US007728023B2

(12) United States Patent
Takeuchi et al.

(10) Patent No.: US 7,728,023 B2
(45) Date of Patent: Jun. 1, 2010

(54) INDOLE COMPOUND AND USE THEREOF

(75) Inventors: Jun Takeuchi, Mishima-gun (JP); Yoshisuke Nakayama, Mishima-gun (JP); Manabu Fujita, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 11/885,018

(22) PCT Filed: Feb. 24, 2006

(86) PCT No.: PCT/JP2006/303374

§ 371 (c)(1), (2), (4) Date: Aug. 24, 2007

(87) PCT Pub. No.: WO2006/090817

PCT Pub. Date: Aug. 31, 2006

(65) Prior Publication Data

US 2008/0188532 A1 Aug. 7, 2008

(30) Foreign Application Priority Data

Feb. 25, 2005 (JP) ............................ 2005-051392
Dec. 7, 2005 (JP) ............................ 2005-352787

(51) Int. Cl.
*A61K 31/41* (2006.01)
*A61K 31/404* (2006.01)
*C07D 257/06* (2006.01)
*C07D 209/04* (2006.01)

(52) U.S. Cl. ...................... 514/381; 514/415; 548/250; 548/254; 548/490

(58) Field of Classification Search ................. 514/381, 514/415; 548/250, 254, 490
See application file for complete search history.

(56) References Cited

U.S. PATENT DOCUMENTS

| | | | |
|---|---|---|---|
| 5,229,413 | A | 7/1993 | Gray et al. |
| 5,530,019 | A | 6/1996 | Okada et al. |
| 5,968,745 | A | 10/1999 | Thorp et al. |
| 6,608,059 | B1 | 8/2003 | Daines et al. |
| 6,833,387 | B1 | 12/2004 | Faull et al. |
| 2003/0207915 | A1 | 11/2003 | Cheng et al. |
| 2005/0004114 | A1 | 1/2005 | Whitehouse et al. |
| 2005/0159474 | A1 | 7/2005 | Arnould |
| 2006/0194797 | A1 | 8/2006 | Takeuchi |

FOREIGN PATENT DOCUMENTS

| | | |
|---|---|---|
| JP | 03-047123 | 2/1991 |
| JP | 7-507574 | 8/1995 |
| JP | 10-512291 | 11/1998 |
| JP | 2002-536362 | 10/2002 |
| WO | 02/00646 | 1/2002 |
| WO | 03/074051 | 9/2003 |
| WO | 03/082271 | 10/2003 |
| WO | 2004/099192 | 11/2004 |
| WO | 2005/021518 | 3/2005 |

OTHER PUBLICATIONS

Stella, Valentino J, Expert Opinion of Therapeutic Patents, Prodrugs as therapeutics, 2004 14(3): 277-280.*

Wolff et al. (Burger's Medicinal Chemistry, 5th Ed., vol. 1, pp. 975-977, 1994).*

Testa, Bernard, Biochemical Pharmacology, Prodrug Research: futile or fertile? 68 (2004) 2097-2106.*

Ettmayer, Peter, Medicinal Chemistry, Lessons Learned from Marketed and Investigational Prodrugs, 47(10) (2004) 2394-2404.*

Morissette et al. Advanced Drug Delivery Reviews 2004, 56, 275-300.*

Vippagunta, Sudha R. "Crystalline Solids." Advanced Drug Delivery Reviews 48(2001): 3-26.*

M. Julia et al., Research in the Indole Series VII. The Cyclization of α-Arylaminoketones, Chemical Abstracts, vol. 58, Abstract No. 12495c, 1963.

R. A. Daines et al., "First X-Ray Cocrystal Structure of a Bacterial FabH Condensing Enzyme and a Small Molecule Inhibitor Achieved using Rational Design and Homology Modeling", Journal of Medicinal Chemistry, vol. 46, No. 1, pp. 5-8, 2003.

(Continued)

*Primary Examiner*—Kamal A Saeed
*Assistant Examiner*—Samantha L Shterengarts
(74) *Attorney, Agent, or Firm*—Wenderoth, Lind & Ponack, LLP.

(57) ABSTRACT

The present invention relates to a compound represented by the formula (I), (I)

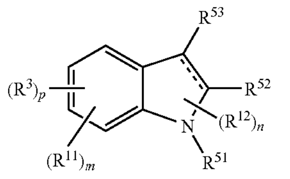

wherein all symbols are as defined in the description, a salt thereof, a solvate thereof, or a prodrug thereof, which has a leukotriene receptor antagonistic activity which is expected to be more effective than those of the leukotriene receptor antagonists currently used in clinical trials. Therefore, it is useful as an agent for the prevention and/or treatment of a leukotriene-mediated disease such as a respiratory diseases such as bronchial asthma, chronic obstructive pulmonary disease, pulmonary emphysema, chronic bronchitis, pneumonia (e.g. interstitial pneumonia etc.), severe acute respiratory syndrome (SARS), acute respiratory distress syndrome (ARDS), allergic rhinitis, sinusitis (e.g. acute sinusitis, chronic sinusitis, etc.), or the like, or as an expectorant or an antiitussive.

6 Claims, No Drawings

OTHER PUBLICATIONS

S. B. Rajur et al., "Synthesis of 1,2,3,4-Tetrahydropyrazino-[1,2-α]indoles and ethyl 1-(2-amino-ethyl)indole-2-carboxylates", Indian Journal of Chemistry, vol. 28B, No. 12, pp. 1065-1068, Dec. 1989.

L. D. Basanagoudar et al., "Synthesis of 10-phenyl-1,2,3,4-tetrahydropyrazino[1,2-α]indoles and ethyl 1-(2-aminoethyl)-3-phenylindole-2-carboxylates", Indian Journal of Chemistry, vol. 30b, No. 11, pp. 1014-1017, Nov. 1991.

F. G. Salituro et al., "3-(2-Carboxyindol-3-yl)propionic Acid-Based Antagonists of the N-Methyl-D-Aspartic Acid Receptor Associated Glycine Binding Site", J. Med. Chem., vol. 35, No. 10, pp. 1791-1799, 1992.

R. D. Fabio et al., "Substituted Indole-2-Carboxylates as in Vivo Potent Antagonists Acting as the Strychnine-Insensitive Glycine Binding Site", J. Med Chem., vol. 40, No. 6, pp. 841-850, 1997.

T. Heinrich et al., "A New Synthesis of Indole 5-Carboxylic Acids and 6-Hydroxy-Indole-5-Carboxylic Acids in the Preparation of an o-Hydroxylated Metabolite of Vilazodone", Bioorganic & Medical Chemistry Letters, vol. 14, No. 10, pp. 2681-2684, 2004.

* cited by examiner

INDOLE COMPOUND AND USE THEREOF

TECHNICAL FIELD

The present invention relates to an indole compound which is useful as a medicament.

More specifically, the present invention relates to:

(1) a compound represented by the formula (I), (I)

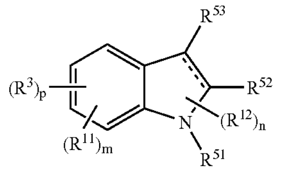

wherein all symbols have the same meanings as defined below;

(2) a pharmaceutical composition containing the compound represented by the formula (I); and (3) a method for the preparation of the compound represented by the formula (I).

BACKGROUND ART

Bronchial asthma is a pathological symptom, in which airway is contracted by airway contraction and inflammation, causing paroxysmal cough, stridor, and breathing difficulty. The drugs for treatment of it include steroidal agents for inhalation, which have a strong antiinflammatory effect, P stimulants and theophyllines which are bronchodilating agents, antiallergic agents which inhibit the effect of chemical mediators, etc.

Histamine, leukotrienes, prostaglandins, TNF-α, etc. are known as various chemical mediators which are released from mast cells or basophils which are concerned in bronchial asthma. Among leukotrienes (LTs), cysteinyl leukotrienes (abbreviated cysLTs hereinafter) represented by $LTC_4$, $LTD_4$ and $LTE_4$ have approximately 1000 times stronger contractile effect on airway as compared to histamine. Moreover, cysLTs promote induction of airway inflammation, typically inflammation cell invasion, airway hypersensitivity and mucus secretion in airway, and they are deeply involved in basic pathology of bronchial asthma.

The leukotriene receptor antagonists which are clinically used, e.g. pranlukast hydrate represented by the formula (A) (See Patent Document 1), montelukast sodium represented by the formula (B) (See Patent Document 2) and zafirlukast represented by the formula (C) (See Patent Document 3) are widely used as useful agents for the treatment of bronchial asthma and allergic rhinitis, which improves various kinds of symptoms and respiratory functions.

(A)

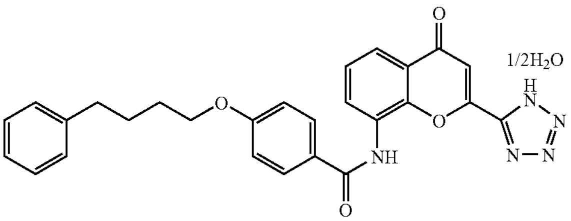

-continued (B)

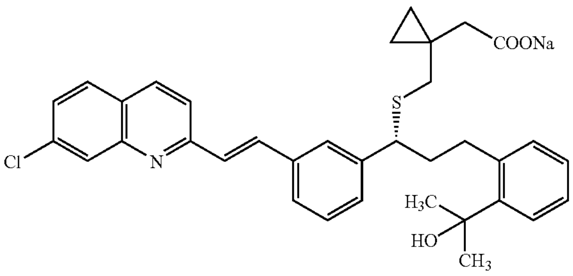

(C)

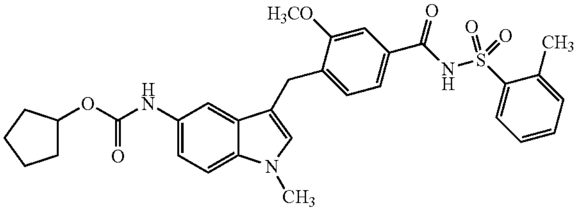

However, it is known these leukotriene receptor antagonists are more effective for mild or moderate symptoms than for severe symptoms. It is also known that there exist some non-responders with mild or moderate symptoms on whom the pharmaceutical agent does not have effect. So agents having higher efficacy than the existing agents have been desired.

Pranlukast hydrate has a strong antagonistic activity against leukotriene receptor, but it also has problems of physical property and systemic absorption.

It is known that a compound represented by the formula (D)

(D)

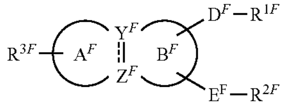

wherein all symbols have the same meanings as described in the document, has an antagonistic activity against $cysLT_2$ receptor.

Pranlukast hydrate which is a leukotriene antagonist is useful for sinusitis (See Patent Document 5), headache such as migraine, migrainous neuralgia or tension-type headache (See Patent Document 6), endometriosis (See Patent Document 7), dysmenorrhea (See Patent Document 8), Meniere's disease, etc.

Patent Document 1: Japan Patent No. 1741466
Patent Document 2: Japan Patent No. 2501385
Patent Document 3: Japan Patent No. 1955810
Patent Document 4: WO2000/18399
Patent Document 5: JP-A-2004-168718
Patent Document 6: JP-A-2002-187855
Patent Document 7: WO2005/058878

DISCLOSURE OF THE INVENTION

Problems to be Solved by the Invention

As described hereinbefore, the leukotriene receptor antagonists which are clinically used are known to act on mild and moderate symptoms of bronchial asthma and it is also known that there exist some non-responders among patients with mild and moderate symptoms, to whom the agents are not effective. Therefore, it has been desired to find a leukotriene receptor antagonist which has stronger activity than that of the existing agents, and those agents for respiratory diseases showing higher efficacy than the existing agents have been desired. And since the indole compound described in patent document 4 has a week antagonistic activity against leukotriene receptor, it is not sufficiently effective when administered orally, so it was desired the improvement to be drug.

Means for Solving the Problems

The present inventors have energetically investigated to solve the above-mentioned problems, and have found out that the compound represented by the formula (I) has a strong antagonistic activity against leukotriene receptor, and an excellent activity when administered orally, and that it is useful as an agent for respiratory diseases to complete the present invention.

That is, the present invention relates to:

[1] A compound represented by the formula (I)

(I)

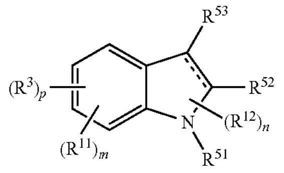

wherein $R^{11}$ and $R^{12}$ each independently represents a substituent, two groups selected from $R^{51}$, $R^{52}$ and $R^{53}$ each independently represents a group having an acidic group which may be protected, the another one selected from $R^{51}$, $R^{52}$ and $R^{53}$ represents a hydrogen atom or a substituent, $R^3$ represents a substituent, m represents 0 or an integer of 1 to 4, n represents 0 or an integer of 1 to 2, p represents 0 or 1, ---------- represents a single bond or a double bond, provided that a sum of m and p is less than or equal to four, a salt thereof, a solvate thereof or a prodrug thereof;

[2] The compound according to the above item [1], wherein p represents 1 and $R^3$ represents a group represented by

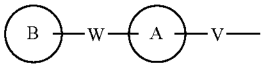

wherein V and W each independently represents a bond or a spacer which has a main chain having 1 to 8 atom(s), ring A and ring B each independently represents a cyclic group which may have a substituent(s);

[3] The compound according to the above item [1], wherein two groups selected from $R^{51}$, $R^{52}$ and $R^{53}$ each independently represents a group selected from -D-$R^1$ and -E-$R^2$ (wherein D and E each independently represents a bond or a spacer which has a main chain having 1 to 8 atom(s), $R^1$ and $R^2$ each independently represents an acidic group which may be protected);

[4] The compound according to the above item [3], wherein $R^1$ and $R^2$ each independently represents —$COOR^A$, —$CONR^AR^B$, —$CONR^BSO_2R^C$, —$SO_2NR^BCOR^C$,

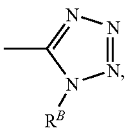 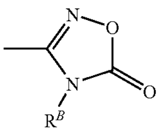 or 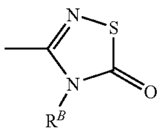

wherein $R^A$ and $R^B$ each independently represents a hydrogen atom or C1-8 alkyl, $R^C$ represents a hydrocarbon group;

[5] The compound according to the above item [2], wherein V represents a divalent radical consisting of 1 to 4 member(s) selected from methylene which may have 1 to 2 substituent(s), ethenylene which may have 1 to 2 substituent(s), ethynylene, a nitrogen atom which may have a substituent —C(O)—, —O—, —S—, —S(O)— and —$SO_2$—;

[6] The compound according to the above item [1], wherein $R^{53}$ represents a group represented by -D-$R^1$(wherein all symbols have the same meanings as in the above item [3]);

[7] The compound according to the above item [1], wherein $R^{51}$ represents a group represented by -E-$R^2$ (wherein all symbols have the same meanings as in the above item [3]);

[8] The compound according to the above item [6], wherein D represents a bond, C1-4 alkylene which may have 1 to 2 substituent(s), —C(O)—(C2-4 alkylene)- which may have 1 to 2 substituent(s), —O—(C1-4 alkylene)- which may have 1 to 2 substituent(s) or —S—(C1-4 alkylene)- which may have 1 to 2 substituent(s); provided that each alkylene group binds to $R^1$;

[9] The compound according to the above item [7], wherein E represents a bond, C1-4 alkylene which may have 1 to 2 substituent(s), —C(O)—(C2-4 alkylene)- which may have 1 to 2 substituent(s), —O—(C1-4 alkylene)- which may have 1 to 2 substituent(s) or —S—(C1-4 alkylene)- which may have 1 to 2 substituent(s); provided that each alkylene group binds to $R^2$;

[10] The compound according to the above item [2], wherein V represents

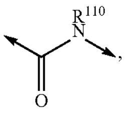, 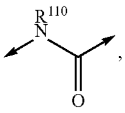, 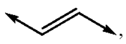, 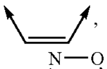, 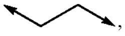,  or 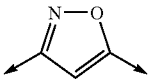

wherein $R^{110}$ represents a hydrogen atom or C1-8 alkyl, and a left arrow binds to ring A;

[11] The compound according to the above item [8], wherein D represents

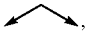, 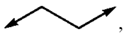, 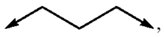, 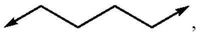, 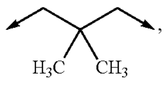,

-continued

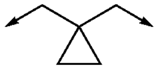
or
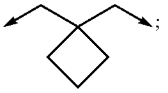;

[12] The compound according to the above item [9], wherein E represents

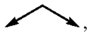, 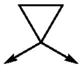, 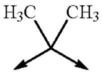, 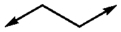 or 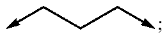;

[13] The compound according to the above item [1], which is a compound represented by the formula (I-a-1)

(I-a-1)

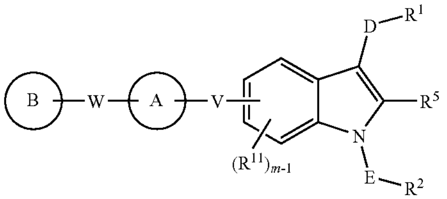

wherein $R^5$ represents a hydrogen atom or a substituent, m-1 represents 0 or an integer of 1 to 3, and the other symbols have the same meanings as in the above items [1], [2] and [3];

[14] The compound according to the above item [1], which is a compound represented by the formula (I-b-1)

(I-b-1)

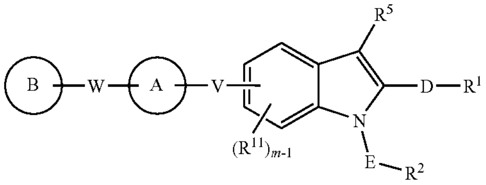

wherein all symbols have the same meanings as in the above items [1], [2], [3] and [11];

[15] The compound according to the above item [1], which is a compound represented by the formula (I-f-2)

(I-f-2)

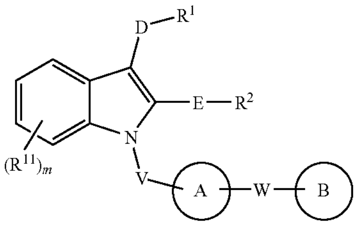

wherein all symbols have the same meanings as in the above items [1], [2] and [3];

[16] The compound according to the above item [13], which is a compound represented by the formula (I-a-1-a)

(I-a-1-a)

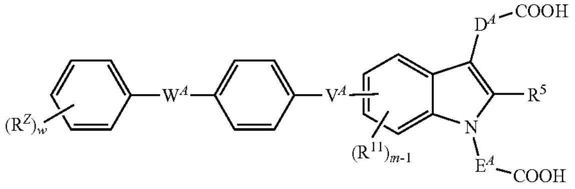

wherein $V^A$ represents

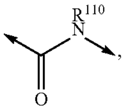, 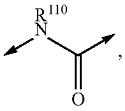, 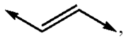, 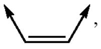, 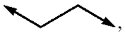,  or 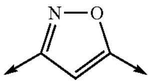

$W^A$ represents —O—(C1-6 allylene)-O—, —O—(C2-6 alkenylene)-O—, —O—(C1-6 alkylene)-C(═O)—, —$CH_2$-phenylene-$CH_2$—, —O—(C1-7 alkylene)- or —(C1-7 alkylene)-O—, $R^5$ represents a hydrogen atom or a substituent, m-1 represents 0 or an integer of 1 to 3, $R^Z$ represents a substituent, w represents 0 or an integer of 1 to 5, DA represents

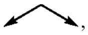, 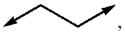, 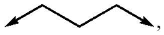, 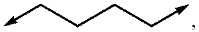, 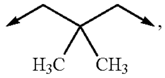, 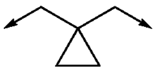 or 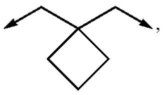, $E^A$ represents

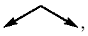, 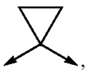, 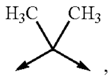, 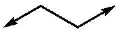 or 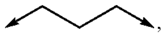, and the other symbols have the same meanings as in the above items [1], [2] and [3];

[17] The compound according to the above item [14], which is a compound represented by the formula (I-b-1-a)

(I-b-1-a)

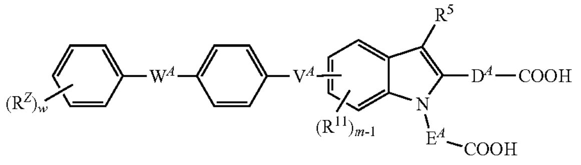

wherein all symbols have the same meanings as in the above items [1], [2], [3] and [16];

[18] The compound according to the above item [1], which is selected from (1) 1-(3-carboxypropyl)-4-{(E)-2-[4-(4-phenylbutoxy)phenyl]vinyl}-1H-indole-3-carboxylic acid,
(2) 4-(3-(carboxymethyl)-4-{(E)-2-[4-(4-phenylbutoxy)phenyl]vinyl}-1H-indol-1-yl)butanoic acid,
(3) 4-(3 carboxymethyl)-4-{(E)-2-[4-(4-phenoxybutoxy)phenyl]vinyl}-1H-indol-1-yl)butanoic acid,
(4) 4-(3-(carboxymethyl)-4-{2-[4-(4-phenylbutoxy)phenyl]ethyl}-1H-indol-1-yl)butanoic acid,
(5) 4-(3-(carboxymethyl)-4-{2-[4-(4-phenoxybutoxy)phenyl]ethyl}-1H-indol-1-yl)butanoic acid,
(6) 4-[4-{(E)-2-[4-(4-phenylbutoxy)phenyl]vinyl}-3-(1H-tetrazol-5-ylmethyl)-1H-indol-1-yl]butanoic acid,
(7) 4-[4-{2-[4-(4-phenylbutoxy)phenyl]ethyl}-3-(1H-tetrazol-5-ylmethyl)-1H-indol-1-yl]butanoic acid,
(8) 4-(3-(carboxymethyl)-4-{(E)-2-[4-(3-phenoxypropoxy)phenyl]vinyl}-1H-indol-1-yl)butanoic acid,
(9) 2,2'-(4-{(E)-2-[4-(4-phenylbutoxy)phenyl]vinyl}-1H-indol-1,3-diyl)diacetic acid,
(10) 4-(3-(carboxymethyl)-4-{(E)-2-[4-(4-phenylbutoxy)phenyl]vinyl}-1H-indol-1-yl)-4-oxobutanoic acid,
(10) 4-(3-(carboxymethyl)-4-{(E)-2-[4-(3-cyclohexylpropoxy)phenyl]vinyl}-1H-indol-1-yl)butanoic acid,
(12) 4-[3-(carboxymethyl)-4-((E)-2-{4-[4-(2-methylphenoxy)butoxy]phenyl}vinyl)-1H-indol-1-yl]butanoic acid,
(13) 4-[4-((E)-2-{4-[4-(2-acetylphenoxy)butoxy]phenyl}vinyl)-3-(carboxymethyl)-1H -indol-1-yl]butanoic acid,
(14) 4-(1-(carboxymethyl)-7-{(E)-2-[4-(4-phenoxybutoxy)phenyl]vinyl}-1H-indol-3-yl)butanoic acid,
(15) 4-[1-(carboxymethyl)-7-((E)-2-{4-[4-(2-chlorophenoxy)butoxy]phenyl}vinyl)-1H-indol-3-yl]butanoic acid,
(16) 4-[1-(carboxymethyl)-7-((E)-2-{4-[4-(2,3-difluorophenoxy)butoxy]phenyl}vinyl)-1H-indol-3-yl]butanoic acid,
(17) 4-[1-(carboxymethyl)-4-fluoro-7-((E)-2-{4-[4-(mesityloxy)butoxy]phenyl}vinyl)-1H-indol-3-yl]butanoic acid,
(18) 4-[1-(carboxymethyl)-7-((E)-2-{4-[4-(2-chloro-3,5-difluorophenoxy)butoxy]phenyl}vinyl)-1H -indol-3-yl]butanoic acid,
(19) 4-[1-(carboxymethyl)-7-((E)-2-{4-[2,6-dichloro-4-methylphenoxy)butoxy]phenyl}vinyl)-1H-indol-3-yl]butanoic acid,
(20) 4-[1-(carboxymethyl)-7-((E)-2-{4-[4-(2,3-difluorophenoxy)butoxy]phenyl}vinyl)-2-methyl-1H-indol-3-yl]butanoic acid,
(21) 4-{1-(carboxymethyl)-7-[(E)-2-(4-{[(2E)-4-(2,3-difluorophenoxy)-2-buten-1-yl]oxy}phenyl)vinyl]-1H-indol-3-yl}butanoic acid,
(22) {[1-(carboxymethyl)-7-((E)-2-{4-[4-(2,3-difluorophenoxy)butoxy]phenyl}vinyl H-indol-3-yl]thio}acetic acid,
(23) {[1-(carboxymethyl)-7-((E)-2-{4-[4-(mesityloxy)butoxy]phenyl}vinyl)-1H-indol-3-yl]thio}acetic acid,
(24) 3-{[1-(carboxymethyl)-7-((E)-2-{4-[4-(2,3-difluorophenoxy)butoxy]phenyl}vinyl)-1H-indol-3-yl]thio}-2-methylpropanoic acid,
(25) 4-(1-(carboxymethyl)-7-{(E)-2-[4-(4-phenoxybutoxy)phenyl]vinyl}-1H-indol-3-yl)-4-oxobutanoic acid,
(26) 4-[1-(carboxymethyl)-5-fluoro-7-((E)-2-{4-[4-(mesityloxy)butoxy]phenyl}vinyl)-1H-indol-3-yl]-4-oxobutanoic acid,
(27) 4-[1-(carboxymethyl)-7-((E)-2-{4-[4-(2,3-difluorophenoxy)butoxy]phenyl}vinyl)-1H-indol-3-yl]-4-oxobutanoic acid,
(28) 3-[1-(carboxymethyl)-7-((E)-2-{4-[4-(2,3-difluorophenoxy)butoxy]phenyl}vinyl)-1H-indol-3-yl]-2,2-dimethyl-3-oxopropanoic acid,
(29) 4-{1-(carboxymethyl)-7-[(E)-2-(4-{[(2E)-4-(mesityloxy)-2-buten-1-yl]oxy}phenyl)vinyl]-1H-indol-3-yl}butanoic acid,
(30) 4-{1-(carboxymethyl)-7-[(E)-2-(4-{[(2E)-4-(2,3-difluorophenoxy)-2-buten-1-yl]oxy}phenyl)vinyl]-2-methyl-1H-indol-3-yl}butanoic acid
(31) [3-{[1-(carboxymethyl)cyclopropyl]methyl}-7-((E)-2-{4-[4-(2,3-difluorophenoxy)butoxy]phenyl}vinyl)-1H-indol-1-yl]acetic acid,
(32) {3-{[1-(carboxymethyl)cyclopropyl]methyl}-7-[(E)-2-(4-{[(2E)-4-(2,3-difluorophenoxy)-2-buten-1-yl]oxy}phenyl)vinyl]-1H-indol-1-yl}acetic acid,
(33) 4-{1-(carboxymethyl)-7-[(E)-2-(4-{[(2E)-4-(2,3-difluorophenoxy-32-buten-1-yl]oxy}phenyl)vinyl]-4-fluoro-2-methyl-1H-indol-3-yl}butanoic acid,
(34) 4-{1 carboxymethyl)-7-[(E)-2-(4-{[(2E)-4-(2-chlorophenoxy)-2-buten-1-yl]oxy}phenyl)vinyl]-2-methyl-1H-indol-3-yl}butanoic acid, and
(35) 4-{1-(carboxymethyl)-7-[(E)-2-(4-{[(2E)-4-(2-chlorophenoxy)-2-buten 1-yl]oxy}phenyl)vinyl]-4-fluoro-2-methyl-1H-indol-3-yl}butanoic acid;

[19] A pharmaceutical composition comprising the compound represented by the formula (I), a salt thereof, a solvate thereof or a prodrug thereof described in the above item [1];

[20] The pharmaceutical composition according to the above item [19], which is a leukotriene receptor antagonist;

[21] The pharmaceutical composition according to the above item [19], which is an agent for the prevention and/or treatment of a leukotriene receptor-mediated disease;

[22] The pharmaceutical composition according to the above item [21], wherein the leukotriene receptor-mediated disease is a respiratory disease;

[23] The pharmaceutical composition according to the above item [22], wherein the respiratory disease is asthma, chronic obstructive pulmonary disease, pulmonary emphysema, chronic bronchitis, pneumonia, severe acute respiratory syndrome, acute respiratory distress syndrome, allergic rhinitis, sinusitis or pulmonary fibrosis;

[24] A medicine comprising the compound represented by the formula (I), a salt thereof, a solvate thereof or a prodrug thereof described in the above item [1] and one or more member(s) selected from a leukotriene receptor antagonist, a steroidal agent, an antihistamine agent, a phosphodiesterase inhibitor, an elastase inhibitor, an anticholinergic agent, a 5-lipoxygenase inhibitor, prostaglandins, a nonsteroidal antiinflammatory agent, a sympathomimetic agent, a thromboxane synthase inhibitor, and a thromboxane receptor antagonist;

[25] A method for the prevention and/or treatment of the leukotriene receptor-mediated disease, characterised by administering to a mammal an effective amount of the compound represented by the formula (I), a salt thereof, a solvate thereof or a prodrug thereof described in the above item [1]; and

[26] Use of the compound represented by the formula (I), a salt thereof, a solvate thereof or a prodrug thereof described in the above item [1], for the manufacture of an agent for the prevention and/or treatment of the leukotriene receptor-mediated disease.

Effect of the Invention

The compound of the present invention represented by the formula (I), a salt thereof, a solvate thereof or a prodrug thereof (abbreviated "the compound of the present invention etc." hereinafter) antagonizes leukotriene receptor, and therefore, it is useful as an inhibitor of airway contraction, an inhibitor of infiltration of inflammatory cells (e.g. eosinophils, neutrophils, lymphocytes, basophils, etc.), an inhibitor of mucus secretion or an inhibitor of increased airway hyperreactivity. Also, the compound of the invention etc. is useful for the prevention and/or treatment of those diseases in which a leukotriene receptor is involved, for example, respiratory diseases (e.g. bronchial asthma, chronic obstructive pulmonary diseases, lung emphysema, chronic bronchitis, pneumonia including interstitial pneumonitis, etc.), severe acute respiratory syndrome (SARS), acute respiratory distress syndrome (ARDS), allergic rhinitis, sinusitis including acute sinusitis, chronic sinusitis, etc., and the like), and as an expectorant or an antiitussive agent. Furthermore, the compound of the present etc. invention is useful as an agent for the improvement of respiratory functions.

The compound of the present invention etc. is useful for the treatment and/or prevention of the diseases which is also concerned with a leukotriene receptor, for example, cardiovascular diseases such as angina pectoris, cardiac infarction, acute coronary syndromes, heart failure, arrhythmia, cardiomyopathy (e.g. dilative cardiomyopathy, hypertrophic cardiomyopathy, etc.), pericarditis, valvulitis, myocarditis, cardiac tamponade, low cardiac output syndrome, mitral stenosis, atherosclerosis, pulmonary fibrosis, cerebral infarction, cerebral edema, aneurysm, headache (migraine, migrainous neuralgia or tension-type headache, etc.), gynecologic disorder (endometriosis, dysmenorrhea, etc.), Meniere's disease, etc.

BEST MODE FOR CARRYING OUT THE INVENTION

In the present specification, among groups represented by $R^{51}$, $R^{52}$ and $R^{53}$, two groups each independently represents a group having an acidic group which may be protected, i.e. a group represented by $-D-R^1$ and $-E-R^2$, and a group remaining one represents a group represented by $R^5$ (wherein $R^5$ represents a hydrogen atom or a substitutent).

As more concrete aspect, a compound of the present invention represented by the formula (I) includes;

(i) a compound, wherein $R^{51}$ represents $-E-R^2$, $R^{52}$ represents $R^5$, $R^{53}$ represents $-D-R^1$, i.e. a compound represented by (I-a)

(I-a)

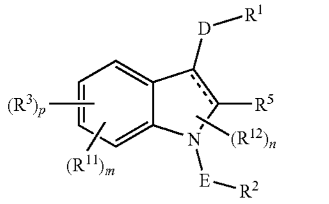

wherein D and E each independently represents a spacer which has a main chain having 1 to 8 atom(s), $R^1$ and $R^2$ each independently represents an acidic group which may be protected, $R^5$ represents a hydrogen atom or a substitutent, other symbols have the same meanings as described hereinbefore;

(ii) a compound, wherein $R^{51}$ represents $-E-R^2$, $R^{52}$ represents $-D-R^1$, $R^{53}$ represents $R^5$, i.e. a compound represented by (I-b)

(I-b)

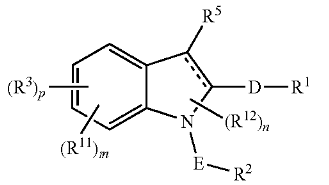

wherein all symbols have the same meanings as described hereinbefore; and (iii) a compound, wherein $R^{51}$ represents $R^5$, $R^{52}$ represents $-E-R^2$, $R^{53}$ represents $-D-R^1$, i.e. a compound represented by (I-c)

(I-c)

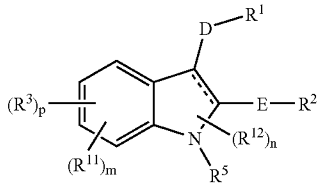

wherein all symbols have the same meanings as described hereinbefore.

In the present specification, a "substituent" represented by $R^{11}$ and $R^{12}$ each independently includes, for example, (1) alkyl which may have a substituent(s), (2) alkenyl which may have a substituent(s), (3) alkynyl which may have a substituent(s), (4) carbocyclic ring which may have a substituent(s), (5) heterocyclic ring which may have a substituent(s), (6) hydroxy which may be protected, (7) mercapto which may be protected, (8) amino which may be protected, (9) carbamoyl which may have a substituent(s), (10) sulfamoyl which may have a substituent(s), (11) carboxy, (12) alkoxycarbonyl (e.g. C1-6 alkoxycarbonyl such as methoxycarbonyl, ethoxycarbonyl, tert-butoxycarbonyl, etc.), (13) sulfo, (14) sulfino, (15) phosphono, (16) nitro, (17) cyano, (18) amidino, (19) imino,

(20) dihydroborono, (21) halogen (e.g. fluorine, chlorine, bromine, iodine), (22) alkylsulfinyl (e.g. C1-4 alkylsulfinyl such as methylsulfinyl, ethylsulfinyl, etc.), (23) aromatic ring-sulfinyl (e.g. C6-10 aromatic ring-sulfinyl such as phenylsulfinyl etc.), (24) alkylsulfonyl (e.g. C1-4 alkylsulfonyl such as methylsulfonyl, ethylsulfonyl, etc.), (25) aromatic ring-sulfonyl (e.g. C6-10 aromatic ring-sulfonyl such as phenylsulfonyl etc.), (26) acyl, (27) oxo, (28) thioxo, (29) (C1-6 alkoxyimino)methyl (e.g. (methoxyimino)methyl etc.), etc., and 1 to 5 of these substituents may be positioned where acceptable.

The alkyl in the "(1) alkyl which may have a substituent(s)" as a substituent represented by $R^{11}$ and $R^{12}$ includes straight or branched C1-20 alkyl such as methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, etc.

Here, a substituent of the (1) alkyl which may have a substituent(s) includes, for example, a substituent(s) selected from the following (a) to (x), and 1 to 4 of these substituents may be positioned where acceptable.

(a) Hydroxy, (b) amino, (c) carboxy, (d) nitro, (e) azido, (f) mono- or di-C1-6 alkylamino (e.g. methylamino, ethylamino, propylamino, dimethylamino, diethylamino, etc.), (g) N-aromatic ring-amino (e.g. N-phenylamino etc.), (h) N-aromatic ring-N-alkylamino (e.g. N-phenyl-N-methylamino, N-phenyl-N-ethylamino, N-phenyl-N-propylamino, N-phenyl-N-butylamino, N-phenyl-N-pentylamino, N-phenyl-N-hexylamino, etc.), (i) acylamino (e.g. C1-6 acylamino such as acetylamino, propionylamino, butyrylamino, valerylamino, hexanoylamino, etc.), (j) N-acyl-N-alkylamino (e.g. N—(C1-6 acyl)-N—(C1-6 alkyl)amino such as N-acetyl-N-methylamino, N-acetyl-N-ethylamino, N-acetyl-N-propylamino, N-acetyl-N-butylamino, N-propionyl-N-methylamino, N-propionyl-N-ethylamino, N-propionyl-N-propylamino, N-propionyl-N-butylamino, etc.), (k) C1-6 alkoxy (e.g. methoxy, ethoxy, propoxy, isopropoxy, hexyloxy, etc.), (l) C3-7 cycloalkyl-C1-6 alkoxy (e.g. cyclohexylmethyloxy, cyclopentylethyloxy, etc.), (m) C3-7 cycloalkyloxy (e.g. cyclopropyloxy, cyclobutyloxy, cycloheptyloxy, cyclohexyloxy etc.), (n) C7-15 aralkyloxy (e.g. benzyloxy, phenethyloxy, phenylpropyloxy, naphthylmethyloxy, naphthylethyloxy, etc.), (o) phenoxy, (p) C1-6 alkoxycarbonyl (e.g. methoxycarbonyl, ethoxycarbonyl, tert-butoxycarbonyl, etc.), (q) C1-6 acyloxy (e.g. acetoxy, propionyloxy, butyryloxy, etc.), (r) C1-4 alkylthio (e.g. methylthio, ethylthio, propylthio, butylthio, etc.), (s) halogen (fluorine, chlorine, bromine, iodine), (t) C1-4 alkylsulfonyl (e.g. methylsulfonyl, ethylsulfonyl; etc.), (u) aromatic ring-sulfonyl (e.g. C6-10 aromatic ring-sulfonyl such as phenylsulfonyl, naphthylsulfonyl, etc., 5 to 10 membered aromatic heterocyclic ring-sulfonyl such as pyridylsulfonyl, thienosulfonyl, furylsulfonyl, etc.), (v) acyl, (w) carbocyclic ring which may have a substituent(s), (x) heterocyclic ring which may have a substituent(s), etc.

Here, a carbocyclic ring in the "(w) carbocyclic ring which may have a substituent(s)" refers to C3-15 carbocyclic ring, for example, optionally partially or completely saturated C3-15 mono- or poly-cyclic aromatic carbocyclic ring. Optionally partially or completely saturated C3-15 mono- or poly-cyclic aromatic carbocyclic ring includes e.g. cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene ring. Optionally partially or completely saturated C3-15 mono- or poly-cyclic aromatic carbocyclic ring also includes a polycyclic carbocyclic ring having a spiro bond, and a bridged polycyclic carbocyclic ring, for example, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane or noradamantane ring.

A substituent in the "(w) carbocyclic ring which may have a substituent(s)" refers to C1-8 alkyl (e.g. methyl, ethyl, n-propyl, isopropyl, n-butyl, isobutyl, sec-butyl, tert-butyl, pentyl, hexyl, heptyl, octyl, etc.), hydroxy, amino, carboxy, nitro, mono- or di-C1-6 alkylamino (e.g. methylamino, ethylamino, propylamino, dimethylamino, diethylamino, etc.), C1-6 alkoxy (e.g. methoxy, ethoxy, propoxy, hexyloxy, etc.), C1-6 alkoxycarbonyl (e.g. methoxycarbonyl, ethoxycarbonyl, tert-butoxycarbonyl, etc.), C1-6 acyloxy (e.g. acetoxy, propionyloxy, butyryloxy, etc.), C1-4 alkylthio (e.g. methylthio, ethylthio, propylthio, butylthio, etc.), halogen (fluorine, chlorine, bromine, iodine), trihalomethyl (e.g. trifluoromethyl etc.), etc, and 1 to 4 of these substituents may be positioned where acceptable.

A heterocyclic ring in the "(x) heterocyclic ring which may have a substituent(s)" refers to 3 to 15 membered heterocyclic ring, for example, optionally partially or completely saturated 3 to 15 membered mono- or poly-cyclic aromatic heterocyclic ring comprising 1 to 5 hetero atom(s) selected from oxygen, nitrogen and sulfur atom, etc.

Among optionally partially or completely saturated 3 to 15 membered mono- or poly-cyclic aromatic heterocyclic ring comprising 1 to 5 hetero atom(s) selected from oxygen, nitrogen and sulfur atom, 3 to 15 membered mono- or poly-cyclic aromatic heterocyclic ring comprising 1 to 5 hetero atom(s) selected from oxygen, nitrogen and sulfur atom includes, for example, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazane, benzothiadiazole, benzotriazole, carbazole, fine, acridine, phenazine, dibenzofuran xanthene, dibenzothiophene, phenothiazine, phenoxazine, phenoxathiin, thianthrene, phenanthridine, phenanthroline, perimidine ring.

Among optionally partially or completely saturated 3 to 15 membered mono- or poly-cyclic aromatic heterocyclic ring comprising 1 to 5 hetero atom(s) selected from oxygen, nitrogen and sulfur atom, partially or completely saturated 3 to 15 membered mono- or poly-cyclic aromatic heterocyclic ring comprising 1 to 5 hetero atom(s) selected from oxygen, nitrogen and sulfur atom includes, for example, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane ring.

A substituent in the "(x) heterocyclic ring which may have a substituent(s)" has the same meaning of the above-mentioned substituent in the "(w) carbocyclic ring which may have a substituent(s)".

An alkenyl in the "(2) alkenyl which may have a substituent(s)" as a substituent represented by $R^{11}$ and $R^{12}$ includes e.g. straight or branched C2-20 alkenyl such as ethenyl, propenyl, butenyl, pentenyl, hexenyl, etc. A "substituent" in the "(2) alkenyl which may have a substituent(s)" has the same meaning of the above-mentioned "substituent" in the "(1) alkyl which may have a substituent(s)".

An alkynyl in the "(3) alkynyl which may have a substituent(s)" as a substituent represented by $R^{11}$ and $R^{12}$ includes e.g. straight or branched C2-20 alkynyl such as ethynyl, propynyl, butynyl, pentynyl, hexynyl, etc. Here a substituent of the "(3) alkynyl which may have a substituent(s)" has the same meaning of the above-mentioned substituent in the "(1) alkyl which may have a substituent(s)".

The "(4) carbocyclic ring which may have a substituent(s)" as a substituent represented by $R^{11}$ and $R^{12}$ has the same meaning of the above-mentioned (w) carbocyclic ring which may have a substituent(s) as a substituent in the "(1) alkyl which may have a substituent(s)" represented by $R^{11}$ and $R^{12}$.

The "(5) Heterocyclic ring which may have a substituent(s)" as a substituent represented by $R^{11}$ and $R^{12}$ has the same meaning of the above-mentioned (x) heterocyclic ring which may have a substituent(s) as a substituent in the "(1) alkyl which may have a substituent(s)" represented by $R^{11}$ and $R^{12}$.

A protective group for protection of "(6) hydroxy which may be protected", "(7) mercapto which may be protected", "(8) amino which may be protected" as a substituent represented by $R^{11}$ and $R^{12}$ includes, for example, alkyl which may have a substituent(s) (it has the same meaning of the above-mentioned "(1) alkyl which may have a substituent(s)"), alkenyl which may have a substituent(s) (it has the same meaning of the above-mentioned "(2) alkenyl which may have a substituent(s)"), alkynyl which may have a substituent(s) (it has the same meaning of the above-mentioned "(3) alkynyl which may have a substituent(s)"), carbocyclic ring which may have a substituent(s) (it has the same meaning of the above-mentioned "(w) carbocyclic ring which may have a substituent(s)"), heterocyclic ring which may have a substituent(s) (it has the same meaning of the above-mentioned "(x) heterocyclic ring which may have a substituent(s)"), alkylsulfonyl (it has the same meaning of the above-mentioned "(t) alklylsulfonyl"), aromatic ring-sulfonyl (it has the same meaning of the above-mentioned "(u) aromatic ring-sulfonyl"), acyl etc. The "(8) amino which may be protected" can be protected by 1 or 2 protective group(s).

The "(9) carbamoyl which may have a substituent(s)" as a substituent represented by $R^{11}$ and $R^{12}$ includes, for example, carbamoyl which has no substituent, N-mono-C1-4 alkylcarbamoyl such as N-methylcarbamoyl, N-ethylcarbamoyl, N-propylcarbamoyl, N-isopropylcarbamoyl, N-butylcarbamoyl, etc., N,N-di-C1-4 alkylcarbamoyl such as N,N-dimethylcarbamoyl, N,N-diethylcarbamoyl, N,N-dipropylcarbamoyl, N,N-dibutylcarbamoyl, etc., 1-piperidiylcarbamoyl etc.

The "(10) sulfamoyl which may have a substituent(s)" as a substituent represented by $R^{11}$ and $R^{12}$ includes, for example, sulfamoyl which has no substituent, N-mono-C1-4 alkylsulfamoyl such as N-methylsulfamoyl, N-ethylsulfamoyl, N-propylsulfamoyl, N-isopropylsulfamoyl, N-butylsulfamoyl, etc., N,N-di-C1-4 alkylsulfamoyl such as N,N-dimethylsulfamoyl, N,N-diethylsulfamoyl, N,N-dipropylsulfamoyl, N,N-dibutylsulfamoyl, etc.) etc.

The "(26) acyl" as a substituent represented by $R^{11}$ and $R^{12}$, "(v) acyl", and "acyl" as a protective group in the "(6) hydroxy which may be protected", "(7) mercapto which may be protected" and "(8) amino which may be protected" include, for example, (i) alkylcarbonyl which may have a substituent(s), (ii) alkenylcarbonyl which may have a substituent(s), (iii) alkynylcarbonyl which may have a substituent(s), (iv) carbocyclic ring—carbonyl which may have a substituent(s), (v) heterocyclic ring—carbonyl which may have a substituent(s). Here an "alkyl which may have a substituent(s)" in the "(i) alkylcarbonyl which may have a substituent(s)" has the same meaning of the above-mentioned "alkyl which may have a substituent(s)" in the "(1) alkyl which may have a substituent(s)". An "alkenyl which may have a substituent(s)" in the "(ii) alkenylcarbonyl which may have a substituent(s)" has the same meaning of the above-mentioned "alkenyl which may have a substituent(s)", in the "(2) alkenyl which may have a substituent(s)". An "alkynyl which may have a substituent(s)" in the "(iii) alkynylcarbonyl which may have a substituent(s)" has the same meaning of the above-mentioned "alkynyl which may have a substituent(s)" in the "(3) alkynyl which may have a substituent(s)". A "carbocyclic ring which may have a substituent(s)" in the "(iv) carbocyclic ring—carbonyl which may have a substituent(s)" has the same meaning of the above-mentioned "carbocyclic ring which may have a substituent(s)" in the "(w) carbocyclic ring which may have a substituent(s)". A "heterocyclic ring which may have a substituent(s)" in the "(v) heterocyclic ring—carbonyl which may have a substituent(s)" has the same meaning of the above-mentioned "heterocyclic ring which may have a substituent(s)" in the "(x) heterocyclic ring which may have a substituent(s)".

In the present specification, a "substituent" represented by $R^3$ includes, for example, (1) alkyl which may have a substituent(s), (2) alkenyl which may have a substituent(s), (3) alkynyl which may have a substituent(s), (4) carbocyclic ring which may have a substituent(s), (5) heterocyclic ring which may have a substituent(s), (6) hydroxy which may be protected, (7) mercapto which may be protected, (8) amino which may be protected, (9) carbamoyl which may have a substituent(s), (10) sulfamoyl which may have a substituent(s), (11) carboxy, (12) alkoxycarbonyl (e.g. C1-6 alkoxycarbonyl such as methoxycarbonyl, ethoxycarbonyl, tert-butoxycarbonyl, etc.), (13) sulfo, (14) sulfino, (15) phosphono, (16) nitro, (17) cyano, (18) amidino, (19) imino, (20) dihydroborono, (21) halogen (e.g. fluorine, chlorine, bromine, iodine), (22) alkylsulfinyl (e.g. CA-4 alkylsulfinyl such as methylsulfinyl, ethylsulfinyl, etc.), (23) aromatic ring-sulfinyl (e.g. C6-10 aromatic ring-sulfinyl such as phenylsulfinyl, naphthylsulfinyl etc.), (24) alkylsulfonyl (e.g. C1-4 alkylsulfonyl such as methylsulfonyl, ethylsulfonyl, etc.), (25) aromatic ring-sulfonyl (e.g. C6-10 aromatic ring-sulfonyl such as phenylsulfonyl, naphthylsulfonyl, etc.), (26) acyl (it has the same meaning of the above-mentioned "(26) acyl"), (27) oxo, (28) thioxo, (29) (C1-6 alkoxyimino)methyl (e.g. (methoxyimino)methyl, (ethoxyimino)methyl, etc.), or (30)

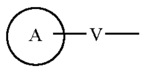

wherein ring A represents a cyclic group which may have a substituent(s), V represents a bond or a spacer which has a main chain having 1 to 8 atom(s).

An (1) Alkyl which may have a substituent(s), (2) alkenyl which may have a substituent(s), (3) alkynyl which may have a substituent(s), (4) carbocyclic ring which may have a substituent(s), (5) heterocyclic ring which may have a substituent(s), (6) hydroxy which may be protected, (7) mercapto which may be protected, (8) amino which may be protected, (9) carbamoyl which may have a substituent(s) and (10) sulfamoyl which may have a substituent(s) as a substituent represented by $R^3$ has the same meaning of the above-mentioned (1) alkyl which may have a substituent(s), (2) alkenyl which may have a substituent(s), (3) alkynyl which may have a substituent(s), (4) carbocyclic ring which may have a substituent(s), (5) heterocyclic ring which may have a substituent(s), (6) hydroxy which may be protected, (7) mercapto which may be protected, (8) amino which may be protected, (9) carbamoyl which may have a substituent(s) and (10) sulfamoyl which may have a substituent(s) as a substituent represented by $R^{11}$ and $R^{12}$, respectively.

In the present specification, a "cyclic group" in the "cyclic group which may have a substituent(s)" represented by ring A refers to, for example, "carbocyclic ring" or "heterocyclic ring".

The "carbocyclic ring" refers to C3-15 carbocyclic ring, for example, C3-15 mono-, or poly-cyclic aromatic carbocyclic ring, partially or completely saturated one thereof, spiro poly-cyclic carbocyclic ring and bridged carbocyclic ring. For example, cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo[2.2.1]hept-2-ene, bicyclo[3.1.1]heptane, bicyclo[3.1.1]hept-2-ene, bicyclo[2.2.2]octane, bicyclo[2.2.2]oct-2-ene, adamantane or noradamantane ring, etc. are included.

The "heterocyclic ring" refers to, for example, optionally partially or completely saturated 3 to 15 membered mono- or poly-cyclic aromatic heterocyclic ring comprising 1 to 5 of hetero atom(s) selected from oxygen, nitrogen and sulfur. For example, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazane, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenantholine, perimidine, pyrazolopyridine, aziridine, azetidine, pyrazoline, pyrrolidine, imidazoline, imidazolidine, triazoline, triazolidine, tetrazoline, tetrzolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothizine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chroman, benzodithiolane, benzodithiane, azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxaspiro[5.5]undecane, azabicyclo[2.2.1]heptane, oxabicyclo[2.2.1]heptane, azabicyclo[3.1.1]heptane, azabicyclo[3.2.1]octane, oxabicyclo[3.2.1]octane, azabicyclo[2.2.2]octane, diazabicyclo[2.2.2]octane, tetrahydro, carboline, hexahydroazepinoindole, oxazaspiro[2.5]octane, hexahydroazepinoindazole, hexahydropyrazolopyridoazepine, tetrahydropyrazoloisoquinoline or tetrahydropyrazolonaphthyridine ring, etc. are included.

In the present specification, a "substituent" in the "cyclic group which may have a substituent(s)" represented by ring A includes, for example, (1) alkyl which may have a substituent(s), (2) alkenyl which may have a substituent(s) (3) alkynyl which may have a substituent(s), (4) carbocyclic ring which may have a substituent(s), (5) heterocyclic ring which may have a substituent(s), (6) hydroxy which may be protected, (7) mercapto which may be protected, (8) amino which may be protected, (9) carbamoyl which may have a substituent(s), (10) sulfamoyl which may have a substituent(s), (11) carboxy, (12) alkoxycarbonyl (e.g. C1-6 alkoxycarbonyl such as methoxycarbonyl, ethoxycarbonyl, tert-butoxycarbonyl, etc.), (13) sulfo, (14) sulfino, (15) phosphono, (16) nitro, (17) cyano, (18) amidino, (19) imino, (20) dihydroborono, (21) halogen (fluorine, chlorine, bromine, iodine), (22) alkylsulfinyl (e.g. C1-4 alkylsulfinyl such as methylsulfinyl, ethylsulfinyl, etc.), (23) aromatic ring-sulfinyl (e.g. C6-10 aromatic ring-sulfinyl such as phenylsulfinyl, naphthylsulfinyl, etc.), (24) alkylsulfonyl (e.g. C1-4 alkylsulfonyl such as methylsulfonyl, ethylsulfonyl, etc.), (25) aromatic ring-sulfonyl (e.g. C6-10 aromatic ring-sulfonyl such as phenylsulfonyl, naphthylsulfonyl, etc.), (26) acyl (it has the same meaning of the above-mentioned "(26) acyl"), (27) oxo, (28) thioxo, (29) (C1-6 alkoxyimino)methyl (e.g. (methoxyimino)methyl, (ethoxyimino)methyl, etc.), (30)

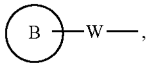, wherein ring B represents a cyclic group which may have a substituent(s), W represents a bond or a spacer which has a main chain having 1 to 8 atom(s), etc., and 1 to 5 of these substituents may be positioned where acceptable.

In the present specification, (1) alkyl which may have a substituent(s), (2) alkenyl which may have a substituents), (3) alkynyl which may have a substituent(s), (4) carbocyclic ring which may have a substituent(s), (5) heterocyclic ring which may have a substituent(s), (6) hydroxy which may be protected, (7) mercapto which may be protected, (8) amino which may be protected, (9) carbamoyl which may have a substituent(s), and (10) sulfamoyl which may have a substituent(s) as a "substituent" in the "cyclic group which may have a substituent(s)" represented by ring A has the same meaning of the above-mentioned (1) alkyl which may have a substituent(s), (2) alkenyl which may have a substituent(s), (3) alkynyl which may have a substituent(s), (4) carbocyclic ring which may have a substituent(s), (5) heterocyclic ring which may have a substituent(s), (6) hydroxy which may be protected, (7) mercapto which may be protected, (8) amino which may be protected, (9) carbamoyl which may have a substituent(s), and (10) sulfamoyl which may have a substituent(s) as a "substituent" represented by $R^{11}$ and $R^{12}$, respectively.

In the present specification, a "cyclic group" in the "cyclic group which may have a substituent(s)" represented by ring B has the same meaning of the above-mentioned "cyclic group" in the "cyclic group which may have a substituent(s)" represented by ring A.

In the present specification, a "substituent" in the "cyclic group which may have a substituent(s)" represented by ring B refers to, for example, the above-mentioned (1)-(29) listed as examples of "substituent" in the "cyclic group which may have a substituent(s)" represented by ring A and

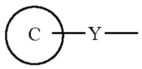

wherein ring C represents a cyclic group which may have a substituent(s), Y represents a bond or a spacer which has a main chain having 1 to 8 atom(s), etc., and 1 to 3 of these substituents may be positioned where acceptable.

A "cyclic group" in the "cyclic group which may have a substituent(s)" represented by ring C has the same meaning of the above-mentioned "cyclic group" in the "cyclic group which may have a substituent(s)" represented by ring A.

A "substituent" in the "cyclic group which may have a substituent(s)" represented by ring C refers to, for example, the above-mentioned (1)-(29) listed as examples of "substituent" in the "cyclic group which may have a substituent(s)" represented by ring A and 1 to 3 of these substituents may be positioned where acceptable.

In the present specification, a "substituent" represented by $R^5$ includes, for example, (1) alkyl which may have a substituent(s), (2) alkenyl which may have a substituent(s), (3) alkynyl which may have a substituent(s), (4) carbocyclic ring which may have a substituent(s), (5) heterocyclic ring which may have a substituent(s), (6) hydroxy which may be protected, (7) mercapto which may be protected, (8) amino which may be protected, (9) carbamoyl which may have a substituent(s), (10) sulfamoyl which may have a substituent(s), (11) carboxy, (12) alkoxycarbonyl (e.g. C1-6 alkoxycarbonyl such as methoxycarbonyl, ethoxycarbonyl, tert-butoxycarbonyl, etc.), (13) sulfo, (14) sulfino, (15) phosphono, (16) nitro, (17) cyano, (18) amidino, (19) imino, (20) dihydroborono, (21) halogen (fluorine, chlorine, bromine, iodine), (22) alkylsulfinyl (e.g. C1-4 alkylsulfinyl such as methylsulfinyl, ethylsulfinyl, etc.), (23) aromatic ring-sulfinyl (e.g. C6-10 aromatic ring-sulfinyl such as phenylsulfinyl, naphthylsulfinyl, etc.), (24) alkylsulfonyl (e.g. C1-4 alkylsulfonyl such as methylsulfonyl, ethylsulfonyl, etc.), (25) aromatic ring-sulfonyl (e.g. C6-10 aromatic ring-sulfonyl such as phenylsulfonyl, naphthylsulfonyl, etc.), (26) acyl (it has the same meaning as described hereinbefore), (27) oxo, (28) thioxo, (29) (C1-6 alkoxyimino)methyl (e.g. (methoxyimino)methyl, (ethoxyimino)methyl, etc.), (30)

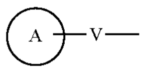

wherein all symbols have the same meanings as described hereinbefore, etc.

(1) Alkyl which may have a substituent(s), (2) alkenyl which may have a substituent(s), (3) alkynyl which may have a substituent(s), (4) carbocyclic ring which may have a substituent(s), (5) heterocyclic ring which may have a substituent(s), (6) hydroxy which may be protected, (7) mercapto which may be protected, (8) amino which may be protected, (9) carbamoyl which may have a substituent(s), and (10) sulfamoyl which may have a substituent(s) as "substituent" represented by $R^5$ has the same meaning of the above-mentioned (1) alkyl which may have a substituent(s), (2) alkenyl which may have a substituent(s), (3) alkynyl which may have a substituent(s), (4) carbocyclic ring which may have a substituent(s), (5) heterocyclic ring which may have a substituent(s), (6) hydroxy which may be protected, (7) mercapto which may be protected, (8) amino which may be protected, (9) carbamoyl which may have a substituent(s), and (10) sulfamoyl which may have a substituent(s) as "substituent" represented by $R^{11}$ and $R^{12}$, respectively.

In the present specification, an "acidic group" in the "acidic group which may be protected" represented by $R^1$ and $R^2$ includes various kinds of Brönsted acid, e.g. carboxy (—COOH), hydroxamic acid (—CONHOH), acylcyanamide (—CONHCN), sulfo (—$SO_3H$), sulfonamide (—$SO_2NH_2$ or $NR^{100}SO_3H$), acylsulfonamide (—$CONHSO_2R^{100}$ or $SO_2NHCOR^{100}$), phosphono (—$P(=O)(OH)_2$), phosphinico (=P(=O)OH), amino(hydroxy)phosphoryl (—P(=O)(OH)($NH_2$)), phenol (—$C_6H_4OH$) or heterocyclic ring residue which comprises a deprotonable hydrogen atom etc., etc.

Here, $R^{100}$ is a hydrogen atom or hydrocarbon group which may have a substituent(s). The "hydrocarbon group" has the same meaning of the below-mentioned "hydrocarbon group" as a protective group in the "acidic group which may be protected". The "Brönsted acid" represents a substance which gives a hydrogen ion to another substance. The "Heterocyclic ring residue which comprises a deprotonable hydrogen atom" includes, for example,

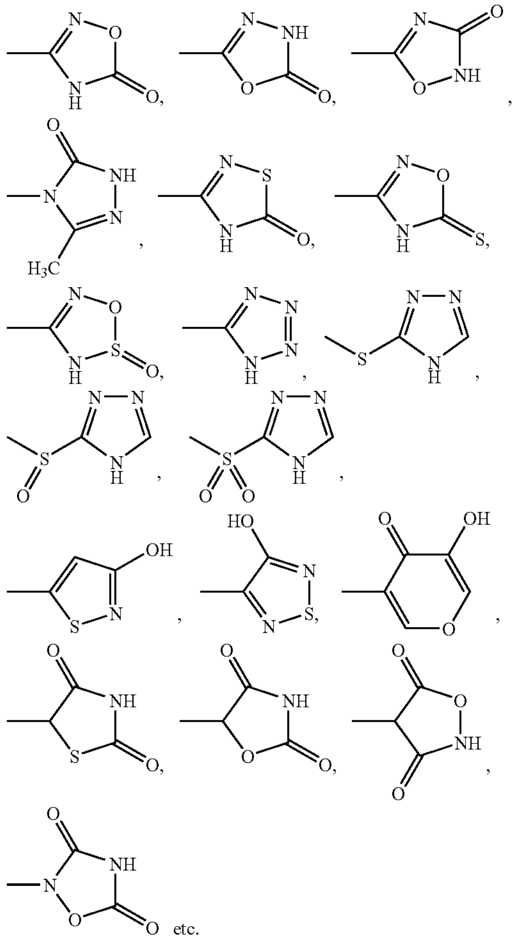

etc.

A "protective group" for protection of the "acidic group which may be protected" represented by $R^1$ and $R^2$ includes, for example, a hydrocarbon group which may have a substituent(s), C1-6 alkoxy, optionally protected amino, 1-piperidinyl or 4-morpholinyl, etc.

Here a "hydrocarbon group" in the "hydrocarbon group which may have a substituent(s)" as a protective group includes, for example, C1-15 alkyl such as methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, etc.; C3-8 cycloalkyl such as cyclopropyl, cyclobutyl, cyclopentyl, cyclohexyl, etc.; C2-10 alkenyl such as vinyl, allyl, 2-methylallyl, 2-butenyl, 3-butenyl, 3-octenyl, etc.; C2-10 alkynyl such as ethynyl, 2-propynyl, 3-hexynyl, etc.; C3-10 cycloalkenyl such as cyclopropenyl, cyclopentenyl, cyclohexenyl, etc.; C6-14 aryl such as phenyl, naphthyl, etc.; C7-16 aralkyl such as benzyl, phenylethyl, etc.; (C3-8 cycloalkyl)(C1-6 alkyl) such as cyclohexylmethyl, cyclohexylethyl, cyclohexylpropyl, 1-methyl-1-cyclohexylmethyl, etc.

A substituent in the "hydrocarbon group which may have a substituent(s)" includes, for example, (1) nitro, (2) hydroxy, (3) oxo, (4) thioxo, (5) cyano, (6) carbamoyl, (7) aminocarbonyl substituted by C1-8 hydrocarbon etc. such as N-butylaminocarbonyl, N-cyclohexylmethylaminocarbonyl, N-butyl-N-cyclohexylmethylaminocarbonyl, N-cyclohexylaminocarbonyl, phenylaminocarbonyl, (8) carboxy, (9) C1-6 alkoxycarbonyl such as methoxycarbonyl, ethoxycarbonyl, etc., (10) sulfo, (11) halogen such as fluorine, chlorine, bromine, iodine, etc., (12) C1-6 alkoxy such as methoxy, ethoxy, propoxy, isopropoxy, butoxy, isobutoxy, sec-butoxy, tert-butoxy, etc., (13) phenoxy, (14) halogenophenoxy such as o-, m- or p-chlorophenoxy, o-, m- or p-bromophenoxy, (15) C1-6 alkylthio such as methylthio, ethylthio, n-propylthio, isopropylthio, n-butylthio, tert-butylthio, etc., (16) phenylthio, (17) C1-6 alkylsulfinyl such as methylsulfinyl, ethylsulfinyl, etc., (18) C1-4 alkylsulfonyl such as methylsulfonyl, ethylsulfonyl, etc., (19) amino, (20) C1-6 acylamino such as acetylamino, propionylamino, etc., (21) primary or secondary amino substituted with hydrocarbon group such as methylamino, ethylamino, n-propylamino, isopropylamino, n-butylamino, dimethylamino, diethylamino, cyclohexylamino, 1-carbamoyl-2-cyclohexylethylamino, N-butyl-N-cyclohexylmethylamino, phenylamino (wherein this "hydrocarbon group" has the same meaning as the above "hydrocarbon group" in the "hydrocarbon group which may have a substituent(s)" and it may be substituted with oxo, amino, carbamoyl, etc.), (22) C1-6 acyl such as formyl, acetyl, etc., (23) benzoyl, (24) 5 to 6 membered heterocyclic ring comprising 1 to 4 hetero atom(s) selected from oxygen, sulfur, nitrogen, etc. besides carbon atom which may have 1 to 4 of substituent selected from 1 to 4 of substituent(s) selected from (a) halogen such as bromine, chlorine, fluorine, (b) hydrocarbon group which may be substituted with oxo, hydroxy, etc., wherein the "hydrocarbon group" (it has the same meaning as the above "hydrocarbon group"), (c) halogenophenoxy such as o-, m- or p-chlorophenoxy, o-, m- or p-bromophenoxy, etc., and (d) oxo, etc., for example, 2- or 3-thienyl, 2- or 3-furyl, 3-, 4- or 5-pyrazolyl, 4-tetrahydropyranyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4- or 5-pyrimidyl, 3- or 4-pyridazinyl, quinolyl, isoquinolyl, indolyl, etc., (25) C1-10 haloalkyl such as difluoromethyl, trifluoromethyl, trifluoroethyl, trichloroethyl, etc., (26) hydroxyimino, or (27) C1-4 alkyloxyimino such as methyloxyimino, ethyloxyimino, etc. The "hydrocarbon group which may have a substituent(s)" may have 1 to 5 of substituent(s) selected from the above (1) to (27) and, when the "hydrocarbon group" is cycloalkyl, cycloalkenyl, aryl or aralkyl, it may have 1 to 4 C1-4 alkyl(s) such as methyl, ethyl, propyl, isopropyl, butyl, etc. as substituent, and also when it has more than one substituent, the substituents may be the same or different.

A "C1-6 alkoxy" as a protective group in the "acidic group which may be protected" represented by $R^1$ and $R^2$ includes, for example, methoxy, ethoxy, propoxy, butoxy, pentyloxy, hexyloxy, etc.

A protective group for protection of an amino in the "amino which may be protected" as a protective group of an acid group in the "acidic group which may be protected" represented by $R^1$ and $R^2$ refers to the above-mentioned "hydrocarbon which may have a substituent(s)". Amino in the "amino which may be protected" can be protected by 1 or 2 protective group(s).

An "acidic group which may be protected" represented by $R^1$ and $R^2$ includes, for example, an ester such as methoxycarbonyl, ethoxycarbonyl, benzyloxycarbonyl, etc., an amide such as carbamoyl, dimethylcarbamoyl, etc., a lactone such as β-lactone, γ-lactone, δ-lactone, etc., a lactam such as β-lactam, γ-lactam, δ-lactam, etc.

In the present specification, a "spacer which has a main chain having 1 to 8 atom(s)" represented by D, E, V W and Y means an interval of 1 to 8 of atom in succession. Here an atom in the main chain is counted so as to minimize the atom in the main chain. D, E, V, W and Y each independently represents a spacer which has a main chain having 1 to 8 atom(s).

The "spacer which has a main chain having 1 to 8 atom(s)" includes, for example, a divalent radical consisting of 1 to 8 member(s) selected from methylene which may have 1 to 2 substituent(s), ethenylene which may have 1 to 2 substituent(s) ethynylene, a nitrogen atom which may have a substituent, —C(O)—, —O—, —S—, —S(O)—, and —$SO_2$—. Here, a substituent of methylene, ethenylene and nitrogen atom has the same meaning of the above-mentioned "substituent" in the "cyclic group which may have a substituent(s)" represented by ring A. Two substituents in the spacer may be taken together to form a C3-8 carbocyclic ring or a 3 to 8 membered heterocyclic ring.

More specifically, a spacer which has a main chain having 1 to 8 atom(s) represented by D, E, V, W and Y includes, for example, a radical consisting of member(s) selected from —$CR^{101}R^{102}$—, —$NR^{103}$—, —CO—, —O—, —S—, —$NR^{103}CO$—, $CONR^{103}$—, —$NR^{103}COCR^{101}R^{102}$—, —$CONR^{103}CR^{101}R^{102}$—, —$C(R^{101})$=$C(R^{102})$— and —C≡C— (wherein $R^{101}$, $R^{102}$ and $R^{103}$ represent a hydrogen atom or have the same meanings of the above-mentioned "substituent" in the "cyclic group which may have a substituent(s)" represented by ring A). Concretely, For example, C1-8 alkylene such as methylene, ethylene, propylene, butylene, pentylene, hexylene, heptylene, octylene and an isomer thereof, —O—C1-6 alkylene-O— such as oxymethyloxy, oxyethyloxy, oxypropyloxy, oxybutyloxy, oxypentyloxy, oxyhexyloxy and an isomer thereof, C2-8 alkenylene such as ethenylene, propenylene, butenylene, pentenylene, hexenylene, heptenylene, octenylene and an isomer thereof, —C1-7 alkylene-O such as methyleneoxy, ethyleneoxy, propyleneoxy, butyleneoxy, pentyleneoxy, hexyleneoxy, heptyleneoxy and an isomer thereof, —C(=O)—C1-6 alkylene-O— such as carbonylmethyloxy, carbonylethyloxy, carbonylpropyloxy, carbonylbutyloxy, carbonylpentyloxy, carbonylhexyloxy and an isomer thereof, —S—(C1-6 alkylene)O— such as thiomethyloxy, thioethyloxy, thiopropyloxy, thiobutyloxy, thiopentyloxy, thiohexyloxy and an isomer thereof, —S—(C1-7 alkylene)- such as thiomethyl thioethyl, thiopropyl, thiobutyl, thiopentyl, thiohexyl, thioheptyl and an isomer thereof, —C(=O)—C1-7 alkylene- such as carbonylmethyl, carbonylethyl, carbonylpropyl, carbonylbutyl, carbonylpentyl, carbonylhexyl, carbonylheptyl and an isomer thereof, etc., etc.

When two substituents in the spacer are taken together to form C3-8 carbocyclic ring or 3 to 8 membered heterocyclic ring, the C3-8 carbocyclic ring which is formed by two substituents in the spacer taken together refers to, for example, benzene, cyclopropane, cyclobutane, cyclopentane, cyclohexane, cycloheptane, cyclooctane, cyclobutene, cyclopentene, cyclohexene, cycloheptene, cyclooctene, cyclooctadiene, etc. The 3 to 8 membered heterocyclic ring which is formed by two substituents in the spacer taken together refers to, for example, pyrrole, pyridine, pyrazine, oxazole, thiazole, aziridine, azetidine, pyrrolidine, piperidine, morpholine, thiomorpholine, furan, thiophene, tetrahydrofuran, tetrahydrothiophene, isooxazole, isothiazole, etc.

In the present specification, a preferable aspect is as follows.

Both of single bond and double bond are preferable for 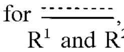, but it is double bond particularly preferably.

$R^1$ and $R^2$ is each independently preferably, —$COOR^A$, —$CONR^BSO_2R^C$, —$SO_2NR^BCOR^C$,

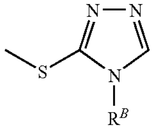, 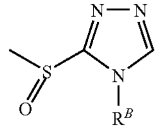,

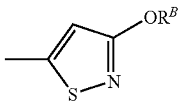, 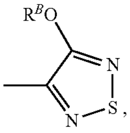,

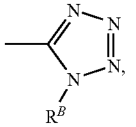, 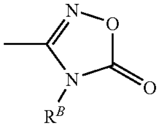 or 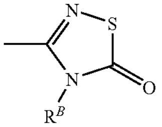

wherein $R^A$ and $R^B$ each independently represents a hydrogen atom or C1-8 alkyl, $R^C$ represents hydrocarbon group, and more preferably —$COOR^A$, —$CONR^BSO_2R^C$, —$SO_2NR^BCOR^C$,

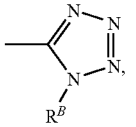, 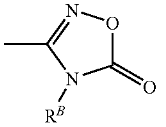 or 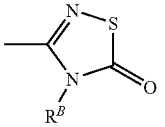

wherein all symbols have the same meanings as described hereinbefore.

A C1-8 alkyl represented by $R^A$ and $R^B$ includes, for example, methyl, ethyl, propyl, isopropyl, butyl, isobutyl, sec-butyl, tert-butyl, pentyl, hexyl, heptyl, octyl, etc. A hydrocarbon group represented by $R^C$ includes, for example, C1-8 alkyl such as methyl, ethyl, propyl, isopropyl, butyl, isobutyl, sec-butyl, tert-butyl, pentyl, hexyl, heptyl, octyl, etc., C3-8 cycloalkyl such as cyclopropyl, cyclobutyl, cyclopentyl, cyclohexyl, etc., C2-8 alkenyl such as vinyl, allyl, 2-methylallyl, 2-butenyl, 3-butenyl, 3-octenyl, etc., C2-8 alkynyl such as ethynyl, 2-propynyl, 3-hexynyl, etc., C3-8 cycloalkenyl such as cyclobutenyl, cyclopentenyl, cyclohexenyl, etc., C6-8 aryl such as phenyl etc., C7-8 aralkyl such as benzyl, phenylethyl, etc., (C3-8 cycloalkyl)-C1-4 alkyl) such as cyclohexylmethyl, cyclohexylethyl, cyclopentylmethyl, 1-methyl-1-cyclopentylmethyl, etc.

D and E is each independently preferably a bond or a spacer consisting of 1 to 5 of atom in the main chain, more preferably, a divalent radical consisting of a combination of 1 to 5 member(s) selected from a bond, methylene which may have 1 to 2 substituent(s), nitrogen atom which may have a substituent, —C(O)—, —O—, —S—, —S(O)— and —$SO_2$—, furthermore preferably, a bond, C1-4 alkylene which may have 1 to 4 substituent(s), —C(O)C2-4 alkylene)- which may have 1 to 4 substituent(s), (C1-4 alkylene)- which may have 1 to 4 substituent(s) or —S—(C1-4 alkylene)- which may have 1 to 4 substituent(s) (an alkylene in each group binds to $R^1$ or $R^2$), and a bond, C1-4 alkylene which may have 1 to 2 substituent(s), —C(O)C2-4 alkylene)- which may have 1 to 2 substituent(s) or —S—(C1-4 alkylene)- which may have 1 to 2 substituent(s) are most preferable. In these groups, C1-4 alkylene represents methylene, ethylene, propylene, butylene and an isomer thereof, and C2-4 alkylene represents ethylene, propylene, butylene and an isomer thereof. Both of straight or branched alkylene are preferable.

A substituent in the group in the D and E is preferably C3-6 carbocyclic ring such as cyclopropyl, cyclobutyl, cyclopentyl, cyclohexyl, cycloheptyl, cyclooctyl, phenyl, etc., hydroxy, C1-4 alkoxy, amino, dimethylamino, etc. It is also preferable that two substituents in the D and E are taken together to form C3-6 carbocyclic ring such as cyclopropane, cyclobutane, cyclopentane, cyclohexane, benzene.

More specifically, D is preferably

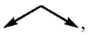, 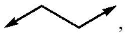, 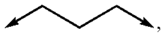,

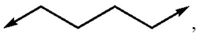, 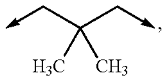,

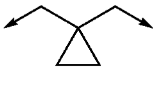 or 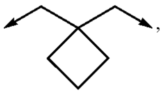, and E is preferably

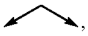, 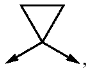, 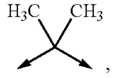,

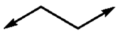 or 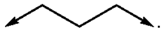.

$R^3$ is preferably

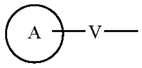

wherein all symbols have the same meanings as described hereinbefore.

Ring A is preferably C3-10 mono- or bi-cyclic aromatic carbocyclic ring, partially or completely saturated carbocyclic ring, or optionally partially or completely saturated 3 to 10 membered mono- or bi-cyclic aromatic heterocyclic ring comprising 1 to 3 hetero atom(s) selected from oxygen, sulfur and nitrogen atom, and cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, pyridine, pyrrole, quinoline, isoquinoline, oxazole, thiazole, benzooxazole or benzothiazole ring are more preferable.

Ring A may have a substituent(s), and the substituent is preferably the 1 to 5 group(s) selected from C1-8 alkyl which may have a substituent(s), C2-8 alkenyl which may have a substituent(s), C1-8 alkoxy which may have a substituent(s), C2-8 alkenyloxy which may have a substituent(s), C5-10 mono- or bi-cyclic carbocyclic ring which may have a substituent(s), 5 to 10 membered mono- or bi-cyclic heterocyclic ring which may have a substituent(s), hydroxy which may be protected, mercapto which may be protected, amino which may be protected, carbamoyl which may have a substituent(s), carboxy, alkoxycarbonyl, nitro, cyano, halogen, acyl, oxo and

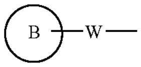

wherein all symbols have the same meanings as described hereinbefore, and these substituents may be positioned where acceptable. As a substituent of ring A, methoxy, ethoxy, hexenyloxy, and

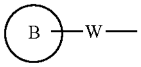

wherein all symbols have the same meanings as described hereinbefore, are more preferable.

Ring B is preferably C3-10 mono- or bi-cyclic aromatic carbocyclic ring, partially or completely saturated carbocyclic ring, or optionally partially or completely saturated 3 to 10 membered mono- or bi-cyclic aromatic heterocyclic ring comprising 1 to 3 hetero atom(s) selected from oxygen, sulfur and nitrogen atom, and cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, pyridine, pyrrole, quinoline, isoquinoline, oxazole, thiazole, benzdooxazole or benzothiazole ring are more preferable.

Ring B may have a substituent, and the substituent is preferably 1 to 3 group(s) selected from hydroxy, C1-8 alkyl, C2-8 alkenyl, C2-8 alkynyl, halogen, C1-8 alkoxy, C2-8 alkenyloxy, C2-8 alkynyloxy, C1-8 alkylthio, C1-8 acyl, C1-4 alkyl substituted with 1 to 3 halogen(s), C1-4 alkyl substituted with hydroxy, C1-4 alkyl substituted with mercapto, C1-4 alkoxy substituted with 1 to 3 halogen(s), and 1 to 3 group(s) selected from hydroxy, methyl, ethyl, propyl, n-butyl, n-pentyl, n-hexyl, isobutyl, propenyl, fluoro, chloro, bromo, methoxy, ethoxy, propoxy, butoxy, propenyloxy, butenyloxy, propynyloxy, butyntloxy, methylthio, ethylthio, acetyl, propanoyl, trifluoromethyl, trifluoromethoxy and

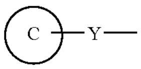

wherein all symbols have the same meanings as described hereinbefore, are more preferable, and these substituents may be positioned where acceptable.

V which binds to ring A etc. is preferably, a bond or spacer which has a main chain having 1 to 5 atom(s) and a divalent radical consisting of 1 to 4 member(s) selected from a bond, methylene which may have 1 to 2 substituent(s), ethenylene which may have 1 to 2 substituent(s), ethynylene, a nitrogen atom which may have a substituent, —O—, —S—, —S(O)— and —S and —$CR^{10}R^{102}$—, —$CR^{101}R^{102}CR^{103}R^{14}$—, —$CR^{100}$=$CR^{102}$—, —$CONR^{103}$—, —$CR^{101}R^{102}NR^{103}$—, —$NR^{103}CO$—, —$NR^{103}COCR^{101}R^{102}$—, —$CONR^{103}CR^{101}R^{102}$—, —$OCR^{101}R^{102}$— or —$CR^{11}R^{102}$—O— (wherein $R^{101}$ to $R^{103}$ have the same meanings as described hereinbefore), are more preferable, and

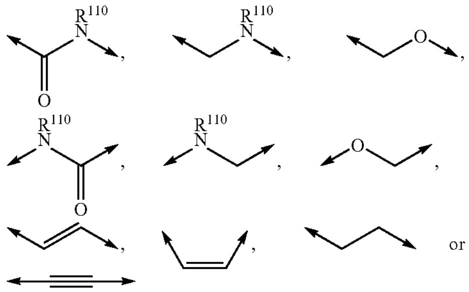

or wherein $R^{110}$ represents a hydrogen atom or a C1-8 alkyl such as methyl, ethyl, propyl, isopropyl, butyl, isobutyl, sec-butyl, tert-butyl, pentyl, hexyl, heptyl, octyl, etc., a left arrow binds to ring A, and a right arrow binds to indole ring, are most preferable.

V is also preferably a carbocyclic ring or heterocyclic ring which the substituents of ethenylene are taken together to form. For example,

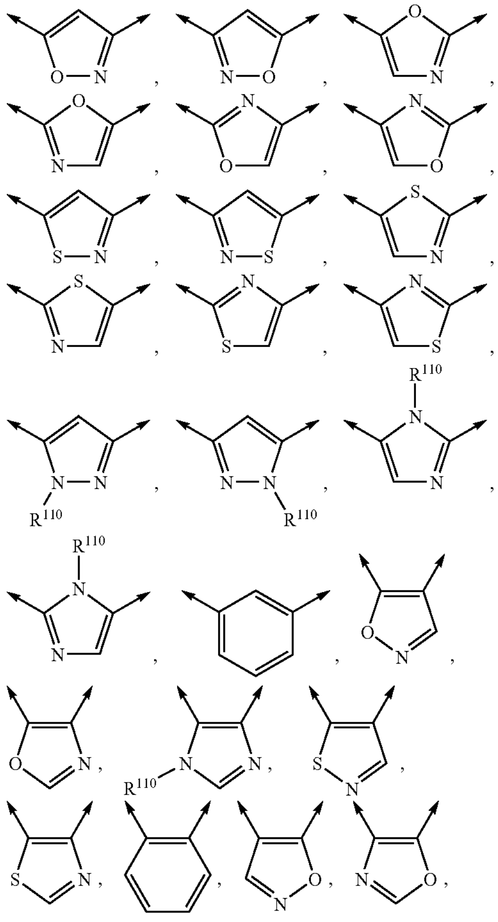

-continued

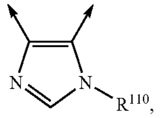

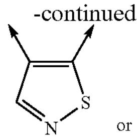

or

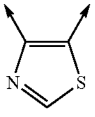

wherein all symbols have the same meanings as described hereinbefore, are preferable.

V is much preferably a group represented by

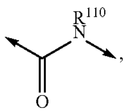

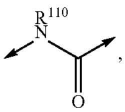

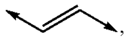

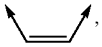

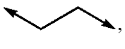

or

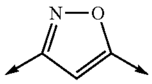

W is preferably a divalent radical consisting of 1 to 8 member(s) selected from a bond, methylene which may have 1 to 2 substituent(s), a nitrogen atom which may have a substituent, —C(O)—, —O—, —S—, —S(O)— and —$SO_2$—, and —O—(C1-6 alkylene)-O—, —O—(C2-6 alkenylene)-O—, —O—(C1-6 alkylene)-C(=O)—, —$CH_2$-phenylene-$CH_2$—, —O—(C1-7 alkylene or 4 C1-7 alkylene)-O—, etc. are more preferable.

Specifically, W is preferably a group represented by

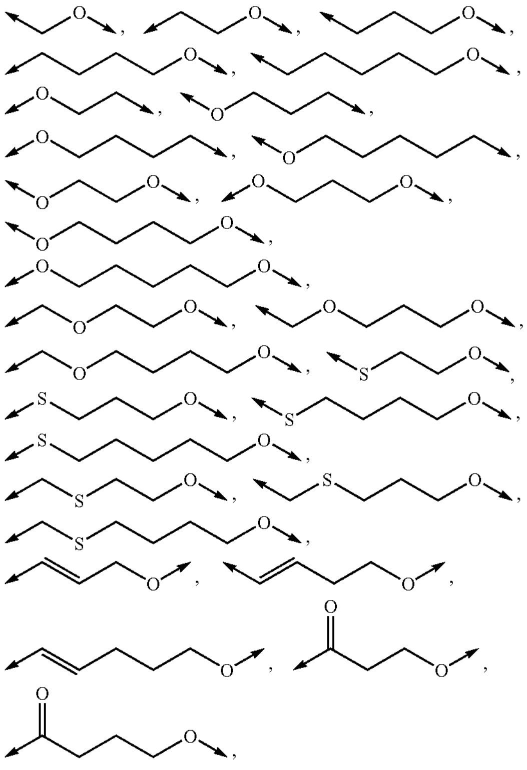

-continued

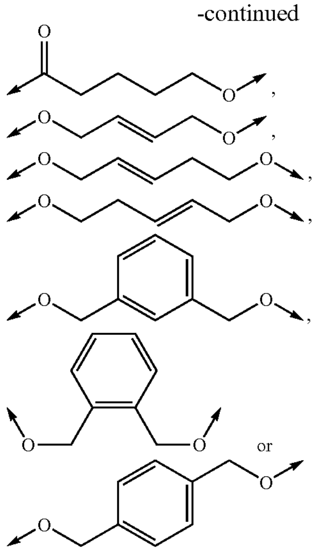

wherein a left arrow binds to ring B, and a right arrow binds to ring A.

Y which binds to ring C etc. is preferably a bond or a spacer which has a main chain having 1 to 6 atom(s), and a divalent radical consisting of 1 to 6 member(s) selected from a bond, methylene which may have 1 to 2 substituent(s), a nitrogen atom which may have a substituent, —C(O)—, —O—, —S—, —S(O)— and —$SO_2$— are more preferable, and ←O—$(CH_2)_2$→, ←O—$(CH_2)_3$→, ←O—$(CH_2)_4$→, ←O—$(CH_2)_5$→, ←O—$(CH_2)_2$→, ←$(CH_2)_3$—O→, ←$(CH_2)_4$—O→, ←$(CH_2)_5$—O→, ←O—$(CH_2)_2$—O→, ←O—$(CH_2)_3$—O→, ←O—$(CH_2)_4$—O→, ←$(CH_2)_5$—O→, ←S—$(CH_2)_2$ —O→, ←S—$(CH_2)_3$—O→, ←S—$(CH_2)_4$—O—, ←S—$(CH_2)_5$—O→, —C(O)—$(CH_2)_4$—, —C(O)—$(CH_2)_5$—, —C(O)—$(CH_2)_4$—O, —C(O)—$(CH_2)_5$—O— are most preferable. A left arrow binds to ring C, and a right arrow binds to ring B.

Ring C is preferably optionally partially or completely saturated C3-10 mono- or bi-cyclic aromatic carbocyclic ring, or optionally partially or completely saturated 3 to 10 membered mono- or bi-cyclic aromatic heterocyclic ring comprising 1 to 3 hetero atom(s) selected from oxygen, sulfur and nitrogen atom and cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, pyridine, pyrrole, quinoline, isoquinoline, oxazole, thiazole, benzooxazole or benzothiazole ring are more preferable.

When ring C has a substituent(s), the substituent of ring C is preferably 1 to 3 group(s) selected from hydroxy, C1-8 alkyl C2-8 alkenyl, C2-8 alkynyl, halogen, C1-8 alkoxy, C2-8 alkenyloxy, C2-8 alkynyloxy, C1-8 alkylthio, C1-8 acyl, C1-4 alkyl substituted by 1 to 3 halogen(s), C1-4 alkoxy substituted by 1 to 3 halogen(s), C5-10 carbocyclic ring, 5 to 10 membered heterocyclic ring, and 1 to 3 group(s) selected from hydroxy, methyl, ethyl, propyl, n-butyl, n-pentyl, n-hexyl, fluoro, chloro, bromo, methoxy, ethoxy, propoxy, butoxy, acetyl, propanoyl, trifluoromethyl and methylthio are more preferable, and these substituents may be positioned where acceptable.

$R^5$ is preferably a group selected from a hydrogen atom, hydroxy, C1-8 alkyl, C2-8 alkenyl, C2-8 alkynyl, halogen, C1-8 alkoxy, C2-8 alkenyloxy, C2-8 alkynyloxy, C1-8 alkylthio, C1-8 acyl, C1-4 alkyl substituted with 1 to 3 halogen(s), C1-4 alkoxy substituted with 1 to 3 halogen(s), C5-10 carbocyclic ring, and 5 to 10 membered heterocyclic ring, and a hydrogen atom, hydroxy, methyl, ethyl, propyl, n-butyl, n-pentyl, n-hexyl, fluoro, chloro, bromo, methoxy, ethoxy, propoxy, butoxy, acetyl, propanoyl, trifluoromethyl or methylthio are more preferable.

In the present invention, a compound represented by the formula (I), a salt thereof, a solvate thereof, or a prodrug thereof, which contains the combinations listed above as preferable groups, preferable rings, and preferable atoms are preferable. More preferable compound of the present invention is exemplified below. For example, a compound of the present invention represented by the formula (I-a-0)

(I-a-0)

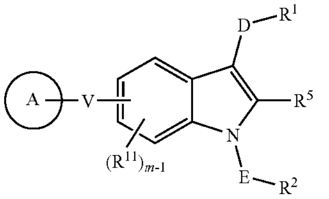

wherein m-1 represents 0 or an integer of 1 to 3, and other symbols have the same meanings as described hereinbefore, a compound of the present invention represented by the formula (I-b-0)

(I-b-0)

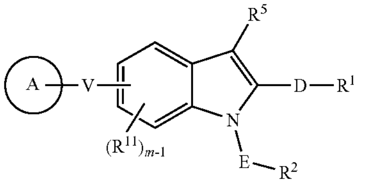

wherein all symbols have the same meanings as described hereinbefore, a compound of the present invention represented by the formula (I-c-0)

(I-c-0)

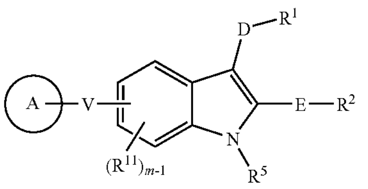

wherein all symbols have the same meanings as described hereinbefore, a compound of the present invention represented by the formula (I-d-0)

(I-d-0)

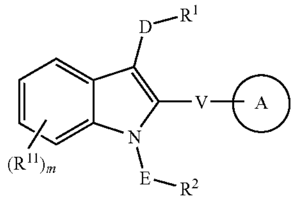

wherein all symbols have the same meanings as described hereinbefore, a compound of the present invention represented by the formula (I-e-0)

(I-e-0)

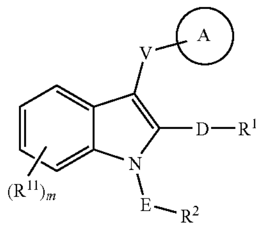

wherein all symbols have the same meanings as described hereinbefore, and a compound of the present invention represented by the formula (I-f-0)

(I-f-0)

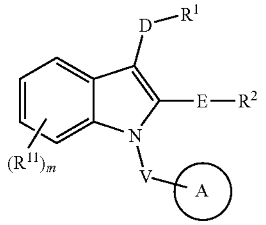

wherein all symbols have the same meanings as described hereinbefore.

Further more preferable compound of the present invention is exemplified below. For example, a compound of the present invention represented by the formula (I-a-1)

(I-a-1)

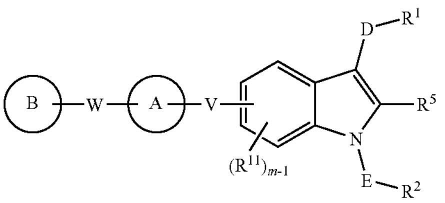

wherein all symbols have the same meanings as described hereinbefore, a compound of the present invention represented by the formula (I-b-1)

(I-b-1)

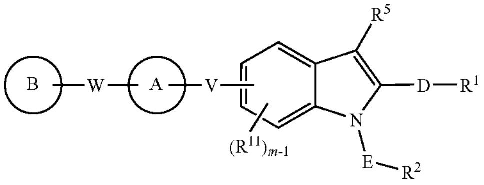

wherein all symbols have the same meanings as described hereinbefore, a compound of the present invention represented by the formula (I-c-1)

(I-c-1)

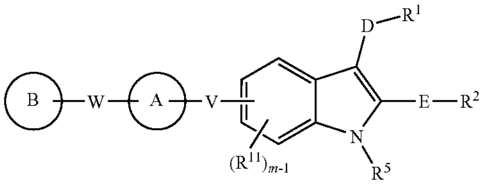

wherein all symbols have the same meanings as described hereinbefore, and a compound of the present invention represented by the formula (I-f-1)

(I-f-1)

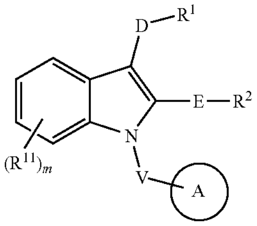

wherein all symbols have the same meanings as described hereinbefore.

Most preferable compound of the present invention is exemplified below. For example, a compound of the present invention represented by the formula (I-a-2)

(I-a-2)

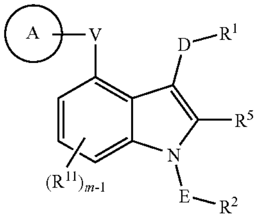

wherein all symbols have the same meanings as described hereinbefore, a compound of the present invention represented by the formula (I-b-2)

(I-b-2)

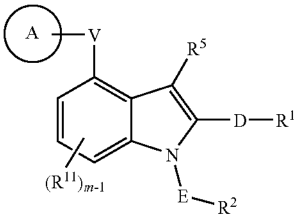

wherein all symbols have the same meanings as described hereinbefore, a compound of the present invention represented by the formula (I-c-2)

(I-c-2)

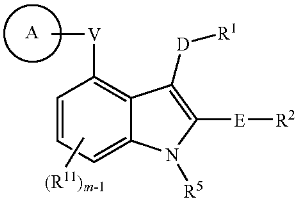

wherein all symbols have the same meanings as described hereinbefore, a compound of the present invention represented by the formula (I-a-3)

(I-a-3)

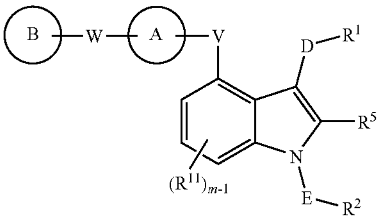

wherein all symbols have the same meanings as described hereinbefore, a compound of the present invention represented by the formula (I-b-3)

(I-b-3)

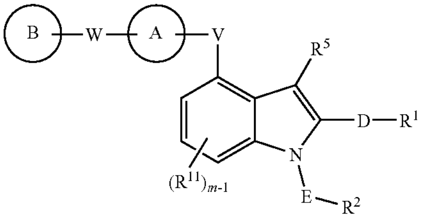

wherein all symbols have the same meanings as described hereinbefore, a compound of the present invention represented by the formula (I-c-3)

(I-c-3)

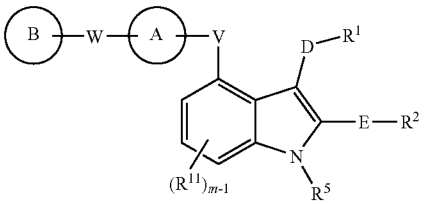

wherein all symbols have the same meanings as described hereinbefore, a compound of the present invention represented by the formula (I-f-2)

(I-f-2)

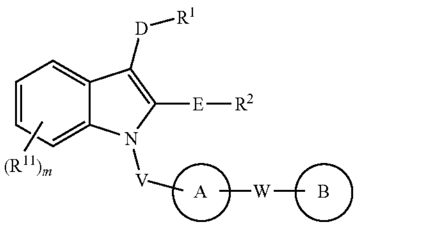

wherein all symbols have the same meanings as described hereinbefore, a compound of the present invention represented by the formula (I-a-4)

(I-a-4)

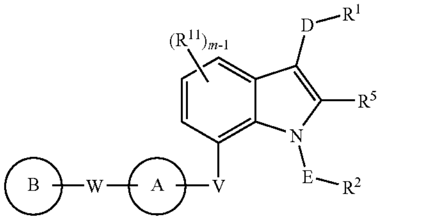

wherein all symbols have the same meanings as described hereinbefore, a compound of the present invention represented by the formula (I-b-4)

(I-b-4)

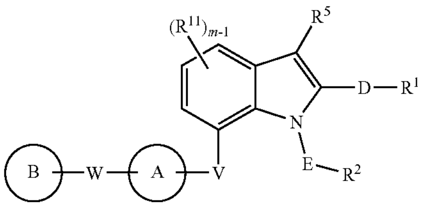

wherein all symbols have the same meanings as described hereinbefore, a compound of the present invention represented by the formula (I-c-4)

(I-c-4)

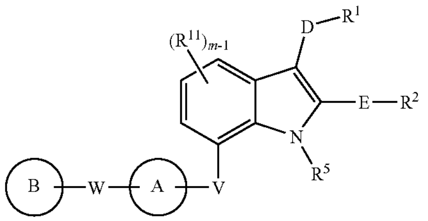

wherein all symbols have the same meanings as described hereinbefore, a compound of the present invention represented by the formula (I-a-1-a)

(I-a-1-a)

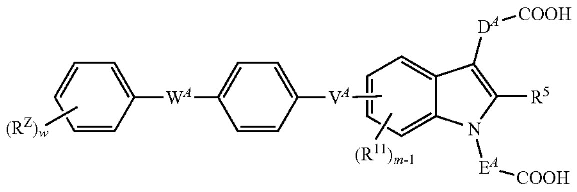

wherein $V^A$ represents

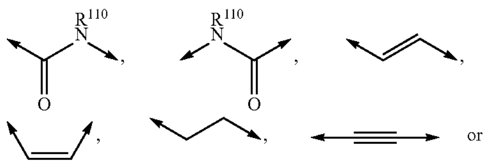

or

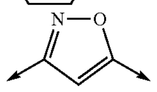

$W^A$ represents (C1-6 alkylene)-O—, —O—(C2-6 alkenylene)-O—, —O—(C2-6 alkylene)-O—, —O—(C1-6 alkylene)-C(=O)—, —$CH_2$-phenylene-$CH_2$—, —O—(C1-7 alkylene)- or —(C1-7 alkylene)-O—, m-1 represents 0 or an integer of 1 to 3, $R^Z$ represents a substituents, w represents 0 or an integer of 1 to 5, $D^A$ represents

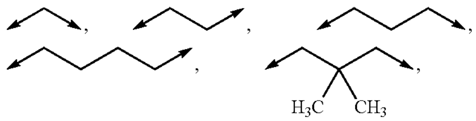

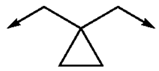

or

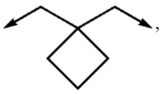

$E^A$ represents

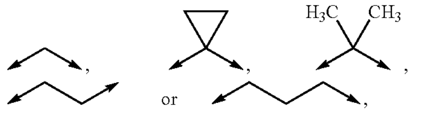

or and other symbols have the same meanings as described hereinbefore, and a compound of the present invention represented by the formula (I-b-1-a)

(I-b-1-a)

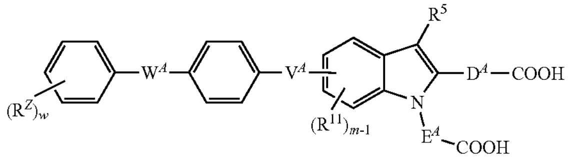

wherein all symbols have the same meanings as described hereinbefore, and a salt thereof, a solvate thereof, and a prodrug thereof.

A "substituent" represented by $R^Z$ in the formulae (I-a-1-a) and (I-b-1-a) has the same meaning of the "substituent" in the "cyclic group which may have a substituent(s)" represented by ring B. As $R^Z$, alkyl which may have a substituent(s) alkenyl which may have a substituent(s), carbocyclic ring which may have a substituent(s), heterocyclic ring which may have a substituent(s), hydroxy which may be protected, amino which may be protected, carboxy, alkoxycarbonyl, halogen, acyl, etc. are preferable, and methyl, ethyl, propyl, butyl, isobutyl, pentyl, trifluoromethyl, benzyl, phenethyl, benzoyl, phenylsulfonyl, vinyl, allyl, phenyl, pyridyl, furyl, thienyl, hydroxy, methoxy, ethoxy, phenoxy, benzyloxy, amino, dimethylamino, diethylamino, carboxy, methoxycarbonyl, ethoxycarbonyl, fluoro, chloro, bromo, iodo, acetyl, propionyl, etc. are more preferable. w is preferably 0 or an integer of 1 to 3, when w is two or more, and a plurality of $R^Z$s are the same or different from each other.

In the present invention, all compounds of the present invention described in examples are preferable. Particularly preferable compound are, for example, 1-(3-carboxypropyl-4-{(E)-2-[4-phenylbutoxy)phenyl]vinyl}-1H-indole-3-carboxylic acid, 4-(3-(carboxymethyl)-4-{(E)-2-[4-(4-phenylbutoxy)phenyl]vinyl}-1H-indol-1-yl)butanoic acid, 4-(3-(carboxymethyl)-4-{(E)-2-[4-(4-phenoxybutoxy)phenyl] vinyl}-1H-indol-1-yl)butanoic acid, 4-(3-carboxymethyl)-4-{2-[4-(4-phenylbutoxy)phenyl]ethyl}-1H-indol-1-yl) butanoic acid, 4-(3-(carboxymethyl)-4-{2-[4-(4-phenoxybutoxy)phenyl]ethyl}-1H-indol-1-yl)butanoic acid, 4-[4-{(E)-2-[4-(4-phenylbutoxy)phenyl]vinyl}-3-(1H-tetrazol-5-ylmethyl)-1H-indol-1-yl]butanoic acid, 4-[4-{2-[4-(4-phenylbutoxy)phenyl]ethyl}-3-(1H-tetrazol-5-ylmethyl)-1H-indol-1-yl]butanoic acid, 4-(3-(carboxymethyl)-4-{(E)-2-[4-(3-phenoxypropoxy)phenyl]vinyl}-1H-indol-1-yl)butanoic acid, 2,2'-(4-{(E)-2-[4-(4-phenylbutoxy)phenyl]vinyl}-1H-indol-1,3-diyl)diacetic acid, 4-(3-(carboxymethyl)-4-{(E)-2-[4-(4-phenylbutoxy)phenyl]vinyl}-1H-indol-1-yl)-4-oxobutanoic acid, 4-(3-(carboxymethyl)-4-{(E)-2-[4-(3-cyclohexylpropoxy)phenyl]vinyl}-1H-indol-1-yl)butanoic acid, 4-[3-(carboxymethyl)-4-((E)-2-{4-[4-(2-methylphenoxy)butoxy]phenyl}vinyl)-1H-indol-1-yl]butanoic acid, 4-[4-((E)-2-{4-[4-(2-acetylphenoxy)butoxy]phenyl}vinyl)-3-(carboxymethyl)-1H-indol-1-yl]butanoic acid, 4-(1-(carboxymethyl)-7-((E)-2-[4 (4-phenoxybutoxy)phenyl]vinyl-1H-indol-3-yl)butanoic acid, 4-[1-(carboxymethyl)-7-((E)-2-{4-[4-(2-chlorophenoxy)butoxy]phenyl}vinyl)-1H-indol-3-yl]butanoic acid, 4-[1-(carboxymethyl-7-((E)-2-{4-[4-(2, fluorophenoxy)butoxy]phenyl}vinyl H-indol-3-yl]butanoic acid, 4-[1-(carboxymethyl)-4-fluoro-7-((E)-2-{4-[4-(mesityloxy)butoxy]phenyl}vinyl) 1H-indol-3-yl]butanoic acid, 4-[1-(carboxymethyl)-7-((E)-2-{4-[4-(2-chloro-3,5-difluorophenoxy)butoxy]phenyl}vinyl)-1H-indol-3-yl]butanoic acid, 4-[1-(carboxymethyl)-7-((E)-2-{4-[4-(2,6-dichloro methylphenoxy)butoxy]phenyl}vinyl)-1H-indol-3-yl]butanoic acid, 4-[1-carboxymethyl)-7-((E)-2-{4-[4-(2,3-difluorophenoxy)butoxy]phenyl}vinyl)-2-methyl-1H-indol-3-yl]butanoic acid, 4-{1-(carboxymethyl-7-[(E)-2-(4-{[(2E)-4-(2,3-difluorophenoxy)-2-buten-1-yl]oxy}phenyl)vinyl]-1H-indol-3-yl}butanoic acid, {[1-(carboxymethyl)-7-((E)-2-{4-[4-(2,3-difluorophenoxy)butoxy]phenyl}vinyl)-1H-indol-3-yl]thio}acetic acid, {[1-(carboxymethyl)-7-((E)-2-{4-[4-(mesityloxy)butoxy]phenyl}vinyl)-1H-indol-3-yl] thio}acetic acid, 3-{[1-(carboxymethyl)-7-((E)-2-{4-[4-(2, 3-difluorophenoxy)butoxy]phenyl}vinyl)-1H-indol-3-yl] thio}-2-methylpropanoic acid, 4-(1-(carboxymethyl)-7-{ (E)-2-[4-(4-phenoxybutoxy)phenyl]vinyl}-1H-indol-3-yl)-4-oxobutanoic acid, 4-[1-carboxymethyl)-5-fluoro-7-((E)-2-{4-[4-(mesityloxy)butoxy]phenyl}vinyl)-1H-indol-3-yl]-4-oxobutanoic acid, 4-[1-(carboxymethyl)-7-((E)-2-{4-[4-(2, 3-difluorophenoxy)butoxy]phenyl}vinyl)-1H-indol-3-yl]-4-oxobutanoic acid, and 3-[1-(carboxymethyl)-7-((E)-2-{4-[4-(2,3-difluorophenoxy)butoxy]phenyl}vinyl)-1H-indol-3-yl]-2,2-dimethyl-3-oxopropanoic acid.

Additionally, in the present invention, compounds listed in Tables 1 to 47, and salts thereof, solvates thereof, or prodrugs thereof are preferable. In the tables, $R^4$ represents alkyl optionally having substituent(s), alkenyl optionally having substituent(s), alkynyl optionally having substituent(s), or

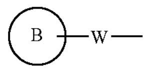

wherein all symbols have the same meanings as described hereinbefore,

"Me" represents methyl, "Ph" represents phenyl, "Ac" represents acetyl, "Bn" represents benzyl, respectively.

TABLE 1
(I-A)
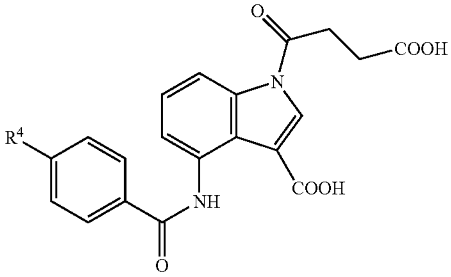
| | $R^4$— |
|---|---|
| 1 | $n$-$C_4H_9$— |
| 2 | $n$-$C_5H_{11}$— |
| 3 | $n$-$C_6H_{13}$— |
| 4 | $n$-$C_4H_9$—O— |
| 5 | $n$-$C_5H_{11}$—O— |
| 6 | $n$-$C_6H_{13}$—O— |
| 7 | 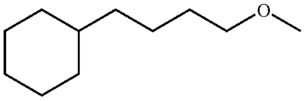 |
| 8 | 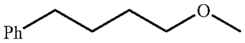 |
| 9 | 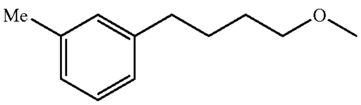 |
| 10 | 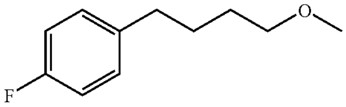 |
| 11 | 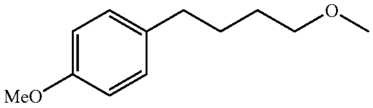 |
| 12 | 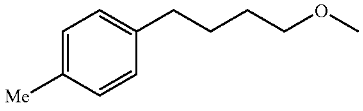 |
| 13 | 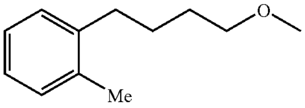 |
| 14 | 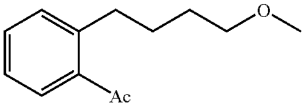 |
| 15 | 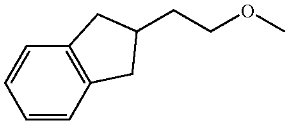 |
TABLE 1-continued
(I-A)
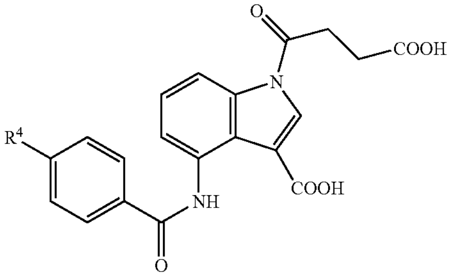
| | $R^4$— |
|---|---|
| 16 | 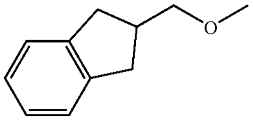 |
| 17 | 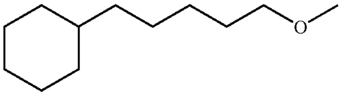 |
| 18 | 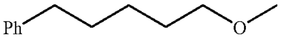 |
| 19 | 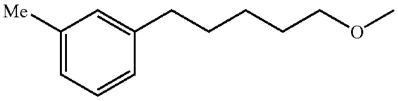 |
| 20 | 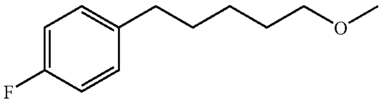 |
| 21 | 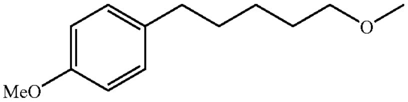 |
| 22 | 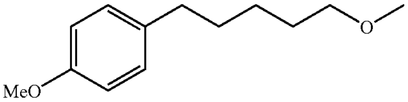 |
| 23 | 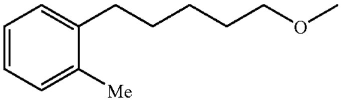 |
| 24 | 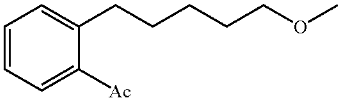 |
| 25 | 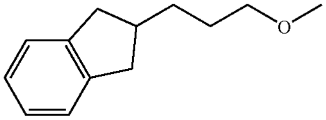 |
| 26 | 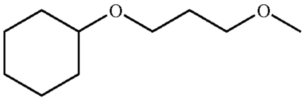 |

TABLE 1-continued
(I-A)
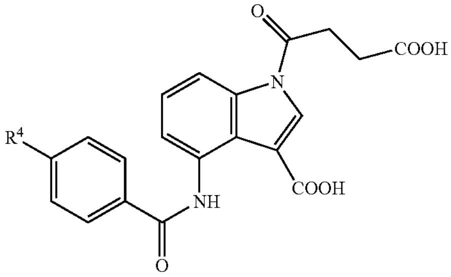
| | R⁴— |
| --- | --- |
| 27 | 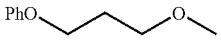 |
| 28 | 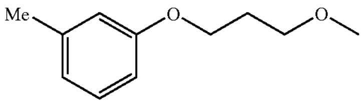 |
| 29 | 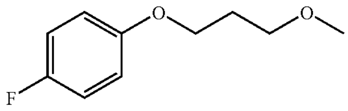 |
| 30 | 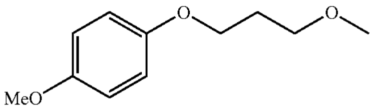 |
| 31 | 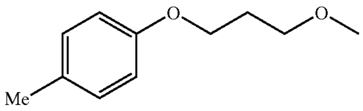 |
| 32 | 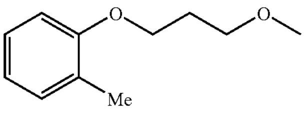 |
| 33 | 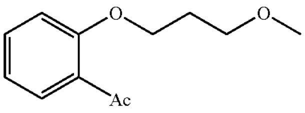 |
| 34 | 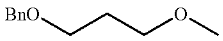 |
| 35 | 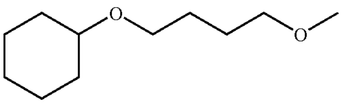 |
| 36 | 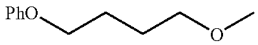 |
| 37 | 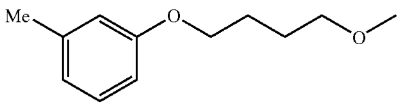 |
| 38 | 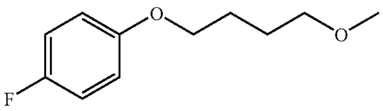 |
TABLE 1-continued
(I-A)
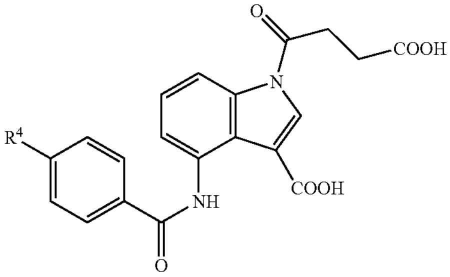
| | R⁴— |
| --- | --- |
| 39 | 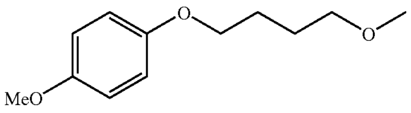 |
| 40 | 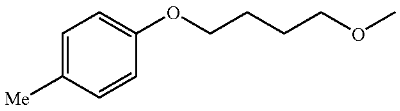 |
| 41 | 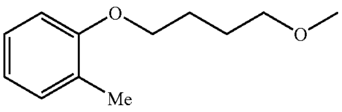 |
| 42 | 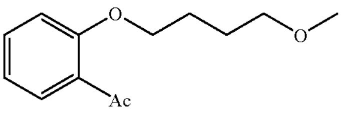 |
| 43 | 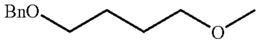 |
| 44 | 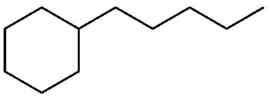 |
| 45 | 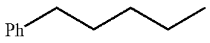 |
| 46 | 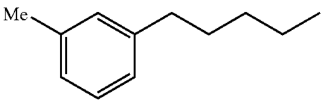 |
| 47 | 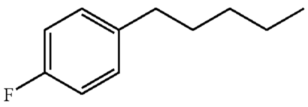 |
| 48 | 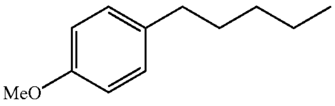 |
| 49 | 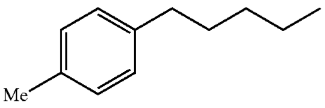 |

TABLE 1-continued
(I-A)
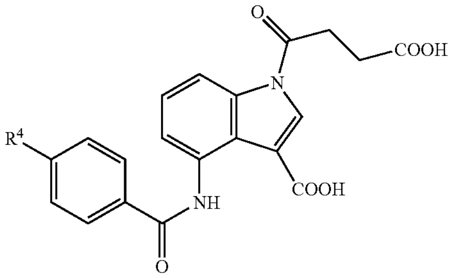
| | $R^4$— |
|---|---|
| 50 | 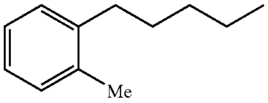 |
| 51 | 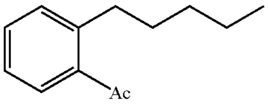 |
| 52 | 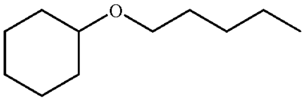 |
| 53 | 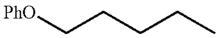 |
| 54 | 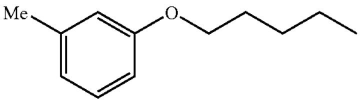 |
| 55 | 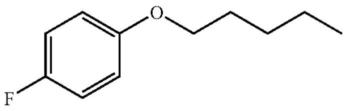 |
| 56 | 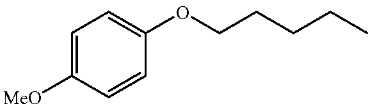 |
| 57 | 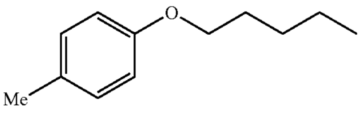 |
| 58 | 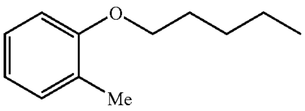 |
| 59 | 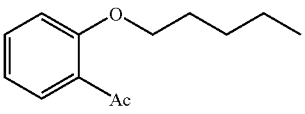 |
TABLE 1-continued
(I-A)
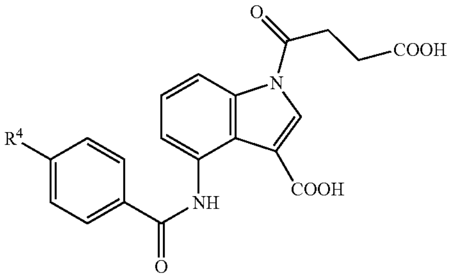
| | $R^4$— |
|---|---|
| 60 | 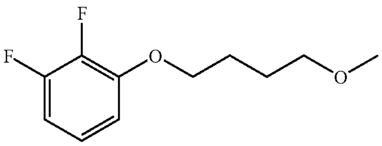 |
| 61 | 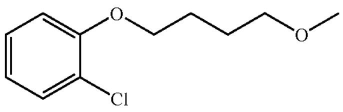 |
| 62 | 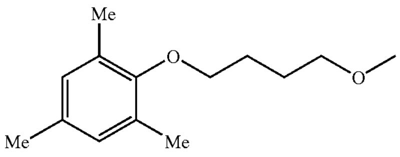 |
| 63 | 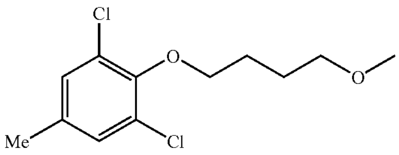 |
| 64 | 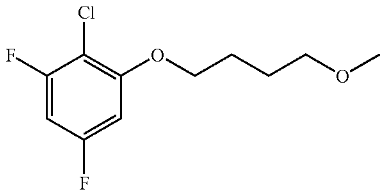 |
| 65 | 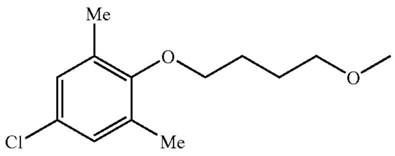 |
| 66 | 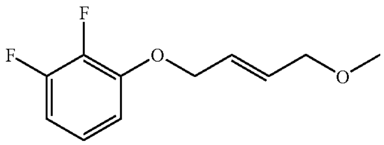 |
| 67 | 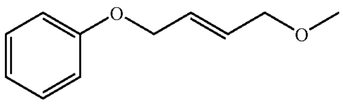 |

TABLE 1-continued
(I-A)
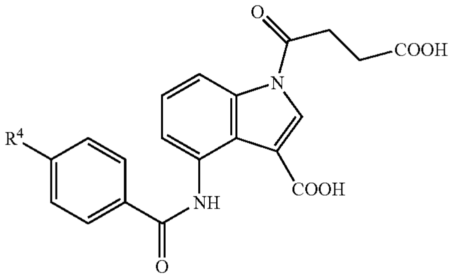
| | R$^4$— |
|---|---|
| 68 | 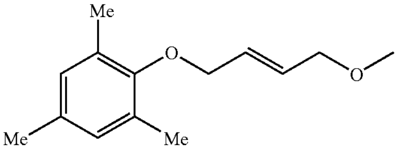 |
| 69 | 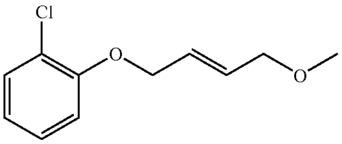 |
TABLE 2
(I-B)
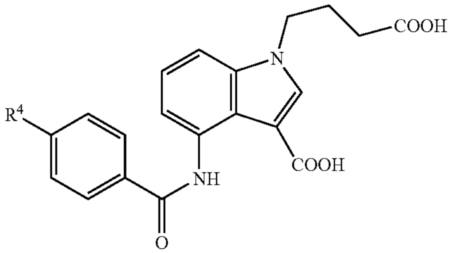
| | R$^4$— |
|---|---|
| 1 | $n\text{-}C_4H_9^-$ |
| 2 | $n\text{-}C_5H_{11}^-$ |
| 3 | $n\text{-}C_6H_{13}^-$ |
| 4 | $n\text{-}C_4H_9—O^-$ |
| 5 | $n\text{-}C_5H_{11}—O^-$ |
| 6 | $n\text{-}C_6H_{13}—O^-$ |
| 7 | 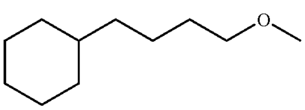 |
| 8 | 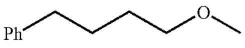 |
| 9 | 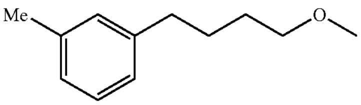 |
TABLE 2-continued
(I-B)
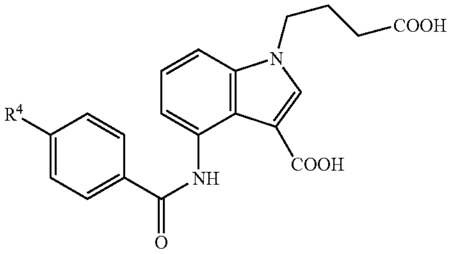
| | R$^4$— |
|---|---|
| 10 | 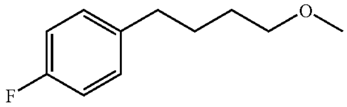 |
| 11 | 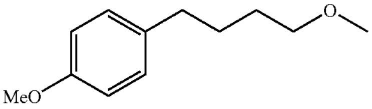 |
| 12 | 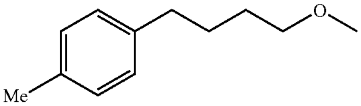 |
| 13 | 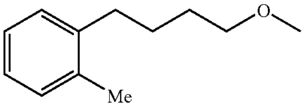 |
| 14 | 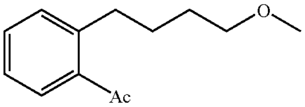 |
| 15 | 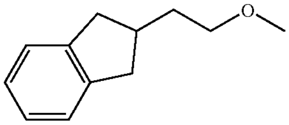 |
| 16 | 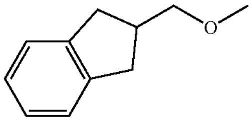 |
| 17 | 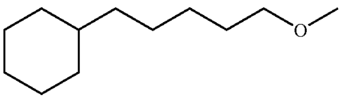 |
| 18 | 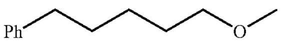 |
| 19 | 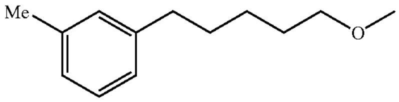 |
| 20 | 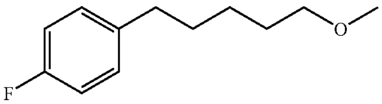 |

TABLE 2-continued
(I-B)
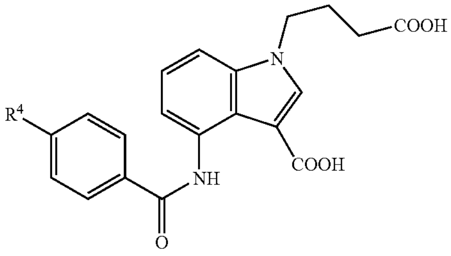
| | R$^4$— |
|---|---|
| 21 | 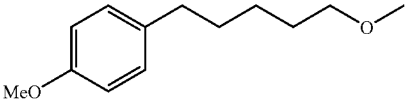 |
| 22 | 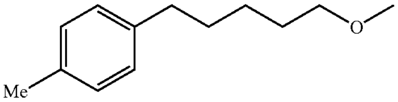 |
| 23 | 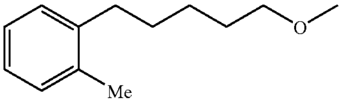 |
| 24 | 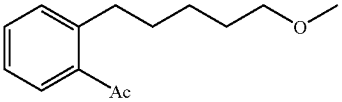 |
| 25 | 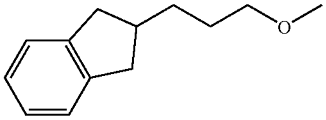 |
| 26 | 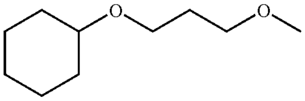 |
| 27 | 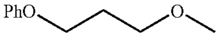 |
| 28 | 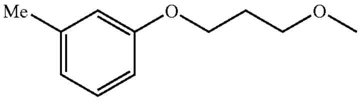 |
| 29 | 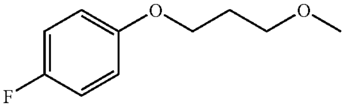 |
| 30 | 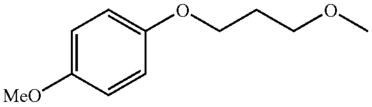 |
| 31 | 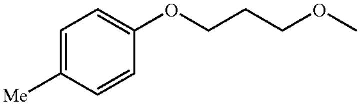 |
TABLE 2-continued
(I-B)
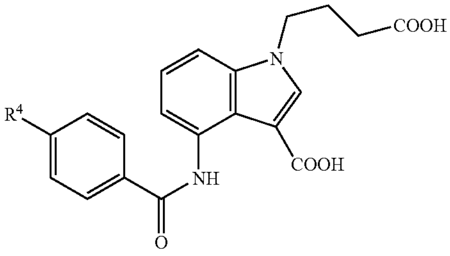
| | R$^4$— |
|---|---|
| 32 | 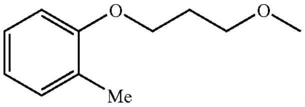 |
| 33 | 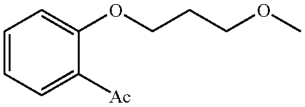 |
| 34 | 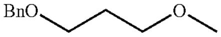 |
| 35 | 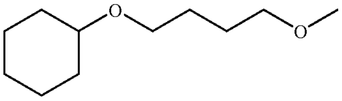 |
| 36 | 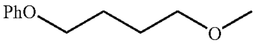 |
| 37 | 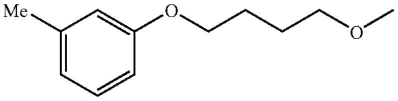 |
| 38 | 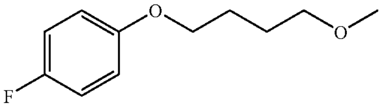 |
| 39 | 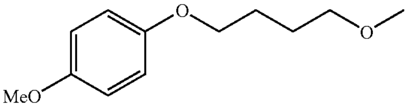 |
| 40 | 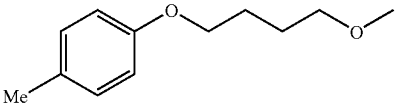 |
| 41 | 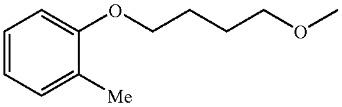 |
| 42 | 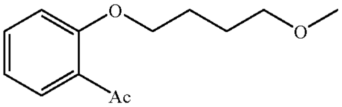 |
| 43 | 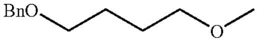 |

TABLE 2-continued
(I-B)
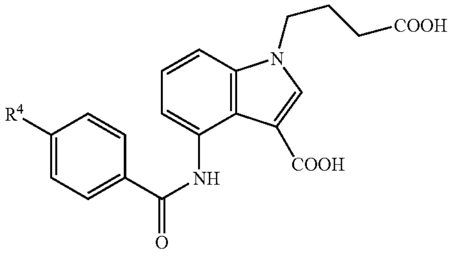
| | $R^4$— |
|---|---|
| 44 | 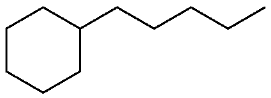 |
| 45 | 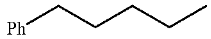 |
| 46 | 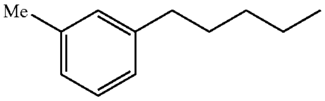 |
| 47 | 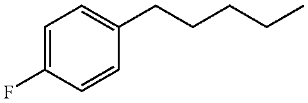 |
| 48 | 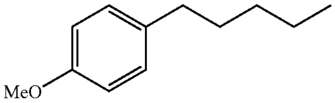 |
| 49 | 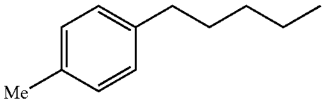 |
| 50 | 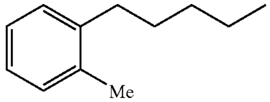 |
| 51 | 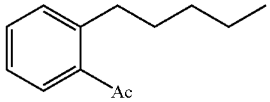 |
| 52 | 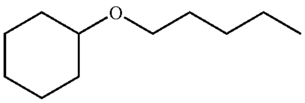 |
| 53 | 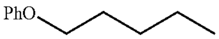 |
| 54 | 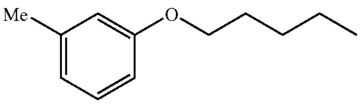 |
| 55 | 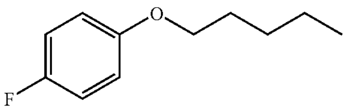 |
TABLE 2-continued
(I-B)
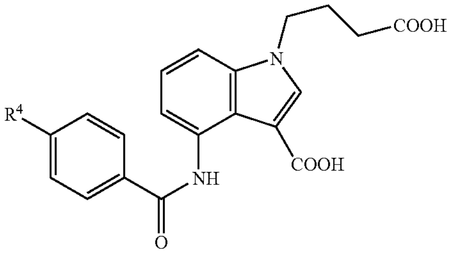
| | $R^4$— |
|---|---|
| 56 | 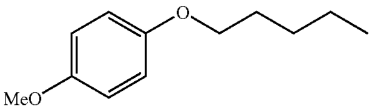 |
| 57 | 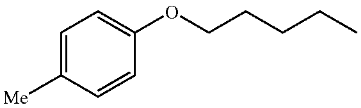 |
| 58 | 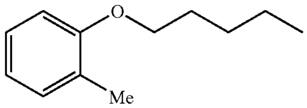 |
| 59 | 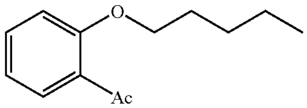 |
| 60 | 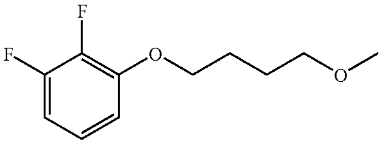 |
| 61 | 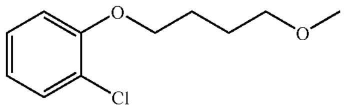 |
| 62 | 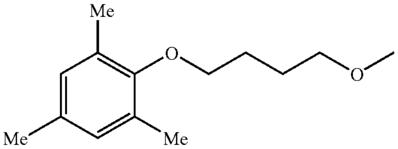 |
| 63 | 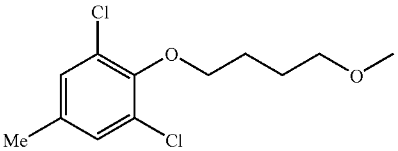 |

TABLE 2-continued
(I-B)
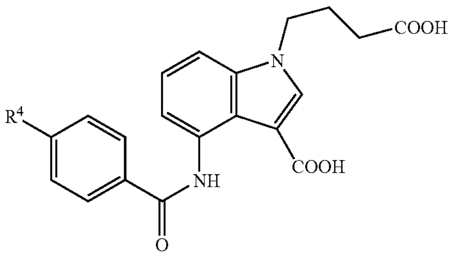
| | $R^4$— |
|---|---|
| 64 | 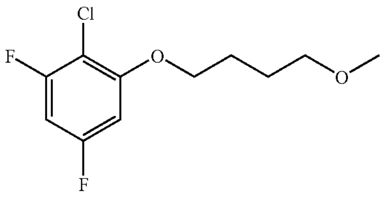 |
| 65 | 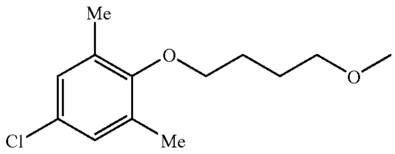 |
| 66 | 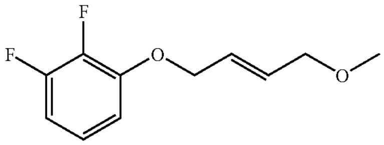 |
| 67 | 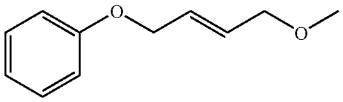 |
| 68 | 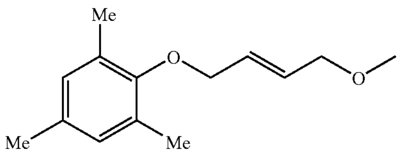 |
| 69 | 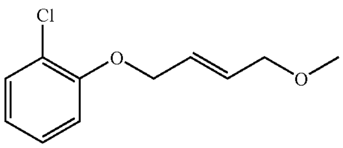 |
TABLE 3
(I-C)
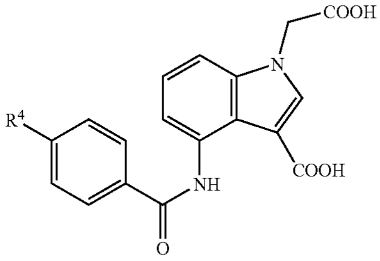
| | $R^4$— |
|---|---|
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |
| 7 | 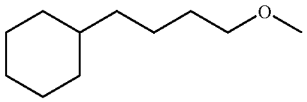 |
| 8 | 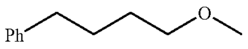 |
| 9 | 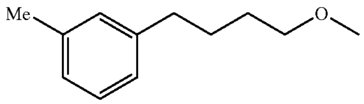 |
| 10 | 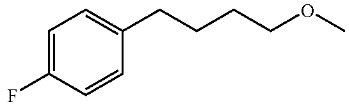 |
| 11 | 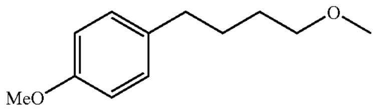 |
| 12 | 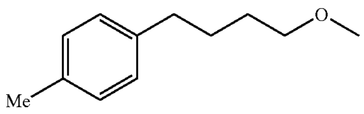 |
| 13 | 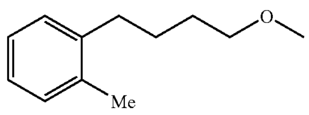 |
| 14 | 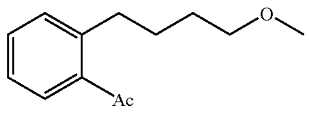 |
| 15 | 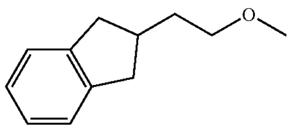 |

TABLE 3-continued
(I-C)
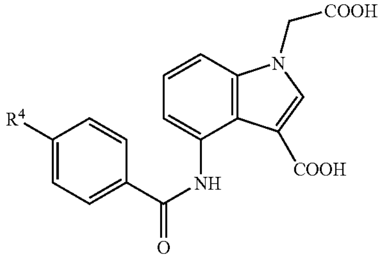
| | R$^4$— |
|---|---|
| 16 | 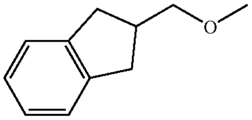 |
| 17 | 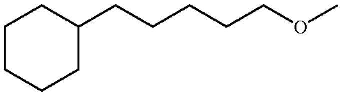 |
| 18 | 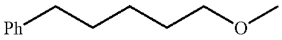 |
| 19 | 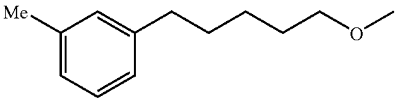 |
| 20 | 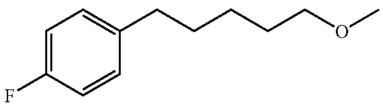 |
| 21 | 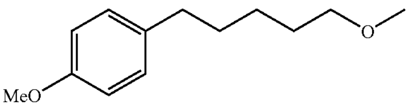 |
| 22 | 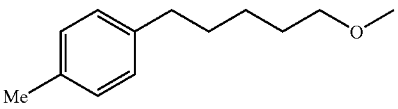 |
| 23 | 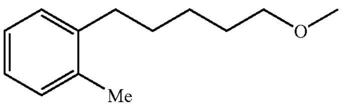 |
| 24 | 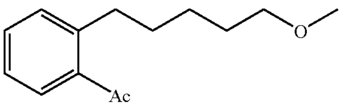 |
| 25 | 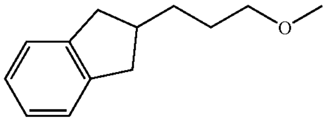 |
| 26 | 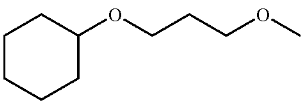 |
TABLE 3-continued
(I-C)
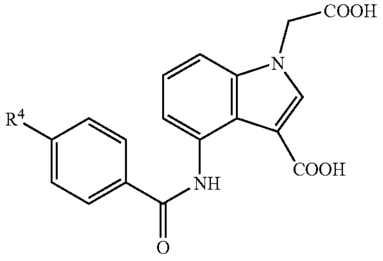
| | R$^4$— |
|---|---|
| 27 | 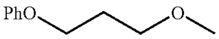 |
| 28 | 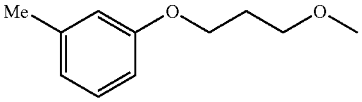 |
| 29 | 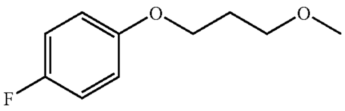 |
| 30 | 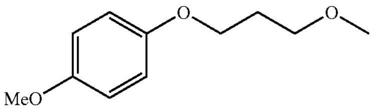 |
| 31 | 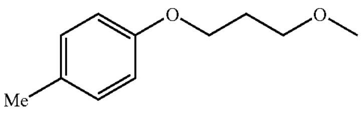 |
| 32 | 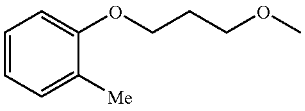 |
| 33 | 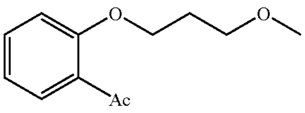 |
| 34 | 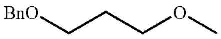 |
| 35 | 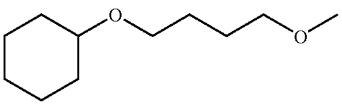 |
| 36 | 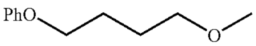 |
| 37 | 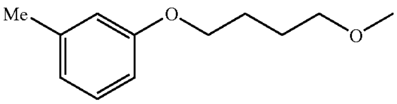 |
| 38 | 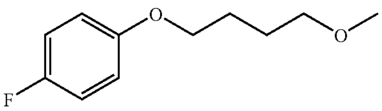 |

TABLE 3-continued
(I-C)
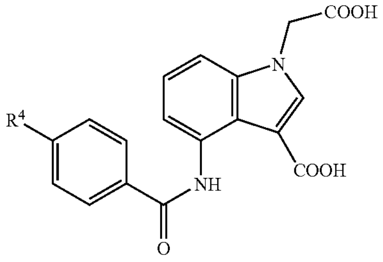
| | $R^4$— |
|---|---|
| 39 | 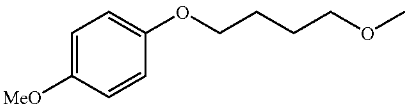 |
| 40 | 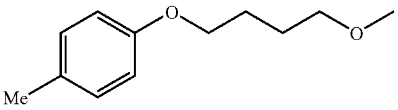 |
| 41 | 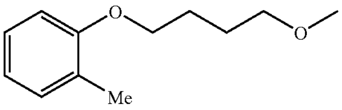 |
| 42 | 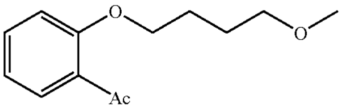 |
| 43 | 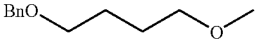 |
| 44 | 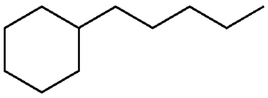 |
| 45 | 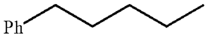 |
| 46 | 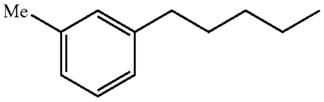 |
| 47 | 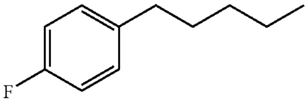 |
| 48 | 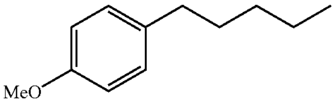 |
| 49 | 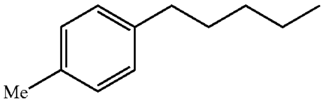 |
TABLE 3-continued
(I-C)
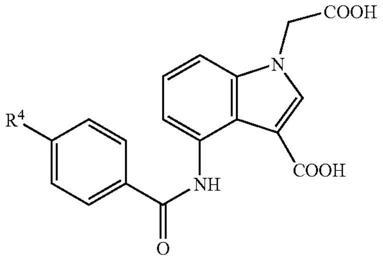
| | $R^4$— |
|---|---|
| 50 | 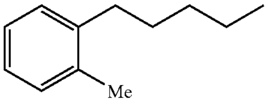 |
| 51 | 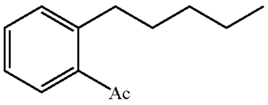 |
| 52 | 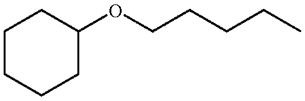 |
| 53 | 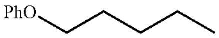 |
| 54 | 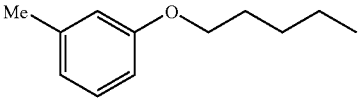 |
| 55 | 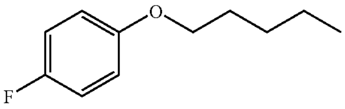 |
| 56 | 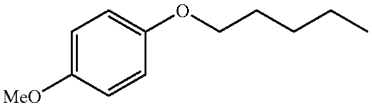 |
| 57 | 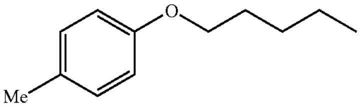 |
| 58 | 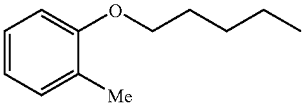 |
| 59 | 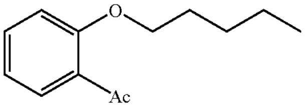 |
| 60 | 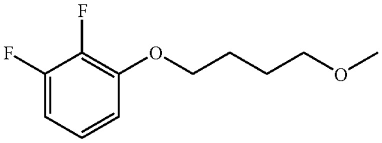 |

TABLE 3-continued
(I-C)
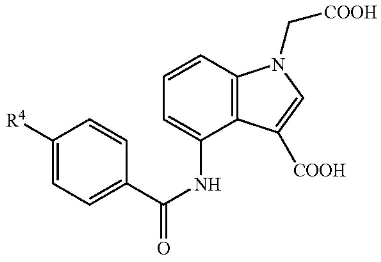
| | R⁴— |
|---|---|
| 61 | 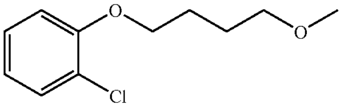 |
| 62 | 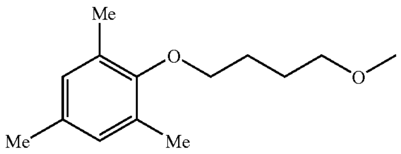 |
| 63 | 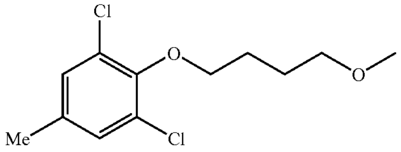 |
| 64 | 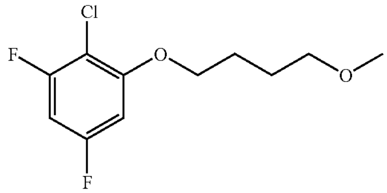 |
| 65 | 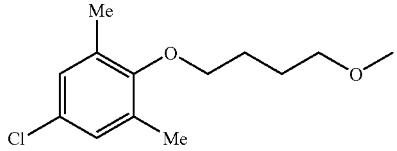 |
| 66 | 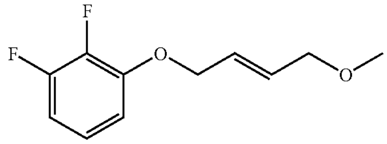 |
| 67 | 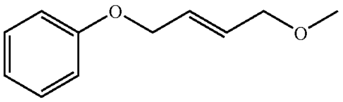 |
| 68 | 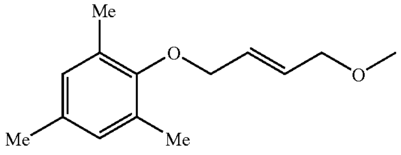 |
TABLE 3-continued
(I-C)
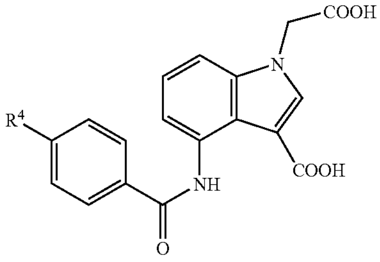
| | R⁴— |
|---|---|
| 69 | 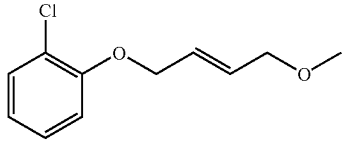 |
TABLE 4
(I-D)
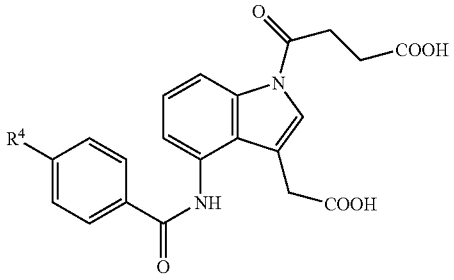
| | $R^4$— |
|---|---|
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |
| 7 | 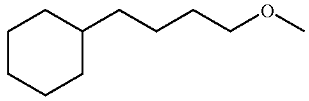 |
| 8 | 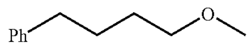 |
| 9 | 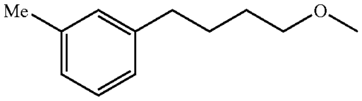 |
| 10 | 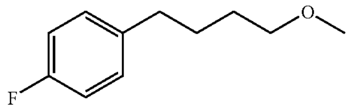 |
| 11 | 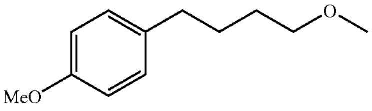 |

TABLE 4-continued
(I-D)
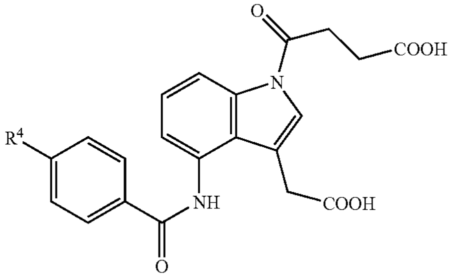
| | $R^4$— |
|---|---|
| 12 | 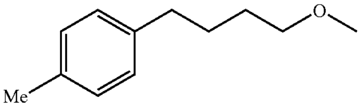 |
| 13 | 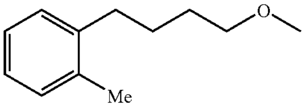 |
| 14 | 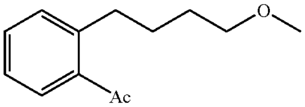 |
| 15 | 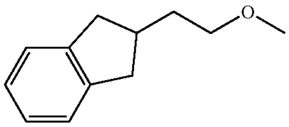 |
| 16 | 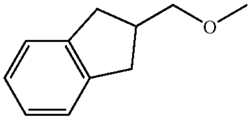 |
| 17 | 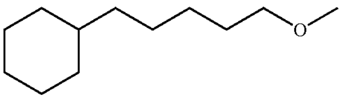 |
| 18 | 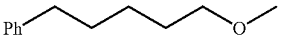 |
| 19 | 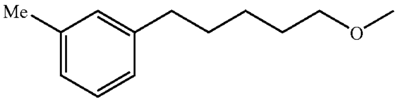 |
| 20 | 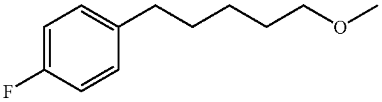 |
| 21 | 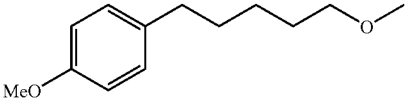 |
| 22 | 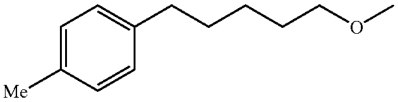 |
TABLE 4-continued
(I-D)
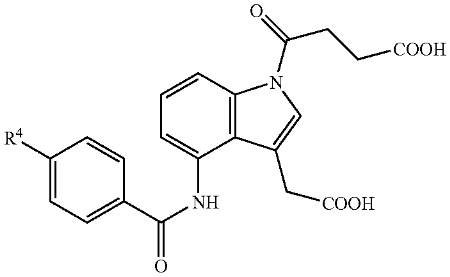
| | $R^4$— |
|---|---|
| 23 | 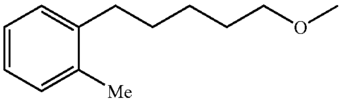 |
| 24 | 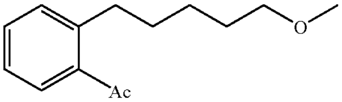 |
| 25 | 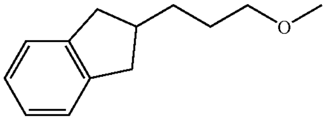 |
| 26 | 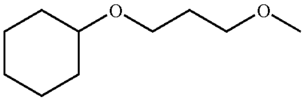 |
| 27 | 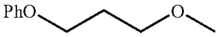 |
| 28 | 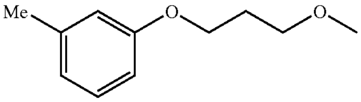 |
| 29 | 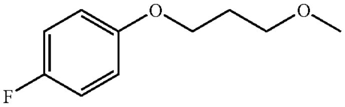 |
| 30 | 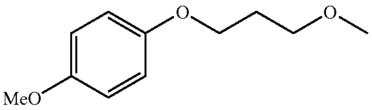 |
| 31 | 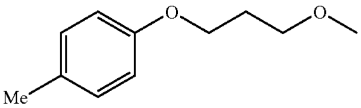 |
| 32 | 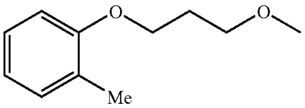 |

TABLE 4-continued
(I-D)
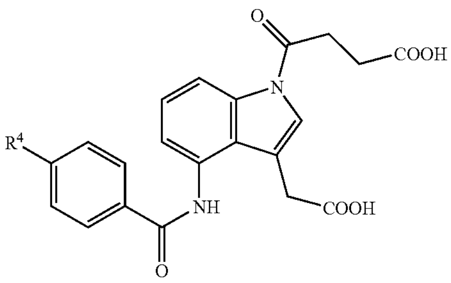
| | $R^4$— |
|---|---|
| 33 | 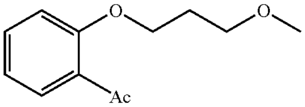 |
| 34 | 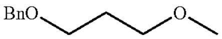 |
| 35 | 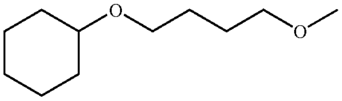 |
| 36 | 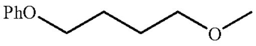 |
| 37 | 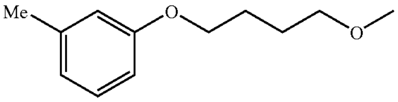 |
| 38 | 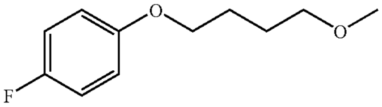 |
| 39 | 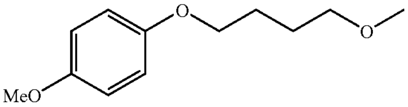 |
| 40 | 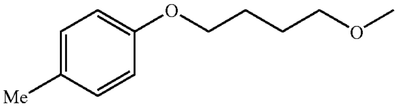 |
| 41 | 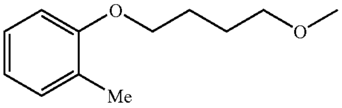 |
| 42 | 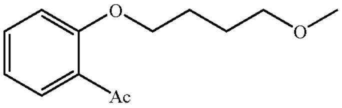 |
| 43 | 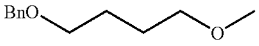 |
| 44 | 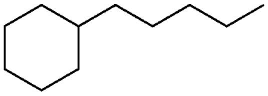 |
TABLE 4-continued
(I-D)
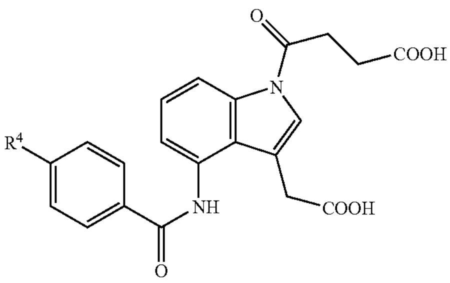
| | $R^4$— |
|---|---|
| 45 | 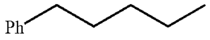 |
| 46 | 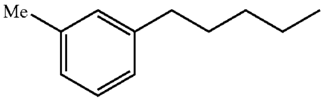 |
| 47 | 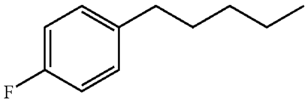 |
| 48 | 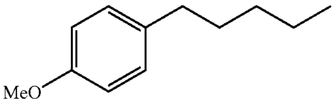 |
| 49 | 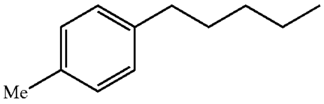 |
| 50 | 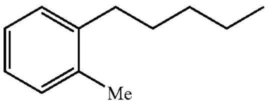 |
| 51 | 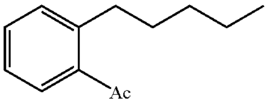 |
| 52 | 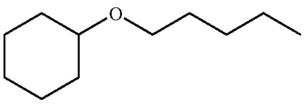 |
| 53 | 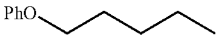 |
| 54 | 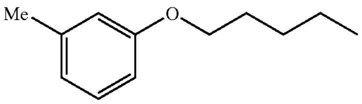 |
| 55 | 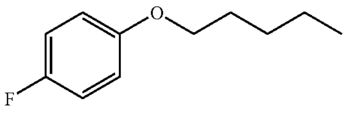 |

TABLE 4-continued
(I-D)
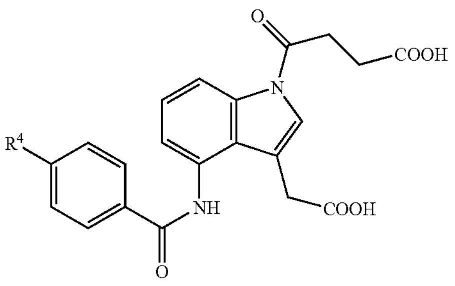
| | R⁴— |
|---|---|
| 56 | 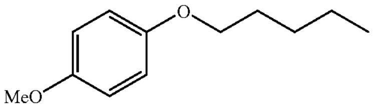 |
| 57 | 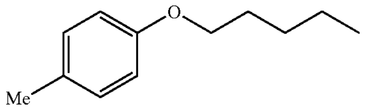 |
| 58 | 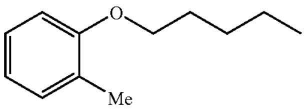 |
| 59 | 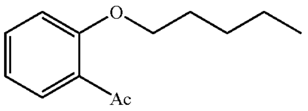 |
| 60 | 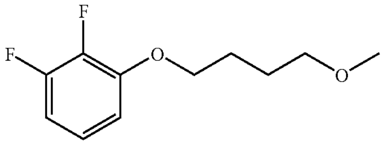 |
| 61 | 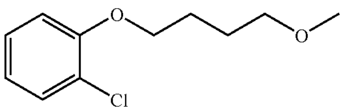 |
| 62 | 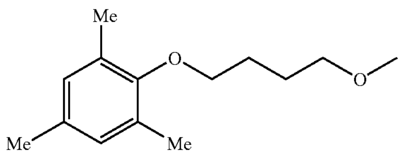 |
| 63 | 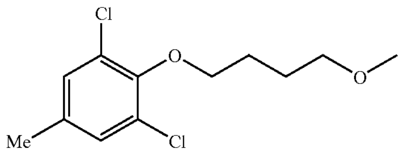 |
TABLE 4-continued
(I-D)
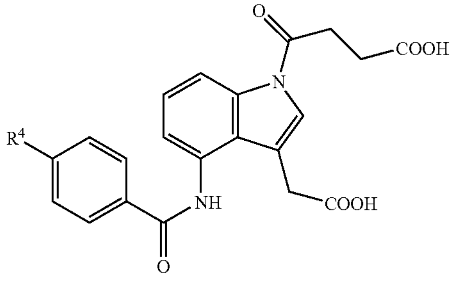
| | R⁴— |
|---|---|
| 64 | 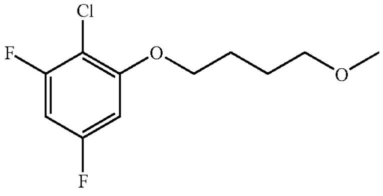 |
| 65 | 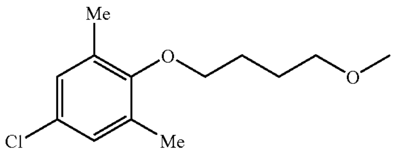 |
| 66 | 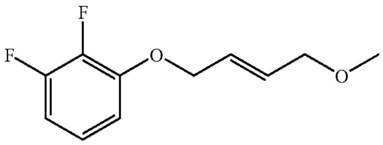 |
| 67 | 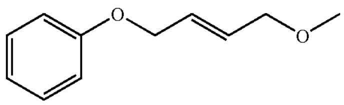 |
| 68 | 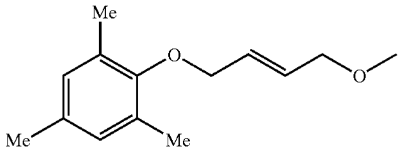 |
| 69 | 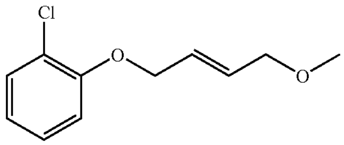 |

TABLE 5
(I-E)
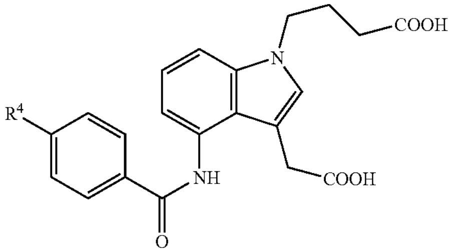
| | $R^4$— |
|---|---|
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |
| 7 | 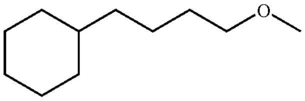 |
| 8 | 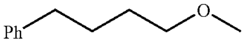 |
| 9 | 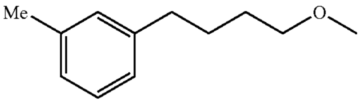 |
| 10 | 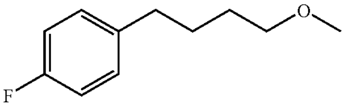 |
| 11 | 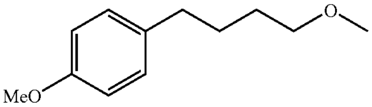 |
| 12 | 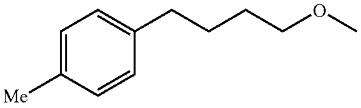 |
| 13 | 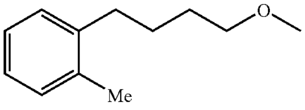 |
| 14 | 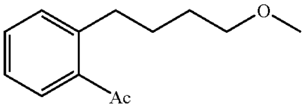 |
| 15 | 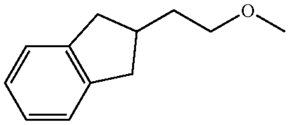 |
TABLE 5-continued
(I-E)
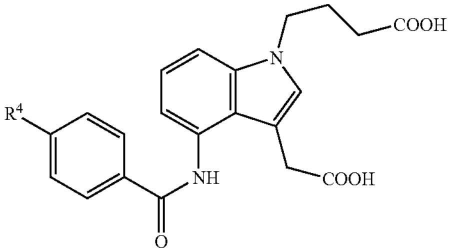
| | $R^4$— |
|---|---|
| 16 | 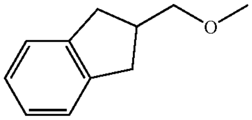 |
| 17 | 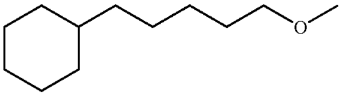 |
| 18 | 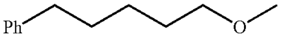 |
| 19 | 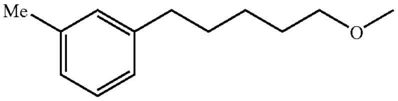 |
| 20 | 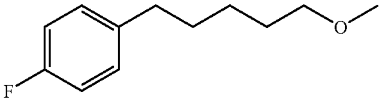 |
| 21 | 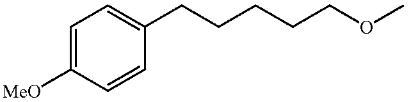 |
| 22 | 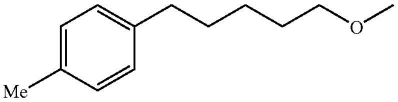 |
| 23 | 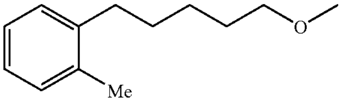 |
| 24 | 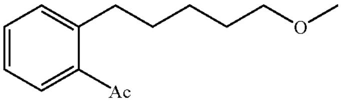 |
| 25 | 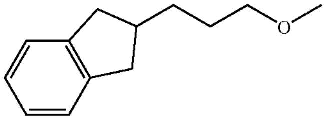 |
| 26 | 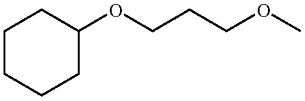 |

TABLE 5-continued
(I-E)
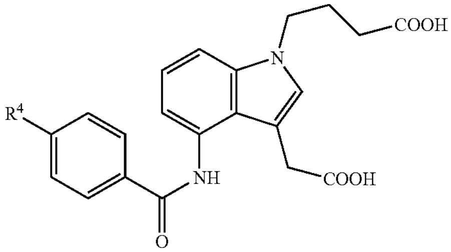
R⁴—
27 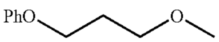
28 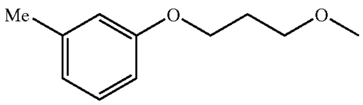
29 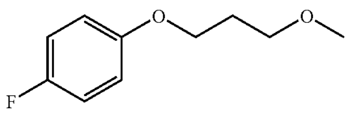
30 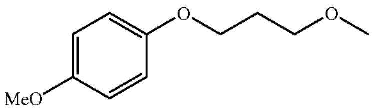
31 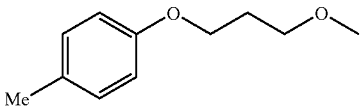
32 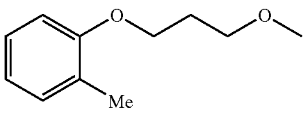
33 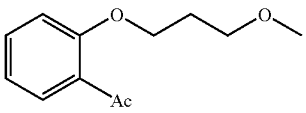
34 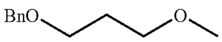
35 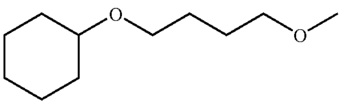
36 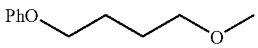
37 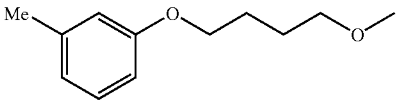
38 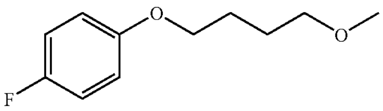
TABLE 5-continued
(I-E)
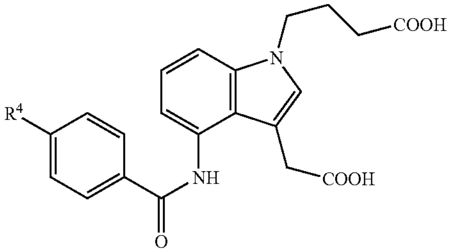
R⁴—
39 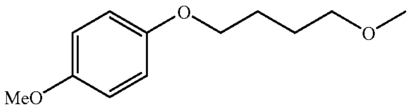
40 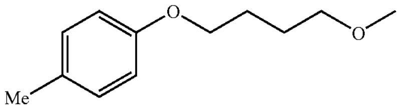
41 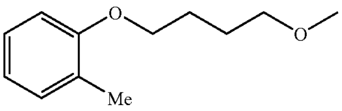
42 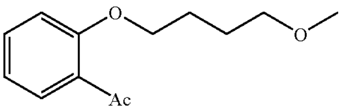
43 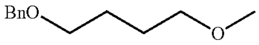
44 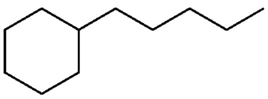
45 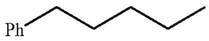
46 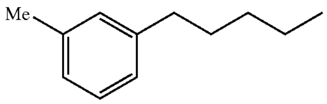
47 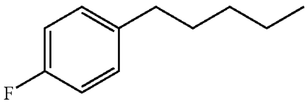
48 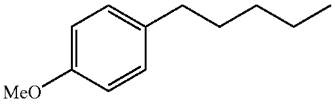
49 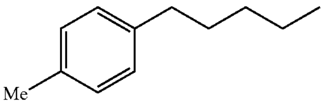
50 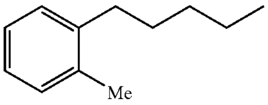

TABLE 5-continued
(I-E)
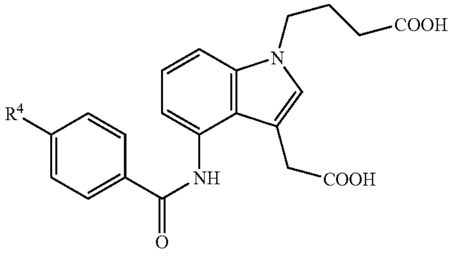
| | $R^4$— |
|---|---|
| 51 | 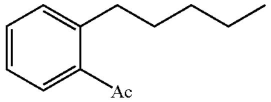 |
| 52 | 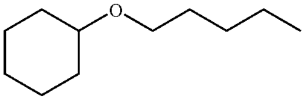 |
| 53 | 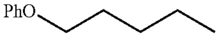 |
| 54 | 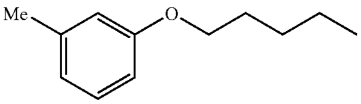 |
| 55 | 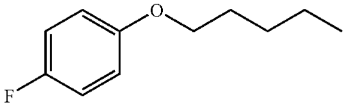 |
| 56 | 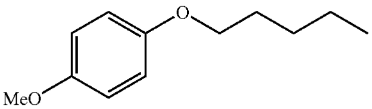 |
| 57 | 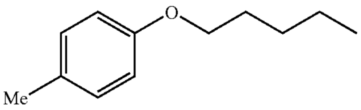 |
| 58 | 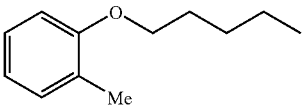 |
| 59 | 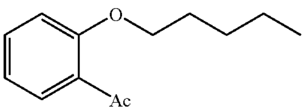 |
| 60 | 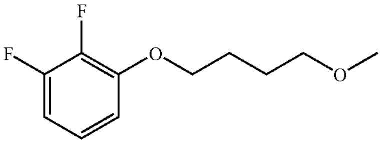 |
TABLE 5-continued
(I-E)
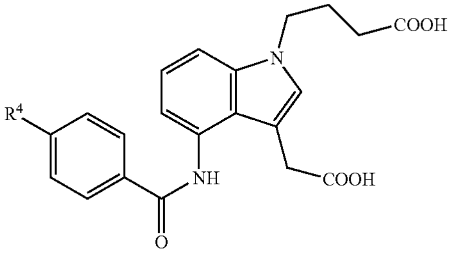
| | $R^4$— |
|---|---|
| 61 | 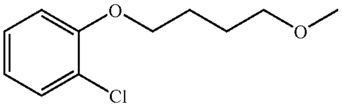 |
| 62 | 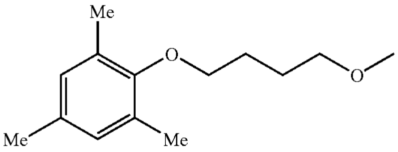 |
| 63 | 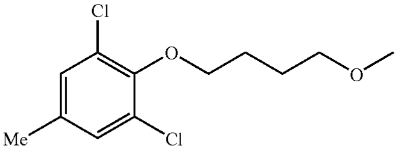 |
| 64 | 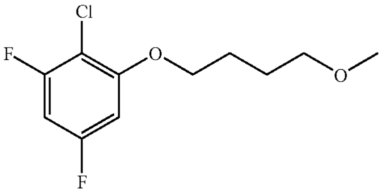 |
| 65 | 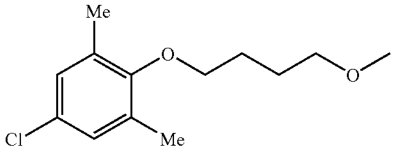 |
| 66 | 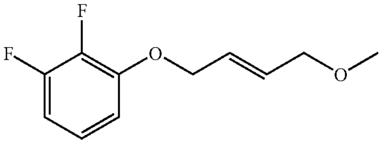 |
| 67 | 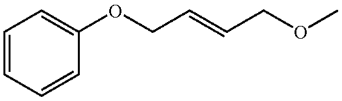 |
| 68 | 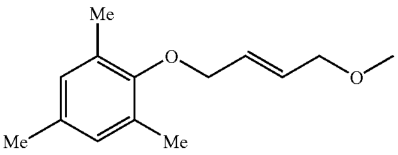 |

TABLE 5-continued
(I-E)
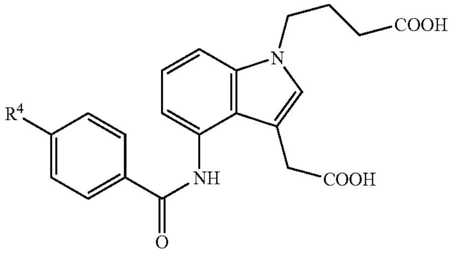
| | $R^4$— |
|---|---|
| 69 | 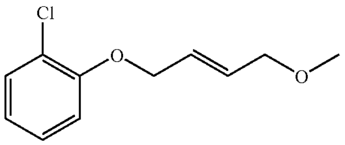 |
TABLE 6
(I-F)
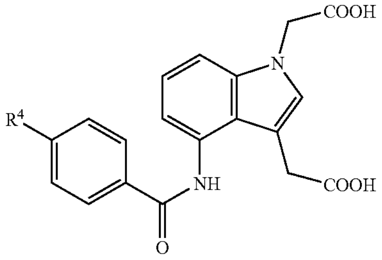
| | $R^4$— |
|---|---|
| 1 | $n\text{-}C_4H_9^-$ |
| 2 | $n\text{-}C_5H_{11}^-$ |
| 3 | $n\text{-}C_6H_{13}^-$ |
| 4 | $n\text{-}C_4H_9$—$O^-$ |
| 5 | $n\text{-}C_5H_{11}$—$O^-$ |
| 6 | $n\text{-}C_6H_{13}$—$O^-$ |
| 7 | 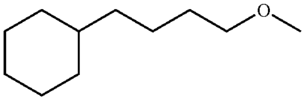 |
| 8 | 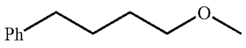 |
| 9 | 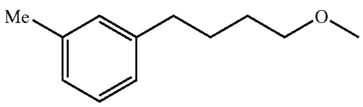 |
| 10 | 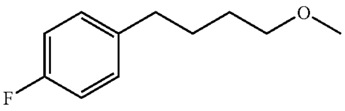 |
| 11 | 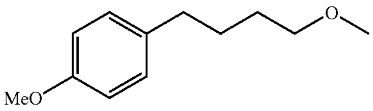 |
TABLE 6-continued
(I-F)
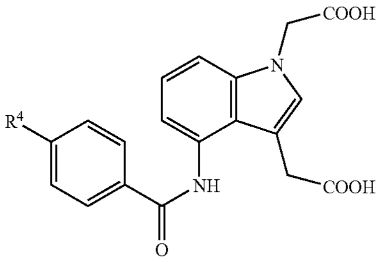
| | $R^4$— |
|---|---|
| 12 | 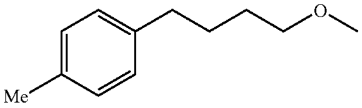 |
| 13 | 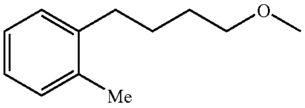 |
| 14 | 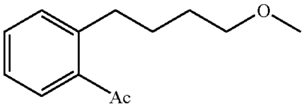 |
| 15 | 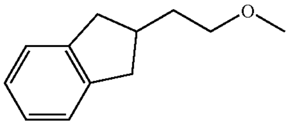 |
| 16 | 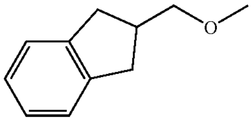 |
| 17 | 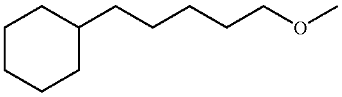 |
| 18 | 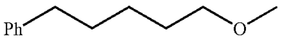 |
| 19 | 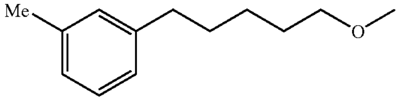 |
| 20 | 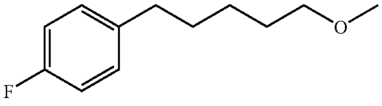 |
| 21 | 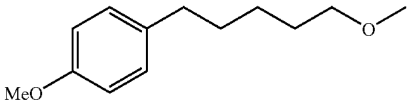 |
| 22 | 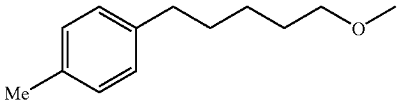 |

TABLE 6-continued
(I-F)
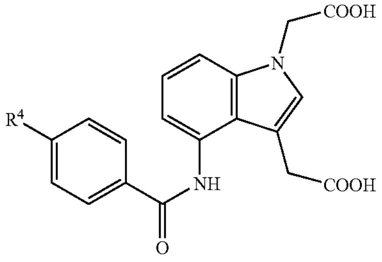
| | R⁴— |
|---|---|
| 23 | 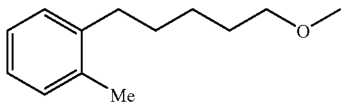 |
| 24 | 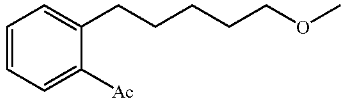 |
| 25 | 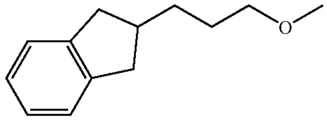 |
| 26 | 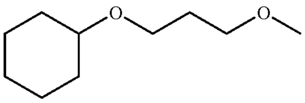 |
| 27 | 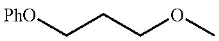 |
| 28 | 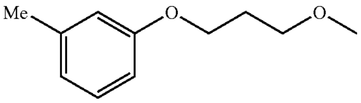 |
| 29 | 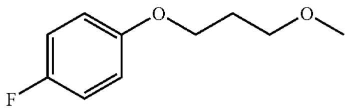 |
| 30 | 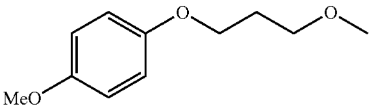 |
| 31 | 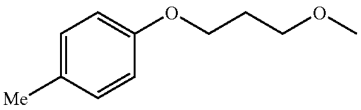 |
| 32 | 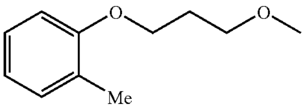 |
| 33 | 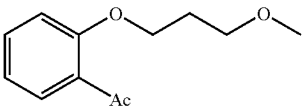 |
TABLE 6-continued
(I-F)
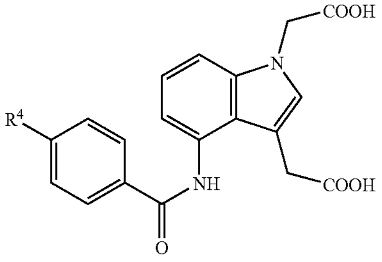
| | R⁴— |
|---|---|
| 34 | 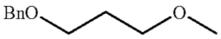 |
| 35 | 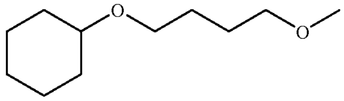 |
| 36 | 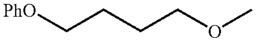 |
| 37 | 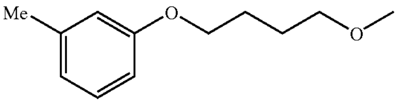 |
| 38 | 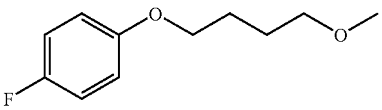 |
| 39 | 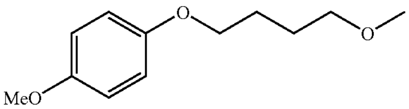 |
| 40 | 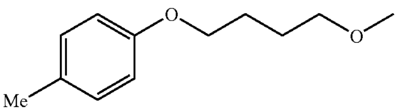 |
| 41 | 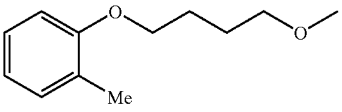 |
| 42 | 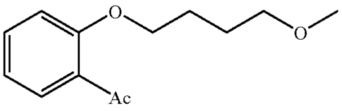 |
| 43 | 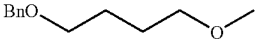 |
| 44 | 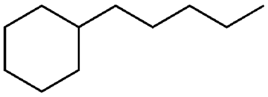 |
| 45 | 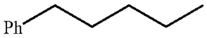 |

TABLE 6-continued
(I-F)
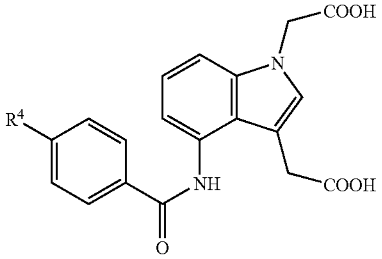
| | R$^4$— |
|---|---|
| 46 | 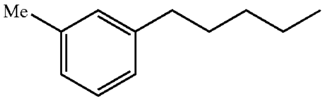 |
| 47 | 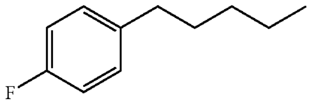 |
| 48 | 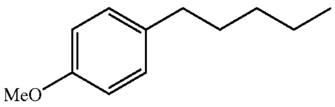 |
| 49 | 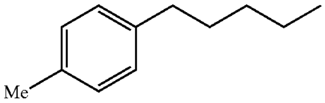 |
| 50 | 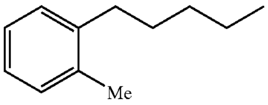 |
| 51 | 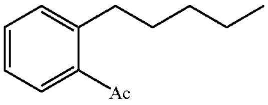 |
| 52 | 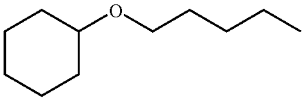 |
| 53 | 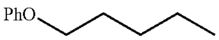 |
| 54 | 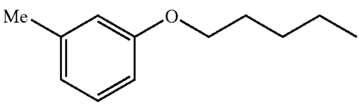 |
| 55 | 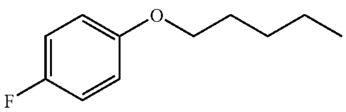 |
| 56 | 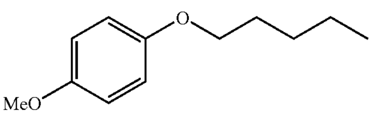 |
TABLE 6-continued
(I-F)
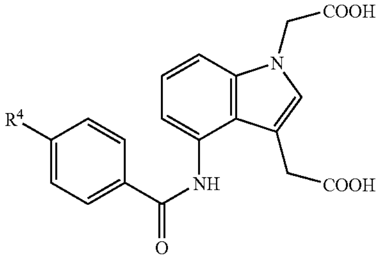
| | R$^4$— |
|---|---|
| 57 | 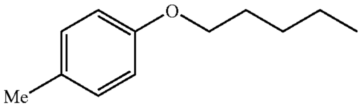 |
| 58 | 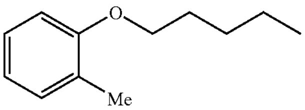 |
| 59 | 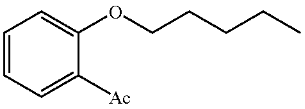 |
| 60 | 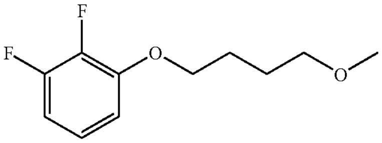 |
| 61 | 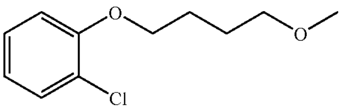 |
| 62 | 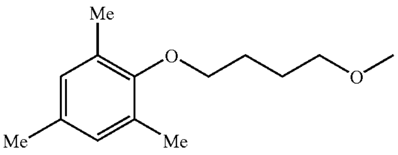 |
| 63 | 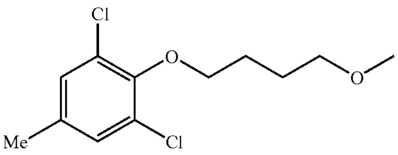 |
| 64 | 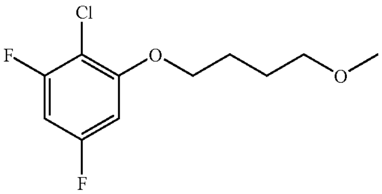 |

TABLE 6-continued
(I-F)
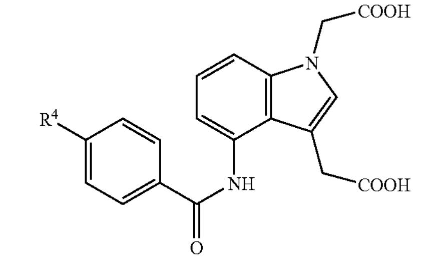
| | $R^4$— |
|---|---|
| 65 | 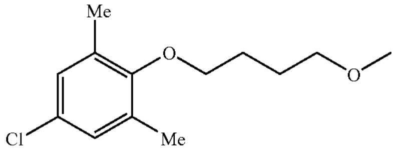 |
| 66 | 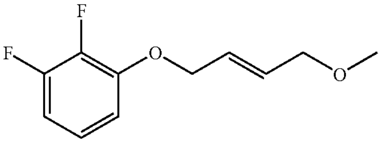 |
| 67 | 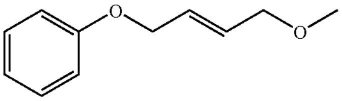 |
| 68 | 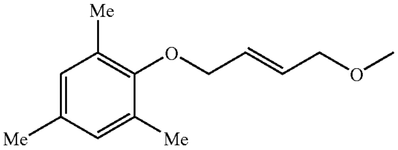 |
| 69 | 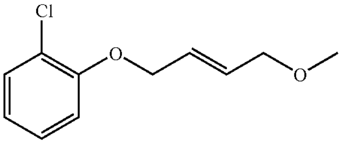 |
TABLE 7
(I-G)
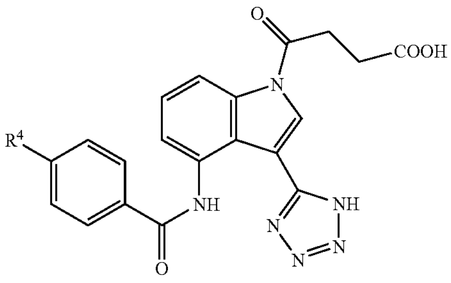
| | $R^4$— |
|---|---|
| 1 | $n-C_4H_9^-$ |
| 2 | $n-C_5H_{11}^-$ |
| 3 | $n-C_6H_{13}^-$ |
| 4 | $n-C_4H_9$—$O^-$ |
TABLE 7-continued
(I-G)
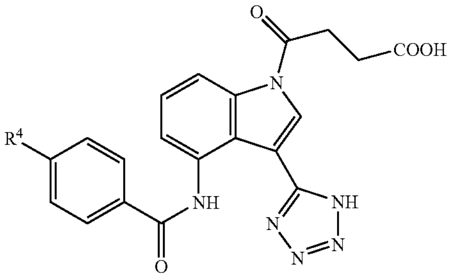
| | $R^4$— |
|---|---|
| 5 | $n-C_5H_{11}$—$O^-$ |
| 6 | $n-C_6H_{13}$—$O^-$ |
| 7 | 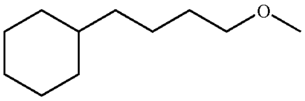 |
| 8 | 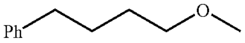 |
| 9 | 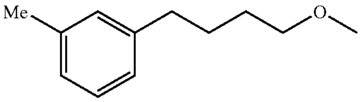 |
| 10 | 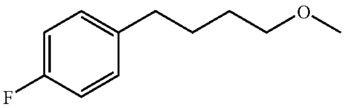 |
| 11 | 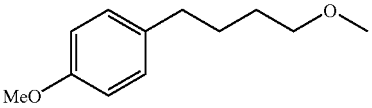 |
| 12 | 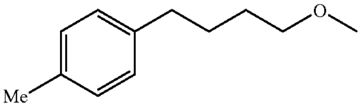 |
| 13 | 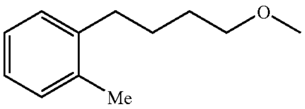 |
| 14 | 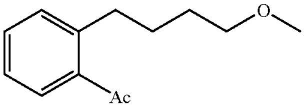 |
| 15 | 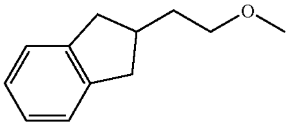 |
| 16 | 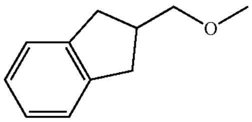 |

TABLE 7-continued
(I-G)
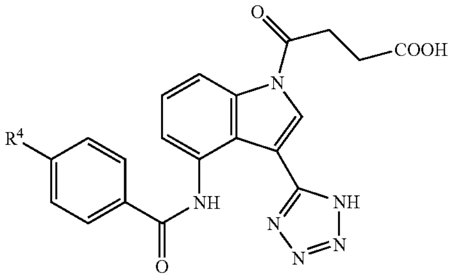
| | $R^4$— |
|---|---|
| 17 | 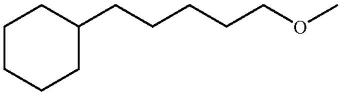 |
| 18 | 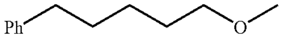 |
| 19 | 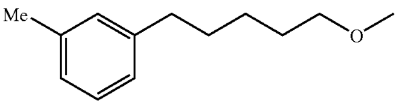 |
| 20 | 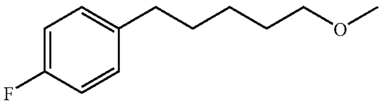 |
| 21 | 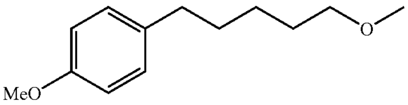 |
| 22 | 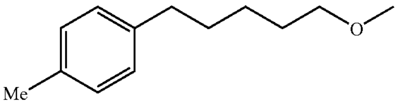 |
| 23 | 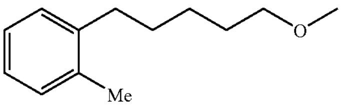 |
| 24 | 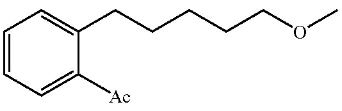 |
| 25 | 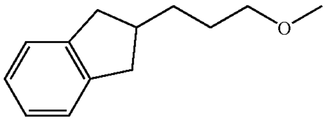 |
| 26 | 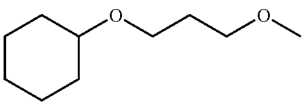 |
| 27 | 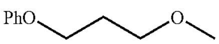 |
TABLE 7-continued
(I-G)
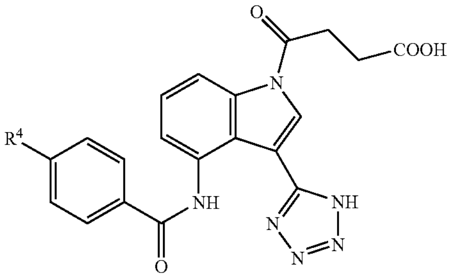
| | $R^4$— |
|---|---|
| 28 | 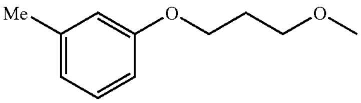 |
| 29 | 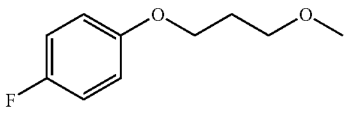 |
| 30 | 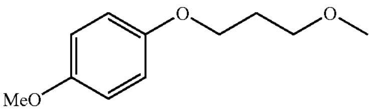 |
| 31 | 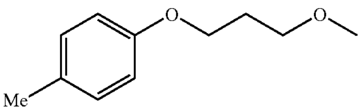 |
| 32 | 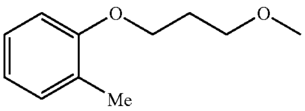 |
| 33 | 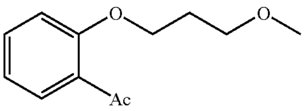 |
| 34 | 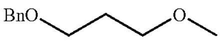 |
| 35 | 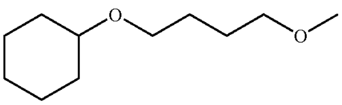 |
| 36 | 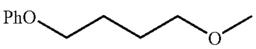 |
| 37 | 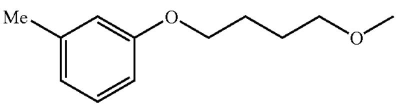 |
| 38 | 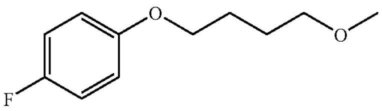 |

TABLE 7-continued
(I-G)
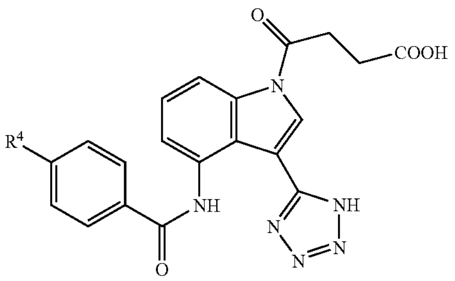
| | R⁴— |
| --- | --- |
| 39 | 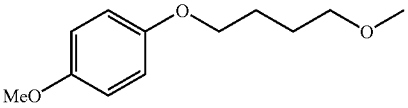 |
| 40 | 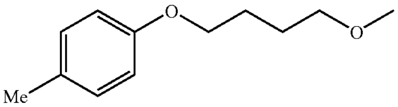 |
| 41 | 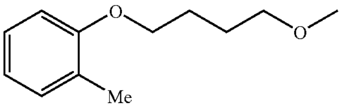 |
| 42 | 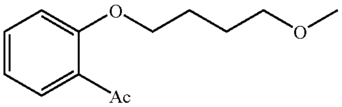 |
| 43 | 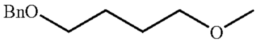 |
| 44 | 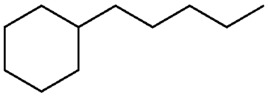 |
| 45 | 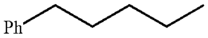 |
| 46 | 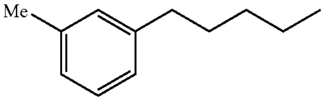 |
| 47 | 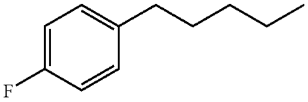 |
| 48 | 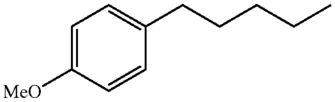 |
| 49 | 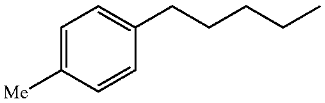 |
TABLE 7-continued
(I-G)
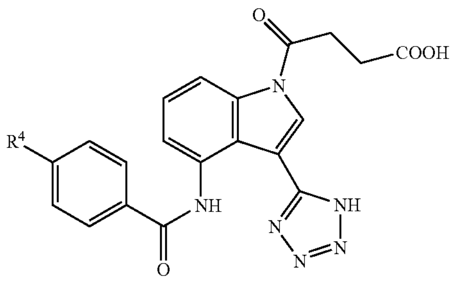
| | R⁴— |
| --- | --- |
| 50 | 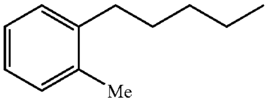 |
| 51 | 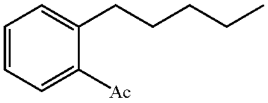 |
| 52 | 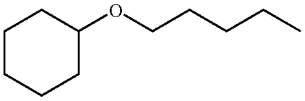 |
| 53 | 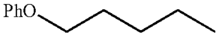 |
| 54 | 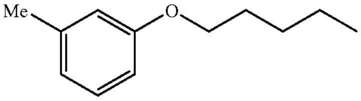 |
| 55 | 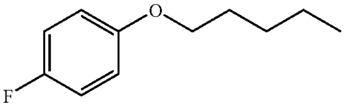 |
| 56 | 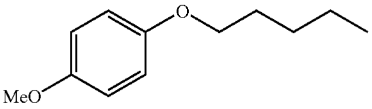 |
| 57 | 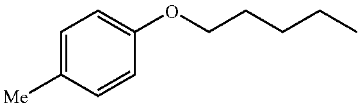 |
| 58 | 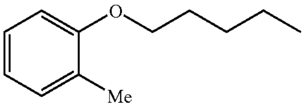 |
| 59 | 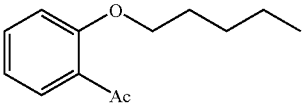 |

TABLE 7-continued
(I-G)
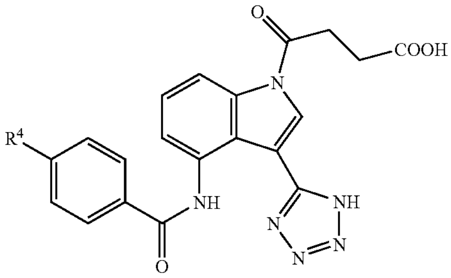
| | $R^4$— |
|---|---|
| 60 | 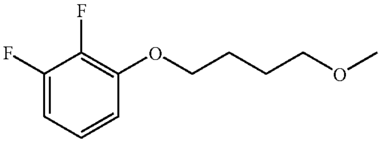 |
| 61 | 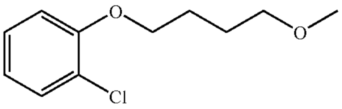 |
| 62 | 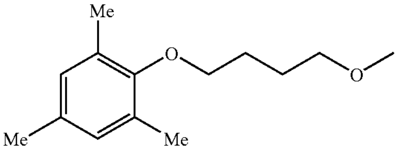 |
| 63 | 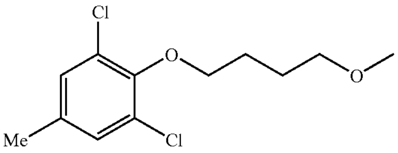 |
| 64 | 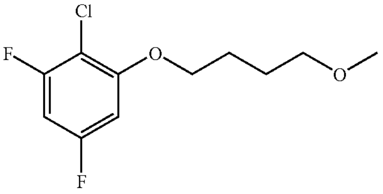 |
| 65 | 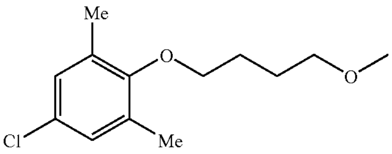 |
| 66 | 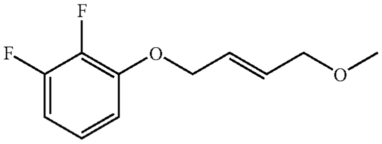 |
| 67 | 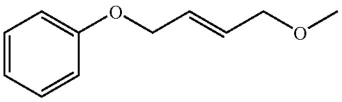 |
TABLE 7-continued
(I-G)
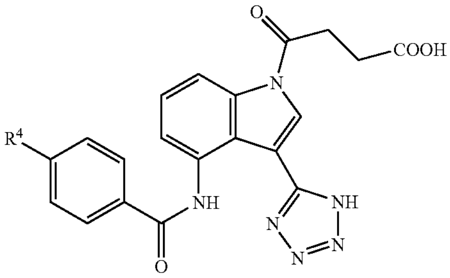
| | $R^4$— |
|---|---|
| 68 | 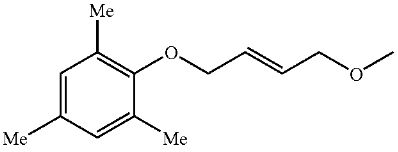 |
| 69 | 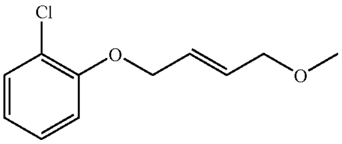 |
TABLE 8
(I-H)
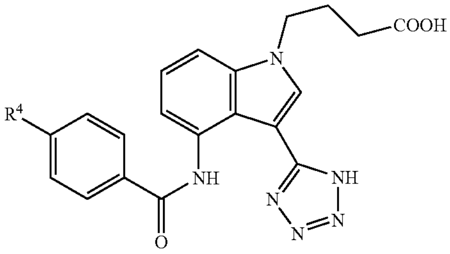
| | $R^4$— |
|---|---|
| 1 | $n\text{-}C_4H_9^-$ |
| 2 | $n\text{-}C_5H_{11}^-$ |
| 3 | $n\text{-}C_6H_{13}^-$ |
| 4 | $n\text{-}C_4H_9\text{—}O^-$ |
| 5 | $n\text{-}C_5H_{11}\text{—}O^-$ |
| 6 | $n\text{-}C_6H_{13}\text{—}O^-$ |
| 7 | 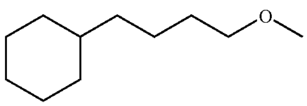 |
| 8 | 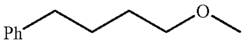 |
| 9 | 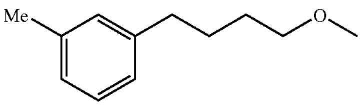 |

TABLE 8-continued
(I-H)
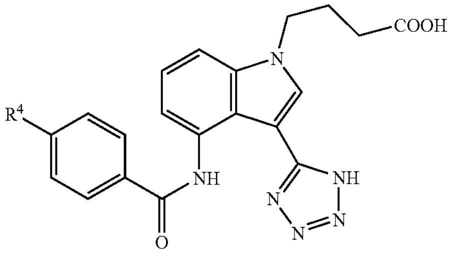
| | $R^4$— |
|---|---|
| 10 | 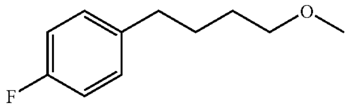 |
| 11 | 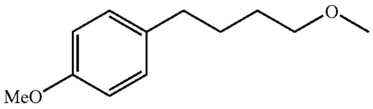 |
| 12 | 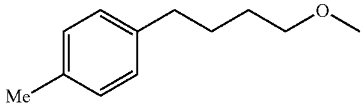 |
| 13 | 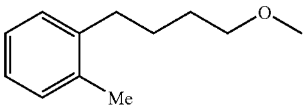 |
| 14 | 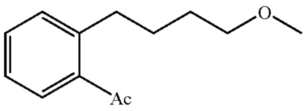 |
| 15 | 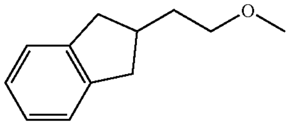 |
| 16 | 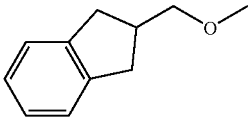 |
| 17 | 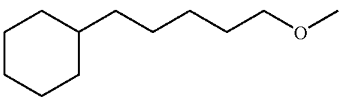 |
| 18 | 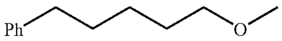 |
| 19 | 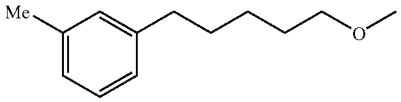 |
| 20 | 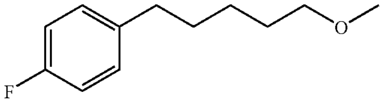 |
TABLE 8-continued
(I-H)
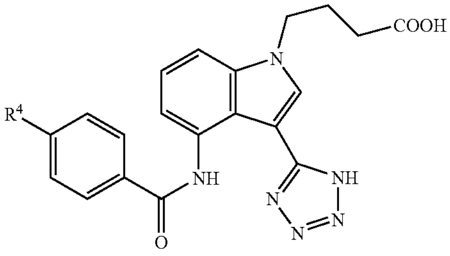
| | $R^4$— |
|---|---|
| 21 | 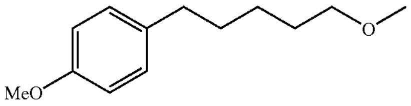 |
| 22 | 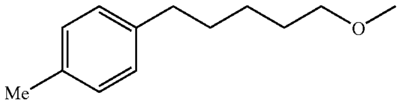 |
| 23 | 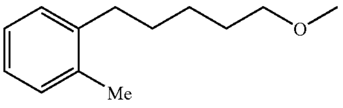 |
| 24 | 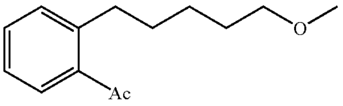 |
| 25 | 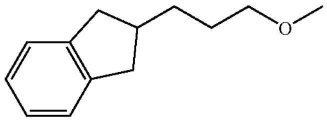 |
| 26 | 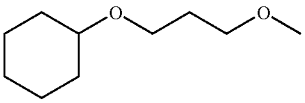 |
| 27 | 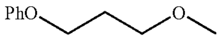 |
| 28 | 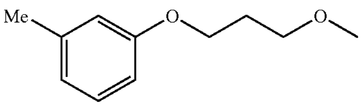 |
| 29 | 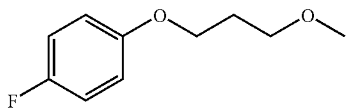 |
| 30 | 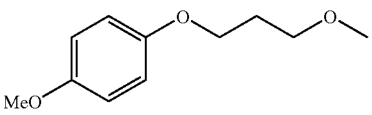 |
| 31 | 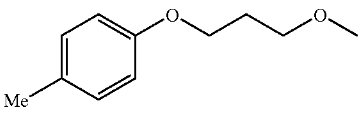 |

TABLE 8-continued
(I-H)
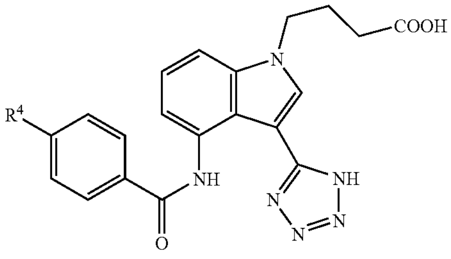
$R^4$—
32 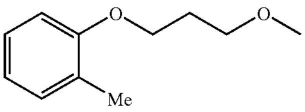
33 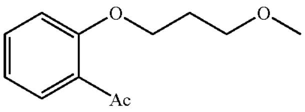
34 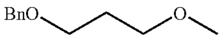
35 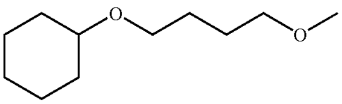
36 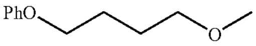
37 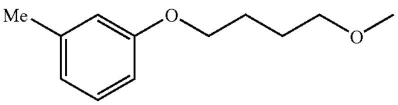
38 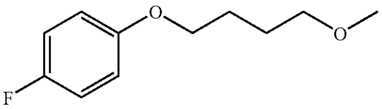
39 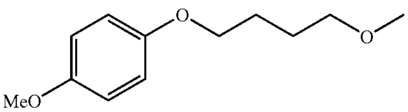
40 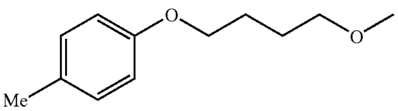
41 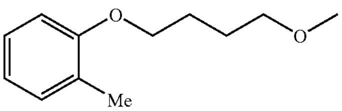
42 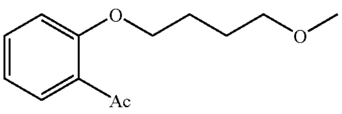
TABLE 8-continued
(I-H)
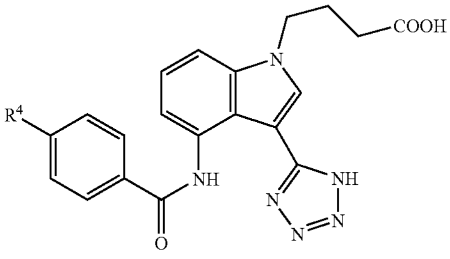
$R^4$—
43 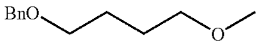
44 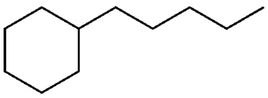
45 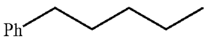
46 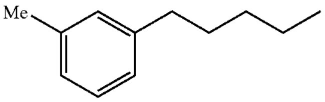
47 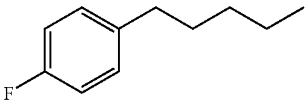
48 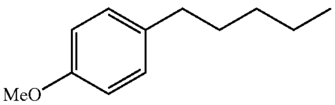
49 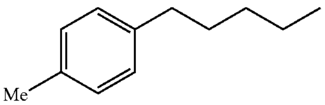
50 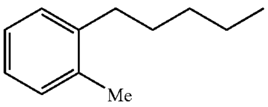
51 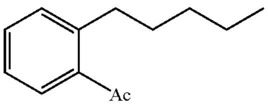
52 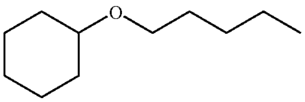
53 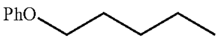
54 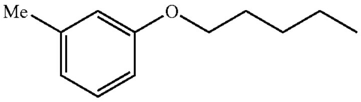

TABLE 8-continued
(I-H)
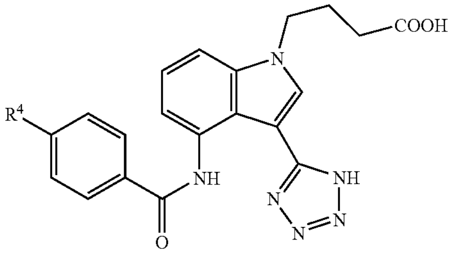
| R⁴— | |
|---|---|
| 55 | 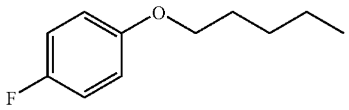 |
| 56 | 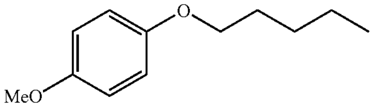 |
| 57 | 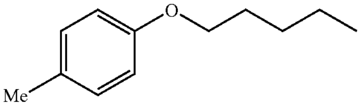 |
| 58 | 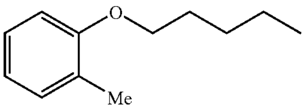 |
| 59 | 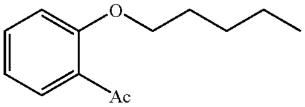 |
| 60 | 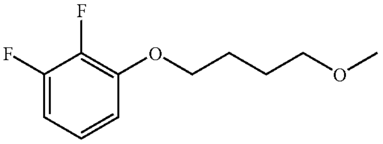 |
| 61 | 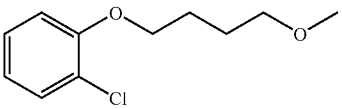 |
| 62 | 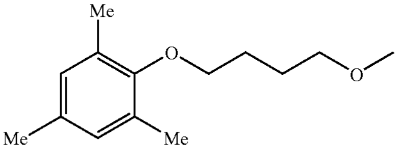 |
| 63 | 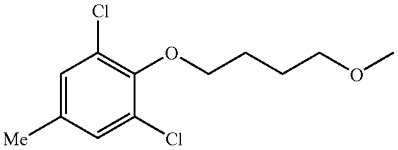 |
TABLE 8-continued
(I-H)
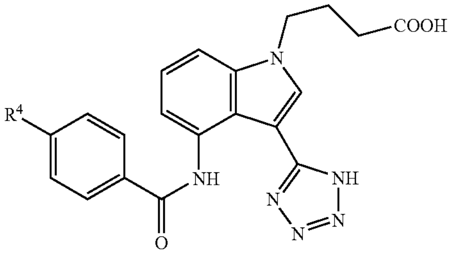
| R⁴— | |
|---|---|
| 64 | 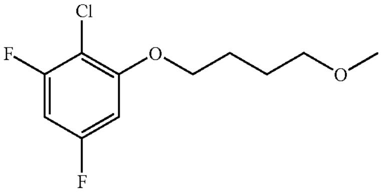 |
| 65 | 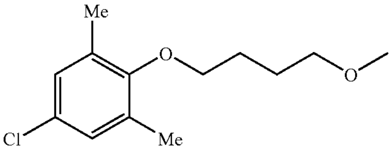 |
| 66 | 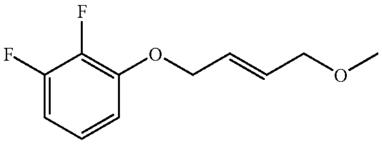 |
| 67 | 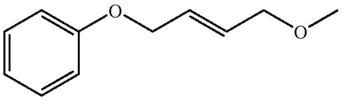 |
| 68 | 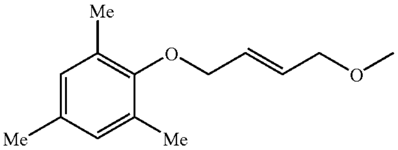 |
| 69 | 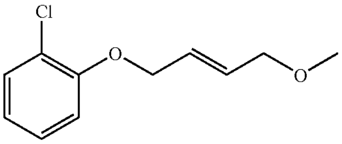 |

TABLE 9
(I-J)
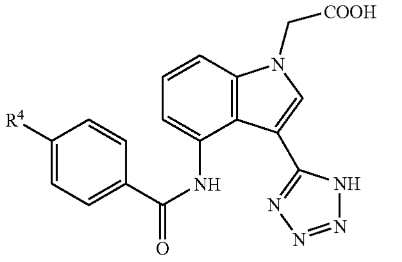
| | $R^4$— |
| --- | --- |
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |
| 7 | 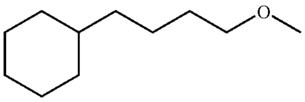 |
| 8 | 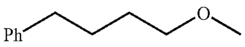 |
| 9 | 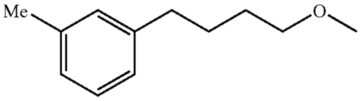 |
| 10 | 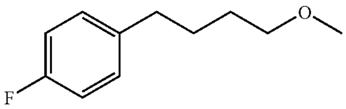 |
| 11 | 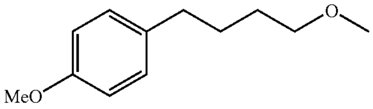 |
| 12 | 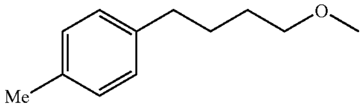 |
| 13 | 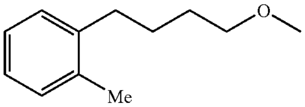 |
| 14 | 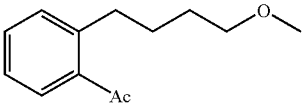 |
| 15 | 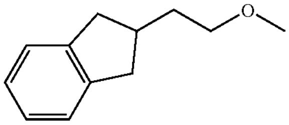 |
TABLE 9-continued
(I-J)
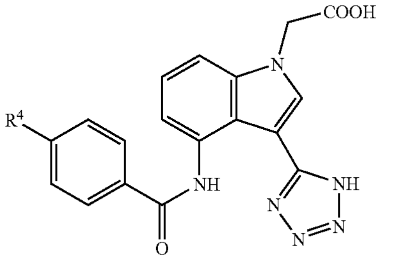
| | $R^4$— |
| --- | --- |
| 16 | 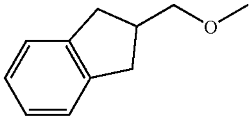 |
| 17 | 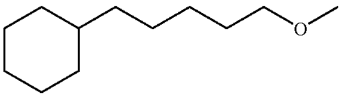 |
| 18 | 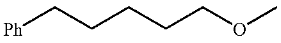 |
| 19 | 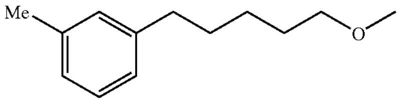 |
| 20 | 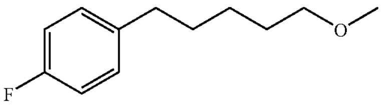 |
| 21 | 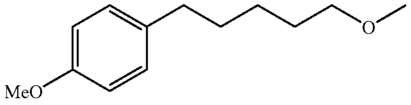 |
| 22 | 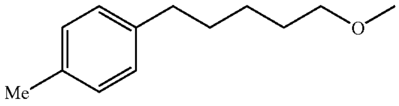 |
| 23 | 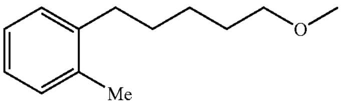 |
| 24 | 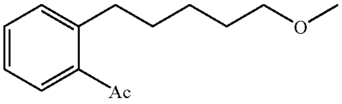 |
| 25 | 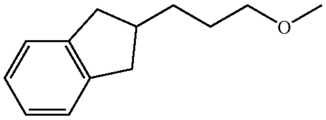 |
| 26 | 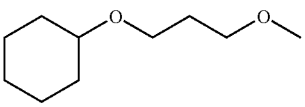 |

TABLE 9-continued
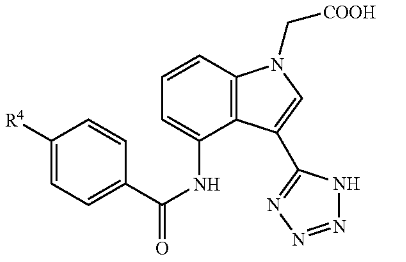
(I-J)
| | $R^4$— |
|---|---|
| 27 | 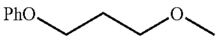 |
| 28 | 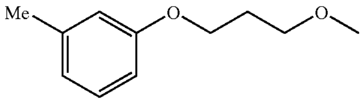 |
| 29 | 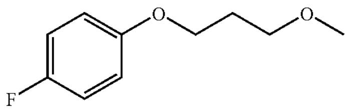 |
| 30 | 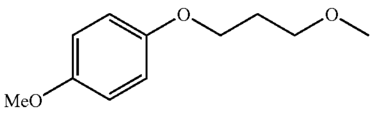 |
| 31 | 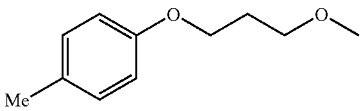 |
| 32 | 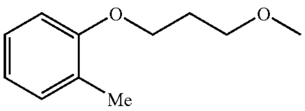 |
| 33 | 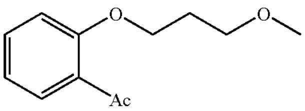 |
| 34 | 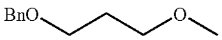 |
| 35 | 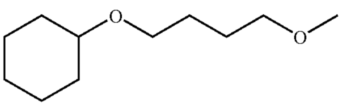 |
| 36 | 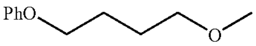 |
| 37 | 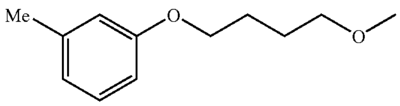 |
| 38 | 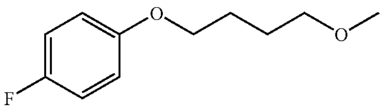 |
TABLE 9-continued
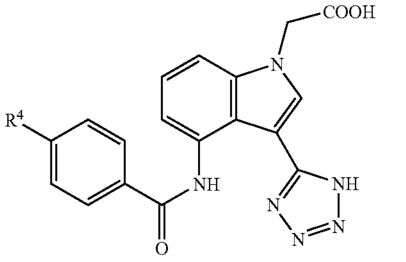
(I-J)
| | $R^4$— |
|---|---|
| 39 | 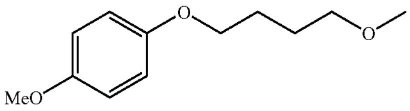 |
| 40 | 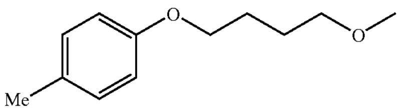 |
| 41 | 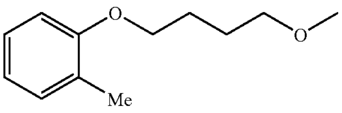 |
| 42 | 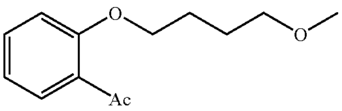 |
| 43 | 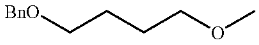 |
| 44 | 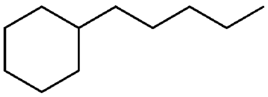 |
| 45 | 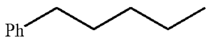 |
| 46 | 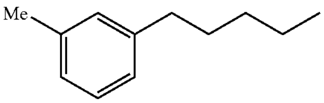 |
| 47 | 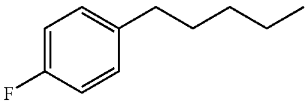 |
| 48 | 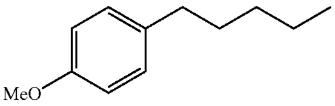 |
| 49 | 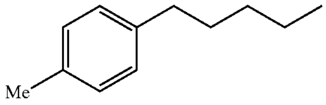 |

TABLE 9-continued
(I-J)
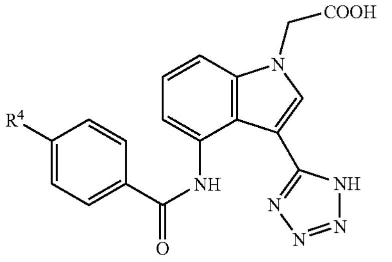
| | $R^4$— |
|---|---|
| 50 | 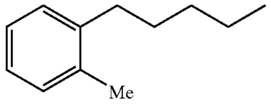 |
| 51 | 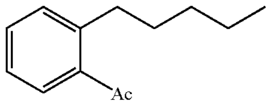 |
| 52 | 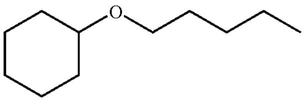 |
| 53 | 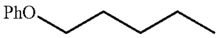 |
| 54 | 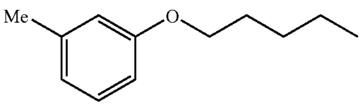 |
| 55 | 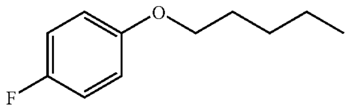 |
| 56 | 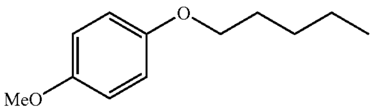 |
| 57 | 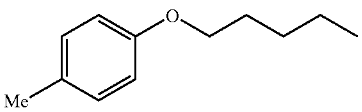 |
| 58 | 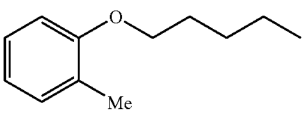 |
| 59 | 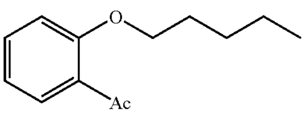 |
| 60 | 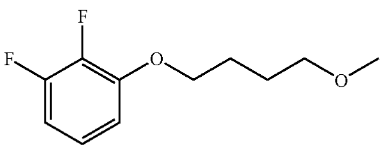 |
TABLE 9-continued
(I-J)
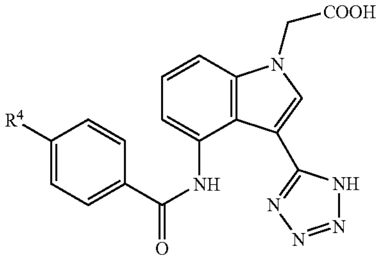
| | $R^4$— |
|---|---|
| 61 | 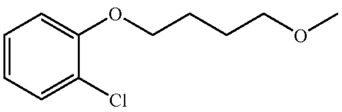 |
| 62 | 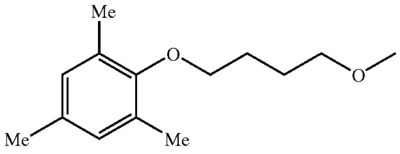 |
| 63 | 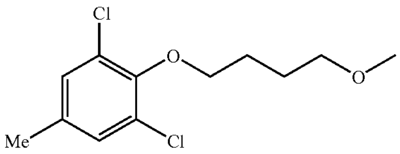 |
| 64 | 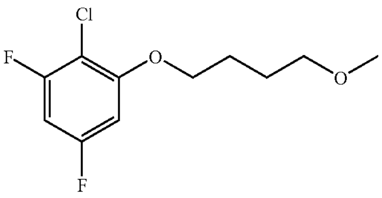 |
| 65 | 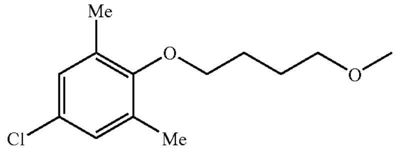 |
| 66 | 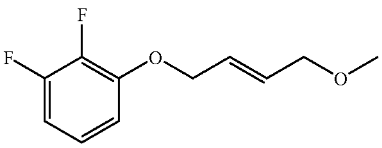 |
| 67 | 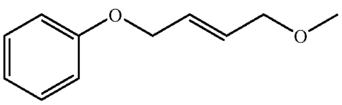 |
| 68 | 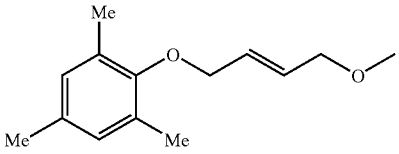 |

TABLE 9-continued
(I-J)
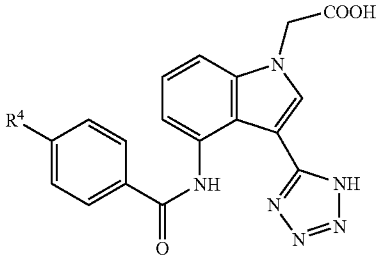
| | $R^4$— |
|---|---|
| 69 | 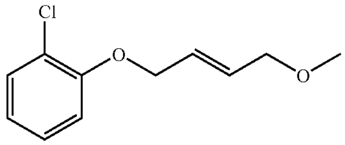 |
TABLE 10
(I-K)
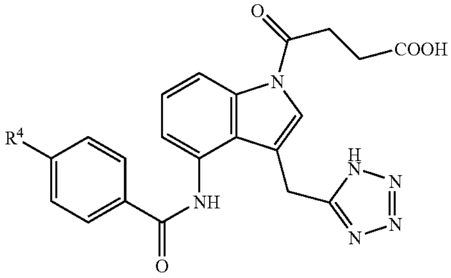
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 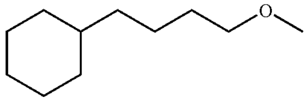 |
| 8 | 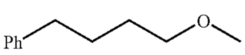 |
| 9 | 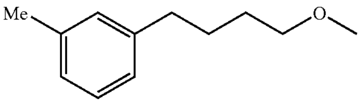 |
| 10 | 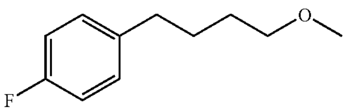 |
| 11 | 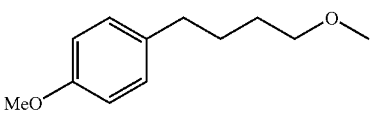 |
TABLE 10-continued
(I-K)
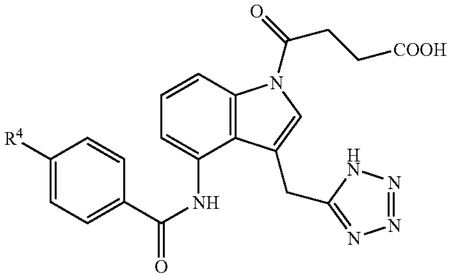
| | $R^4$— |
|---|---|
| 12 | 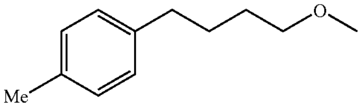 |
| 13 | 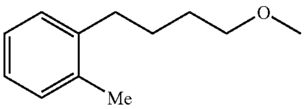 |
| 14 | 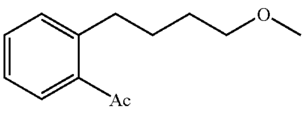 |
| 15 | 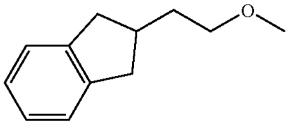 |
| 16 | 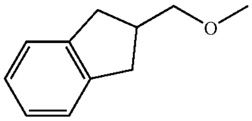 |
| 17 | 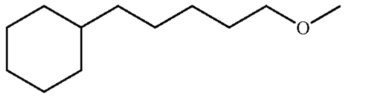 |
| 18 | 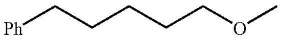 |
| 19 | 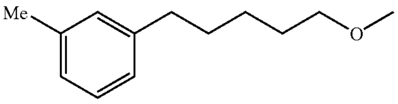 |
| 20 | 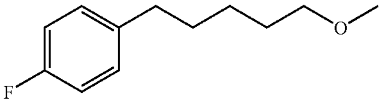 |
| 21 | 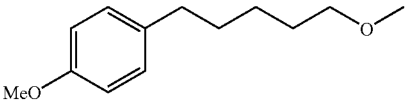 |
| 22 | 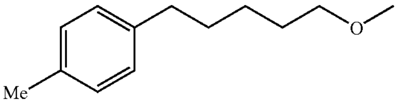 |

TABLE 10-continued
(I-K)
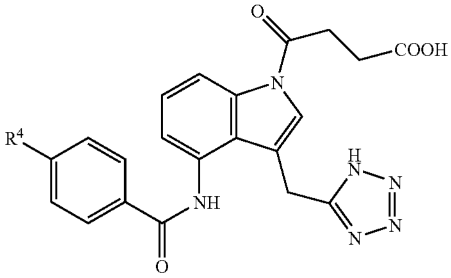
| | $R^4$— |
|---|---|
| 23 | 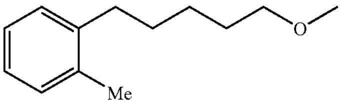 |
| 24 | 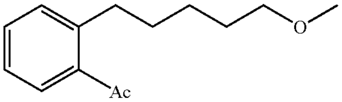 |
| 25 | 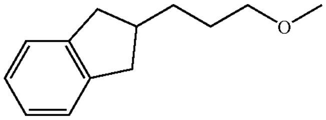 |
| 26 | 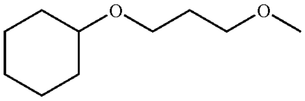 |
| 27 | 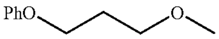 |
| 28 | 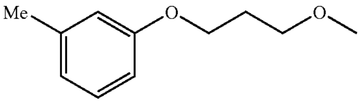 |
| 29 | 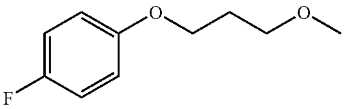 |
| 30 | 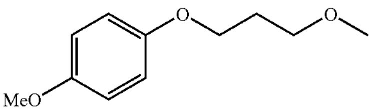 |
| 31 | 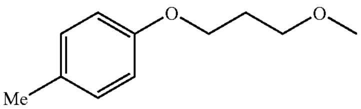 |
| 32 | 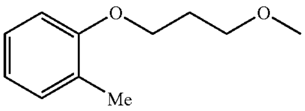 |
TABLE 10-continued
(I-K)
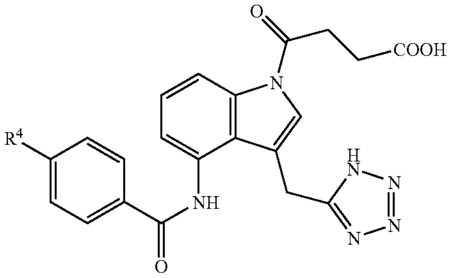
| | $R^4$— |
|---|---|
| 33 | 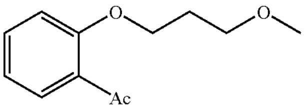 |
| 34 | 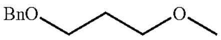 |
| 35 | 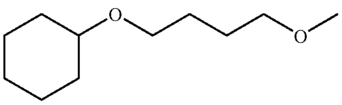 |
| 36 | 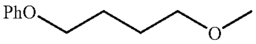 |
| 37 | 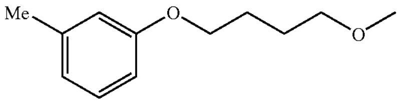 |
| 38 | 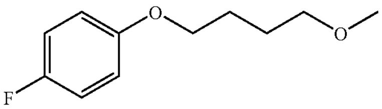 |
| 39 | 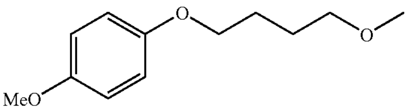 |
| 40 | 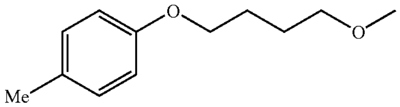 |
| 41 | 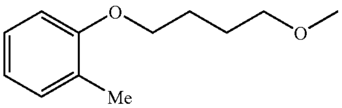 |
| 42 | 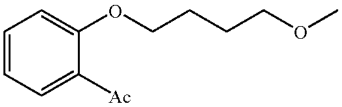 |
| 43 | 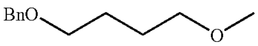 |
| 44 | 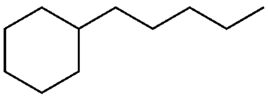 |

TABLE 10-continued
(I-K)
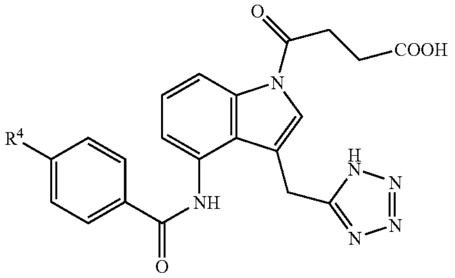
| | $R^4$— |
|---|---|
| 45 | 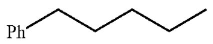 |
| 46 | 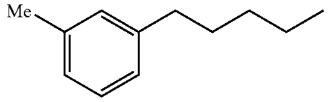 |
| 47 | 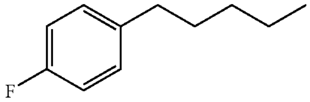 |
| 48 | 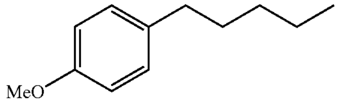 |
| 49 | 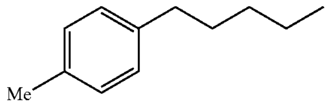 |
| 50 | 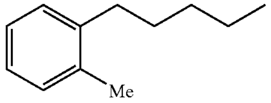 |
| 51 | 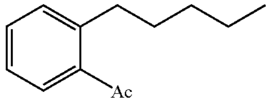 |
| 52 | 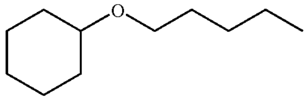 |
| 53 | 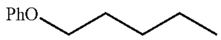 |
| 54 | 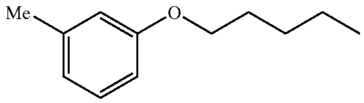 |
| 55 | 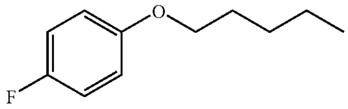 |
TABLE 10-continued
(I-K)
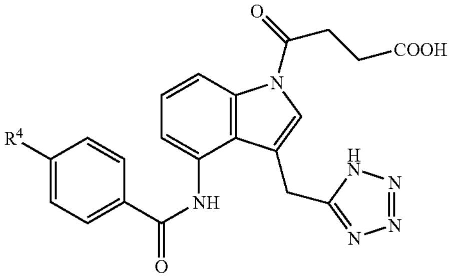
| | $R^4$— |
|---|---|
| 56 | 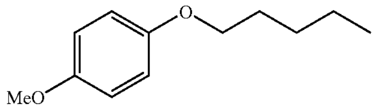 |
| 57 | 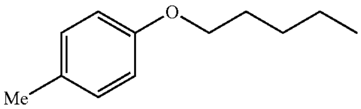 |
| 58 | 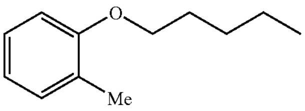 |
| 59 | 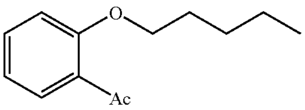 |
| 60 | 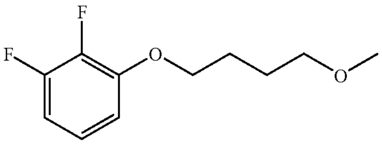 |
| 61 | 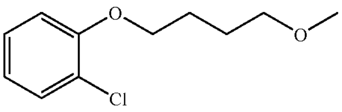 |
| 62 | 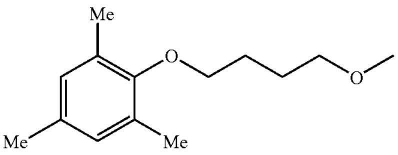 |
| 63 | 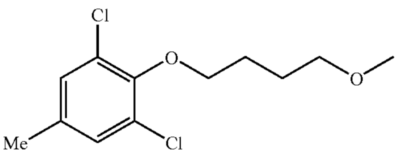 |

TABLE 10-continued
(I-K)
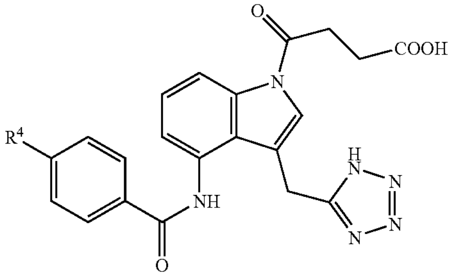
| | $R^4$— |
|---|---|
| 64 | 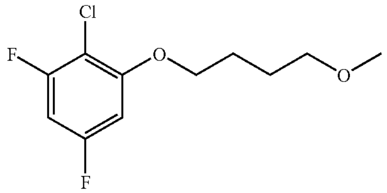 |
| 65 | 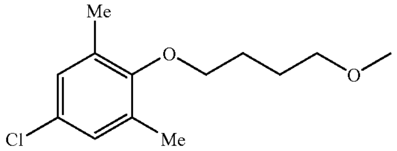 |
| 66 | 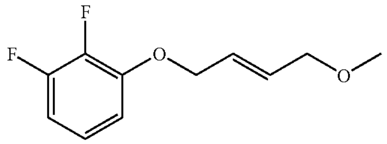 |
| 67 | 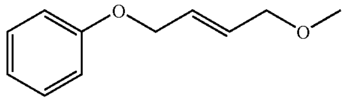 |
| 68 | 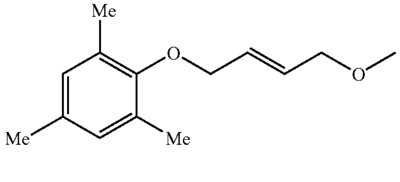 |
| 69 | 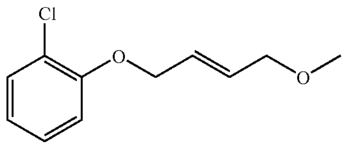 |
TABLE 11
(I-L)
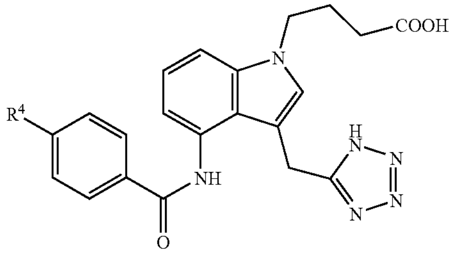
| | $R^4$— |
|---|---|
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |
| 7 | 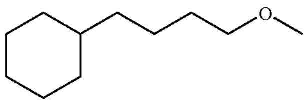 |
| 8 | 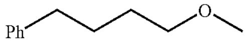 |
| 9 | 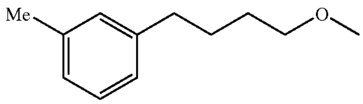 |
| 10 | 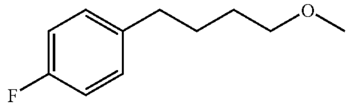 |
| 11 | 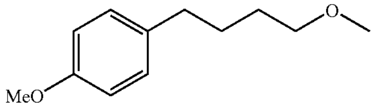 |
| 12 | 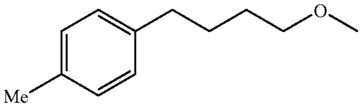 |
| 13 | 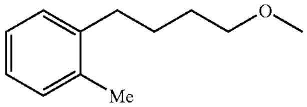 |
| 14 | 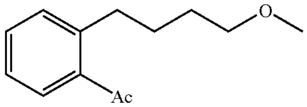 |
| 15 | 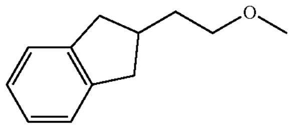 |

TABLE 11-continued
(I-L)
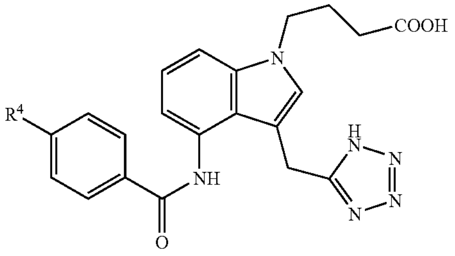
| | $R^4$— |
|---|---|
| 16 | 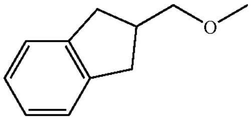 |
| 17 | 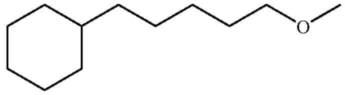 |
| 18 | 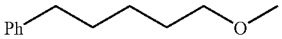 |
| 19 | 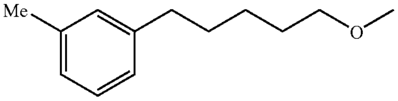 |
| 20 | 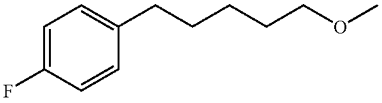 |
| 21 | 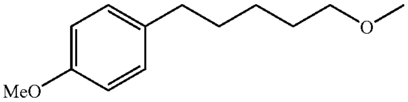 |
| 22 | 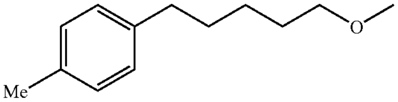 |
| 23 | 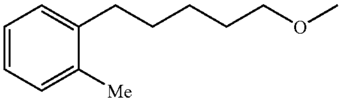 |
| 24 | 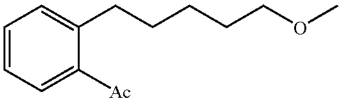 |
| 25 | 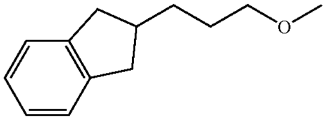 |
| 26 | 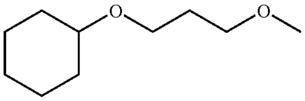 |
TABLE 11-continued
(I-L)
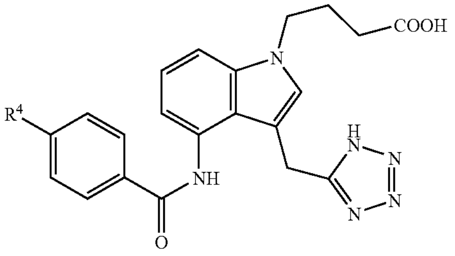
| | $R^4$— |
|---|---|
| 27 | 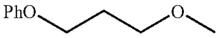 |
| 28 | 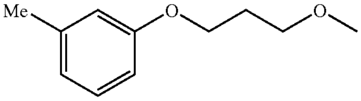 |
| 29 | 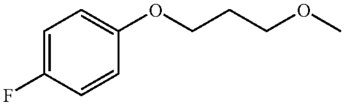 |
| 30 | 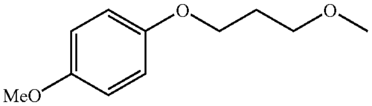 |
| 31 | 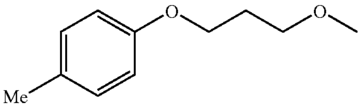 |
| 32 | 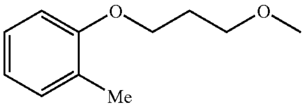 |
| 33 | 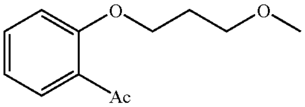 |
| 34 | 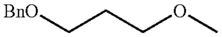 |
| 35 | 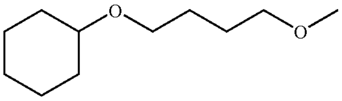 |
| 36 | 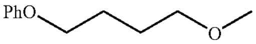 |
| 37 | 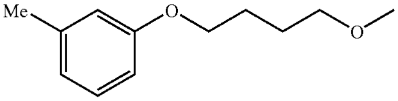 |
| 38 | 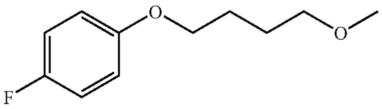 |

TABLE 11-continued
(I-L)
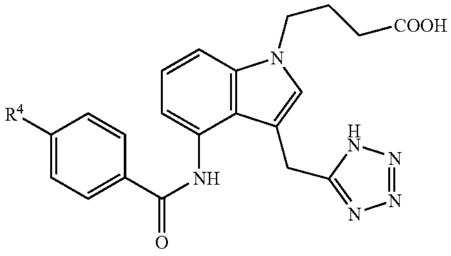
| | $R^4$— |
|---|---|
| 39 | 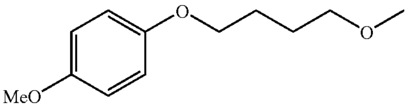 |
| 40 | 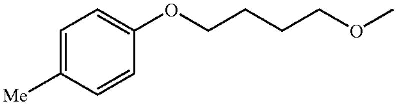 |
| 41 | 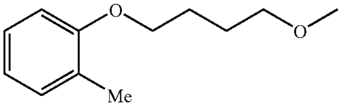 |
| 42 | 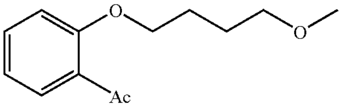 |
| 43 | 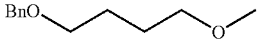 |
| 44 | 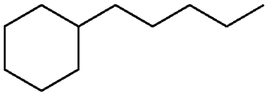 |
| 45 | 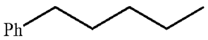 |
| 46 | 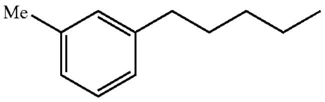 |
| 47 | 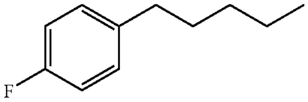 |
| 48 | 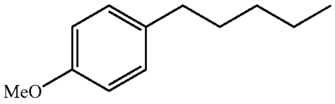 |
| 49 | 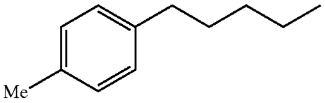 |
| 50 | 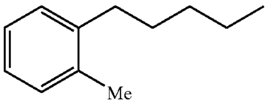 |
TABLE 11-continued
(I-L)
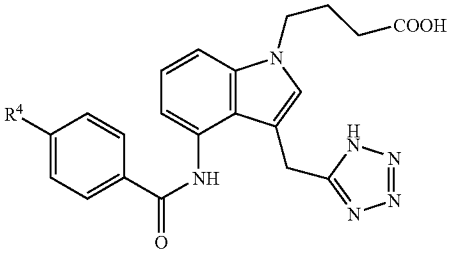
| | $R^4$— |
|---|---|
| 51 | 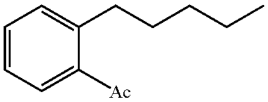 |
| 52 | 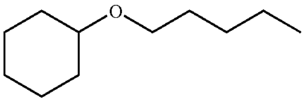 |
| 53 | 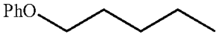 |
| 54 | 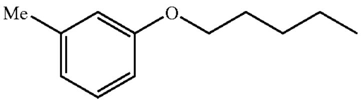 |
| 55 | 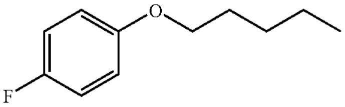 |
| 56 | 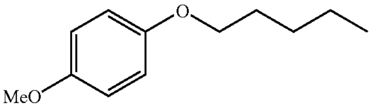 |
| 57 | 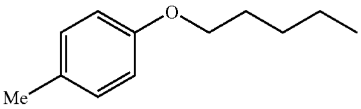 |
| 58 | 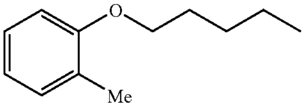 |
| 59 | 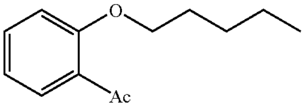 |
| 60 | 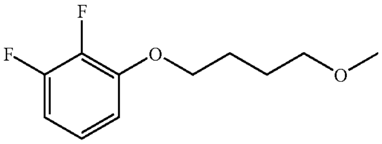 |

TABLE 11-continued
(I-L)
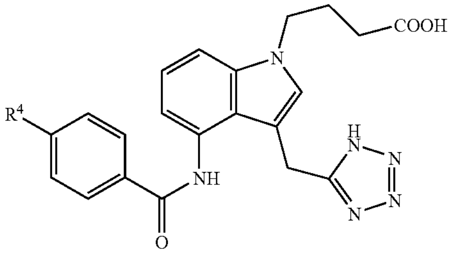
| | R⁴— |
|---|---|
| 61 | 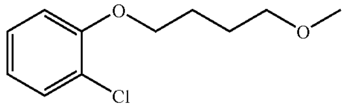 |
| 62 | 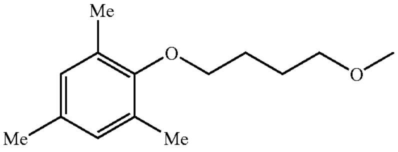 |
| 63 | 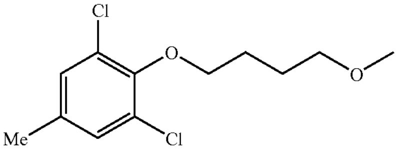 |
| 64 | 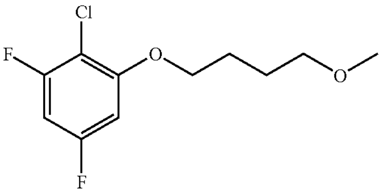 |
| 65 | 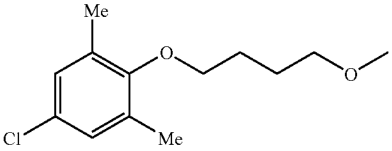 |
| 66 | 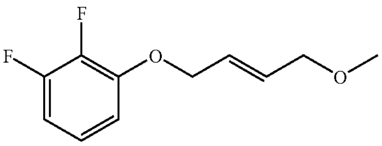 |
| 67 | 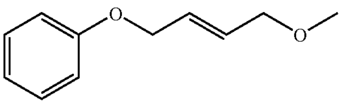 |
| 68 | 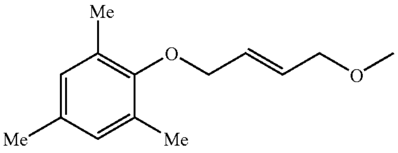 |
TABLE 11-continued
(I-L)
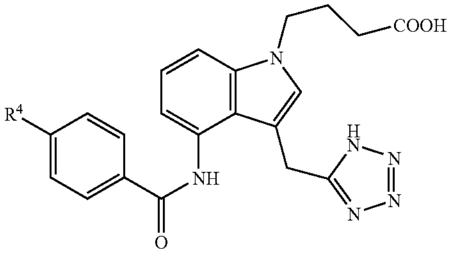
| | R⁴— |
|---|---|
| 69 | 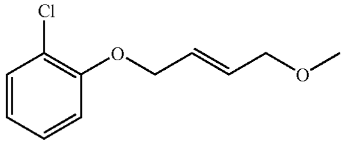 |
TABLE 12
(I-M)
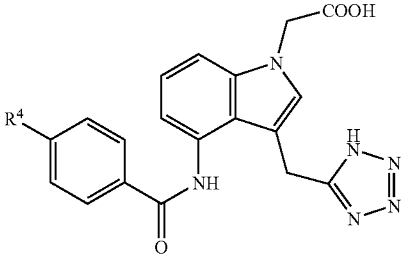
| | R⁴— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 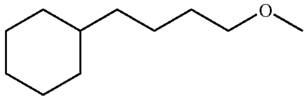 |
| 8 | 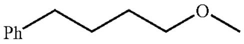 |
| 9 | 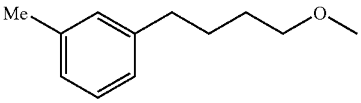 |
| 10 | 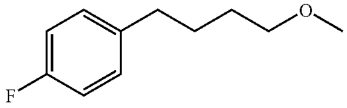 |
| 11 | 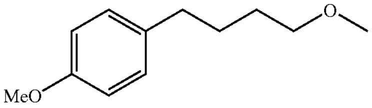 |

TABLE 12-continued
(I-M)
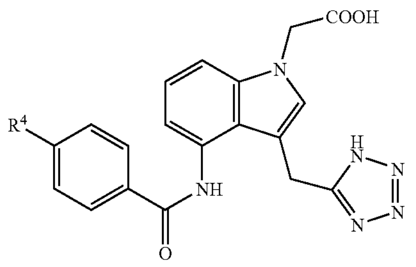
| | $R^4$— |
|---|---|
| 12 | 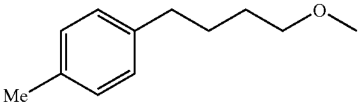 |
| 13 | 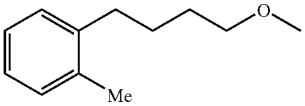 |
| 14 | 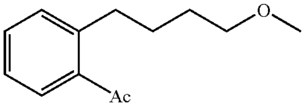 |
| 15 | 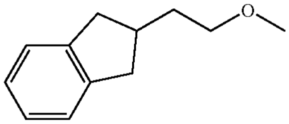 |
| 16 | 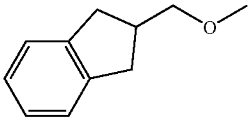 |
| 17 | 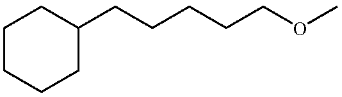 |
| 18 | 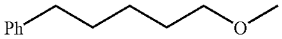 |
| 19 | 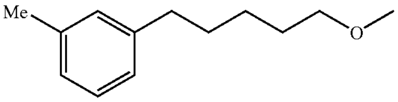 |
| 20 | 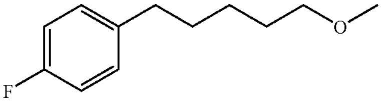 |
| 21 | 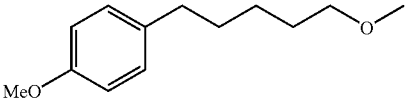 |
| 22 | 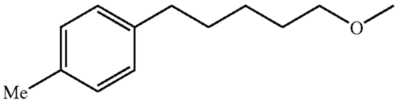 |
TABLE 12-continued
(I-M)
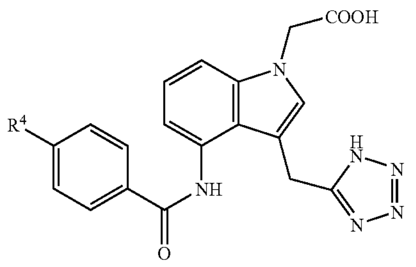
| | $R^4$— |
|---|---|
| 23 | 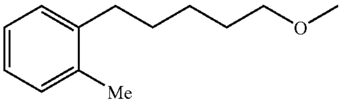 |
| 24 | 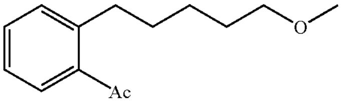 |
| 25 | 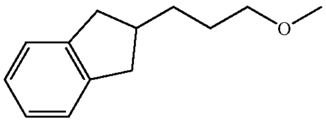 |
| 26 | 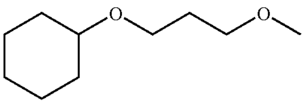 |
| 27 | 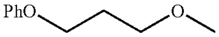 |
| 28 | 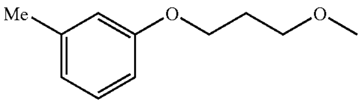 |
| 29 | 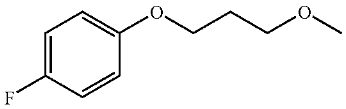 |
| 30 | 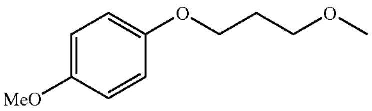 |
| 31 | 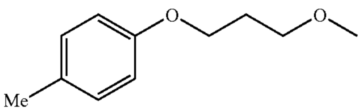 |
| 32 | 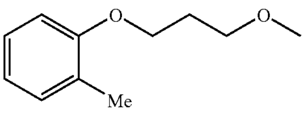 |

TABLE 12-continued
(I-M)
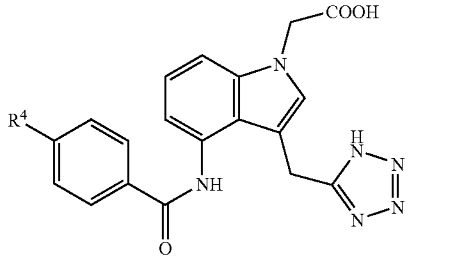
| | $R^4$— |
|---|---|
| 33 | 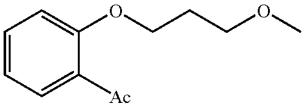 |
| 34 | 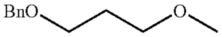 |
| 35 | 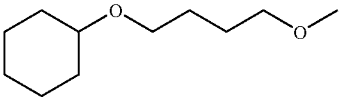 |
| 36 | 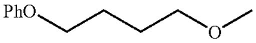 |
| 37 | 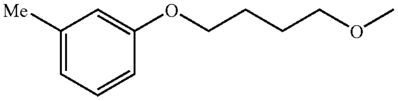 |
| 38 | 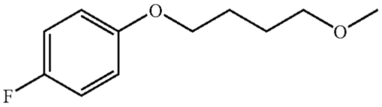 |
| 39 | 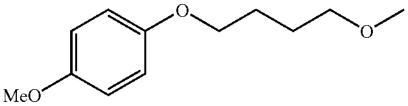 |
| 40 | 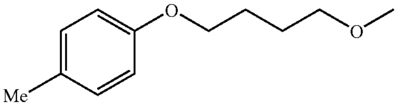 |
| 41 | 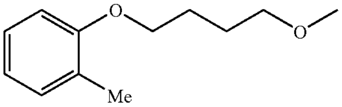 |
| 42 | 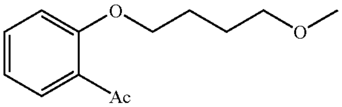 |
| 43 | 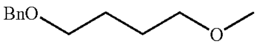 |
| 44 | 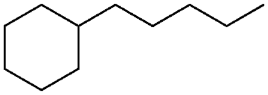 |
TABLE 12-continued
(I-M)
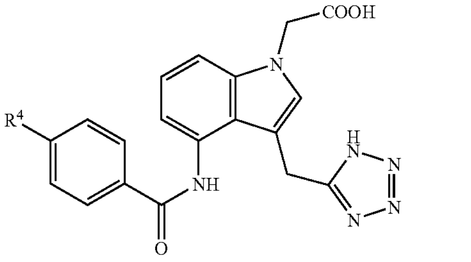
| | $R^4$— |
|---|---|
| 45 | 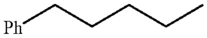 |
| 46 | 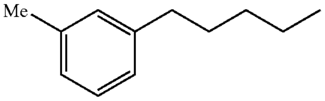 |
| 47 | 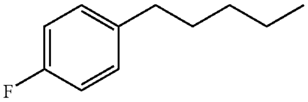 |
| 48 | 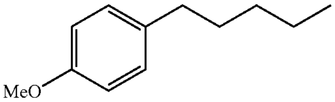 |
| 49 | 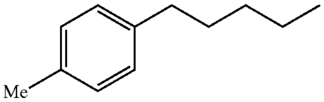 |
| 50 | 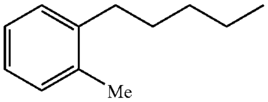 |
| 51 | 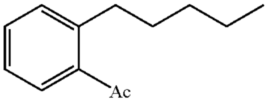 |
| 52 | 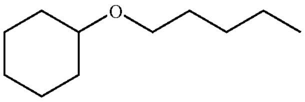 |
| 53 | 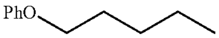 |
| 54 | 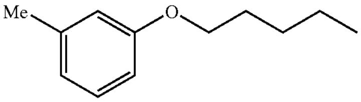 |
| 55 | 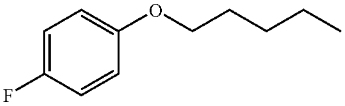 |
| 56 | 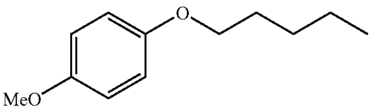 |

TABLE 12-continued
(I-M)
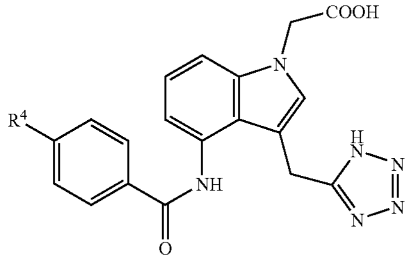
| | $R^4$— |
|---|---|
| 57 | 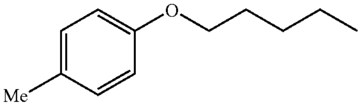 |
| 58 | 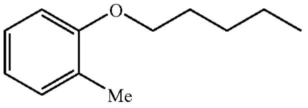 |
| 59 | 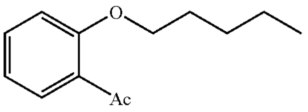 |
| 60 | 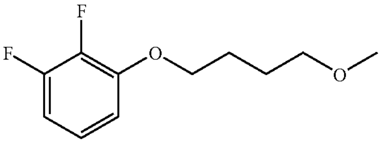 |
| 61 | 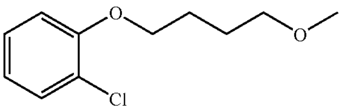 |
| 62 | 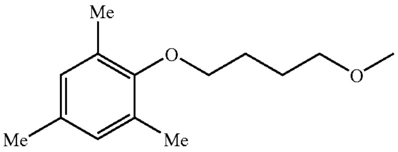 |
| 63 | 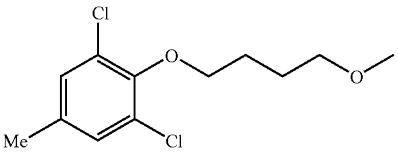 |
| 64 | 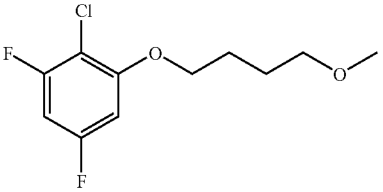 |
TABLE 12-continued
(I-M)
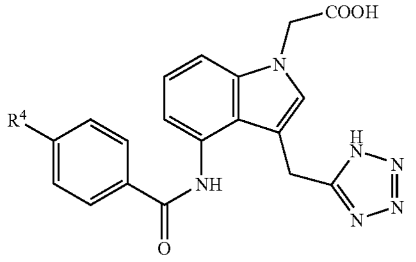
| | $R^4$— |
|---|---|
| 65 | 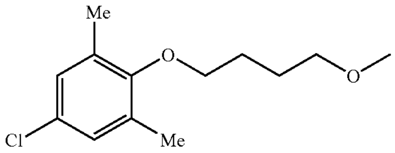 |
| 66 | 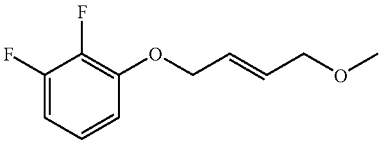 |
| 67 | 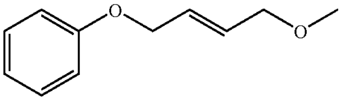 |
| 68 | 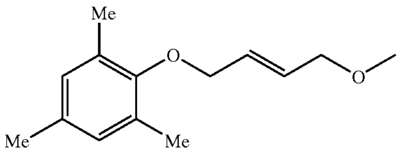 |
| 69 | 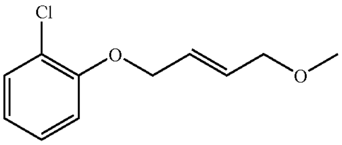 |
TABLE 13
(I-N)
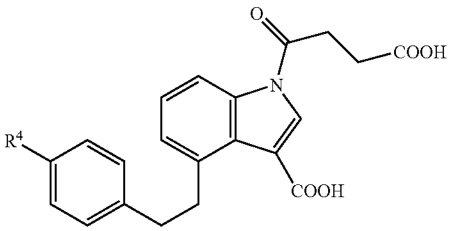
| | $R^4$— |
|---|---|
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |

TABLE 13-continued
| | |
|---|---|
| | 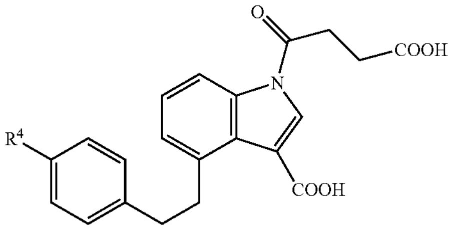 (I-N) |
| | $R^4$— |
| 7 | 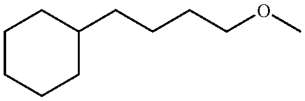 |
| 8 | 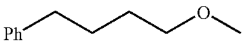 |
| 9 | 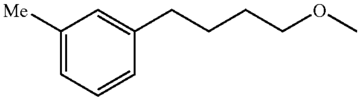 |
| 10 | 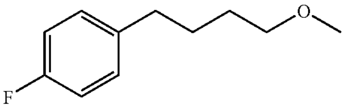 |
| 11 | 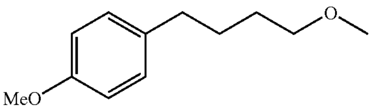 |
| 12 | 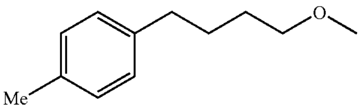 |
| 13 | 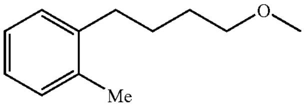 |
| 14 | 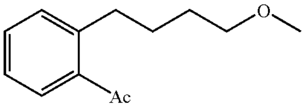 |
| 15 | 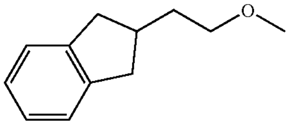 |
| 16 | 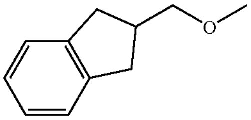 |
| 17 | 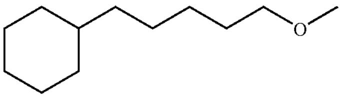 |
TABLE 13-continued
| | |
|---|---|
| | 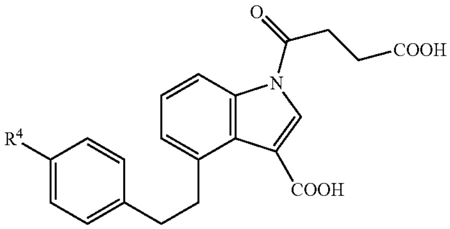 (I-N) |
| | $R^4$— |
| 18 | 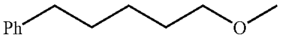 |
| 19 | 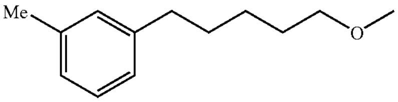 |
| 20 | 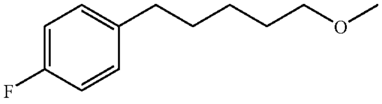 |
| 21 | 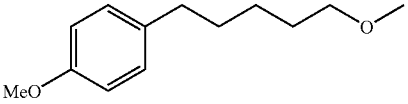 |
| 22 | 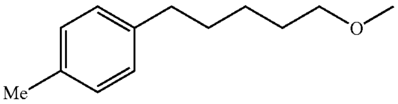 |
| 23 | 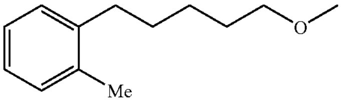 |
| 24 | 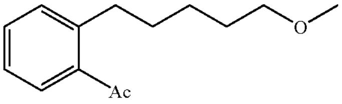 |
| 25 | 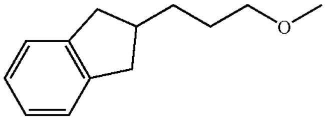 |
| 26 | 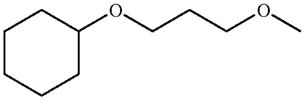 |
| 27 | 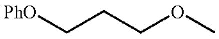 |
| 28 | 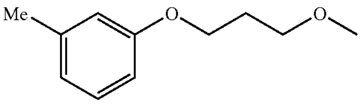 |
| 29 | 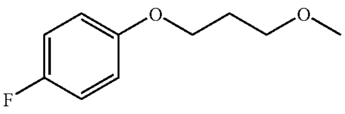 |

TABLE 13-continued
(I-N)
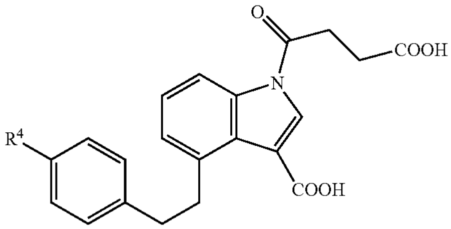
| R⁴— | |
|---|---|
| 30 | 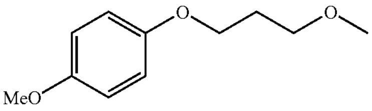 |
| 31 | 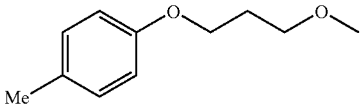 |
| 32 | 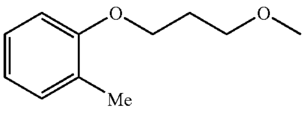 |
| 33 | 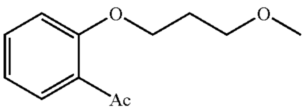 |
| 34 | 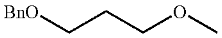 |
| 35 | 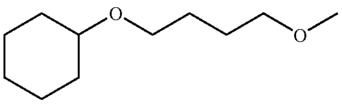 |
| 36 | 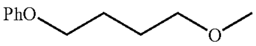 |
| 37 | 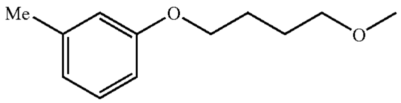 |
| 38 | 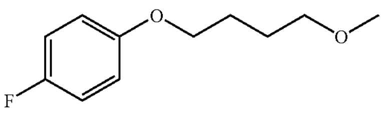 |
| 39 | 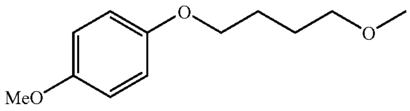 |
| 40 | 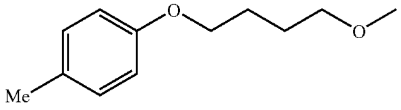 |
TABLE 13-continued
(I-N)
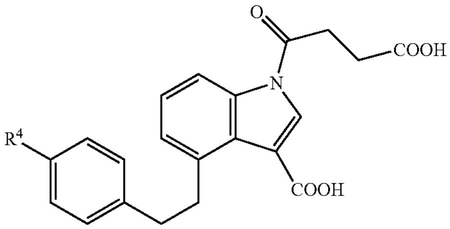
| R⁴— | |
|---|---|
| 41 | 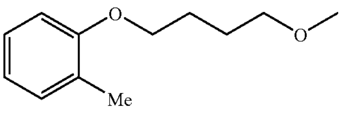 |
| 42 | 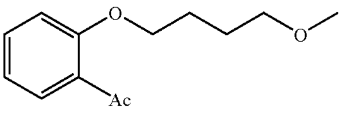 |
| 43 | 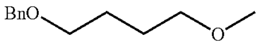 |
| 44 | 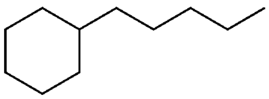 |
| 45 | 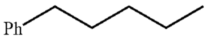 |
| 46 | 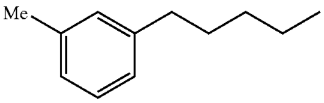 |
| 47 | 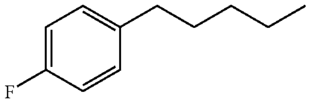 |
| 48 | 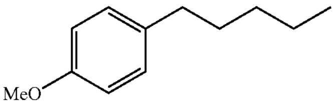 |
| 49 | 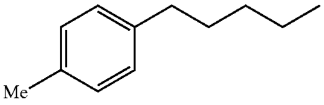 |
| 50 | 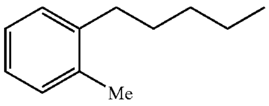 |
| 51 | 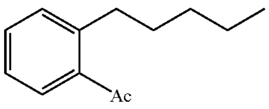 |
| 52 | 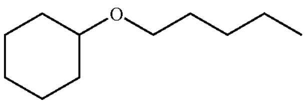 |

TABLE 13-continued
(I-N)
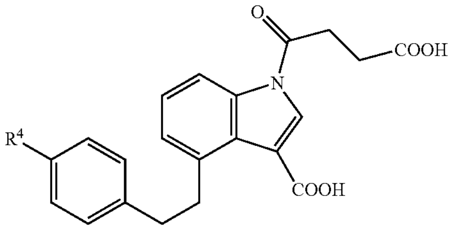
| | $R^4$— |
|---|---|
| 53 | 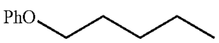 |
| 54 | 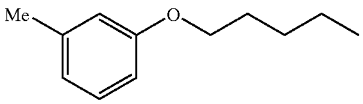 |
| 55 | 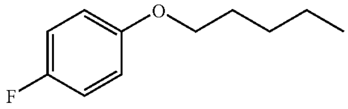 |
| 56 | 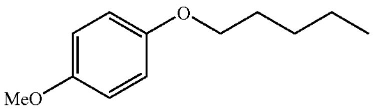 |
| 57 | 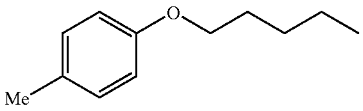 |
| 58 | 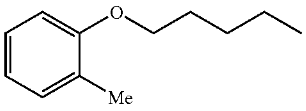 |
| 59 | 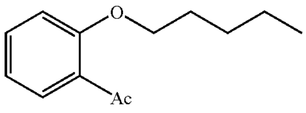 |
| 60 | 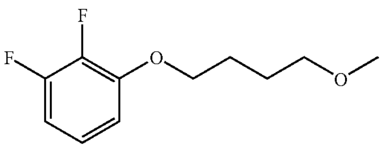 |
| 61 | 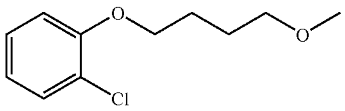 |
| 62 | 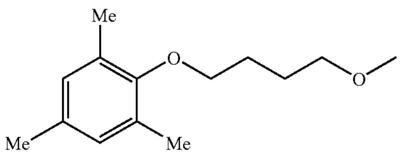 |
TABLE 13-continued
(I-N)
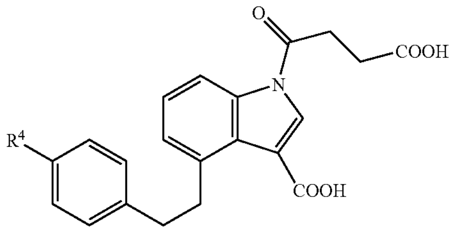
| | $R^4$— |
|---|---|
| 63 | 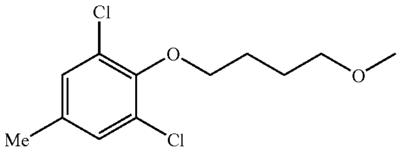 |
| 64 | 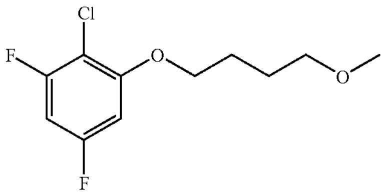 |
| 65 | 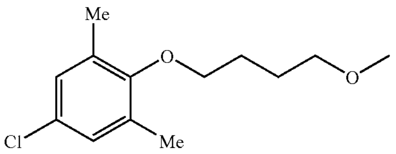 |
| 66 | 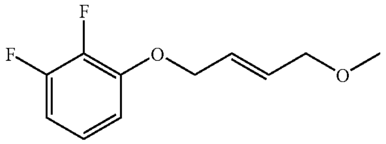 |
| 67 | 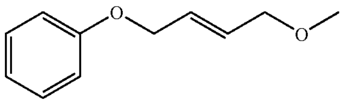 |
| 68 | 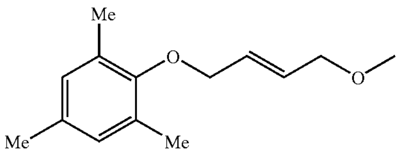 |
| 69 | 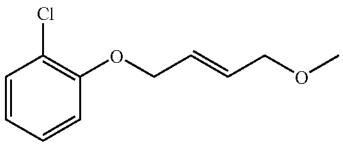 |

TABLE 14
(I-O)
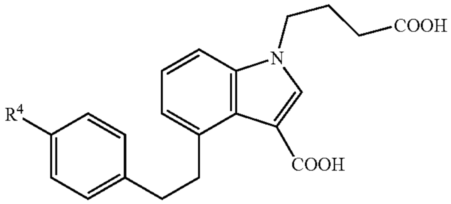
| | $R^4$— |
|---|---|
| 1 | $n\text{-}C_4H_9^-$ |
| 2 | $n\text{-}C_5H_{11}^-$ |
| 3 | $n\text{-}C_6H_{13}^-$ |
| 4 | $n\text{-}C_4H_9\text{—}O^-$ |
| 5 | $n\text{-}C_5H_{11}\text{—}O^-$ |
| 6 | $n\text{-}C_6H_{13}\text{—}O^-$ |
| 7 | 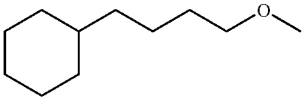 |
| 8 | 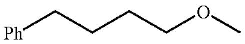 |
| 9 | 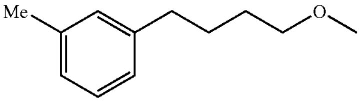 |
| 10 | 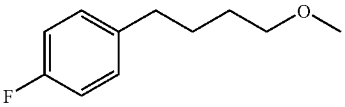 |
| 11 | 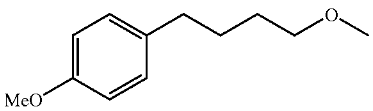 |
| 12 | 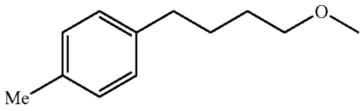 |
| 13 | 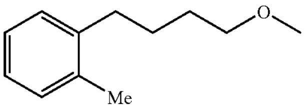 |
| 14 | 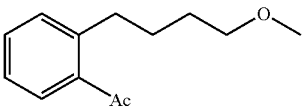 |
| 15 | 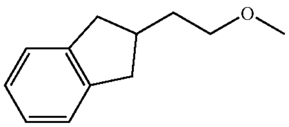 |
| 16 | 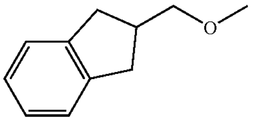 |
TABLE 14-continued
(I-O)
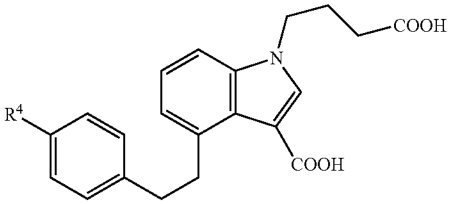
| | $R^4$— |
|---|---|
| 17 | 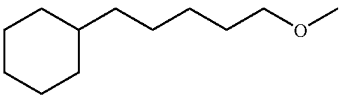 |
| 18 | 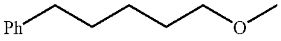 |
| 19 | 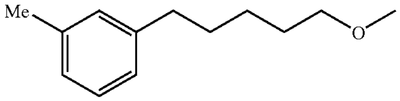 |
| 20 | 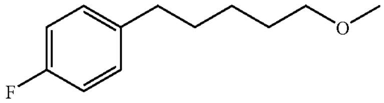 |
| 21 | 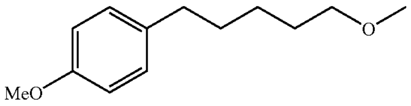 |
| 22 | 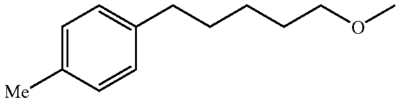 |
| 23 | 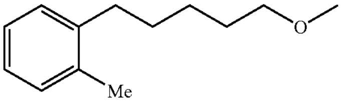 |
| 24 | 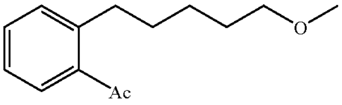 |
| 25 | 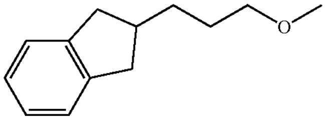 |
| 26 | 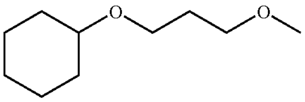 |
| 27 | 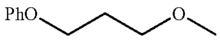 |
| 28 | 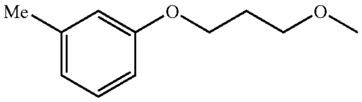 |

TABLE 14-continued
(I-O)
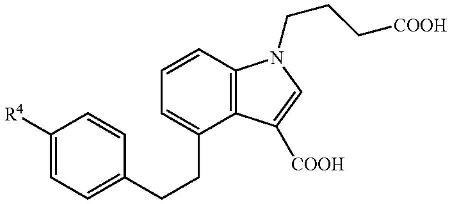
| | $R^4$— |
|---|---|
| 29 | 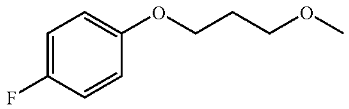 |
| 30 | 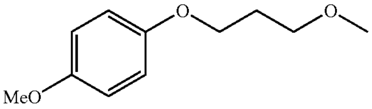 |
| 31 | 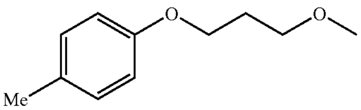 |
| 32 | 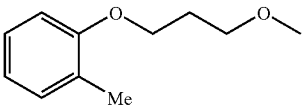 |
| 33 | 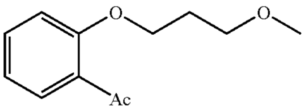 |
| 34 | 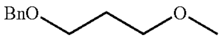 |
| 35 | 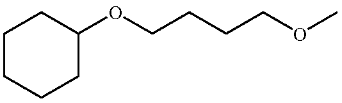 |
| 36 | 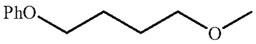 |
| 37 | 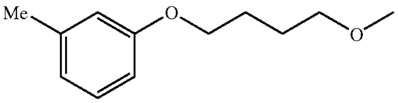 |
| 38 | 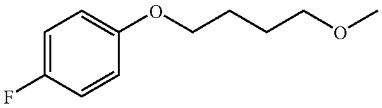 |
| 39 | 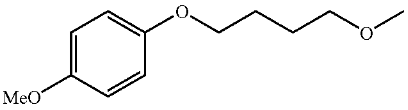 |
| 40 | 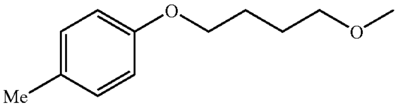 |
TABLE 14-continued
(I-O)
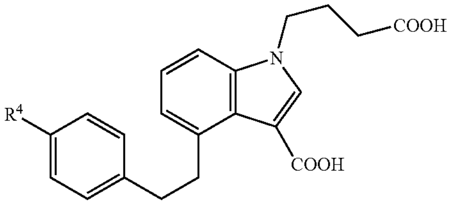
| | $R^4$— |
|---|---|
| 41 | 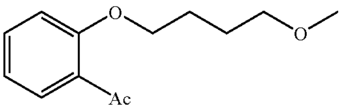 |
| 42 | 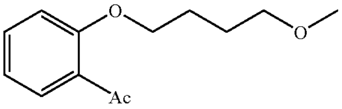 |
| 43 | 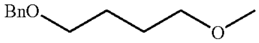 |
| 44 | 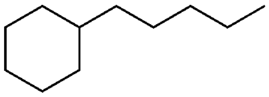 |
| 45 | 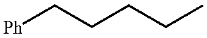 |
| 46 | 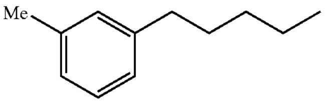 |
| 47 | 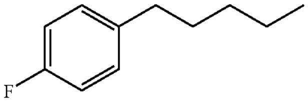 |
| 48 | 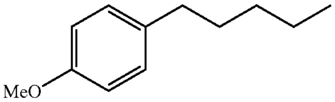 |
| 49 | 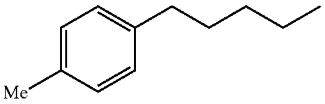 |
| 50 | 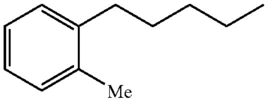 |
| 51 | 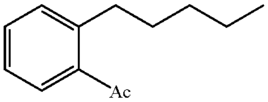 |
| 52 | 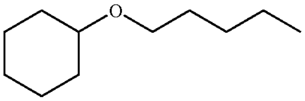 |

TABLE 14-continued
(I-O)
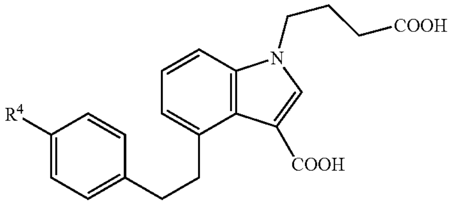
| | R⁴— |
|---|---|
| 53 | 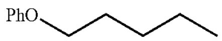 |
| 54 | 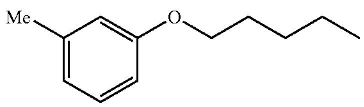 |
| 55 | 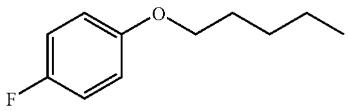 |
| 56 | 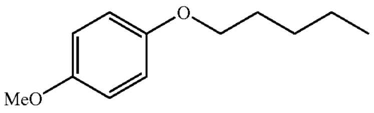 |
| 57 | 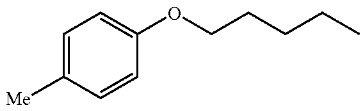 |
| 58 | 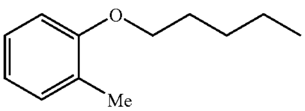 |
| 59 | 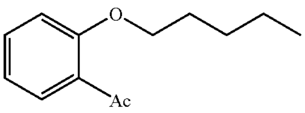 |
| 60 | 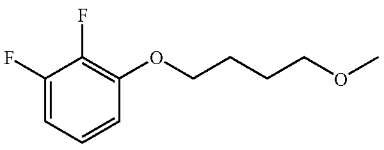 |
| 61 | 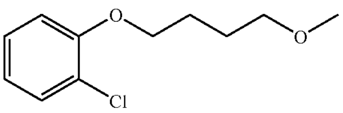 |
| 62 | 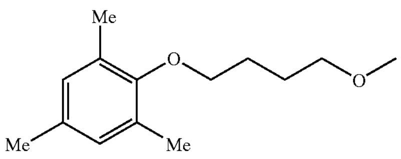 |
TABLE 14-continued
(I-O)
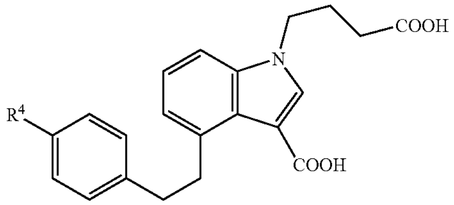
| | R⁴— |
|---|---|
| 63 | 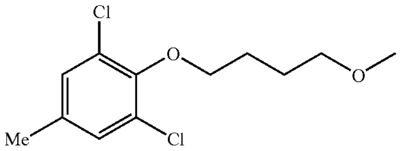 |
| 64 | 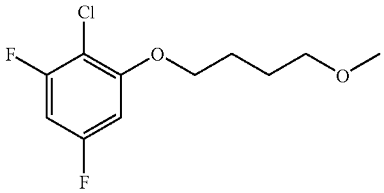 |
| 65 | 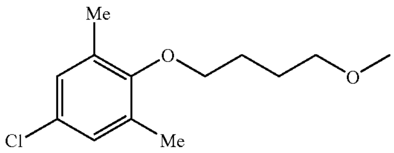 |
| 66 | 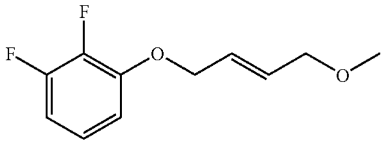 |
| 67 | 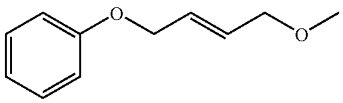 |
| 68 | 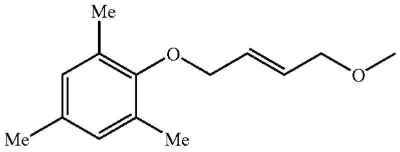 |
| 69 | 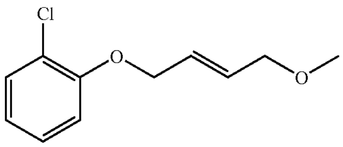 |

TABLE 15
(I-P)
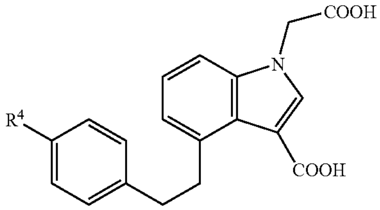
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 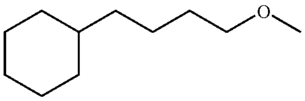 |
| 8 | 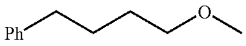 |
| 9 | 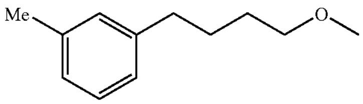 |
| 10 | 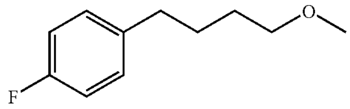 |
| 11 | 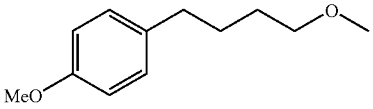 |
| 12 | 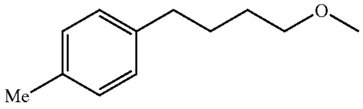 |
| 13 | 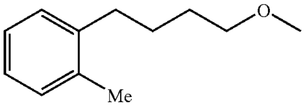 |
| 14 | 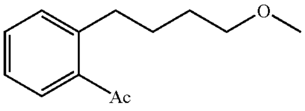 |
| 15 | 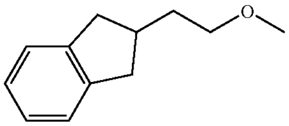 |
| 16 | 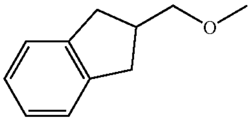 |
TABLE 15-continued
(I-P)
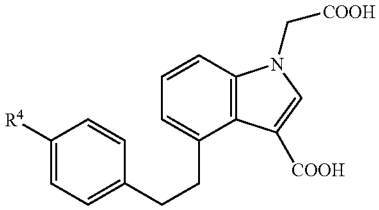
| | $R^4$— |
|---|---|
| 17 | 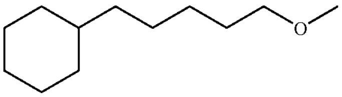 |
| 18 | 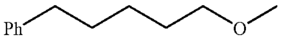 |
| 19 | 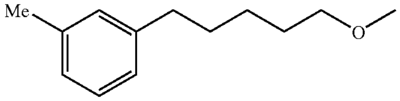 |
| 20 | 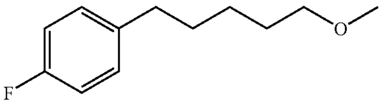 |
| 21 | 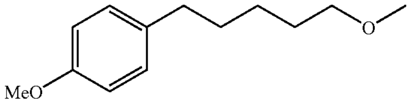 |
| 22 | 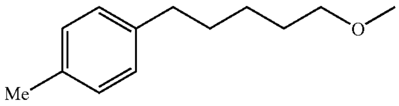 |
| 23 | 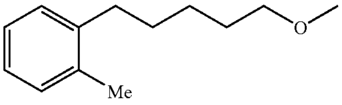 |
| 24 | 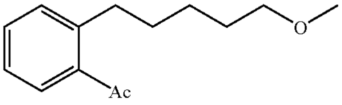 |
| 25 | 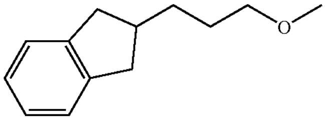 |
| 26 | 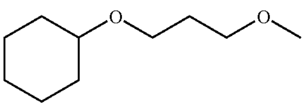 |
| 27 | 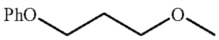 |
| 28 | 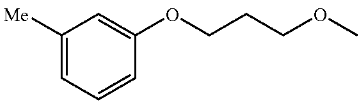 |

TABLE 15-continued
(I-P)
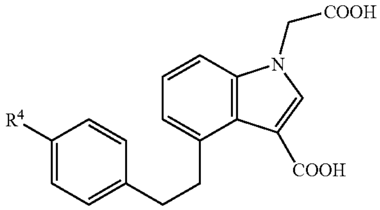
| | $R^4$— |
|---|---|
| 29 | 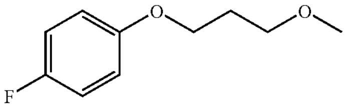 |
| 30 | 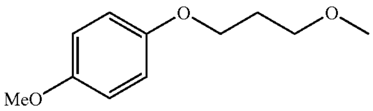 |
| 31 | 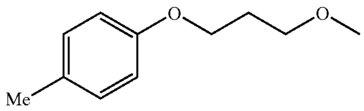 |
| 32 | 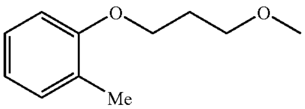 |
| 33 | 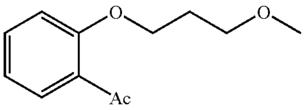 |
| 34 | 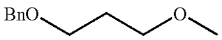 |
| 35 | 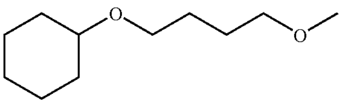 |
| 36 | 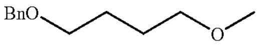 |
| 37 | 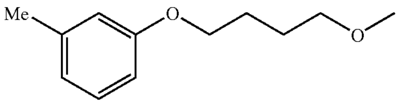 |
| 38 | 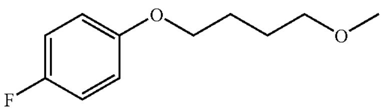 |
| 39 | 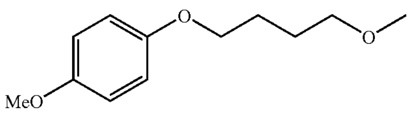 |
| 40 | 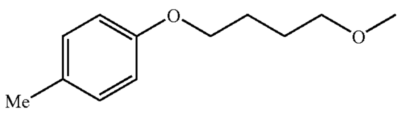 |
TABLE 15-continued
(I-P)
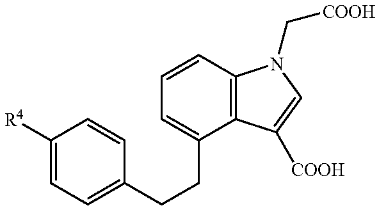
| | $R^4$— |
|---|---|
| 41 | 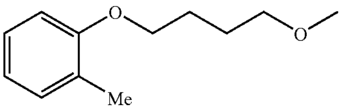 |
| 42 | 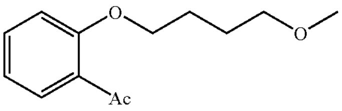 |
| 43 | 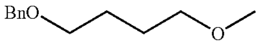 |
| 44 | 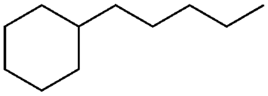 |
| 45 | 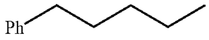 |
| 46 | 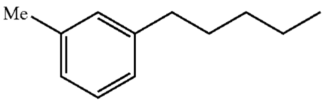 |
| 47 | 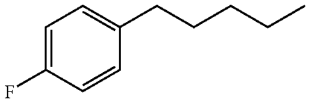 |
| 48 | 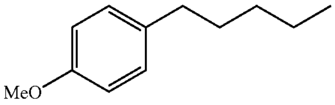 |
| 49 | 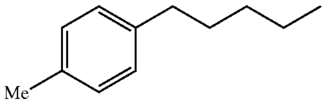 |
| 50 | 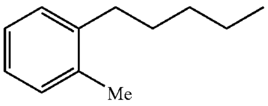 |
| 51 | 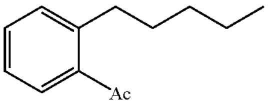 |
| 52 | 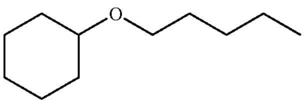 |

TABLE 15-continued
(I-P)
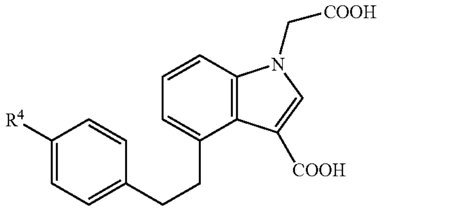
| | $R^4$— |
|---|---|
| 53 | 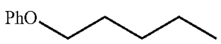 |
| 54 | 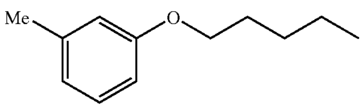 |
| 55 | 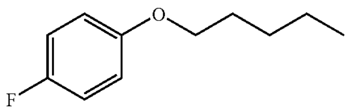 |
| 56 | 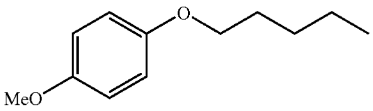 |
| 57 | 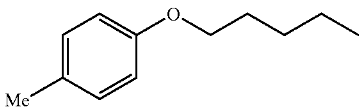 |
| 58 | 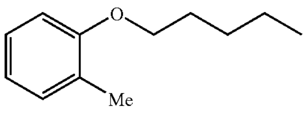 |
| 59 | 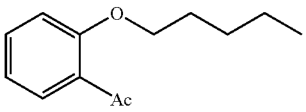 |
| 60 | 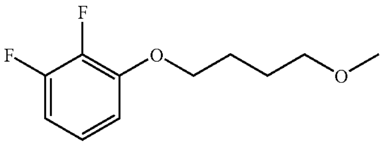 |
| 61 | 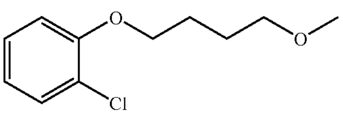 |
| 62 | 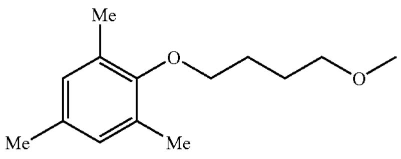 |
TABLE 15-continued
(I-P)
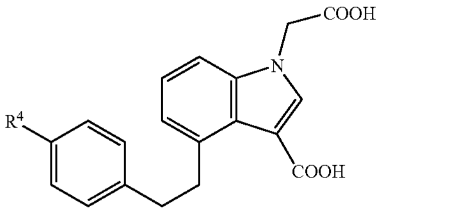
| | $R^4$— |
|---|---|
| 63 | 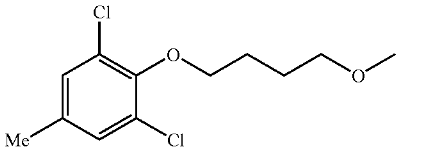 |
| 64 | 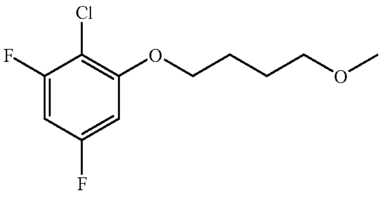 |
| 65 | 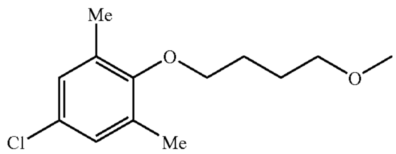 |
| 66 | 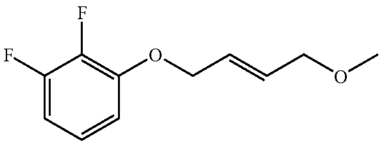 |
| 67 | 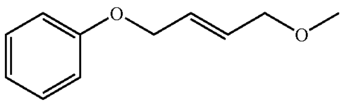 |
| 68 | 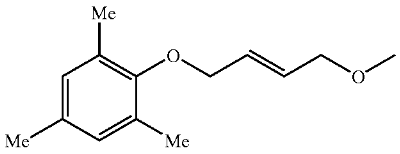 |
| 69 | 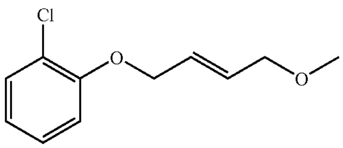 |

TABLE 16
(I-Q)
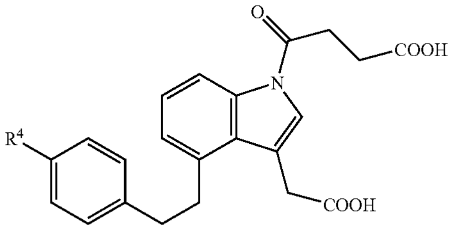
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 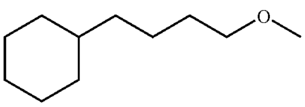 |
| 8 | 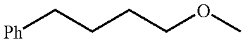 |
| 9 | 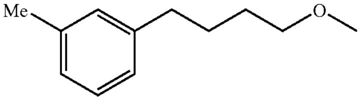 |
| 10 | 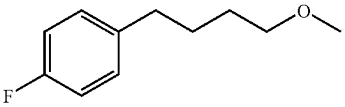 |
| 11 | 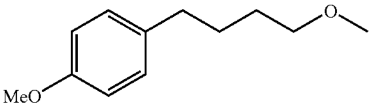 |
| 12 | 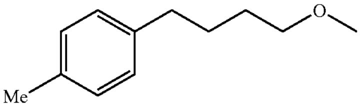 |
| 13 | 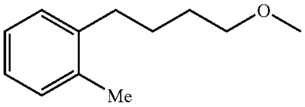 |
| 14 | 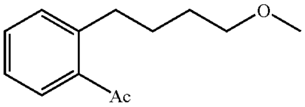 |
| 15 | 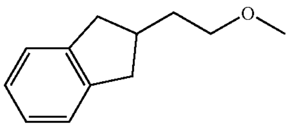 |
| 16 | 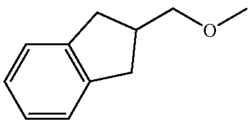 |
TABLE 16-continued
(I-Q)
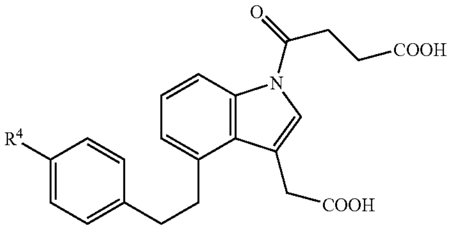
| | $R^4$— |
|---|---|
| 17 | 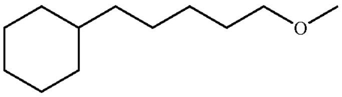 |
| 18 | 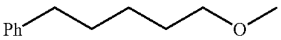 |
| 19 | 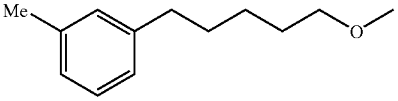 |
| 20 | 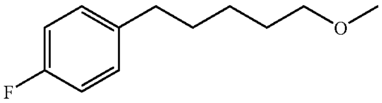 |
| 21 | 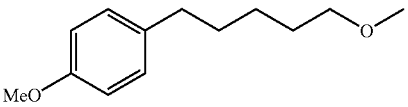 |
| 22 | 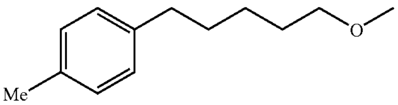 |
| 23 | 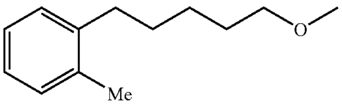 |
| 24 | 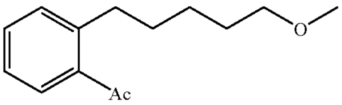 |
| 25 | 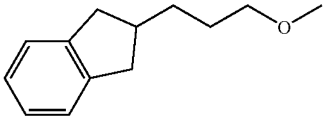 |
| 26 | 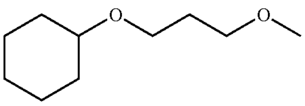 |
| 27 | 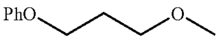 |
| 28 | 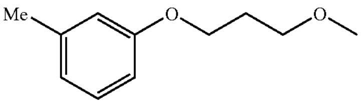 |

TABLE 16-continued
(I-Q)
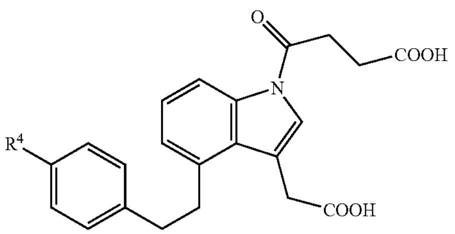
| | $R^4$— |
|---|---|
| 29 | 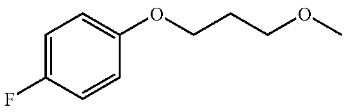 |
| 30 | 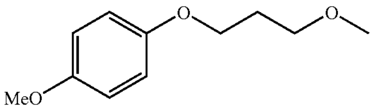 |
| 31 | 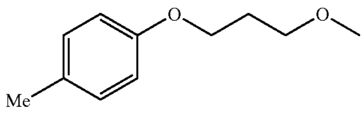 |
| 32 | 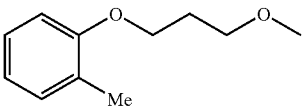 |
| 33 | 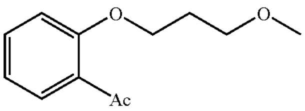 |
| 34 | 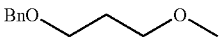 |
| 35 | 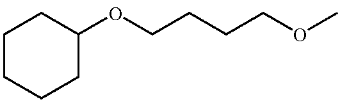 |
| 36 | 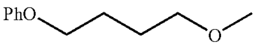 |
| 37 | 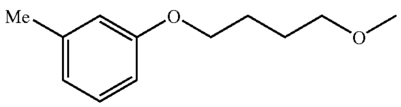 |
| 38 | 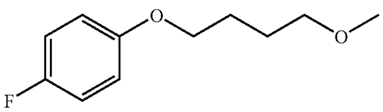 |
| 39 | 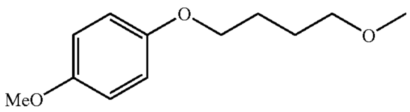 |
TABLE 16-continued
(I-Q)
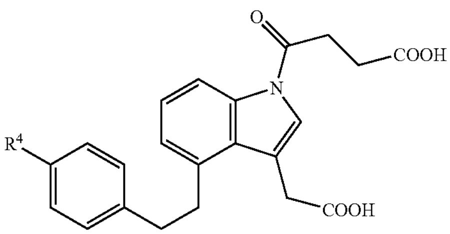
| | $R^4$— |
|---|---|
| 40 | 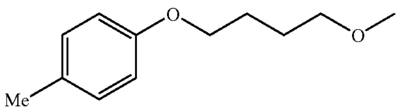 |
| 41 | 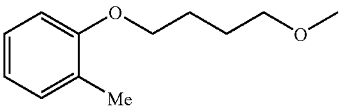 |
| 42 | 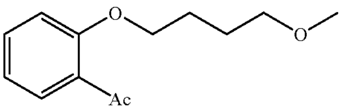 |
| 43 | 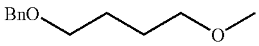 |
| 44 | 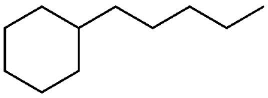 |
| 45 | 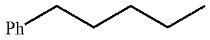 |
| 46 | 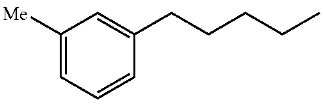 |
| 47 | 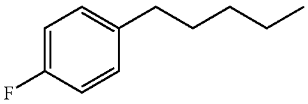 |
| 48 | 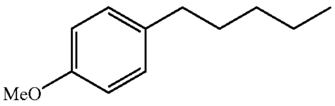 |
| 49 | 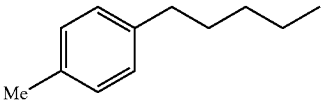 |
| 50 | 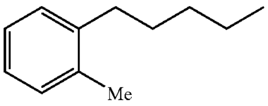 |
| 51 | 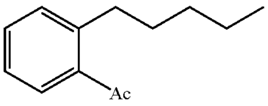 |

TABLE 16-continued
| | (I-Q) |
|---|---|
| | 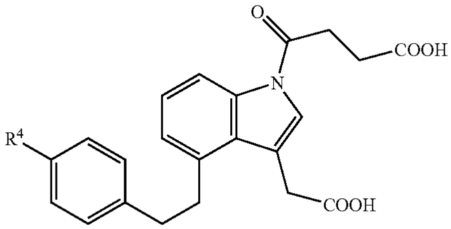 |
| | $R^4$— |
| 52 | 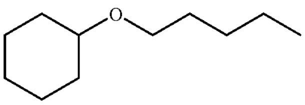 |
| 53 | 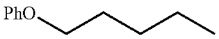 |
| 54 | 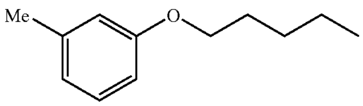 |
| 55 | 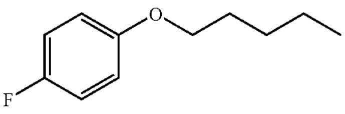 |
| 56 | 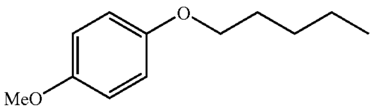 |
| 57 | 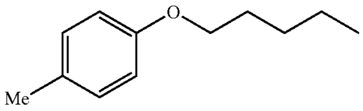 |
| 58 | 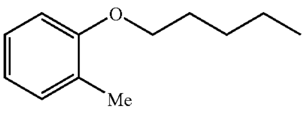 |
| 59 | 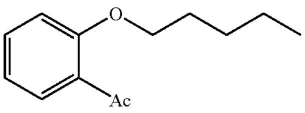 |
| 60 | 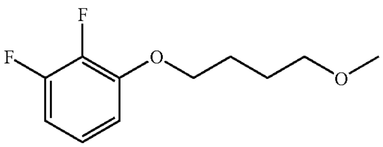 |
| 61 | 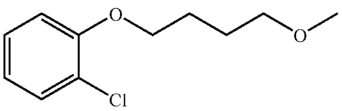 |
TABLE 16-continued
| | (I-Q) |
|---|---|
| | 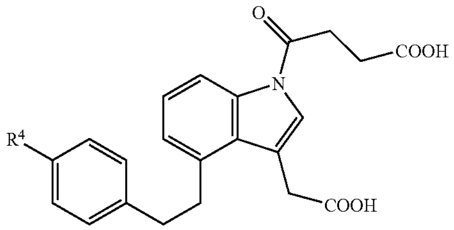 |
| | $R^4$— |
| 62 | 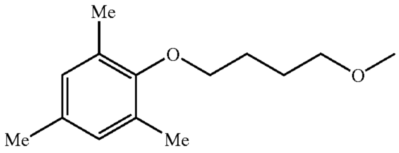 |
| 63 | 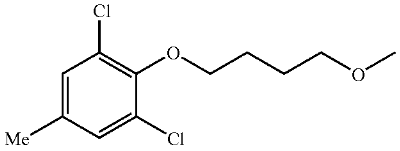 |
| 64 | 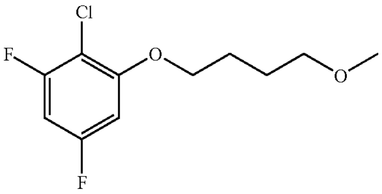 |
| 65 | 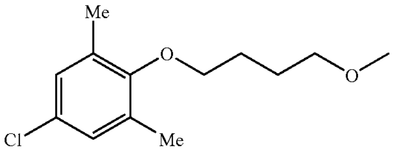 |
| 66 | 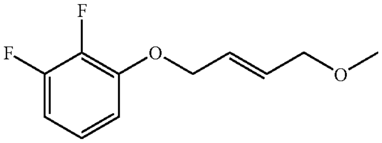 |
| 67 | 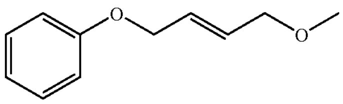 |
| 68 | 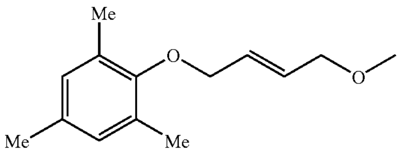 |
| 69 | 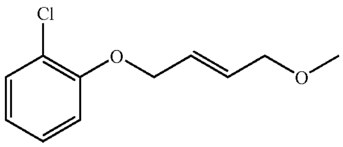 |

TABLE 17
(I-R)
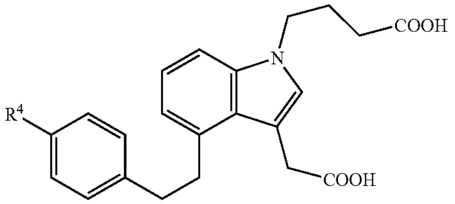
| | $R^4$— |
|---|---|
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |
| 7 | 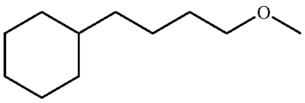 |
| 8 | 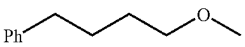 |
| 9 | 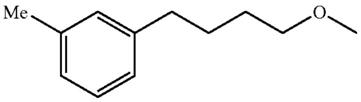 |
| 10 | 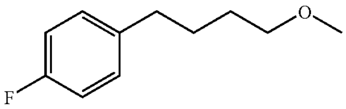 |
| 11 | 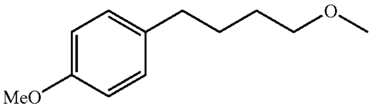 |
| 12 | 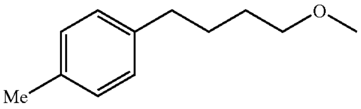 |
| 13 | 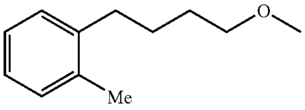 |
| 14 | 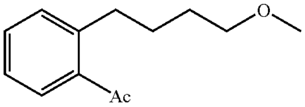 |
| 15 | 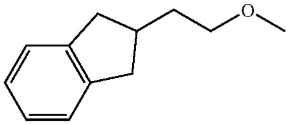 |
| 16 | 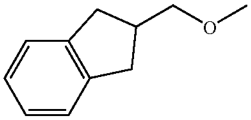 |
| 17 | 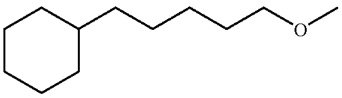 |
| 18 | 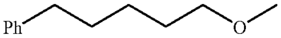 |
| 19 | 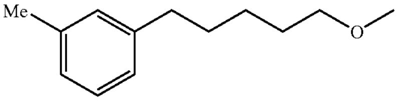 |
| 20 | 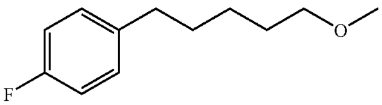 |
| 21 | 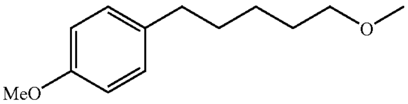 |
| 22 | 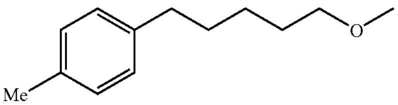 |
| 23 | 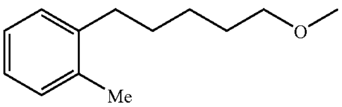 |
| 24 | 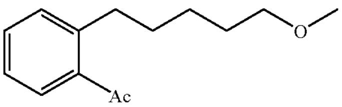 |
| 25 | 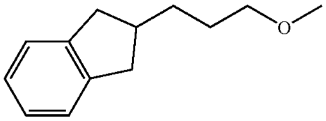 |
| 26 | 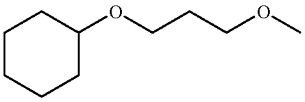 |
| 27 | 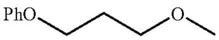 |
| 28 | 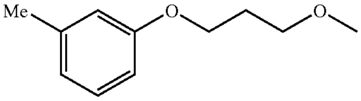 |
TABLE 17-continued
(I-R)
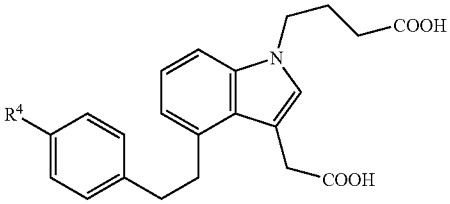

TABLE 17-continued
(I-R)
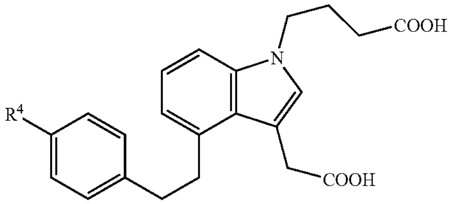
| | R$^4$— |
|---|---|
| 29 | 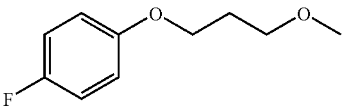 |
| 30 | 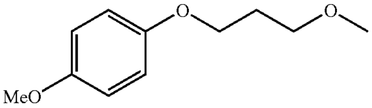 |
| 31 | 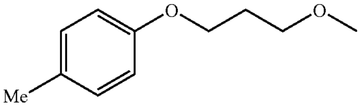 |
| 32 | 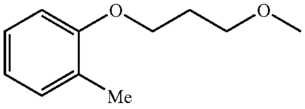 |
| 33 | 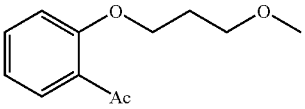 |
| 34 | 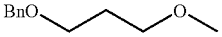 |
| 35 | 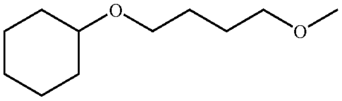 |
| 36 | 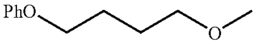 |
| 37 | 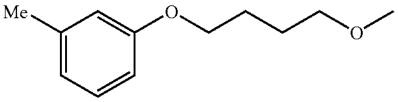 |
| 38 | 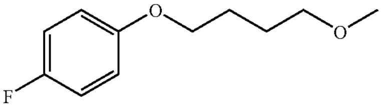 |
| 39 | 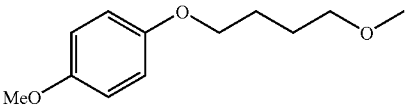 |
| 40 | 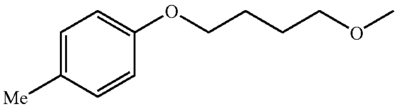 |
TABLE 17-continued
(I-R)
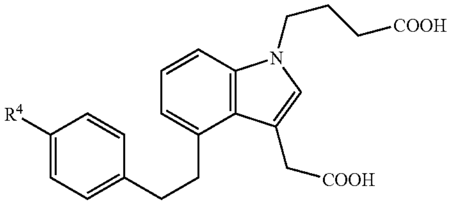
| | R$^4$— |
|---|---|
| 41 | 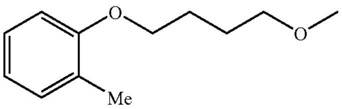 |
| 42 | 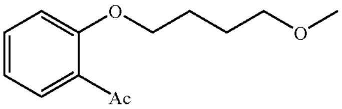 |
| 43 | 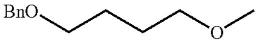 |
| 44 | 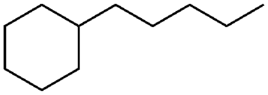 |
| 45 | 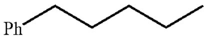 |
| 46 | 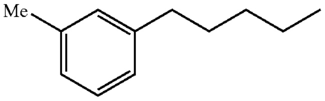 |
| 47 | 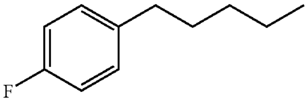 |
| 48 | 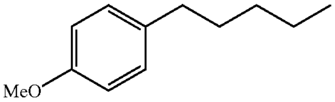 |
| 49 | 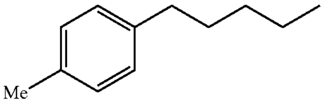 |
| 50 | 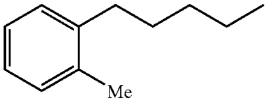 |
| 51 | 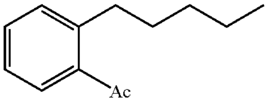 |
| 52 | 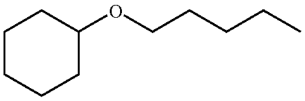 |
| 53 | 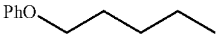 |

TABLE 17-continued
(I-R)
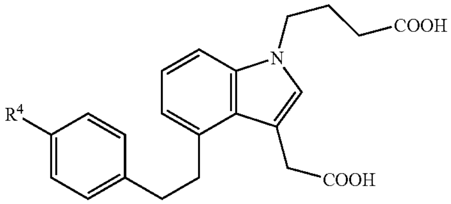
| | R$^4$— |
|---|---|
| 54 | 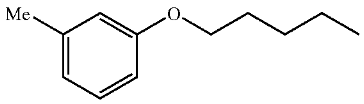 |
| 55 | 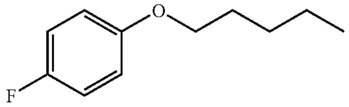 |
| 56 | 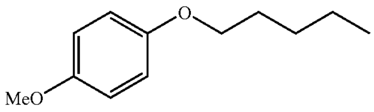 |
| 57 | 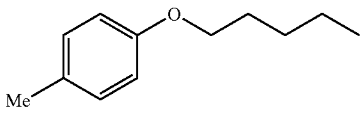 |
| 58 | 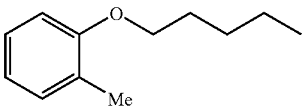 |
| 59 | 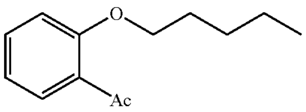 |
| 60 | 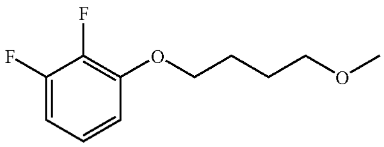 |
| 61 | 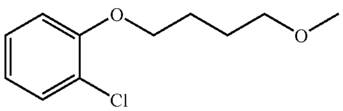 |
| 62 | 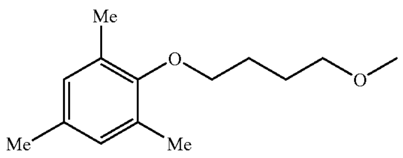 |
| 63 | 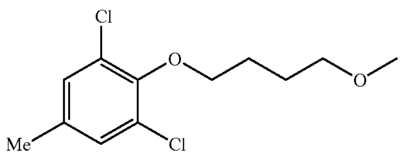 |
TABLE 17-continued
(I-R)
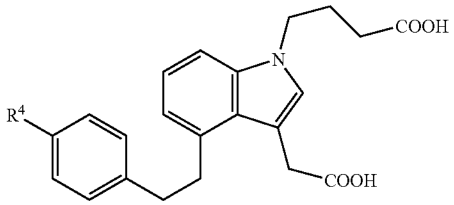
| | R$^4$— |
|---|---|
| 64 | 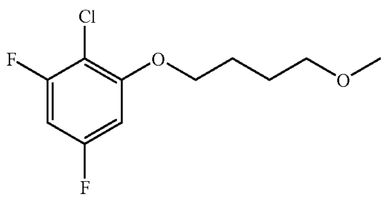 |
| 65 | 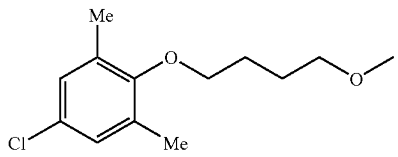 |
| 66 | 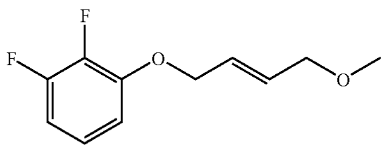 |
| 67 | 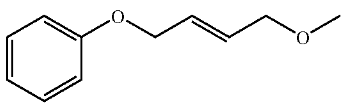 |
| 68 | 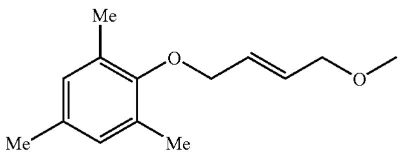 |
| 69 | 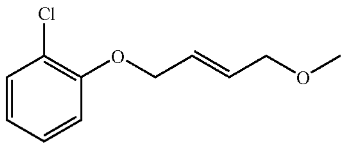 |

TABLE 18
(I-S)
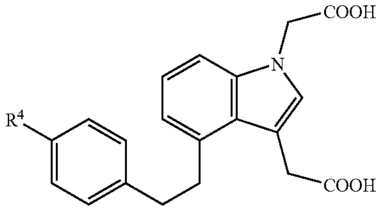
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 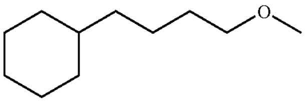 |
| 8 | 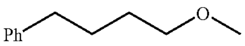 |
| 9 | 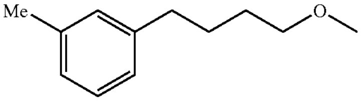 |
| 10 | 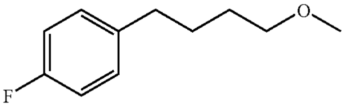 |
| 11 | 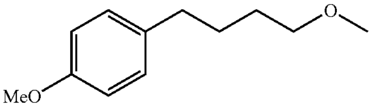 |
| 12 | 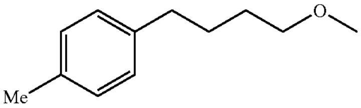 |
| 13 | 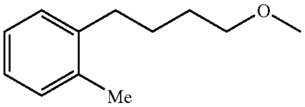 |
| 14 | 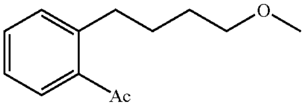 |
| 15 | 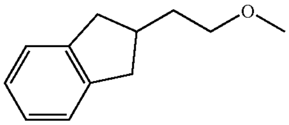 |
| 16 | 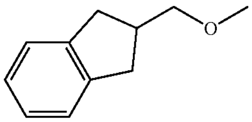 |
TABLE 18-continued
(I-S)
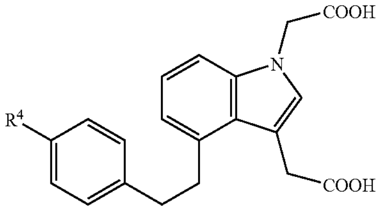
| | $R^4$— |
|---|---|
| 17 | 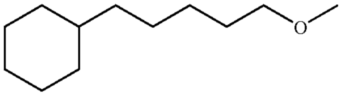 |
| 18 | 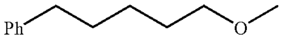 |
| 19 | 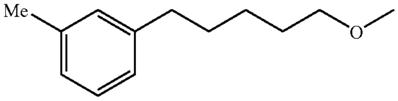 |
| 20 | 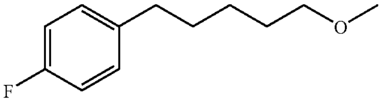 |
| 21 | 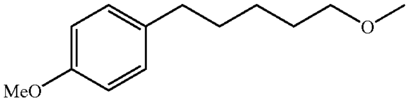 |
| 22 | 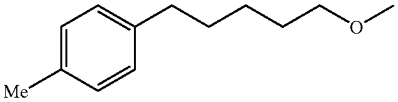 |
| 23 | 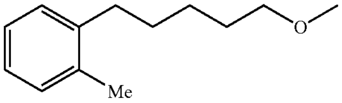 |
| 24 | 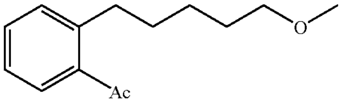 |
| 25 | 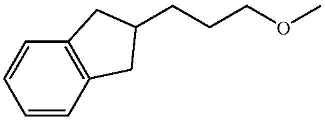 |
| 26 | 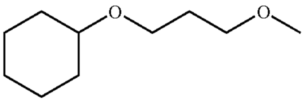 |
| 27 | 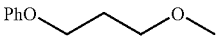 |
| 28 | 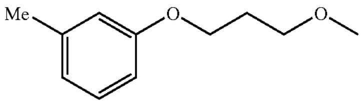 |

TABLE 18-continued
(I-S)
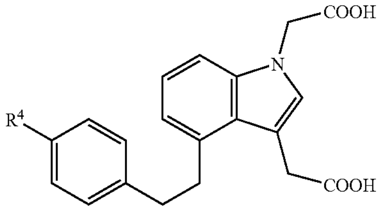
| | $R^4$— |
|---|---|
| 29 | 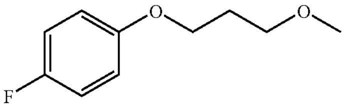 |
| 30 | 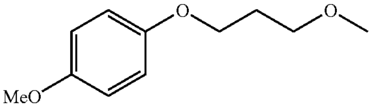 |
| 31 | 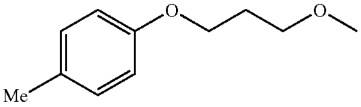 |
| 32 | 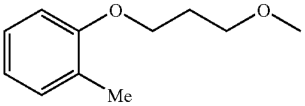 |
| 33 | 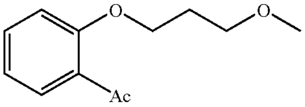 |
| 34 | 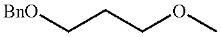 |
| 35 | 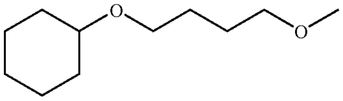 |
| 36 | 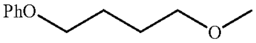 |
| 37 | 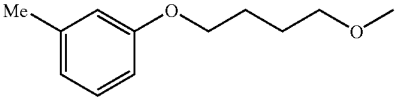 |
| 38 | 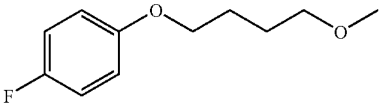 |
| 39 | 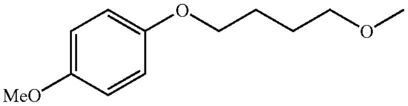 |
| 40 | 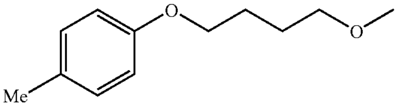 |
TABLE 18-continued
(I-S)
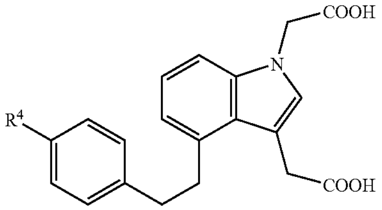
| | $R^4$— |
|---|---|
| 41 | 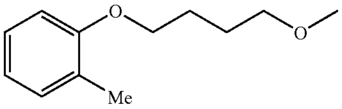 |
| 42 | 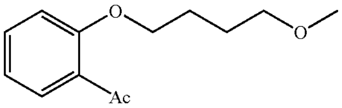 |
| 43 | 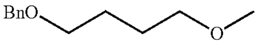 |
| 44 | 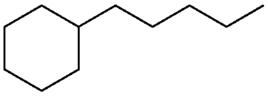 |
| 45 | 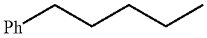 |
| 46 | 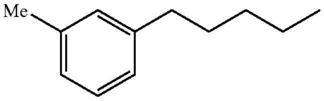 |
| 47 | 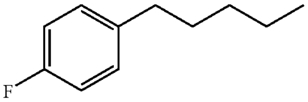 |
| 48 | 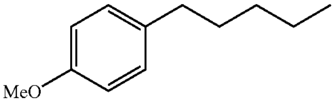 |
| 49 | 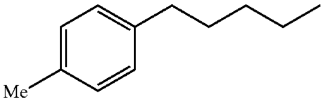 |
| 50 | 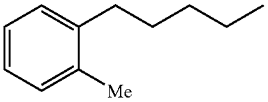 |
| 51 | 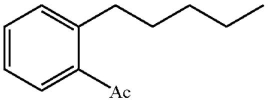 |
| 52 | 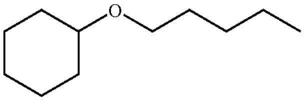 |

TABLE 18-continued
(I-S)
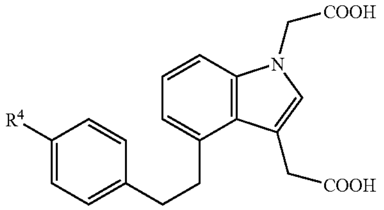
R⁴—
| | |
|---|---|
| 53 | 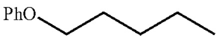 |
| 54 | 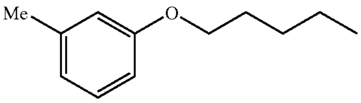 |
| 55 | 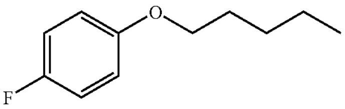 |
| 56 | 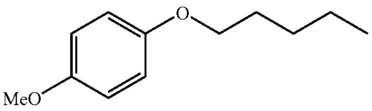 |
| 57 | 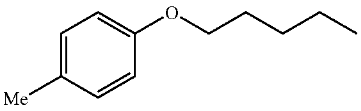 |
| 58 | 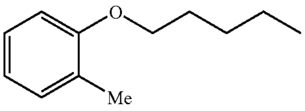 |
| 59 | 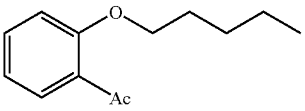 |
| 60 | 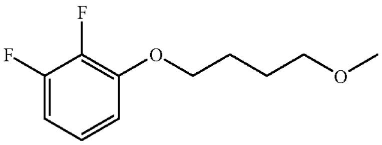 |
| 61 | 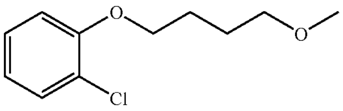 |
| 62 | 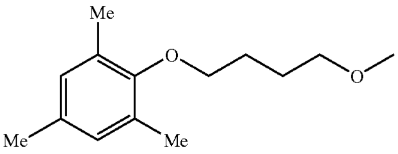 |
TABLE 18-continued
(I-S)
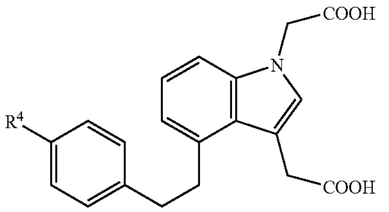
R⁴—
| | |
|---|---|
| 63 | 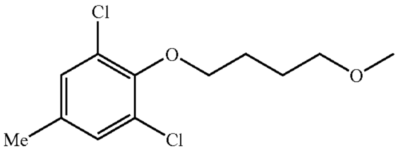 |
| 64 | 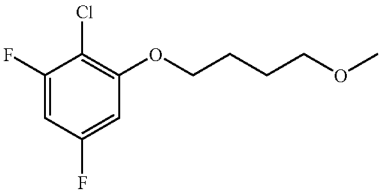 |
| 65 | 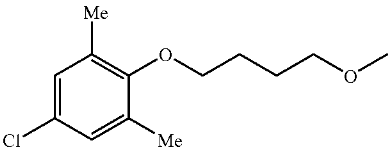 |
| 66 | 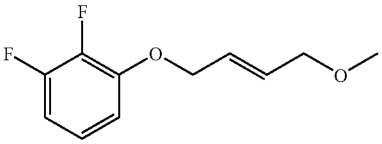 |
| 67 | 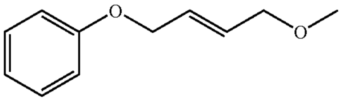 |
| 68 | 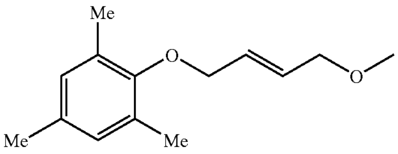 |
| 69 | 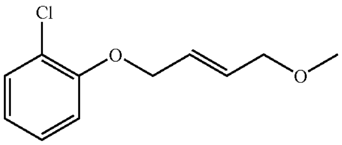 |

TABLE 19
(I-T)
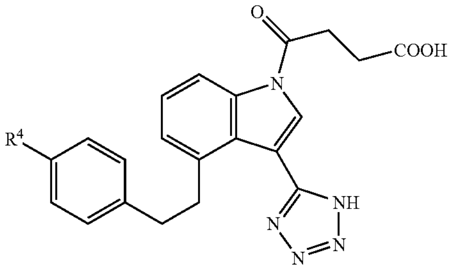
| | R$^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 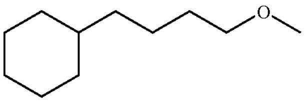 |
| 8 | 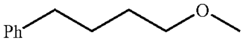 |
| 9 | 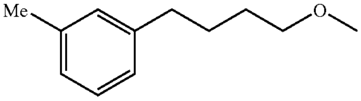 |
| 10 | 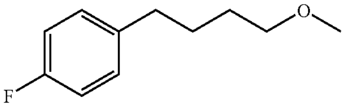 |
| 11 | 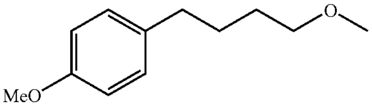 |
| 12 | 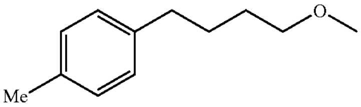 |
| 13 | 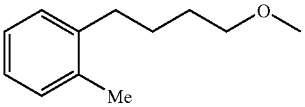 |
| 14 | 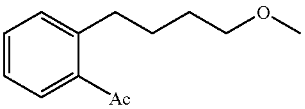 |
| 15 | 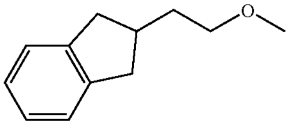 |
TABLE 19-continued
(I-T)
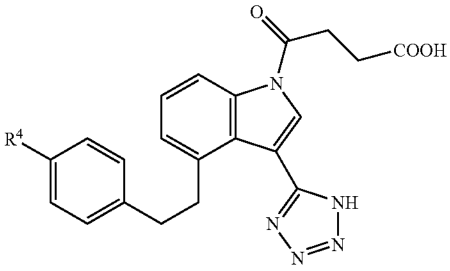
| | R$^4$— |
|---|---|
| 16 | 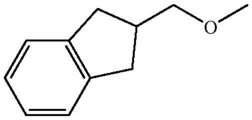 |
| 17 | 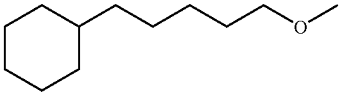 |
| 18 | 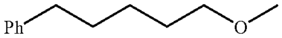 |
| 19 | 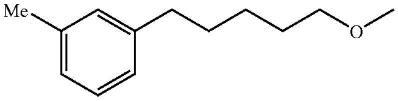 |
| 20 | 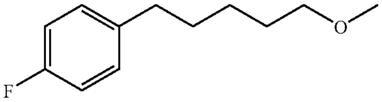 |
| 21 | 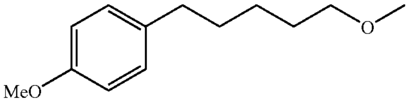 |
| 22 | 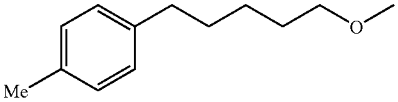 |
| 23 | 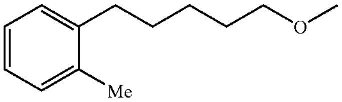 |
| 24 | 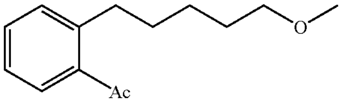 |
| 25 | 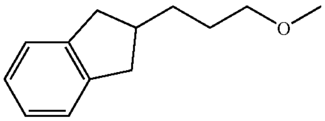 |
| 26 | 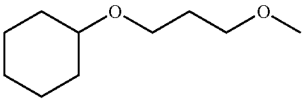 |

TABLE 19-continued
(I-T)
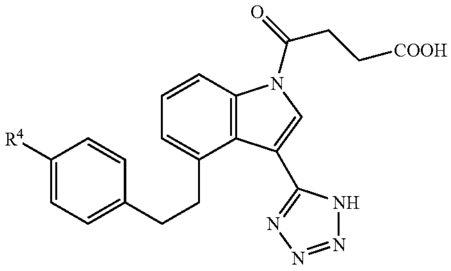
| | $R^4$— |
|---|---|
| 27 | 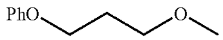 |
| 28 | 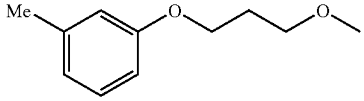 |
| 29 | 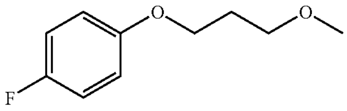 |
| 30 | 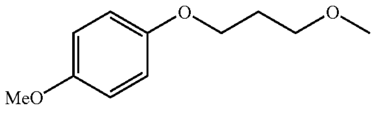 |
| 31 | 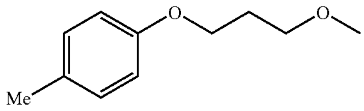 |
| 32 | 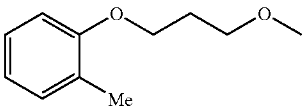 |
| 33 | 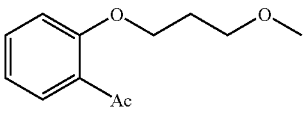 |
| 34 | 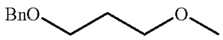 |
| 35 | 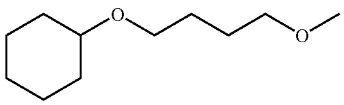 |
| 36 | 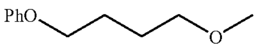 |
| 37 | 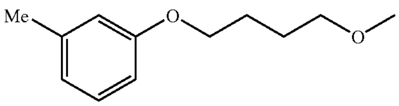 |
| 38 | 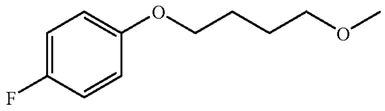 |
TABLE 19-continued
(I-T)
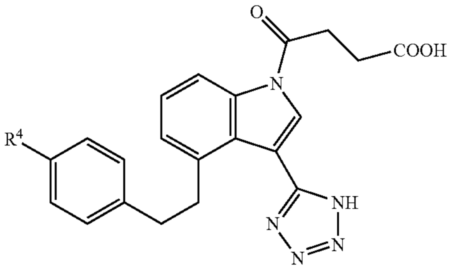
| | $R^4$— |
|---|---|
| 39 | 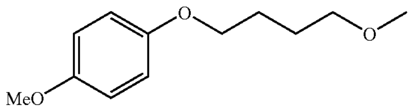 |
| 40 | 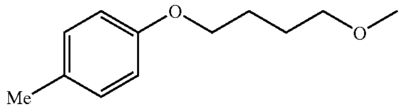 |
| 41 | 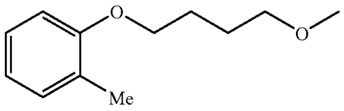 |
| 42 | 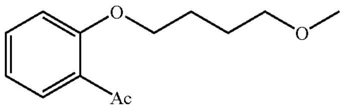 |
| 43 | 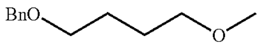 |
| 44 | 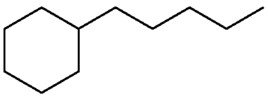 |
| 45 | 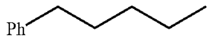 |
| 46 | 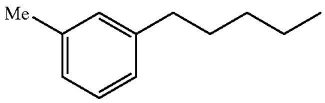 |
| 47 | 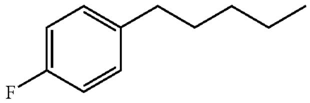 |
| 48 | 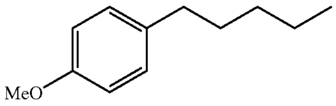 |
| 49 | 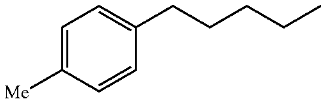 |

TABLE 19-continued
(I-T)
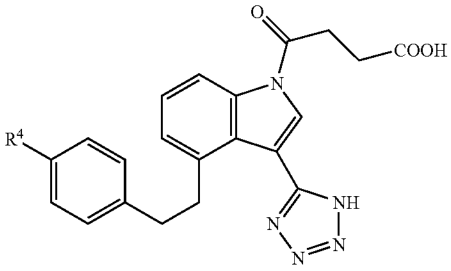
| | $R^4$— |
|---|---|
| 50 | 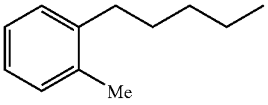 |
| 51 | 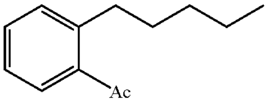 |
| 52 | 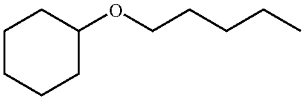 |
| 53 | 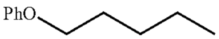 |
| 54 | 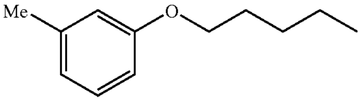 |
| 55 | 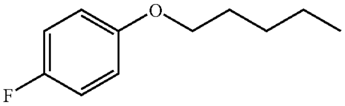 |
| 56 | 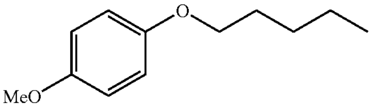 |
| 57 | 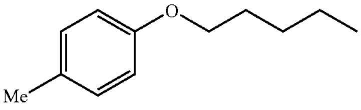 |
| 58 | 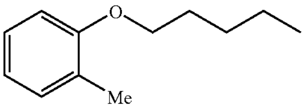 |
| 59 | 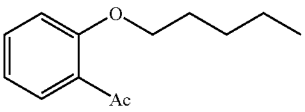 |
TABLE 19-continued
(I-T)
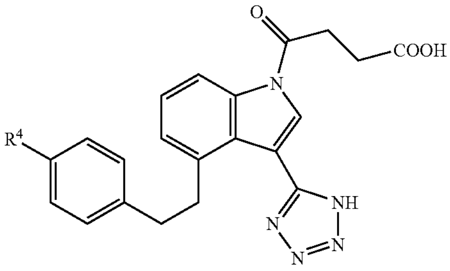
| | $R^4$— |
|---|---|
| 60 | 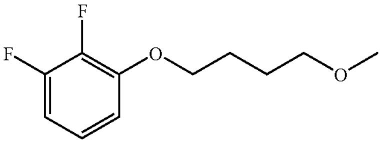 |
| 61 | 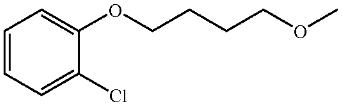 |
| 62 | 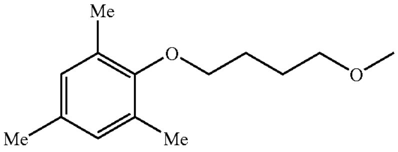 |
| 63 | 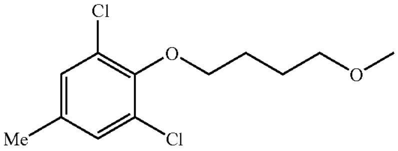 |
| 64 | 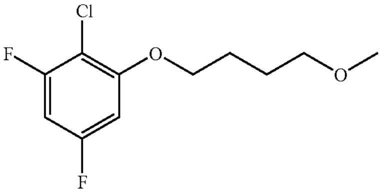 |
| 65 | 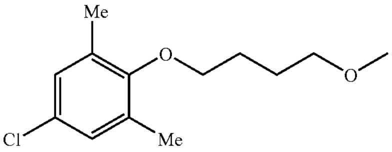 |
| 66 | 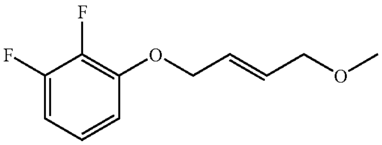 |
| 67 | 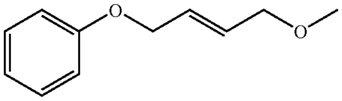 |

TABLE 19-continued
(I-T)
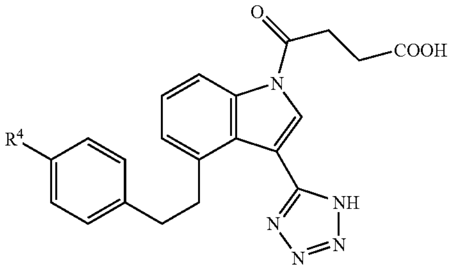
| | R4— |
|---|---|
| 68 | 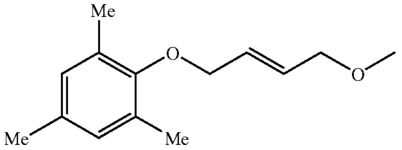 |
| 69 | 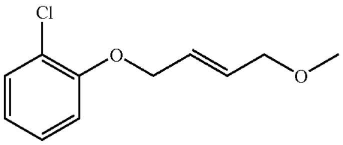 |
TABLE 20
(I-U)
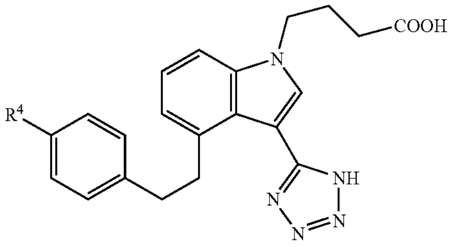
| | R4— |
|---|---|
| 1 | $n\text{-}C_4H_9$— |
| 2 | $n\text{-}C_5H_{11}$— |
| 3 | $n\text{-}C_6H_{13}$— |
| 4 | $n\text{-}C_4H_9$—O— |
| 5 | $n\text{-}C_5H_{11}$—O— |
| 6 | $n\text{-}C_6H_{13}$—O— |
| 7 | 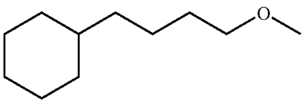 |
| 8 | 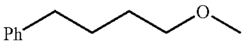 |
| 9 | 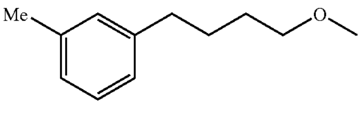 |
| 10 | 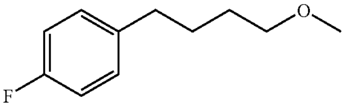 |
TABLE 20-continued
(I-U)
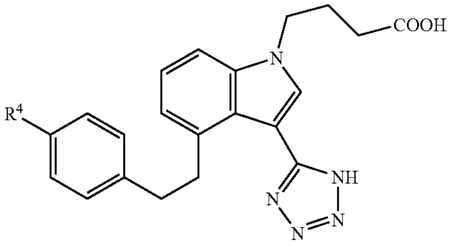
| | R4— |
|---|---|
| 11 | 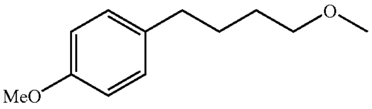 |
| 12 | 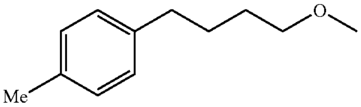 |
| 13 | 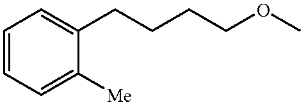 |
| 14 | 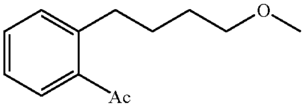 |
| 15 | 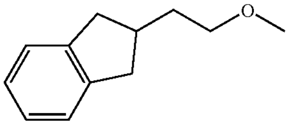 |
| 16 | 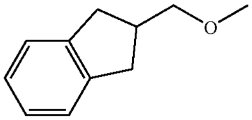 |
| 17 | 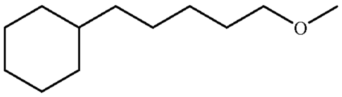 |
| 18 | 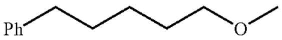 |
| 19 | 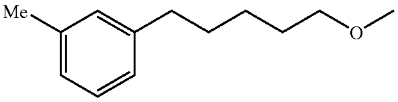 |
| 20 | 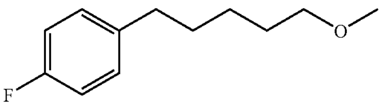 |
| 21 | 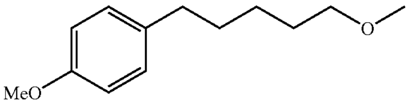 |

TABLE 20-continued
(I-U)
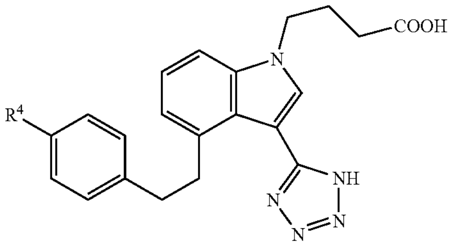
| | $R^4$— |
|---|---|
| 22 | 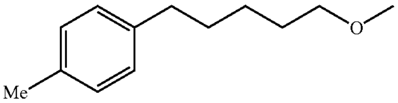 |
| 23 | 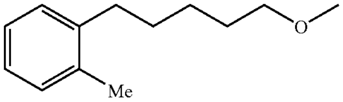 |
| 24 | 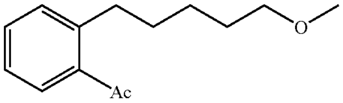 |
| 25 | 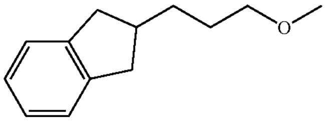 |
| 26 | 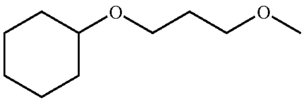 |
| 27 | 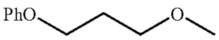 |
| 28 | 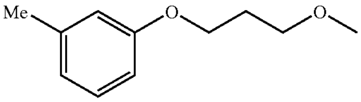 |
| 29 | 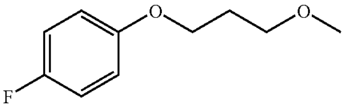 |
| 30 | 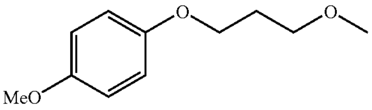 |
| 31 | 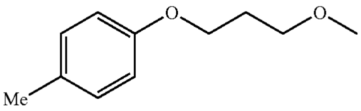 |
| 32 | 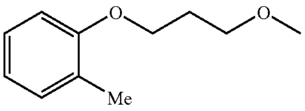 |
TABLE 20-continued
(I-U)
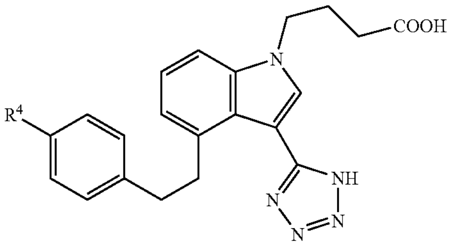
| | $R^4$— |
|---|---|
| 33 | 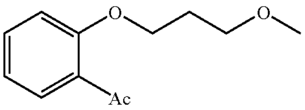 |
| 34 | 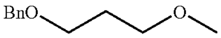 |
| 35 | 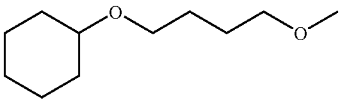 |
| 36 | 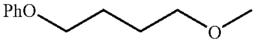 |
| 37 | 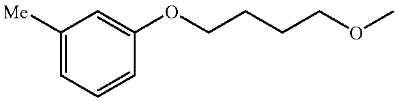 |
| 38 | 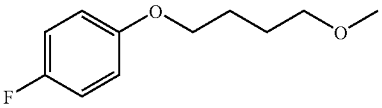 |
| 39 | 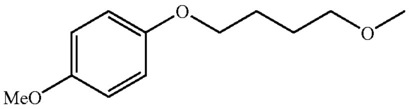 |
| 40 | 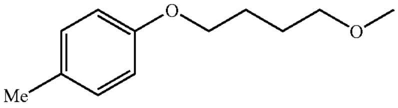 |
| 41 | 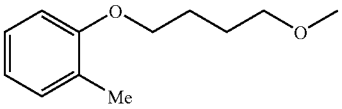 |
| 42 | 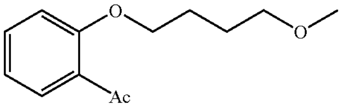 |
| 43 | 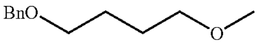 |
| 44 | 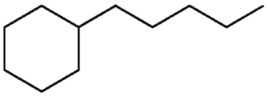 |

TABLE 20-continued
(I-U)
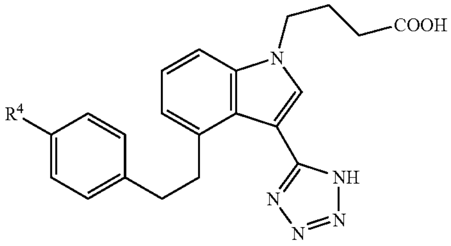
| | R⁴— |
|---|---|
| 45 | 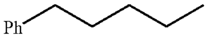 |
| 46 | 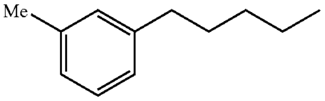 |
| 47 | 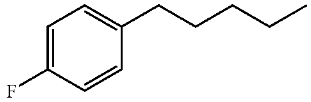 |
| 48 | 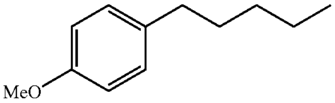 |
| 49 | 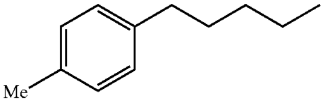 |
| 50 | 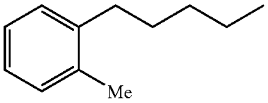 |
| 51 | 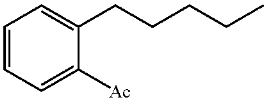 |
| 52 | 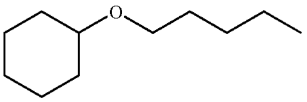 |
| 53 | 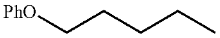 |
| 54 | 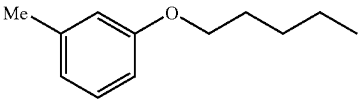 |
| 55 | 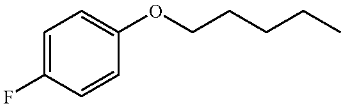 |
| 56 | 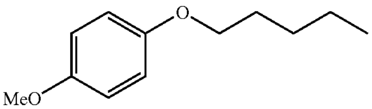 |
TABLE 20-continued
(I-U)
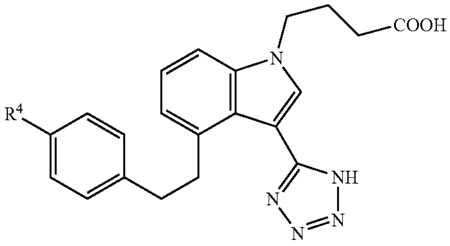
| | R⁴— |
|---|---|
| 57 | 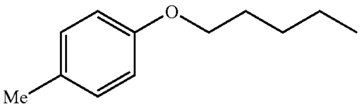 |
| 58 | 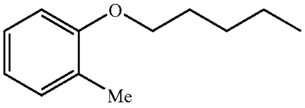 |
| 59 | 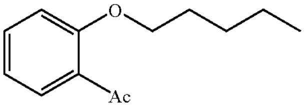 |
| 60 | 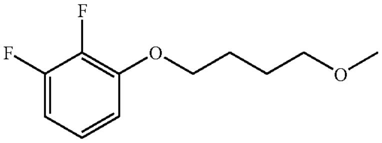 |
| 61 | 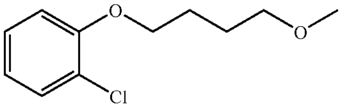 |
| 62 | 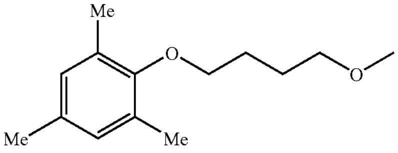 |
| 63 | 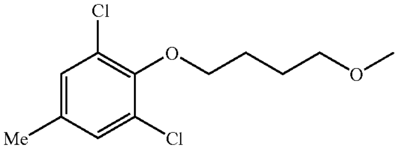 |
| 64 | 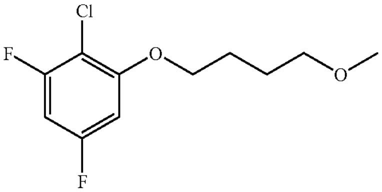

TABLE 20-continued
(I-U)
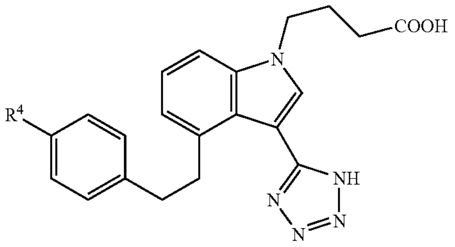
| | $R^4$— |
|---|---|
| 65 | 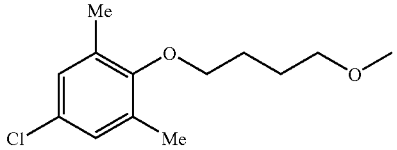 |
| 66 | 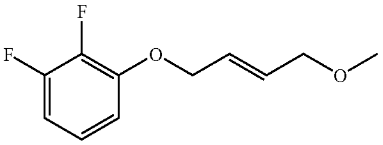 |
| 67 | 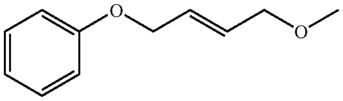 |
| 68 | 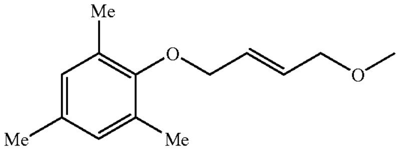 |
| 69 | 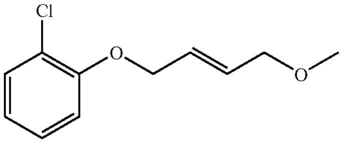 |
TABLE 21
(I-V)
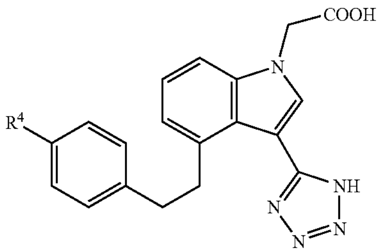
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
TABLE 21-continued
(I-V)
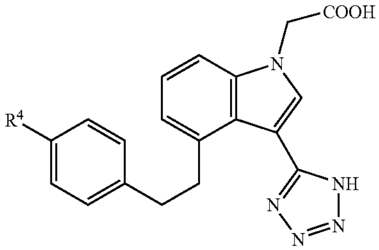
| | $R^4$— |
|---|---|
| 7 | 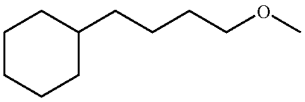 |
| 8 | 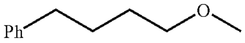 |
| 9 | 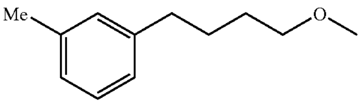 |
| 10 | 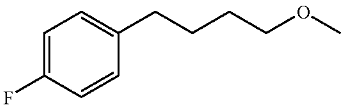 |
| 11 | 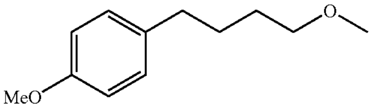 |
| 12 | 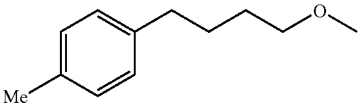 |
| 13 | 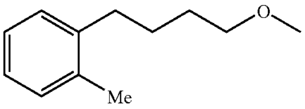 |
| 14 | 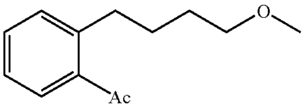 |
| 15 | 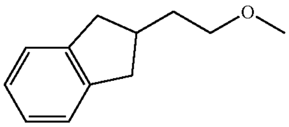 |
| 16 | 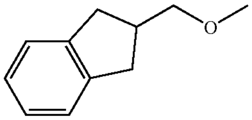 |

TABLE 21-continued
(I-V)
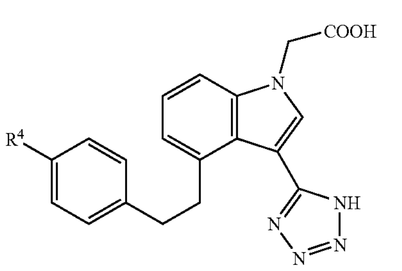
| | R⁴— |
|---|---|
| 17 | 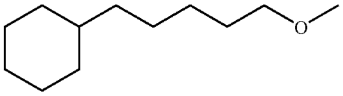 |
| 18 | 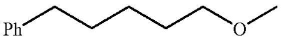 |
| 19 | 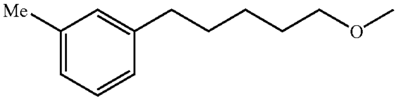 |
| 20 | 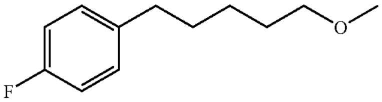 |
| 21 | 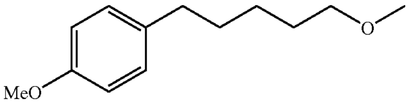 |
| 22 | 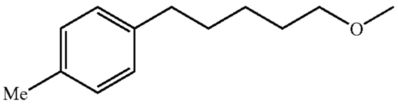 |
| 23 | 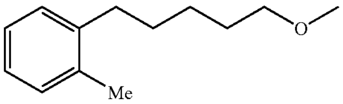 |
| 24 | 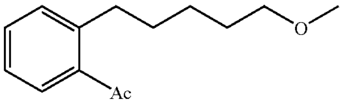 |
| 25 | 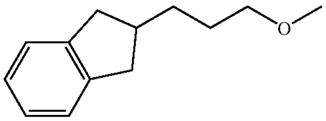 |
| 26 | 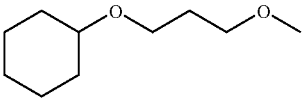 |
| 27 | 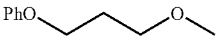 |
| 28 | 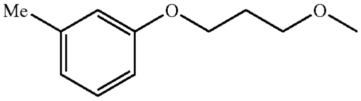 |
TABLE 21-continued
(I-V)
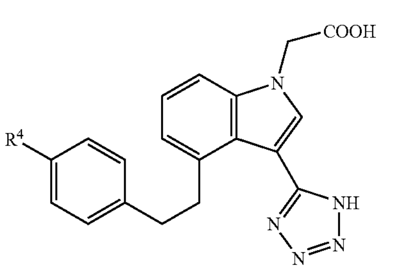
| | R⁴— |
|---|---|
| 29 | 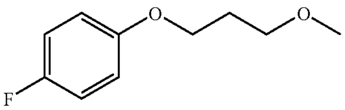 |
| 30 | 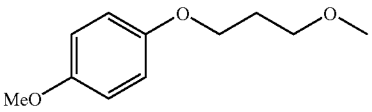 |
| 31 | 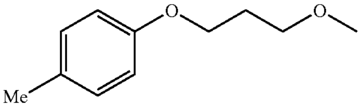 |
| 32 | 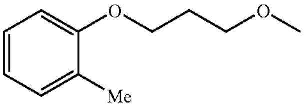 |
| 33 | 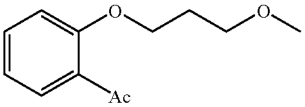 |
| 34 | 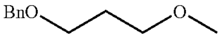 |
| 35 | 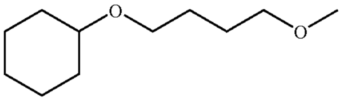 |
| 36 | 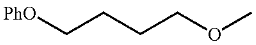 |
| 37 | 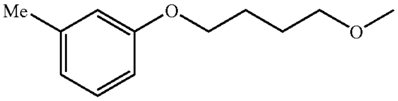 |
| 38 | 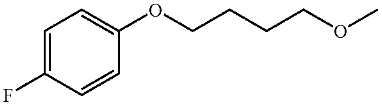 |
| 39 | 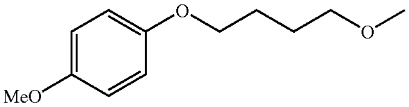 |

TABLE 21-continued
(I-V)
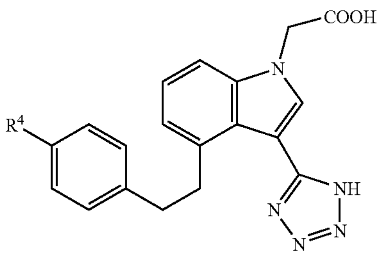
(I-V)
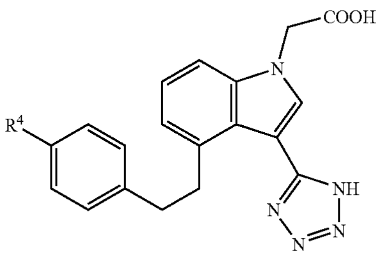
| | $R^4$— |
| --- | --- |
| 40 | 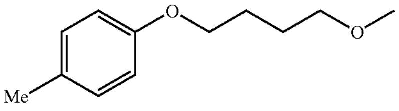 |
| 41 | 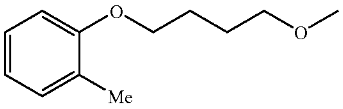 |
| 42 | 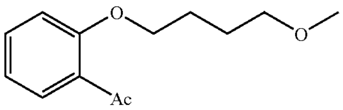 |
| 43 | 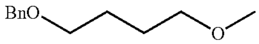 |
| 44 | 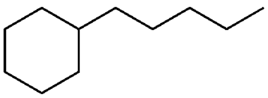 |
| 45 | 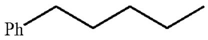 |
| 46 | 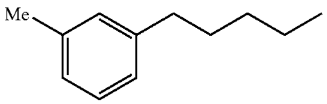 |
| 47 | 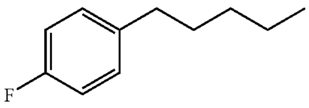 |
| 48 | 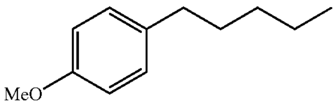 |
| 49 | 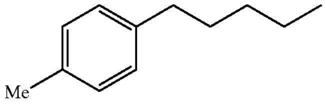 |
| 50 | 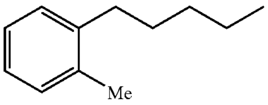 |
| 51 | 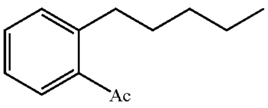 |
| 52 | 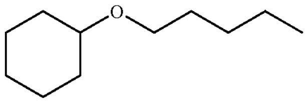 |
| 53 | 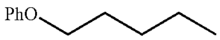 |
| 54 | 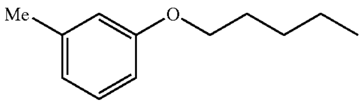 |
| 55 | 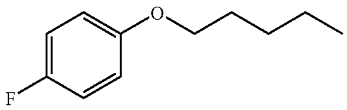 |
| 56 | 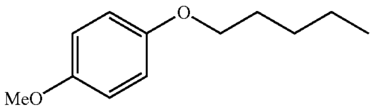 |
| 57 | 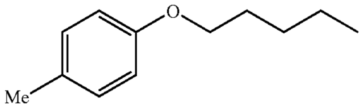 |
| 58 | 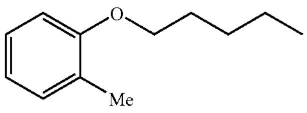 |
| 59 | 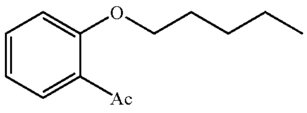 |
| 60 | 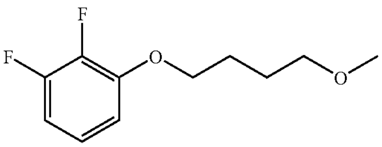 |
| 61 | 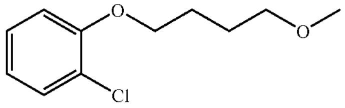 |

TABLE 21-continued
(I-V)
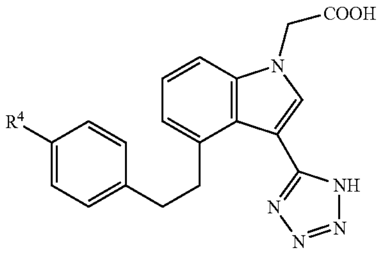
| | $R^4$— |
|---|---|
| 62 | 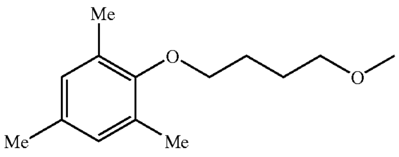 |
| 63 | 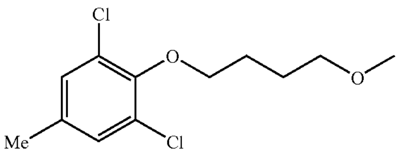 |
| 64 | 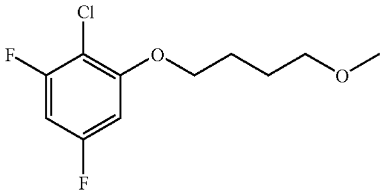 |
| 65 | 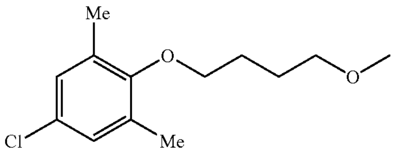 |
| 66 | 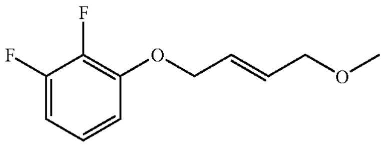 |
| 67 | 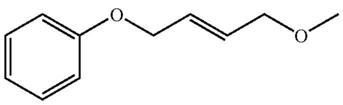 |
| 68 | 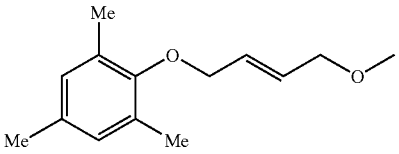 |
TABLE 21-continued
(I-V)
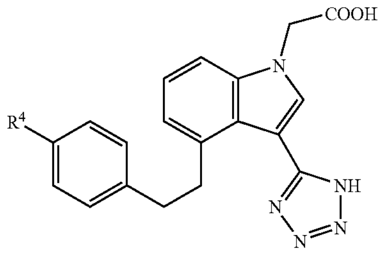
| | $R^4$— |
|---|---|
| 69 | 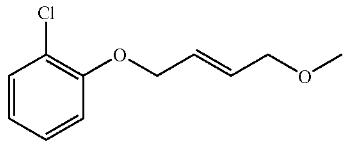 |
TABLE 22
(I-W)
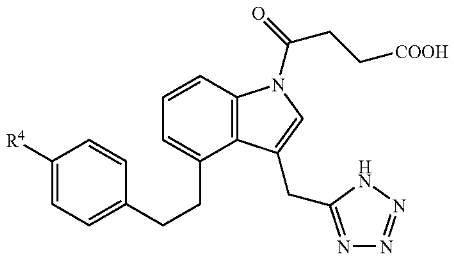
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 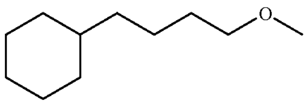 |
| 8 | 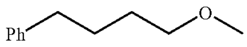 |
| 9 | 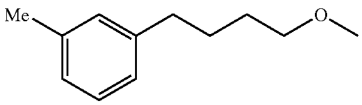 |
| 10 | 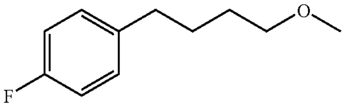 |

TABLE 22-continued
(I-W)
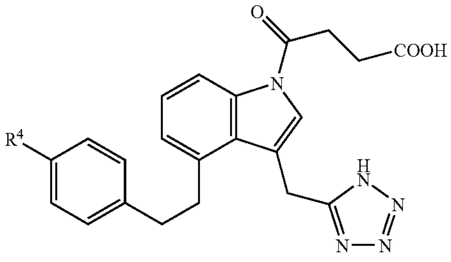
| | $R^4$— |
|---|---|
| 11 | 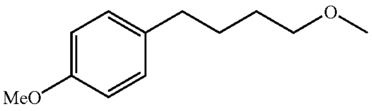 |
| 12 | 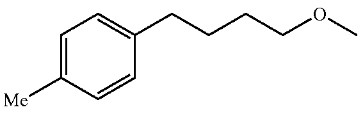 |
| 13 | 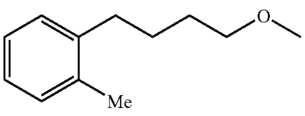 |
| 14 | 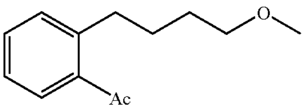 |
| 15 | 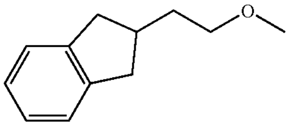 |
| 16 | 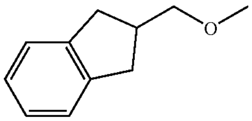 |
| 17 | 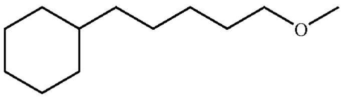 |
| 18 | 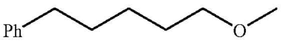 |
| 19 | 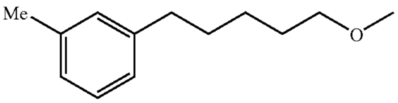 |
| 20 | 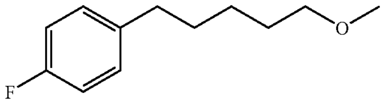 |
TABLE 22-continued
(I-W)
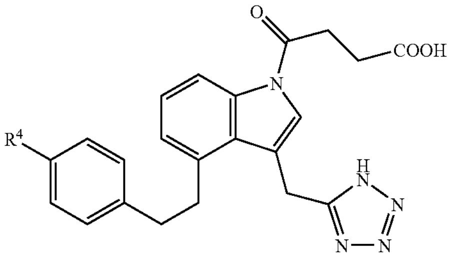
| | $R^4$— |
|---|---|
| 21 | 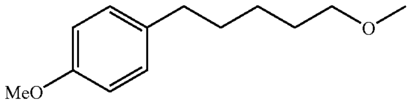 |
| 22 | 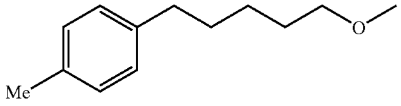 |
| 23 | 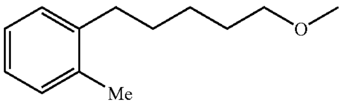 |
| 24 | 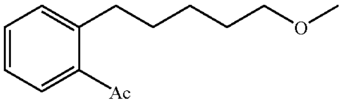 |
| 25 | 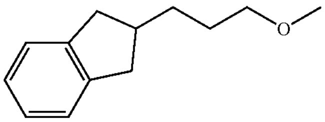 |
| 26 | 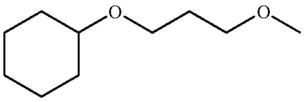 |
| 27 | 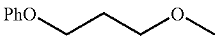 |
| 28 | 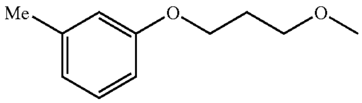 |
| 29 | 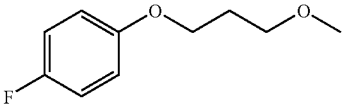 |
| 30 | 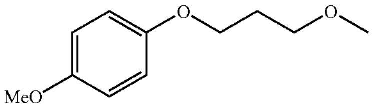 |
| 31 | 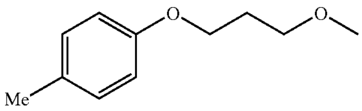 |

TABLE 22-continued
(I-W)
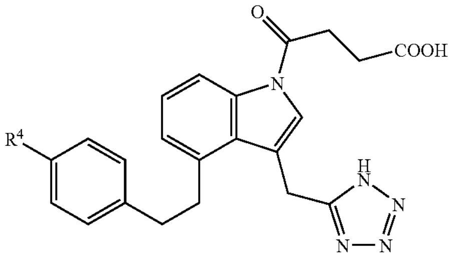
| | $R^4$— |
|---|---|
| 32 | 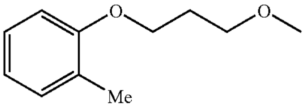 |
| 33 | 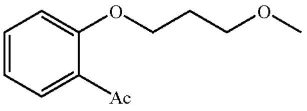 |
| 34 | 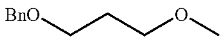 |
| 35 | 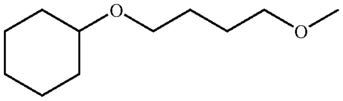 |
| 36 | 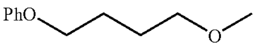 |
| 37 | 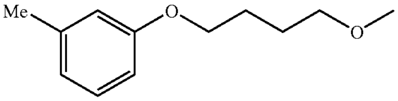 |
| 38 | 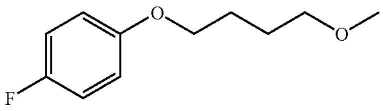 |
| 39 | 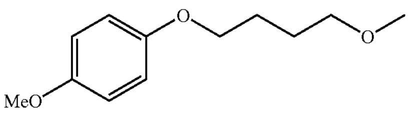 |
| 40 | 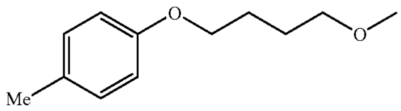 |
| 41 | 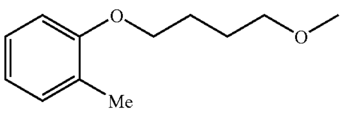 |
| 42 | 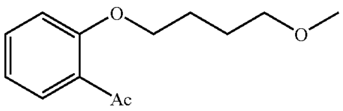 |
| 43 | 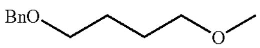 |
TABLE 22-continued
(I-W)
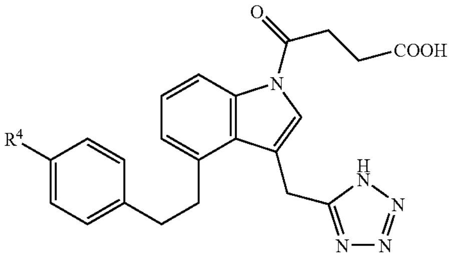
| | $R^4$— |
|---|---|
| 44 | 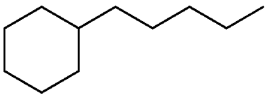 |
| 45 | 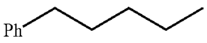 |
| 46 | 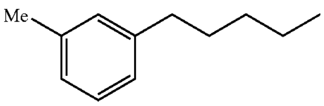 |
| 47 | 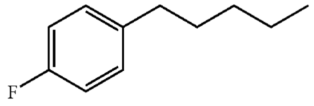 |
| 48 | 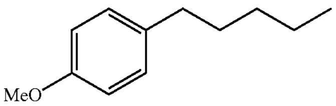 |
| 49 | 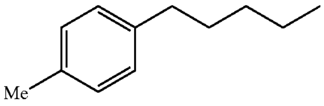 |
| 50 | 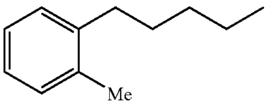 |
| 51 | 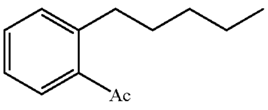 |
| 52 | 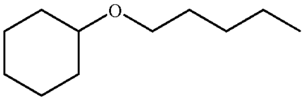 |
| 53 | 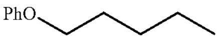 |
| 54 | 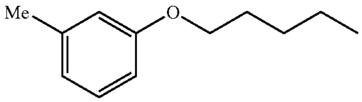 |

TABLE 22-continued
(I-W)
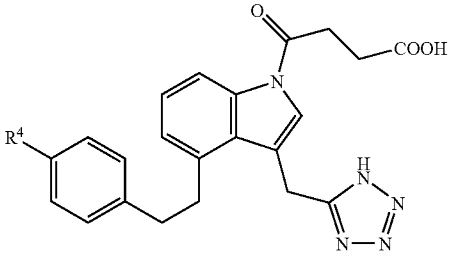
| | $R^4$— |
|---|---|
| 55 | 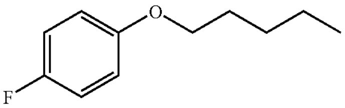 |
| 56 | 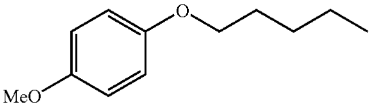 |
| 57 | 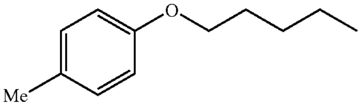 |
| 58 | 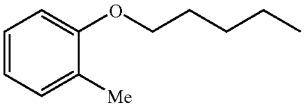 |
| 59 | 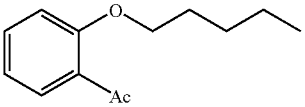 |
| 60 | 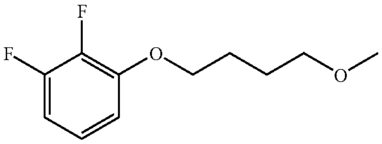 |
| 61 | 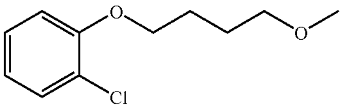 |
| 62 | 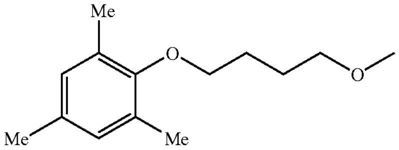 |
| 63 | 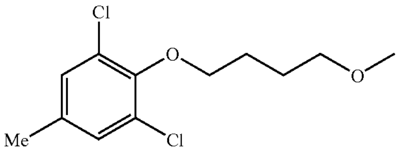 |
TABLE 22-continued
(I-W)
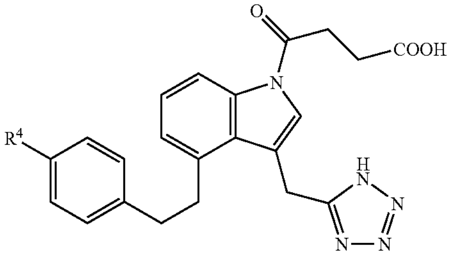
| | $R^4$— |
|---|---|
| 64 | 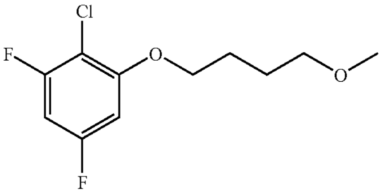 |
| 65 | 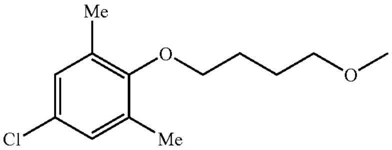 |
| 66 | 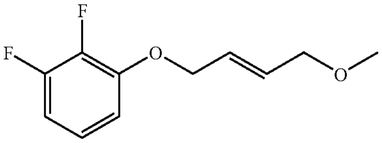 |
| 67 | 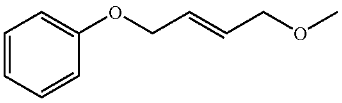 |
| 68 | 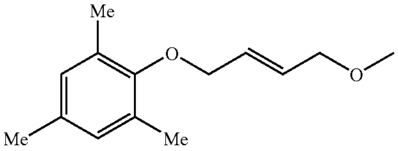 |
| 69 | 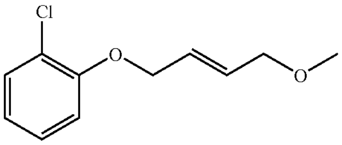 |

TABLE 23
(I-X)
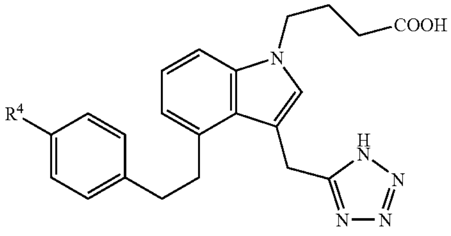
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 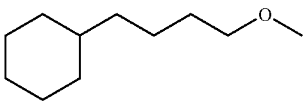 |
| 8 | 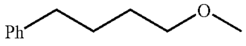 |
| 9 | 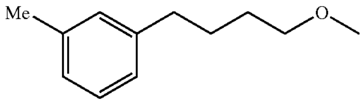 |
| 10 | 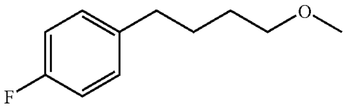 |
| 11 | 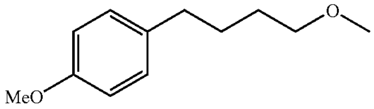 |
| 12 | 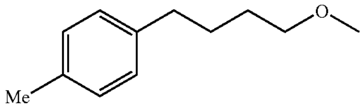 |
| 13 | 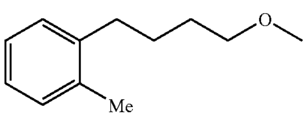 |
| 14 | 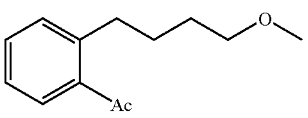 |
| 15 | 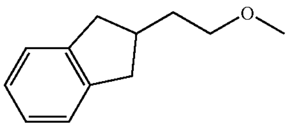 |
| 16 | 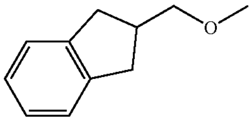 |
TABLE 23-continued
(I-X)
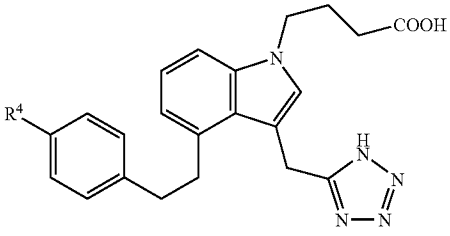
| | $R^4$— |
|---|---|
| 17 | 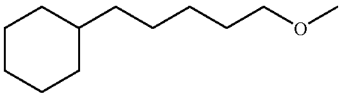 |
| 18 | 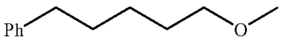 |
| 19 | 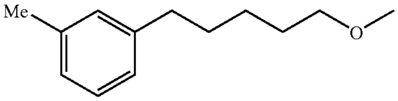 |
| 20 | 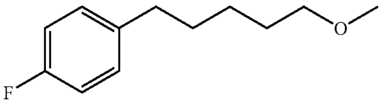 |
| 21 | 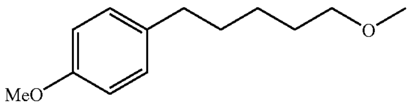 |
| 22 | 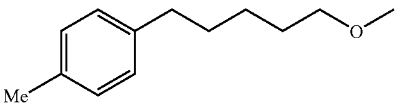 |
| 23 | 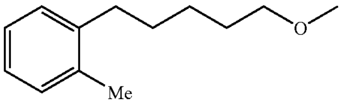 |
| 24 | 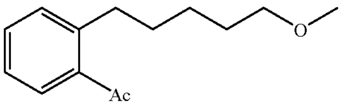 |
| 25 | 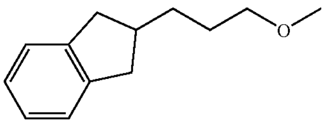 |
| 26 | 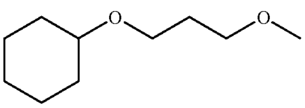 |
| 27 | 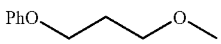 |
| 28 | 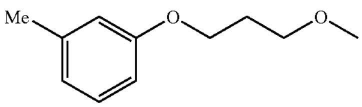 |

TABLE 23-continued
(I-X)
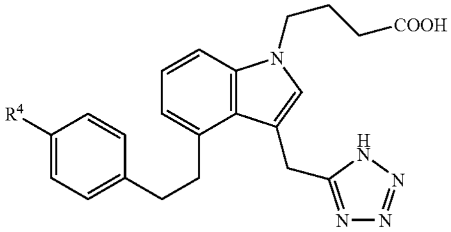
| | $R^4$— |
|---|---|
| 29 | 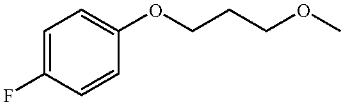 |
| 30 | 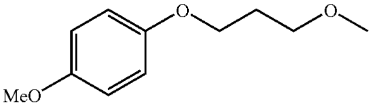 |
| 31 | 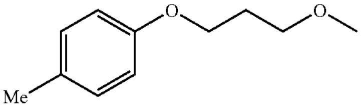 |
| 32 | 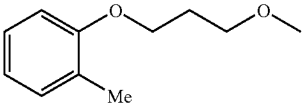 |
| 33 | 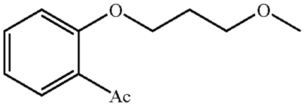 |
| 34 | 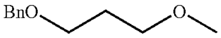 |
| 35 | 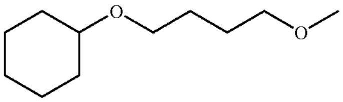 |
| 36 | 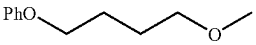 |
| 37 | 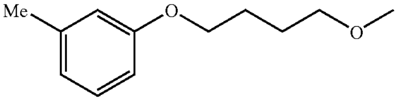 |
| 38 | 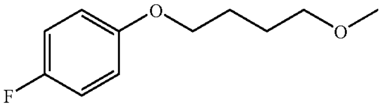 |
| 39 | 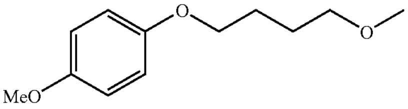 |
TABLE 23-continued
(I-X)
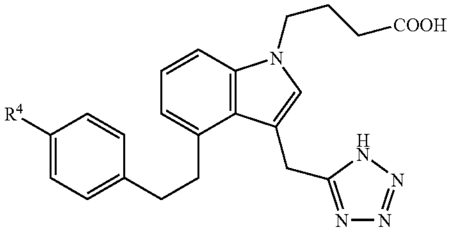
| | $R^4$— |
|---|---|
| 40 | 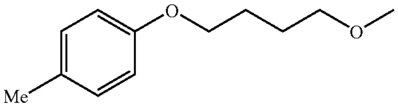 |
| 41 | 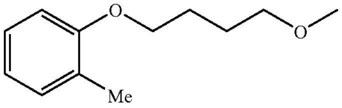 |
| 42 | 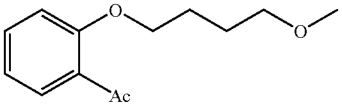 |
| 43 | 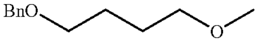 |
| 44 | 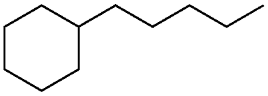 |
| 45 | 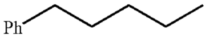 |
| 46 | 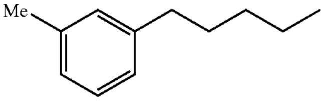 |
| 47 | 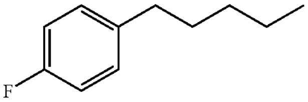 |
| 48 | 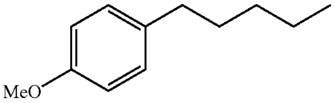 |
| 49 | 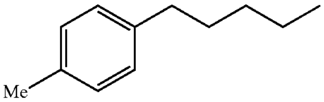 |
| 50 | 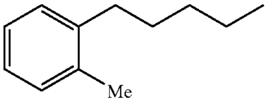 |
| 51 | 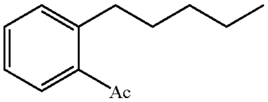 |

TABLE 23-continued
(I-X)
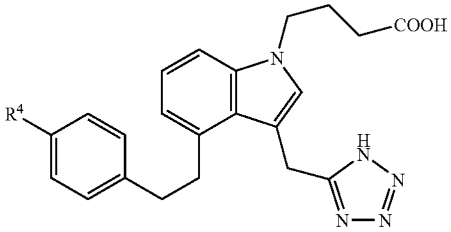
| | R⁴— |
|---|---|
| 52 | 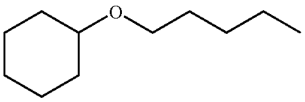 |
| 53 | 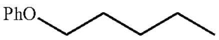 |
| 54 | 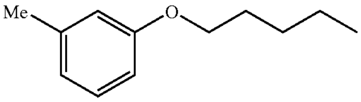 |
| 55 | 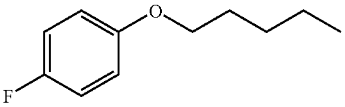 |
| 56 | 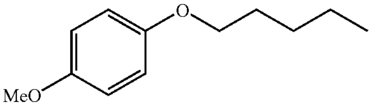 |
| 57 | 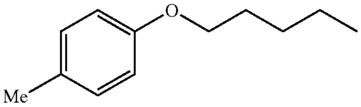 |
| 58 | 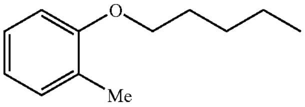 |
| 59 | 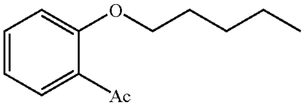 |
| 60 | 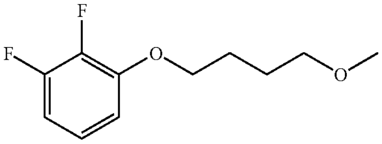 |
| 61 | 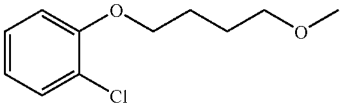 |
TABLE 23-continued
(I-X)
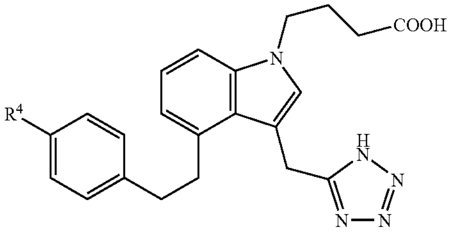
| | R⁴— |
|---|---|
| 62 | 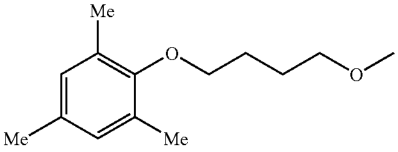 |
| 63 | 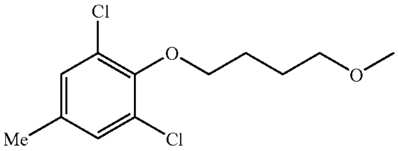 |
| 64 | 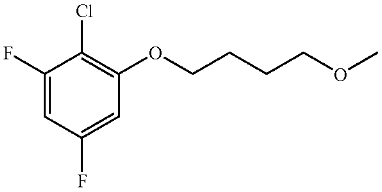 |
| 65 | 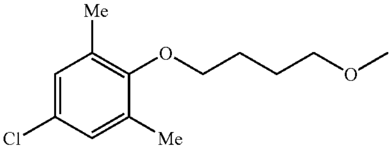 |
| 66 | 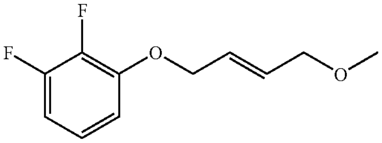 |
| 67 | 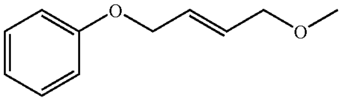 |
| 68 | 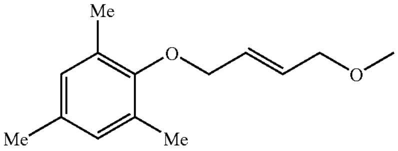 |
| 69 | 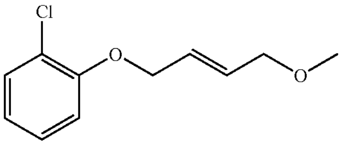 |

TABLE 24
(I-Y)
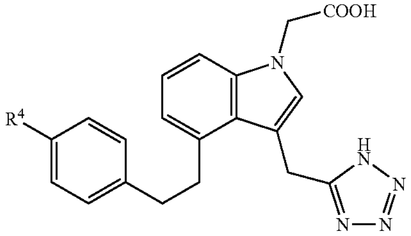
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 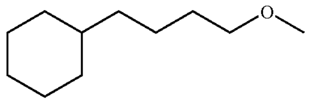 |
| 8 | 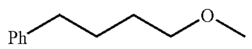 |
| 9 | 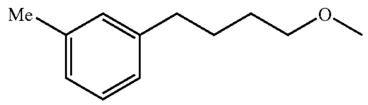 |
| 10 | 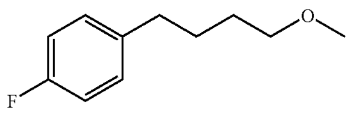 |
| 11 | 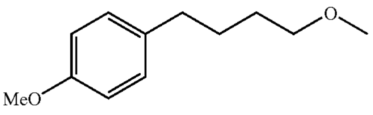 |
| 12 | 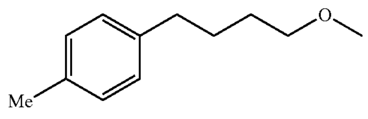 |
| 13 | 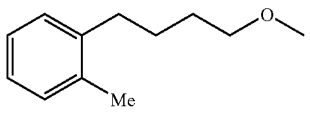 |
| 14 | 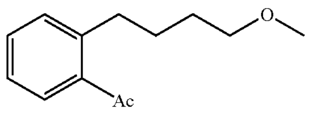 |
| 15 | 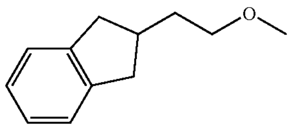 |
TABLE 24-continued
(I-Y)
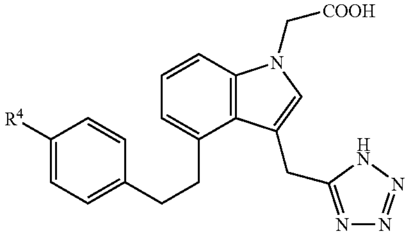
| | $R^4$— |
|---|---|
| 16 | 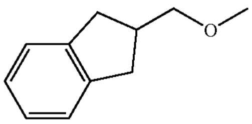 |
| 17 | 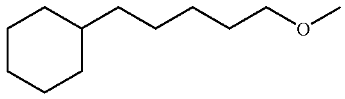 |
| 18 | 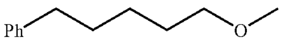 |
| 19 | 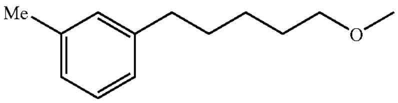 |
| 20 | 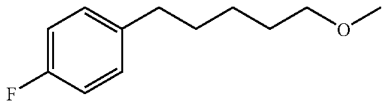 |
| 21 | 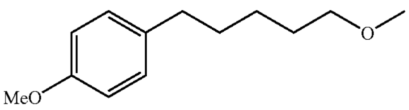 |
| 22 | 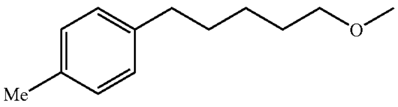 |
| 23 | 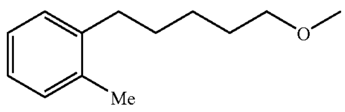 |
| 24 | 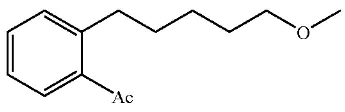 |
| 25 | 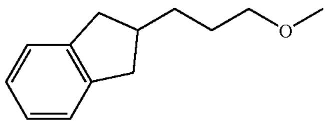 |
| 26 | 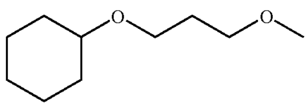 |
| 27 | 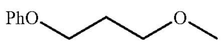 |

TABLE 24-continued
(I-Y)
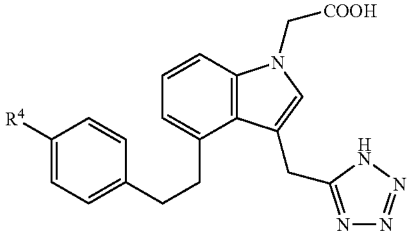
| | $R^4$— |
|---|---|
| 28 | 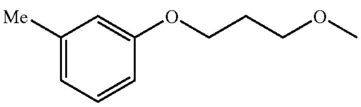 |
| 29 | 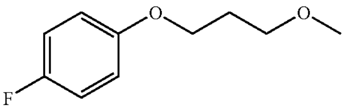 |
| 30 | 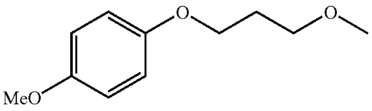 |
| 31 | 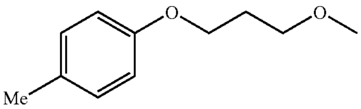 |
| 32 | 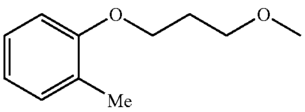 |
| 33 | 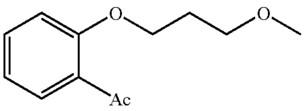 |
| 34 | 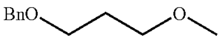 |
| 35 | 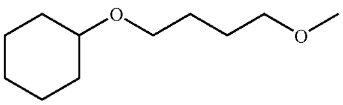 |
| 36 | 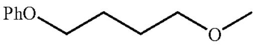 |
| 37 | 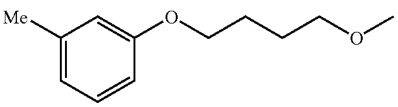 |
| 38 | 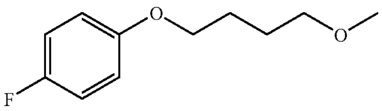 |
TABLE 24-continued
(I-Y)
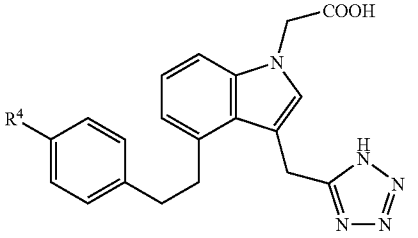
| | $R^4$— |
|---|---|
| 39 | 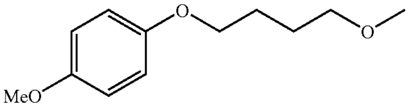 |
| 40 | 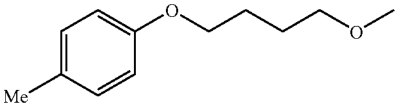 |
| 41 | 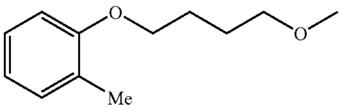 |
| 42 | 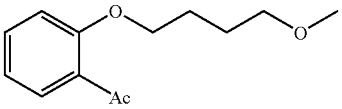 |
| 43 | 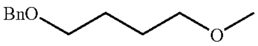 |
| 44 | 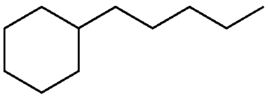 |
| 45 | 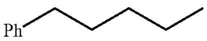 |
| 46 | 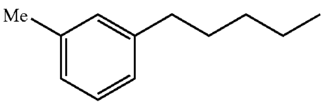 |
| 47 | 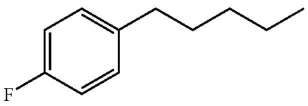 |
| 48 | 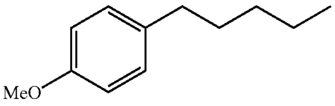 |
| 49 | 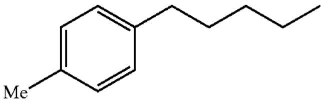 |
| 50 | 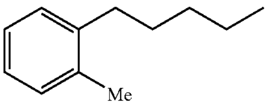 |

TABLE 24-continued
(I-Y)
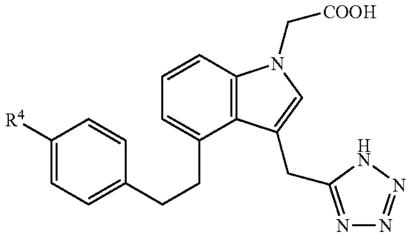
R$^4$—
51
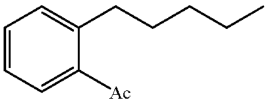
52
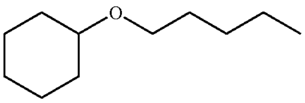
53
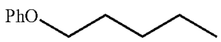
54
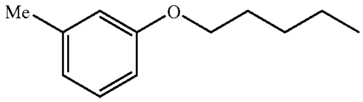
55
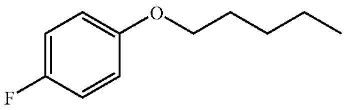
56
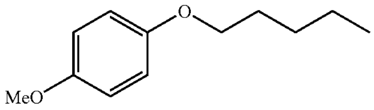
57
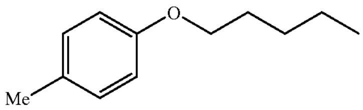
58
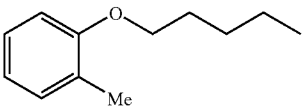
59
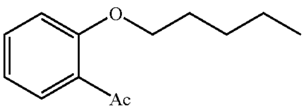
60
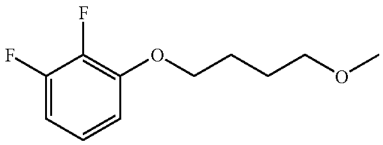
TABLE 24-continued
(I-Y)
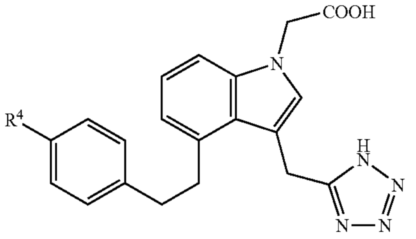
R$^4$—
61
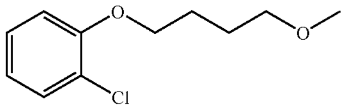
62
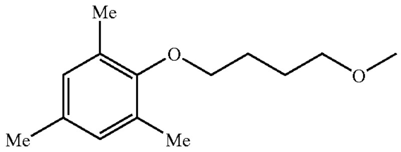
63
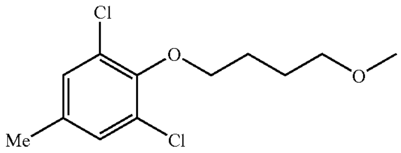
64
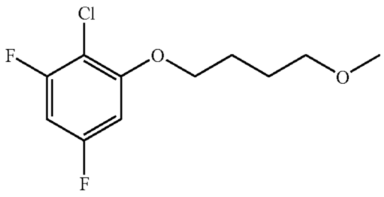
65
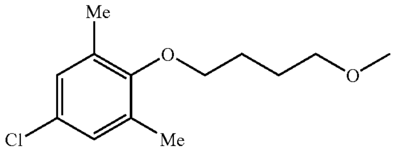
66
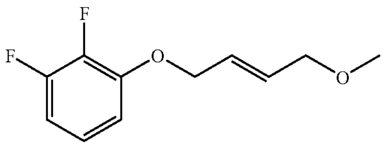
67
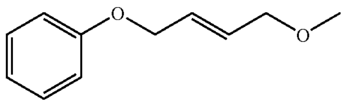
68
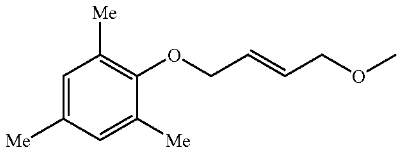

TABLE 24-continued
(I-Y)
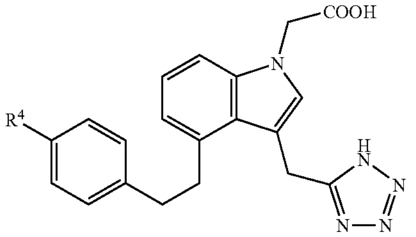
| | $R^4$— |
|---|---|
| 69 | 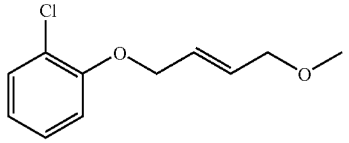 |
TABLE 25
(I-Z)
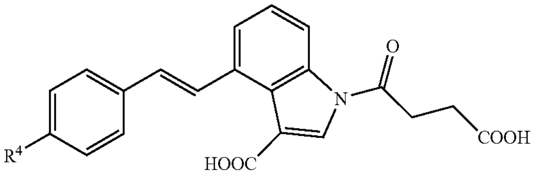
| | $R^4$— |
|---|---|
| 1 | n-$C_4H_9$$^-$ |
| 2 | n-$C_5H_{11}$$^-$ |
| 3 | n-$C_6H_{13}$$^-$ |
| 4 | n-$C_4H_9$—$O^-$ |
| 5 | n-$C_5H_{11}$—$O^-$ |
| 6 | n-$C_6H_{13}$—$O^-$ |
| 7 | 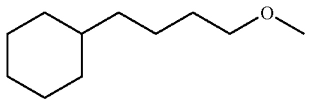 |
| 8 | 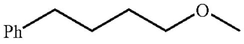 |
| 9 | 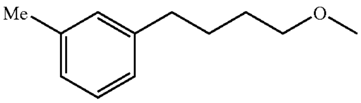 |
| 10 | 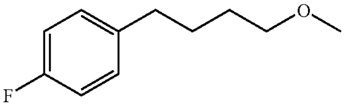 |
| 11 | 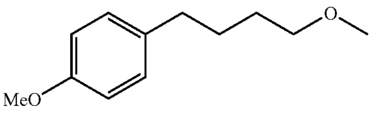 |
| 12 | 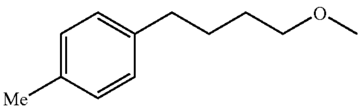 |
TABLE 25-continued
(I-Z)
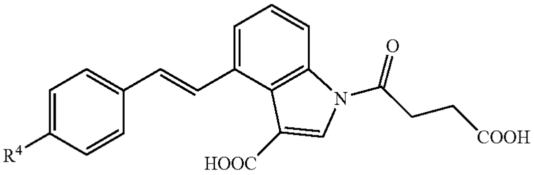
| | $R^4$— |
|---|---|
| 13 | 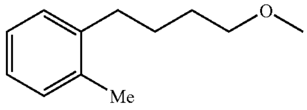 |
| 14 | 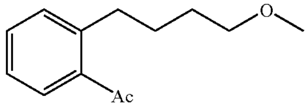 |
| 15 | 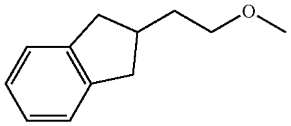 |
| 16 | 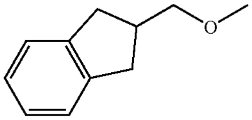 |
| 17 | 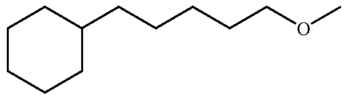 |
| 18 | 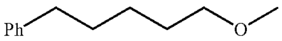 |
| 19 | 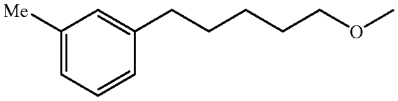 |
| 20 | 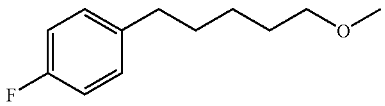 |
| 21 | 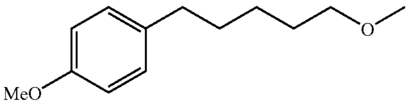 |
| 22 | 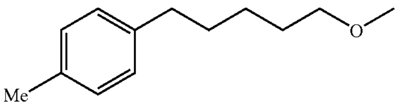 |
| 23 | 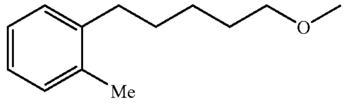 |

TABLE 25-continued
(I-Z)
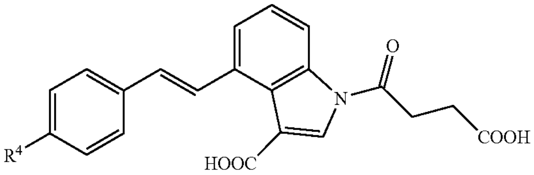
| | $R^4$— |
|---|---|
| 24 | 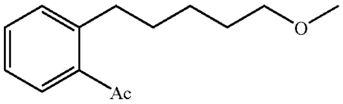 |
| 25 | 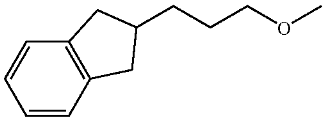 |
| 26 | 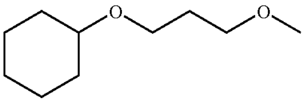 |
| 27 | 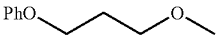 |
| 28 | 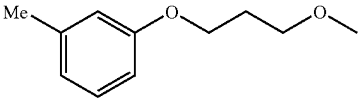 |
| 29 | 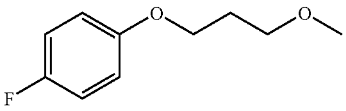 |
| 30 | 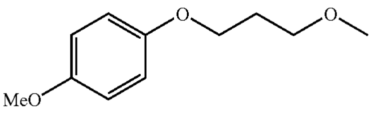 |
| 31 | 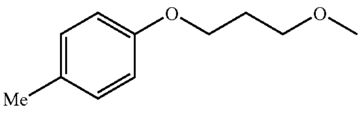 |
| 32 | 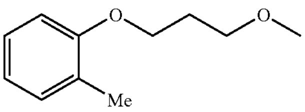 |
| 33 | 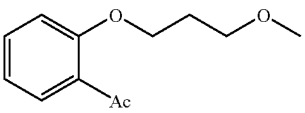 |
| 34 | 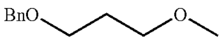 |
| 35 | 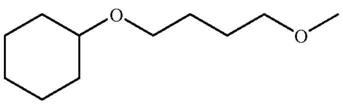 |
TABLE 25-continued
(I-Z)
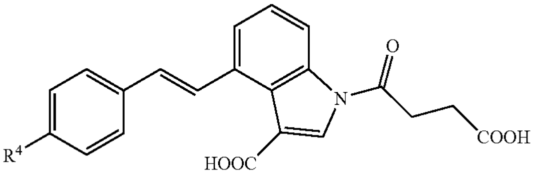
| | $R^4$— |
|---|---|
| 36 | 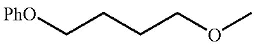 |
| 37 | 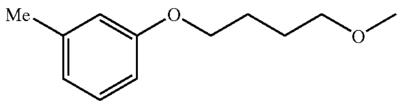 |
| 38 | 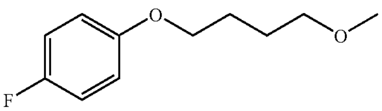 |
| 39 | 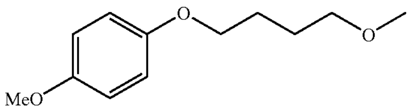 |
| 40 | 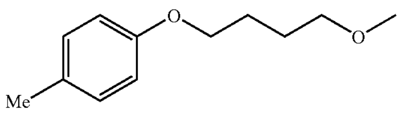 |
| 41 | 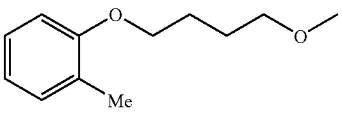 |
| 42 | 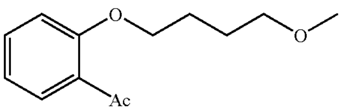 |
| 43 | 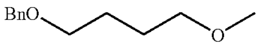 |
| 44 | 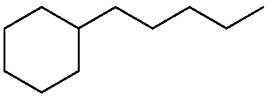 |
| 45 | 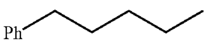 |
| 46 | 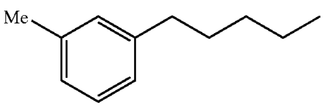 |
| 47 | 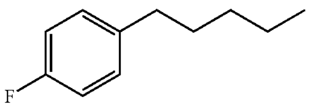 |
| 48 | 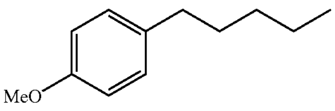 |

TABLE 25-continued
(I-Z)
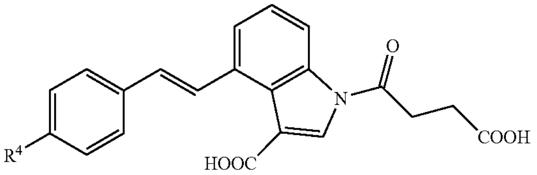
| | $R^4$— |
|---|---|
| 49 | 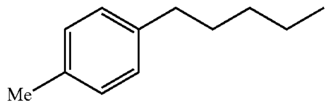 |
| 50 | 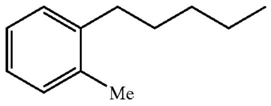 |
| 51 | 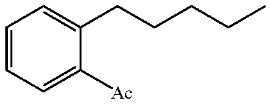 |
| 52 | 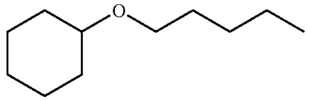 |
| 53 | 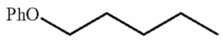 |
| 54 | 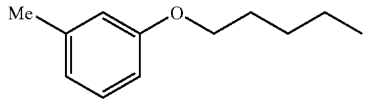 |
| 55 | 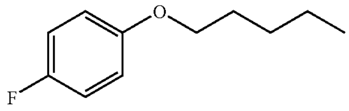 |
| 56 | 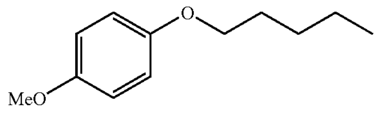 |
| 57 | 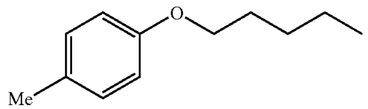 |
| 58 | 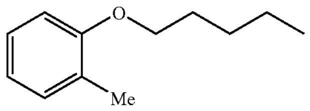 |
| 59 | 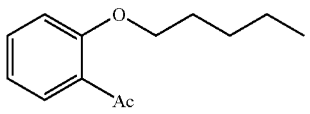 |
TABLE 25-continued
(I-Z)
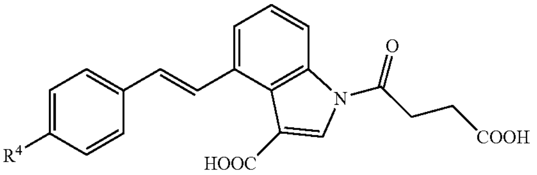
| | $R^4$— |
|---|---|
| 60 | 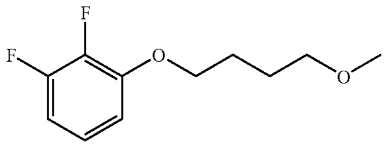 |
| 61 | 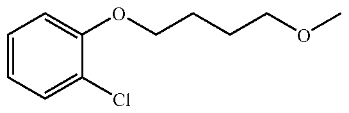 |
| 62 | 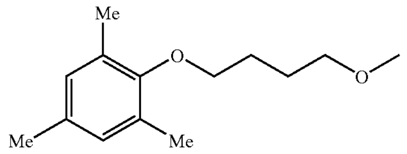 |
| 63 | 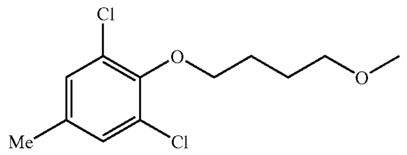 |
| 64 | 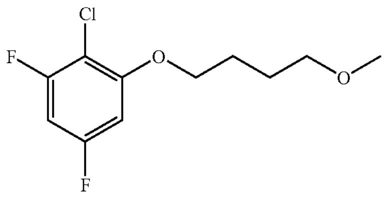 |
| 65 | 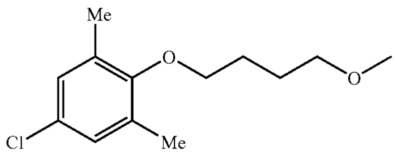 |
| 66 | 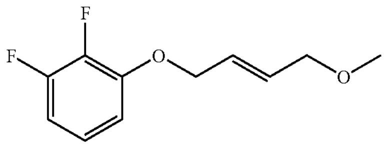 |
| 67 | 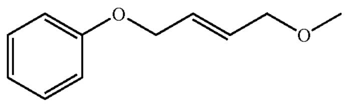 |

TABLE 25-continued
(I-Z)
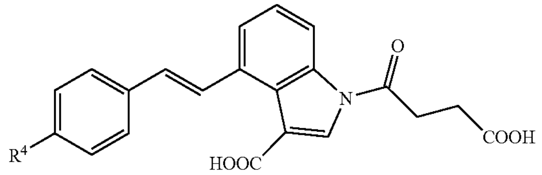
| | $R^4$— |
|---|---|
| 68 | 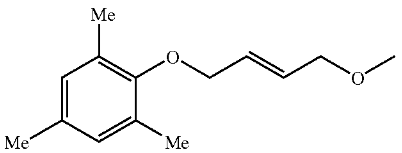 |
| 69 | 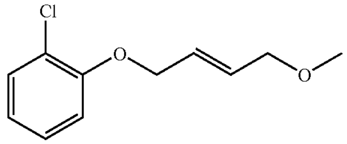 |
TABLE 26
(I-AA)
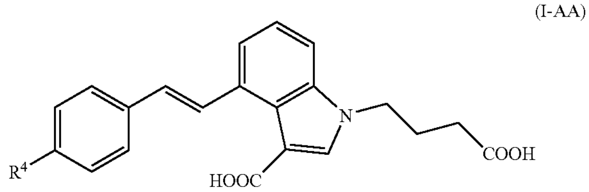
| | $R^4$— |
|---|---|
| 1 | $n\text{-}C_4H_9^-$ |
| 2 | $n\text{-}C_5H_{11}^-$ |
| 3 | $n\text{-}C_6H_{13}^-$ |
| 4 | $n\text{-}C_4H_9$—$O^-$ |
| 5 | $n\text{-}C_5H_{11}$—$O^-$ |
| 6 | $n\text{-}C_6H_{13}$—$O^-$ |
| 7 | 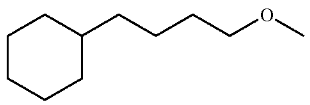 |
| 8 | 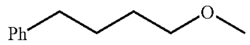 |
| 9 | 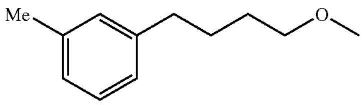 |
| 10 | 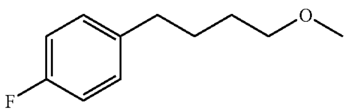 |
| 11 | 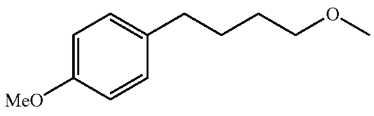 |
TABLE 26-continued
(I-AA)
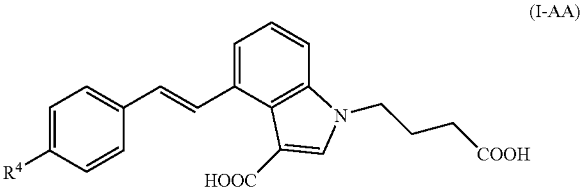
| | $R^4$— |
|---|---|
| 12 | 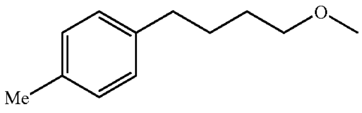 |
| 13 | 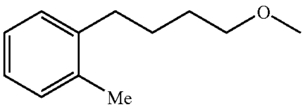 |
| 14 | 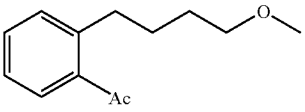 |
| 15 | 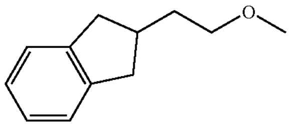 |
| 16 | 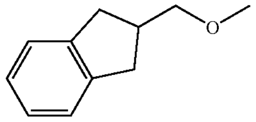 |
| 17 | 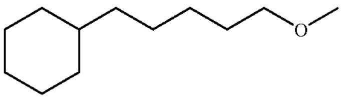 |
| 18 | 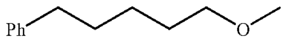 |
| 19 | 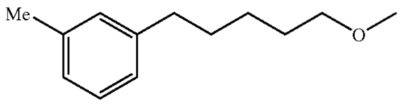 |
| 20 | 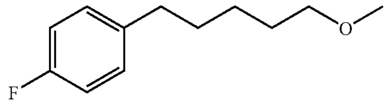 |
| 21 | 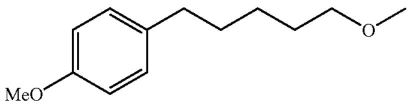 |
| 22 | 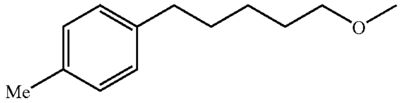 |

TABLE 26-continued
(I-AA)
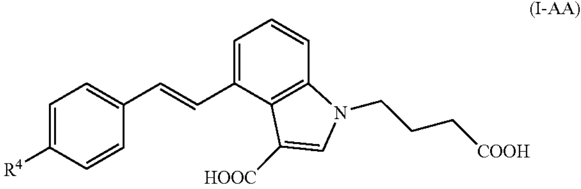
| | $R^4$— |
|---|---|
| 23 | 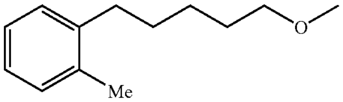 |
| 24 | 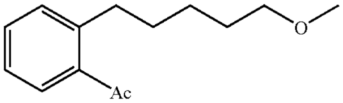 |
| 25 | 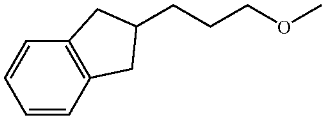 |
| 26 | 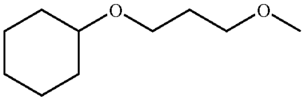 |
| 27 | 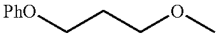 |
| 28 | 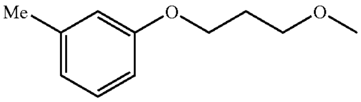 |
| 29 | 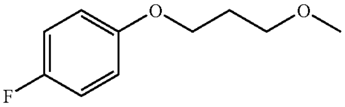 |
| 30 | 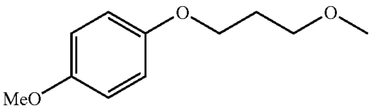 |
| 31 | 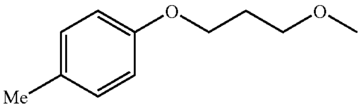 |
| 32 | 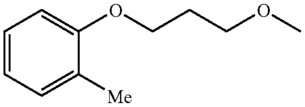 |
| 33 | 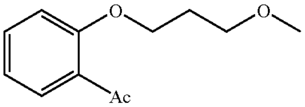 |
| 34 | 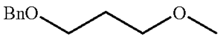 |
TABLE 26-continued
(I-AA)
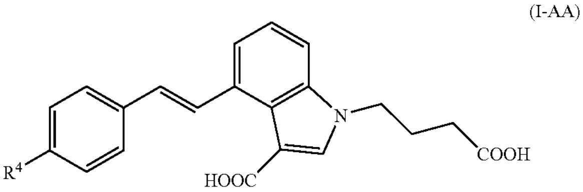
| | $R^4$— |
|---|---|
| 35 | 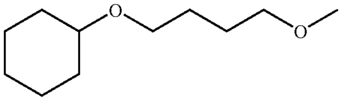 |
| 36 | 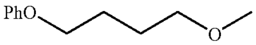 |
| 37 | 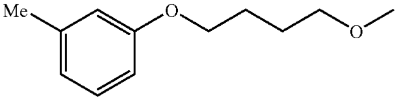 |
| 38 | 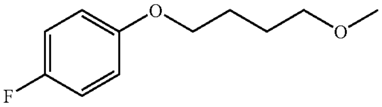 |
| 39 | 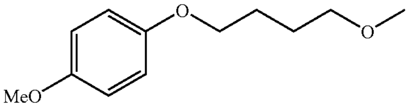 |
| 40 | 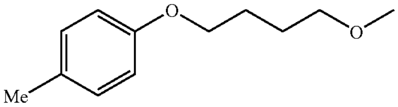 |
| 41 | 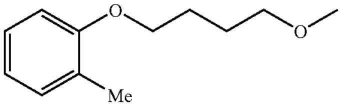 |
| 42 | 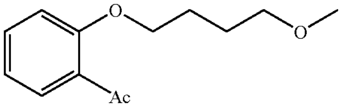 |
| 43 | 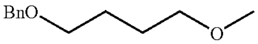 |
| 44 | 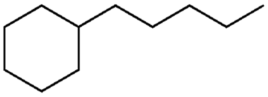 |
| 45 | 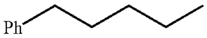 |
| 46 | 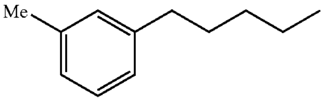 |
| 47 | 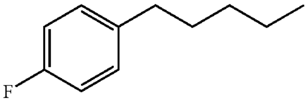 |

TABLE 26-continued
(I-AA)
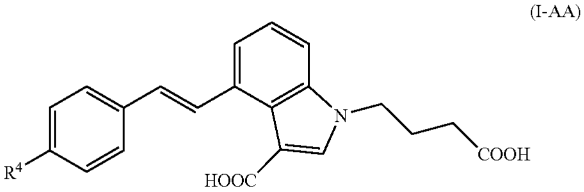
| | $R^4$— |
|---|---|
| 48 | 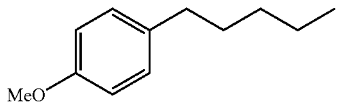 |
| 49 | 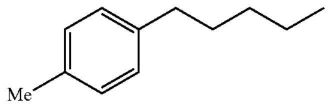 |
| 50 | 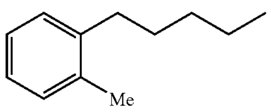 |
| 51 | 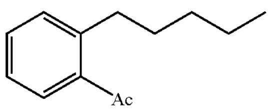 |
| 52 | 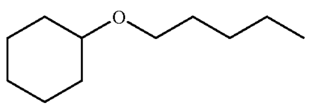 |
| 53 | 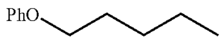 |
| 54 | 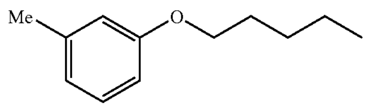 |
| 55 | 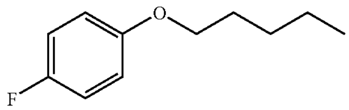 |
| 56 | 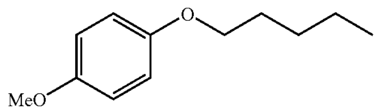 |
| 57 | 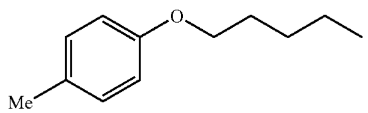 |
| 58 | 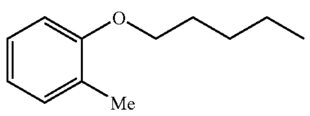 |
TABLE 26-continued
(I-AA)
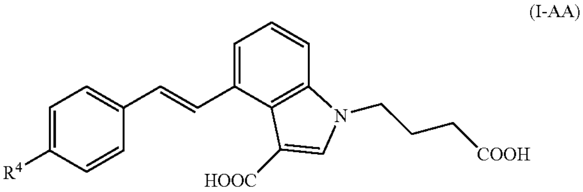
| | $R^4$— |
|---|---|
| 59 | 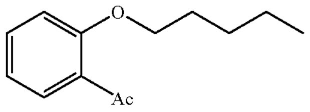 |
| 60 | 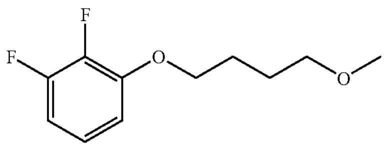 |
| 61 | 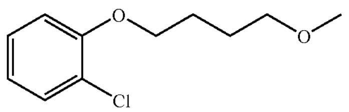 |
| 62 | 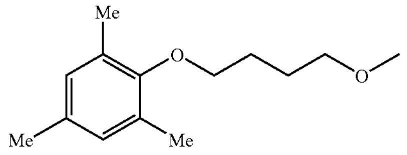 |
| 63 | 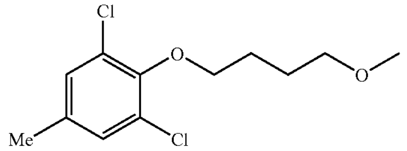 |
| 64 | 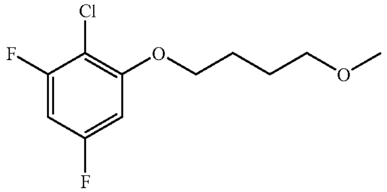 |
| 65 | 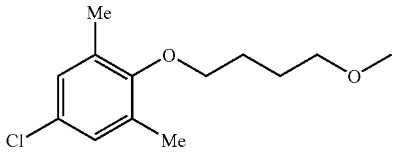 |
| 66 | 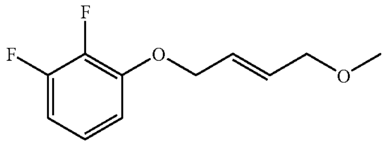 |
| 67 | 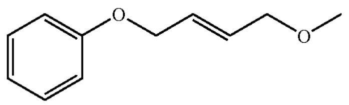 |

TABLE 26-continued
(I-AA)
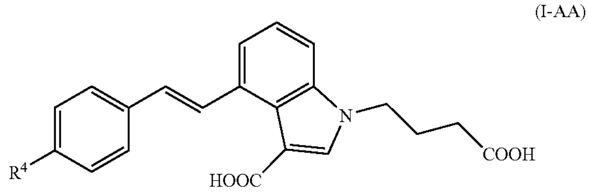
| | R⁴— |
|---|---|
| 68 | 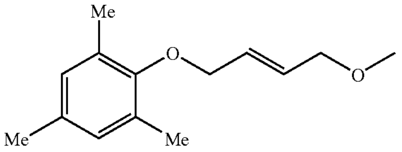 |
| 69 | 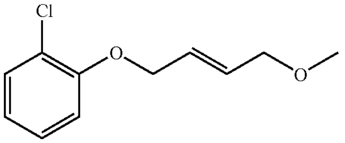 |
TABLE 27
(I-BB)
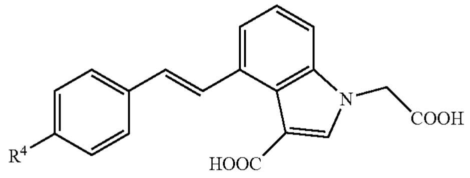
| | R⁴— |
|---|---|
| 1 | $n\text{-}C_4H_9$— |
| 2 | $n\text{-}C_5H_{11}$— |
| 3 | $n\text{-}C_6H_{13}$— |
| 4 | $n\text{-}C_4H_9$—O— |
| 5 | $n\text{-}C_5H_{11}$—O— |
| 6 | $n\text{-}C_6H_{13}$—O— |
| 7 | 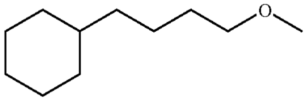 |
| 8 | 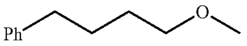 |
| 9 | 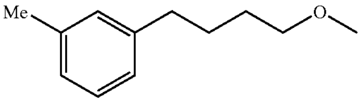 |
| 10 | 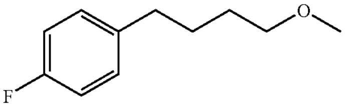 |
| 11 | 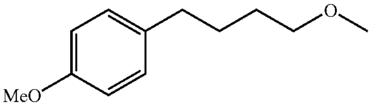 |
TABLE 27-continued
(I-BB)
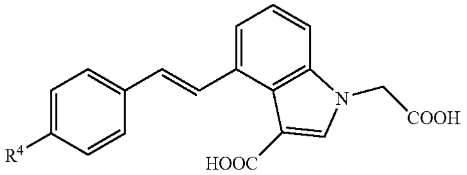
| | R⁴— |
|---|---|
| 12 | 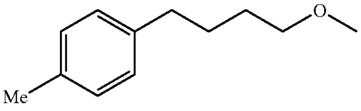 |
| 13 | 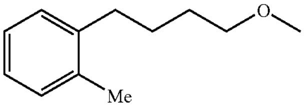 |
| 14 | 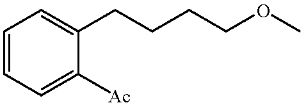 |
| 15 | 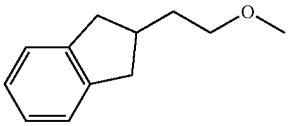 |
| 16 | 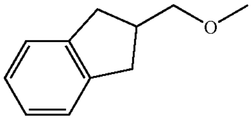 |
| 17 | 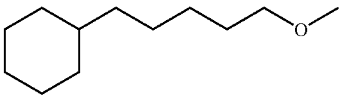 |
| 18 | 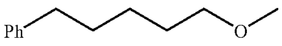 |
| 19 | 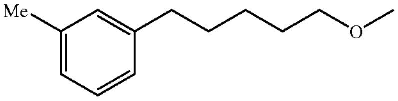 |
| 20 | 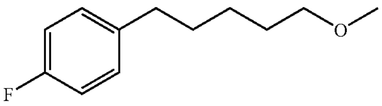 |
| 21 | 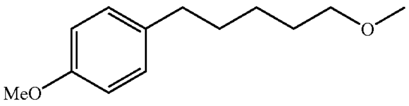 |
| 22 | 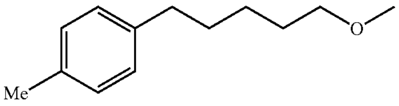 |

TABLE 27-continued
(I-BB)
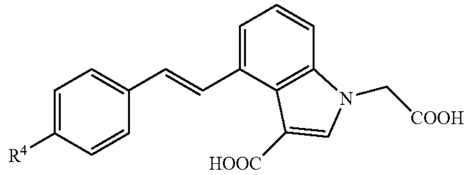
| | $R^4$— |
|---|---|
| 23 | 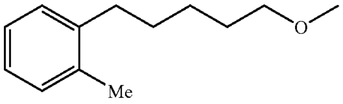 |
| 24 | 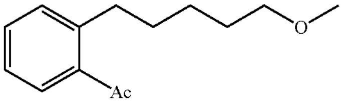 |
| 25 | 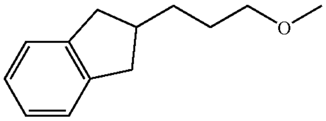 |
| 26 | 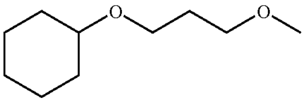 |
| 27 | 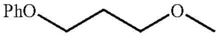 |
| 28 | 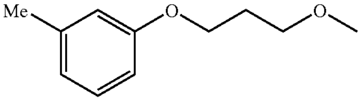 |
| 29 | 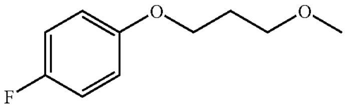 |
| 30 | 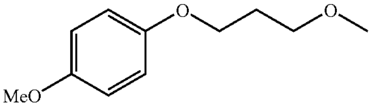 |
| 31 | 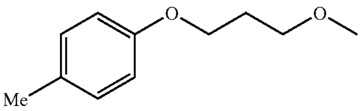 |
| 32 | 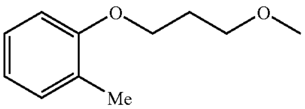 |
| 33 | 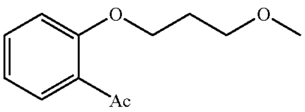 |
| 34 | 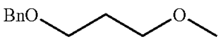 |
TABLE 27-continued
(I-BB)
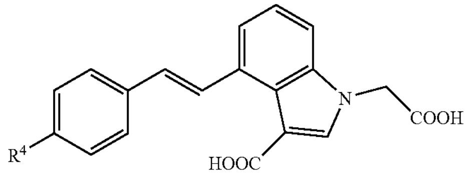
| | $R^4$— |
|---|---|
| 35 | 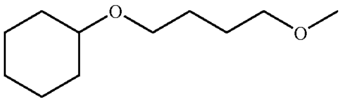 |
| 36 | 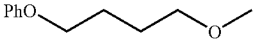 |
| 37 | 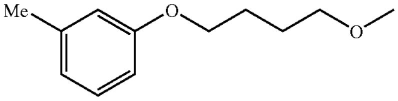 |
| 38 | 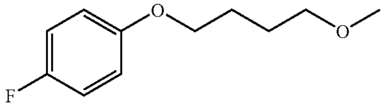 |
| 39 | 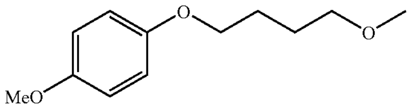 |
| 40 | 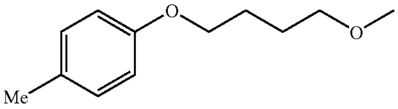 |
| 41 | 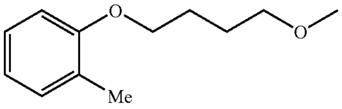 |
| 42 | 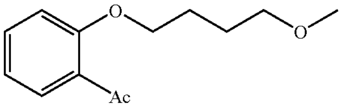 |
| 43 | 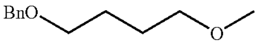 |
| 44 | 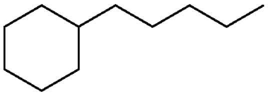 |
| 45 | 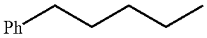 |
| 46 | 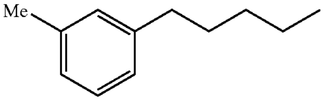 |

TABLE 27-continued
(I-BB)
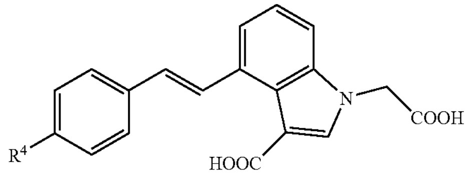
| | $R^4$— |
|---|---|
| 47 | 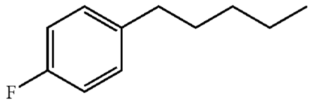 |
| 48 | 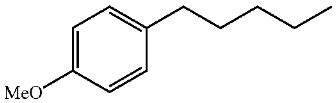 |
| 49 | 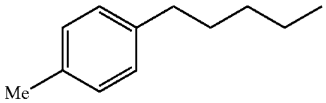 |
| 50 | 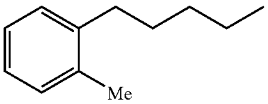 |
| 51 | 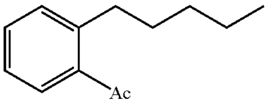 |
| 52 | 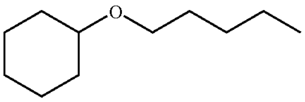 |
| 53 | 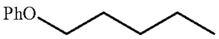 |
| 54 | 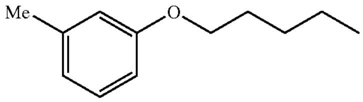 |
| 55 | 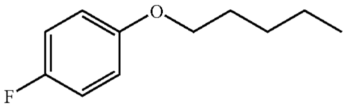 |
| 56 | 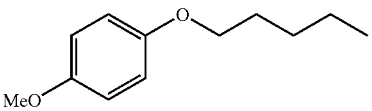 |
| 57 | 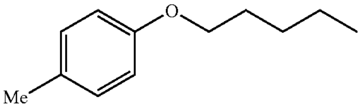 |
| 58 | 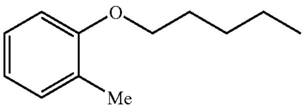 |
TABLE 27-continued
(I-BB)
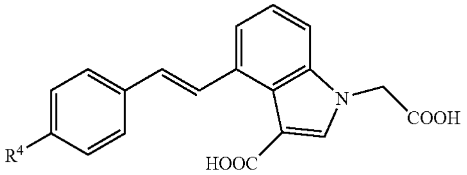
| | $R^4$— |
|---|---|
| 59 | 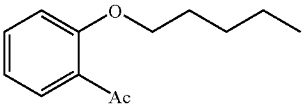 |
| 60 | 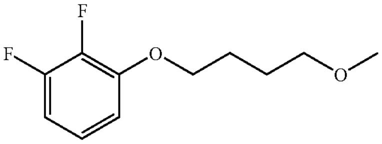 |
| 61 | 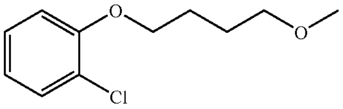 |
| 62 | 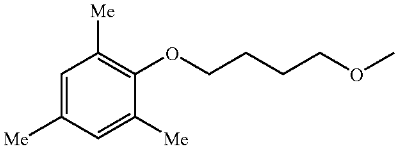 |
| 63 | 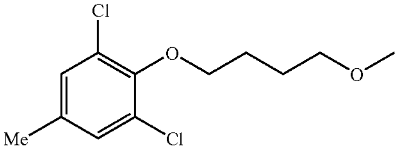 |
| 64 | 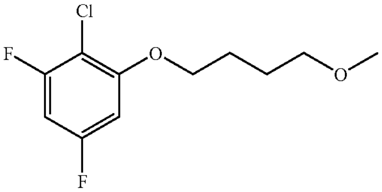 |
| 65 | 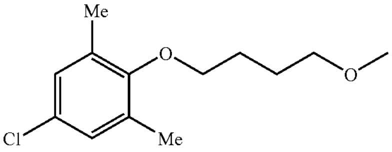 |
| 66 | 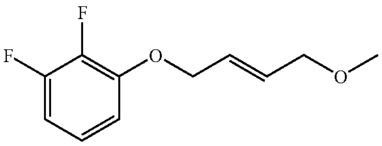 |

TABLE 27-continued
(I-BB)
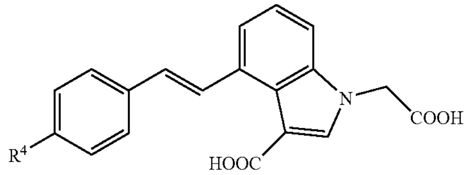
R4—
| | |
|---|---|
| 67 | 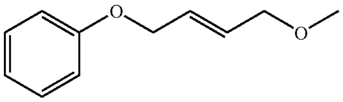 |
| 68 | 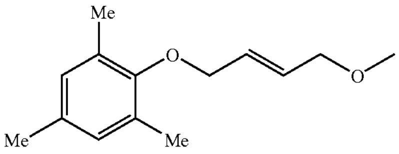 |
| 69 | 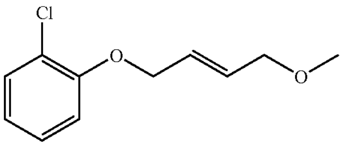 |
TABLE 28
(I-CC)
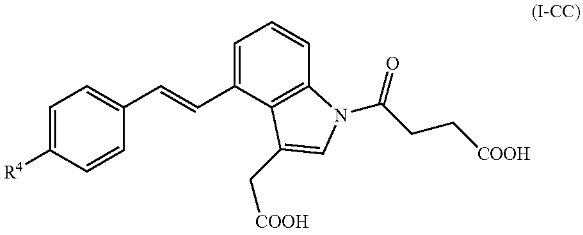
R4—
| | |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 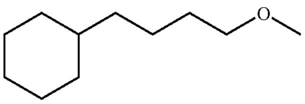 |
| 8 | 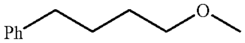 |
| 9 | 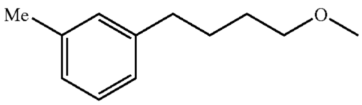 |
| 10 | 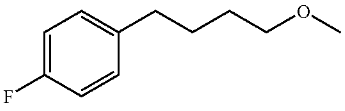 |
TABLE 28-continued
(I-CC)
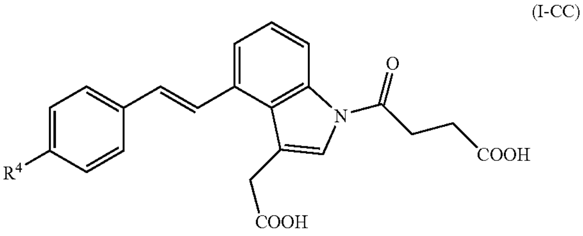
R4—
| | |
|---|---|
| 11 | 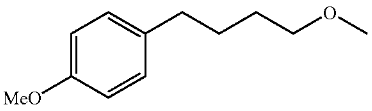 |
| 12 | 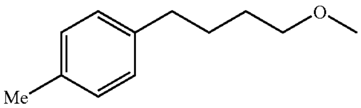 |
| 13 | 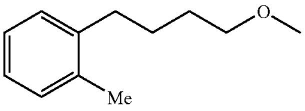 |
| 14 | 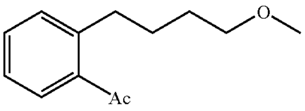 |
| 15 | 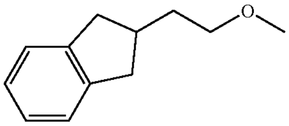 |
| 16 | 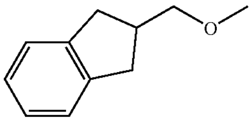 |
| 17 | 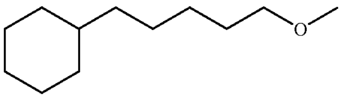 |
| 18 | 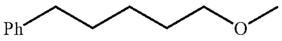 |
| 19 | 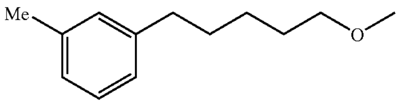 |
| 20 | 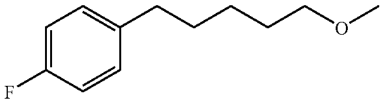 |
| 21 | 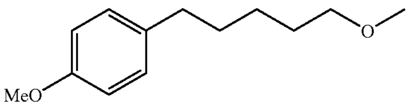 |

TABLE 28-continued
(I-CC)
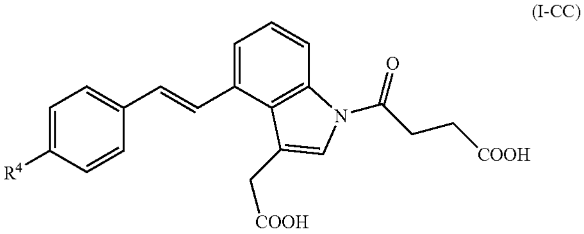
| | $R^4$— |
|---|---|
| 22 | 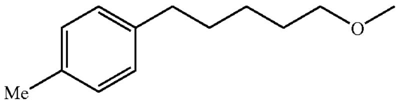 |
| 23 | 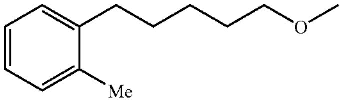 |
| 24 | 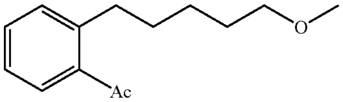 |
| 25 | 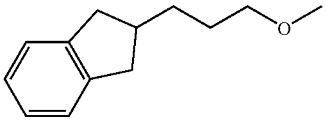 |
| 26 | 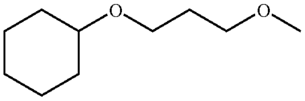 |
| 27 | 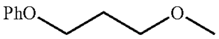 |
| 28 | 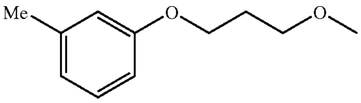 |
| 29 | 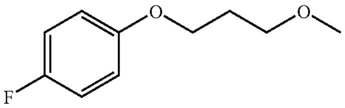 |
| 30 | 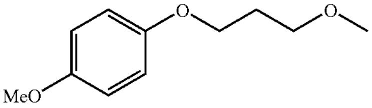 |
| 31 | 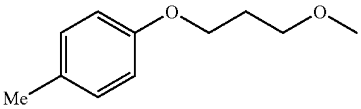 |
| 32 | 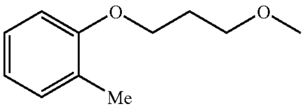 |
TABLE 28-continued
(I-CC)
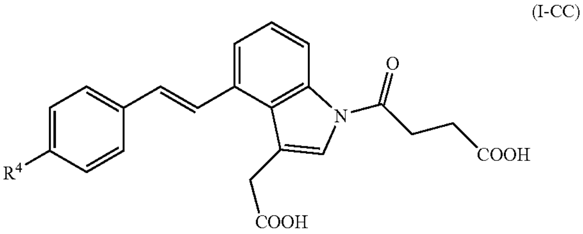
| | $R^4$— |
|---|---|
| 33 | 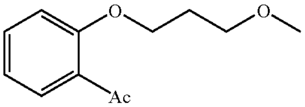 |
| 34 | 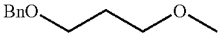 |
| 35 | 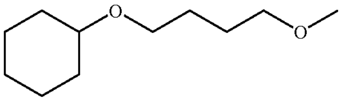 |
| 36 | 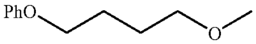 |
| 37 | 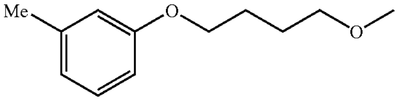 |
| 38 | 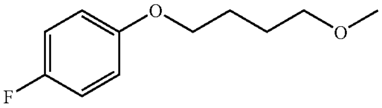 |
| 39 | 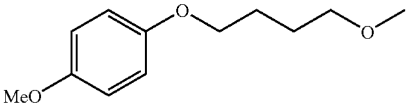 |
| 40 | 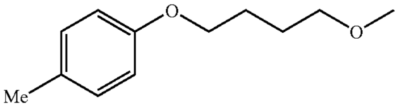 |
| 41 | 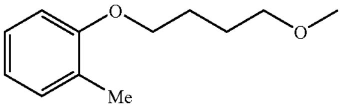 |
| 42 | 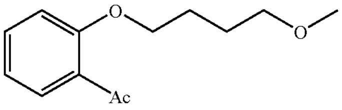 |
| 43 | 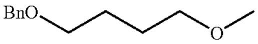 |
| 44 | 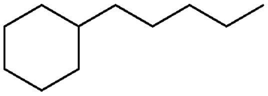 |
| 45 | 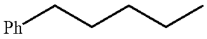 |

TABLE 28-continued
(I-CC)
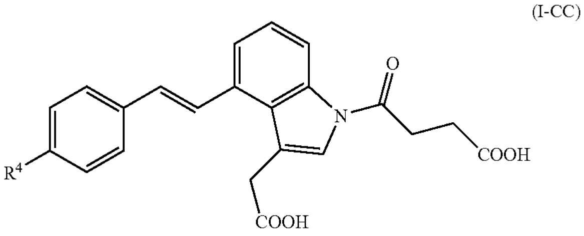
| | R⁴— |
|---|---|
| 46 | 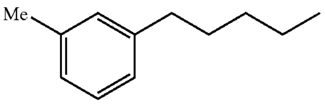 |
| 47 | 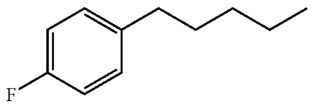 |
| 48 | 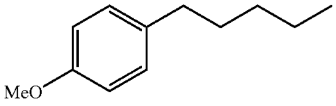 |
| 49 | 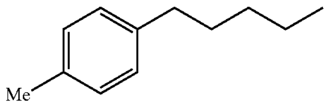 |
| 50 | 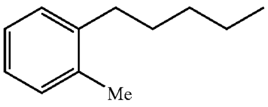 |
| 51 | 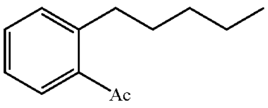 |
| 52 | 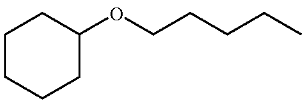 |
| 53 | 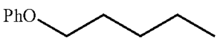 |
| 54 | 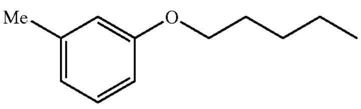 |
| 55 | 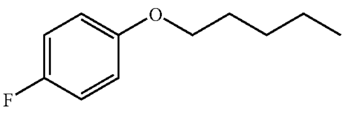 |
| 56 | 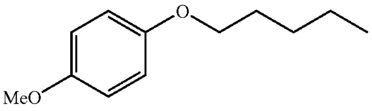 |
TABLE 28-continued
(I-CC)
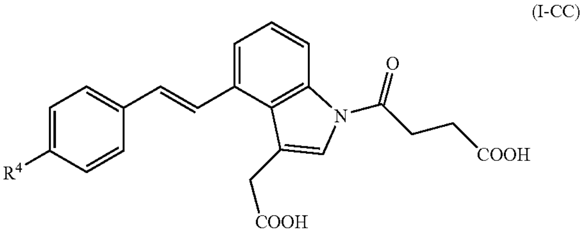
| | R⁴— |
|---|---|
| 57 | 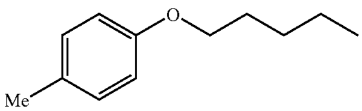 |
| 58 | 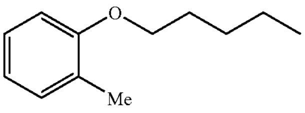 |
| 59 | 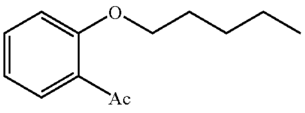 |
| 60 | 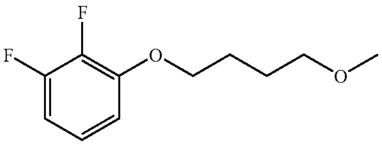 |
| 61 | 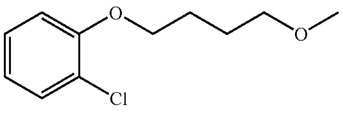 |
| 62 | 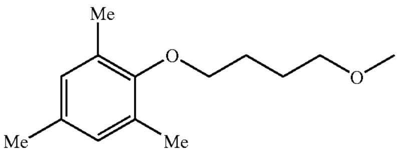 |
| 63 | 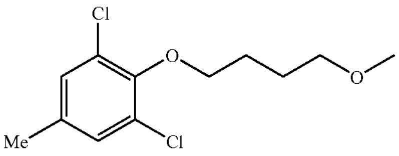 |
| 64 | 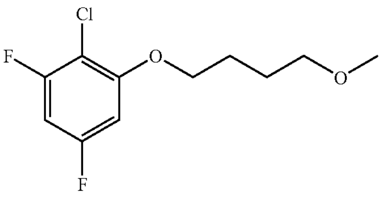 |
| 65 | 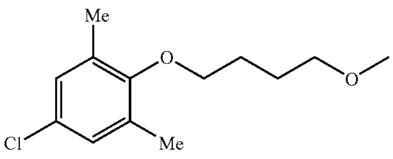 |

TABLE 28-continued
(I-CC)
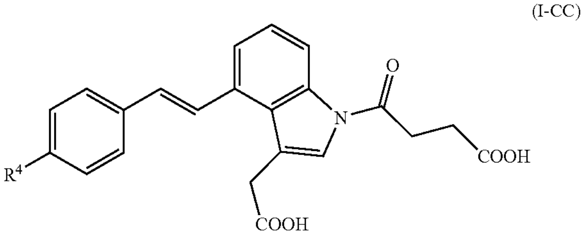
| | $R^4$— |
|---|---|
| 66 | 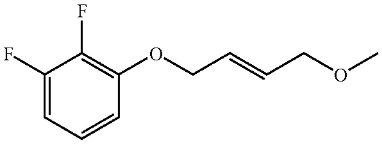 |
| 67 | 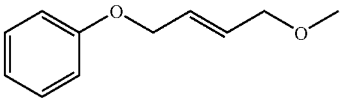 |
| 68 | 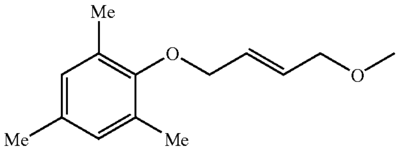 |
| 69 | 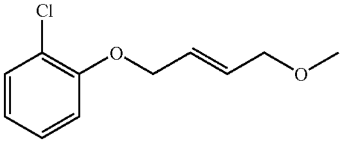 |
TABLE 29
(I-DD)
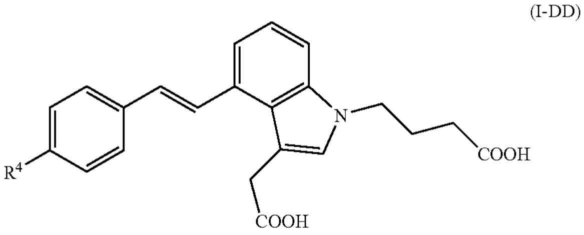
| | $R^4$— |
|---|---|
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |
| 7 | 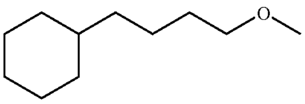 |
TABLE 29-continued
(I-DD)
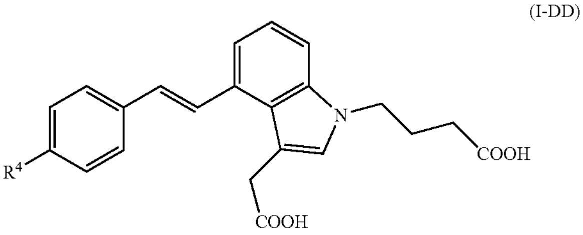
| | $R^4$— |
|---|---|
| 8 | 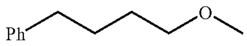 |
| 9 | 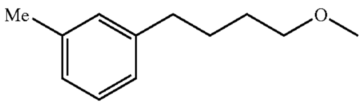 |
| 10 | 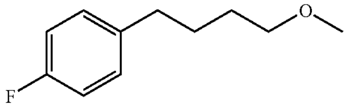 |
| 11 | 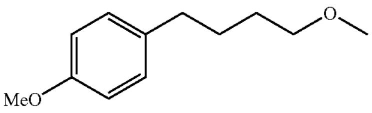 |
| 12 | 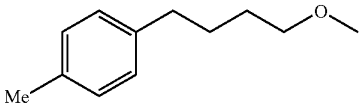 |
| 13 | 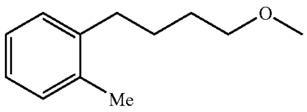 |
| 14 | 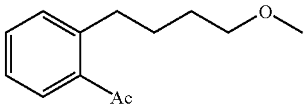 |
| 15 | 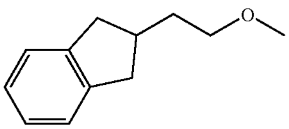 |
| 16 | 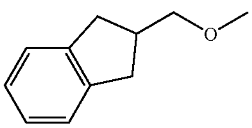 |
| 17 | 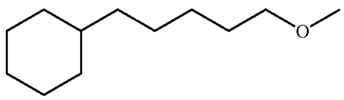 |
| 18 | 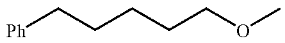 |

TABLE 29-continued
(I-DD)
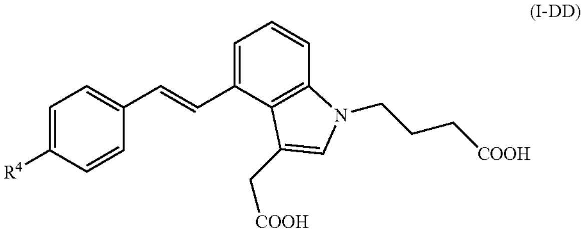
| | $R^4$— |
|---|---|
| 19 | 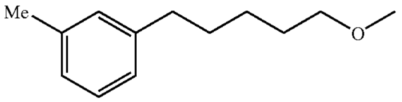 |
| 20 | 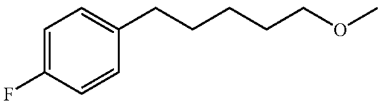 |
| 21 | 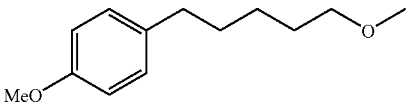 |
| 22 | 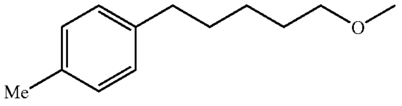 |
| 23 | 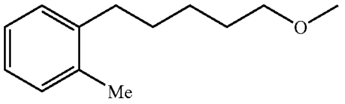 |
| 24 | 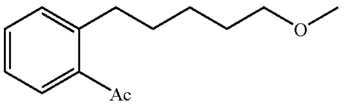 |
| 25 | 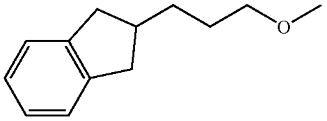 |
| 26 | 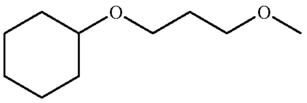 |
| 27 | 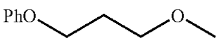 |
| 28 | 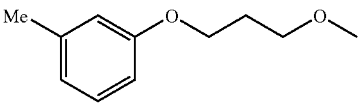 |
| 29 | 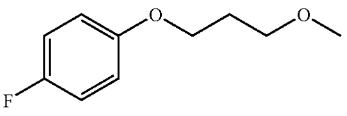 |
TABLE 29-continued
(I-DD)
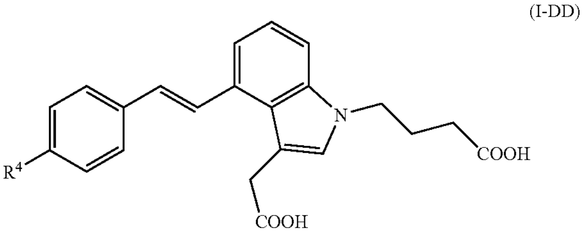
| | $R^4$— |
|---|---|
| 30 | 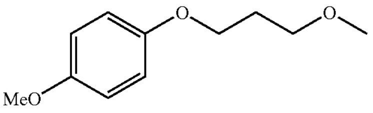 |
| 31 | 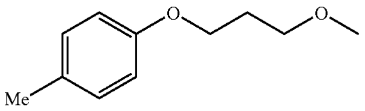 |
| 32 | 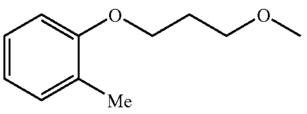 |
| 33 | 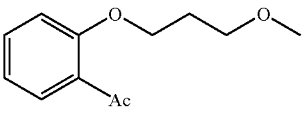 |
| 34 | 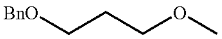 |
| 35 | 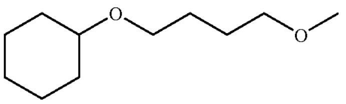 |
| 36 | 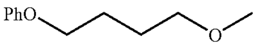 |
| 37 | 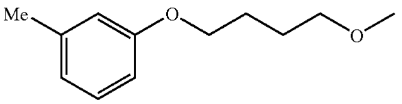 |
| 38 | 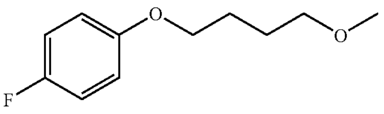 |
| 39 | 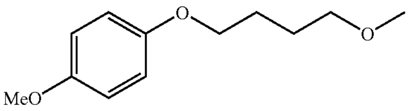 |
| 40 | 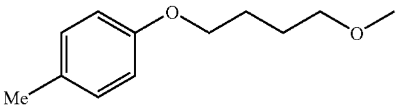 |
| 41 | 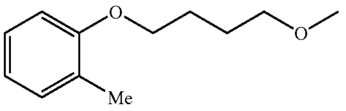 |

TABLE 29-continued
(I-DD)
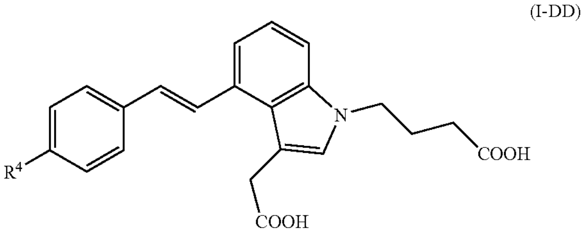
| | R⁴— |
|---|---|
| 42 | 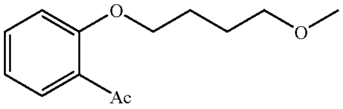 |
| 43 | 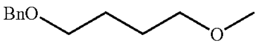 |
| 44 | 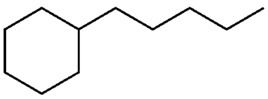 |
| 45 | 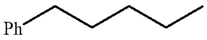 |
| 46 | 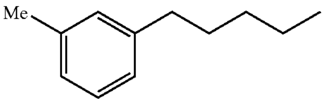 |
| 47 | 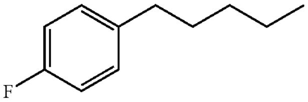 |
| 48 | 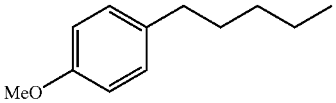 |
| 49 | 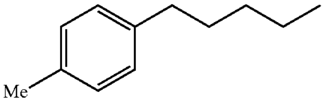 |
| 50 | 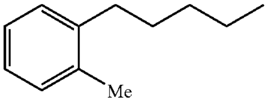 |
| 51 | 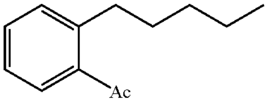 |
| 52 | 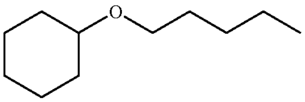 |
| 53 | 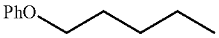 |
| 54 | 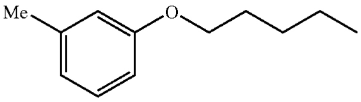 |
TABLE 29-continued
(I-DD)
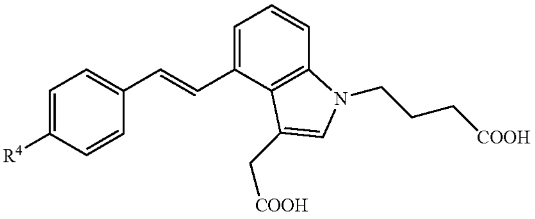
| | R⁴— |
|---|---|
| 55 | 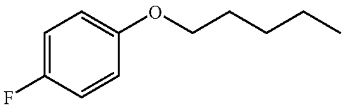 |
| 56 | 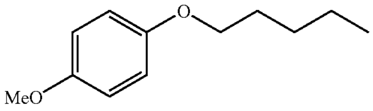 |
| 57 | 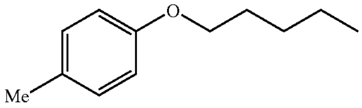 |
| 58 | 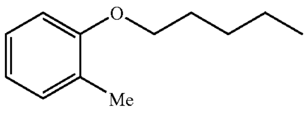 |
| 59 | 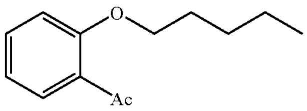 |
| 60 | 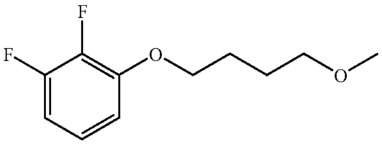 |
| 61 | 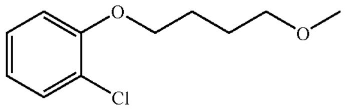 |
| 62 | 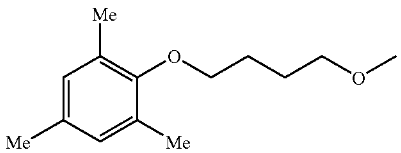 |

TABLE 29-continued
(I-DD)
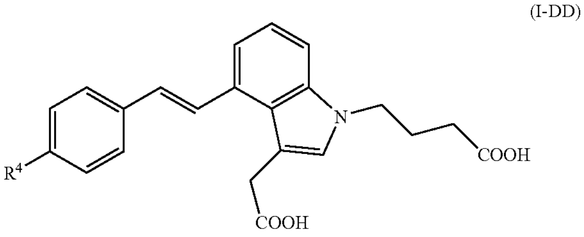
| | $R^4$— |
|---|---|
| 63 | 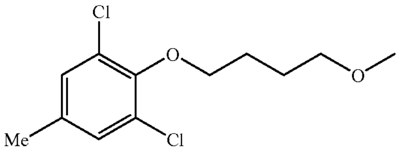 |
| 64 | 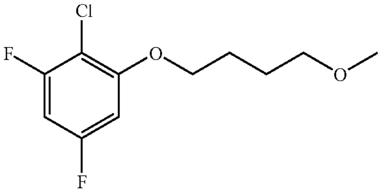 |
| 65 | 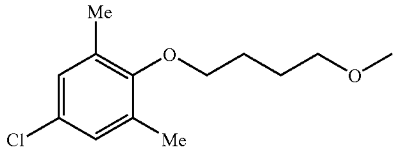 |
| 66 | 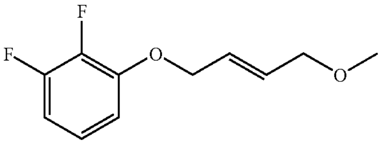 |
| 67 | 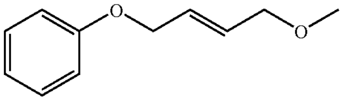 |
| 68 | 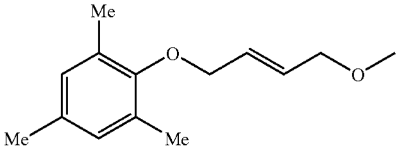 |
| 69 | 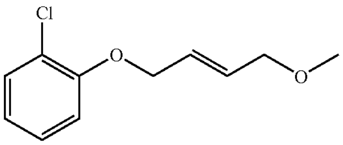 |
TABLE 30
(I-EE)
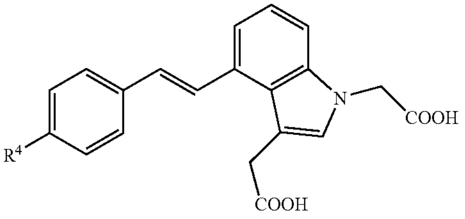
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 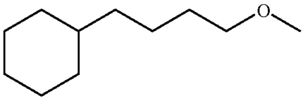 |
| 8 | 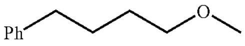 |
| 9 | 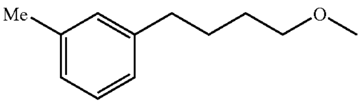 |
| 10 | 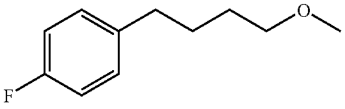 |
| 11 | 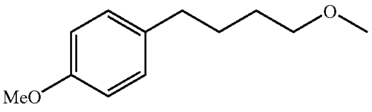 |
| 12 | 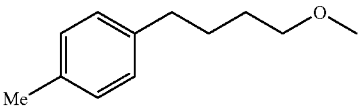 |
| 13 | 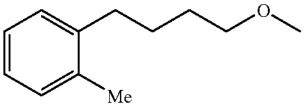 |
| 14 | 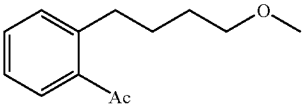 |
| 15 | 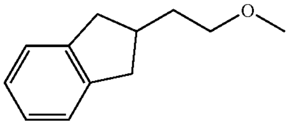 |
| 16 | 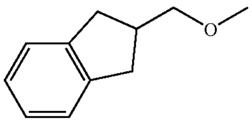 |

TABLE 30-continued
(I-EE)
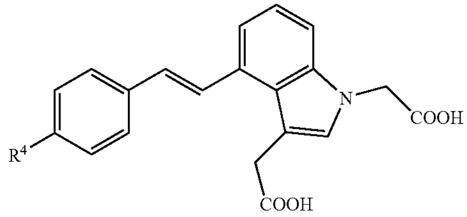
| | $R^4$— |
|---|---|
| 17 | 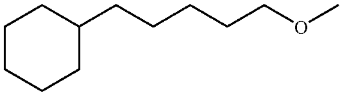 |
| 18 | 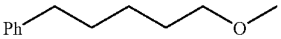 |
| 19 | 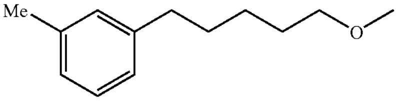 |
| 20 | 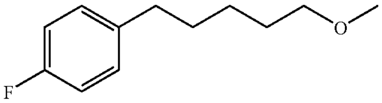 |
| 21 | 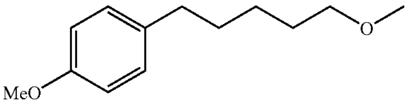 |
| 22 | 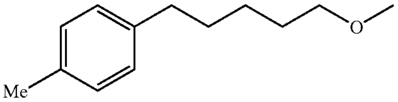 |
| 23 | 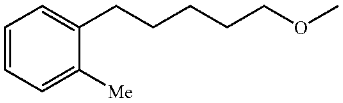 |
| 24 | 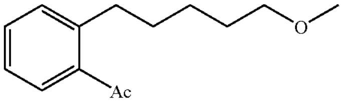 |
| 25 | 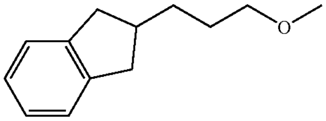 |
| 26 | 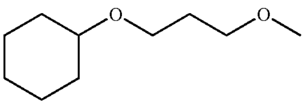 |
| 27 | 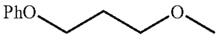 |
| 28 | 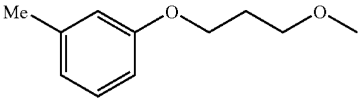 |
TABLE 30-continued
(I-EE)
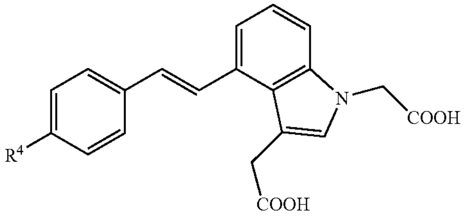
| | $R^4$— |
|---|---|
| 29 | 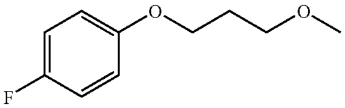 |
| 30 | 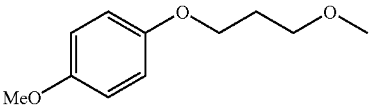 |
| 31 | 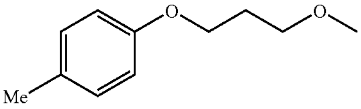 |
| 32 | 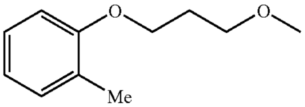 |
| 33 | 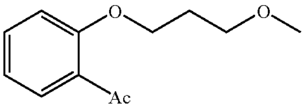 |
| 34 | 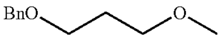 |
| 35 | 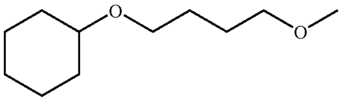 |
| 36 | 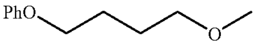 |
| 37 | 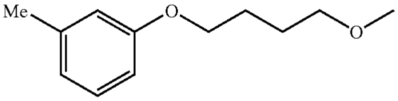 |
| 38 | 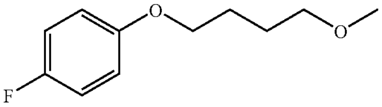 |
| 39 | 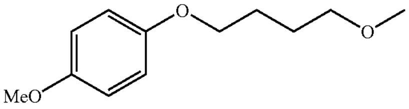 |
| 40 | 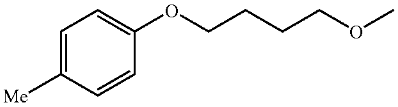 |

TABLE 30-continued
(I-EE)
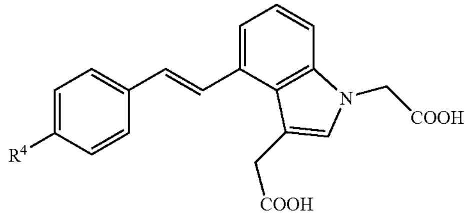
| | R⁴— |
|---|---|
| 41 | 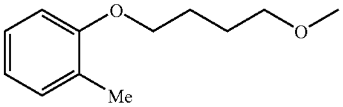 |
| 42 | 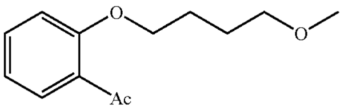 |
| 43 | 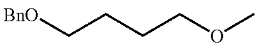 |
| 44 | 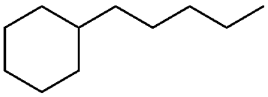 |
| 45 | 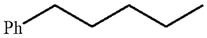 |
| 46 | 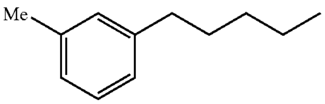 |
| 47 | 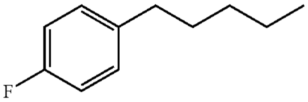 |
| 48 | 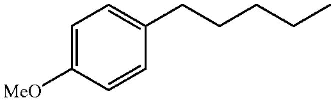 |
| 49 | 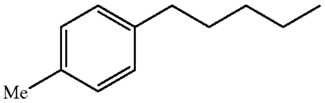 |
| 50 | 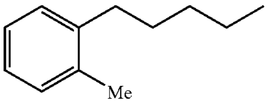 |
| 51 | 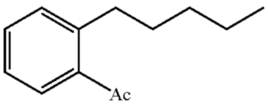 |
| 52 | 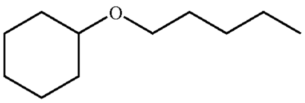 |
TABLE 30-continued
(I-EE)
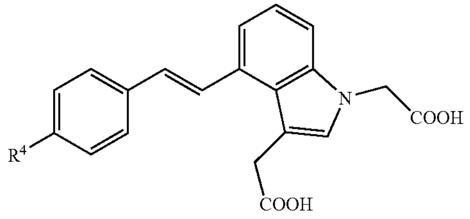
| | R⁴— |
|---|---|
| 53 | 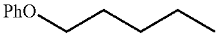 |
| 54 | 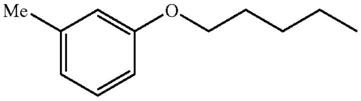 |
| 55 | 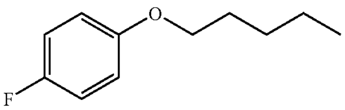 |
| 56 | 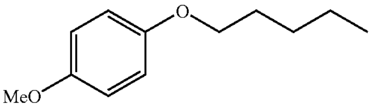 |
| 57 | 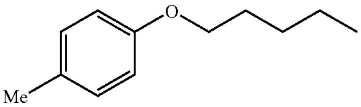 |
| 58 | 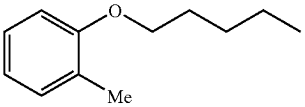 |
| 59 | 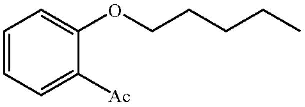 |
| 60 | 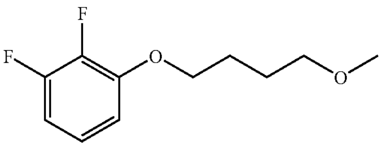 |
| 61 | 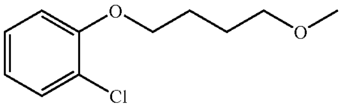 |
| 62 | 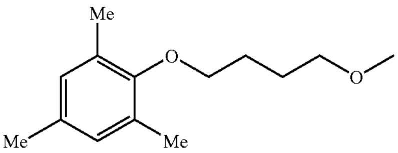 |

TABLE 30-continued
(I-EE)
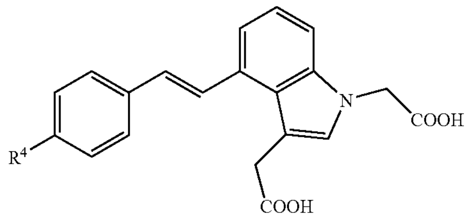
| | $R^4$— |
|---|---|
| 63 | 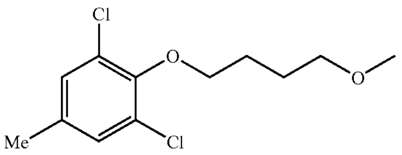 |
| 64 | 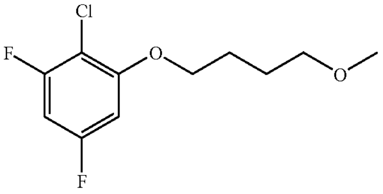 |
| 65 | 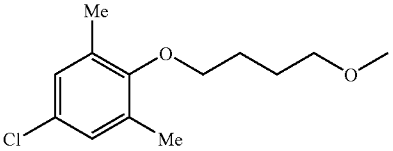 |
| 66 | 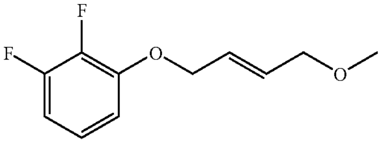 |
| 67 | 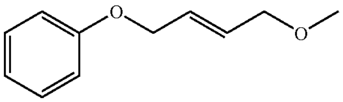 |
| 68 | 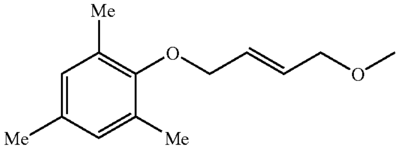 |
| 69 | 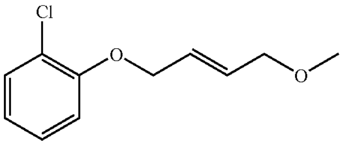 |
TABLE 31
(I-FF)
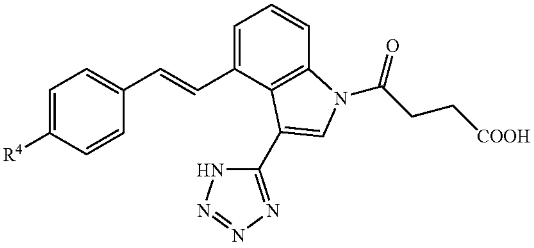
| | $R^4$— |
|---|---|
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |
| 7 | 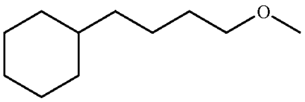 |
| 8 | 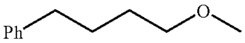 |
| 9 | 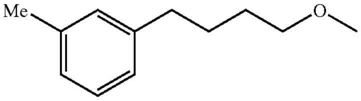 |
| 10 | 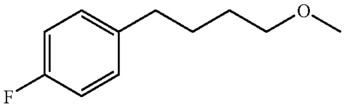 |
| 11 | 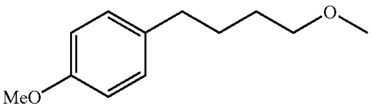 |
| 12 | 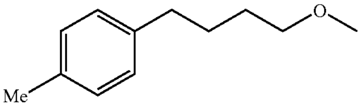 |
| 13 | 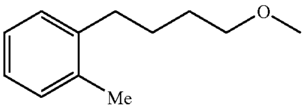 |
| 14 | 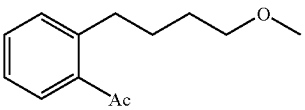 |
| 15 | 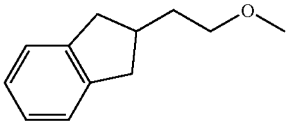 |

TABLE 31-continued
(I-FF)
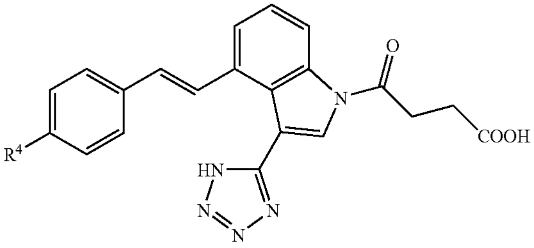
| | $R^4$— |
|---|---|
| 16 | 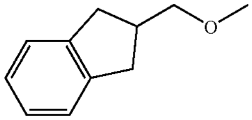 |
| 17 | 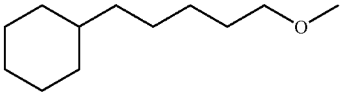 |
| 18 | 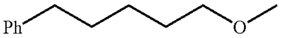 |
| 19 | 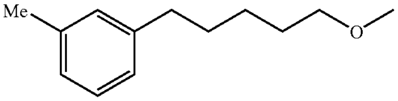 |
| 20 | 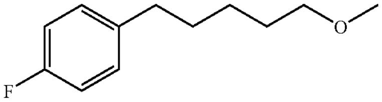 |
| 21 | 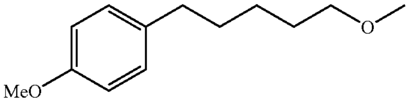 |
| 22 | 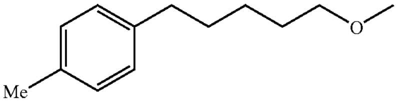 |
| 23 | 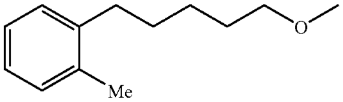 |
| 24 | 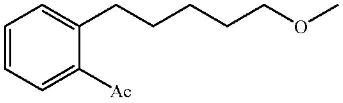 |
| 25 | 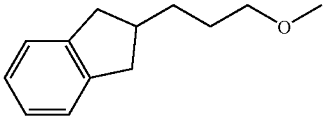 |
| 26 | 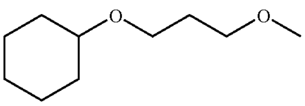 |
| 27 | 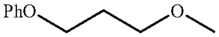 |
TABLE 31-continued
(I-FF)
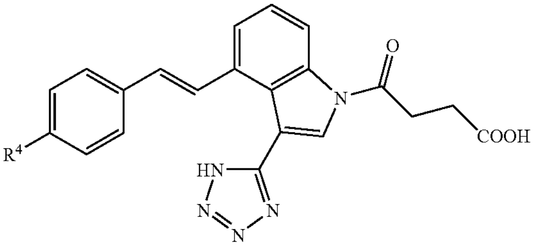
| | $R^4$— |
|---|---|
| 28 | 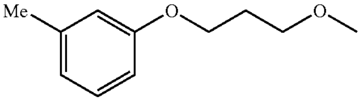 |
| 29 | 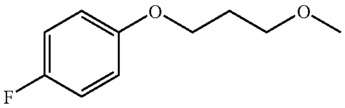 |
| 30 | 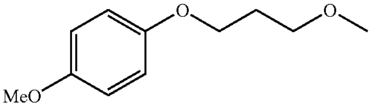 |
| 31 | 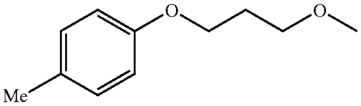 |
| 32 | 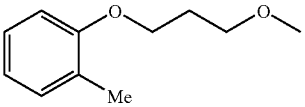 |
| 33 | 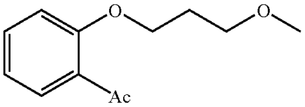 |
| 34 | 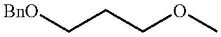 |
| 35 | 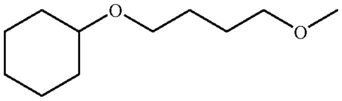 |
| 36 | 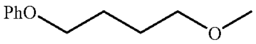 |
| 37 | 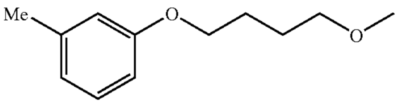 |
| 38 | 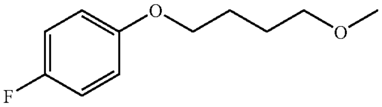 |

TABLE 31-continued
(I-FF)
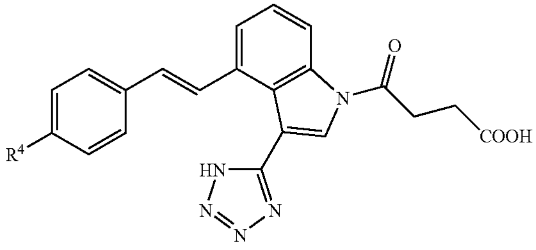
| | $R^4$— |
|---|---|
| 39 | 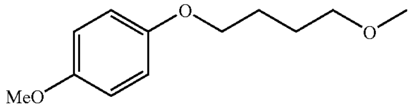 |
| 40 | 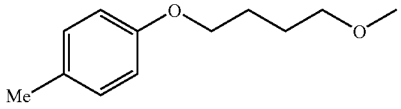 |
| 41 | 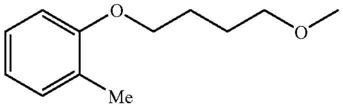 |
| 42 | 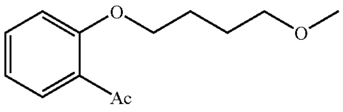 |
| 43 | 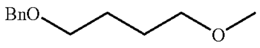 |
| 44 | 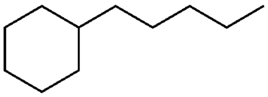 |
| 45 | 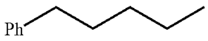 |
| 46 | 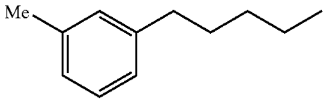 |
| 47 | 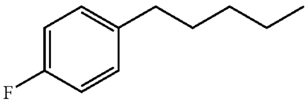 |
| 48 | 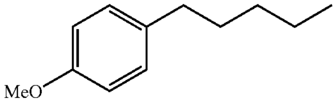 |
| 49 | 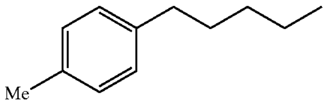 |
| 50 | 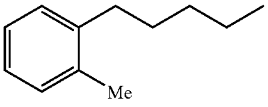 |
TABLE 31-continued
(I-FF)
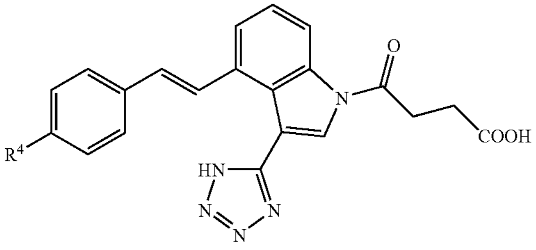
| | $R^4$— |
|---|---|
| 51 | 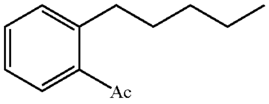 |
| 52 | 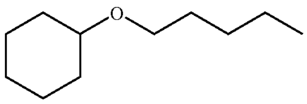 |
| 53 | 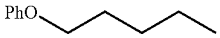 |
| 54 | 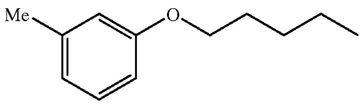 |
| 55 | 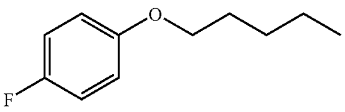 |
| 56 | 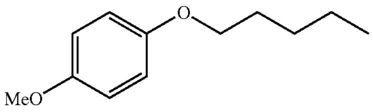 |
| 57 | 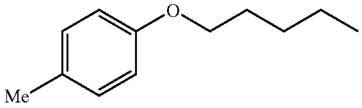 |
| 58 | 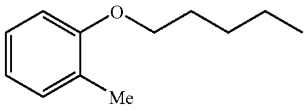 |
| 59 | 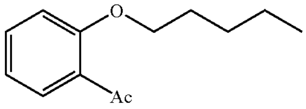 |
| 60 | 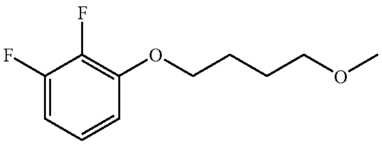 |

TABLE 31-continued
(I-FF)
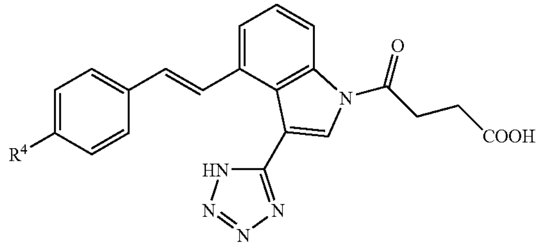
| R⁴— |
|---|
| 61 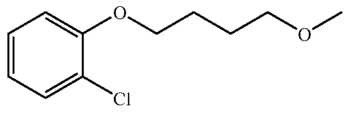 |
| 62 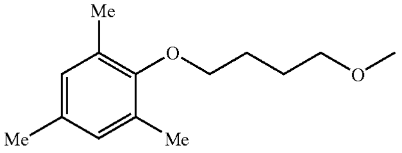 |
| 63 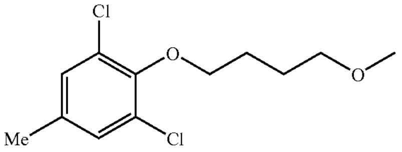 |
| 64 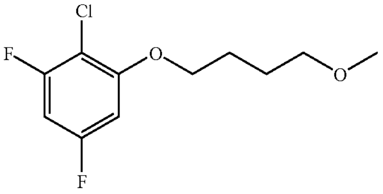 |
| 65 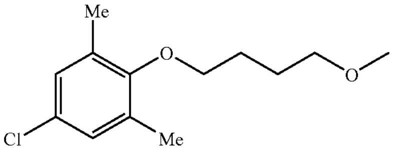 |
| 66 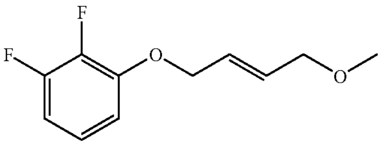 |
| 67 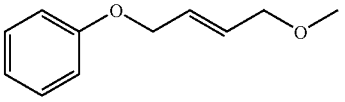 |
| 68 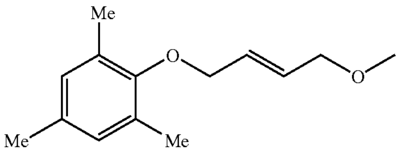 |
TABLE 31-continued
(I-FF)
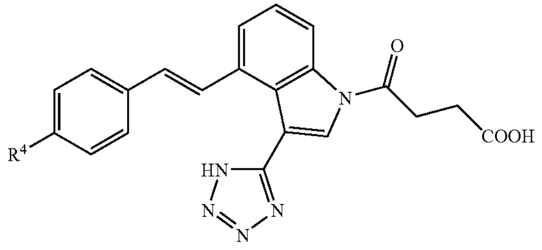
| R⁴— |
|---|
| 69 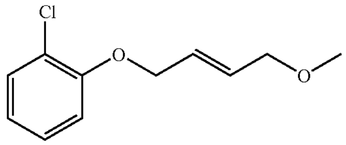 |
TABLE 32
(I-GG)
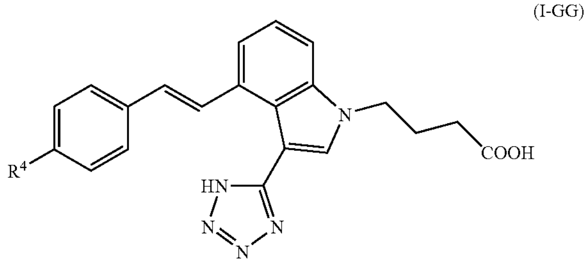
| | R⁴— |
|---|---|
| 1 | $n\text{-}C_4H_9^-$ |
| 2 | $n\text{-}C_5H_{11}^-$ |
| 3 | $n\text{-}C_6H_{13}^-$ |
| 4 | $n\text{-}C_4H_9\text{—}O^-$ |
| 5 | $n\text{-}C_5H_{11}\text{—}O^-$ |
| 6 | $n\text{-}C_6H_{13}\text{—}O^-$ |
| 7 | 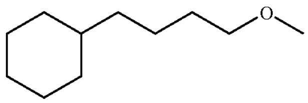 |
| 8 | 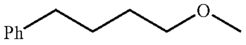 |
| 9 | 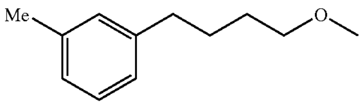 |
| 10 | 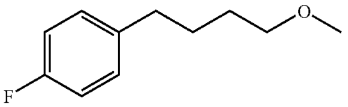 |
| 11 | 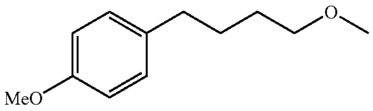 |

TABLE 32-continued
(I-GG)
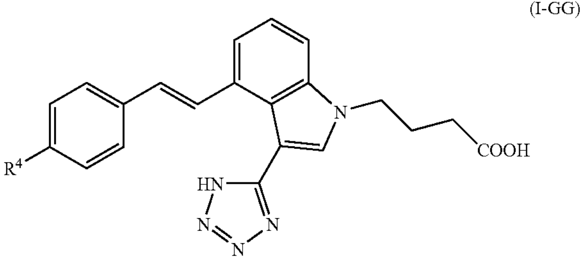
| | $R^4$— |
|---|---|
| 12 | 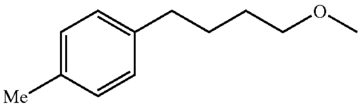 |
| 13 | 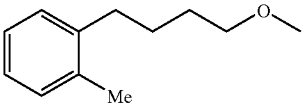 |
| 14 | 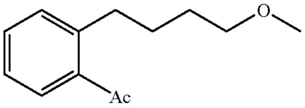 |
| 15 | 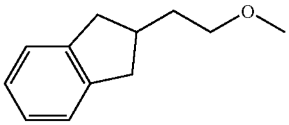 |
| 16 | 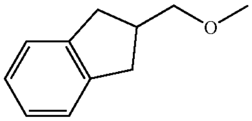 |
| 17 | 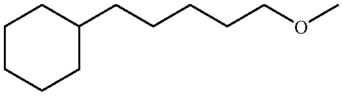 |
| 18 | 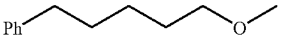 |
| 19 | 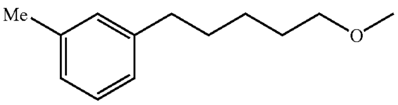 |
| 20 | 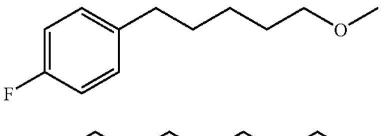 |
| 21 | 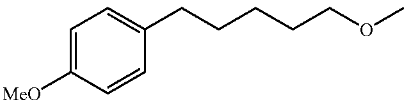 |
| 22 | 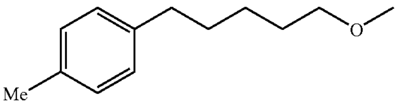 |
TABLE 32-continued
(I-GG)
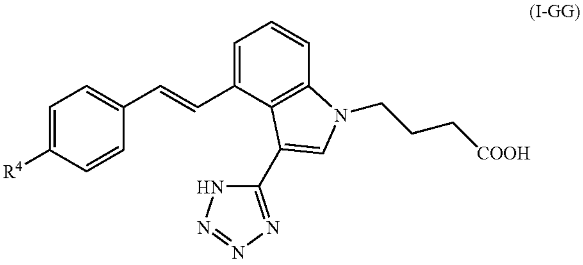
| | $R^4$— |
|---|---|
| 23 | 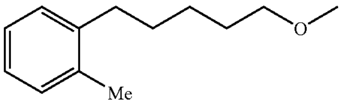 |
| 24 | 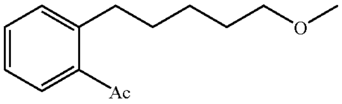 |
| 25 | 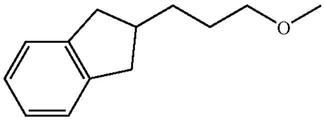 |
| 26 | 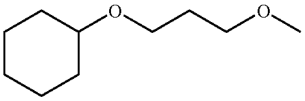 |
| 27 | 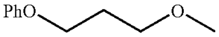 |
| 28 | 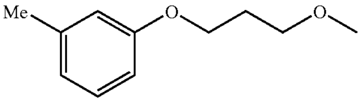 |
| 29 | 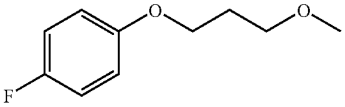 |
| 30 | 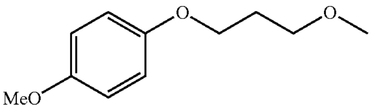 |
| 31 | 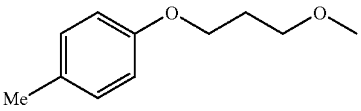 |
| 32 | 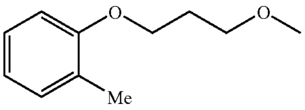 |
| 33 | 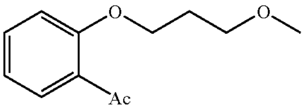 |

TABLE 32-continued
(I-GG)
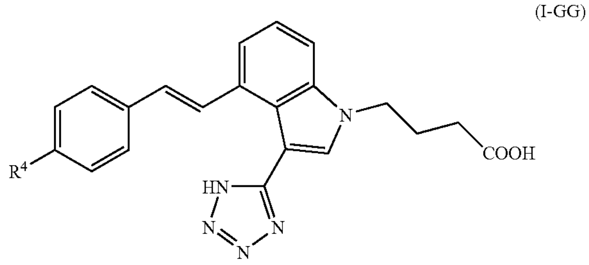
| | $R^4$— |
|---|---|
| 34 | 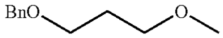 |
| 35 | 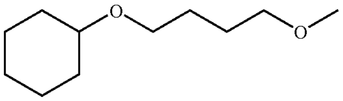 |
| 36 | 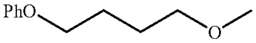 |
| 37 | 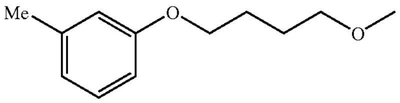 |
| 38 | 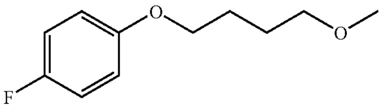 |
| 39 | 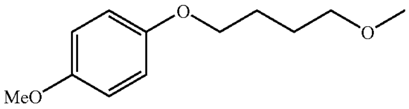 |
| 40 | 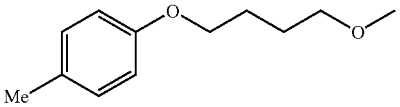 |
| 41 | 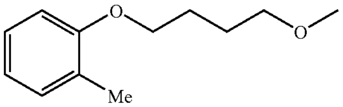 |
| 42 | 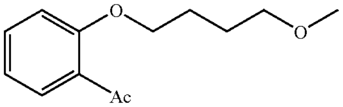 |
| 43 | 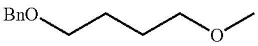 |
| 44 | 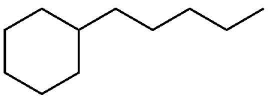 |
| 45 | 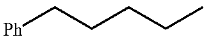 |
| 46 | 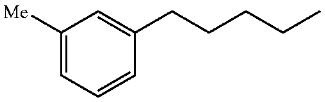 |
TABLE 32-continued
(I-GG)
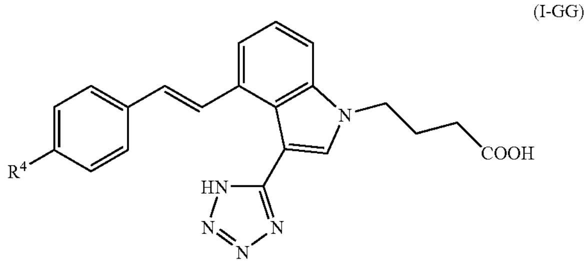
| | $R^4$— |
|---|---|
| 47 | 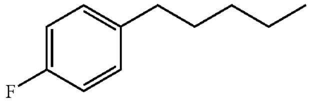 |
| 48 | 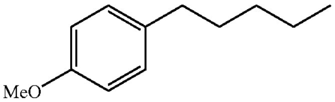 |
| 49 | 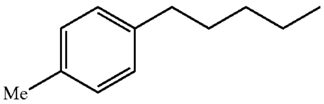 |
| 50 | 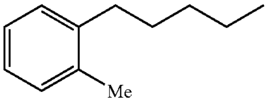 |
| 51 | 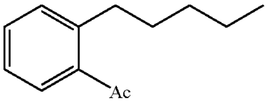 |
| 52 | 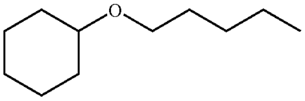 |
| 53 | 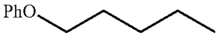 |
| 54 | 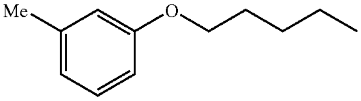 |
| 55 | 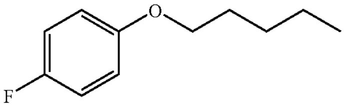 |
| 56 | 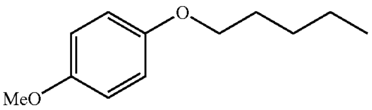 |
| 57 | 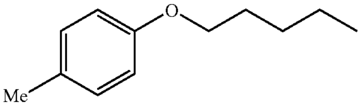 |

TABLE 32-continued
(I-GG)
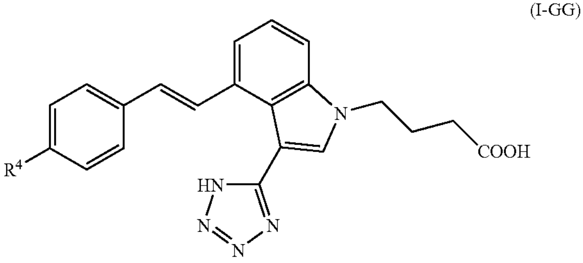
| | $R^4$— |
|---|---|
| 58 | 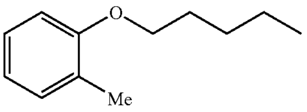 |
| 59 | 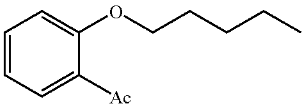 |
| 60 | 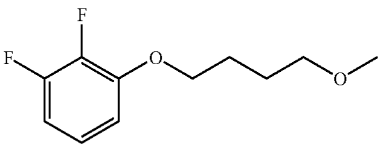 |
| 61 | 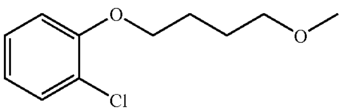 |
| 62 | 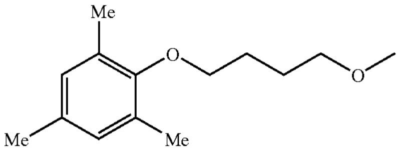 |
| 63 | 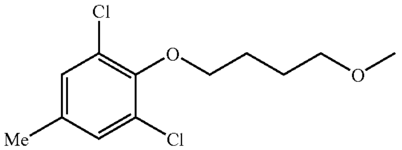 |
| 64 | 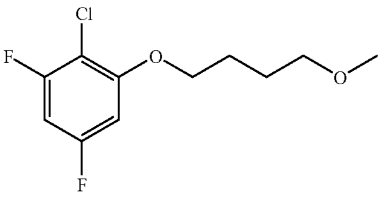 |
| 65 | 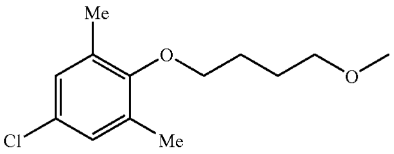 |
TABLE 32-continued
(I-GG)
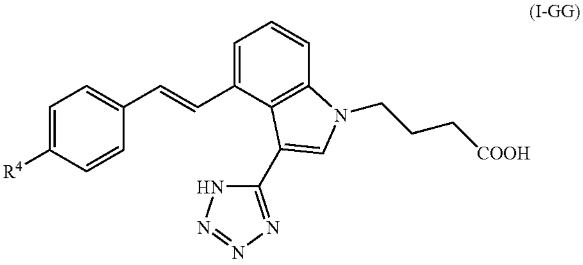
| | $R^4$— |
|---|---|
| 66 | 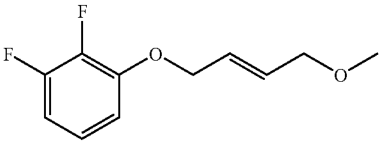 |
| 67 | 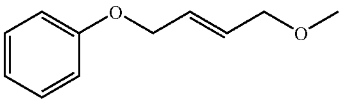 |
| 68 | 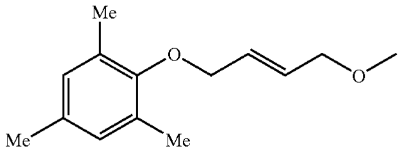 |
| 69 | 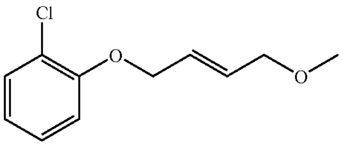 |
TABLE 33
(I-HH)
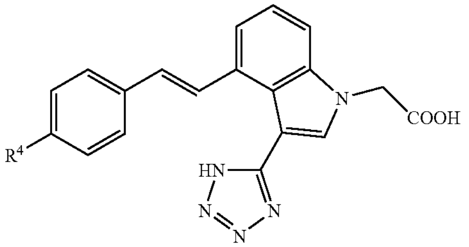
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 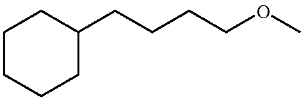 |
| 8 | 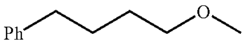 |

TABLE 33-continued
(I-HH)
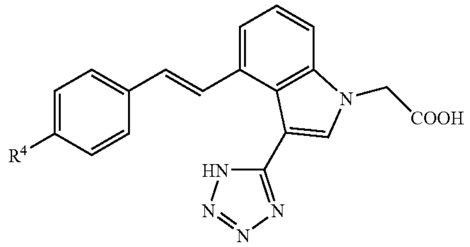
| | $R^4$— |
|---|---|
| 9 | 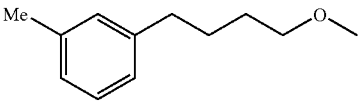 |
| 10 | 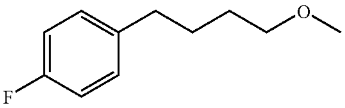 |
| 11 | 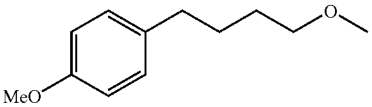 |
| 12 | 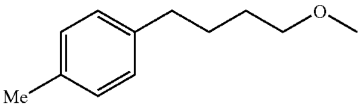 |
| 13 | 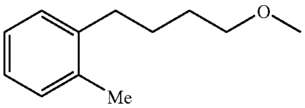 |
| 14 | 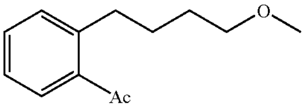 |
| 15 | 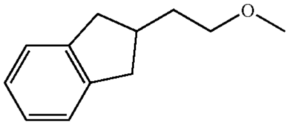 |
| 16 | 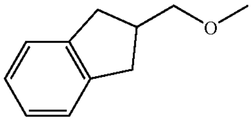 |
| 17 | 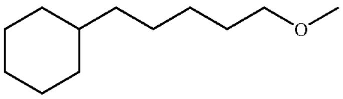 |
| 18 | 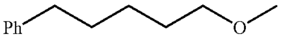 |
TABLE 33-continued
(I-HH)
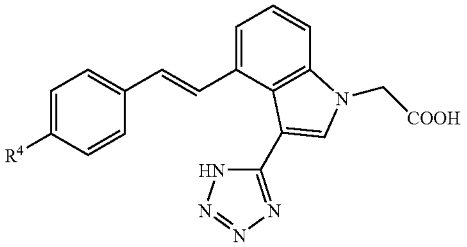
| | $R^4$— |
|---|---|
| 19 | 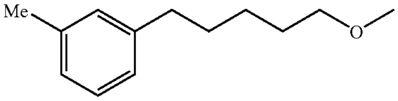 |
| 20 | 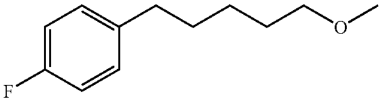 |
| 21 | 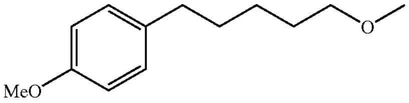 |
| 22 | 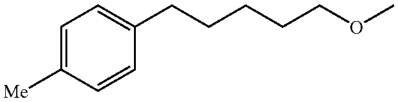 |
| 23 | 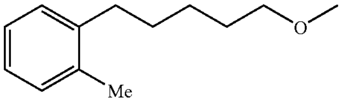 |
| 24 | 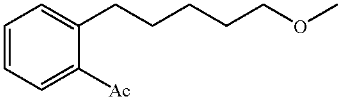 |
| 25 | 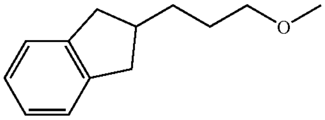 |
| 26 | 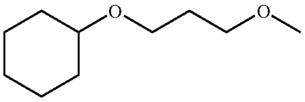 |
| 27 | 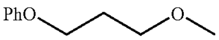 |
| 28 | 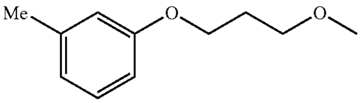 |
| 29 | 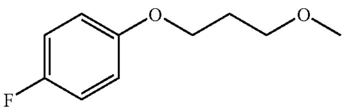 |

TABLE 33-continued
(I-HH)
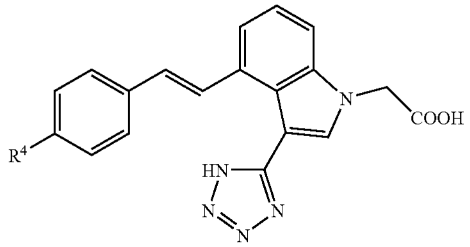
| | $R^4$— |
|---|---|
| 30 | 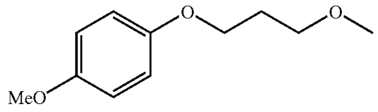 |
| 31 | 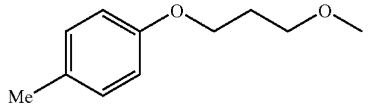 |
| 32 | 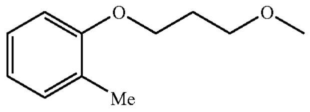 |
| 33 | 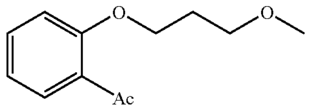 |
| 34 | 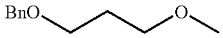 |
| 35 | 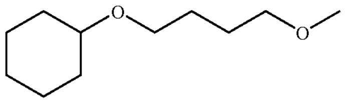 |
| 36 | 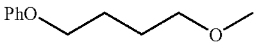 |
| 37 | 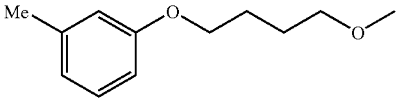 |
| 38 | 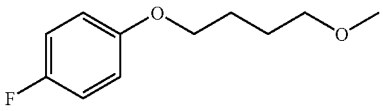 |
| 39 | 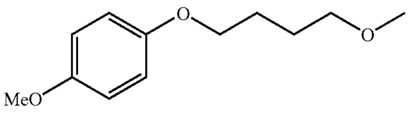 |
| 40 | 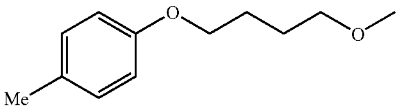 |
TABLE 33-continued
(I-HH)
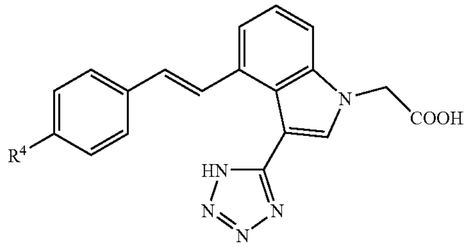
| | $R^4$— |
|---|---|
| 41 | 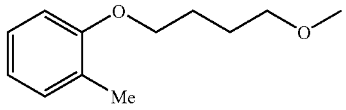 |
| 42 | 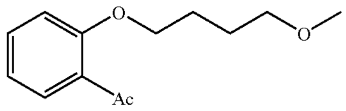 |
| 43 | 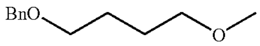 |
| 44 | 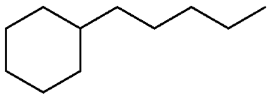 |
| 45 | 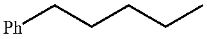 |
| 46 | 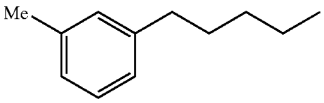 |
| 47 | 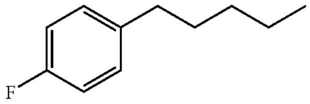 |
| 48 | 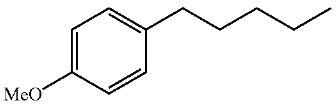 |
| 49 | 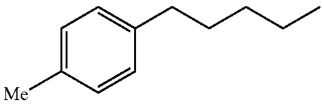 |
| 50 | 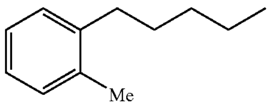 |
| 51 | 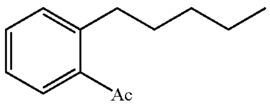 |
| 52 | 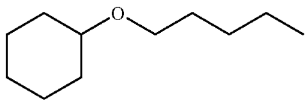 |

TABLE 33-continued
(I-HH)
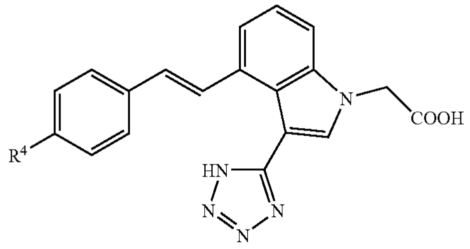
| | $R^4$— |
| --- | --- |
| 53 | 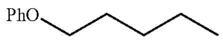 |
| 54 | 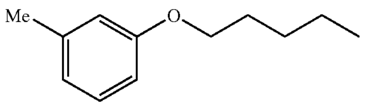 |
| 55 | 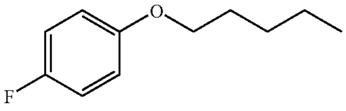 |
| 56 | 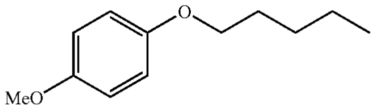 |
| 57 | 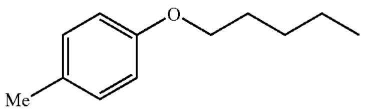 |
| 58 | 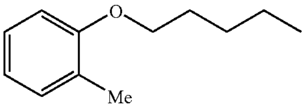 |
| 59 | 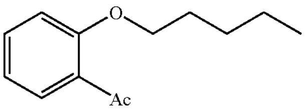 |
| 60 | 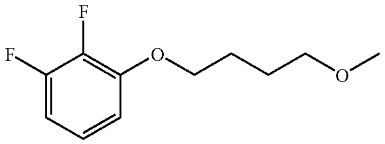 |
| 61 | 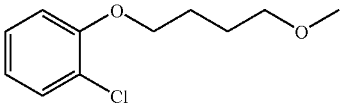 |
| 62 | 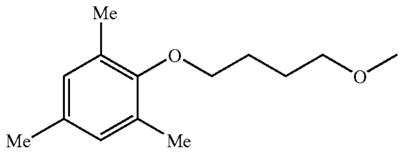 |
TABLE 33-continued
(I-HH)
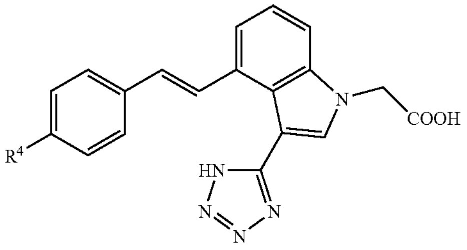
| | $R^4$— |
| --- | --- |
| 63 | 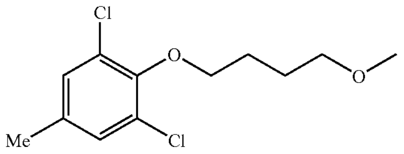 |
| 64 | 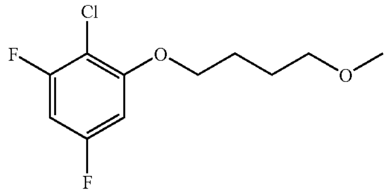 |
| 65 | 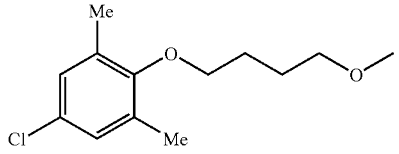 |
| 66 | 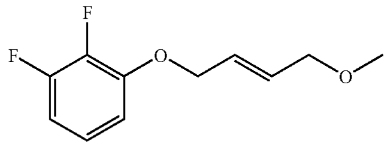 |
| 67 | 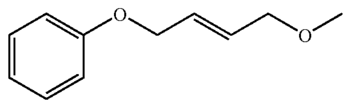 |
| 68 | 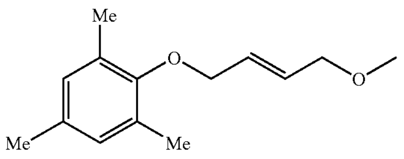 |
| 69 | 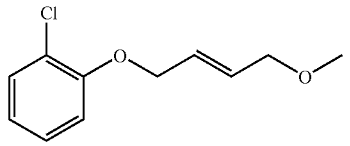 |

TABLE 34
(I-JJ)
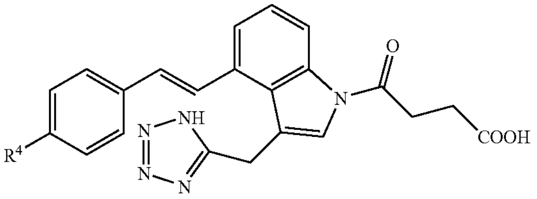
| | $R^4$— |
|---|---|
| 1 | $n-C_4H_9^-$ |
| 2 | $n-C_5H_{11}^-$ |
| 3 | $n-C_6H_{13}^-$ |
| 4 | $n-C_4H_9—O^-$ |
| 5 | $n-C_5H_{11}—O^-$ |
| 6 | $n-C_6H_{13}—O^-$ |
| 7 | 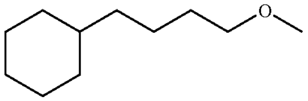 |
| 8 | 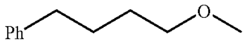 |
| 9 | 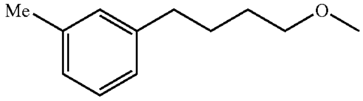 |
| 10 | 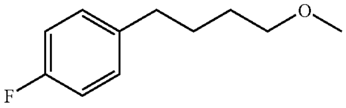 |
| 11 | 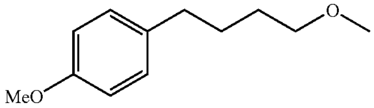 |
| 12 | 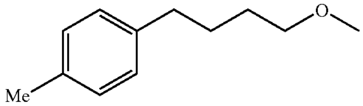 |
| 13 | 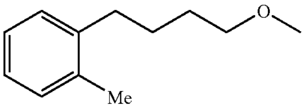 |
| 14 | 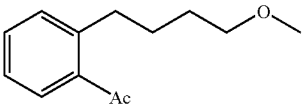 |
| 15 | 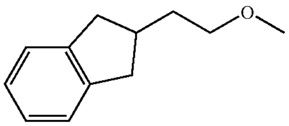 |
| 16 | 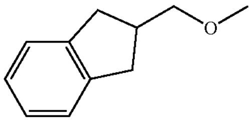 |
TABLE 34-continued
(I-JJ)
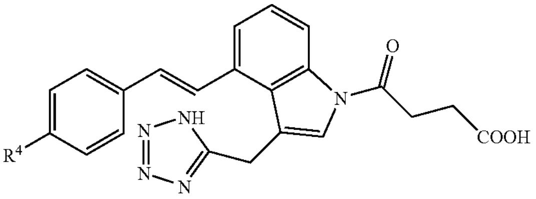
| | $R^4$— |
|---|---|
| 17 | 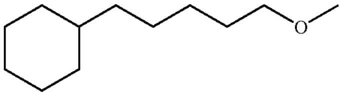 |
| 18 | 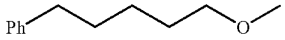 |
| 19 | 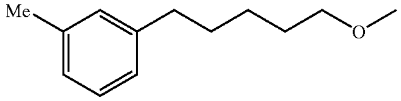 |
| 20 | 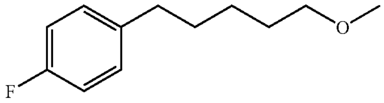 |
| 21 | 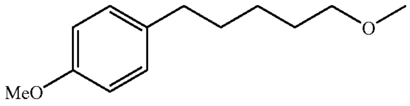 |
| 22 | 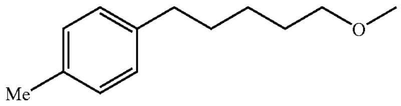 |
| 23 | 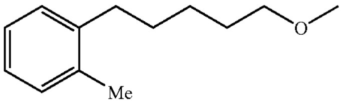 |
| 24 | 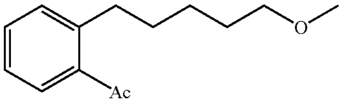 |
| 25 | 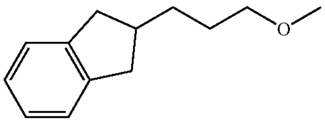 |
| 26 | 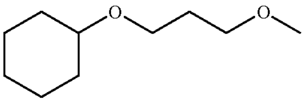 |
| 27 | 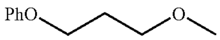 |
| 28 | 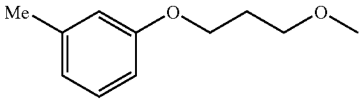 |

TABLE 34-continued
(I-JJ)
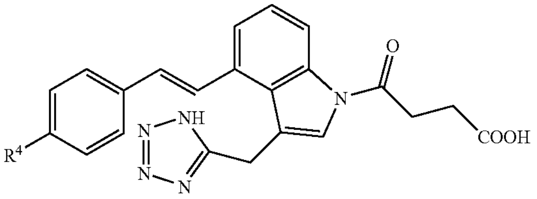
| | $R^4$— |
|---|---|
| 29 | 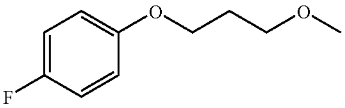 |
| 30 | 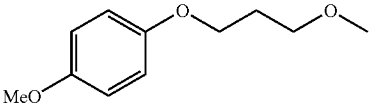 |
| 31 | 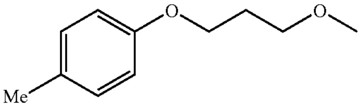 |
| 32 | 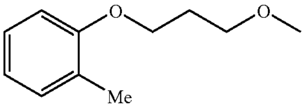 |
| 33 | 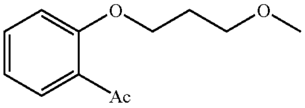 |
| 34 | 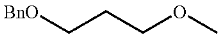 |
| 35 | 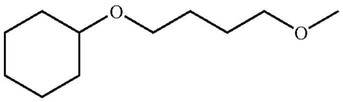 |
| 36 | 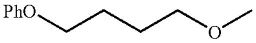 |
| 37 | 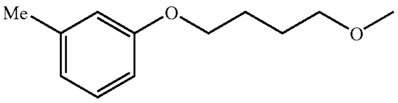 |
| 38 | 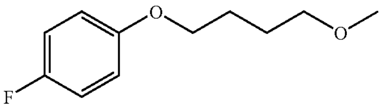 |
| 39 | 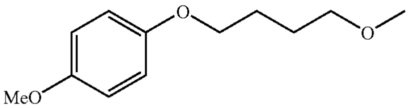 |
| 40 | 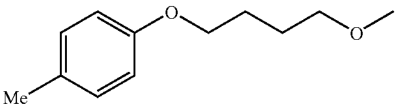 |
TABLE 34-continued
(I-JJ)
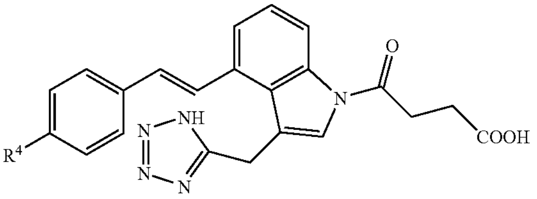
| | $R^4$— |
|---|---|
| 41 | 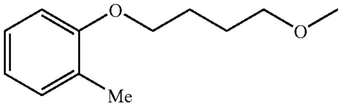 |
| 42 | 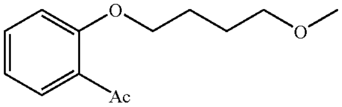 |
| 43 | 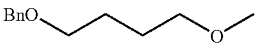 |
| 44 | 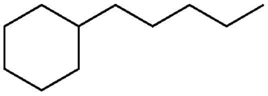 |
| 45 | 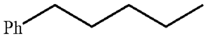 |
| 46 | 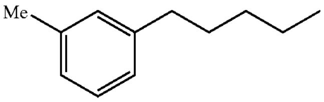 |
| 47 | 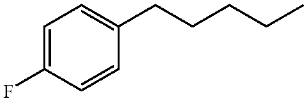 |
| 48 | 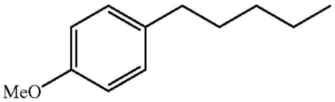 |
| 49 | 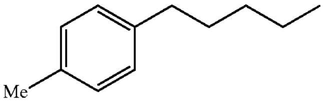 |
| 50 | 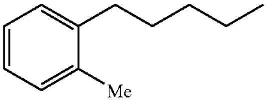 |
| 51 | 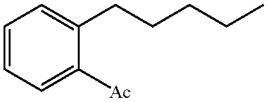 |
| 52 | 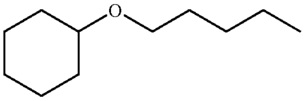 |

TABLE 34-continued
(I-JJ)
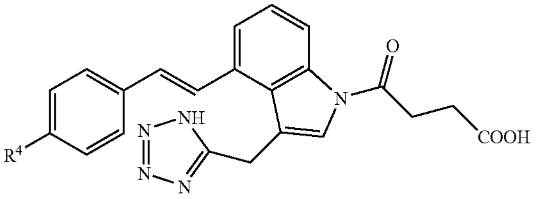
| | $R^4$— |
|---|---|
| 53 | 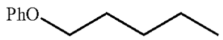 |
| 54 | 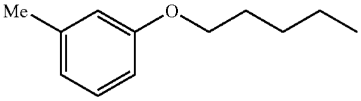 |
| 55 | 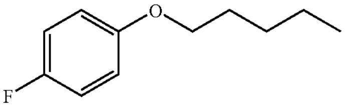 |
| 56 | 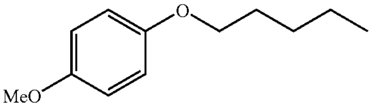 |
| 57 | 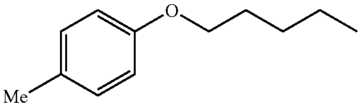 |
| 58 | 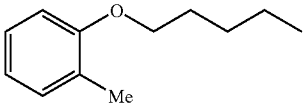 |
| 59 | 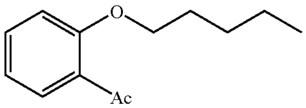 |
| 60 | 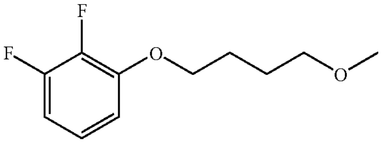 |
| 61 | 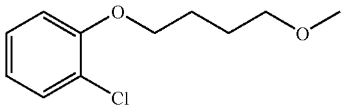 |
| 62 | 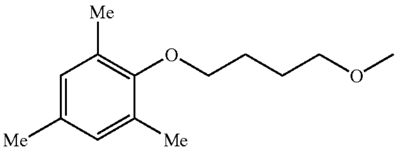 |
TABLE 34-continued
(I-JJ)
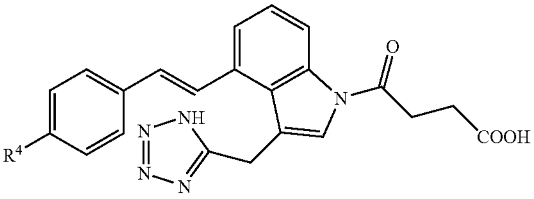
| | $R^4$— |
|---|---|
| 63 | 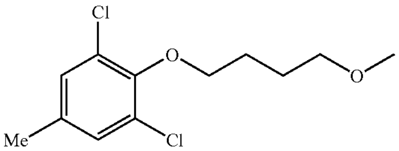 |
| 64 | 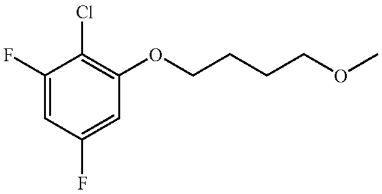 |
| 65 | 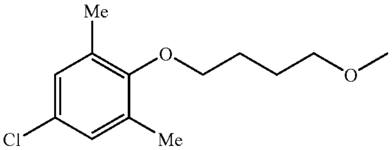 |
| 66 | 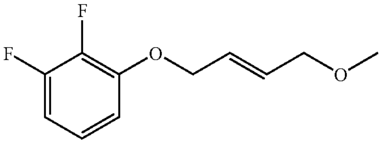 |
| 67 | 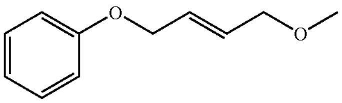 |
| 68 | 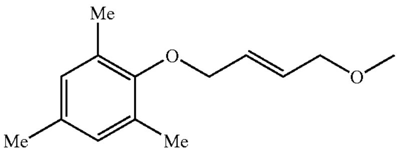 |
| 69 | 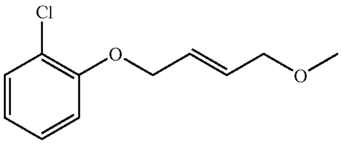 |

TABLE 35
(I-KK)
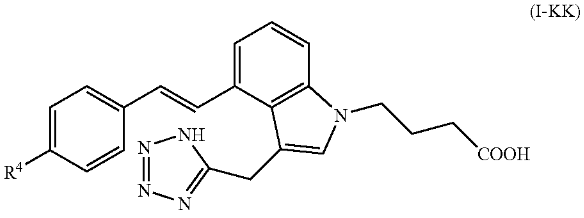
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 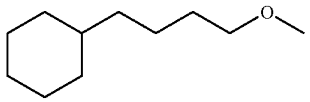 |
| 8 | 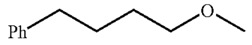 |
| 9 | 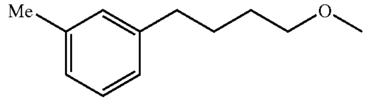 |
| 10 | 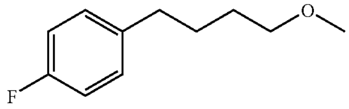 |
| 11 | 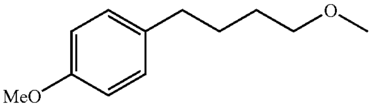 |
| 12 | 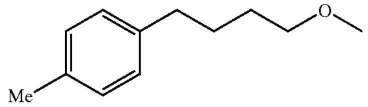 |
| 13 | 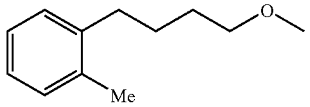 |
| 14 | 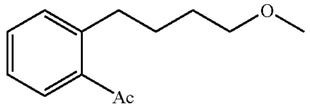 |
| 15 | 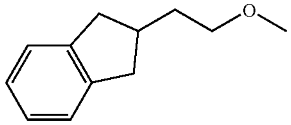 |
| 16 | 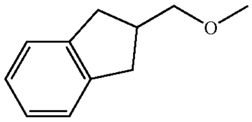 |
TABLE 35-continued
(I-KK)
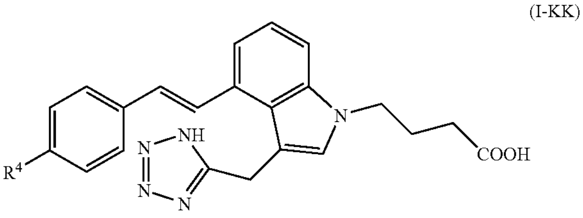
| | $R^4$— |
|---|---|
| 17 | 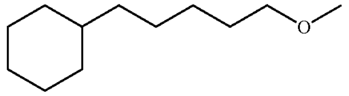 |
| 18 | 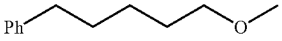 |
| 19 | 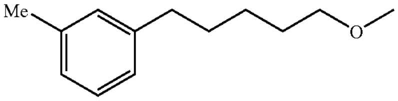 |
| 20 | 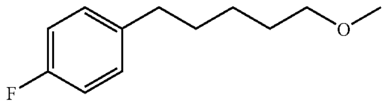 |
| 21 | 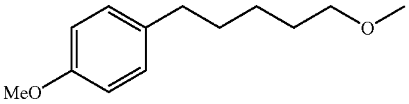 |
| 22 | 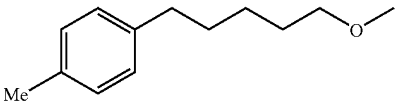 |
| 23 | 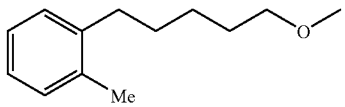 |
| 24 | 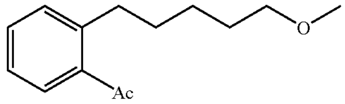 |
| 25 | 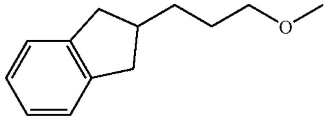 |
| 26 | 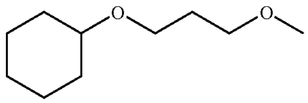 |
| 27 | 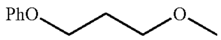 |
| 28 | 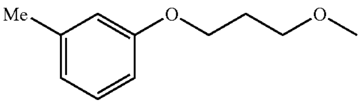 |

TABLE 35-continued
(I-KK)
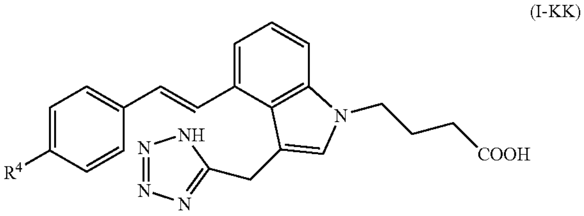
| | $R^4$— |
|---|---|
| 29 | 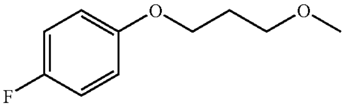 |
| 30 | 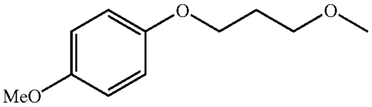 |
| 31 | 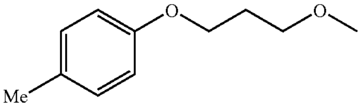 |
| 32 | 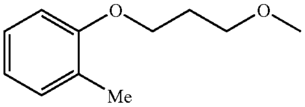 |
| 33 | 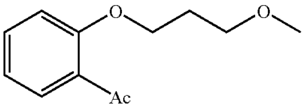 |
| 34 | 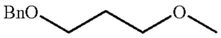 |
| 35 | 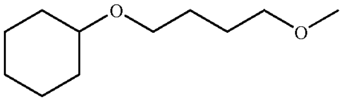 |
| 36 | 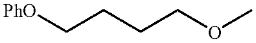 |
| 37 | 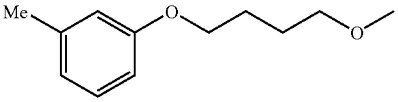 |
| 38 | 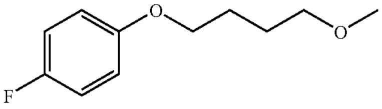 |
| 39 | 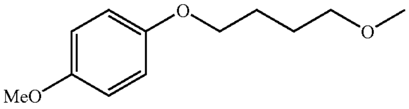 |
| 40 | 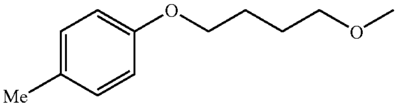 |
TABLE 35-continued
(I-KK)
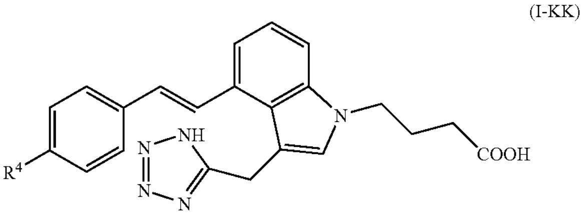
| | $R^4$— |
|---|---|
| 41 | 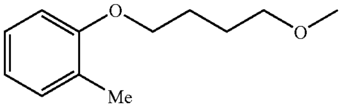 |
| 42 | 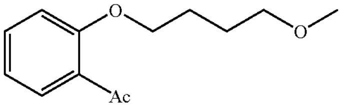 |
| 43 | 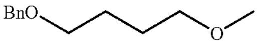 |
| 44 | 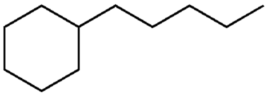 |
| 45 | 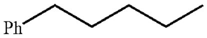 |
| 46 | 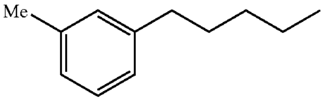 |
| 47 | 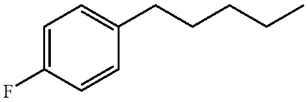 |
| 48 | 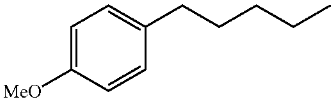 |
| 49 | 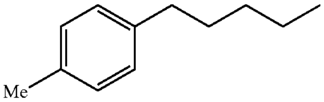 |
| 50 | 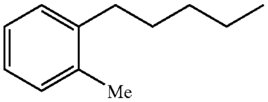 |
| 51 | 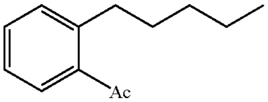 |
| 52 | 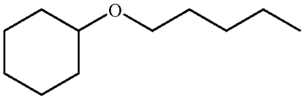 |
| 53 | 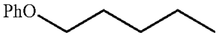 |

TABLE 35-continued
(I-KK)
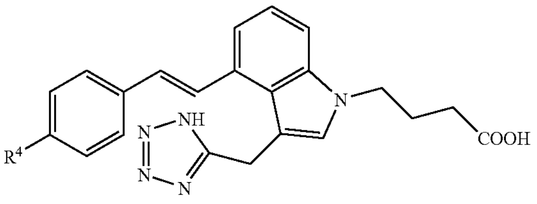
| | $R^4$— |
|---|---|
| 54 | 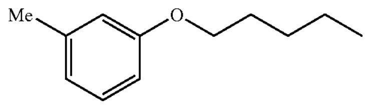 |
| 55 | 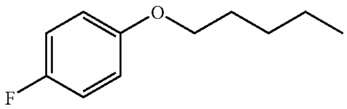 |
| 56 | 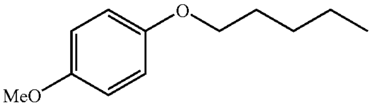 |
| 57 | 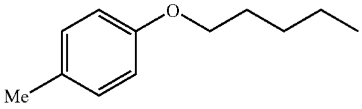 |
| 58 | 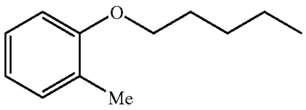 |
| 59 | 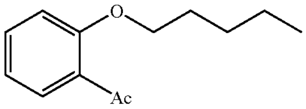 |
| 60 | 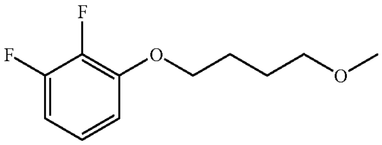 |
| 61 | 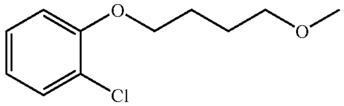 |
TABLE 35-continued
(I-KK)
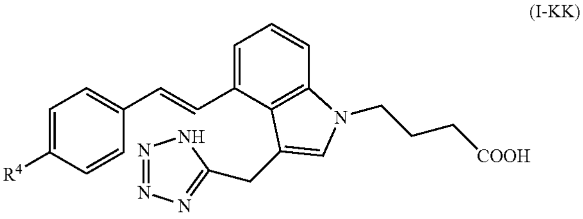
| | $R^4$— |
|---|---|
| 62 | 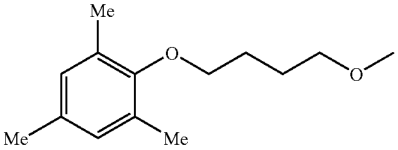 |
| 63 | 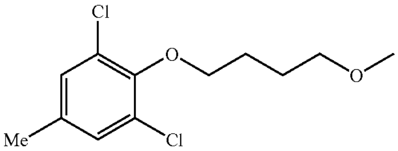 |
| 64 | 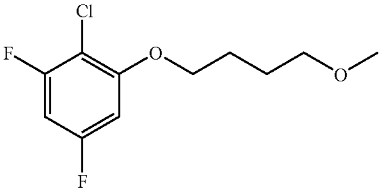 |
| 65 | 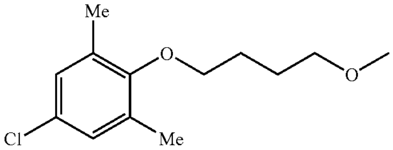 |
| 66 | 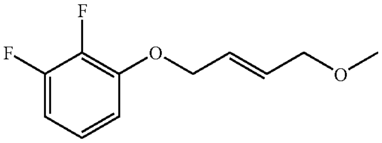 |
| 67 | 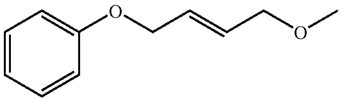 |
| 68 | 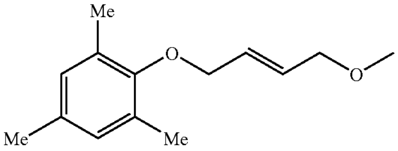 |
| 69 | 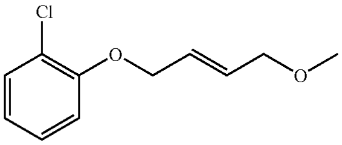 |

TABLE 36
(I-LL)
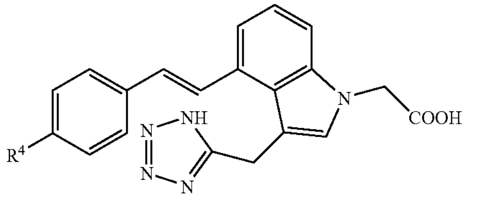
| | $R^4$— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 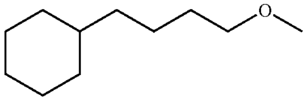 |
| 8 | 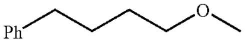 |
| 9 | 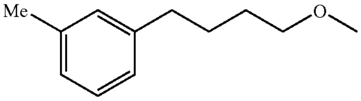 |
| 10 | 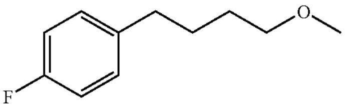 |
| 11 | 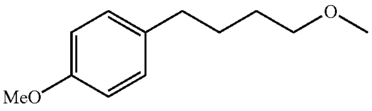 |
| 12 | 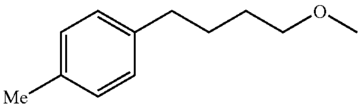 |
| 13 | 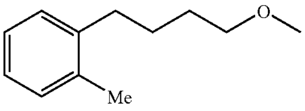 |
| 14 | 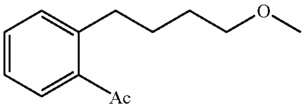 |
| 15 | 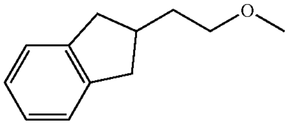 |
| 16 | 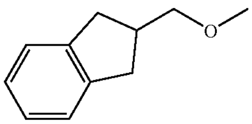 |
TABLE 36-continued
(I-LL)
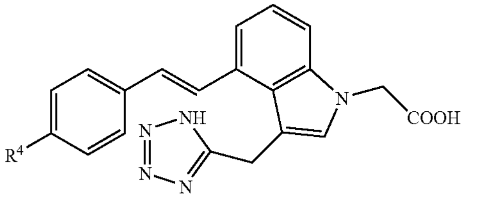
| | $R^4$— |
|---|---|
| 17 | 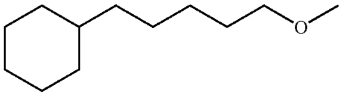 |
| 18 | 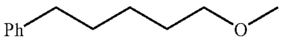 |
| 19 | 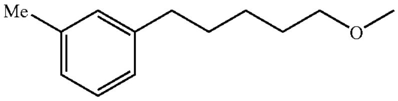 |
| 20 | 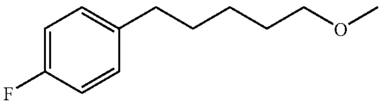 |
| 21 | 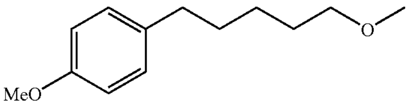 |
| 22 | 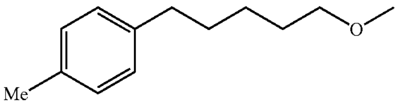 |
| 23 | 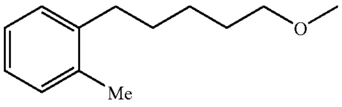 |
| 24 | 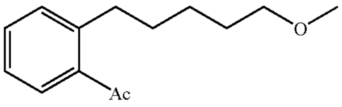 |
| 25 | 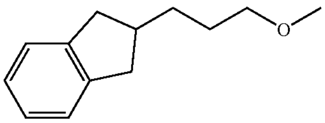 |
| 26 | 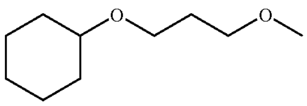 |
| 27 | 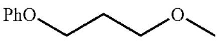 |
| 28 | 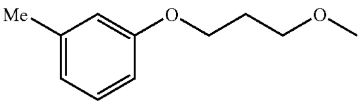 |

TABLE 36-continued
(I-LL)
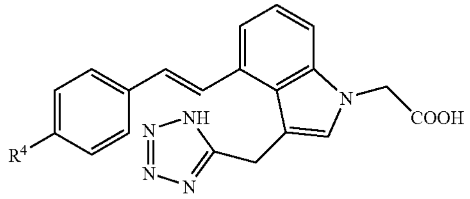
| | R⁴— |
|---|---|
| 29 | 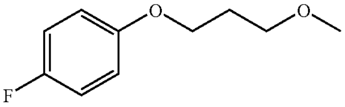 |
| 30 | 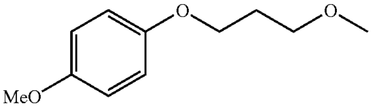 |
| 31 | 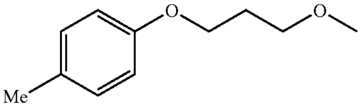 |
| 32 | 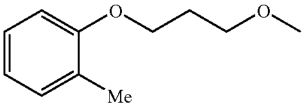 |
| 33 | 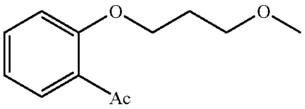 |
| 34 | 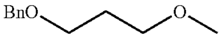 |
| 35 | 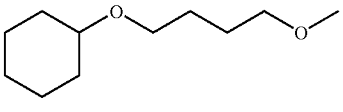 |
| 36 | 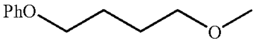 |
| 37 | 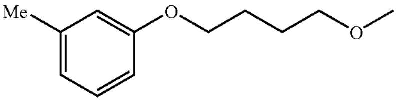 |
| 38 | 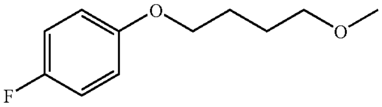 |
| 39 | 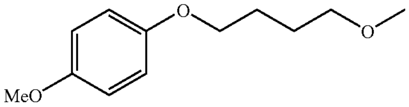 |
| 40 | 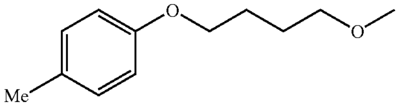 |
TABLE 36-continued
(I-LL)
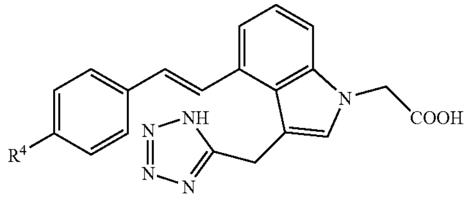
| | R⁴— |
|---|---|
| 41 | 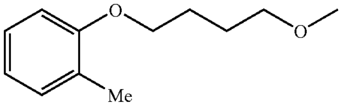 |
| 42 | 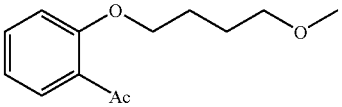 |
| 43 | 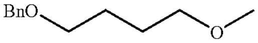 |
| 44 | 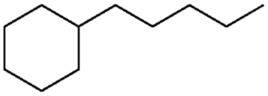 |
| 45 | 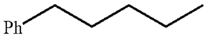 |
| 46 | 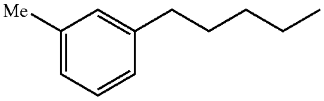 |
| 47 | 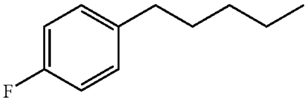 |
| 48 | 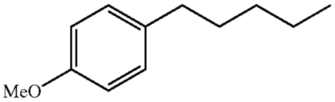 |
| 49 | 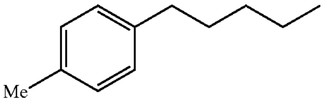 |
| 50 | 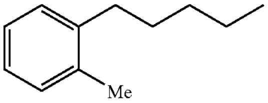 |
| 51 | 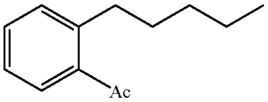 |
| 52 | 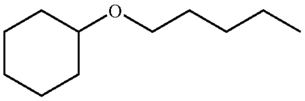 |
| 53 | 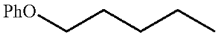 |

TABLE 36-continued
(I-LL)
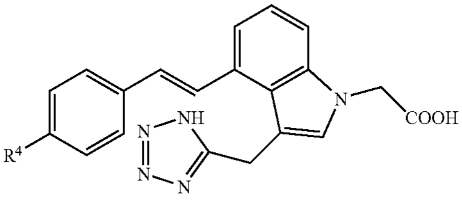
| | $R^4$— |
|---|---|
| 54 | 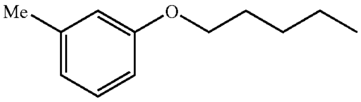 |
| 55 | 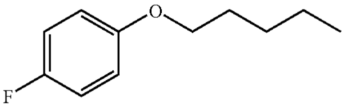 |
| 56 | 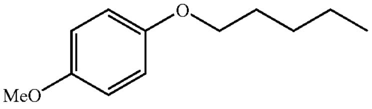 |
| 57 | 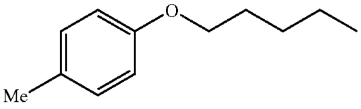 |
| 58 | 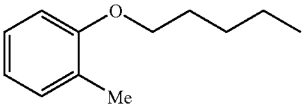 |
| 59 | 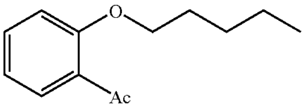 |
| 60 | 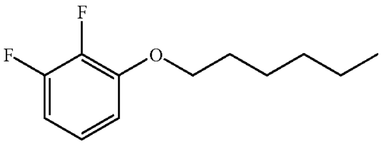 |
| 61 | 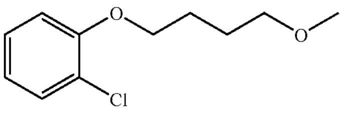 |
| 62 | 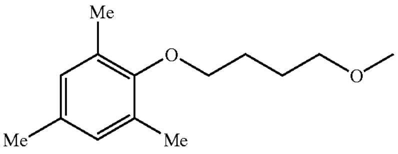 |
TABLE 36-continued
(I-LL)
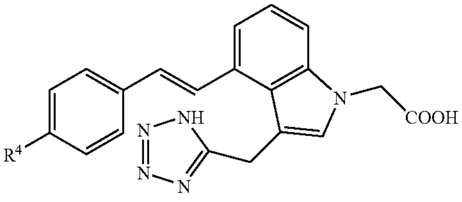
| | $R^4$— |
|---|---|
| 63 | 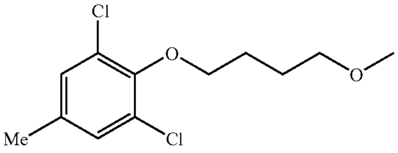 |
| 64 | 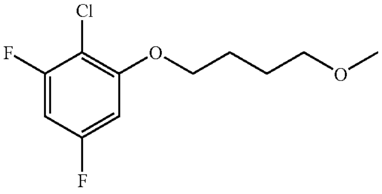 |
| 65 | 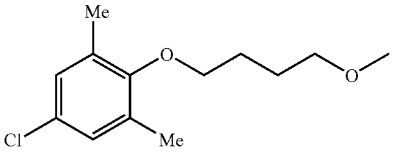 |
| 66 | 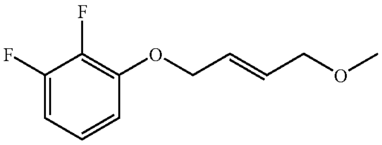 |
| 67 | 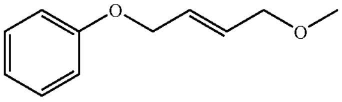 |
| 68 | 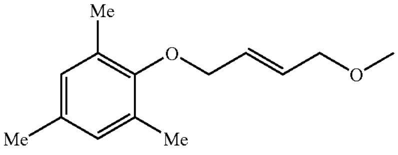 |
| 69 | 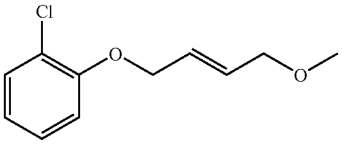 |

TABLE 37
(I-MM)
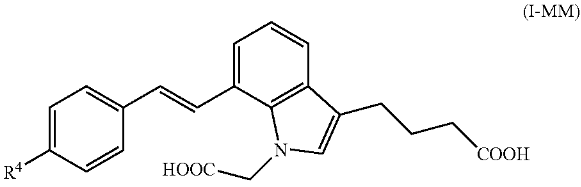
| | $R^4$— |
|---|---|
| 1 | $n-C_4H_9^-$ |
| 2 | $n-C_5H_{11}^-$ |
| 3 | $n-C_6H_{13}^-$ |
| 4 | $n-C_4H_9—O^-$ |
| 5 | $n-C_5H_{11}—O^-$ |
| 6 | $n-C_6H_{13}—O^-$ |
| 7 | 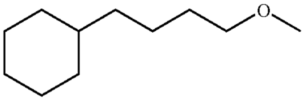 |
| 8 | 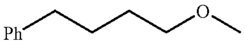 |
| 9 | 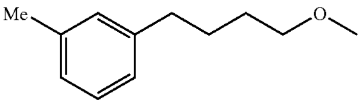 |
| 10 | 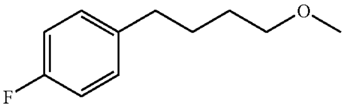 |
| 11 | 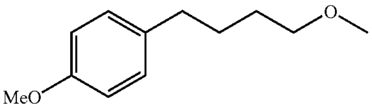 |
| 12 | 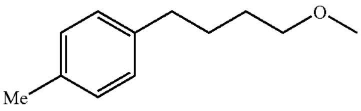 |
| 13 | 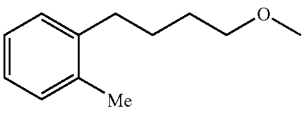 |
| 14 | 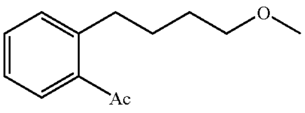 |
| 15 | 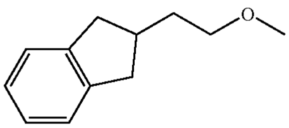 |
| 16 | 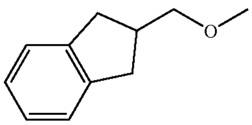 |
TABLE 37-continued
(I-MM)
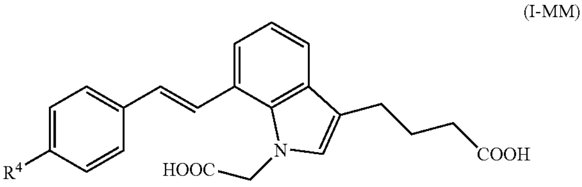
| | $R^4$— |
|---|---|
| 17 | 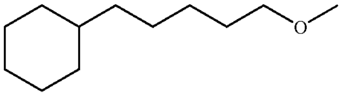 |
| 18 | 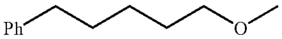 |
| 19 | 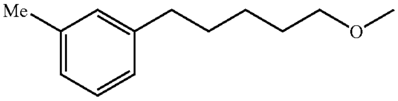 |
| 20 | 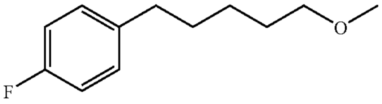 |
| 21 | 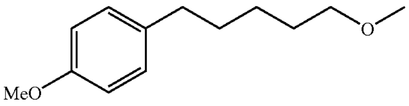 |
| 22 | 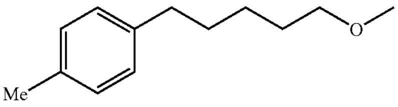 |
| 23 | 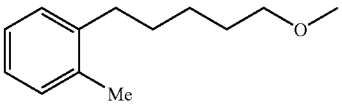 |
| 24 | 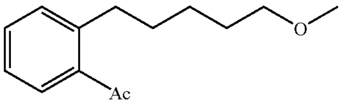 |
| 25 | 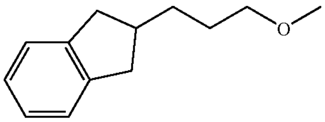 |
| 26 | 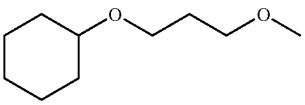 |
| 27 | 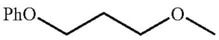 |
| 28 | 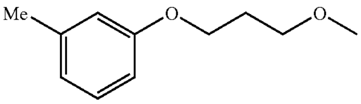 |

TABLE 37-continued
(I-MM)
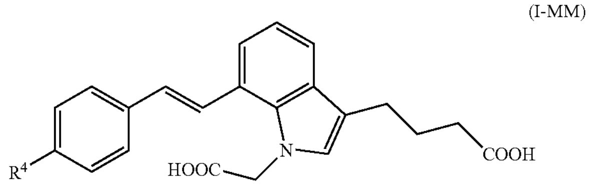
| | $R^4$— |
|---|---|
| 29 | 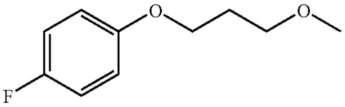 |
| 30 | 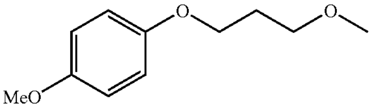 |
| 31 | 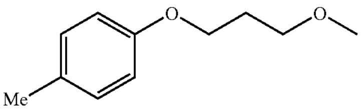 |
| 32 | 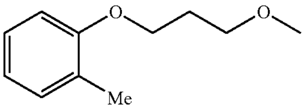 |
| 33 | 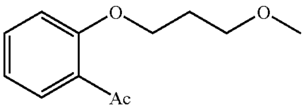 |
| 34 | 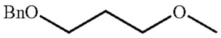 |
| 35 | 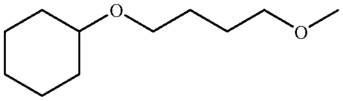 |
| 36 | 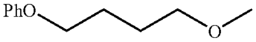 |
| 37 | 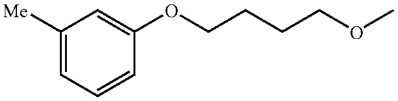 |
| 38 | 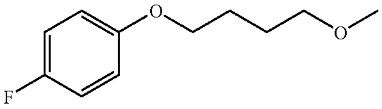 |
| 39 | 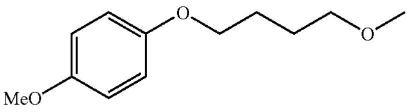 |
| 40 | 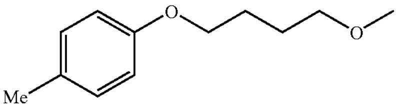 |
TABLE 37-continued
(I-MM)
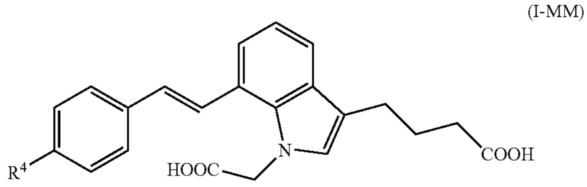
| | $R^4$— |
|---|---|
| 41 | 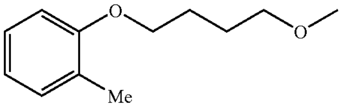 |
| 42 | 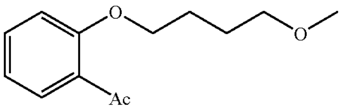 |
| 43 | 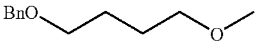 |
| 44 | 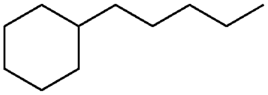 |
| 45 | 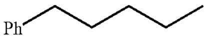 |
| 46 | 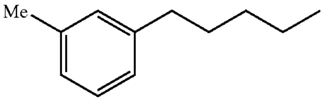 |
| 47 | 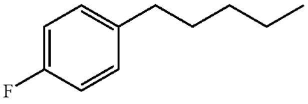 |
| 48 | 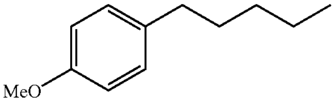 |
| 49 | 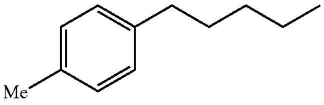 |
| 50 | 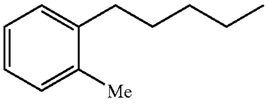 |
| 51 | 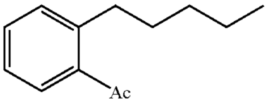 |
| 52 | 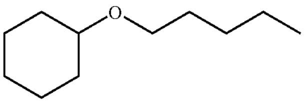 |
| 53 | 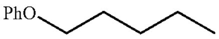 |

TABLE 37-continued
(I-MM)
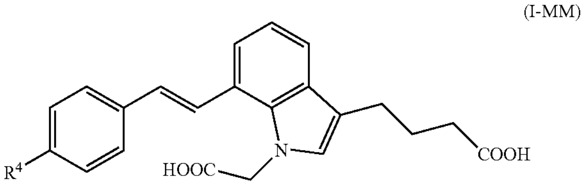
| | R4— |
|---|---|
| 54 | 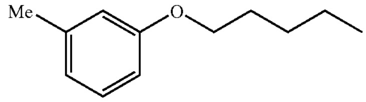 |
| 55 | 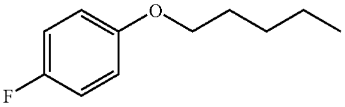 |
| 56 | 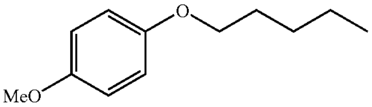 |
| 57 | 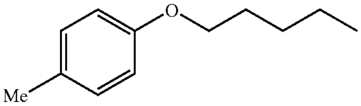 |
| 58 | 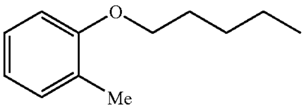 |
| 59 | 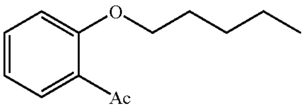 |
| 60 | 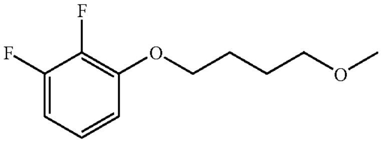 |
| 61 | 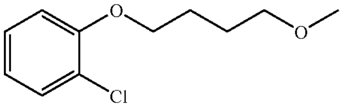 |
| 62 | 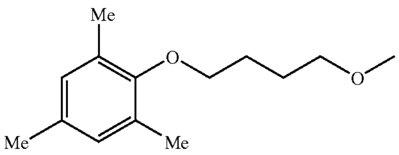 |
| 63 | 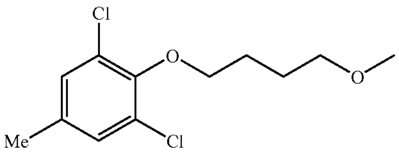 |
TABLE 37-continued
(I-MM)
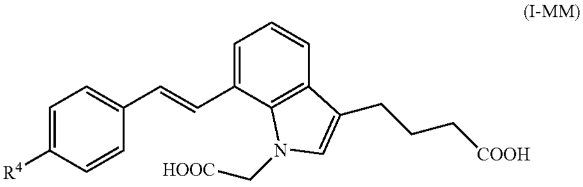
| | R4— |
|---|---|
| 64 | 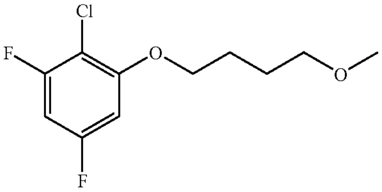 |
| 65 | 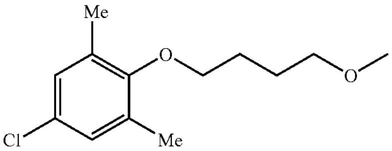 |
| 66 | 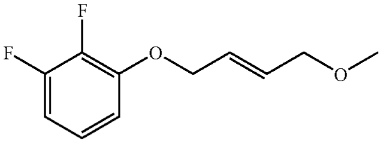 |
| 67 | 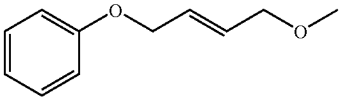 |
| 68 | 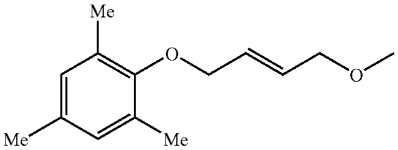 |
| 69 | 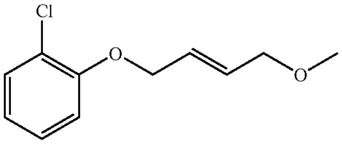 |
TABLE 38
(I-NN)
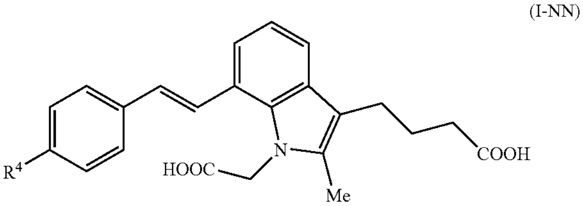
| | R4— |
|---|---|
| 1 | n-$C_4H_9^-$ |
| 2 | n-$C_5H_{11}^-$ |

TABLE 38-continued
(I-NN)
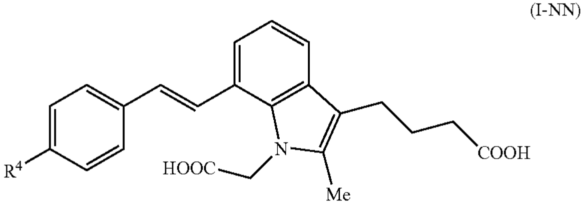
| | R⁴— |
|---|---|
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 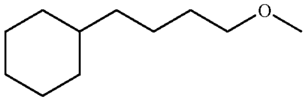 |
| 8 | 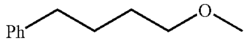 |
| 9 | 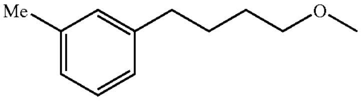 |
| 10 | 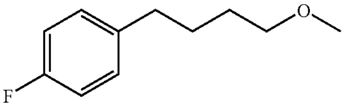 |
| 11 | 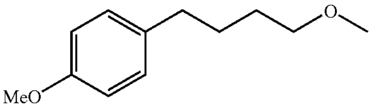 |
| 12 | 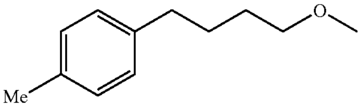 |
| 13 | 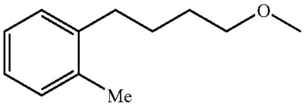 |
| 14 | 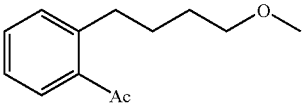 |
| 15 | 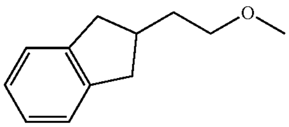 |
| 16 | 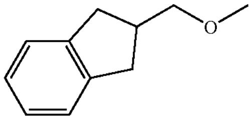 |
TABLE 38-continued
(I-NN)
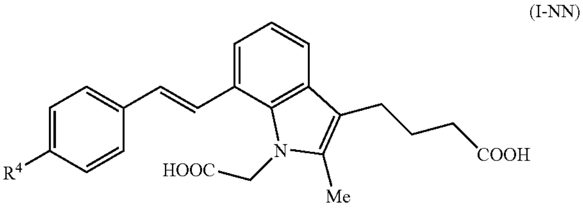
| | R⁴— |
|---|---|
| 17 | 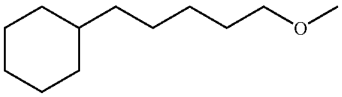 |
| 18 | 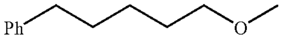 |
| 19 | 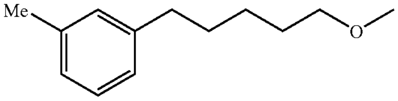 |
| 20 | 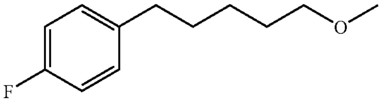 |
| 21 | 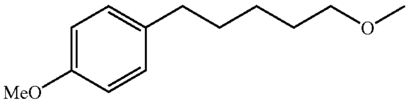 |
| 22 | 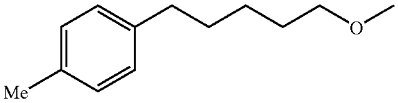 |
| 23 | 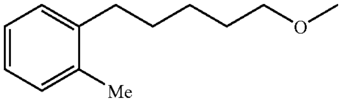 |
| 24 | 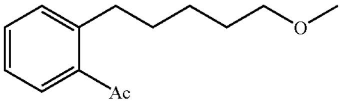 |
| 25 | 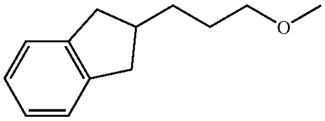 |
| 26 | 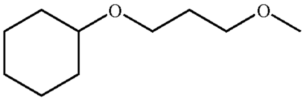 |
| 27 | 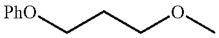 |
| 28 | 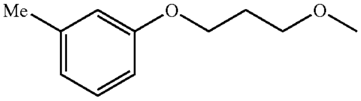 |

TABLE 38-continued
(I-NN)
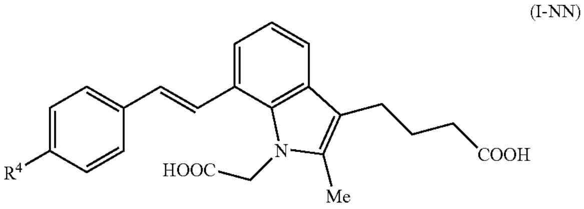
| | R4— |
|---|---|
| 29 | 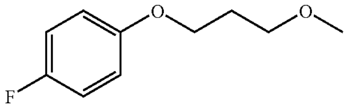 |
| 30 | 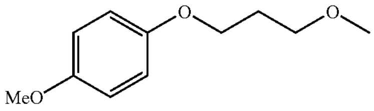 |
| 31 | 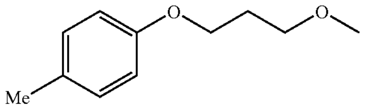 |
| 32 | 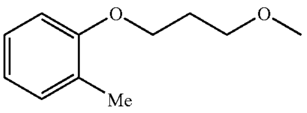 |
| 33 | 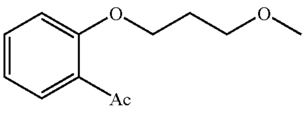 |
| 34 | 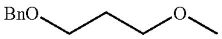 |
| 35 | 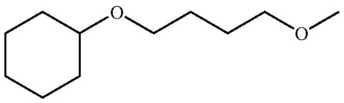 |
| 36 | 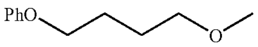 |
| 37 | 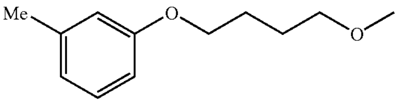 |
| 38 | 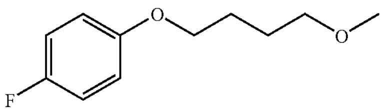 |
| 39 | 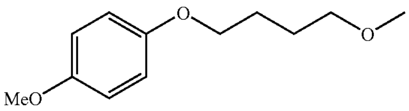 |
| 40 | 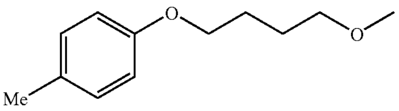 |
TABLE 38-continued
(I-NN)
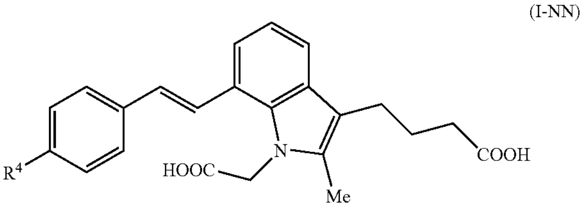
| | R4— |
|---|---|
| 41 | 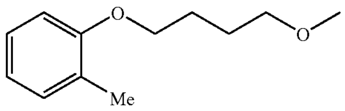 |
| 42 | 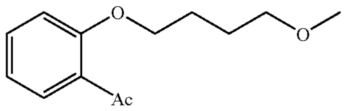 |
| 43 | 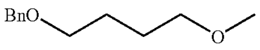 |
| 44 | 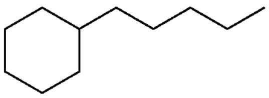 |
| 45 | 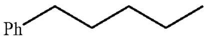 |
| 46 | 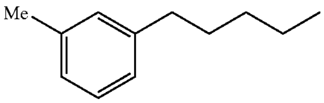 |
| 47 | 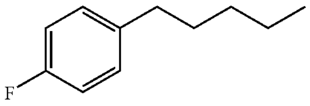 |
| 48 | 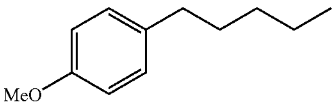 |
| 49 | 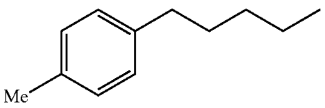 |
| 50 | 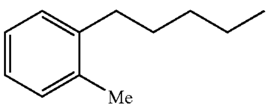 |
| 51 | 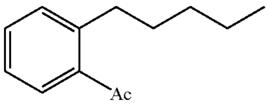 |
| 52 | 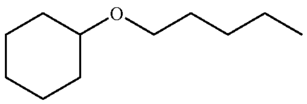 |
| 53 | 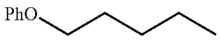 |

TABLE 38-continued
(I-NN)
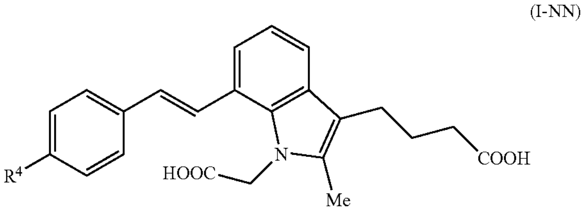
| | R4— |
| --- | --- |
| 54 | 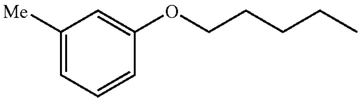 |
| 55 | 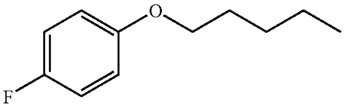 |
| 56 | 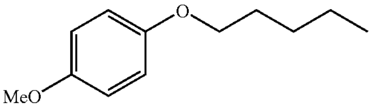 |
| 57 | 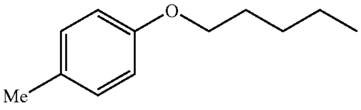 |
| 58 | 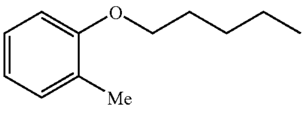 |
| 59 | 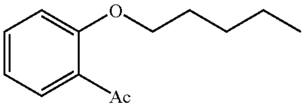 |
| 60 | 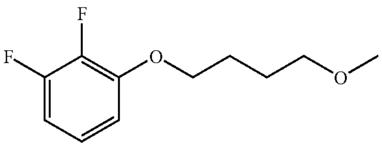 |
| 61 | 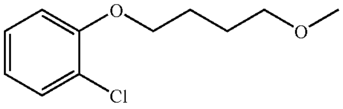 |
TABLE 38-continued
(I-NN)
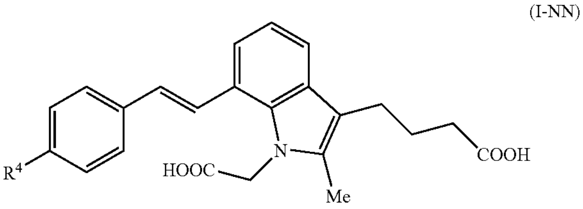
| | R4— |
| --- | --- |
| 62 | 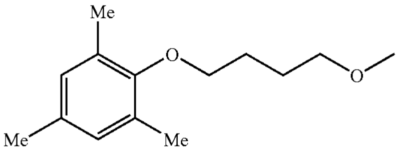 |
| 63 | 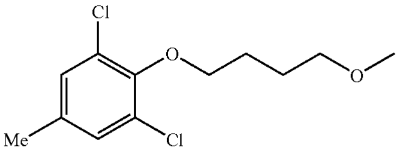 |
| 64 | 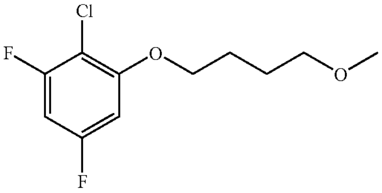 |
| 65 | 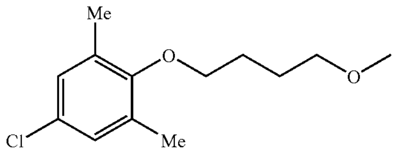 |
| 66 | 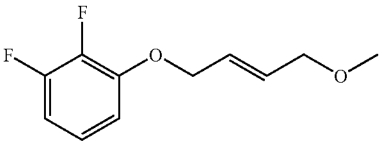 |
| 67 | 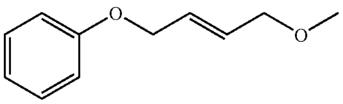 |
| 68 | 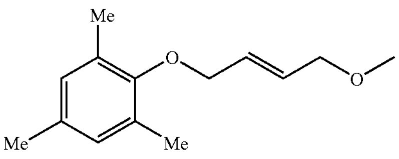 |
| 69 | 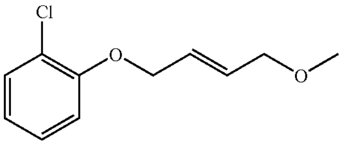 |

TABLE 39
(I-OO)
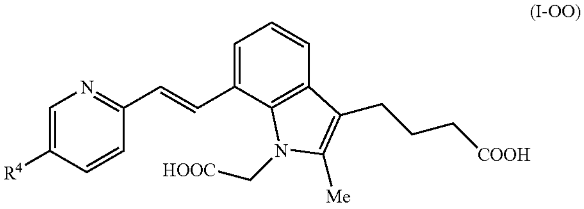
| | R4— |
|---|---|
| 1 | n-$C_4H_9$— |
| 2 | n-$C_5H_{11}$— |
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 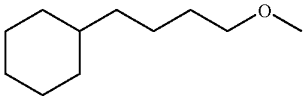 |
| 8 | 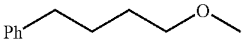 |
| 9 | 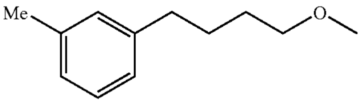 |
| 10 | 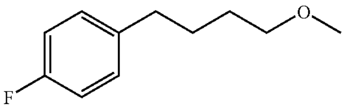 |
| 11 | 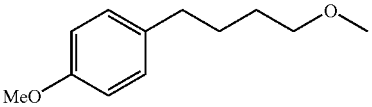 |
| 12 | 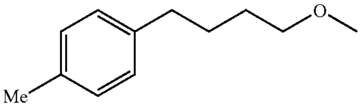 |
| 13 | 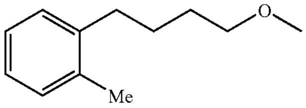 |
| 14 | 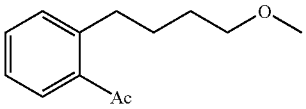 |
| 15 | 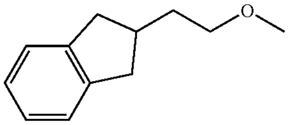 |
| 16 | 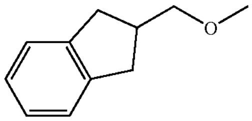 |
TABLE 39-continued
(I-OO)
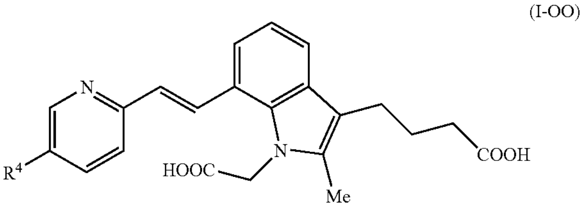
| | R4— |
|---|---|
| 17 | 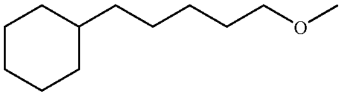 |
| 18 | 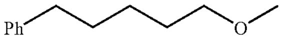 |
| 19 | 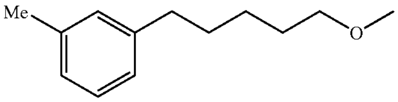 |
| 20 | 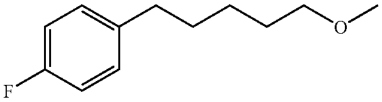 |
| 21 | 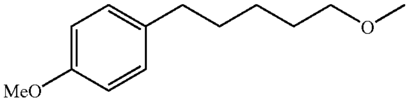 |
| 22 | 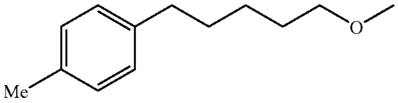 |
| 23 | 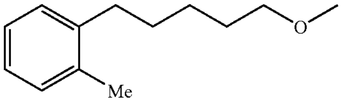 |
| 24 | 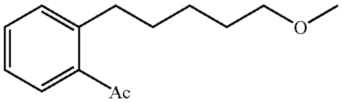 |
| 25 | 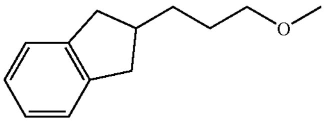 |
| 26 | 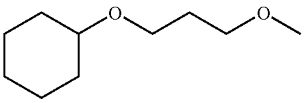 |
| 27 | 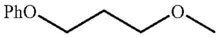 |
| 28 | 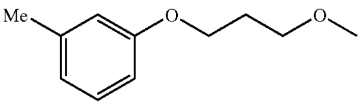 |

TABLE 39-continued
(I-OO)
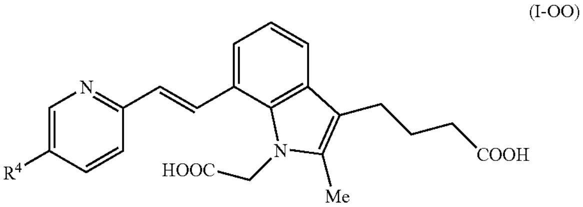
| | $R^4$— |
|---|---|
| 29 | 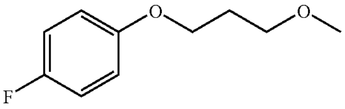 |
| 30 | 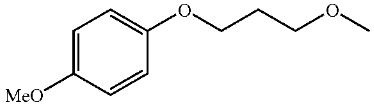 |
| 31 | 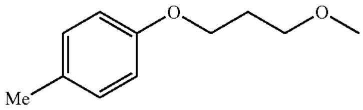 |
| 32 | 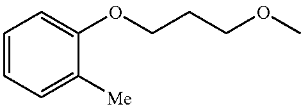 |
| 33 | 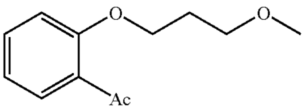 |
| 34 | 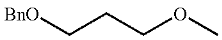 |
| 35 | 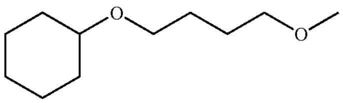 |
| 36 | 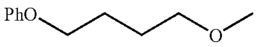 |
| 37 | 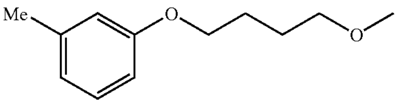 |
| 38 | 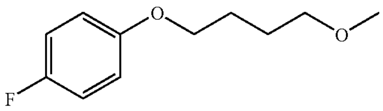 |
| 39 | 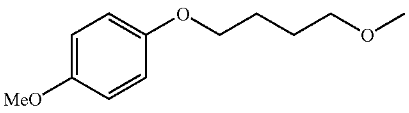 |
| 40 | 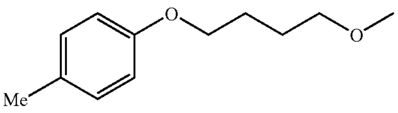 |
TABLE 39-continued
(I-OO)
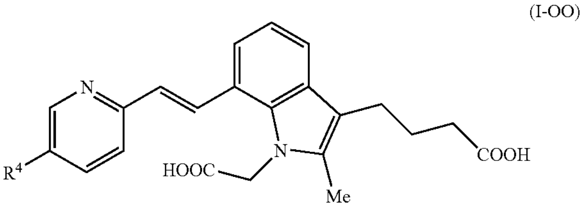
| | $R^4$— |
|---|---|
| 41 | 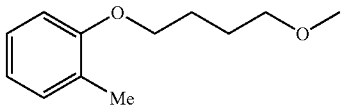 |
| 42 | 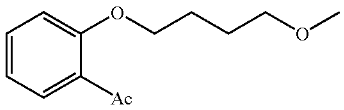 |
| 43 | 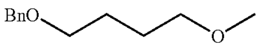 |
| 44 | 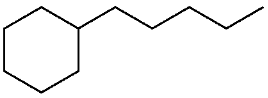 |
| 45 | 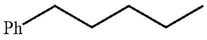 |
| 46 | 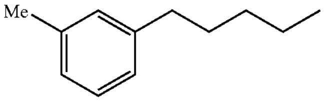 |
| 47 | 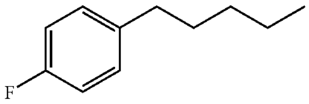 |
| 48 | 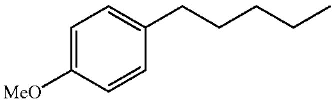 |
| 49 | 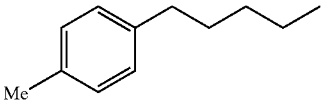 |
| 50 | 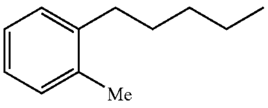 |
| 51 | 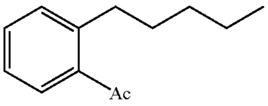 |
| 52 | 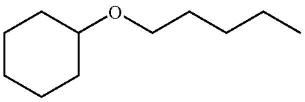 |
| 53 | 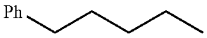 |

TABLE 39-continued
| | |
|---|---|
| (I-OO) | 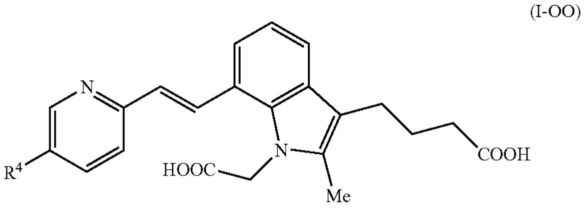 |
| | $R^4$— |
| 54 | 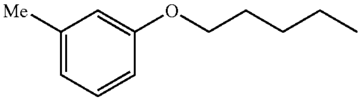 |
| 55 | 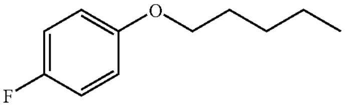 |
| 56 | 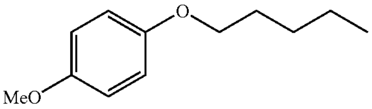 |
| 57 | 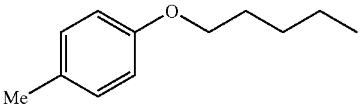 |
| 58 | 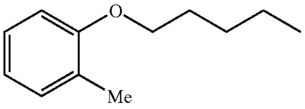 |
| 59 | 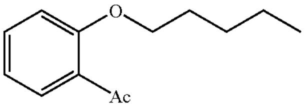 |
| 60 | 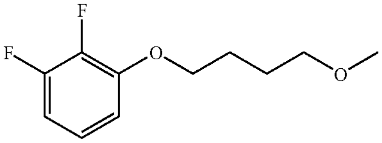 |
| 61 | 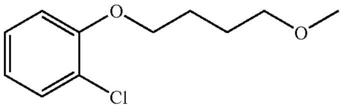 |
| 62 | 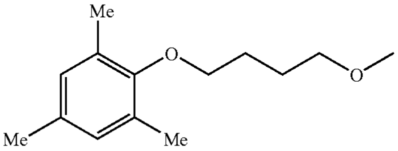 |
TABLE 39-continued
| | |
|---|---|
| (I-OO) | 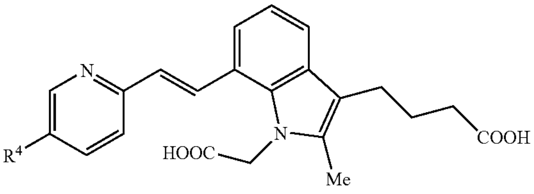 |
| | $R^4$— |
| 63 | 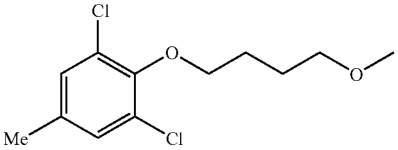 |
| 64 | 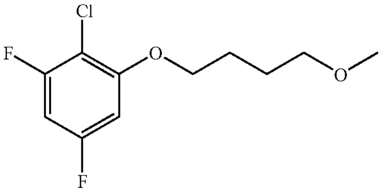 |
| 65 | 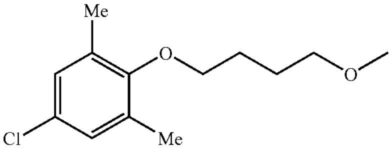 |
| 66 | 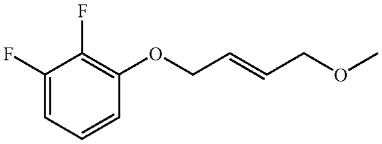 |
| 67 | 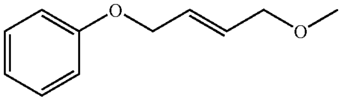 |
| 68 | 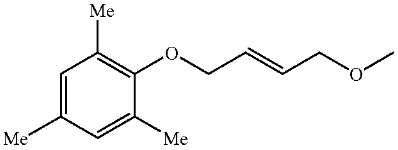 |
| 69 | 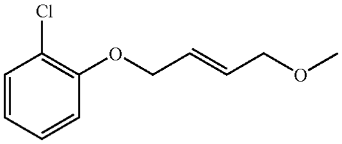 |

TABLE 40
(I-QQ)
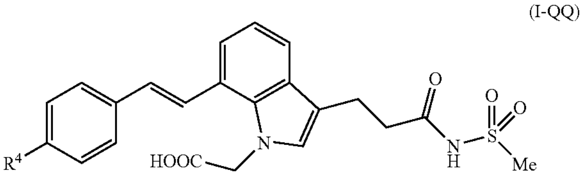
| | $R^4$— |
|---|---|
| 1 | n-$C_4H_9$$^-$ |
| 2 | n-$C_5H_{11}$$^-$ |
| 3 | n-$C_6H_{13}$$^-$ |
| 4 | n-$C_4H_9$—$O^-$ |
| 5 | n-$C_5H_{11}$—$O^-$ |
| 6 | n-$C_6H_{13}$—$O^-$ |
| 7 | 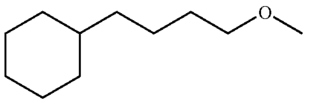 |
| 8 | 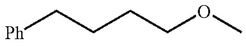 |
| 9 | 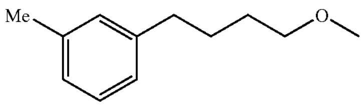 |
| 10 | 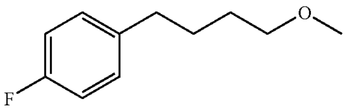 |
| 11 | 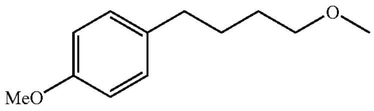 |
| 12 | 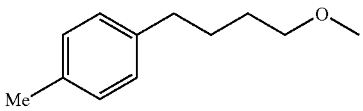 |
| 13 | 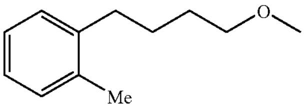 |
| 14 | 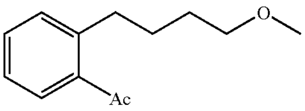 |
| 15 | 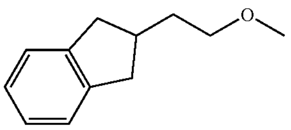 |
| 16 | 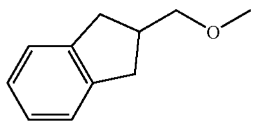 |
TABLE 40-continued
(I-QQ)
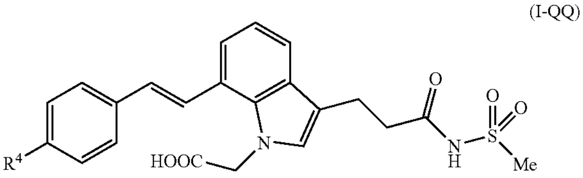
| | $R^4$— |
|---|---|
| 17 | 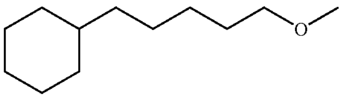 |
| 18 | 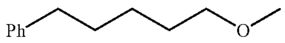 |
| 19 | 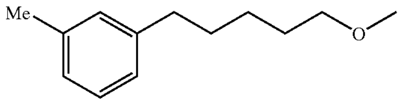 |
| 20 | 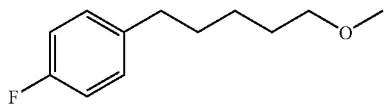 |
| 21 | 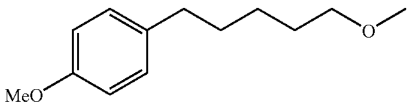 |
| 22 | 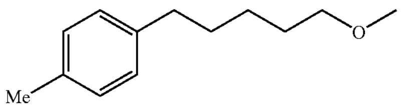 |
| 23 | 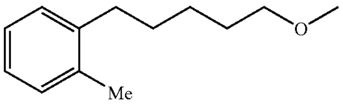 |
| 24 | 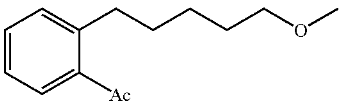 |
| 25 | 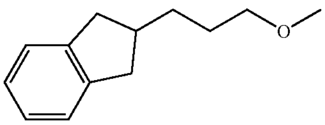 |
| 26 | 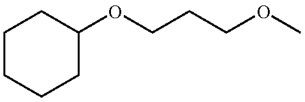 |
| 27 | 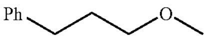 |
| 28 | 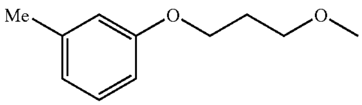 |

TABLE 40-continued
(I-QQ)
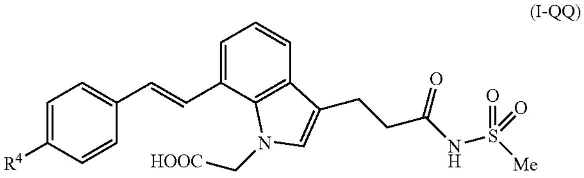
| | $R^4$— |
|---|---|
| 29 | 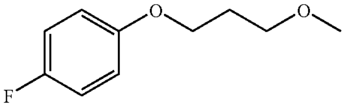 |
| 30 | 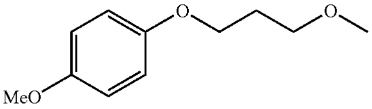 |
| 31 | 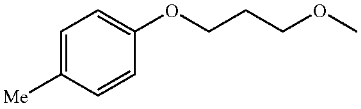 |
| 32 | 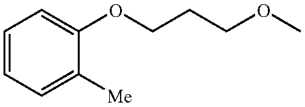 |
| 33 | 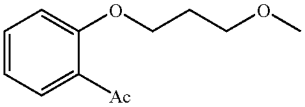 |
| 34 | 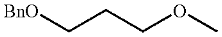 |
| 35 | 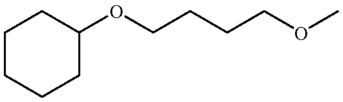 |
| 36 | 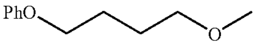 |
| 37 | 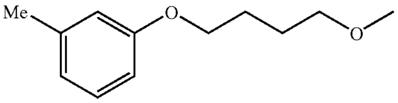 |
| 38 | 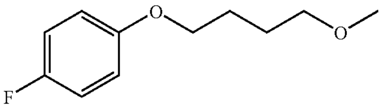 |
| 39 | 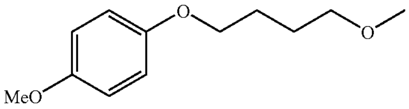 |
| 40 | 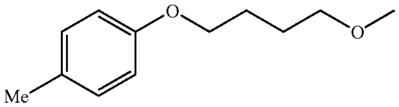 |
TABLE 40-continued
(I-QQ)
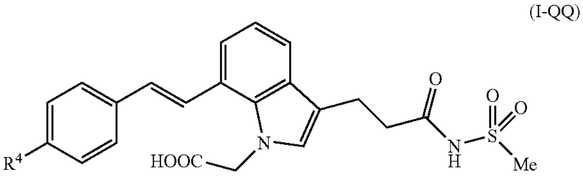
| | $R^4$— |
|---|---|
| 41 | 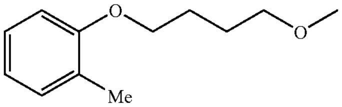 |
| 42 | 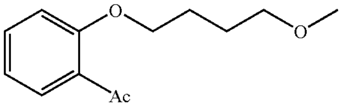 |
| 43 | 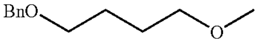 |
| 44 | 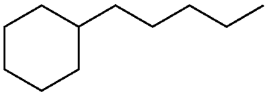 |
| 45 | 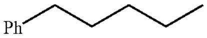 |
| 46 | 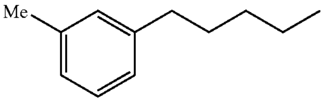 |
| 47 | 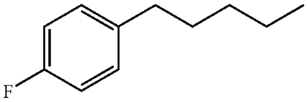 |
| 48 | 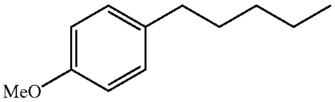 |
| 49 | 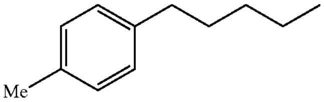 |
| 50 | 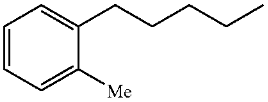 |
| 51 | 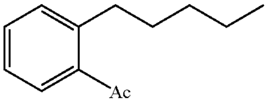 |
| 52 | 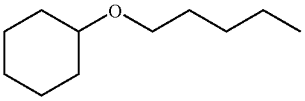 |
| 53 | 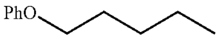 |

TABLE 40-continued
(I-QQ)
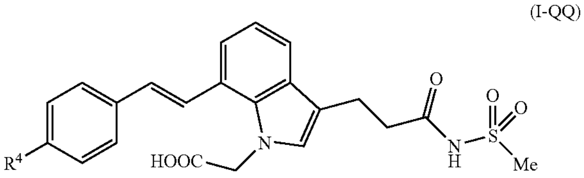
| | R⁴— |
|---|---|
| 54 | 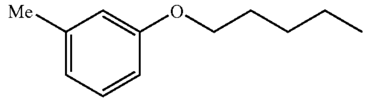 |
| 55 | 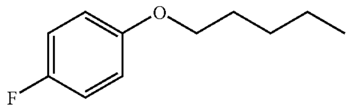 |
| 56 | 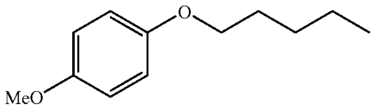 |
| 57 | 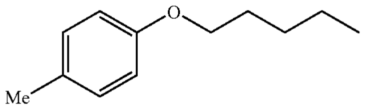 |
| 58 | 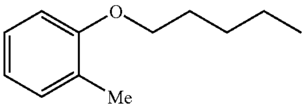 |
| 59 | 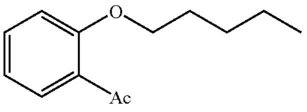 |
| 60 | 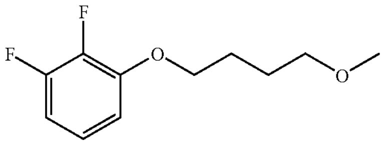 |
| 61 | 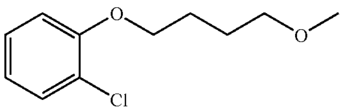 |
| 62 | 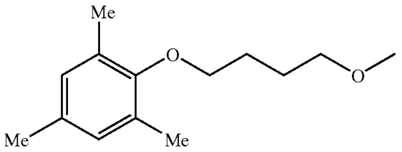 |
| 63 | 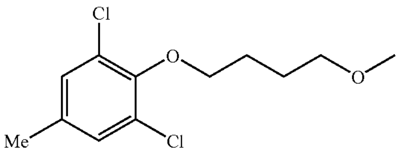 |
TABLE 40-continued
(I-QQ)
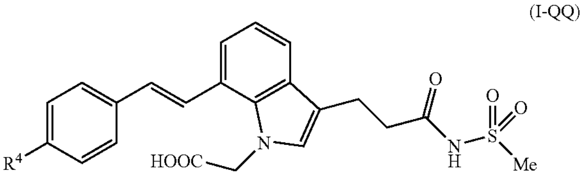
| | R⁴— |
|---|---|
| 64 | 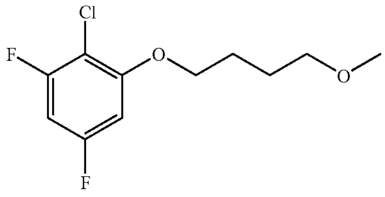 |
| 65 | 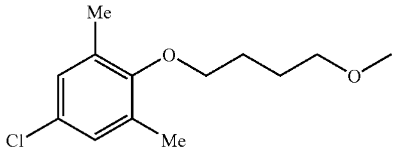 |
| 66 | 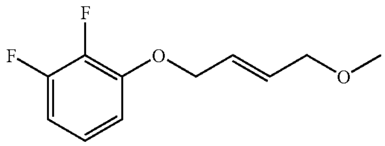 |
| 67 | 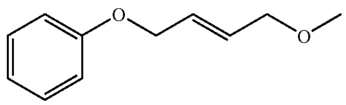 |
| 68 | 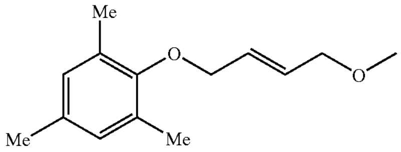 |
| 69 | 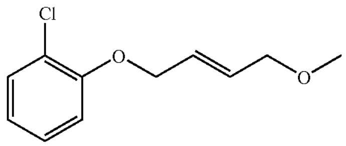 |
TABLE 41
(I-RR)
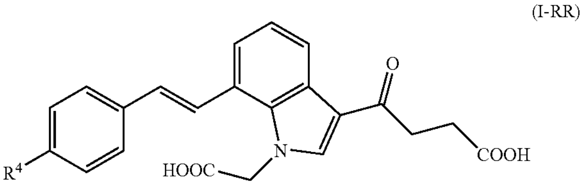
| | $R^4$— |
|---|---|
| 1 | $n\text{-}C_4H_9^-$ |
| 2 | $n\text{-}C_5H_{11}^-$ |
| 3 | $n\text{-}C_6H_{13}^-$ |
| 4 | $n\text{-}C_4H_9$—$O^-$ |

TABLE 41-continued
(I-RR)
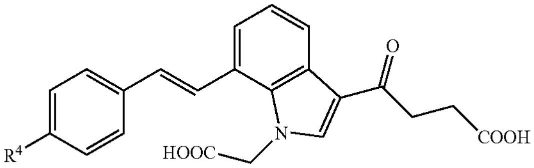
| | $R^4$— |
|---|---|
| 5 | n-$C_5H_{11}$—$O^-$ |
| 6 | n-$C_6H_{13}$—$O^-$ |
| 7 | 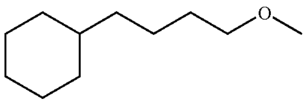 |
| 8 | 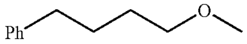 |
| 9 | 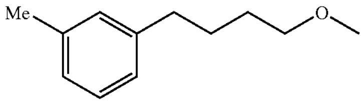 |
| 10 | 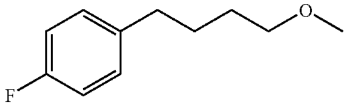 |
| 11 | 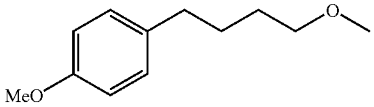 |
| 12 | 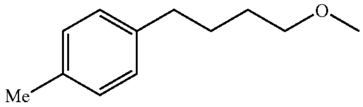 |
| 13 | 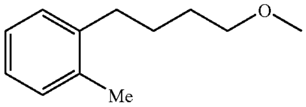 |
| 14 | 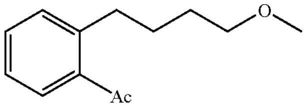 |
| 15 | 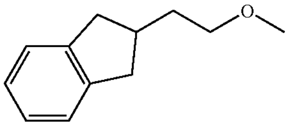 |
| 16 | 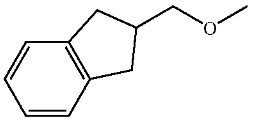 |
| 17 | 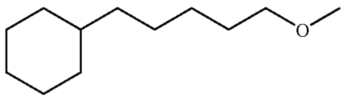 |
TABLE 41-continued
(I-RR)
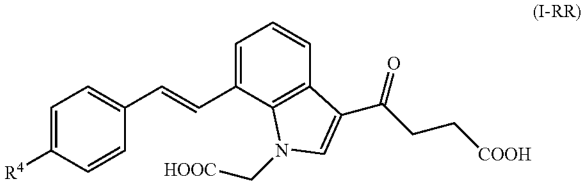
| | $R^4$— |
|---|---|
| 18 | 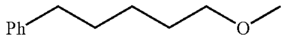 |
| 19 | 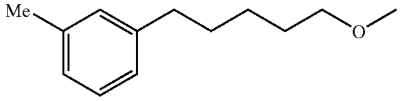 |
| 20 | 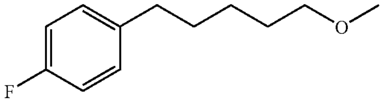 |
| 21 | 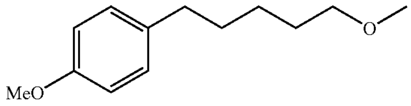 |
| 22 | 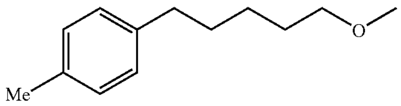 |
| 23 | 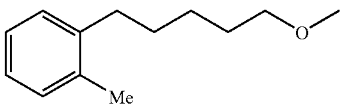 |
| 24 | 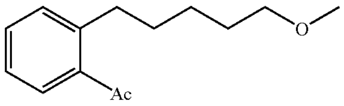 |
| 25 | 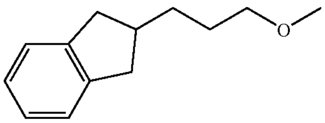 |
| 26 | 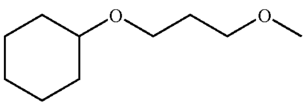 |
| 27 | 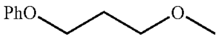 |
| 28 | 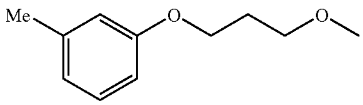 |
| 29 | 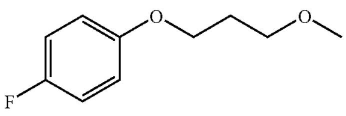 |

TABLE 41-continued
(I-RR)
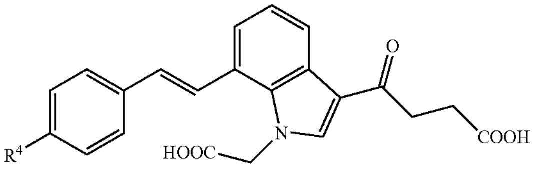
| R$^4$— | |
|---|---|
| 30 | 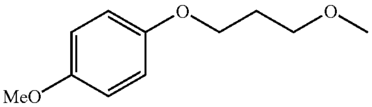 |
| 31 | 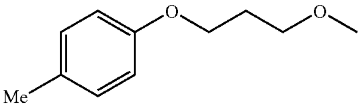 |
| 32 | 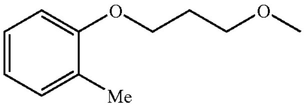 |
| 33 | 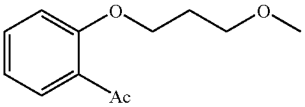 |
| 34 | 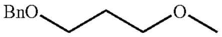 |
| 35 | 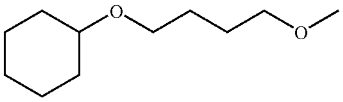 |
| 36 | 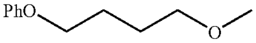 |
| 37 | 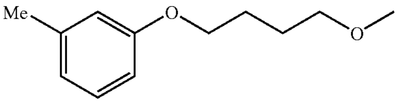 |
| 38 | 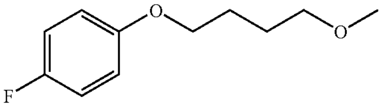 |
| 39 | 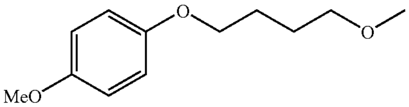 |
| 40 | 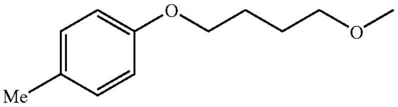 |
| 41 | 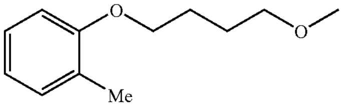 |
TABLE 41-continued
(I-RR)
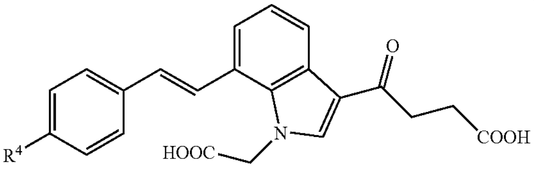
| R$^4$— | |
|---|---|
| 42 | 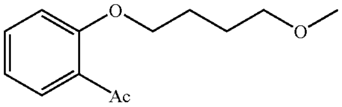 |
| 43 | 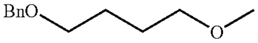 |
| 44 | 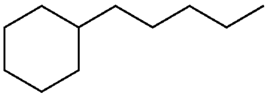 |
| 45 | 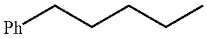 |
| 46 | 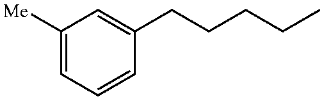 |
| 47 | 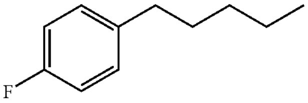 |
| 48 | 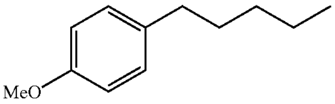 |
| 49 | 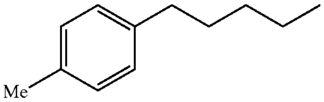 |
| 50 | 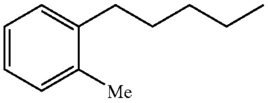 |
| 51 | 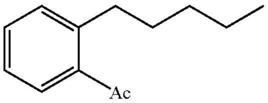 |
| 52 | 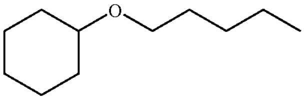 |
| 53 | 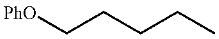 |
| 54 | 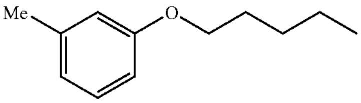 |

TABLE 41-continued
(I-RR)
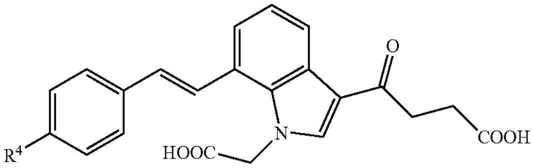
| | R⁴— |
|---|---|
| 55 | 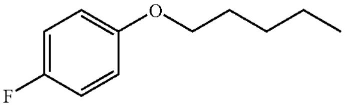 |
| 56 | 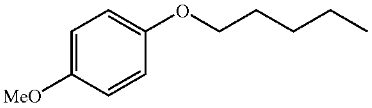 |
| 57 | 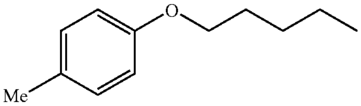 |
| 58 | 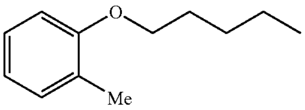 |
| 59 | 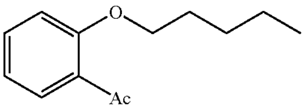 |
| 60 | 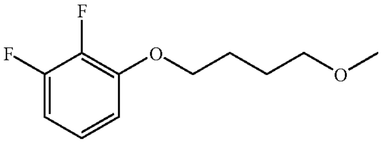 |
| 61 | 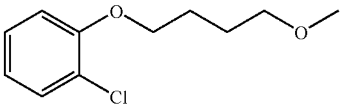 |
| 62 | 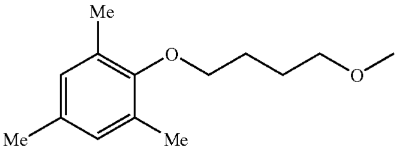 |
| 63 | 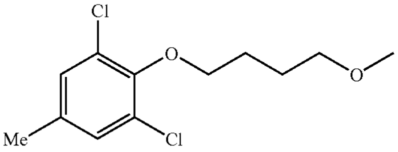 |
TABLE 41-continued
(I-RR)
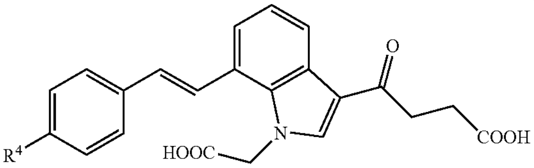
| | R⁴— |
|---|---|
| 64 | 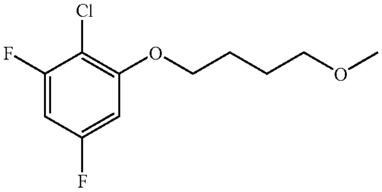 |
| 65 | 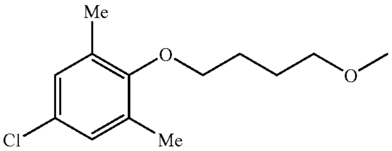 |
| 66 | 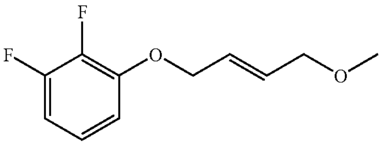 |
| 67 | 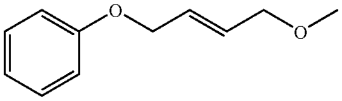 |
| 68 | 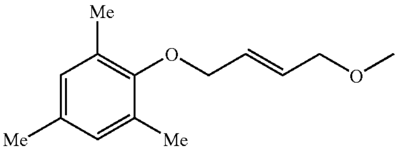 |
| 69 | 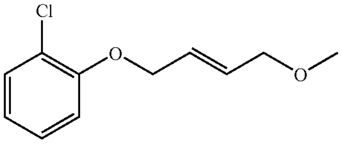 |
TABLE 42
(I-SS)
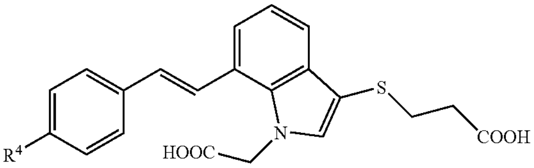
| | $R^4$— |
|---|---|
| 1 | $n\text{-}C_4H_9^-$ |
| 2 | $n\text{-}C_5H_{11}^-$ |
| 3 | $n\text{-}C_6H_{13}^-$ |

TABLE 42-continued
(I-SS)
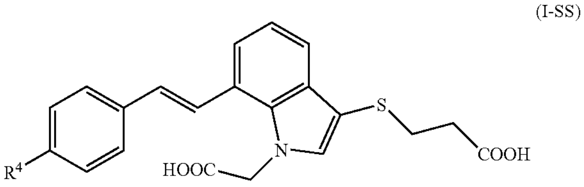
| | R⁴— |
|---|---|
| 4 | n-$C_4H_9$—$O^-$ |
| 5 | n-$C_5H_{11}$—$O^-$ |
| 6 | n-$C_6H_{13}$—$O^-$ |
| 7 | 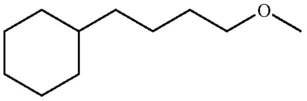 |
| 8 | 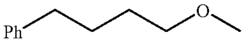 |
| 9 | 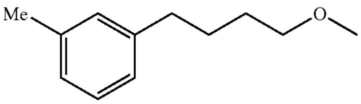 |
| 10 | 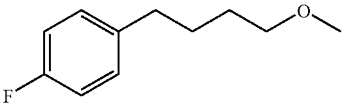 |
| 11 | 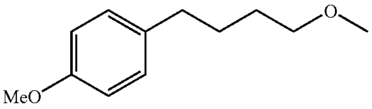 |
| 12 | 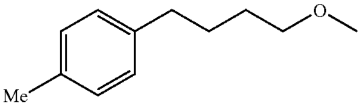 |
| 13 | 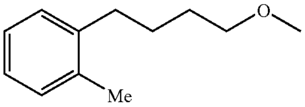 |
| 14 | 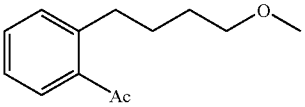 |
| 15 | 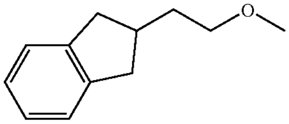 |
| 16 | 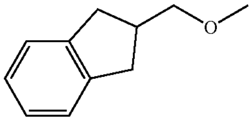 |
| 17 | 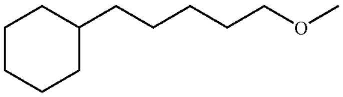 |
TABLE 42-continued
(I-SS)
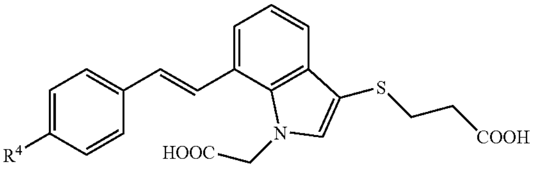
| | R⁴— |
|---|---|
| 18 | 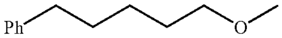 |
| 19 | 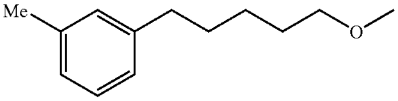 |
| 20 | 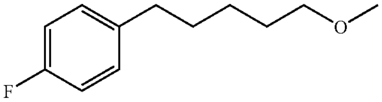 |
| 21 | 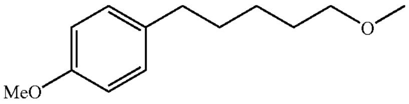 |
| 22 | 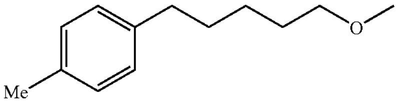 |
| 23 | 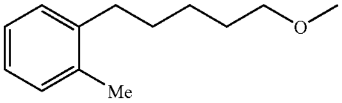 |
| 24 | 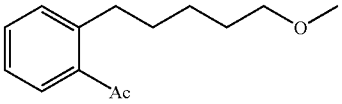 |
| 25 | 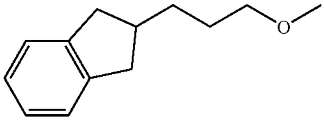 |
| 26 | 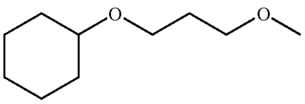 |
| 27 | 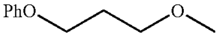 |
| 28 | 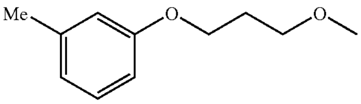 |
| 29 | 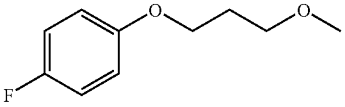 |

TABLE 42-continued
(I-SS)
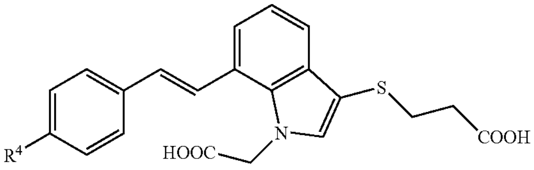
| | $R^4$— |
|---|---|
| 30 | 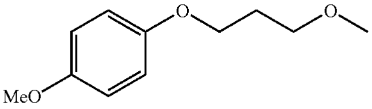 |
| 31 | 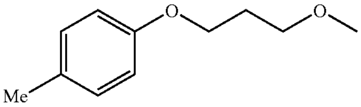 |
| 32 | 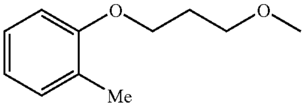 |
| 33 | 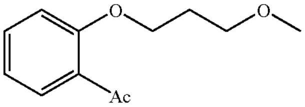 |
| 34 | 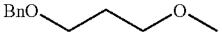 |
| 35 | 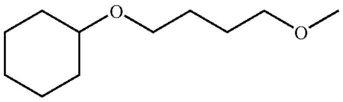 |
| 36 | 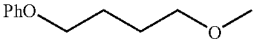 |
| 37 | 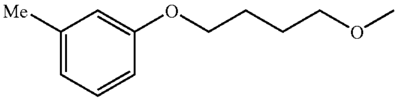 |
| 38 | 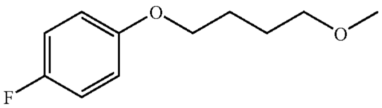 |
| 39 | 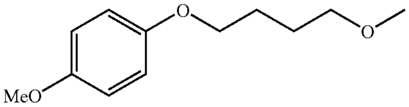 |
| 40 | 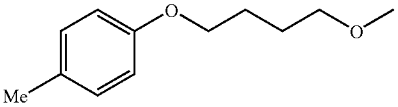 |
| 41 | 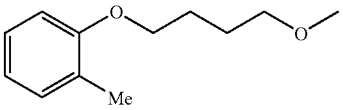 |
TABLE 42-continued
(I-SS)
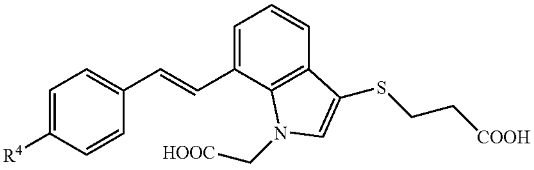
| | $R^4$— |
|---|---|
| 42 | 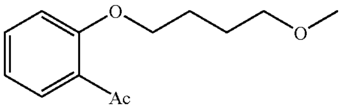 |
| 43 | 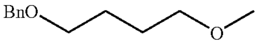 |
| 44 | 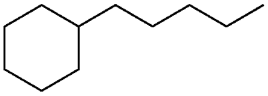 |
| 45 | 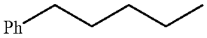 |
| 46 | 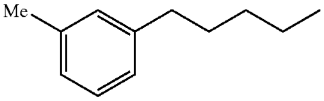 |
| 47 | 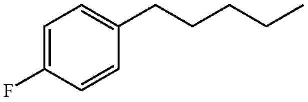 |
| 48 | 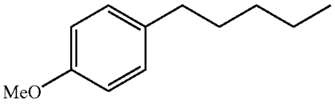 |
| 49 | 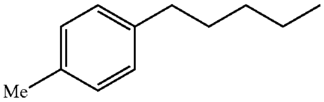 |
| 50 | 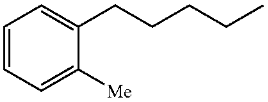 |
| 51 | 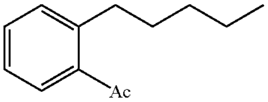 |
| 52 | 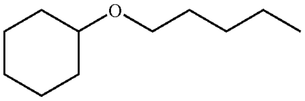 |
| 53 | 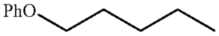 |
| 54 | 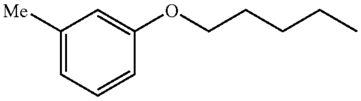 |

TABLE 42-continued
(I-SS)
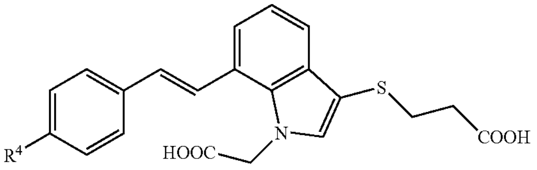
| | $R^4$— |
|---|---|
| 55 | 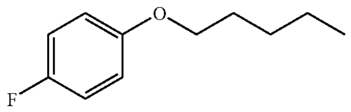 |
| 56 | 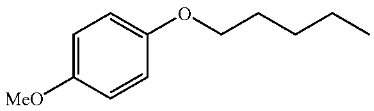 |
| 57 | 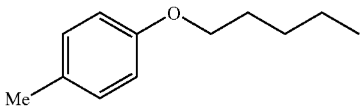 |
| 58 | 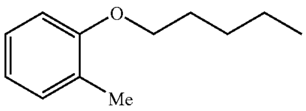 |
| 59 | 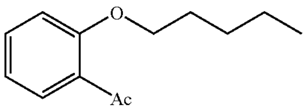 |
| 60 | 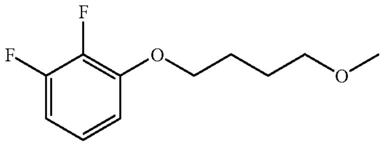 |
| 61 | 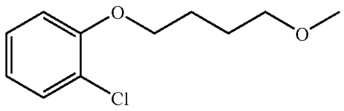 |
| 62 | 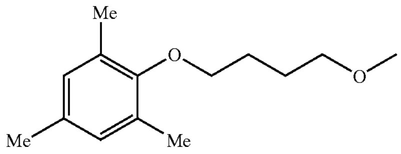 |
| 63 | 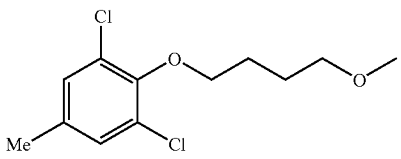 |
TABLE 42-continued
(I-SS)
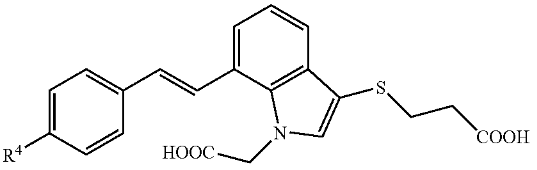
| | $R^4$— |
|---|---|
| 64 | 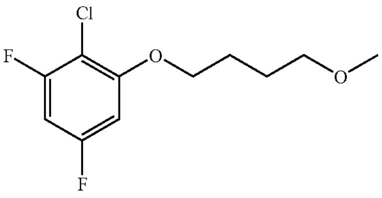 |
| 65 | 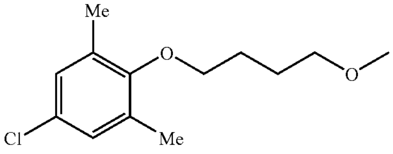 |
| 66 | 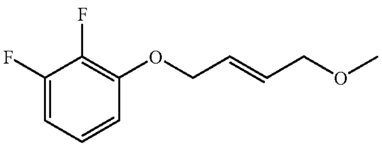 |
| 67 | 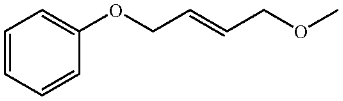 |
| 68 | 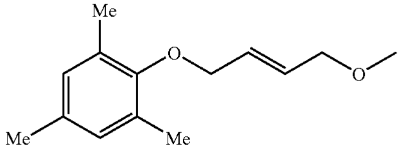 |
| 69 | 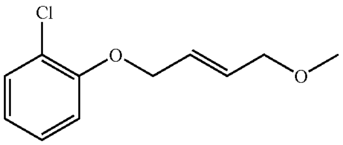 |
TABLE 43
(I-TT)
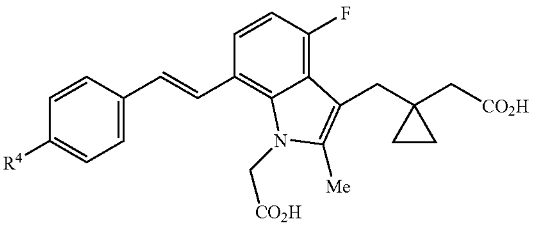
| | $R^4$— |
|---|---|
| 1 | $n\text{-}C_4H_9^-$ |
| 2 | $n\text{-}C_5H_{11}^-$ |

TABLE 43-continued
(I-TT)
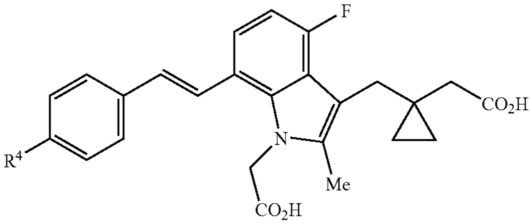
| | R$^4$— |
|---|---|
| 3 | n-$C_6H_{13}$— |
| 4 | n-$C_4H_9$—O— |
| 5 | n-$C_5H_{11}$—O— |
| 6 | n-$C_6H_{13}$—O— |
| 7 | 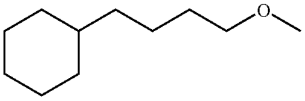 |
| 8 | 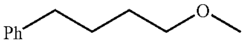 |
| 9 | 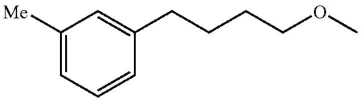 |
| 10 | 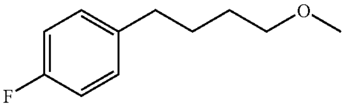 |
| 11 | 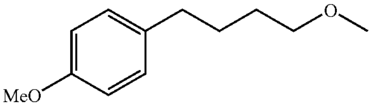 |
| 12 | 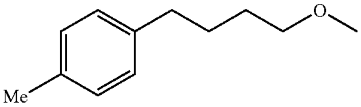 |
| 13 | 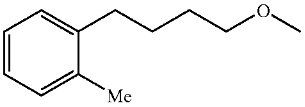 |
| 14 | 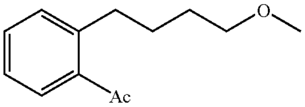 |
| 15 | 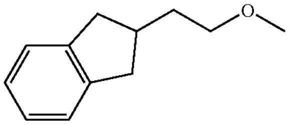 |
| 16 | 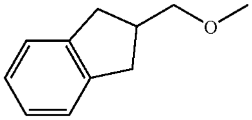 |
TABLE 43-continued
(I-TT)
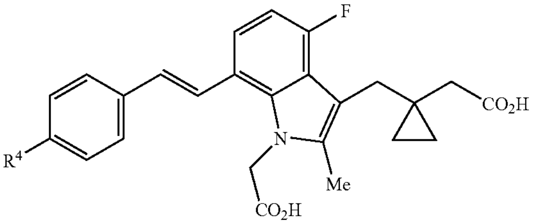
| | R$^4$— |
|---|---|
| 17 | 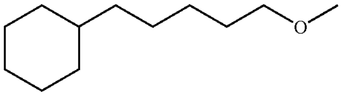 |
| 18 | 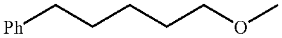 |
| 19 | 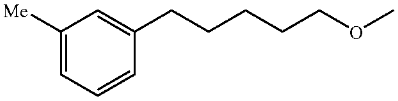 |
| 20 | 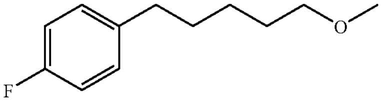 |
| 21 | 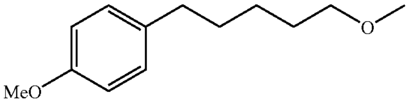 |
| 22 | 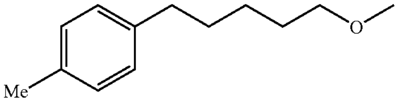 |
| 23 | 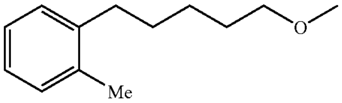 |
| 24 | 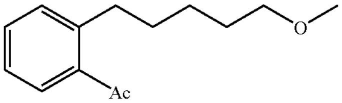 |
| 25 | 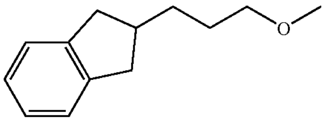 |
| 26 | 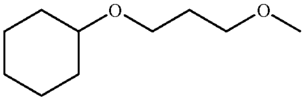 |
| 27 | 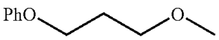 |
| 28 | 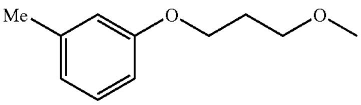 |

TABLE 43-continued
(I-TT)
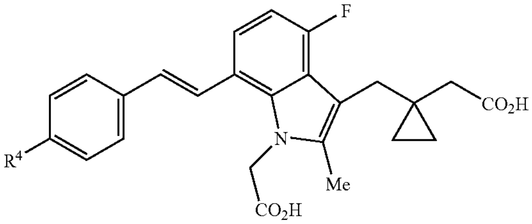
| | $R^4$— |
|---|---|
| 29 | 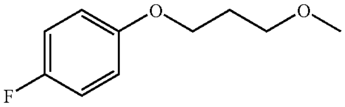 |
| 30 | 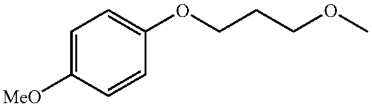 |
| 31 | 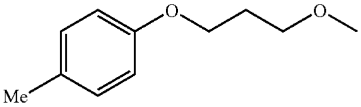 |
| 32 | 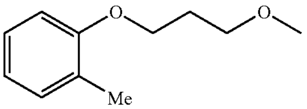 |
| 33 | 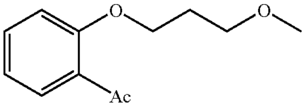 |
| 34 | 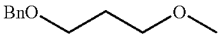 |
| 35 | 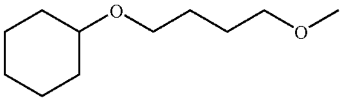 |
| 36 | 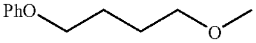 |
| 37 | 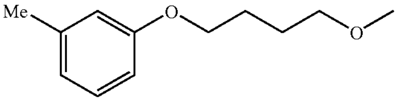 |
| 38 | 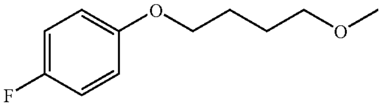 |
| 39 | 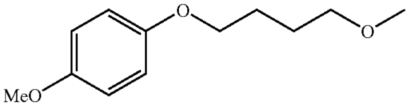 |
| 40 | 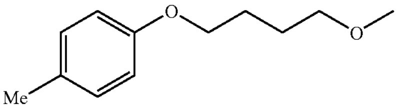 |
TABLE 43-continued
(I-TT)
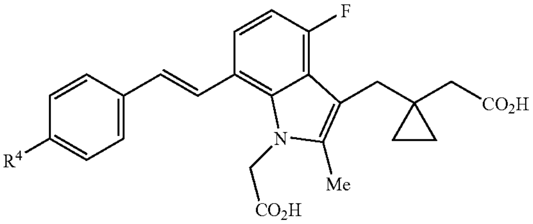
| | $R^4$— |
|---|---|
| 41 | 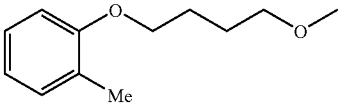 |
| 42 | 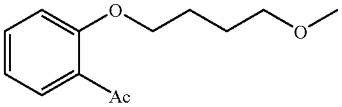 |
| 43 | 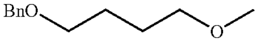 |
| 44 | 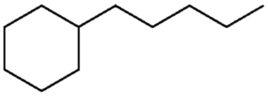 |
| 45 | 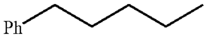 |
| 46 | 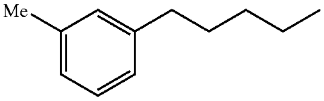 |
| 47 | 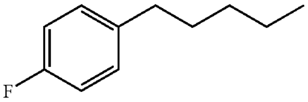 |
| 48 | 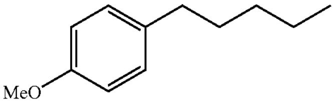 |
| 49 | 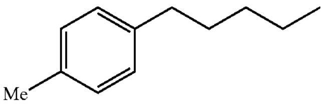 |
| 50 | 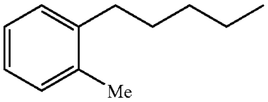 |
| 51 | 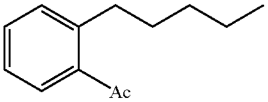 |
| 52 | 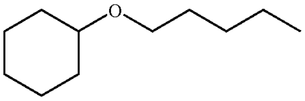 |
| 53 | 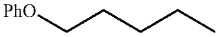 |

TABLE 43-continued
(I-TT)
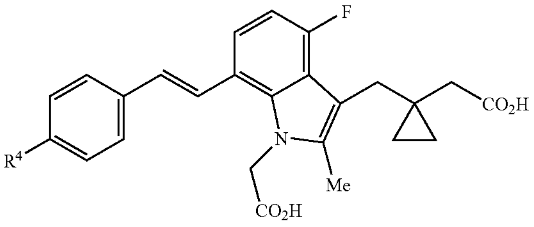
| | R⁴— |
|---|---|
| 54 | 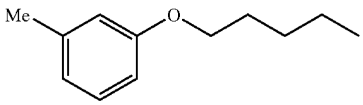 |
| 55 | 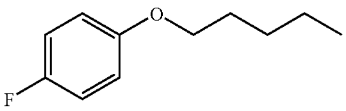 |
| 56 | 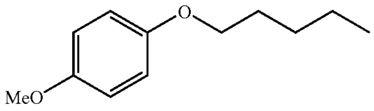 |
| 57 | 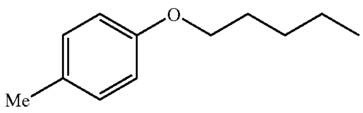 |
| 58 | 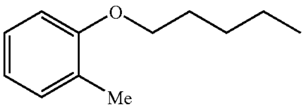 |
| 59 | 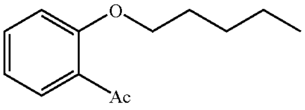 |
| 60 | 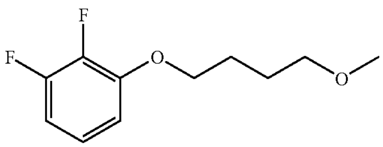 |
| 61 | 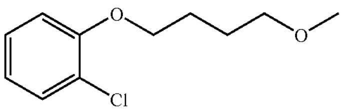 |
| 62 | 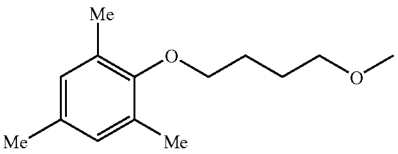 |
TABLE 43-continued
(I-TT)
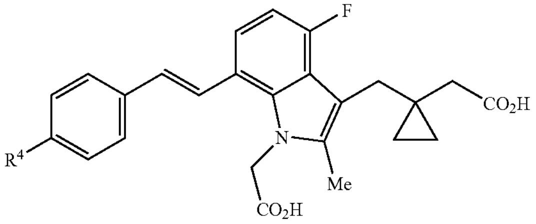
| | R⁴— |
|---|---|
| 63 | 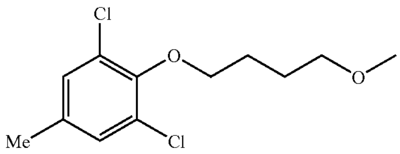 |
| 64 | 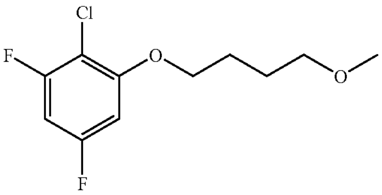 |
| 65 | 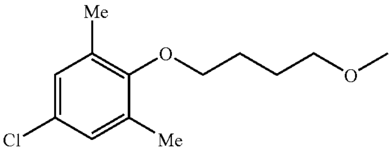 |
| 66 | 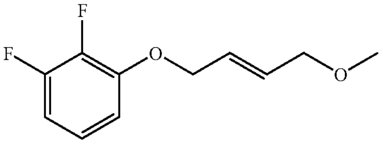 |
| 67 | 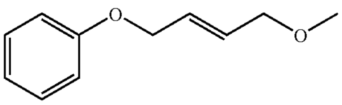 |
| 68 | 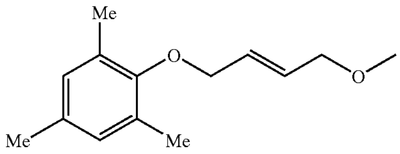 |
| 69 | 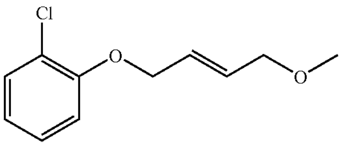 |

TABLE 44
(I-UU)
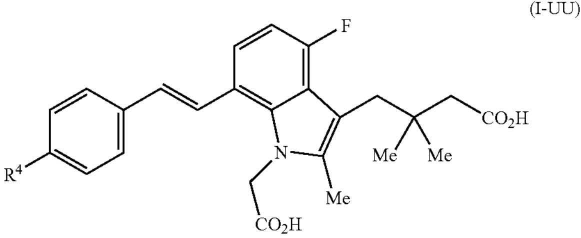
| | $R^4$— |
|---|---|
| 1 | $n\text{-}C_4H_9^-$ |
| 2 | $n\text{-}C_5H_{11}^-$ |
| 3 | $n\text{-}C_6H_{13}^-$ |
| 4 | $n\text{-}C_4H_9—O^-$ |
| 5 | $n\text{-}C_5H_{11}—O^-$ |
| 6 | $n\text{-}C_6H_{13}—O^-$ |
| 7 | 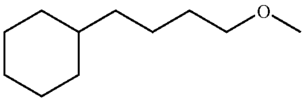 |
| 8 | 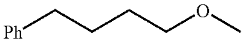 |
| 9 | 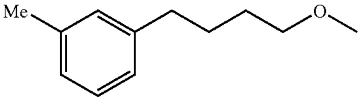 |
| 10 | 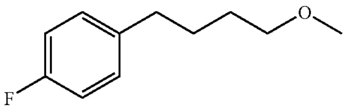 |
| 11 | 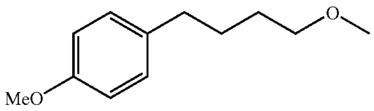 |
| 12 | 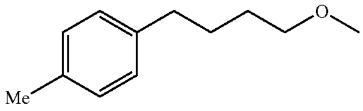 |
| 13 | 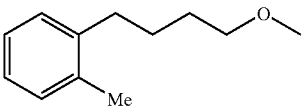 |
| 14 | 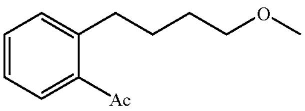 |
| 15 | 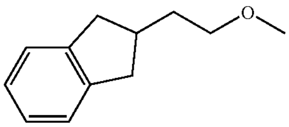 |
| 16 | 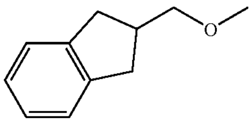 |
TABLE 44-continued
(I-UU)
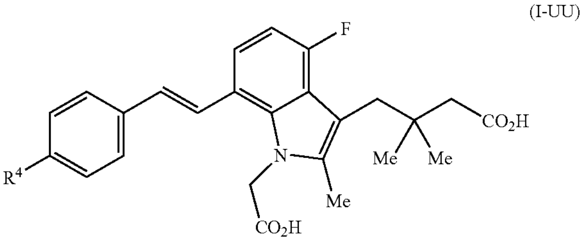
| | $R^4$— |
|---|---|
| 17 | 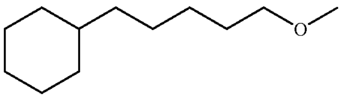 |
| 18 | 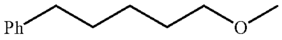 |
| 19 | 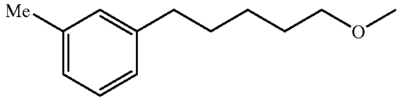 |
| 20 | 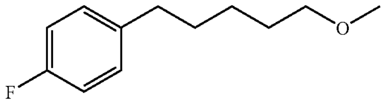 |
| 21 | 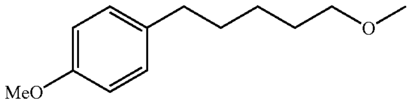 |
| 22 | 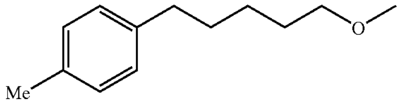 |
| 23 | 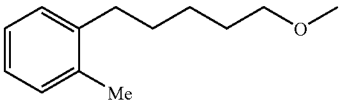 |
| 24 | 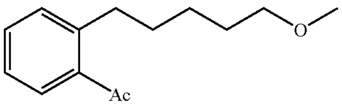 |
| 25 | 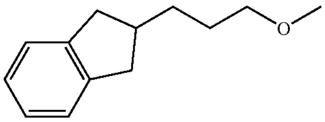 |
| 26 | 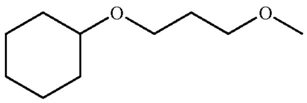 |
| 27 | 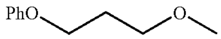 |
| 28 | 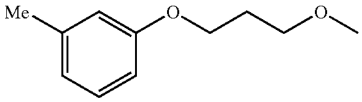 |

TABLE 44-continued
(I-UU)
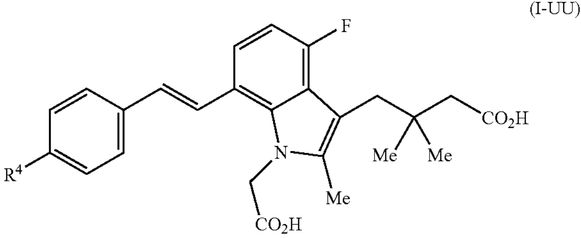
| | $R^4$— |
|---|---|
| 29 | 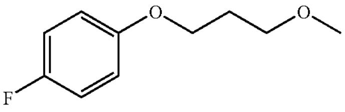 |
| 30 | 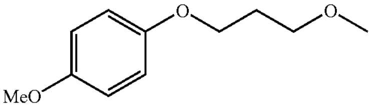 |
| 31 | 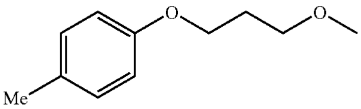 |
| 32 | 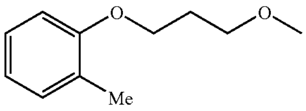 |
| 33 | 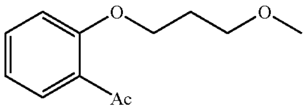 |
| 34 | 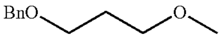 |
| 35 | 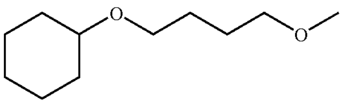 |
| 36 | 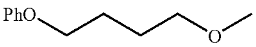 |
| 37 | 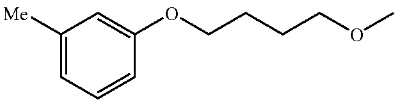 |
| 38 | 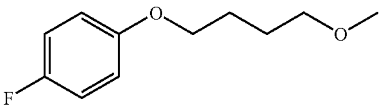 |
| 39 | 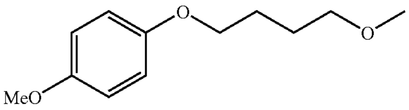 |
TABLE 44-continued
(I-UU)
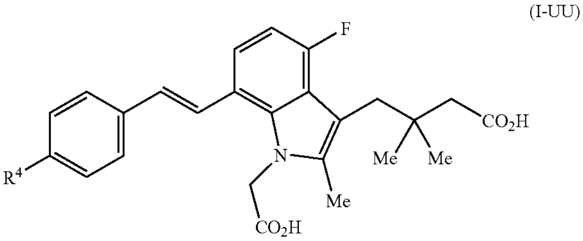
| | $R^4$— |
|---|---|
| 40 | 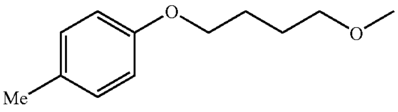 |
| 41 | 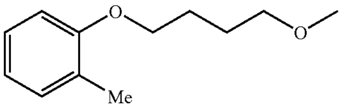 |
| 42 | 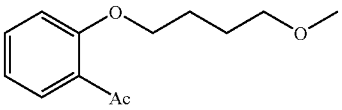 |
| 43 | 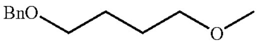 |
| 44 | 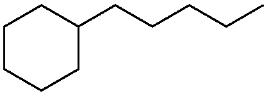 |
| 45 | 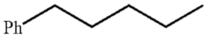 |
| 46 | 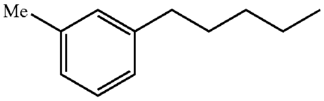 |
| 47 | 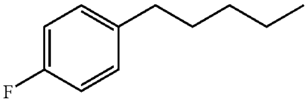 |
| 48 | 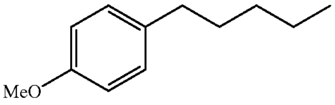 |
| 49 | 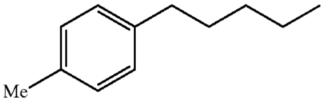 |
| 50 | 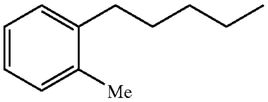 |
| 51 | 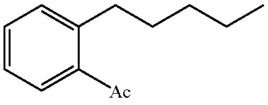 |

TABLE 44-continued
(I-UU)
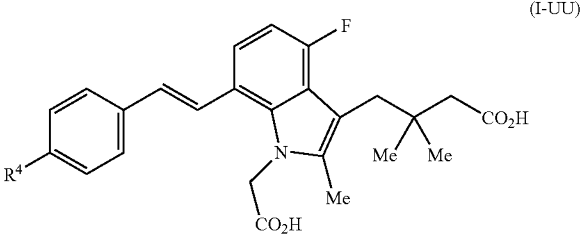
| | R⁴— |
|---|---|
| 52 | 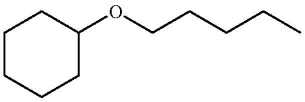 |
| 53 | 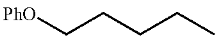 |
| 54 | 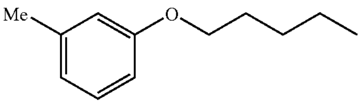 |
| 55 | 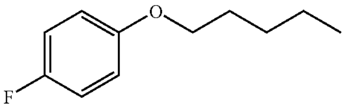 |
| 56 | 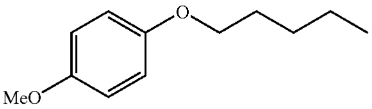 |
| 57 | 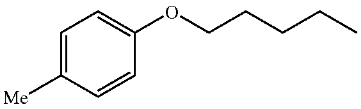 |
| 58 | 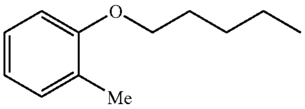 |
| 59 | 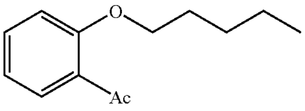 |
| 60 | 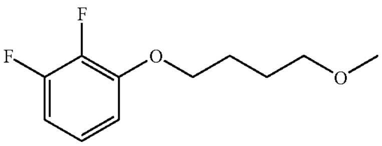 |
| 61 | 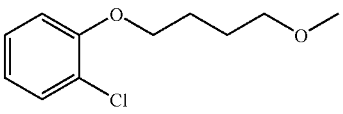 |
TABLE 44-continued
(I-UU)
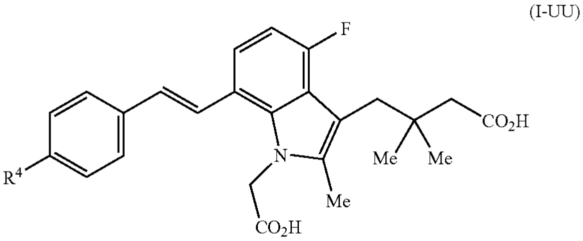
| | R⁴— |
|---|---|
| 62 | 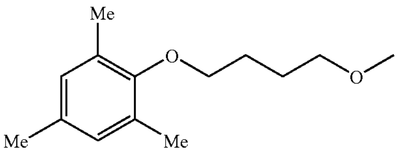 |
| 63 | 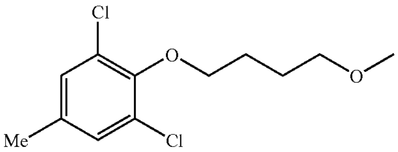 |
| 64 | 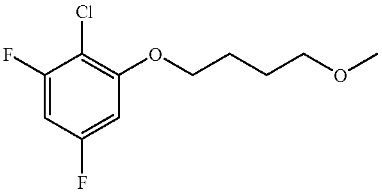 |
| 65 | 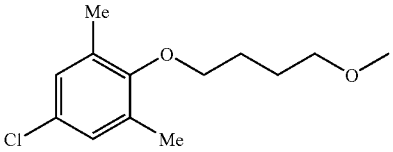 |
| 66 | 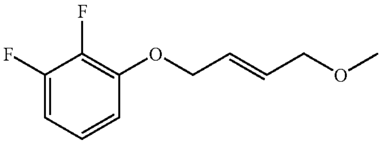 |
| 67 | 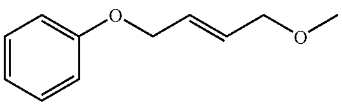 |
| 68 | 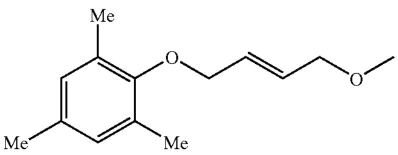 |
| 69 | 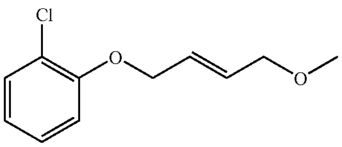 |

TABLE 45
(I-VV)
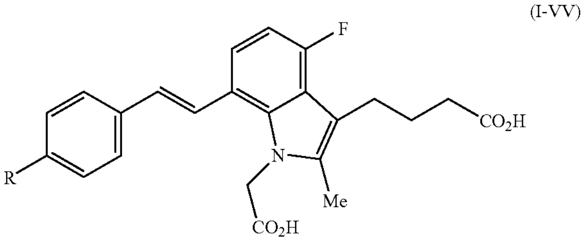
| | $R^4$— |
|---|---|
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |
| 7 | 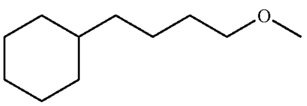 |
| 8 | 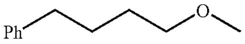 |
| 9 | 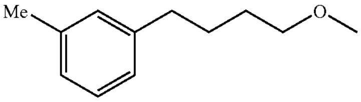 |
| 10 | 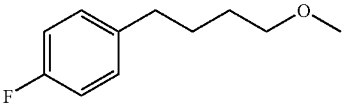 |
| 11 | 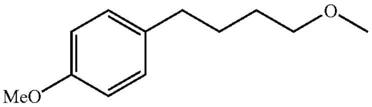 |
| 12 | 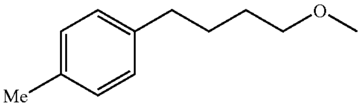 |
| 13 | 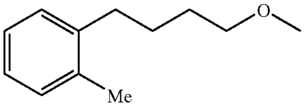 |
| 14 | 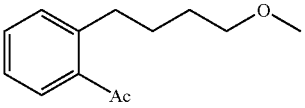 |
| 15 | 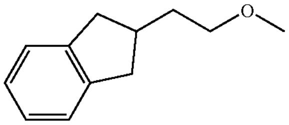 |
TABLE 45-continued
(I-VV)
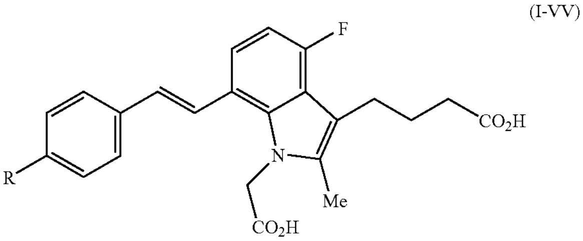
| | $R^4$— |
|---|---|
| 16 | 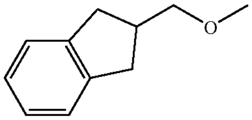 |
| 17 | 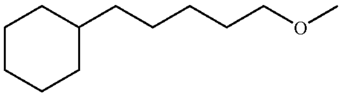 |
| 18 | 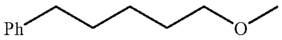 |
| 19 | 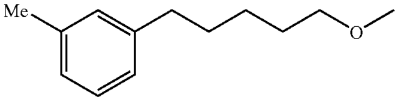 |
| 20 | 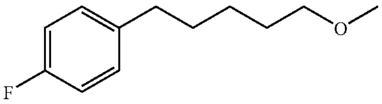 |
| 21 | 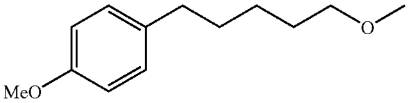 |
| 22 | 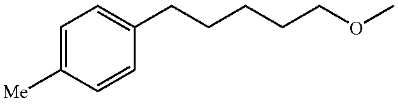 |
| 23 | 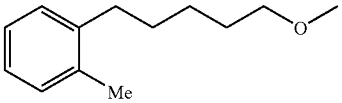 |
| 24 | 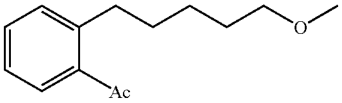 |
| 25 | 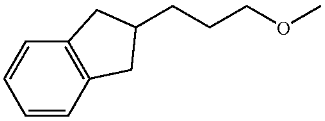 |
| 26 | 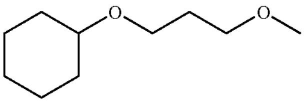 |
| 27 | 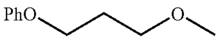 |

TABLE 45-continued
(I-VV)
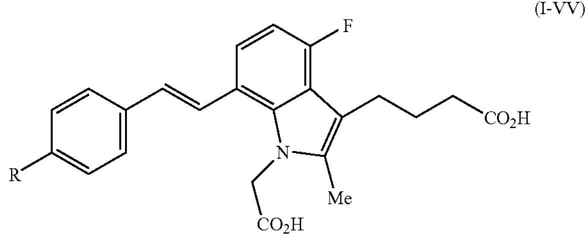
| | R⁴— |
|---|---|
| 28 | 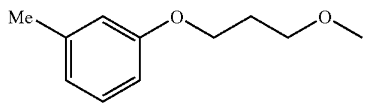 |
| 29 | 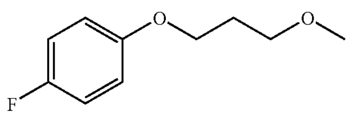 |
| 30 | 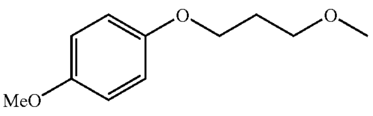 |
| 31 | 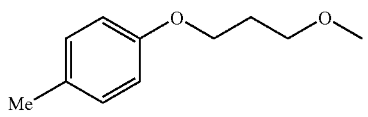 |
| 32 | 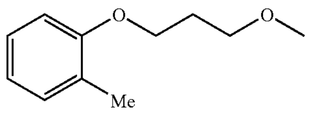 |
| 33 | 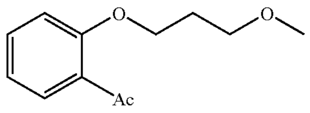 |
| 34 | 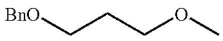 |
| 35 | 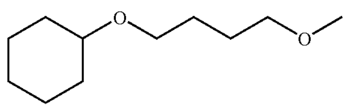 |
| 36 | 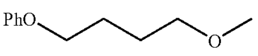 |
| 37 | 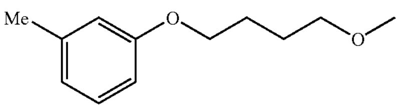 |
| 38 | 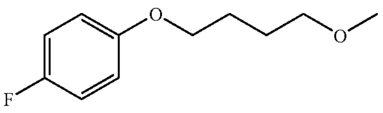 |
TABLE 45-continued
(I-VV)
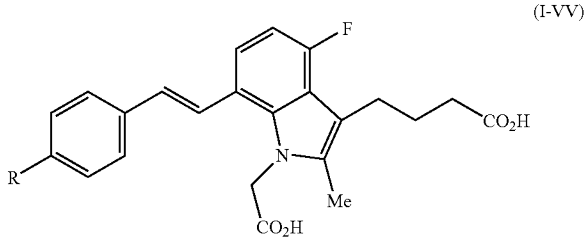
| | R⁴— |
|---|---|
| 39 | 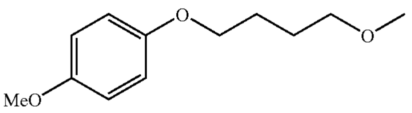 |
| 40 | 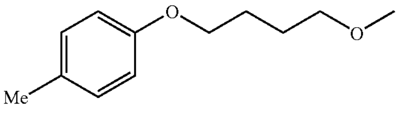 |
| 41 | 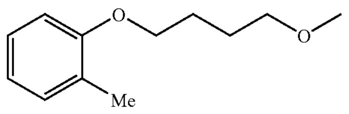 |
| 42 | 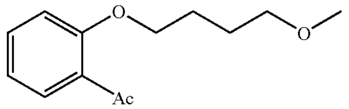 |
| 43 | 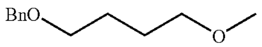 |
| 44 | 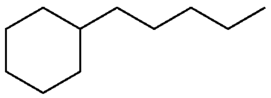 |
| 45 | 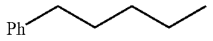 |
| 46 | 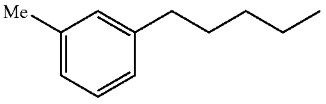 |
| 47 | 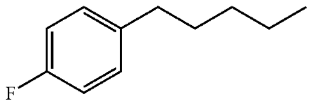 |
| 48 | 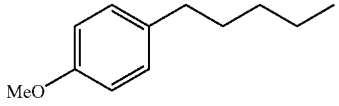 |
| 49 | 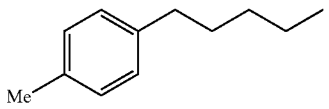 |
| 50 | 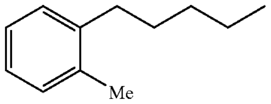 |

TABLE 45-continued
(I-VV)
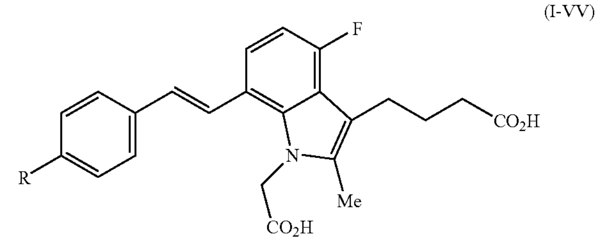
| | $R^4$— |
|---|---|
| 51 | 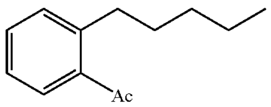 |
| 52 | 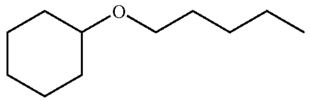 |
| 53 | 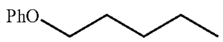 |
| 54 | 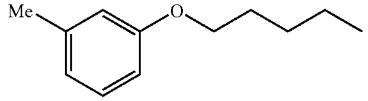 |
| 55 | 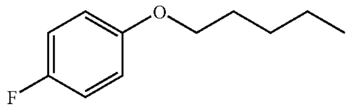 |
| 56 | 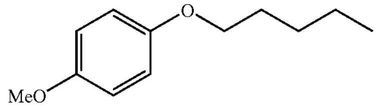 |
| 57 | 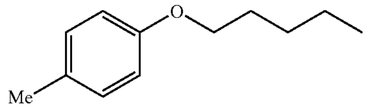 |
| 58 | 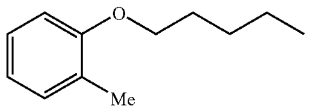 |
| 59 | 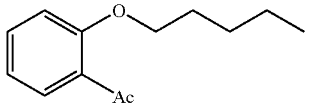 |
| 60 | 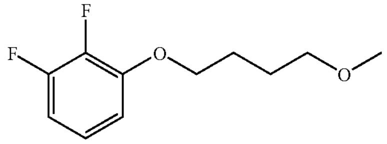 |
| 61 | 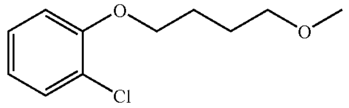 |
TABLE 45-continued
(I-VV)
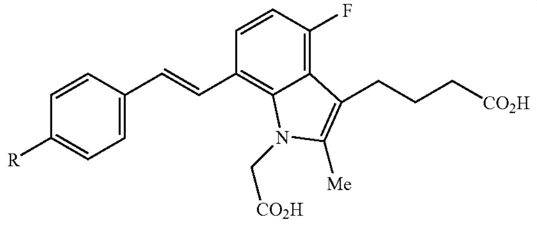
| | $R^4$— |
|---|---|
| 62 | 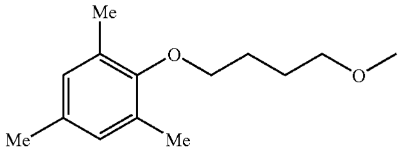 |
| 63 | 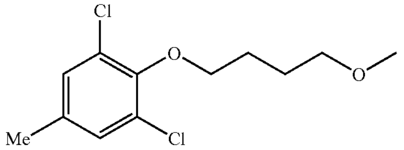 |
| 64 | 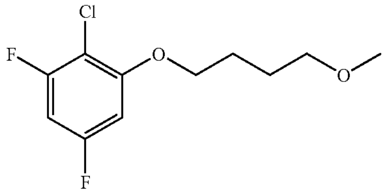 |
| 65 | 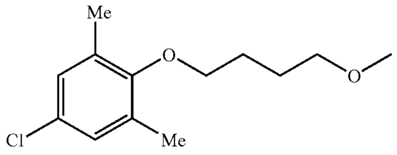 |
| 66 | 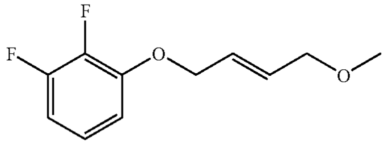 |
| 67 | 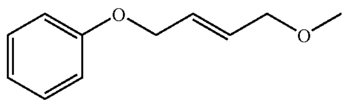 |
| 68 | 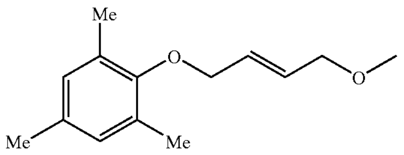 |
| 69 | 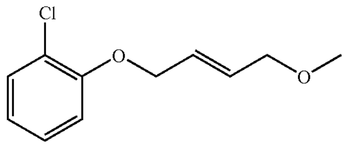 |

TABLE 46
(I-WW)
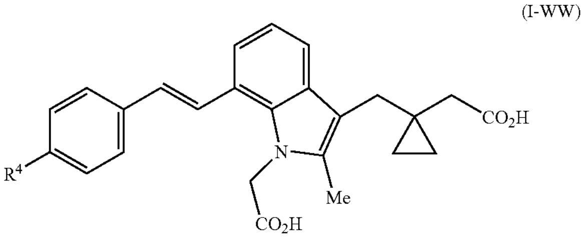
| | $R^4$— |
|---|---|
| 1 | n-$C_4H_9^-$ |
| 2 | n-$C_5H_{11}^-$ |
| 3 | n-$C_6H_{13}^-$ |
| 4 | n-$C_4H_9$—$O^-$ |
| 5 | n-$C_5H_{11}$—$O^-$ |
| 6 | n-$C_6H_{13}$—$O^-$ |
| 7 | 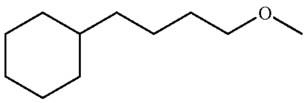 |
| 8 | 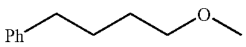 |
| 9 | 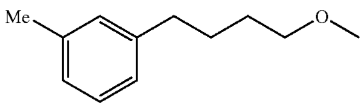 |
| 10 | 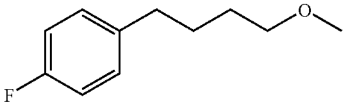 |
| 11 | 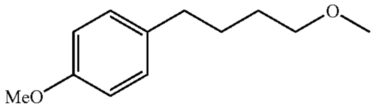 |
| 12 | 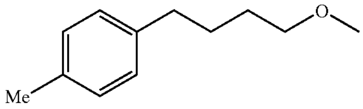 |
| 13 | 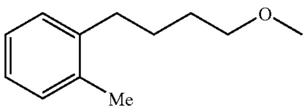 |
| 14 | 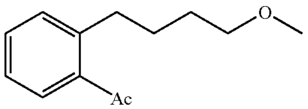 |
| 15 | 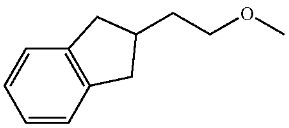 |
| 16 | 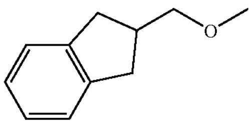 |
TABLE 46-continued
(I-WW)
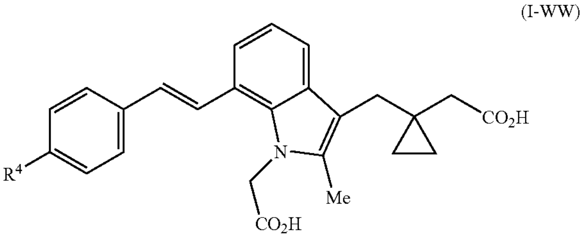
| | $R^4$— |
|---|---|
| 17 | 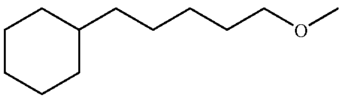 |
| 18 | 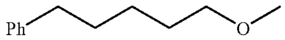 |
| 19 | 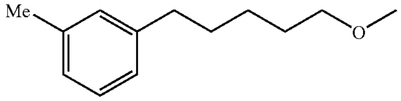 |
| 20 | 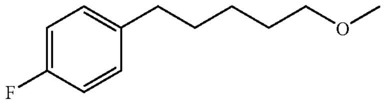 |
| 21 | 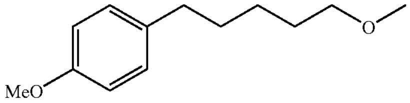 |
| 22 | 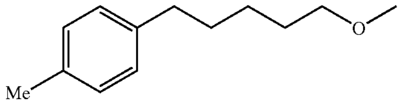 |
| 23 | 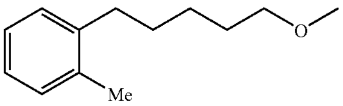 |
| 24 | 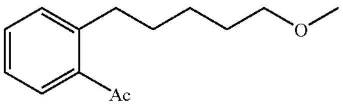 |
| 25 | 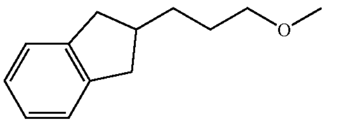 |
| 26 | 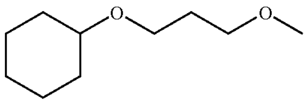 |
| 27 | 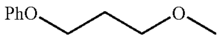 |
| 28 | 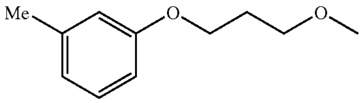 |

TABLE 46-continued
(I-WW)
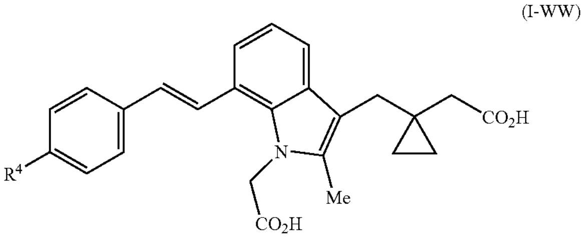
| | $R^4$— |
|---|---|
| 29 | 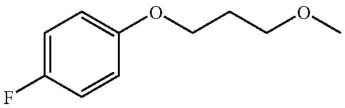 |
| 30 | 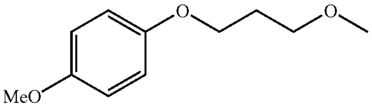 |
| 31 | 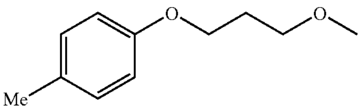 |
| 32 | 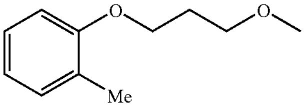 |
| 33 | 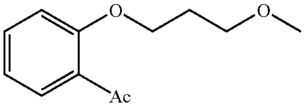 |
| 34 | 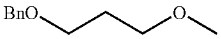 |
| 35 | 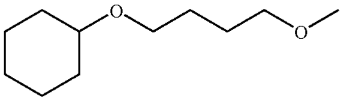 |
| 36 | 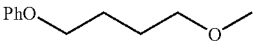 |
| 37 | 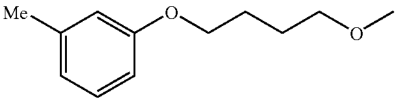 |
| 38 | 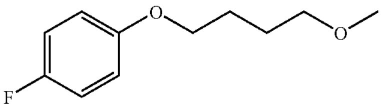 |
| 39 | 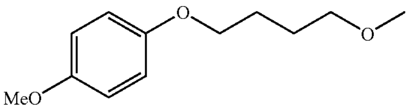 |
TABLE 46-continued
(I-WW)
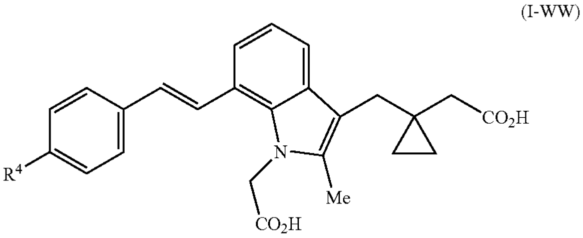
| | $R^4$— |
|---|---|
| 40 | 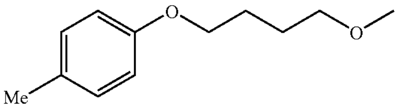 |
| 41 | 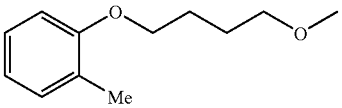 |
| 42 | 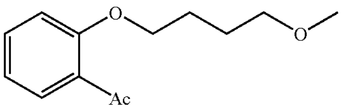 |
| 43 | 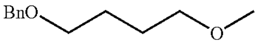 |
| 44 | 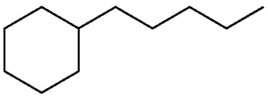 |
| 45 | 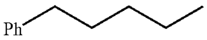 |
| 46 | 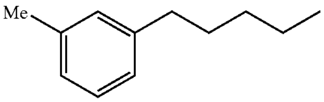 |
| 47 | 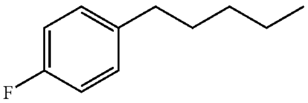 |
| 48 | 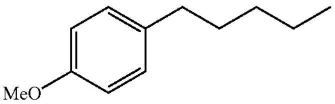 |
| 49 | 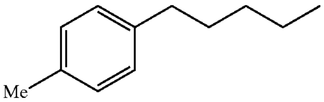 |
| 50 | 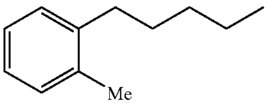 |
| 51 | 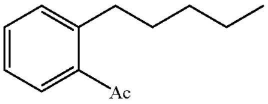 |

TABLE 46-continued
(I-WW)
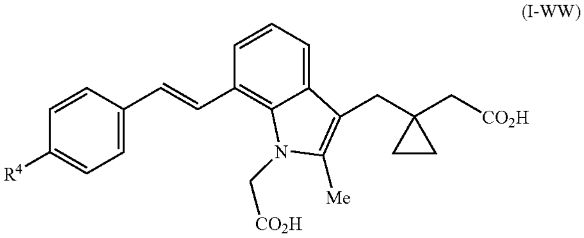
| | $R^4$— |
|---|---|
| 52 | 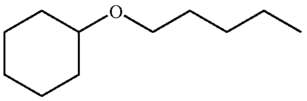 |
| 53 | 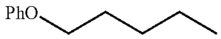 |
| 54 | 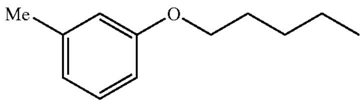 |
| 55 | 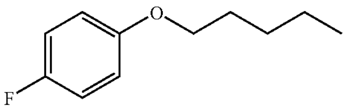 |
| 56 | 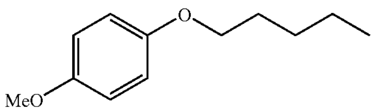 |
| 57 | 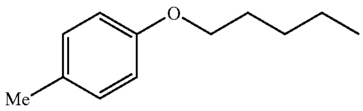 |
| 58 | 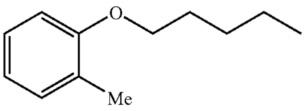 |
| 59 | 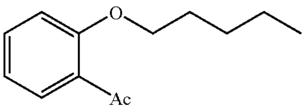 |
| 60 | 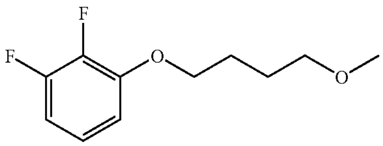 |
| 61 | 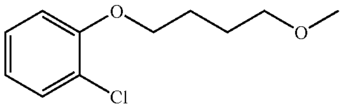 |
TABLE 46-continued
(I-WW)
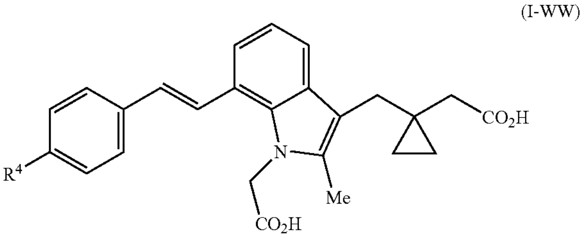
| | $R^4$— |
|---|---|
| 62 | 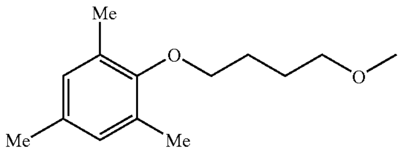 |
| 63 | 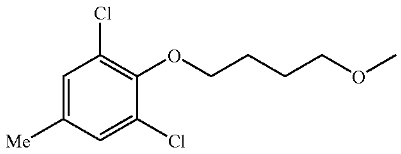 |
| 64 | 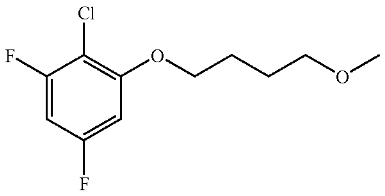 |
| 65 | 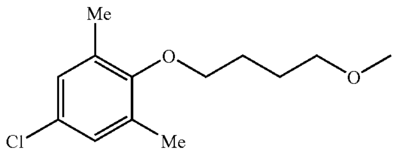 |
| 66 | 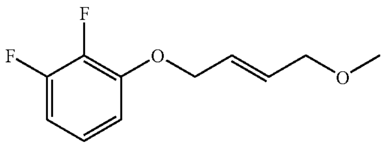 |
| 67 | 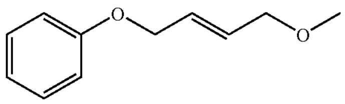 |
| 68 | 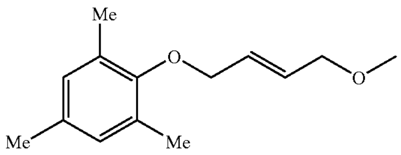 |
| 69 | 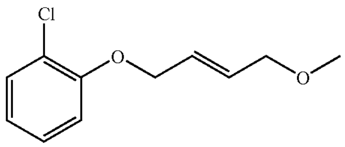 |

TABLE 47
(I-XX)
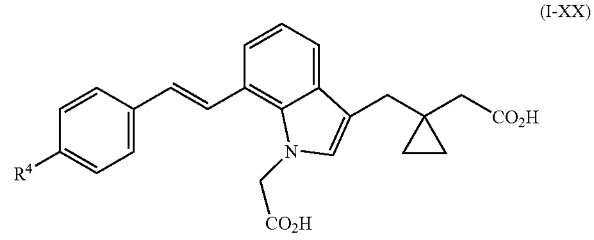
| | $R^4$— |
|---|---|
| 1 | $n\text{-}C_4H_9^-$ |
| 2 | $n\text{-}C_5H_{11}^-$ |
| 3 | $n\text{-}C_6H_{13}^-$ |
| 4 | $n\text{-}C_4H_9$—$O^-$ |
| 5 | $n\text{-}C_5H_{11}$—$O^-$ |
| 6 | $n\text{-}C_6H_{13}$—$O^-$ |
| 7 | 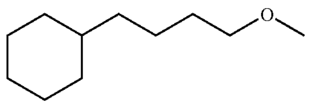 |
| 8 | 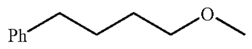 |
| 9 | 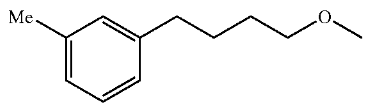 |
| 10 | 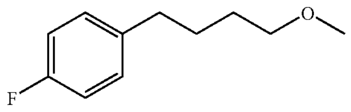 |
| 11 | 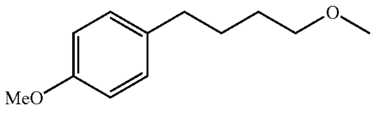 |
| 12 | 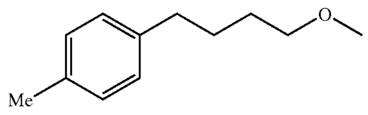 |
| 13 | 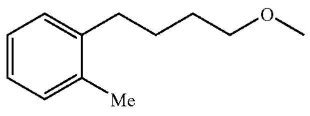 |
| 14 | 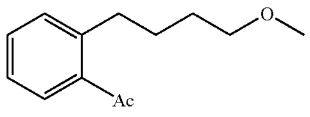 |
| 15 | 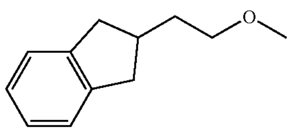 |
| 16 | 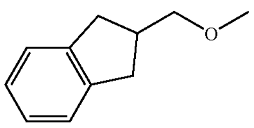 |
TABLE 47-continued
(I-XX)
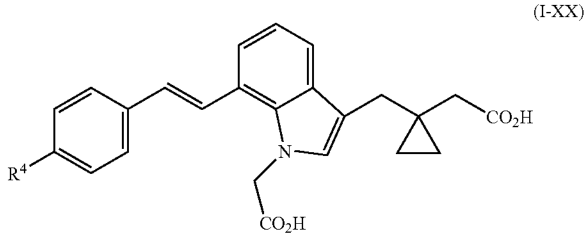
| | $R^4$— |
|---|---|
| 17 | 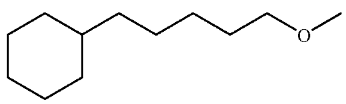 |
| 18 | 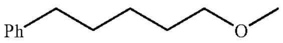 |
| 19 | 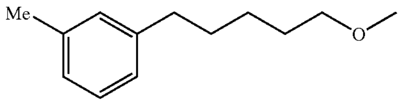 |
| 20 | 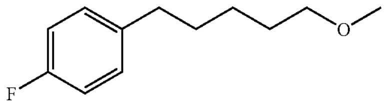 |
| 21 | 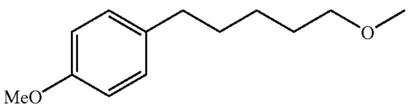 |
| 22 | 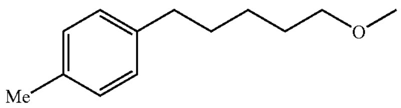 |
| 23 | 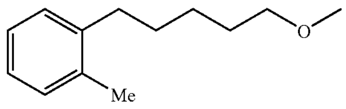 |
| 24 | 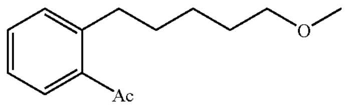 |
| 25 | 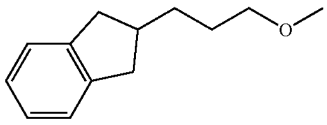 |
| 26 | 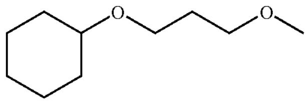 |
| 27 | 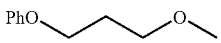 |
| 28 | 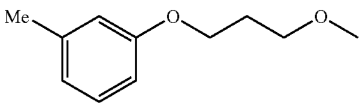 |

TABLE 47-continued
(I-XX)
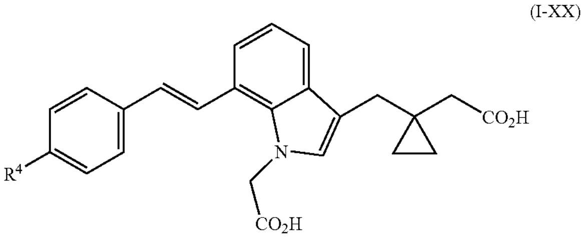
| | $R^4$— |
|---|---|
| 29 | 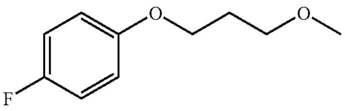 |
| 30 | 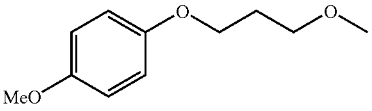 |
| 31 | 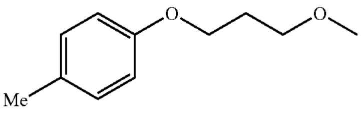 |
| 32 | 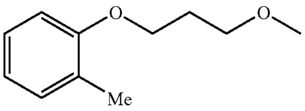 |
| 33 | 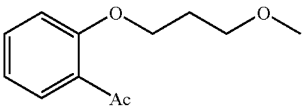 |
| 34 | 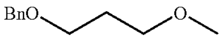 |
| 35 | 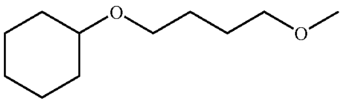 |
| 36 | 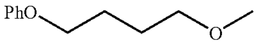 |
| 37 | 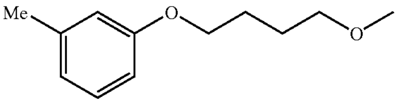 |
| 38 | 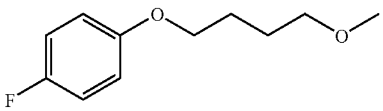 |
| 39 | 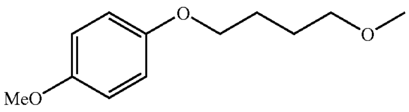 |
TABLE 47-continued
(I-XX)
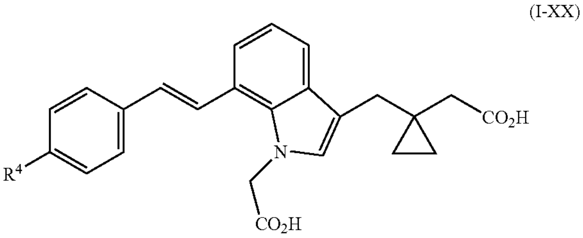
| | $R^4$— |
|---|---|
| 40 | 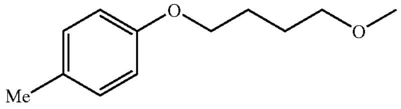 |
| 41 | 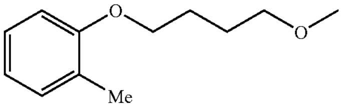 |
| 42 | 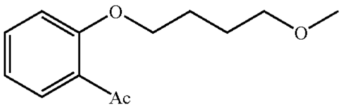 |
| 43 | 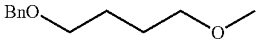 |
| 44 | 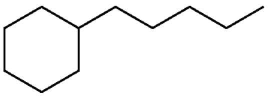 |
| 45 | 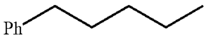 |
| 46 | 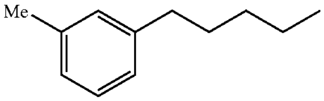 |
| 47 | 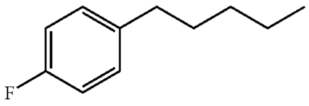 |
| 48 | 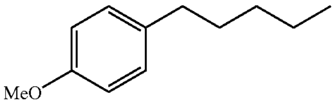 |
| 49 | 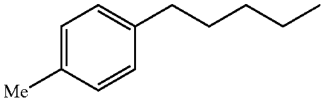 |
| 50 | 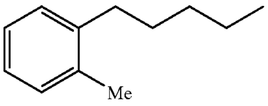 |
| 51 | 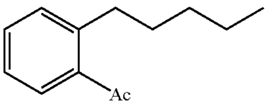 |

TABLE 47-continued
(I-XX)
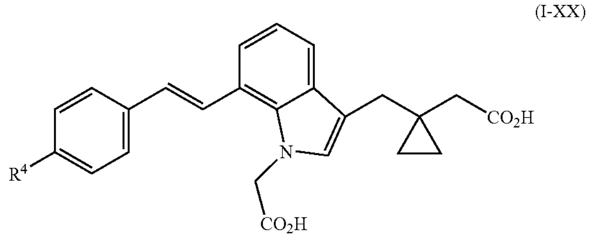
| | $R^4$— |
|---|---|
| 52 | 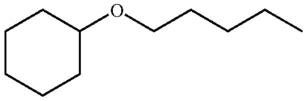 |
| 53 | 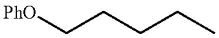 |
| 54 | 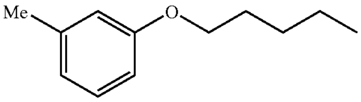 |
| 55 | 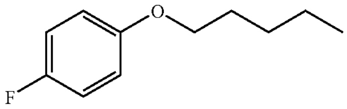 |
| 56 | 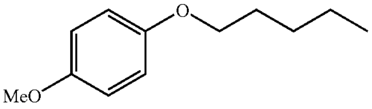 |
| 57 | 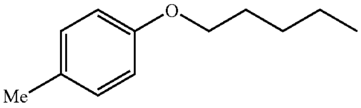 |
| 58 | 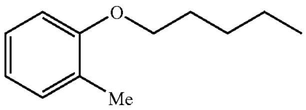 |
| 59 | 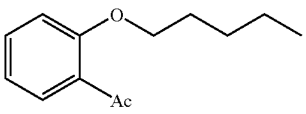 |
| 60 | 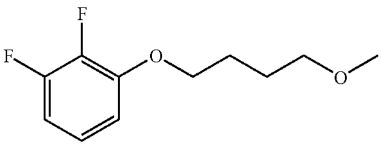 |
| 61 | 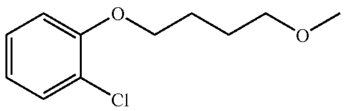 |
TABLE 47-continued
(I-XX)
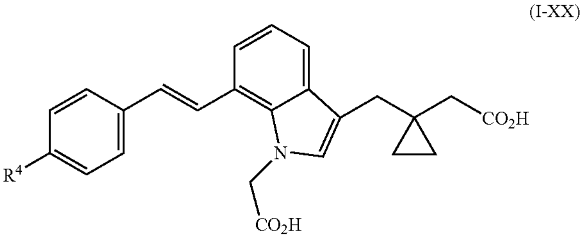
| | $R^4$— |
|---|---|
| 62 | 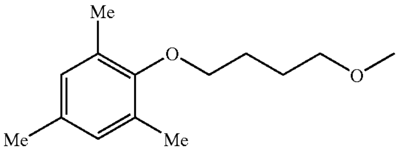 |
| 63 | 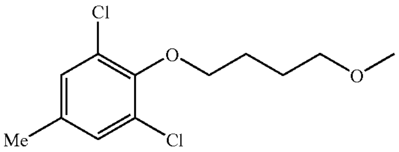 |
| 64 | 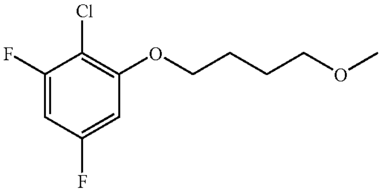 |
| 65 | 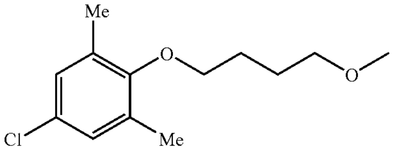 |
| 66 | 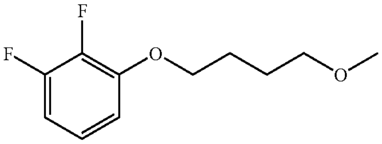 |
| 67 | 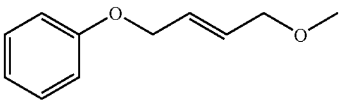 |
| 68 | 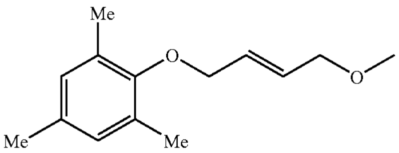 |
| 69 | 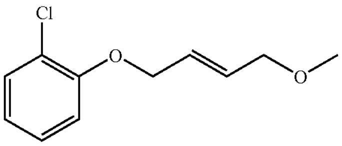 |

[The Method for the Preparation of the Compound of the Present Invention]

The compound of the present invention represented by the formula (I) may be prepared by known methods, for example, a method combining the following methods, the method according to these method, the methods described in Examples and/or methods described in Comprehensive Organic Transformations: A Guide to Functional Group Preparations, 2nd Edition (Richard C. Larock, John Wiley & Sons Inc, 1999), etc., which are appropriately modified In each following method for the preparation, salts of the starting materials may be used. The below-mentioned salts of the compound (I) can be used as the salts.

1) Among the compound of the present invention represented by the formula (I), a compound wherein $R^{51}$ is $-E-CO_2H$, one of $R^{52}$ and $R^{53}$ is $-D-R^1$, the other of $R^{52}$ and $R^{53}$ is $R^5$, $R^1$ is carboxy or 5-tetrazolyl, p is 1, i.e. the compound of the present invention represented by the formula (I-1)

(I-1)

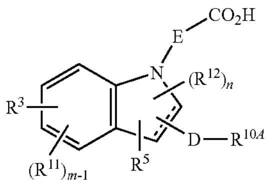

wherein $R^{10A}$ represents carboxy or 5-tetrazolyl, and other symbols have the same meanings as described hereinbefore, may be prepared according to the following method.

1-a) Among the compound of the present invention represented by the formula (I-1), which E binds to indole ring with carbonyl, i.e. the compound of the present invention represented by the formula (I-1-a)

(I-1-a)

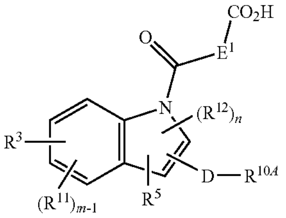

wherein $E^1$ represents a spacer which has a main chain having 1 to 7 atom(s), and other symbols have the same meanings as described hereinbefore, may be prepared by subjecting a compound represented by the formula (II)

(II)

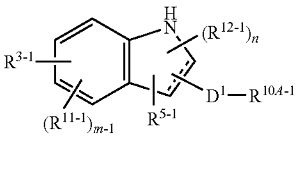

wherein $R^{10A-1}$ represents carboxy which is protected, or 5-tetrazolyl, $R^{3-1}$, $D^1$, $R^{5-1}$, $R^{11-1}$ and $R^{12-1}$ have the same meanings of $R^3$, D, $R^5$, $R^{11}$ and $R^{12}$, and when carboxy, hydroxy, amino or mercapto group exists in the group, it is protected if the protection is necessary, to a amidation with a carboxylic acid represented by the formula (III-1)

(III-1)

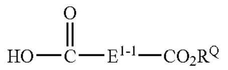

wherein $E^{1-1}$ has the same meaning of $E^1$, and when carboxy, hydroxy, amino or mercapto group exists in the group, it is protected if the protection is necessary, $R^Q$ represents a protective group of carboxy, optionally followed by subjecting to a deprotection reaction of the protective groups of $R^Q$, followed by a deprotection reaction of a protective group of carboxy, hydroxy, amino, mercapto or tetrazolyl group, if necessary.

The amidation reaction may be carried out by, for example, (1) a method using acid halide, (2) a method using mixed anhydride, (3) a method using a condensing agent, etc.

To explain these methods specifically;

(1) The method using acid halide is carried out, for example, by subjecting a carboxylic acid to a reaction with an acid-halogenating agent (e.g. oxalyl chloride, thionyl chloride, etc.) in an organic solvent (e.g. chloroform, dichloromethane, diethyl ether, tetrahydrofuran, dimethoxyethane, etc.) or without a solvent, at a temperature of −20° C. to a refluxing temperature, and then subjecting the thus obtained acid halide to a reaction with an amine in the presence of a base (e.g. pyridine, triethylamine, dimethylaniline, dimethylaminopyridine, diisopropylethylamine, etc.) in an organic solvent (e.g. chloroform, dichloromethane, diethyl ether, tetrahydrofuran, acetonitorile, ethyl acetate, etc.) at a temperature of 0 to 40° C. Also, the reaction may be carried out by subjecting the thus obtained acidic halide to a reaction with an amine in an organic solvent (e.g. dioxane, tetrahydrofuran, dichloromethane, etc.) using an alkali aqueous solution (e.g. an aqueous solution of sodium bicarbonate, sodium hydroxide, etc.) in the presence or absence of a phase-transfer catalyst (e.g. quaternary ammonium salts such as tetrabutylammonium chloride, triethylbenzylammonium chloride, tri-n-octylmethylammonium chloride, trimethyldecylammonium chloride, tetramethylammonium bromide, etc.) at a temperature of between 0 to 40° C.;

(2) The method using mixed anhydride is carried out, for example, by subjecting a carboxylic acid to a reaction with an acid halide (e.g. pivaloyl chloride, tosyl chloride, mesyl chloride, etc.) or an acid derivative (e.g. ethyl chloroformate, isobutyl chloroformate, etc.) in an organic solvent (e.g. chloroform, dichloromethane, diethyl ether, tetrahydrofuran, etc.) or without a solvent in the presence of a base (pyridine, triethylamine, dimethylaniline, dimethylaminopyridine, diisopropylethylamine, etc.) at a temperature of 0 to 40° C., and then subjecting the thus obtained mixed anhydride to a reaction with an amine in an organic solvent (e.g. chloroform, dichloromethane, diethyl ether, tetrahydrofuran, etc.) at a temperature of 0 to 40° C.;

(3) The method using a condensing agent is carried out, for example, by subjecting a carboxylic acid to a reaction with an amine in an organic solvent (e.g. chloroform, dichloromethane, N,N-dimethylformamide, diethyl ether, tetrahydrofuran, etc.) or without a solvent, in the presence or absence of a base (e.g. pyridine, triethylamine, dimethylaniline, dimethylaminopyridine, etc.), using a condensing agent (e.g. 1,3-dicyclohexylcarbodiimide (DCC), 1-ethyl-3-[3-dimethylamino)propyl]carbodiimide (EDC), 1,1'-carbonyldiimidazole (CDI), 2-chloro-1-methylpyridinium iodide, 1-propylphosphonic acid cyclic anhydride (1-propanephosphonic acid cyclic anhydride; PPA), etc.) in the presence or absence of 1-hydroxybenzotriazole (1-HOBt) at a temperature of 0 to 40° C.

The reactions of (1), (2) and (3) are desirably carried out under atmosphere of inert gas (argon, nitrogen, etc.) and anhydrous conditions.

The deprotective reaction of $R^Q$ is known, and for example, when $R^Q$ is methyl or ethyl, it may be carried out by deprotection reaction by alkali hydrolysis, and when $R^Q$ is tert-butyl, it may be carried out by deprotection reaction under acidic conditions.

The deprotection reaction by alkali hydrolysis is carried out, for example, in an organic solvent (methanol, tetrahydrofuran, 1,4-dioxane, etc.) using a hydroxide of alkali metals (sodium hydroxide, potassium hydroxide, lithium hydroxide, etc.), hydroxide of alkaline earth metals (barium hydroxide, calcium hydroxide, etc.), carbonate (sodium carbonate, potassium carbonate, etc.) or a solution thereof or a mixture thereof at a temperature of 0 to 40° C.

The deprotection reaction under acidic conditions is carried out, for example, in an organic solvent (dichloromethane, chloroform, dioxane, ethyl acetate, anisole, etc.), in an organic acid (acetic acid, trifluoroacetic acid, methanesulfonic acid, p-toluenesulfonic acid, etc.) or an inorganic acid (hydrochloric acid, sulfuric acid, etc.) or a mixture thereof (hydrobromic acid/acetic acid, etc.) in the presence or absence of 2,2,2-trifluoroethanol at a temperature of 0 to 100° C.

The deprotection reaction of the protective groups of carboxy, hydroxy, amino, mercapto or tetrazolyl group is well-known and includes, for example, (1) a deprotection reaction by alkali hydrolysis, (2) a deprotection under acidic conditions, (3) a deprotection reaction by hydrogenolysis, (4) a deprotection reaction of silyl group, (5) a deprotection reaction using a metal, (6) a deprotection reaction using a metal complex, etc.

To explain these methods concretely, (1) a deprotection reaction by alkali hydrolysis and (2) a deprotection under acidic conditions can be performed in accordance with the method as described above.

(3) The deprotection reaction by hydrogenolysis is, for example, carried out in a solvent (e.g. ethers such as tetrahydrofuran, 1,4-dioxane, dimethoxyethane, diethyl ether, etc.; alcohols such as methanol, ethanol, etc.; benzenes such as benzene, toluene, etc.; ketones such as acetone, methyl ethyl ketone, etc.; nitriles such as acetonitrile etc.; amides such as N,N-dimethylformamide, N,N-dimethylacetamide etc.; water, ethyl acetate, acetic acid or a mixture of two or more thereof, etc.) in the presence of a catalyst (palladium-carbon, palladium black, palladium hydroxide, platinum oxide, Raney nickel, etc.) under the atmosphere of hydrogen of normal or suppressed pressure, or in the presence of ammonium formate at a temperature of 0 to 200° C.

(4) The deprotection reaction of a silyl group is, for example, carried out in a water-miscible organic solvent (tetrahydrofuran, acetonitrile, etc.) using tetrabutylammonium fluoride at a temperature of 0 to 40° C.

(5) The deprotection reaction using a metal is carried out, for example, in an acidic solvent (acetic acid, a buffer of pH 4.2 to 7.2 or a mixture of the solution thereof and an organic solvent such as tetrahydrofuran etc.) in the presence of zinc powder at a temperature of 0 to 40° C. optionally under sonication.

(6) The deprotection reaction using a metal complex is carried out, for example, in an organic solvent (dichloromethane, N,N-dimethylformamide, tetrahydrofuran, ethyl acetate, acetonitrile, dioxane, ethanol, etc.), water or a mixture thereof, in the presence of a trap reagent (tributyltin hydride, triethylsilane, dimedone, morpholine, diethylamine, pyrrolidine, etc.), an organic acid (acetic acid, formic acid, 2-ethylhexanecarboxylic acid, etc.) and/or a salt of an organic acid (sodium 2-ethylhexanoate, potassium 2-ethylhexanoate, etc.) in the presence or absence of a phosphine reagent (triphenylphosphine etc.) using a metal complex (palladium tetrakis(triphenylphosphine (0)), palladium bis(triphenylphosphosphine) dichloride (II), palladium acetate (II), rhodium tris(triphenylphosphine) chloride (I) etc. at a temperature of 0 to 40° C.

In addition to the above, deprotection reaction may be carried out by the method, for example, described in T. W. Greene, Protective Groups in Organic Synthesis, Wiley, New York, 1999.

A protective group for carboxy includes, for example, methyl, ethyl, allyl, tert-butyl, trichloroethyl, benzyl (Bn), phenacyl, p-methoxybenzyl, trityl, 2-chlorotrityl or a solid carrier containing these structure, etc.

A protective group for hydroxy includes, for example, methyl, trityl, methoxymethyl (MOM), 1-ethoxyethyl (EE), methoxyethoxymethyl (MEM), 2-tetrahydropyranyl (LIP), trimethylsilyl (TMS), triethylsilyl (TES), tert-butyldimethylsilyl (TBDMS), tert-butyldiphenylsilyl (TBDPS), acetyl (Ac), pivaolyl, benzoyl, benzyl (Bn), p-methoxybenzyl, allyloxycarbonyl (Alloc) or 2,2,2-trichloroethoxycarbonyl (Troc), etc.

A protective group for amino includes, for example, benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), p-methoxybenzyl, benzyloxymethyl (BOM), 2-(trimethylsilyl)ethoxymethyl (SEM), etc.

A protective group for mercapto includes, for example, benzyl, methoxybenzyl, methoxymethyl (MOM), 2-tetrahydropyranyl (THP), diphenylmethyl, acetyl (Ac), etc.

A protective group for tetrazolyl includes, for example, tert-butyl, methyloxycarbonyl, benzyloxycarbonyl, tert-butoxycarbonyl, allyloxycarbonyl (Alloc), 1-methyl-1-(4-biphenyl)ethoxycarbonyl (Bpoc), trifluoroacetyl, 9-fluorenylmethoxycarbonyl, benzyl (Bn), α,α-dimethylbenzyl, trityl, p-methoxybenzyl, benzyloxymethyl (BOM), 2-(trimethylsilyl)ethoxymethyl (SEM), trimethylsilyl (TMS), triethylsilyl (TES) or 2-cyanoethyl, etc.

Protective groups for carboxy, hydroxy, amino, mercapto or tetrazolyl group are not limited to the above ones, but those groups which are easily and selectively eliminated are also acceptable. For example, those groups described in T. W. Greene, Protective Groups in Organic Synthesis, Wiley, New York, 1999 are used.

As is easily understood by those skilled in the art, the target compound of the present invention may be prepared easily by selecting these deprotection reactions.

1-b) Among the compound of the present invention represented by the formula (I-1), which E binds to indole ring with methylene, i.e. the compound of the present invention represented by the formula (I-1-b)

(I-1-b)

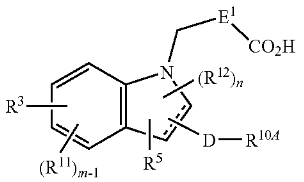

wherein all symbols have the same meanings as described hereinbefore, may be prepared by subjecting a compound represented by the formula (II) and a compound represented by the formula (III-2)

(III-2)

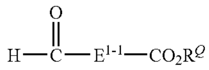

wherein all symbols have the same meanings as described hereinbefore, to reductive amination, optionally followed by subjecting to a deprotection reaction of the protective groups of $R^Q$, followed by a deprotection reaction of a protective group of carboxy, hydroxy, amino, mercapto or tetrazolyl group, if necessary.

The reductive amination is carried out, for example, by reaction at a temperature of from 0 to 40° C. in an organic solvent (tetrahydrofuran, diethyl ether, dichloroethane, dichloromethane, N,N-dimethylformamide, acetic acid, methanol ethanol and a mixed solvent thereof, etc.), in the presence of a reducing agent (sodium triacetoxyborohydride sodium cyanoborohydride, sodium borohydride, zinc borohydride, diisobutylaluminium hydride, etc.), or by reaction at a temperature of from 0 to 200° C. in an organic solvent (ethers such as tetrahydrohuran, dioxane, dimethoxyethane, diethyl ether, etc., alcohols such as methanol, ethanol, etc., benzens such as benzene, toluene, etc., ketones such as acetone, methyl ethyl ketone, etc., nitriles such as acetonitrile etc., amides such as N,N-dimethylformamide, N,N-dimethylacetamide, etc., water, ethyl acetate, acetic acid or a mixed solvent thereof, etc.), in the presence of a catalyst (palladium on carbon, palladium black, palladium hydroxide, platinum oxide, Raney Nickel, etc., under atmosphere of hydrogen at normal pressure or under pressure.

The deprotective reaction of $R^Q$ and the deprotection reaction of the protective groups of carboxy, hydroxy, amino, mercapto or tetrazolyl group is known may be carried out by the same method as described hereinbefore.

1-c) Among the compound of the present invention represented by the formula (I-1), which nitrogen atom of indole ring binds to saturated carbon atom, i.e. the compound of the present invention represented by the formula (I-1-c)

(I-1-c)

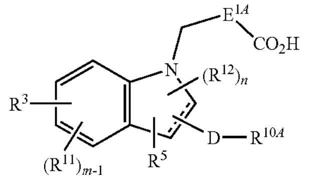

wherein $E^{1A}$ represents a bond or a spacer which has a main chain having 1 to 7 atom(s), and other symbols have the same meanings as described hereinbefore, may be prepared by subjecting an above-mentioned compound represented by the formula (II) and a compound represented by the formula (III-3)

$$X—CH_2\text{-}E^{1A}\text{-}CO_2R^Q \quad \text{(III-3)}$$

wherein X represents a leaving group such as halogen, mesyloxy, tosyloxy, etc., and other symbols have the same meanings as described hereinbefore, to N-alkylation, optionally followed by subjecting to a deprotection reaction of the protective groups of $R^Q$, followed by a deprotection reaction of a protective group of carboxy, hydroxy, amino, mercapto or tetrazolyl group, if necessary.

The N-alkylation is carried out, for example, by reaction at a temperature of from −78° C. to reflux temperature in an organic solvent (tetrahydrofuran, dichloromethane, chloroform, benzene, toluene, xylene, hexane, heptane, cyclohexane, diethyl ether, dioxane, acetone, ethyl methyl ketone, acetonitrile, dimethylsulfoxide, N,N-dimethylformamide, N,N-dimethylacetamide, ethyl acetate, etc.), in the presence or absence of base (sodium hydride, triethylamine, dimethylaminopyridine, pyridine, etc.).

The deprotective reaction of $R^Q$ and the deprotection reaction of the protective groups of carboxy, hydroxy, amino, mercapto or tetrazolyl is known may be carried out by the same method as described hereinbefore.

1-2) Among the compound of the present invention represented by the formula (I-1), a compound wherein $R^3$ represents

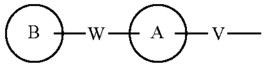

wherein all symbols have the same meanings as described hereinbefore, and V is ethenylene, i.e. the compound of the present invention represented by the formula (I-1-2)

(I-1-2)

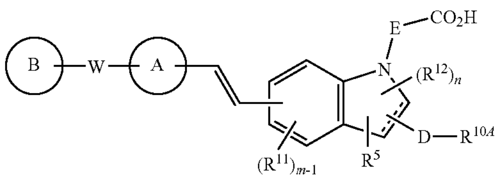

wherein all symbols have the same meanings as described hereinbefore, may be prepared by subjecting a compound represented by the formula (Y-1)

(Y-1)

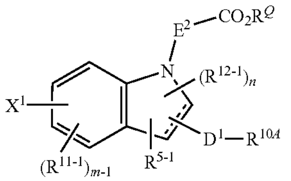

wherein $X^1$ represents halogen (chlorine, bromine or fluorine) or trifluoromethanesulfonyloxy, $E^2$ has the same meaning of E, and when carboxy, hydroxy, amino or mercapto group exists in the group, it is protected if the protection is necessary, and other symbols have the same meanings as described hereinbefore, and a compound represented by the formula (Y-2)

(Y-2)

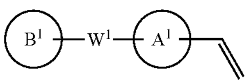

wherein ring $A^1$, $W^1$ and ring $B^1$ have the same meanings of ring A, W and ring B, respectively, and when carboxy, hydroxy, amino or mercapto group exists in the group, it is protected if the protection is necessary, to Heck reaction, optionally followed by subjecting to a deprotection reaction of the protective groups of $R^Q$, followed by a deprotection reaction of a protective group of carboxy, hydroxy, amino, mercapto or tetrazolyl group if necessary.

The Heck reaction can be carried out according to known method, for example, a reaction at a temperature of from 0 to 180° C. in an organic solvent (dimethylformamide, dimethylacetamide, N-methylpyrrolidone, acetonitrile, toluene, xylenen, dioxane, etc.), in the presence of palladium catalyst (palladium acetate (II), palladium chloride (II), tris(dibenzylideneacetone) dipalladium (0), [1,1'-bis(diphenylphosphino)ferrocene]palladium (II), etc.), in the presence of phosphine reagent (triphenylphosphine, tri-n-butylphosphine, tri-t-butylphosphine, tris(2,4,6-trimethylphenyl)phosphine, tris(4-methylphenyl)phosphine, etc.), in the presence of base (potassium carbonate, sodium carbonate, sodium hydrogen carbonate, diisopropylethylamine, triethylamine, N,N-dicyclohexylmethylamine, etc.) if necessary, in the presence or absence of additive (tetra-n-butylammonium chloride, tetra-n-butylammonium bromide, tetra-n-butylammonium hydrogen sulfate, etc.). This reaction is desirably carried out under atmosphere of inert gas (argon, nitrogen, etc.) and anhydrous conditions. This reaction may be carried out by method described in Chem. Rev., 100, 3009 (2000), handbook of Organopalladium Chemistry for Organic Synthesis (Wiley Interscience), etc. as reference.

The deprotective reaction of $R^Q$ and the deprotection reaction of the protective groups of carboxy, hydroxy, amino, mercapto or tetrazolyl group is known and may be carried out by the same method as described hereinbefore.

1-3) Among the compound of the present invention represented by the formula (I-1), a compound wherein $R^3$ represents a group represented by

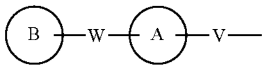

wherein all symbols have the same meanings as described hereinbefore, and V is —C(O)—NH- (wherein a left bond binds to ring A), i.e. the compound of the present invention represented by the formula (I-1-3)

(I-1-3)

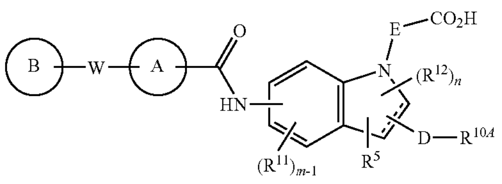

wherein all symbols have the same meanings as described hereinbefore, may be prepared by subjecting a compound represented by the formula (Y3)

(Y-3)

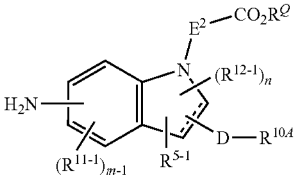

wherein all symbols have the same meanings as described hereinbefore, and a compound represented by the formula (Y4)

(Y-4)

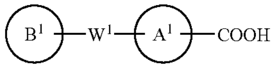

wherein all symbols have the same meanings as described hereinbefore, to amidation, optionally followed by subjecting to a deprotection reaction of the protective groups of $R^Q$, followed by a deprotection reaction of a protective group of carboxy, hydroxy, amino, mercapto or tetrazolyl group if necessary.

The amidation, the deprotective reaction of $R^Q$ and the deprotection reaction of the protective groups of carboxy, hydroxy, amino, mercapto or tetrazolyl group is known and may be carried out by the same method as described hereinbefore.

2-1) Among the compound represented by the formula (I), a compound wherein $R^{51}$ is -E-$CO_2$H, the one of $R^{52}$ and $R^{53}$ is -D-C(O)—$NR^BSO_2R^C$, the other of $R^{52}$ and $R^{53}$ is $R^5$, i.e. the compound of the present invention represented by the formula (I-2-1)

(I-2-1)

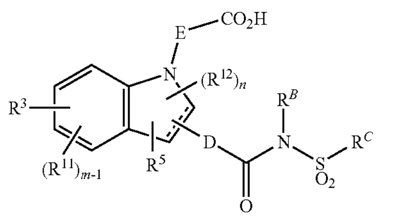

wherein all symbols have the same meanings as described hereinbefore, may be prepared by subjecting a compound represented by the formula (Y-5)

(Y-5)

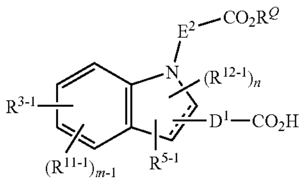

wherein all symbols have the same meanings as described hereinbefore, and a compound represented by the formula (Y6)

(Y-6)

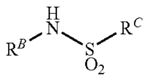

wherein $R^B$ and $R^C$ have the same meaning as described hereinbefore, respectively, to amidation, followed by a deprotection reaction of a protective groups of carboxy, hydroxy, amino, mercapto or tetrazolyl group. The amidation and the deprotection reaction of the protective groups of carboxy, hydroxy, amino or mercapto group is known and may be carried out by the same method as described hereinbefore.

An above-mentioned compound represented by the formula (Y-5) may be prepared by subjecting a compound wherein $R^{10A-1}$ is carboxy which is protected by protective group among a compound represented by the formula (II), i.e. the compound represented by the formula (II-A)

(II-A)

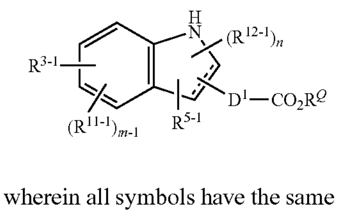

wherein all symbols have the same meanings as described hereinbefore, and a compound represented by the formulae (III-1), (III-2) or (III-3) to the reaction, followed by a selective deprotection reaction of $R^{10A-1}$.

2-2) Among the compound represented by the formula (I), a compound wherein $R^{51}$ is -E-C(O)—$NR^B$—$SO_2R^C$, one of $R^{52}$ and $R^{53}$ is -D-$CO_2H$, for example, a compound of the present invention represented by the formula (I-2-2)

(I-2-2)

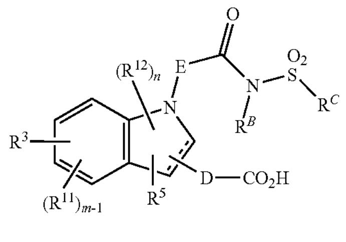

wherein all symbols have the same meanings as described hereinbefore, may also be prepared by subjecting a compound represented by the formula (Y-7)

(Y-7)

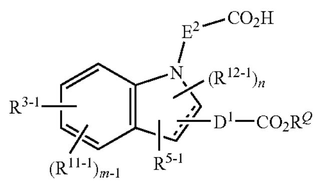

wherein $R^Q$ represents a protective group of carboxyl, and other symbols have the same meanings as described hereinbefore, and a compound represented by the formula (Y6) to amidation, followed by a deprotection reaction of a protective group of carboxy, hydroxy, amino, mercapto or tetrazolyl group. The amidation, the deprotective reaction of $R^Q$ and the deprotection reaction of the protective groups of carboxy, hydroxy, amino, mercapto or tetrazolyl group is known and may be carried out by the same method as described hereinbefore.

An above-mentioned compound represented by the formula (Y-7) may be prepared by subjecting an above-mentioned compound represented by the formula (II-A) and a compound represented by the formulae (III-1), (III-2) or (III-3) to the reaction, followed by a selective deprotection reaction of a protective group of $R^Q$.

3) Among the compound of the present invention represented by the formula (I), a compound wherein $R^{51}$ is -E-$CO_2H$, one $R^{52}$ and $R^{53}$ is

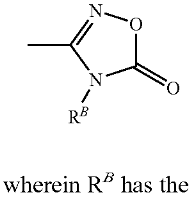

or

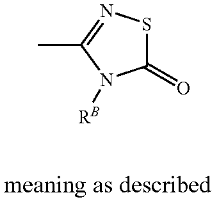

wherein $R^B$ has the same meaning as described hereinbefore, the other of $R^{52}$ and $R^{53}$, is $R^5$, i.e. the compound of the present invention represented by the formula (I-3)

(I-3)

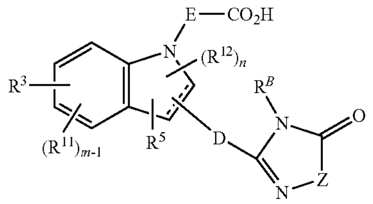

wherein Z represents an oxygen atom or a sulfur atom, and other symbols have the same meanings as described hereinbefore, may be prepared by subjecting the compound represented by the formula (Y-8)

(Y-8)

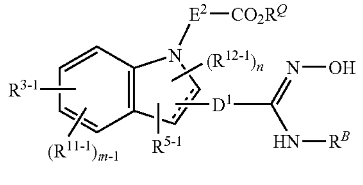

wherein all symbols have the same meanings as described hereinbefore, to a reaction with carbonyldiimidazole (CDI) or thiocarbonyldiimidazole (TCDI), then subjecting to a deprotection reaction of $R^Q$, followed by a deprotection reaction of a protective group of carboxy, hydroxy, amino or mercapto group, if necessary.

The reaction of the compound represented by the formula (Y-8) with CDI or TCDI can be carried out by the method according to known method. For example, it may be carried out in the presence of CDI or TCDI in an organic solvent (ethyl acetate, tetrahydrofuran, dichloromethane, chloroform, benzene, toluene, etc.) at a temperature of −20° C. to refluxing temperature.

The deprotective reaction of $R^Q$ and the deprotection reaction of the protective groups of carboxy, hydroxy, amino or mercapto group is known and may be carried out by the same method as described hereinbefore.

4-1) Among the compound of the present invention represented by the formula (I), a compound wherein $R^{51}$ is $-E-CO_2H$, one of $R^{52}$ and $R^{53}$ is

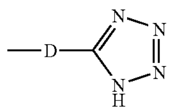

wherein $D^1$ has the same meaning as described hereinbefore, the other of $R^{52}$ and $R^{53}$ is $R^5$, i.e. the compound of the present invention represented by the formula (I-4-1)

(I-4-1)

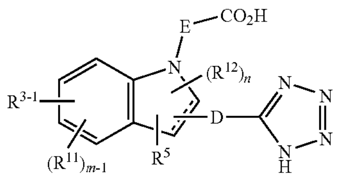

wherein all symbols have the same meanings as described hereinbefore, may be prepared by subjecting a compound represented by the formula (Y-9)

(Y-9)

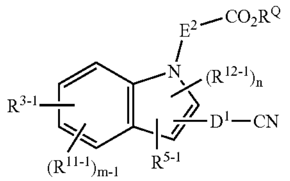

wherein all symbols have the same meanings as described hereinbefore, to ring closure reaction with an azide reagent, optionally followed by subjecting to a deprotection reaction of the protective groups of $R^Q$, followed by a deprotection reaction of a protective group of carboxy, hydroxy, amino or mercapto group, if necessary.

4-2) Among the compound of the present invention represented by the formula (I), a compound wherein $R^{51}$ is

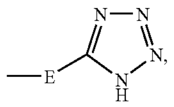

the one of $R^{52}$ and $R^{53}$ is $-D-CO_2H$, the other of $R^{52}$ and $R^{53}$ is $R^5$, i.e. the compound represented by the formula (I-4-2)

(I-4-2)

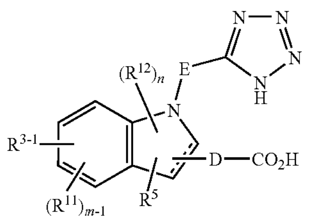

wherein all symbols have the same meanings as described hereinbefore, may also be prepared by subjecting a compound represented by the formula (Y-10)

(Y-10)

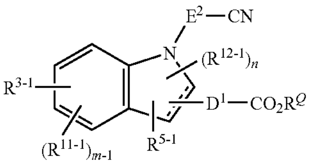

wherein all symbols have the same meanings as described hereinbefore, to ring closure reaction with an azide reagent, followed by a deprotection reaction of a protective group of carboxy, hydroxy, amino or mercapto group, if necessary.

The ring closure reaction of a compound represented by the formula (Y-9) or (Y-10) with an azide reagent may be carried out according to known method, for example, by reaction at a temperature of 0 to 180° C. in an organic solvent (dimethylformamide, toluene, tetrahydrofuran, xylene, dimethoxyethane, dioxane, o-dichlorobenzene, etc.), in the presence of an azide reagent (hydrogen azide, sodium azide, potassium azide, calcium azide, trimethylsilylazide, trimethyltin azide, ammonium azide, tri-n-butyltin azide, dimethylammonium azide, aluminium azide, amino[bis(dimethylamino)]methylazide, etc.), in the presence or absence of additive (ammounium chloride, lithium chloride, dibutyltin oxide, triethylamine, tetrabutylammonium fluoride, aluminium chloride, trimethylaluminium, dimethyltin oxide, tri-n-butyltin chloride).

The deprotective reaction of $R^Q$ and the deprotection reaction of the protective groups of carboxy, hydroxy, amino or mercapto group is known and may be carried out by the same method as described hereinbefore.

5) Among the compound represented by the formula (I), a compound wherein $R^{3-1}$ is

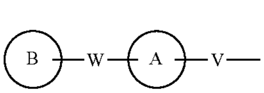,

V is 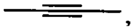, i.e. the compound represented by the formula (I-5)

(I-5)

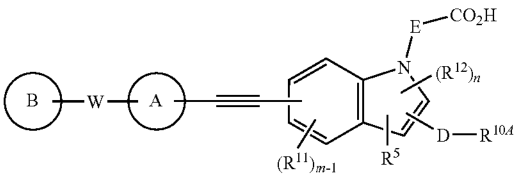

wherein all symbols have the same meanings as described hereinbefore, may be prepared, for example, by subjecting a compound represented by the formula (Y-1) and a compound represented by the formula (Y-11)

(Y-11)

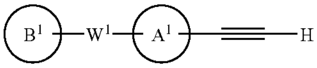

wherein all symbols have the same meanings as described hereinbefore, to Heck reaction, followed by a deprotection reaction. The Heck reaction and the deprotection reaction may be carried out by the same method as described hereinbefore.

6) Among the compound represented by the formula (I-1), a compound wherein $R^{3-1}$ is

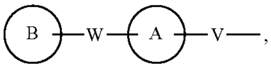,

V is

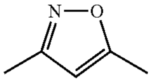, i.e. the compound represented by the formula (I-6)

(I-6)

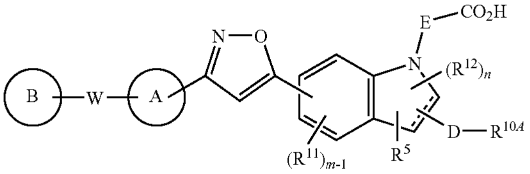

wherein all symbols have the same meanings as described hereinbefore, may be prepared, for example, by subjecting a compound represented by the formula (Y-12)

(Y-12)

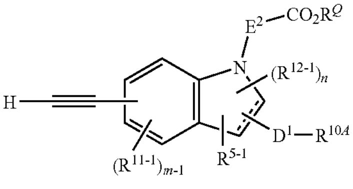

wherein all symbols have the same meanings as described hereinbefore, and a compound represented by the formula (Y-13)

(Y-13)

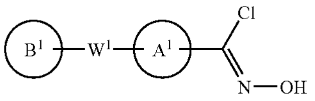

wherein all symbols have the same meanings as described hereinbefore, to a reaction, followed by a deprotection reaction.

The reaction of a compound represented by the formula (Y-12) and a compound represented by the formula (Y-13) is known, and can be carried out in an organic solvent (ethyl acetate, dichloromethane, chloroform, tetrahydrofuran, diethylel ether, N,N-dimethylformamide, etc.), in the presence of base (triethylamine, diisopropylethylamine, etc.), at a temperature under ice cooling to refluxing temperature.

Each compound used as a stating material or a reagent, is known per se, or may be prepared by method described in following reaction schemes.

The representative compound among compounds represented by the formula (II), for example, compounds represented by the formulae (II-1) to (II-13) may be prepared, for example, by the methods described in reaction schemes 1 to 5. Compounds represented by the formulae (Y-1) and (Y-3) may be prepared, for example, by the method described in reaction scheme 6, a compound represented by the formula (Y-8) may be prepared, for example, by the method described in reaction scheme 7, compounds represented by the formulae (Y-9) and (Y-10) may be prepared, for example, by the method described in reaction scheme 8.

A compound represented by the formula (Y-12) is known and may be prepared, for example, by subjecting a compound represented by the formula (Y-1) and a compound represented by the formula

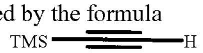

wherein TMS represents trimethylsilyl group, to Heck reaction, followed by a deprotection reaction of TMS, for example, the above-mentioned deprotective reaction under alkali condition.

Reaction Scheme 1

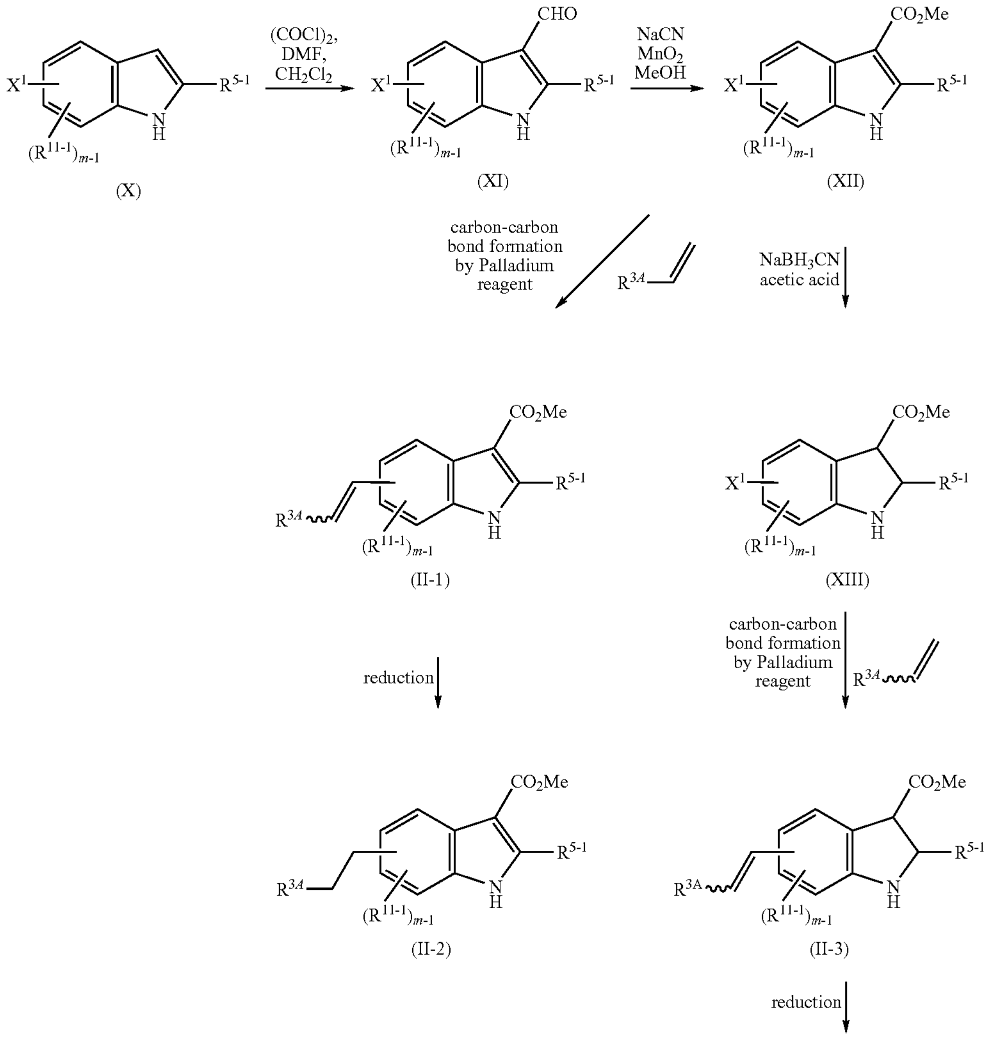

-continued
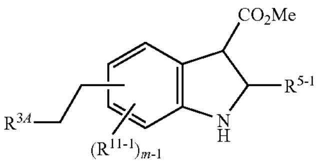
(II-4)
Reaction Scheme 2
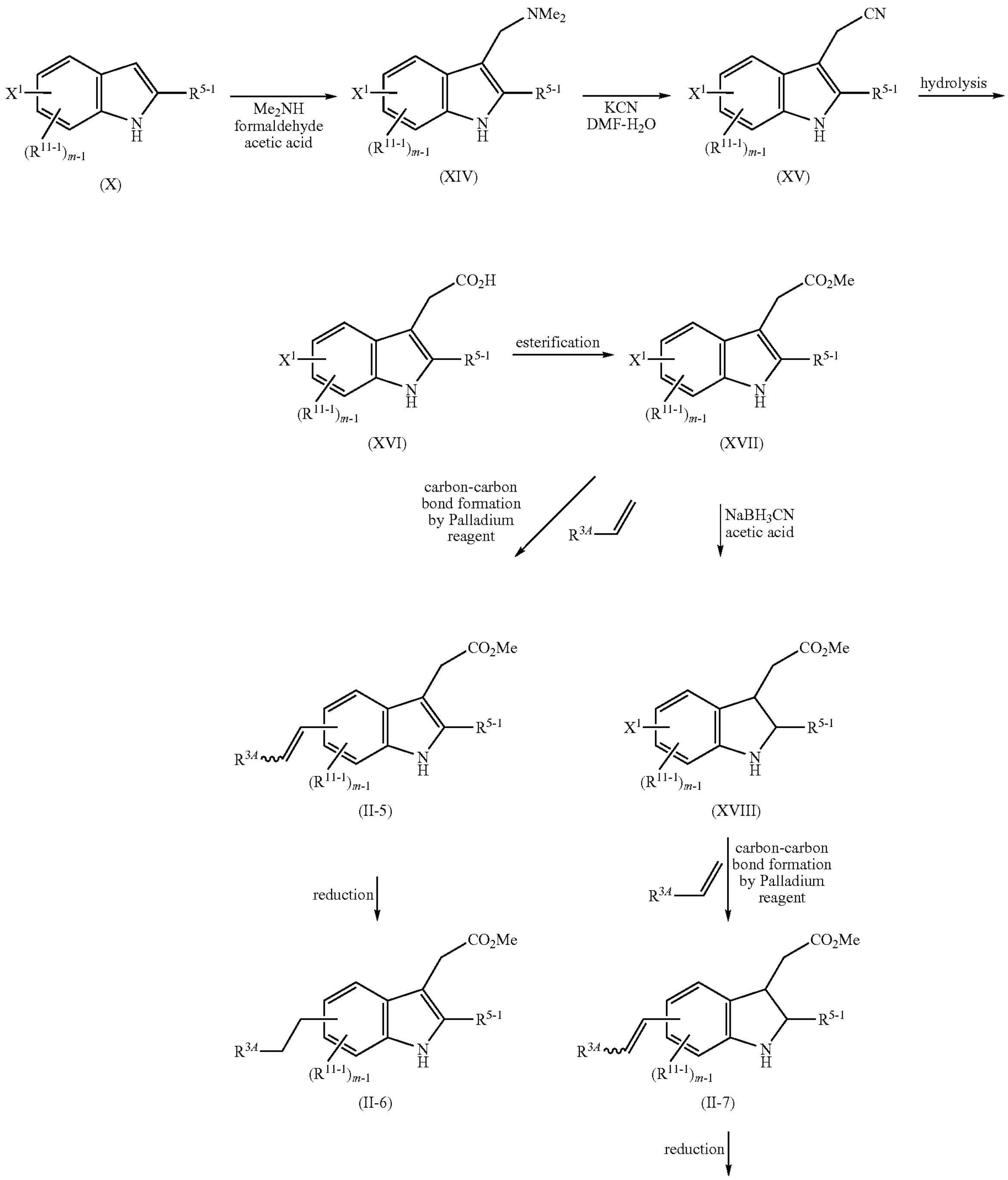
(X) (XIV) (XV) (XVI) (XVII) (II-5) (XVIII) (II-6) (II-7)

-continued
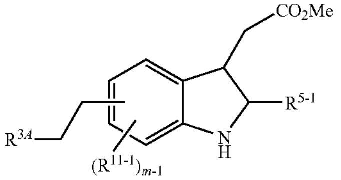
(II-8)
Reaction Scheme 3
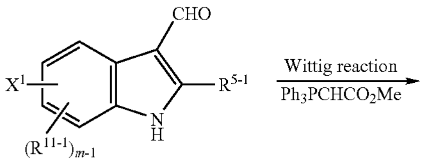
(XI)
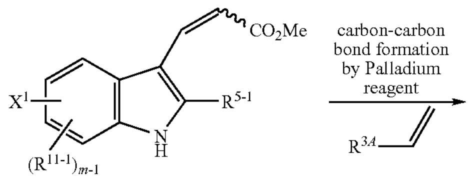
(XIX)
-continued
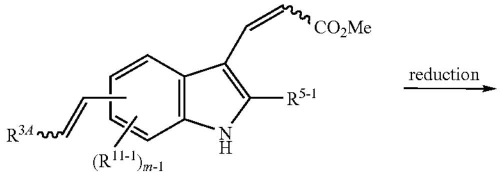
(II-9)
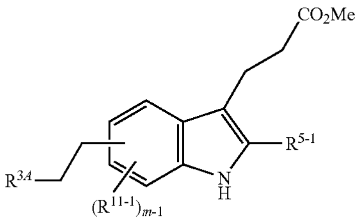
(II-10)
Reaction Scheme 4
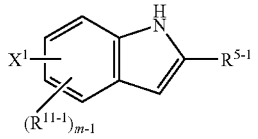
(X)
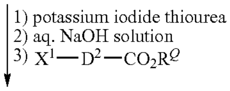
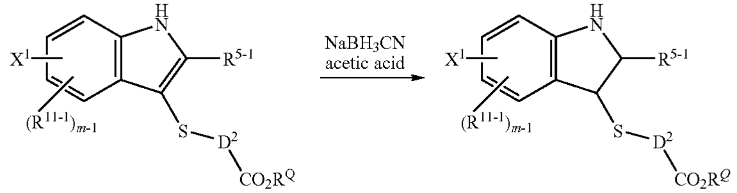
(XX) (XXI)
introduction of $R^{3-1}$
introduction of $R^{3-1}$ -continued
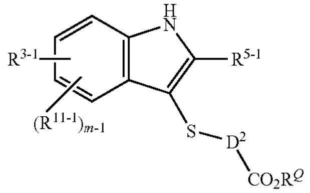
(II-9)
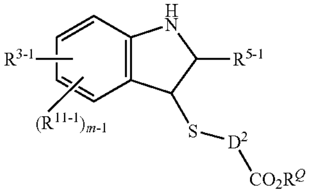
(II-10)
Reaction Scheme 5
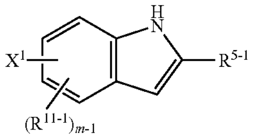
(X)
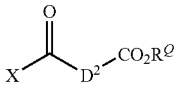
(XXII)
Lewis acid
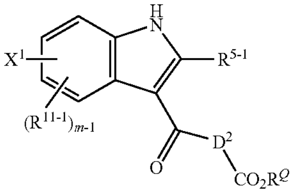
(XXIII)
introduction of $R^{3-1}$
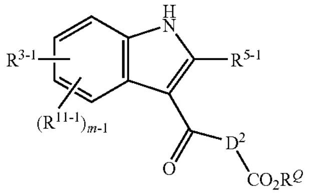
(II-11)
reduction
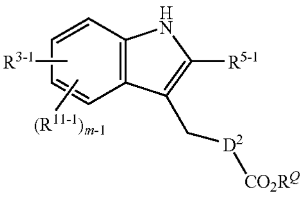
(II-12)
$NaBH_3CN$
acetic acid
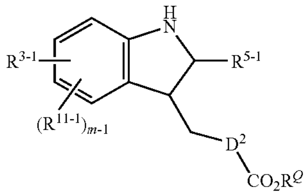
(II-13)
Reaction Scheme 6
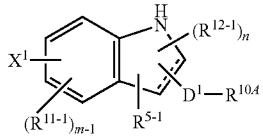
(XXIV)
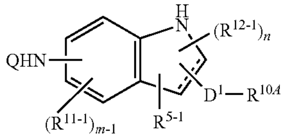
(XXV)
introduction of $—E^2—CO_2R^Q$
introduction of $—E^2—CO_2R^Q$
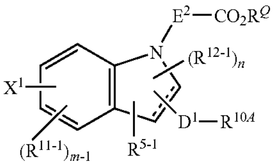
(Y-1)
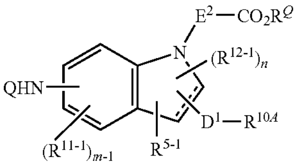
(XXVI)
deprotection of protective group of amino
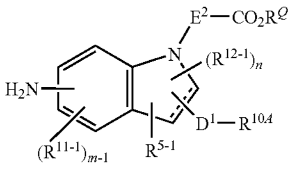
(Y-3)
Reaction Scheme 7
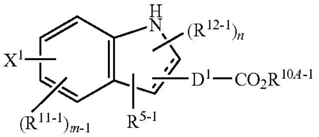
(XXVII)
1) introduction of $—E^2—CO_2R^Q$
2) introduction of $R^{3-1}$ -continued

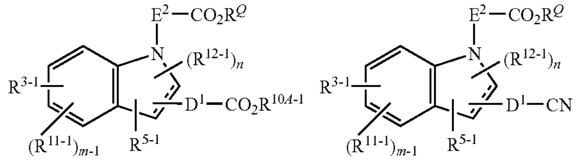

(XXVIII) (Y-9)

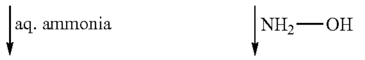

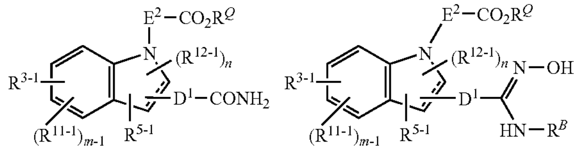

(XXIX) (Y-8)

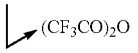

Reaction Scheme 8

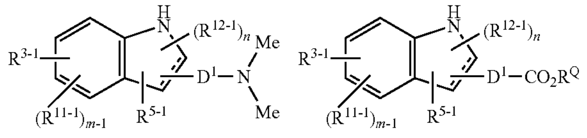

(XXXI) (XXXIV)

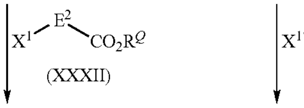

(XXXII) (XXXV)

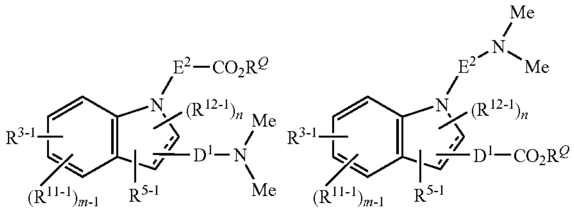

(XXXIII) (XXXVI)

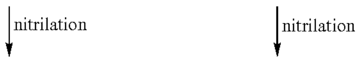

-continued

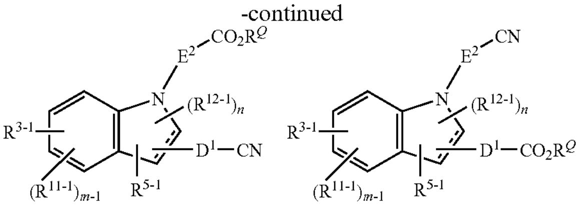

(Y-9) (Y-10)

In each reaction scheme, $R^{3A}$ is a group represented by

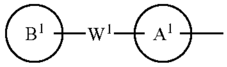

wherein all symbols have the same meanings as described hereinbefore, when a part corresponding to $R^3$ is a group represented by

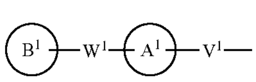

wherein $V^1$ represents ethylene or ethenylene, and other symbols have the same meanings as described hereinbefore;

a group represented by —S-$D^2$- is a spacer represented by D which a sulfur atom included the spacer binds to indole or indoline ring; a group represented by —C(O)-$D^2$- is a spacer represented by D which a carbonyl group included the spacer binds to indole or indoline ring; Q represents a protective group of amino; DMF is N,N-dimethylformamide; Me represents methyl; q represents 0 or 1; and other symbols have the same meanings as described hereinbefore.

The compounds represented by the formulae (III-1), (III-2), (III-3), (Y-2), (Y4), (Y6), (X), (XXII), (XXIV), (XXV), (XXXI), (XXXII), (XXXIV) and (XXXV), which are used as starting materials or reagents, are known per se, or may be prepared by known methods, e.g. described in “Comprehensive Organic Transformations: A Guide to Functional Group Preparations 2nd Edition (Richard C. Larock, John Wiley & Sons Inc, 1999)” or a method which improved arbitrarily the methods described in the above-mentioned reaction schemes, etc. by using known compounds.

The compound represented by the formula (XXVII) may be prepared by, for example, a method same as one shown in the above-mentioned 1-1-a), 1-1-b) or 1-1-c).

Among the compounds represented by the formula (I), the compounds other than those described above may be prepared by combining the methods described in the examples of the present specification and/or known methods, e.g. described in “Comprehensive Organic Transformations: A Guide to Functional Group Preparations 2nd Edition (Richard C. Larock, John Wiley & Sons Inc, 1999)”.

In each reaction of the present specification, the reactions accompanied by heating, as is obvious to those skilled in the art, may be carried out in a water bath, an oil bath, a sand bath or they may be carried out using a microwave.

In each reaction of the present specification, if required, reagents which are supported with high molecular polymers (e.g. polystyrene, polyacrylamide, polypropylene, polyethyleneglycol, etc.) may also be used.

In each reaction of the present specification, reaction products may be purified by conventional techniques, e.g. distillation under atmospheric or reduced pressure, high performance liquid chromatography, thin layer chromatography or ion exchange chromatography using silica gel or magnesium silicate, washing, recrystallization, etc. Purification may be carried out after each reaction, or after a series of reactions.

In the present specification, unless otherwise specified, as is easily understood by those skilled in the art, the symbol  indicates that the substituent attached thereto is behind the sheet (i.e. α-configuration), the symbol  indicates that the substituent attached thereto is in front of the sheet (i.e. β-configuration), and the symbol 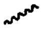 indicates that the substituent attached thereto is in α-configuration, β-configuration, or a mixture thereof by an arbitrary ratio, and the symbol 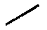 indicates that the substituent attached thereto is a mixture of α-configuration or β-configuration by an arbitrary ratio.

Unless otherwise specified, all isomers are included in the present invention. For example, alkyl, alkenyl, alkynyl, alkoxy, alkylthio, alkylene, alkenylene alkynylene, alkylidene, and alkenylidene group, etc. includes straight one or branched one. In addition, isomers on double bonds, rings, fused rings (E)-, Z-, cis-, trans-isomer), isomers due to an asymmetric carbon atom(s) (R—, S-form, α-,β-configuration, enantiomer, diastereomer), optically active isomers having optical activity (D-, L-, d-, l-isomer), polar compounds generated by chromatographic separation (more polar compounds, less polar compounds), equilibrium compounds, rotamers, mixtures thereof at optional ratios and racemic mixtures are also included in the present invention.

In addition, other enantiomer of less than 50% may be included in the compound which is optical activity in the present invention as well as the one which is 100% purity.

[Salts, Solvates and N-oxide Forms]

The salts of the compounds represented by the formula (I) include all pharmaceutically acceptable ones. Law-toxic, and water-soluble pharmaceutically acceptable salts are preferable. Preferable salts include, for example, salts of alkali metals (potassium, sodium, lithium, etc.), salts of alkaline earth metals (calcium, magnesium, etc.), ammonium salts (tetramethylammonium salt, tetrabutylammonium salt, etc.), organic amine salts (triethylamine, methylamine, ethylamine, dimethylamine, cyclopentylamine, benzylamine, phenethylamine, piperidine, monoethanolamine, diethanolamine, tris(hydroxymethyl)methylamine, lysine, arginine, ornithine, N-methyl-D-glucamine, etc.), acid addition salts (inorganic acid salts such as hydrochloride, hydrobromide, hydroiodide, sulfate, phosphate, nitrate, etc.; organic acid salts such as formate, acetate, propionate, trifluoroacetate, lactate, tartrate, oxalate, malonate, succinate, fumarate, malate, maleate, benzoate, citrate, methanesulfonate, ethanesulfonate, benzenesulfonate, toluenesulfonate, isethionate, glucuronate, gluconate, aspartate, glutamate, etc.; etc).

The salt of the compound represented by the formula (I) includes an N-oxide form. An N-oxide form of the compound represented by the formula (I) represents one in which the nitrogen atom of the compound represented by the formula (I) is oxidized. In addition, the N-oxide form of the present invention may be an alkali (earth) metal salt, an ammonium salt, organic amine salts, and acid addition salts as described hereinbefore.

The salt of the compound represented by the formula (I) further includes a quaternary ammonium salt. The quaternary ammonium salt means the compound represented by the formula (I) which nitrogen atom is quaterinized by a proper group, for example, alkyl which may have a substituent(s) such as C1-8 alkyl which may be substituted by phenyl (i.e. methyl, ethyl, propyl, butyl, pentyl, hexyl, heptyl, octyl, benzyl, phenethyl, phenylpropyl, phenylbutyl, phenylpentyl, phenylhexyl, phenylheptyl, phenyloctyl, and an isomer thereof), etc., etc.

Appropriate solvates of the compound represented by the formula (I) include, for example, the solvates of water or alcohol solvents (ethanol etc.). Solvates are preferably non-toxic and water-soluble ones. In the present invention, the solvates include solvates of salts of alkali (earth) metals, (quaternary) ammonium salts, organic amine salts, acid addition salts or N-oxides as described hereinbefore.

The compound of the present invention may be converted into a salt, an N-oxide, a solvate as described hereinbefore according to the known methods.

[Prodrugs]

The prodrugs of the compound represented by the formula (I) mean the compounds which are converted into the compound (I) by an enzyme, gastric acid, etc. in the body. The prodrugs of the compound represented by the formula (I) are, when the compound represented by the formula (I) possesses an amino group, the amino group is acylated, alkylated, phosphorylated (e.g. the amino group of the compound represented by the formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, t-butylated, etc.); when the compound represented by the formula (I) possesses a hydroxy group, the hydroxy group is acylated, alkylated, phosphorylated, borated (e.g. the hydroxy group of the compound represented by the formula (I) is acetylated, palmitoylated, propanoylated, pivaloylated, succinylated, fumarylated, alanylated, dimethylaminomethylcarbonylated, etc., when the compound represented by the formula (I) possesses a carboxy group, the carboxy group is esterified, or amidated (e.g. the carboxy group of the compound represented by the formula (I) is converted into ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.), etc. These compounds may be prepared by known methods. The prodrug of the compound (I) may be a salvate or a non-solvate. Also, the prodrugs of the compound represented by the formula (I) may be converted into the compounds represented by the formula (I) under such physiological conditions as described in "Molecular Design" pages 163-198, in the "*Development of pharmaceuticals*" Vol. 7, 1990.

[Toxicity]

The toxicity of the compound represented by the formula (I), a salt thereof, a solvate thereof or a prodrug thereof (abbreviated "the compound of the present invention etc." hereinafter), is very low, and therefore it is considered to be sufficiently safe when used as a drug.

[Application for Pharmaceuticals Preparations]

The compound of the present invention etc. antagonizes leukotriene receptor, and therefore, it is useful as an inhibitor of airway contraction, an inhibitor of infiltration of inflammatory cells (e.g. eosinophils, neutrophils, lymphocytes, basophils, etc.), an inhibitor of mucus secretion or an inhibitor of increased airway hyperreactivity. Also, the compound of the present invention etc. is useful for the prevention and/or treatment of those diseases in which leukotriene receptor is involved, for example, respiratory diseases (e.g. asthma (bronchial asthma etc.), chronic obstructive pulmonary diseases (COPD), lung emphysema, chronic bronchitis, pneumonia including interstitial pneumonitis, etc.), severe acute respiratory syndrome (SARS), acute respiratory distress syndrome (ARDS), allergic rhinitis, sinusitis including acute sinusitis, chronic sinusitis, pulmonary fibrosis, etc.), and as an expectorant or an antiitussive agent. Furthermore, the compound of the present invention etc. is useful as an agent for the improvement of respiratory functions. The respiratory function is defined as, e.g. a function of taking air in and out (i.e. a function of pulmonary capacity), a function of taking oxygen from lungs into blood and taking carbon dioxide from blood out of the body (i.e. a function of oxygen exchange), and a function of respiratory resistance.

In the present invention, respiratory organs mean, body parts concerned with a respiration e.g. airway, oral cavity, nasal cavity, nasal sinuses, trachea, bronchus, bronchiole, lungs, etc.

Furthermore, the compound of the present invention etc. is useful for the treatment and/or prevention of cardiovascular diseases which are known as leukotriene receptor-mediated diseases, e.g. angina pectoris, cardiac infarction, acute coronary syndromes, heart failure, arrhythmia, cardiomyopathy (dilative cardiomyopathy, hypertrophic cardiomyopathy, etc.), pericarditis, valvulitis, myocarditis, cardiac tamponade, low cardiac output syndrome, mitral stenosis, atherosclerosis, pulmonary fibrosis, cerebral infarction, cerebral edema, aneurysm, headache (migraine, migrainous neuralgia or tension-type headache, etc.), gynecologic disorder (endometriosis, dysmenorrhea, etc.), Meniere's disease, etc.

In the present invention, non-responders are defined as those patients to whom existing leukotriene receptor antagonists give insufficient effect or no effect. Since the agent for the treatment of the present invention is more useful for respiratory diseases than an existing leukotriene receptor antagonist, it is preferable to administer it to non-responders and those patients with severe disorders in respiratory functions (e.g. severe bronchial asthma patients).

The compound of the present invention etc. may be administered in combination with other agents for the purpose of (1) supplementing and/or reinforcement of preventive and/or treating effect of the compound of the present invention etc., (2) improvement in kinetics and absorption and reduction of dose of the compound of the present invention etc., and/or (3) reduction of side effect of the compound of the present invention etc.

Concomitant agents of the compound of the present invention etc. with other agents may be administered in a mode of an agent in which both components are comprised in a single preparation or in a mode of separate preparations. When administration is conducted using separate preparations, a simultaneous administration and administrations with time difference are included. In the case of administrations with time difference, the compound of the present invention etc. may be firstly administered and then the other drug may be administered, and vice versa. Each of the methods for the administration may be the same or different.

The other agents as described above may be low molecular compounds, high molecular proteins, polypeptides, polynucleotides (DNA, RNA, genes), anti-sense, decoys, antibodies, vaccines, etc. The dose of the other agents may be determined taking the clinically used dose as a reference appropriately. The ratio of the compound of the present invention etc. and the other agents may be determined according to a patients' age, weight, route of administration, time of administration, the target disease, symptom or combination, etc. For example, approximately 0.01 to 100 of the other agents in weight ratio may be used versus the compound of the present invention etc. One or more of the other agent(s) may be selected from the same group or different groups described hereafter, and may be administered alone or in combination thereof in optional ratios. The other agents which supplement and/or reinforce the preventing and/or treating effect of the compound of the present invention etc. include not only those have been found out so far, but also those are to be found out from now on, based on the above mechanism.

Diseases on which the concomitant agents show the preventing and/or treating effect are not limited in particular, and those diseases in which the preventing and/or treating effect of the compound of the present invention etc. are supplemented and/or reinforced are included.

The other agents for supplement and/or reinforcement of the preventing and/or treating effect of the compound of the present invention etc. against asthma include, for example, leukotriene receptor antagonists, antihistamine agents, phosphodiesterase inhibitors, elastase inhibitors, anticholinergic agents, antiallergic agents (e.g. chemical mediator release inhibitors, histamine antagonists, thromboxane synthase inhibitors, thromboxane receptor antagonists, Th2 cytokine inhibitors), steroidal agents, bronchodilating agents (e.g. xanthine derivatives, sympathomimetic agents, parasympatholytic agents), vaccine therapy agents, gold formulations, Chinese medicines, non-steroidal antiinflammatory agents, 5-lipoxygenase inhibitors, 5-lipoxygenase activated protein antagonists, leukotriene synthesis inhibitors, prostaglandin agents, cannabinoid-2 receptor agonists, antiitussive agents, expectorant agents or extract from inflammatory rabbit skin inoculated by vaccinia virus, etc.

Leukotriene receptor antagonists include, for example, pranlukast hydrate, montelukast sodium, zafirlukast MK-571, LY-203647, WY-46016, WY-48422, WY-49353, WY-49451, RG-12553, MDL-43291, CGP-44044A, RG-14524, LY-287192, LY-290324, L-695499, RPR-105735B, WAY-125007, OT-4003, LM-1376, LY-290154, SR-2566, L-740515, LM-1453, CP-195494, LM-1484, CR-3465, ablukast pobilukast sulukast, L-648051, RG-12525, RG-7152, SK&F-106203, SR-2640, WY-50295, iralukast sodium, verlukast, MCC-847, BAY-x-7195, ritolukast, cinalukast, CGP-44826, FK-011, YM-158, MEN-91507, KCA-757, RS-601, RS-635, S-36496, ZD-13523, DS-4574, pirodomast AS-35, YM-57158, MC-1826, NZ-107, 4414-CERM, YM-16638, Wy-48252, Wy-44329, Wy-48090, VUF-4679, tomelukast SM-11044, SC-39070, OT-3473, N-2401, LY-243364, L-649923, doqualast, DP-1934, YM-17551, Wy-47120, VUF-K-8707, SK&F-88046, SK&F-101132, SK&F-102922, LY-137617, LY-163443, LY-302905, L-647438, L-708738, KY-234, FPL-55712, CP-288886, S-36527, CGP-35949, CS-615, MDL-19301D, SCH-40120, or ZD-3705, etc.

Leukotriene receptor antagonists are preferably, pranlukast hydrate, montelukast sodium, zafirlukast or MK-571, more preferably, pranlukast hydrate, montelukast sodium or zafirlukast.

Antihistamine agents include, for example, diphenhydramine, diphenylpyraline hydrochloride, diphenylpyraline chlorotheophyllinate, clemastine fumarate, dimenhydrinate, dl-chlorpheniramine maleate, d-chlorpheniramine maleate, triprolidine hydrochloride, promethazine hydrochloride, alimemazine tartrate, isothipendyl hydrochloride, homochlorcyclizine hydrochloride, hydroxyzine, cyproheptadine hydrochloride, levocabastine hydrochloride, astemizole, bepotastine, desloratadine, TAK427, ZCR-2060, NIP-530, mometasone furoate, mizolastine, BP-294, andolast, auranofin, acrivastine, etc.

Phosphodiesterase 4 inhibitors are preferable as phosphodiesterase inhibitors, phosphodiesterase 4 inhibitors include, for example, rolipram, cilomilast (brand name: Ariflo), Bay19-8004, NIK-616, roflumilast (BY-217), cipamfylline (BRL-61063), atizoram (CP-80633), SCH-351591, YM-976, V-11294A, PD-168787, D-4396 or IC-485, etc.

Elastase inhibitors include, for example, sivelestat sodium hydrate (ONO-5046), ONO-6818, MR-889, PBI-1101, EPI-HNE-4, R-665, ZD-0892, ZD-8321, GW-311616, AE-3763, DMP-777, L-659286, L-658758, L-680833, L-683845, etc.

Anticholinergic agents include, for example, ipratropium bromide, oxitropium bromide, flutropium bromide, cimetropium, temiverine, tiotropium bromide, revatropate (UK-112166), etc.

Among the antiallergic agents, chemical mediator release inhibitors include, for example, sodium cromoglicate, tranilast, anlexanox, repirinast, ibudilast, potassium pemilolast, tazanolast, nedocromil, cromoglicate, israpafant, etc.

Among the antiallergic agents, histamine antagonists include, for example, ketotifen fuimarate, azelastine hydrochloride, oxatomide, mequitaaine, terfenadine, emedastine difumarate, epinastine hydrochloride, ebastin, cetirzine hydrochloride, olopatadine hydrochloride, loratadine, fexofenadine, etc.

Among the antiallergic agents, thromboxane synthase inhibitors include, for example, ozagrel hydrochloride or imitrodast sodium, etc.

Among the antiallergic agents, thromboxane receptor antagonists are, for example, seratrodast ramatoroban, domitroban calcium hydrate, KT-2-962, etc.

Among the antiallergic agents, Th2 cytokine inhibitors include, for example, suplatast tosylate, etc.

Steroidal agents as external medicines include, for example, clobetasol propionate, diflorasone acetate, fluocinonide, mometasone furoate, betamethasone dipropionate, betamethasone butyrate propionate, betamethasone valerate, difluprednate, budesonide, diflucortolone valerate, amcinonide, halcinonide, dexamene, dexamethasone propionate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone dipropionate, triamcinolone acetonide, flumethasone pivalate, alclometasone dipropionate, clobetasone butyrate, prednisolone, beclomethasone dipropionate, fludroxycortide, etc.

Steroidal agents as internal medicines and injections include, for example, cortisone acetate, hydrocortisone, sodium hydrocortisone phosphate, sodium hydrocortisone succinate, fludrocortisone acetate, prednisolone, prednisolone acetate, sodium prednisolone succinate, butyl prednisolone acetate, prednisolone sodium phosphate, halopredone acetate, methyl prednisolone, methyl prednisolone acetate, sodium methyl prednisolone succinate, triamcinolone, triamcinolone acetate, triamcinolone acetonide, dexamethasone, dexamethasone acetate, sodium dexamethasone phosphate, dexamethasone palmitate, paramethasone acetate, betamethasone, etc. Inhalant medicines include, for example, beclometasone dipropionate, fluticasone propionate, budesonide, flunisolide, triamcinolone, ST-126P, ciclesonide, dexamethasone palmitate, mometasone furoate, prasterone sulfonate, deflazacort, methylprednisolone sleptanate, methylprednisolone sodium succinate, etc.

Among the bronchodilating agents, the xanthine derivabives include, for example, aminophylline, theophylline, doxophylline, cipamphilline, diprophilline, proxyphylline, choline theophylline, etc.

Among the bronchodilating agents, sympathomimetic agents include, for example, epinephrine, ephedrine hydrochloride, dl-methylephedrine hydrochloride, methoxyphenamine hydrochloride, isoproterenol sulfate, isoproterenol hydrochloride, orciprenaline sulfate, clorprenaline hydrochloride, trimetoquinol hydrochloride, salbutamol sulfate, terbutaline sulfate, hexoprenaline sulfate, tulobuterol hydrochloride, procaterol hydrochloride, fenoterol hydrobromide, formoterol fumarate, clenbuterol hydrochloride, mabuterol hydrochloride, salmeterol xinafoate, R,R-formoterol, tulobuterol, pirbuterol hydrochloride, ritodrine hydrochloride, bambuterol, dopexamine hydrochloride, meluadrine tartrate, AR-C68397, levosalbutamol, KUR-1246, KUL-7211, AR-C89855, S-1319, etc.

Among the bronchodilating agents, parasympatholytic agents include, for example, ipratropium bromide, flutropium bromide, oxitropium bromide, cimetropium bromide, temiverine, tiotropium bromide, revatropate (UK-112166), etc.

Vaccine therapy agents include, for example, paspat, astremesin, broncasma bema, CS-560, etc.

Gold formulations include, for example, gold sodium thiomalate etc.

Basic non-steroidal antiinflammatory agents include, for example, tiaramide hydrochloride, tinoridine hydrochloride, epirizole, emorfazone, etc.

5-Lipoxygenase inhibitors include, for example, Zileuton (Zyflo), docebenone, piripost, SCH-40120, WY-50295, E-6700, ML-3000, TMK-688, ZD-2138, darbufelone mesylate, R-68151, E-6080, DuP-654, SC-45662, CV-6504, NE-11740, CMI-977, NC-2000, E-3040, PD-136095, CMI-392, TZI-41078, Orf-20485, IDB-18024, BF-389, A-78773, TA-270, FLM-5011, CGS-23885, A-79175 or ET1-615, etc.

5-Lipoxygenase activating protein antagonists include, for example, MK-591 or MK-886, etc.

Leukotriene synthase inhibitors include, for example, auranofin, proglumetacin maleate, L-674636, A-81834, UPA-780, A-93178, MK-886, REV-5901A, SCH-40120, MK-591, Bay-x-1005, Bay-y-1015, Dn-0026, amlexanox or E-6700, etc.

Prostaglandins (abbreviated as PG hereinafter) include, for example, PG receptor agonists, PG receptor antagonists, etc.

PG receptors include, for example, PGE receptors ($EP_1$, $EP_2$, $EP_3$, $EP_4$), PGD receptors (DP, $CRTH_2$), PGF receptor (FP) PGI receptor (IP), or TX receptor (IP), etc Antitussive agents include, for example, codeine phosphate, dihydrocodeine phosphate, oxymetebanol, dextromethorphan hydrobromide, pentoxyverine citrate, dimemorfan phosphate, oxeladin citrate, chloperaste, benproperine phosphate, clofedanol hydrochloride, fominoben hydrochloride, noscapine, tipepidine hibenzate, eprazinone hydrochloride, plantago, etc.

Expectorants include, for example, fennel ammonium spirit, sodium bicarbonate, potassium iodide, bromhexine hydrochloride, cherry bark extract, carbocysteine, fudostein, ambroxol hydrochloride, ambroxol hydrochloride extended release drug, methylcysteine hydrochloride, acetylcysteine, Lethylcycleine hydrochloride, tyloxapol, etc.

The other agents to be used in combination with the compound of the present invention etc. are preferably, leukotriene receptor antagonists, steroidal agents or sympathomimetics.

The formulation to be used in the present invention may contain a leukotriene receptor antagonist and the other agent(s) supplementing and/or reinforcing the treating effect of the compound which are compounded in a single preparation or in separate preparations. These are formulated by known methods.

Using for the purpose of superscription, a pharmaceutical composition comprising of a compound of the present invention etc., or a concomitant agents of a compound of the present invention etc. with other agents is administered normally systemically or topically, orally or parenterally.

The dosages are determined depending on age, body weight, symptom, therapeutic effect, administration route, duration of the treatment and the like. Generally, for an adult, 1 mg to 1000 mg per dose is orally administered once to several times per day, or 0.1 mg to 100 mg is parenterally administered once to several times per day, or continuously administered from vein for 1 to 24 hours per day.

As described hereinbefore, since the dosage changes depending on various conditions as described above, there are cases in which doses lower than or greater than the above ranges may be used.

The compound is administered in the form of solid formulations for oral administration or liquid formulations for oral administration, or injectable formulations, external medicine, suppositories, eye drops, inhalants and the like for parenteral administration, for the purpose of the present invention.

The solid formulation for oral administration includes, for example, tablets, pills, capsules, powdered drugs, granulated drugs, etc. Capsules include hard capsules and soft capsules.

In such solid formulations, said one or more active agent(s) are formulated according to usual methods as it is, or mixed with one or more of an excipient (lactose, mannitol, glucose, microcrystalline cellulose, starch, etc.), a binding agent (hydroxypropyl cellulose, polyvinylpyrrolidone, magnesium aluminometasilicate, etc.), a disintegrating agent (calcium glycolate cellulose, etc.), a lubricant (magnesium stearate etc.), a stabilizing agent or a solubilizing agent (glutamic acid, aspartic acid, etc.), etc. If necessary, the formulations may be coated with a coating agent such as sugar, gelatin, hydroxypropyl cellulose, hydroxypropylmethyl cellulose phthalate, or may be coated with two or more layers thereof. Alternatively, the solid agent may be capsulized by an absorbable material such as gelatin.

The liquid formulation for oral administration includes pharmaceutically acceptable aqueous solution, suspension, emulsion, syrup, elixir, etc. In such liquid formulations, one or more of the active agents) are dissolved, suspended or emulsified in a commonly used diluent (e.g., purified water, ethanol, or a mixture thereof). Furthermore, such liquid formulations may comprise a wetting agent, a suspending agent, an emulsifier, a sweetening agent, a flavoring agent, an aromatic agent, a preservative, a buffer, etc.

The injectable formulation for parenteral administration includes, for example, a solution, a suspension, an emulsion or a solid formulation for injection which is dissolved, suspended or emulsified in use. The injectable formulation is prepared by dissolving, suspending or emulsifying one or more of active substance in a solubilizing agent. The solubilizing agent includes, for example, distilled water for injection, saline, vegetable oil, propylene glycol, polyethyleneglycol or alcohols such as ethanol, and a combination thereof. The injectable formulation may further contain a stabilizing agent, a solubilizing agent (glutarnic acid, aspartic acid, polysorbate 80 (registered trademark), etc.), a suspending agent, an emulsifying agent, a soothing agent, a buffer or a preservative, etc. These are sterilized in the final step or are prepared by aseptic manipulation. Sterile solid formulation, such as freeze-dried formulation, may be prepared, to sterilize or to solve in sterile distilled water for injection or other sterile solvents before use.

The eye drops for parenteral administration may be in the form of liquid eye drops, suspended eye drops, emulsified eye drops or eyedrops which is used by dissolving in a solvent in use or eye ointment.

These eye drops are prepared by known methods. For example, in the case of liquid eye drops, they may be prepared by appropriately selecting and comprising one or more agent(s) such as an isotonic agent (sodium chloride, concentrated glycerin, etc.), a buffer (sodium phosphate, sodium acetate, etc.), a surface active agent (Polysolvate 80 (trade name), polyoxyl stearate 40, polyoxyethylene-hardened castor oil, etc.), a stabilizer (sodium citrate, sodium edentate, etc.), and a preservative (benzalconium chloride, Paraben, etc.), and the like depending on the needs. The eye drops are sterilized at the final step or prepared by an aseptic process.

The inhalable formulation for parenteral administration may be in the form of aerosol, inhalable liquid formulation or inhalable powder. The inhalable liquid formulation may be dissolved, suspended or emulsified in water or other appropriate medium in use.

These inhalable formulations may be prepared according to known methods. For example, inhalable liquid formulations may further contain antiseptics (benzalkonium chloride, paraben, etc.), a coloring agent, a buffer (sodium phosphate, sodium acetate, etc.), a tonicity agent (sodium chloride, concentrated glycerine, etc.), a thickening agent (carboxyvinyl polymer, etc.), an absorption promoter, and the like.

Inhalable powders may be prepared by appropriately selecting and comprising one or more agent(s) such as a lubricant (stearic acid, a salt thereof (e.g. magnesium stearate), etc.), a binding agent (starch, dextrin, etc.), an excipient (lactose, cellulose, etc.), a coloring agent, an antiseptic agent (benzalchonium chloride, parabens, etc.), an absorption promoter, and the like.

Inhalable liquid formulations may normally be administered by sprayer (e.g. atomizer, nebulizer, etc.) and inhalable powders may be administered by using inhalers for powder formulations.

The other compositions for parenteral administration include a liquid preparation for external application, an ointment, a liniment, a spray formulation, a suppository, a pessary for intravaginal administration, and the like. The spray formulation may include, besides generally used diluents, a stabilizing agent such as sodium hydrogensulfite etc., a buffer for tonicity such as a tonicity agent (e.g. sodium chloride, sodium citrate, or citric acid etc.). For the preparation of the spray formulation, for example, the methods described in the U.S. Pat. No. 2,868,691 and ibid. U.S. Pat. No. 3,095,355 may be used.

EXAMPLES

The present invention will be described in detail by following Examples, but is not limited thereto.

The solvent in the parenthesis described in the position of separation through chromatography and TLC indicates an elution solvent or a developing solvent used, and the proportion is expressed by a volume ratio.

The solvent in the parenthesis described in $^1$H-NMR indicates a solvent used in the measurement.

Including compounds in the following Examples, compounds used in the present specification were commonly named using a computer program capable of naming in accordance with IUPAC rules, ACD/Name® manufactured by Advanced Chemistry Development Inc., or IUPAC nomenclature. In each of the following Examples, the name of the objective compound of the Example is described subsequently to the number of Example, and the compound is sometimes referred to as the "titled compound".

Example 1 methyl 4-bromo-1H-indole-3-carboxylate

To a methanol (40 mL) solution of 4-bromo-1H-indole-3-carboaldehyde [Chem. Pharm. Bull. 33,3696 (1985)] (395 mg), sodium cyanide (432 mg) and manganese dioxide (15.3 g) were sequentially added and the mixture was stirred overnight at room temperature. To the reaction mixture, ethyl acetate (50 mL) was added and insoluble matters were removed. The filtrate was concentrated and water was added to the residue, and then the solution was extracted with ethyl acetate. The organic layer was washed in turn with water and saturated saline, dried and then concentrated. The residue was washed with diisopropyl ether and n-hexane and then concentrated to obtain the titled compound having the following physical properties (375 mg).

TLC: Rf 0.50 (n-hexane:ethyl acetate=1:1); $^1$H-NMR ($CDCl_3$): δ 3.90 (s, 3H), 7.08 (t, 1H), 7.36 (dt, 1H), 7.48 (dt, 1H), 7.89 (d, 1H), 8.79 (brs, 1H).

Example 2 methyl 4-bromo-1-(4-methoxy-4 oxobutyl)-1H-indole-3 carboxylate

To an N,N-dimethylformamide (5 mL) solution of the compound prepared in Example 1 (370 mg), sodium hydride (60% oily suspended, 70 mg) and the mixture was stirred at room temperature for 30 minutes. To the mixture, methyl 4-bromobutyrate (317 mg) was added, followed by stirring at room temperature for 3 hours. To the reaction mixture, an aqueous saturated ammonium chloride solution was added, followed by extraction with n-hexane/ethyl acetate (1:2). The organic layer was washed in turn with water and saturated saline, dried and then concentrated. The residue was purified by the column chromatography to obtain the titled compound having the following physical properties (126 mg).

TLC: Rf 0.56 (toluene:ethyl acetate=2:1); $^1$H-NMR ($CDCl_3$): δ 2.12-2.22 (m, 2H), 2.32 (t, 2H), 3.68 (s, 3H), 3.88 (s, 3H), 4.21 (t, 2H), 7.11 (t, 1H), 7.35 (d, 1H), 7.48 (d, 1H), 7.80 (s, 1H).

Example 3 methyl 4-{(E)-2-[4-acetyloxy)phenyl]vinyl}-1-(4-methoxy-4-oxobutyl)-1H-indole-3 carboxylate To an acetonitrile (4.5 triethylamine (1.5 mL) solution of the compound prepared in Example 2 (130 mg), 4-vinylphenyl acetate (60 mg), tris(2-methylphenyl)phosphine (89 mg) and palladium acetate (8 mg) were sequentially added under an argon atmosphere and the mixture was stirred at 85° C. for 2 hours. To the reaction mixture, an aqueous saturated ammonium chloride solution was added, followed by extraction with ethyl acetate. The organic layer was washed in turn with water and saturated saline, dried and then concentrated. The residue was purified by the column chromatography to obtain the titled compound having the following physical properties (145 mg).

TLC: Rf 0.53 (toluene:ethyl acetate=2:1); $^1$H-NMR ($CDCl_3$): δ 2.15-2.36 (m, 7H), 3.68 (s, 3H), 3.87 (s, 3H), 4.23 (t, 2H), 7.02 (d, 1H), 7.10 (d, 2H), 7.28-7.32 (m, 2H), 7.56-7.60 (m, 1H), 7.66 (d, 2H), 7.90 (s, 1H), 8.81 (d, 1H).

Example 4 methyl 4-[(E)-2-(4-hydroxyphenyl)vinyl]-1-(4-methoxy-4-oxobutyl)-1H-indole-3-carboxylate To a methanol (1 mL)tetrahydrofuran (2 mL) solution of the compound prepared in Example 3 (140 mg), potassium carbonate (89 mg) was added and the mixture was stirred at room temperature for 2 hours. An aqueous saturated ammonium chloride solution was poured into the reaction mixture, followed by extraction with ethyl acetate. The organic layer was washed in turn with water and saturated saline, dried and then concentrated. The residue was purified by the column chromatography to obtain the titled compound having the following physical properties (118 mg).

TLC: Rf 0.34 (n-hexane:ethyl acetate=1:1); $^1$H-NMR ($CDCl_3$): δ 2.15-2.25 (m, 2H), 2.31-2.36 (m, 2H), 3.68 (s, 3H), 3.87 (s, 3H), 4.22 (t, 2H), 5.00 (s, 1H), 6.85 (d, 2H), 6.99 (d, 1H), 7.27-7.29 (m, 2H), 7.52-7.58 (m, 3H), 7.89 (s, 1H), 8.68 (d, 1H).

Example 5 methyl 1-(4-methoxy-4-oxobutyl)-4-{(E)-2-[4-(4-phenylbutoxy)phenyl]vinyl}-1H-indole-3-carboxylate To an N,N-dimethylformamide (3 mL) solution of the compound prepared in Example 4 (100 mg), potassium carbonate (176 mg), 1-chloro-4-phenylbutane (176 mg) and potassium iodide (8 mg) were added and the mixture was stirred at 95° C. for 2 hours. To the reaction mixture, water was added, followed by extraction with n-hexane/ethyl acetate (1:1). The organic layer was washed in turn with water and saturated saline, dried and then concentrated. The residue was purified by the column chromatography to obtain the titled compound having the following physical properties (125 mg).

TLC: Rf 0.33 (n-hexane:ethyl acetate=2:1); $^1$H-NMR ($CDCl_3$): δ 1.56-1.59 (m, 2), 1.72-1.92 (m, 4H), 2.14-2.25 (m, 2H), 2.33 (t, 2H), 2.65 (t, 2H), 3.68 (s, 3H), 3.87 (s, 3H), 4.00 (t, 2H), 4.22 (t, 2H), 6.90 (d, 2M), 7.00 (d, 1H), 7.16-7.32 (m, 7H), 7.54-7.60 (m, 3H), 7.89 (s, 1H), 8.68 (d, 1H).

Example 6

1-(3-carboxypropyl)-4-{(E)-2-[4-(4-phenylbutoxy)phenyl]vinyl}-1H-indole-3-carboxylic acid

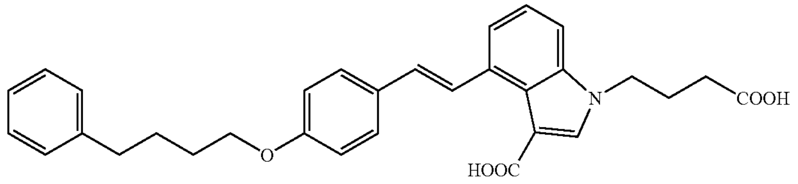

To a tetrahydrofuran (2 mL)methanol (2 mL) solution of the compound prepared in Example 5 (120 mg), an aqueous 2M sodium hydroxide solution (2 mL) was added and the mixture was stirred at 60° C. for 5 days. To the reaction mixture, 2M hydrochloric acid (2 mL) was added, followed by extraction with ethyl acetate. The organic layer was washed in turn with water and saturated saline, dried and then concentrated. The residue was washed with diisopropyl ether to obtain the titled compound having the following physical properties (94 mg).

TLC: Rf 0.26 (dichloromethane:methanol=9:1); $^1$H-NMR (DMSO-$d_6$): δ 1.58-1.81 (m, 4H), 1.90-2.07 (m, 2H), 2.21 (t, 2H), 2.64 (t, 2H), 3.93-4.06 (m, 2H), 4.25 (t, 2H), 6.92 (d, 2H), 7.06 (d, 1H), 7.11-7.34 (m, 6H), 7.40-7.71 (m, 4H), 8.15 (s, 1H), 8.87 (d, 1H).

Example 6(1) to Example 6(9)

The same operation as in Example 1→Example 2→Example 3→Example 4→Example 5→Example 6 was conducted to obtain the titled compound having the following physical properties. In the step corresponding to Example 2 in the operation, the compound prepared in Example 1 or a corresponding halide compound was used and, in the step corresponding to Example 5, 1-chloro-4-phenylbutane or a corresponding halide compound was used.

Example 6(1)

1-(3-carboxypropyl-5){(E)-2-[4-(4-phenylbutoxy)phenyl]vinyl}-1H-indole-3-carboxylic acid TLC: Rf 0.32 (dichloromethane:methanol=9:1); $^1$H-NMR (DMSO-$d_6$): δ 1.58-1.82 (m, 4H), 1.88-2.08 (m, 2H), 2.20 (t, 2H), 2.58-2.69 (m, 2H), 3.93-4.06 (m, 2H), 4.25 (t, 2H), 6.91 (d, 2H), 7.04-7.34 (m, 6H), 7.47-7.62 (m, 4H), 8.02 (s, 1H), 8.12 (s, 1H).

Example 6(2)

1-(3-carboxypropyl)-4-{(E)-2-[4-(4-phenylbutoxy)phenyl]vinyl}-1H-indole-2-carboxylic acid TLC: Rf 0.32 (chloroform:methanol:acetic acid=90:10:1); $^1$H-NMR (DMSO-$d_6$): δ 1.67-1.78 (m, 4H), 1.88-1.98 (m, 2H), 2.19 (t, 2H), 2.62-2.66 (m, 2H), 3.98-4.03 (m, 2H), 4.61 (t, 2H), 6.93 (d, 2H), 7.14-7.31 (m, 7H), 7.39-7.47 (m, 3H), 7.52-7.59 (d, 1H), 7.64 (d, 2H), 12.39 (bs, 2H).

Example 6(3)

1-(3-carboxypropyl)-4-{(E)-2-[4-(4-phenylbutoxy)phenyl]vinyl}-1H-indole-2-carboxylic acid TLC: Rf 0.44 (chloroform:methanol:acetic acid=90:10:1); $^1$H-NMR (DMSO-$d_6$): δ 1.85-1.93 (m, 4H), 1.93-2.03 (m, 2H), 2.20 (t, 2H), 4.00-4.06 (m, 4H), 4.25 (t, 2H), 6.88-6.96 (m, 5H), 7.07 (d, 1H), 7.23-7.30 (m, 3H), 7.48-7.60 (m, 4H), 8.15 (s, 1H), 8.88 (d, 1H), 11.94 (bs, 2H).

Example 6(4)

1-(3-carboxypropyl)-4-((E)-2-{4-[(5-phenylbutoxy)oxy]phenyl}vinyl)-1H-indole-3-carboxylic acid TLC: Rf 0.48 (chloroform:methanol:acetic acid=90:10:1); $^1$H-NMR (DMSO-$d_6$): δ 1.52-1.62 (m, 2H), 1.74-1.83 (m, 4H), 1.98 (quintet, 2H), 2.20 (t, 2H), 3.96-4.03 (m, 4H), 4.25 (t, 2H), 6.88-6.95 (m, 5H), 7.07 (d, 1H), 7.23-7.29 (m, 3H), 7.47-7.59 (m, 4H), 8.15 (s, 1H), 8.88 (d, 1H), 12.01 (bs, 2H).

Example 6(5)

1-(3-carboxypropyl)-4-{(E)-2-[4-(2,3-dihydro-1H-inden-2-ylmethoxy)phenyl]vinyl}-1H-indole-3-carboxylic acid TLC: Rf 0.39 (chloroform:methanol:acetic acid=90:10:1); $^1$H-NMR (DMSO-$d_6$): δ 1.94-2.03 (m, 2H), 2.21 (t, 2H), 2.76-2.83 (m, 2H), 2.83-2.95 (m, 1H), 3.05-3.12 (m, 2H), 3.99 (d, 2H), 4.26 (t, 2H), 6.96 (d, 2H), 7.04-7.14 (m, 3H), 7.20-7.28 (m, 3H), 7.47-7.60 (m, 4H), 8.16 (s, 1H), 8.80-8.94 (m, 1H), 12.05 (bs, 2H).

Example 6(6)

1-(3-carboxypropyl)-4-{(E)-2-[4-({3-[(7-chloro-2-quinolinyl)methoxyl]benzyl}oxy)phenyl]vinyl}-1H-indole-3-carboxylic acid TLC: Rf 0.45 (chloroform:methanol:acetic acid=90:10:1); $^1$H-NMR (DMSO-$d_6$): δ 1.93-2.04 (m, 2H), 2.21 (t, 2H), 4.25 (t, 2H), 5.09 (s, 2H), 5.38 (s, 2H), 6.95-7.08 (m, 5H), 7.16 (s, 1H), 7.23-7.34 (m, 2H), 7.47-7.71 (m, 6H), 8.03-8.07 (m, 2H), 8.16 (s, 1H), 8.45 (d, 1H), 8.88 (d, 1H), 11.78 (bs, 2H).

Example 6(7)

1-(3-carboxypropyl)-4-{(E)-2-[4-(3-phenylpropoxy) phenyl]vinyl}-1H-indole-3-carboxylic acid TLC: Rf 0.36 (dichloromethane:methanol=9:1); $^1$H-NMR (DMSO-$d_6$): δ 1.80-2.12 (m, 4H), 2.13-2.35 (m, 2H), 2.63-2.82 (m, 2H), 3.98 (t, 2H), 4.26 (t, 2H), 6.94 (d, 2H), 7.07 (d, 1H), 7.12-7.39 (m, 6H), 7.40-7.69 (m, 4H), 8.16 (s, 1H), 8.87 (d, 1H).

Example 6(8)

1-(3-carboxypropyl)-4-((E)-2-{4-[(5-phenylpentyl) oxy]phenyl}vinyl)-1H-indole-3 carboxylic acid TLC: Rf 0.38 (dichloromethane:methanol=9:1); $^1$H-NMR (DMSO-$d_6$): δ 1.30-1.54 (m, 2H), 1.53-1.83 (m, 4H), 1.88-2.10 (m, 2H), 2.13-2.29 (m, 2H), 2.53-2.66 (m, 2H), 3.92-4.01 (m, 2H), 4.26 (t, 2H), 6.92 (d, 2H), 7.06 (d, 1H), 7.11-7.33 (m, 6H), 7.42-7.64 (m, 4H), 8.16 (s, 1H), 8.87 (d, 1H), 12.06 (s, 1H).

Example 6(9)

1-(3-carboxypropyl)-4-((E)-2-{4-[(7-chloro-2-chloro-2-quinolinyl)methoxy]phenyl}vinyl)-1H-indole-3-carboxylic acid TLC: Rf 0.52 (chloroform:methanol:acetic acid=90:10:1); $^1$H-NMR (DMSO-$d_6$): δ 1.98 (m, 2H), 2.21 (t, 2H), 4.25 (t, 2H), 5.39 (s, 2H), 7.03-7.09 (m, 3H), 7.25 (t, 1H), 7.49 (d, 1H), 7.54-7.59 (m, 3H), 7.64-7.68 (m, 1H), 7.72 (d, 1H), 8.05-8.08 (m, 2H), 8.15 (s, 1H) 8.47 (d, 1H), 8.89 (d, 1H), 11.96 (bs, 2H).

Example 7 methyl (4-bromo-1H-indol-3-yl)acetic acid

To methanol (10 mL), thionyl chloride (0.76 mL) was added dropwise at −15 to −10° C., followed by stirring for 30 minutes. To the mixture, (4-bromo-1H-indol-3-yl)acetic acid (Chemical and Pharmaceutical Bulletin, 33(9), 3696-3708 (1985), 1.32 g) was added, followed by stifling at room temperature for 2 hours. To the reaction mixture, an aqueous saturated sodium hydrogen carbonate solution was added, followed by extraction with ethyl acetate. The organic layer was washed in turn with water and saturated saline, dried and then concentrated. The residue was washed with diisopropyl ether/n-hexane (1:2) to obtain the titled compound having the following physical properties (1.26 g).

TLC: Rf 0.41 (n-hexane:ethyl acetate=1:1); $^1$H-NMR ($CDCl_3$): δ 3.74 (s, 3H), 4.06 (s, 2H), 6.98 (t, 1H), 7.10 (d, 1H), 7.23-7.27 (m, 2H), 8.25 (brs, 1H).

Example 8 to Example 8(51)

The same operation as in Example 2→Example 3→Example 4→Example 5→Example 6 was conducted to obtain the titled compound having the following physical properties. In the step corresponding to Example 2 in the operation, the compound prepared in Example 7 was used in place of the compound prepared in Example 1 and methyl 4-bromobutyrate or a corresponding halide compound was used and, in the step corresponding to Example 5, 1-chloro-4-phenylbutane or a corresponding halide compound was used.

Example 8

4-(3-(carboxymethyl)-4-{(E)-2-[4-(4-phenylbutoxy) phenyl]vinyl}-1H-indol-1-yl)butanoic acid

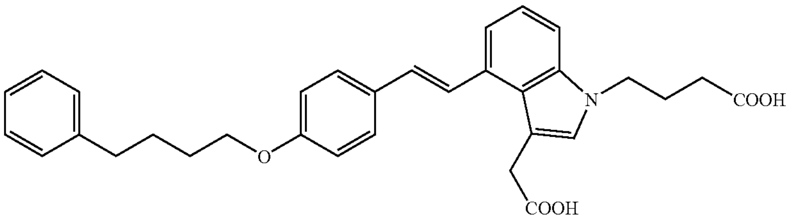

TLC: Rf 0.32 (dichloromethane:methanol=9:1); $^1$H-NMR (DMSO-$d_6$): δ 1.61-1.80 (m, 4H), 1.85-2.03 (m, 2H), 2.20 (t, 2H), 2.64 (t, 2H), 3.83 (s, 2H), 4.00 (t, 2H), 4.14 (t, 2H), 6.92 (d, 2H), 6.98-7.44 (m, 10H), 7.52 (d, 2H), 7.63 (d, 1H), 12.25 (s, 2H).

Example 8(1)

4-(3-(carboxymethyl)-4-{(E)-2-[4-(4-phenylbutoxy) phenyl]vinyl}-1H-indol-1-yl)butanoic acid TLC: Rf 0.32 (dichloromethane:methanol=9:1); $^1$H-NMR (DMSO-$d_6$): δ 1.71-2.04 (m, 6H), 2.20 (t, 2H), 3.83 (s, 2H), 3.94-4.10 (m, 4H), 4.14 (t 2H), 6.85-6.99 (m, 5H), 7.00-7.19 (m, 2H), 7.21-7.42 (m, 5H), 7.53 (d, 2H), 7.63 (d, 1H), 12.23 (s, 2H).

Example 8(2)

4-[3-(carboxymethyl)-4-((E)-2-{4-[(5-phenylpentyl) oxy]phenyl}vinyl) 1H-indol-1-yl]butanoic acid TLC: Rf 0.33 (dichloromethane:methanol=9:1); $^1$H-NMR (DMSO-$d_6$): δ 1.36-1.52 (m, 2H), 1.55-1.83 (m, 4H), 1.86-2.02 (m, 2H), 2.19 (t, 2H), 2.55-2.64 (m, 2H), 3.83 (s, 2H), 3.98 (t, 2H), 4.14 (t, 2H), 6.91 (d, 2H), 7.05 (d, 1H), 7.09-7.41 (m, 9H), 7.52 (d, 2H), 7.63 (d, 1H).

Example 8(3)

3-[(3-carboxymethyl)-4-{(E)-2-[4-(4-phenylbutoxy) phenyl]vinyl}-1H-indol-1-yl)methyl]benzoic acid TLC: Rf 0.21 (dichloromethane:methanol=9:1); $^1$H-NMR (DMSO-$d_6$): δ 1.66-1.80 (m, 4H), 2.63 (t 2H), 3.85 (s, 2H), 3.99 (t 2H), 5.44 (s, 2H), 6.91 (d, 2H), 6.99-7.35 (m, 9H), 7.37-7.46 (m, 3H), 7.51 (d, 2H) 7.63 (d, 1H), 7.73-7.87 (m, 2H), 12.66 (s, 2H).

Example 8(4)

5-(3-carboxymethy-4-{(E)-2-[4-(4-phenylbutoxy) phenyl]vinyl}-1H-indol-1-yl)pentanoic acid TLC: Rf 0.53 (dichloromethane:methanol:acetic acid=9:1:0.05); $^1$H-NMR (DMSO-$d_6$): δ 1.41-1.54 (m, 2H), 1.66-1.78 (m, 6H), 2.22 (t 2H), 2.64 (t 2H), 3.82 (s, 2H), 4.00 (t, 2H), 4.12 (t, 2H), 6.92 (d, 2H) 7.05 (d, 1H), 7.08-7.39 (m, 9H), 7.52 (d, 2H), 7.64 (d, 1H), 12.13 (s, 2H).

Example 8(5)

3-(3-carboxymethyl-4-{(E)-2-[4-(4-phenylbutoxy) phenyl]vinyl}-1H-indol-1-yl)pentanoic acid TLC: Rf 0.49 (dichloromethane:methanol:acetic acid=9:1:0.05); $^1$H-NMR (DMSO-$d_6$): δ 1.68-1.78 (m, 4H), 2.64 (t, 2H) 2.71 (t, 2H), 3.81 (s, 2H), 4.00 (t, 2H), 4.34 (t, 2H), 6.92 (d, 2H) 7.05 (d, 1H), 7.09-7.41 (m, 9H), 7.51 (d, 2H), 7.62 (d, 1H), 12.32 (s, 2H).

Example 8(6)

4-(3-carboxymethyl)-4-{(E)-2-[4-(3-phenylpropoxy) phenyl]vinyl}-1H-indol-1-yl)butanoic acid TLC: Rf 0.29 (dichloromethane:methanol=9:1); $^1$H-NMR (DMSO-$d_6$): δ 1.86-2.10 (m, 4H), 2.20 (t, 2H), 2.75 (dd, 2H), 3.84 (s, 2H), 3.99 (t 2H), 4.14 (t, 2H), 6.93 (d, 2H), 7.06 (d, 1H), 7.09-7.41 (m, 9H), 7.53 (d, 2H), 7.63 (d, 1H), 12.25 (s, 2H).

Example 8(7)

4-(3-(carboxymethyl)-4-{(E)-2-[4-(3-phenoxypropoxy)phenyl]vinyl}-1H-indol-1-yl)butanoic acid TLC: Rf 0.30 (dichloromethane:methanol=9:1); $^1$H-NMR (DMSO-$d_6$): δ 1.87-2.02 (m, 2H), 2.11-2.25 (m, 4H), 3.83 (s, 2H), 4.06-4.24 (m, 6H), 6.86-7.01 (m, 5H), 7.06 (d, 1H), 7.13 (t, 1H), 7.22-7.41 (m, 5H), 7.53 (d, 2H), 7.63 (d, 1H), 12.24 (s, 2H).

Example 8(8)

4-[3-carboxymethyl)-4-((E)-2-{4-[2-(5-methyl-2-phenyl-1,3-oxazol-4-yl)ethoxy]phenyl}vinyl)-1H-indol-1-yl]butanoic acid TLC: Rf 0.26 (dichloromethane:methanol:acetic acid=95:4:1); $^1$H-NMR (DMSO-$d_6$): δ 1.86-2.02 (m, 2H) 2.20 (t 2H), 2.37 (s, 3H), 2.94 (t, 2H), 3.83 (s, 2H), 4.14 (t, 2H), 4.24 (t, 2H), 6.95 (d, 2H), 7.06 (d, 1H), 7.12 (dd, 1H) 7.26 (s, 1H), 7.32 (d, 1H), 7.36 (d, 1H), 7.44-7.58 (m, 5H), 7.63 (d, 1H), 7.83-7.99 (m, 2H) 12.08-12.41 (m, 2H).

Example 8(9)

2,2'-4-{(E)-2-[4-(4-phenylbutoxy)phenyl]vinyl}-1H-indol-1,3-diyl)diacetic acid

TLC: Rf 0.24 (dichloromethane:methanol:acetic acid=9:1:0.05); $^1$H-NMR (DMSO-$d_6$): δ 1.65-1.78 (m, 4H), 2.59-2.69 (m, 2H), 3.83 (s, 2H), 3.95-4.05 (m, 2H), 4.95 (s, 2H), 6.92 (d, 2H), 7.06 (d, 1H), 7.12-7.38 (m, 9H), 7.53 (d, 2H), 7.64 (d, 1H), 12.37 (s, 1H), 12.89 (s, 1H).

Example 8(10)

4-(3-(carboxymethyl)-4-{(E)-2-[4-(4-penten-1-yloxy)phenyl]vinyl}-1H-indol-1-yl)butanoic acid TLC: Rf 0.52 (dichloromethane:methanol:acetic acid=9:1:0.05); $^1$H-NMR (DMSO-$d_6$): δ 1.73-1.86 (m, 2H), 1.87-2.01 (m, 2H), 2.19 (q, 4H), 3.83 (s, 2H), 3.99 (t, 2H), 4.14 (t, 2H), 4.96-5.09 (m, 2H), 5.78-5.95 (m, 1H), 6.93 (d, 2H), 7.06 (d, 1H), 7.13 (dd, 1H), 7.22-7.41 (m, 3H), 7.52 (d, 2H), 7.63 (d, 1H), 12.24 (s, 2H).

Example 8(11)

4-{3-(carboxymethyl)-4-[(E)-2-(4-{[(2E)-3-phenyl-2-propen-1-yl]oxy}phenyl)vinyl]-1H-indol-1-yl}butanoic acid TLC: Rf 0.33 (dichloromethane:methanol=9:1); $^1$H-NMR (DMSO-$d_6$): δ 1.87-2.02 (m, 2H), 2.20 (t, 2H), 3.84 (s, 2H), 4.14 (t, 2H), 4.76 (d, 2H), 6.52 (dt, 1H), 6.70-6.85 (m, 1H), 6.94-7.19 (m, 4H), 7.20-7.42 (m, 6H), 7.43-7.59 (m, 4H), 7.64 (d, 1H), 12.26 (s, 2H).

Example 8(12)

4-(3-(carboxymethyl)-4-{(E)-2-[4-(2-pentyn-1-yloxy)phenyl]vinyl}-1H-indol-1-yl)butanoic acid TLC: Rf 0.28 (dichloromethane:methanol=9:1); $^1$H-NMR (DMSO-$d_6$): δ 1.06 (t, 3H), 1.87-2.01 (m, 2H), 2.13-2.29 (m, 4H), 1-3.84 (s, 2H), 4.14 (t, 2H), 4.77 (s, 2H), 6.97 (d, 2H), 7.07 (d, 1H), 7.13 (dd, 1H), 7.27 (s, 1H), 7.33 (d, 1H), 7.36 (d, 1H), 7.55 (d, 2H), 7.65 (d, 1H), 12.28 (s, 2H).

Example 8(13)

4-[3-(carboxymethyl)-4-((E)-2-{4-[(7-chloro)-2-quinolinylmethoxy]phenyl}vinyl)-1H-indol-1-yl] butanoic acid TLC: Rf 0.60 (dichloromethane:methanol:acetic acid=9:1:0.05); $^1$H-NMR (DMSO-$d_6$): δ 1.88-2.01 (m, 2H), 2.20 (t, 2H), 3.83 (s, 2H), 4.14 (t, 2H), 5.41 (s, 2H), 7.02-7.16 (m, 4H), 7.25-7.38 (m, 3H) 7.55 (d, 2H) 7.59-7.69 (m, 2H) 7.72 (d, 1H), 8.04-8.09 (m, 2H), 8.48 (d, 1H), 12.22 (s, 2H).

Example 8(14)

4-[3-(carboxymethyl)-4-((E)-2-{4-[(4-methyl-3-penten-1-yl)oxy]phenyl}vinyl)-1H-indol-1-yl]butanoic acid TLC: Rf 0.42 (dichloromethane:methanol=9:1); $^1$H-NMR (DMSO-$d_6$): δ 1.62 (s, 3H), 1.69 (d, 3H), 1.87-2.00 (m, 2H), 2.19 (t, 2H), 2.41 (q, 2H), 3.83 (s, 2H), 3.96 (t, 2H), 4.14 (t, 2H), 5.16-5.26 (m, 1H), 6.92 (d, 2H), 7.05 (d, 1H), 7.12 (dd, 1H), 7.26 (s, 1H), 7.32 (d, 1H), 7.35 (d, 1H), 7.52 (d, 2H), 7.63 (d, 1H), 12.26 (s, 2H).

Example 8(15)

4-(3-(carboxymethyl)-4-{(E)-2-[4-(3-cyclohexylpropoxy)phenyl]vinyl}-1H-indol-1-yl)butanoic acid TLC: Rf 0.44 (dichloromethane:methanol=9:1); $^1$H-NMR (DMSO-$d_6$): δ 0.78-0.99 (m, 2H), 1.06-1.37 (m, 6H), 1.53-1.80 (m, 7H), 1.88-2.01 (m, 2H), 2.19 (t, 2H), 3.83 (s, 2H), 3.96 (t, 2H), 4.14 (t, 2H), 6.91 (d, 2H), 7.05 (d, 1H), 7.12 (dd, 1H), 7.26 (s, 1H), 7.32 (d, 1H), 7.35 (d, 1H), 7.52 (d, 2H), 7.63 (d, 1H) 12.26 (s, 2H).

Example 8(16)

4-[3-(carboxymethyl)-4-((E)-2-{4-[2-(5-methyl-2-phenyl-1,3-thiazol-4-yl)ethoxy]phenyl}vinyl)-1H-indol-1-yl]butanoic acid TLC: Rf 0.44 (dichloromethane:methanol=9:1); $^1$H-NMR (DMSO-$d_6$): δ 1.86-2.01 (m, 2H), 2.19 (t, 2H), 2.45 (s, 3H), 3.14 (t, 2H), 3.83 (s, 2H), 4.13 (t, 2H), 4.33 (t, 2H), 6.95 (d, 2H), 7.05 (d, 1H) 7.12 (dd, 1H), 7.26 (s, 1H), 7.32 (d, 1H), 7.35 (d, 1H), 7.39-7.58 (m, 5H), 7.63 (d, 1H), 7.85 (dd, 2H), 12.21 (s, 2H).

Example 8(17)

4-[4-((E)-2-{4-[2-(1,3-benzothiazol-2-ylthio)ethoxy}phenyl]vinyl)-3-(carboxymethyl)-1H-indol-1-yl]butanoic acid TLC: Rf 0.37 (dichloromethane:methanol=9:1); $^1$H-NMR (DMSO-$d_6$): δ 1.87-2.02 (m, 2H), 2.20 (t, 2H), 3.78 (t 2H), 3.84 (s, 2H), 4.14 (t, 2H), 4.39 (t, 2H), 6.97-7.19 (m, 4H), 7.27 (s, 1H), 7.29-7.42 (m, 3H), 7.48 (td, 1H), 7.55 (d, 2H), 7.65 (d, 1H), 7.90 (d, 1H), 8.02 (dd, 1H), 12.24 (s, 2H).

Example 8(18)

4-[3-carboxymethyl-4-((E)-2-{4-[2-phenylthio)ethoxy]phenyl}vinyl)-1H-indol-1-yl]butanoic acid TLC: Rf 0.42 (dichloromethane:methanol=9:1); $^1$H-NMR (DMSO-$d_6$): δ 1.87-2.01 (m, 2H), 2.20 (t 2H), 3.37 (t, 2H) 3.83 (s, 2H), 4.07-4.24 (m, 4H), 6.90 (d, 2H) 7.06 (d, 1H), 7.12 (dd, 1H), 7.17-7.46 (m, 8H), 7.52 (d, 2H), 7.63 (d, 1H), 12.24 (s, 2H).

Example 8(19)

4-[3-carboxymethyl-4-((E)-2-{4-[4-(2-methylphenoxy)butoxy]phenyl}vinyl)-1H-indol-1-yl]butanoic acid TLC: Rf 0.60 (dichloromethane:methanol:acetic acid=9:1:0.05); $^1$H-NMR (DMSO-$d_6$A): δ 1.85-1.97 (m, 6H), 2.14 (s, 3H), 2.20 (t, 2H), 3.84 (s, 2H), 3.97-4.19 (m, 6H), 6.81 (dd, 1H), 6.89-6.97 (m, 3H), 7.01-7.19 (m, 4H), 7.23-7.39 (m, 3H), 7.53 (d, 2H), 7.63 (d, 1H), 12.24 (s, 2H).

Example 8(20)

4-[4-((E)-2-{4-[4-(2-acetylphenoxy)butoxy]phenyl}vinyl)-3-carboxymethyl) 1H-indol-1-yl]butanoic acid TLC: Rf 0.43 (dichloromethane:methanol:acetic acid=9:1:0.05); $^1$H-NMR (DMSO-$d_6$): δ 1.82-2.03 (m, 6H), 2.19 (t, 2H), 2.54 (s, 3H), 3.82 (s, 2H), 4.02-4.23 (m, 6H), 6.87-7.19 (m, 6H), 7.23-7.40 (m, 3H), 7.44-7.59 (m, 4H), 7.63 (d, 1H), 1220 (s, 2H).

Example 8(21)

4-[3-carboxymethyl)-4-((E)-2-{4-[4-(2-ethylphenoxy)butoxy]phenyl}vinyl)-1H-indol-1-yl]butanoic acid TLC: Rf 0.70 (dichloromethane:methanol:acetic acid=9:1:0.05); $^1$H-NMR (DMSO-$d_6$): δ 1.12 (t, 3H), 1.82-2.02 (m, 6H), 2.20 (t, 2H), 2.56 (q, 2H), 3.84 (s, 2H), 3.99-4.10 (m, 4H), 4.14 (t, 2H), 6.80-6.88 (m, 1H), 6.90-6.99 (m, 3H), 7.06 (d, 1H), 7.10-7.18 (m, 3H), 7.27 (s, 1H), 7.32 (d, 1H), 7.36 (d, 1H), 7.53 (d, 2H), 7.63 (d, 1H), 12.24 (brs, 2H).

Example 8(22)

4-[3-carboxymethyl)-4-((E)-2-{4-[2-(3-thienyl)ethoxy]phenyl}vinyl)-1H-indol-1-yl]butanoic acid TLC: Rf 0.33 (dichloromethane:methanol=9:1); $^1$H-NMR (DMSO-$d_6$): δ 1.85-2.00 (m, 2H), 2.17 (t, 2H), 3.05 (t, 2H), 3.80 (s, 2H), 4.12 (t, 2H), 4.21 (t, 2H), 6.95 (d, 2H), 7.05 (d, 1H), 7.08-7.17 (m, 2H), 7.24 (s, 1H), 7.27-7.40 (m, 3H), 7.47 (dd, 1H), 7.54 (d, 2H), 7.68 (d, 1H).

Example 8(23)

4-[3-carboxymethyl)-4-((E)-2-{4-[4-(4-methoxyphenyl)butoxy]phenyl}vinyl)-1H-indol-1-yl]butanoic acid TLC: Rf 0.36 (dichloromethane:methanol=9:1); $^1$H-NMR (DMSO-$d_6$): δ 1.60-1.80 (m, 4H), 1.87-2.01 (m, 2H), 2.20 (t, 2H), 2.57 (t, 2H), 3.71 (s, 3H), 3.83 (s, 2H), 3.95-4.04 (m, 2H), 4.14 (t, 2H), 6.84 (d, 2H), 6.92 (d, 2H), 7.06 (d, 1H), 7.09-7.17 (m, 3H), 7.26 (s, 1H), 7.32 (d, 1H), 7.36 (d, 1H), 7.52 (d, 2H), 7.62 (d, 1H), 12.24 (s, 2H).

Example 8(24)

4-[3-(carboxymethyl-4-((E)-2-{4-[4-(2,6-dichlorophenoxy)butoxy]phenyl}vinyl)-1H-indol-1-yl]butanoic acid TLC: Rf 0.47 (dichloromethane:methanol:acetic acid=9:1:0.05); $^1$H-NMR (DMSO-$d_6$): δ 1.87-2.00 (m, 6H), 2.20 (t, 2H), 3.84 (s, 2H), 4.00-4.19 (m, 6H), 6.95 (d, 2H), 7.02-7.23 (m, 3H), 7.27 (s, 1H), 7.32 (d, 1H), 7.36 (d, 1H), 7.49 (d, 2H), 7.53 (d, 2H), 7.58-7.69 (d, 1H), 12.25 (s, 2H).

Example 8(25)

4-[3-(carboxymethyl)-4-((E)-2-{4-[4-(4-methylphenoxy)butoxy]phenyl}vinyl)-1H-indol-1-yl]butanoic acid TLC: Rf 0.59 (dichloromethane:methanol:acetic acid=9:1:0.05); $^1$H-NMR (DMSO-$d_6$): δ 1.80-2.02 (m, 6H), 2.13-2.26 (m, 5H), 3.83 (s, 2H), 3.92-4.01 (m, 2H), 4.05 (t, 2H), 4.14 (t, 2H), 6.75-6.86 (m, 2H), 6.94 (d, 2H), 7.02-7.18 (m, 4H), 7.26 (s, 1H), 7.30-7.42 (m, 2H), 7.53 (d, 2H), 7.63 (d, 1H), 12.24 (s, 2H).

Example 8(26)

2,2'-(4-{(E)-2-[4-(3-phenylpropoxy)phenyl]vinyl}-1H-indol-1,3-diyl)diacetic acid TLC: Rf 0.26 (dichloromethane:methanol:acetic acid=9:1:0.05); $^1$H-NMR (DMSO-$d_6$): δ 1.95-2.11 (m, 2H), 2.68-2.80 (m, 2H), 3.84 (s, 2H), 3.99 (t, 2H), 4.93 (s, 2H), 6.93 (d, 2H), 7.02-7.37 (m, 10H), 7.53 (d, 2H), 7.65 (d, 1H), 12.43 (s, 2H).

Example 8(27)

4-[3-(carboxymethyl)-4-((E)-2-{4-[4-(2-fluorophenoxy)butoxy]phenyl}vinyl)-1H-indol-1-yl]butanoic acid TLC: Rf 0.56 (dichloromethane:methanol:acetic acid=9:1:0.05); $^1$H-NMR (DMSO-$d_6$): δ 1.80-2.03 (m, 6H), 2.20 (t 2H), 3.84 (s, 2H), 3.98-4.22 (m, 6H), 6.94 (d, 2H), 7.06 (d, 1H), 7.10-7.24 (m, 5H), 7.27 (s, 1H), 7.32 (d, 1H), 7.36 (d, 1H), 7.53 (d, 2H), 7.63 (d, 1H), 12.25 (brs, 2H).

Example 8(28)

2,2'-(4-{(E)-2-[4-(4-phenoxybutoxy)phenyl]vinyl}-1H-indol-1,3-diyl)diacetic acid TLC: Rf 0.41 (dichloromethane:methanol:acetic acid=18:1:1); $^1$H-NMR (DMSO-$d_6$): δ 1.77-1.96 (m, 4H), 3.84 (s, 2H), 3.95-4.15 (m, 4H), 4.96 (s, 2H), 6.85-7.01 (m, 5H), 7.09 (d, 1H), 7.11 (t, 1H), 7.19-7.38 (m, 5H), 7.54 (d, 2H), 7.65 (d, 1H), 12.37 (s, 1H), 12.90 (s, 1H).

Example 8(29)

2,2'-(4-{(E)-2-[4-(3-phenoxypropoxy)phenyl]vinyl}-1H-indol-1,3-diyl)diacetic acid TLC: Rf 0.41 (dichloromethane:methanol:acetic acid=18:1:1); $^1$H-NMR (DMSO-$d_6$): δ 2.11-2.24 (m, 2H), 3.84 (s, 2H), 4.13 (t, 2H), 4.16 (t, 2H), 4.96 (s, 2H), 6.87-7.00 (m, 5H), 7.09 (d, 1H), 7.11 (dd, 1H), 7.19-7.39 (m, 5H), 7.54 (d, 2H), 7.65 (d, 1H), 12.36 (s, 1H), 12.91 (s, 1H).

Example 8(30)

2,2'-(4-{(E)-2-[4-(4-penten-1-yloxy)phenyl]vinyl}-1H-indol-1,3-diyl)diacetic acid TLC: Rf 0.37 (dichloromethane:methanol:acetic acid=18:1:1); $^1$H-NMR (DMSO-$d_6$): δ 1.74-1.87 (m, 2H), 2.12-2.26 (m, 2H), 3.84 (s, 2H), 4.00 (t, 2H), 4.90-5.11 (m, 2H), 4.96 (s, 2H), 5.79-5.95 (m, 1H),6.93 (d, 2H), 7.07 (d, 1H), 7.08-7.15 (m, 1H), 7.25 (d, 1H), 7.25 (s, 1H), 7.33 (d, 1H), 7.53 (d, 2H), 7.64 (d, 1H), 12.43 (s, 2H).

Example 8(31)

2,2'-[4-((E)-2-{4-[(5-phenylpentyl)oxy]phenyl}vinyl)-1H-indol-1,3-diyl]diacetic acid TLC: Rf 0.24 (dichloromethane:methanol:acetic acid=9:1:0.05); $^1$H-NMR (DMSO-$d_6$): δ 139-1.50 (m, 2H), 1.54-1.69 (m, 2H), 1.70-1.87 (m, 2H), 2.55-2.66 (m, 2H), 3.84 (s, 2H), 3.98 (t, 2H), 4.95 (s, 2H), 6.92 (d, 2H), 7.00-7.30 (m, 9H), 7.33 (d, 1H), 7.53 (d, 2H), 7.64 (d, 1H), 12.36 (s, 2H).

Example 8(32)

2,2'-[4-((E)-2-{4-[(7-chloro-2-quinolinyl)methoxy]phenyl}vinyl)-1H-indol-1,3-diyl]diacetic acid TLC: Rf 0.23 (dichloromethane:methanol:acetic acid=9:1:0.05); $^1$H-NMR (DMSO-$d_6$): δ 3.83 (s, 2H), 4.95 (s, 2H), 5.40 (s, 2H), 7.01-7.17 (m, 4H), 7.20-7.28 (m, 2H), 7.33 (d, 1H), 7.56 (d, 2H), 7.61-7.69 (m, 2H), 7.72 (d, 1H), 8.02-8.16 (m, 2H), 8.47 (d, 1H), 12.42 (s, 2H).

Example 8(33)

2,2'-(4-{(E)-2-[4-(2,3-dihydro-1H-inden-2-ylmethoxy)phenyl]vinyl}-1H-indol-1,3-diyl)diacetic acid TLC: Rf 0.49 (dichloromethane:methanol:acetic acid=90:10:1); $^1$H-NMR (DMSO-$d_6$): δ 2.68-2.99 (m, 3H), 2.99-3.20 (m, 2H), 3.82 (s, 2H) 3.99 (d, 2H), 4.84 (s, 2H), 6.95 (d, 2H), 7.00-7.16 (m, 4H), 7.16-7.27 (m, 4H), 7.31 (d, 1H), 7.53 (d, 2H), 7.66 (d, 1H).

Example 8(34)

2,2'-[4-((E)-2-{4-[(6-phenylhexyl)oxy]phenyl}vinyl)-1H-indol-1,3-diyl]diacetic acid TLC: Rf 0.45 (dichloromethane:methanol:acetic acid=90:10:1); $^1$H-NMR (DMSO-$d_6$): δ 1.04-1.90 (m, 8H), 2.58 (t, 2H), 3.84 (s, 2H), 3.97 (t, 2H), 4.96 (s, 2H), 6.92 (d, 2H), 6.99-7.40 (m, 10H), 7.53 (d, 2H), 7.65 (d, 1H), 12.60 (s, 2H).

Example 8(35)

2,2'-[4-((E)-2-{4-[3-(benzyloxy)propoxy]phenyl}vinyl)-1H-indol-1,3-diyl]diacetic acid TLC: Rf 0.53 (dichloromethane:methanol:acetic acid=90:10:1); $^1$H-NMR (DMSO-$d_6$): δ 1.77-2.12 (m, 2H), 3.59 (t, 2H), 3.83 (s, 2H), 4.08 (t, 2H), 4.49 (s, 2H), 4.87 (s, 2H), 6.93 (d, 2H), 6.99-7.17 (m, 2H), 7.18-7.39 (m, 8H), 7.54 (d, 2H), 7.66 (d, 1H).

Example 8(36)

2,2'-[4-((E)-2-{4-[3-(benzyloxy)propoxy] phenyl}vinyl)-3-carboxymethyl)-1H-indol-1-yl]butanoic acid TLC: Rf 0.63 (dichloromethane:methanol:acetic acid=9:1:0.05); $^1$H-NMR (DMSO-$d_6$): δ 1.86-2.07 (m, 4H), 2.20 (t, 2H), 3.59 (t, 2H), 3.84 (s, 2H), 4.08 (t, 2H), 4.14 (t, 2H), 4.49 (s, 2H), 6.93 (d, 2H), 7.06 (d, 1H), 7.13 (t, 1H), 7.23-7.41 (m, 8H), 7.53 (d, 2H), 7.63 (d, 1H), 12.24 (brs, 2H).

Example 8(37)

4-[3-carboxymethyl)-4-((E)-2-{4-[4-(2,6-dimethylphenoxy)butoxy]phenyl}vinyl)-1H-indol-1-yl] butanoic acid TLC: Rf 0.47 (dichloromethane:methanol:acetic acid=9:1:0.05); $^1$H-NMR (DMSO-$d_6$): δ 1.81-2.02 (m, 6H), 2.10-2.27 (m, 8H), 3.78 (t, 2H), 3.83 (s, 2H), 4.07 (t, 2H), 4.13 (t, 2H), 6.82-7.17 (m, 7H), 723-7.42 (m, 3H), 7.53 (d, 2H), 7.63 (d, 1H), 12.23 (s, 2H).

Example 8(38)

2,2'-[4-((E)-2-{4-[4-(benzyloxy)butoxy] phenyl}vinyl)-1H-indol-1,3-diyl]diacetic acid TLC: Rf 0.31 (dichloromethane:methanol:acetic acid=9:1:0.05); $^1$H-NMR (DMSO-$d_6$): δ 1.63-1.85 (m, 4H), 3.49 (t, 2H), 3.84 (s, 2H), 4.00 (t, 2H), 4.46 (s, 2H), 4.95 (d, 2H), 6.92 (d, 2H), 7.01-7.16 (m, 2H), 7.21-7.38 (m, 8H), 7.53 (d, 2H), 7.65 (d, 1H), 12.52 (s, 2H).

Example 8(39)

4-[4-((E)-2-{4-[4-(benzyloxy)butoxy]phenyl}vinyl )-3-carboxymethyl)-1H-indol-1-yl]butanoic acid TLC: Rf 0.39 (dichloromethane:methanol:acetic acid=9:1:0.05); $^1$H-NMR (DMSO-$d_6$): δ 1.62-1.85 (m, 4H), 1.88-2.03 (m, 2H), 2.20 (t, 2H), 3.49 (t, 2H), 3.83 (s, 2H), 4.00 (t, 2H), 4.14 (t, 2H), 4.41-4.50 (m, 2H) 6.91 (d, 2H), 6.99-7.09 (m, 1H), 7.13 (t, 1H), 7.22-7.41 (m, 8H), 7.52 (d, 2H), 7.63 (d, 1H), 1225 (s, 2H).

Example 8(40)

4-[4-((E)-2-{4-[2-(benzylthio)ethoxy]phenyl}vinyl)-3-carboxymethyl)-1H-indol-1-yl]butanoic acid TLC: Rf 0.44 (dichloromethane:methanol=9:1); $^1$H-NMR (DMSO-$d_6$): δ 1.87-2.03 (m, 2H), 2.20 (t, 2H), 2.77 (t, 2H), 3.84 (s, 2H), 3.85 (s, 2H), 4.11 (t, 2H), 4.15 (t, 2H), 6.91 (d, 2H), 7.07 (d, 1H), 7.13 (t, 1H), 7.20-7.41 (m, 8H), 7.53 (d, 2H), 7.64 (d, 1H), 12.26 (brs, 2H).

Example 8(41)

2,2'-[4-((E)-2-{4-[4-(2-acetylphenoxy)butoxy] phenyl}vinyl)-1H-indol-1,3-diyl]diacetic acid TLC: Rf 0.24 (dichloromethane:methanol:acetic acid=9:1:0.05); $^1$H-NMR (DMSO-$d_6$): δ 1.86-2.03 (m, 4H), 2.55 (s, 3H), 3.84 (s, 2H), 4.08 (t 2H), 4.17 (t, 2H), 4.95 (s, 2H), 6.88-7.28 (m, 8H), 7.33 (d, 1H), 7.47-7.60 (m, 4H), 7.65 (d, 1H), 12.44 (s, 2H).

Example 8(42)

2,2'-[4-((E)-2-{4-[4-(2-fluorophenoxy)butoxy] phenyl}vinyl)-1H-indol-1,3-diyl]diacetic acid TLC: Rf 0.26 (dichloromethane:methanol:acetic acid=9:1:0.05); $^1$H-NMR (DMSO-$d_6$): δ 1.81-1.99 (m, 4H), 3.84 (s, 2H), 3.97-4.21 (m, 4H), 4.93 (s, 2H), 6.84-6.99 (m, 3H), 7.02-7.27 (m, 7H), 7.33 (d, 1H), 7.54 (d, 2H), 7.65 (d, 1H), 12.56 (s, 2H).

Example 8(43)

2,2'-[4-((E)-2-{4-[4-(2-methylphenoxy)butoxy] phenyl}vinyl)-1H-indol-1,3-diyl]diacetic acid TLC: Rf 0.42 (dichloromethane:methanol:acetic acid=90:10:1); $^1$H-NMR (DMSO-$d_6$): δ 1.76-2.00 (m, 4H), 2.15 (s, 3H), 3.83 (s, 2H), 3.91-4.17 (m, 4H), 4.80 (s, 2H), 6.81 (t, 1H), 6.87-6.98 (m, 3H), 6.99-7.18 (m, 4H), 7.18-7.26 (m, 2H), 7.31 (d, 1H), 7.54 (d, 2H), 7.66 (d, 1H).

Example 8(44)

2,2'-[4-((E)-2-{4-[4-(2,6-dimethylphenoxy)butoxy] phenyl}vinyl)-1H-indol-1,3-diyl]diacetic acid TLC: Rf 0.46 (dichloromethane:methanol:acetic acid=90:10:1); $^1$H-NMR (DMSO-$d_6$): δ 1.72-2.06 (m, 44), 2.22 (s, 6H), 3.69-3.91 (m, 4H), 4.08 (t, 2H), 4.87 (s, 2H), 6.81-7.16 (m, 7H), 7.19-7.25 (m, 2H), 7.32 (d, 1H), 7.54 (d, 2H), 7.66 (d, 1H).

Example 8(45)

2,2'-[4-((E)-2-{4-[4-(2,6-dichlorophenoxy)butoxy] phenyl}vinyl)-1H-indol-1,3-diyl]diacetic acid TLC: Rf 0.37 (dichloromethane:methanol:acetic acid=90:10:1); $^1$H-NMR (DMSO-$d_6$): δ 1.81-2.07 (m, 4H), 3.83 (s, 2H), 3.93-4.19 (m, 4H), 4.87 (s, 2H), 6.95 (d, 2H), 7.00-7.26 (m, 5H), 7.32 (d, 1H), 7.45-7.58 (m, 4H), 7.66 (d, 1H).

Example 8(46)

2,2'-[4-((E)-2-{4-[4-(3-methylphenoxy)butoxy] phenyl}vinyl)-1H-indol-1,3-diyl]diacetic acid TLC: Rf 0.48 (dichloromethane:methanol:acetic acid=18:1:1); $^1$H-NMR (DMSO-$d_6$): δ 1.80-1.93 (m, 4H), 2.26 (s, 3H), 3.82 (s, 2H), 3.93-4.11 (m, 4H), 4.72 (s, 2H), 6.67-6.79 (m, 3H), 6.94 (d, 2H), 7.00-7.24 (m, 5H) 7.30 (d, 1H), 7.54 (d, 2H), 7.67 (d, 1H).

Example 8(47)

2,2'-[4-((E)-2-{4-[4-(4-methylphenoxy)butoxy] phenyl}vinyl)-1H-indol-1,3-diyl]diacetic acid TLC: Rf 0.48 (dichloromethane:methanol:acetic acid=18:1:1); $^1$H-NMR (DMSO-$d_6$): δ 1.75-1.95 (m, 4H), 2.21 (s, 3H), 3.82 (s, 2H), 3.93-4.02 (m, 2H), 4.01-4.09 (m, 2H), 4.74 (s, 2H), 6.82 (d, 2H), 6.93 (d, 2H), 7.00-7.13 (m, 4H), 7.16-7.25 (m, 2H), 7.30 (d, 1H), 7.54 (d, 2H), 7.67 (d, 1H).

Example 8(48)

2,2'-[4-((E-2-{4-[4-(4-ethylphenoxy)butoxy]phenyl}vinyl)-1H-indol-1,3-diyl]diacetic acid TLC: Rf 0.27 (dichloromethane:methanol:acetic acid=9:1:0.05); $^1$H-NMR (DMSO-$d_6$): δ 1.12 (t, 3H), 1.83-1.97 (m, 4H), 2.56 (q, 2H), 3.84 (s, 2H), 3.98-4.17 (m, 4H), 4.96 (s, 2H), 6.84 (t, 1H), 6.90-6.98 (m, 3H), 7.07 (d, 1H), 7.10-7.18 (m, 3H), 7.21-7.28 (m, 2H), 7.33 (d, 1H), 7.54 (d, 2H), 7.65 (d, 1H).

Example 8(49)

2,2'-[4-((E)-2-{4-[4-(2-propionylphenoxy)butoxy]phenyl}vinyl)-1H-indol-1,3-diyl]diacetic acid TLC: Rf 0.20 (dichloromethane:methanol:acetic acid=9:1:0.05); $^1$H-NMR (DMSO-$d_6$): δ 1.04 (t 3H), 1.82-2.02 (m, 4H), 2.94 (q, 2H), 3.84 (s, 2H), 4.08 (t, 2H), 4.16 (t, 2H) 4.96 (s, 2H), 6.94 (d, 2H), 7.00 (t, 1H), 7.07 (d, 1H), 7.10 (d, 1H), 7.15 (d, 1H), 7.25 (d, 1H), 7.25 (s, 1H), 7.33 (d, 1H), 7.45-7.57 (m, 4H), 7.65 (d, 1H).

Example 8(50)

2,2'-[4-((E)-2-{4-[4-(2-propylphenoxy)butoxy]phenyl}vinyl)-1H-indol-1,3-diyl]diacetic acid TLC: Rf 0.37 (dichloromethane:methanol:acetic acid=18:1:1); $^1$H-NMR (DMSO-$d_6$): δ 0.87 (t, 3H), 1.46-1.62 (m, 2H), 1.77-2.01 (m, 4H), 2.49-2.57 (m, 2H), 3.82 (s, 2H), 3.96-4.13 (m, 4H), 4.73 (s, 2H), 6.83 (td, 1H), 6.89-6.98 (m, 3H), 7.00-7.17 (m, 4H), 7.17-7.24 (m, 2H), 7.30 (d, 1H), 7.53 (d, 2H), 7.67 (d, 1H).

Example 8(51)

2,2'-[4-((E)-2-{4-[4-(2-chlorophenoxy)butoxy]phenyl}vinyl)-1H-indol-1,3-diyl]diacetic acid TLC: Rf 0.29 (dichloromethane:methanol:acetic acid=9:1:0.05); $^1$H-NMR (DMSO-$d_6$): δ 1.84-1.99 (m, 4H), 3.82 (s, 2H), 4.01-4.19 (m, 4H), 4.79 (s, 2H), 6.89-6.97 (m, 3H), 7.00-7.34 (m, 7H), 7.41 (dd, 1H), 7.53 (d, 2H), 7.66 (d, 1H), 1230 (s, 2H).

Example 9(1) to Example 9(5)

The same operation as in Example 2→Example 6 was conducted to obtain the titled compound having the following physical properties. In the step corresponding to Example 2 in the operation, ethyl 3-(4-methoxy-4-oxobutanoyl)-1H-indole-2-carboxylate [Chem. Pharm. Bull., 38,3261 (1990)] was used in place of the compound prepared in Example 1 and a corresponding compound was used in place of methyl 4-bromobutyrate.

Example 9(1)

3-(3-carboxypropanoyl)-1-(4-phenoxybutyl)-1H-indole-2-carboxylic acid

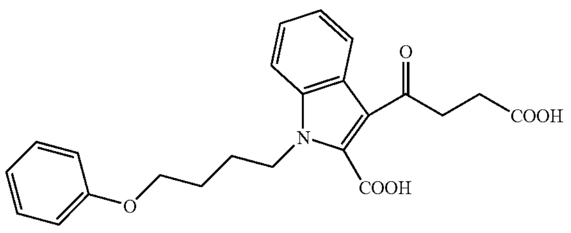

TLC: Rf 0.33 (methanol: dichloromethane=1:4); $^1$H-NMR (DMSO-$d_6$): δ 1.64-1.80 (m, 2H), 1.82-2.00 (m, 2H), 2.57 (t, 2H), 3.16 (t, 2H), 3.94 (t, 2H), 4.38 (t, 2H) 6.83-6.94 (m, 3H), 7.19-7.41 (m, 4H), 7.69 (d, 1H), 8.04 (d, 1H), 12.09 (brs, 1H).

Example 9(2)

3-(3-carboxypropanoyl)-1-{3-[4-(4-phenylbutoxy)phenyl]propyl}-1H-indole-2-carboxylic acid TLC: Rf 0.38 (methanol: dichloromethane:acetic acid=1:9:0.1); $^1$H-NMR (DMSO-$d_6$): δ 1.62-1.78 (m, 4H), 1.92-2.08 (m, 2H), 2.51-2.68 (m, 6H), 3.15 (t, 2H), 3.86-4.00 (m, 2H), 4.29 (t, 2H), 6.81 (d, 2H), 7.06 (d, 2H), 7.11-7.39 (m, 7H), 7.56 (d, 1H), 8.04 (d, 1H), 12.06 (brs, 1H).

Example 9(3)

3-(3-carboxypropanoyl)-1-(6-phenylhexyl)-1H-indole-2-carboxylic acid

TLC: Rf 0.40 (methanol: dichloromethane:acetic acid=1:9:0.1); $^1$H-NMR (DMSO-$d_6$): δ 1.20-1.37 (m, 4H), 1.42-1.59 (m, 2H), 1.64-1.80 (m, 2H), 2.52-2.62 (m, 4H), 3.15 (t, 2H), 4.28 (t, 2H), 7.09-7.18 (m, 3H), 7.19-7.40 (m, 4H), 7.64 (d, 1H), 8.04 (d, 1H), 12.07 (s, 1H).

Example 9(4)

3-(3-carboxypropanoyl)-1-(7-phenylheptyl)-1H-indole-2-carboxylic acid

TLC: Rf 0.30 (methanol:dichloromethane:acetic acid=1:9:0.1); $^1$H-NMR (DMSO-$d_6$): δ 1.15-1.34 (m, 6H), 1.43-1.59 (m, 2H), 1.63-1.79 (m, 2H), 2.50-2.62 (m, 4H), 3.15 (t, 2H), 4.28 (t, 2H), 7.08-7.40 (m, 7H), 7.64 (d, 1H), 8.04 (d, 1H), 12.06 (brs, 1H).

Example 9(5)

3-(3-carboxypropanoyl)-1-{3-[4-(4-phenoxybutoxy)phenyl]propyl}-1H-indole-2-carboxylic acid TLC: Rf 0.54 (dichloromethane:methanol:acetic acid=8:2:0.1); $^1$H-NMR (DMSO-$d_6$): δ 1.77-1.91 (m, 4H), 1.91-2.08 (m, 2H), 2.52-2.63 (m, 4H), 3.15 (t, 2H), 3.91-4.10 (m, 4H), 4.29 (t, 2H), 6.77-6.96 (m, 5H), 7.07 (d, 2H), 7.20-7.38 (m, 4H), 7.56 (d, 1H), 8.05 (d, 1H), 12.09 (brs, 2H).

Example 10 methyl (2E)-3-(4-bromo-1H-indol-3-yl)acrylate

To a toluene (10.0 mL) suspension of 4-bromo-1H-indole-3-carbaldehyde [Chem. Pharm. Bull., 33, 3696 (1985)] (500 mg), methyl triphenylphosphoranilideneacetate (1.11 g) was added at room temperature, followed by stirring at 80° C. for 16 hours. The reaction mixture was cooled to room temperature and then concentrated. The residue was purified by the column chromatography to obtain the titled compound having the following physical properties (410 mg).

TLC: Rf 0.68 (n-hexane:ethyl acetate=1:2); $^1$H-NMR ($CDCl_3$): δ 3.81 (s, 3H), 6.24 (d, 1H), 7.07 (t, 1H), 7.36 (d, 1H), 7.38 (d, 1H), 7.66 (d, 1H), 8.52 (brs, 1H), 8.79 (d, 1H).

Example 11 methyl (2E)-3-[4-bromo-1-(4-methoxy-4-oxobutyl)-1H-indol-3-yl]acrylate

The same operation as in Example 2 was conducted to obtain the titled compound having the following physical properties. In place of the compound prepared in Example 1, the compound prepared in Example 10 was used.

TLC: Rf 0.69 (ethyl acetate: n-hexane=1:1); $^1$H-NMR ($CDCl_3$): δ 2.17 (quint, 2H), 2.32 (t, 2H), 3.68 (s, 3H), 3.80 (s, 3H), 4.22 (t, 2H), 6.20 (d, 1H), 7.08 (t, 1H), 8.33 (d, 1H), 7.37 (d, 1H), 8.79 (d, 1H).

Example 12(1) to Example 12(3)

The same operation as in Example 3→Example 4→Example 5→Example 6 was conducted to obtain the following compound. In the step corresponding to Example 3 in the operation, the compound prepared in Example 11 was used in place of the compound prepared in Example 2 and, in the step corresponding to Example 5, a corresponding compound was used in place of 1-chloro-4-phenylbutane.

Example 12(1)

(2E)-3-(1-(3-carboxypropyl-4-{(E)-2-[4-(4-phenylbutoxy)phenyl]vinyl}-1H-indol-3-yl)acrylic acid

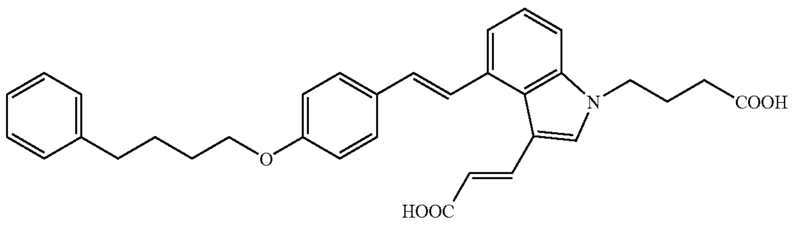

TLC: Rf 0.50 (chloroform:methanol:acetic acid=90:10:1); $^1$H-NMR (DMSO-$d_6$): δ 1.68-1.79 (m, 4H), 2.00 (m, 2H), 2.23 (t, 2H), 2.65 (t, 2H), 4.02 (m, 2H), 4.23 (t, 2H), 6.22 (d, 1H), 6.94 (d, 2H), 7.07 (d, 1H), 7.17-7.35 (m, 7H), 7.46-7.64 (m, 4H), 8.10 (s, 1H), 8.13 (d, 1H) 12.00 (bs, 2H).

Example 12(2)

(2E)-3-(1-(3-carboxypropyl-4-{(E)-2-[4-(3-phenylpropoxy)phenyl]vinyl}-1H-indol-3-yl)acrylic acid TLC: Rf 0.52 (chloroform:methanol:acetic acid=90:10:1); $^1$H-NMR (DMSO-$d_6$): δ 1.95-2.08 (m, 4H), 2.23 (t, 2H), 2.75 (t, 2H), 4.00 (t, 2H), 4.23 (t, 2H), 6.22 (d, 1H), 6.95 (d, 2H), 7.07 (d, 1H), 7.16-7.35 (m, 7H), 7.48 (d, 1H), 7.54 (d, 2H), 7.62 (d, 1H), 8.10 (s, 1H), 8.14 (d, 1H), 12.03 (bs, 2H).

Example 12(3)

(2E)-3-(1-(3-carboxypropyl)-4-{(E)-2-[4-(2-phenylethoxy)phenyl]vinyl}-1H-indol-3-yl)acrylic acid TLC: Rf 0.51 (chloroform:methanol:acetic acid=90:10:91); $^1$H-NMR (DMSO-$d_6$): δ 2.00 (quint, 2H), 2.23 (t, 2H), 3.05 (t, 2H), 4.22 (t, 4H), 6.22 (d, 1H), 6.96 (d, 2H), 7.06 (d, 1H), 7.14-7.43 (m, 7H), 7.48 (d, 1H), 7.54 (d, 2H), 7.62 (d, 1H), 8.10 (s, 1H), 8.13 (d, 1H), 12.02 (brs, 2H).

Example 13

1-(3-carboxypropyl)-4-{2-[4-(4-phenoxybutoxy) phenyl]ethyl}-1H-indole-3-carboxylic acid

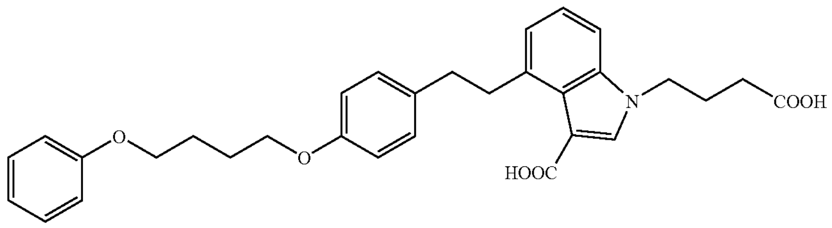

The compound (45 mg) prepared in Example 6(3) and 10% palladium-carbon (50% wet, 10 mg) were added to a methanol (1.0 mL)-tetrahydrofuran (1.0 mL) solution and the mixture was stirred under a hydrogen atmosphere at room temperature for 3 hours. The reaction mixture was filtered and then concentrated to obtain the titled compound having the following physical properties (34 mg).

TLC: Rf 0.37 (chloroform:methanol:acetic acid=90:10:1); $^1$H-NMR (DMSO-$d_6$): δ 1.83-1.88 (m, 4H), 1.92-2.02 (m, 2H), 2.20 (t, 2H), 2.70-2.76 (m, 2H), 3.44-3.50 (m, 2H), 3.94-4.04 (m, 4H), 4.23 (t, 2H), 6.82 (d, 2H), 6.87-6.94 (m, 3H), 6.99 (d, 1H), 7.15 (t, 1H), 7.20-7.30 (m, 4H), 7.42 (d, 1H), 8.08 (s, 1H), 12.01 (bs, 2H).

Example 13(1) to Example 13(19)

Using the compound prepared in Example 6(7), 6(8), 6(5), 8, 8(1), 12(1), 8(6), 8(7), 8(8), 8(30), 8(19), 8(34), 8(43), 8(15), 8(23), 8(28), 8(33), 8(37) or 8(29) in place of the compound prepared in Example 6(3), the same operation as in Example 13 was conducted to obtain the titled compound having the following physical properties.

Example 13(1)

1-(3-carboxypropyl)-4-{2-[4-(3-phenylpropoxy)phenyl]ethyl}-1H-indole-3-carboxylic acid TLC: Rf 0.37 (dichloromethane:methanol=9:1); $^1$H-NMR (DMSO-$d_6$): δ 1.85-2.10 (m, 4H), 2.21 (t, 2H), 2.62-2.83 (m, 4H), 3.38-3.57 (m, 2H), 3.92 (t, 2H), 4.24 (t, 2H), 6.81 (d, 2H), 6.99 (d, 1H), 7.07-7.37 (m, 8H), 7.42 (d, 1H), 8.09 (s, 1H).

Example 13(2)

1-(3-carboxypropyl)-4-(2-{4-[(5-phenylpentyl)oxy] phenyl}ethyl-1H-indole-3-carboxylic acid TLC: Rf 0.39 (dichloromethane:methanol=9:1); $^1$H-NMR (DMSO-$d_6$): δ 1.31-1.51 (m, 2H), 1.51-1.82 (m, 4H), 1.88-2.09 (m, 2H), 2.19 (t, 2H), 2.59 (t, 2H), 2.65-2.80 (m, 2H), 3.38-3.55 (m, 2H), 3.90 (t, 2H), 4.23 (t, 2H), 6.79 (d, 2H), 6.99 (d, 1H), 7.07-7.35 (m, 8H), 7.42 (d, 1H), 8.08 (s, 1H).

Example 13(3)

1-(3-carboxypropyl)-4-{2-[4-(2,3-dihydro-1H-inden-2-ylmethoxy)phenyl]ethyl}-1H-indole-3-carboxylic acid TLC: Rf 0.46 (chloroform:methanol:acetic acid=90:10:1); $^1$H-NMR (DMSO-$d_6$): δ 1.93-2.02 (m, 2H), 2.21 (t 2H), 2.70-2.92 (m, 5H), 3.03-3.11 (m, 2H), 3.41-3.52 (m, 2H), 3.93 (d, 2H), 4.24 (t, 2H), 6.84 (d, 2H), 6.99 (d, 1H), 7.10-7.23 (m, 7H), 7.41 (d, 1H), 8.08 (s, 1H), 11.93 (bs, 2H).

Example 13(4)

4-(3-carboxymethyl)-4-{2-[4-(4-phenylbutoxy)phenyl]ethyl}-1H-indol-1-yl)butanoic acid TLC: Rf 0.39 (dichloromethane:methanol=9:1); $^1$H-NMR (DMSO-$d_6$): δ 1.61-1.79 (m, 4H), 1.81-2.02 (m, 2H), 2.19 (t 2H), 2.55-2.68 (m, 2H), 2.74-2.86 (m, 2H), 3.02-3.16 (m, 2H), 3.78 (s, 2H), 3.87-4.00 (m, 2H), 4.12 (t 2H), 6.78-6.85 (m, 3H), 7.03 (t, 1H), 7.10-7.37 (m, 9H).

Example 13(5)

4-(3-(carboxymethyl)-4-{2-[4-(4-phenoxybutoxy) phenyl]ethyl}-1H-indol-1-yl)butanoic acid TLC: Rf 0.37 (dichloromethane:methanol=9:1); $^1$H-NMR (DMSO-$d_6$): δ 1.75-2.03 (m, 6H), 2.19 (t, 2H), 2.74-2.85 (m, 2H), 3.04-3.15 (m, 2H), 3.78 (s, 2H), 3.95-4.06 (m, 4H), 4.11 (t, 2H), 6.77-6.96 (m, 6H), 7.03 (t, 1H), 7.11-7.34 (m, 6H).

Example 13(6)

4-(3-(2-carboxyethyl)-4-{2-[4-(4-phenylbutoxy)phenyl]ethyl}-1H-indol-1-yl)butanoic acid TLC: Rf 0.47 (chloroform:methanol:acetic acid=90:10:1); $^1$H-NMR (DMSO-$d_6$): δ 1.68-1.73 (m, 4H) 1.89 (m, 2H), 2.12 (t 2H), 2.56-2.65 (m, 4H), 2.79-2.85 (m, 2H), 3.11-3.16 (m, 4H), 3.92-3.96 (m, 2H), 4.08 (t, 2H), 6.80-6.84 (m, 3H), 7.00 (t, 1H), 7.07 (s, 1H), 7.16-7.30 (m, 8H).

Example 13(7)

4-(3-carboxymethyl-4-{2-[4-(3-phenylpropoxy)phenyl]ethyl}-1H-indol-1-yl)butanoic acid TLC: Rf 0.31 (dichloromethane:methanol=9:1); $^1$H-NMR (DMSO-$d_6$): δ 1.86-2.06 (m, 4H), 2.19 (t, 2H), 2.66-2.87 (m, 4H), 3.04-3.16 (m, 2H), 3.78 (s, 2H), 3.92 (t, 2H), 4.12 (t, 2H), 6.78-6.89 (m, 3H), 7.03 (t, 1H), 7.11-7.35 (m, 9H).

Example 13(8)

4-(3-carboxymethyl)-4-{2-[4-(3-phenoxypropoxy)phenyl]ethyl}-1H-indol-1-yl)butanoic acid TLC: Rf 0.32 (dichloromethane:methanol=9:1); $^1$H-NMR (DMSO-$d_6$): δ 1.85-2.00 (m, 2H), 2.08-2.24 (m, 4H), 2.74-2.85 (m, 2H), 3.03-3.15 (m, 2H), 3.78 (s, 2H), 4.03-4.19 (m, 6H), 6.78-6.98 (m, 6H), 6.98-7.08 (m, 1H), 7.11-7.34 (m, 6H), 12.21 (s, 2H).

Example 13(9)

4-[3-(carboxymethyl)-4-(2-{4-[2-(5-methyl-2-phenyl-1,3-oxazol ethoxy]phenyl}ethyl)-1H-indol-1-yl]butanoic acid TLC: Rf 0.26 (dichloromethane:methanol:acetic acid=95:4:1); $^1$H-NMR (DMSO-$d_6$): δ 1.85-2.00 (m, 2H), 2.19 (t, 2H), 2.36 (s, 3H), 2.74-2.85 (m, 2H), 2.91 (t 2H), 3.04-3.15 (m, 2H), 3.78 (s, 2H), 4.12 (t 2H), 4.18 (t, 2H), 6.82 (d, 1H), 6.85 (d, 2H), 7.02 (dd, 1H), 7.18 (d, 2H), 7.20 (s, 1H), 7.27 (d, 1H), 7.44-7.54 (m, 3H), 7.86-7.97 (m, 2H), 12.19 (s, 2H).

Example 13(10)

2,2'-[4-(2-{4-[(5-phenylpentyl)oxy]phenyl}ethyl)-1H-indol-1,3-diyl]diacetic acid TLC: Rf 0.32 (dichloromethane:methanol:acetic acid=9:1:0.05); $^1$H-NMR (DMSO-$d_6$): δ 1.35-1.48 (m, 2H), 1.55-1.79 (m, 4H), 2.59 (t, 2H), 2.75-2.85 (m, 2H), 3.04-3.16 (m, 2H), 3.80 (s, 2H), 3.91 (t, 2H), 4.93 (s, 2H), 6.78-6.87 (m, 3H), 7.01 (dd, 1H), 7.11-7.31 (m, 9H), 12.46 (s, 2H).

Example 13(11)

4-[3-carboxymethyl)-4-(2-{4-[4-(2-methylphenoxy)butoxy]phenyl}ethyl)-1H-indol-1-yl]butanoic acid TLC: Rf 0.60 (dichloromethane:methanol:acetic acid=90:10:0.5); $^1$H-NMR (DMSO-$d_6$): δ 1.72-2.05 (m, 6H), 2.05-2.33 (m, 5H), 2.68-2.92 (m, 2H), 2.96-3.20 (m, 2H), 3.79 (s, 2H), 3.89-4.24 (m, 6H) 6.66-6.97 (m, 5H), 6.96-7.43 (m, 7H), 12.19 (brs, 2H).

Example 13(12)

2,2'-[4-(2-{4-[(6-phenylhexyl)oxy]phenyl}ethyl)-1H-indol-1,3-diyl]diacetic acid

TLC: Rf 0.51 (dichloromethane:methanol:acetic acid=90:10:1); $^1$H-NMR (DMSO-$d_6$): δ 1.19-1.79 (m, 8H), 2.53-2.61 (m, 2H), 2.74-2.90 (m, 2H), 3.01-3.20 (m, 2H), 3.79 (s, 2H), 3.91 (t, 2H), 4.91 (s, 2H), 6.76-6.88 (m, 3H), 6.96-7.05 (m, 1H), 7.08-7.33 (m, 9H).

Example 13(13)

2,2'-[4-(2-{4-[4-(2,6-dichlorophenoxy)butoxy]-phenyl}ethyl-1H-indol-1,3-diyl]diacetic acid TLC: Rf 0.47 (dichloromethane:methanol:acetic acid=90:10:1); $^1$H-NMR (DMSO-$d_6$): δ 1.77-2.01 (m, 4H), 2.73-2.87 (m, 2H), 3.05-3.19 (m, 2H), 3.80 (s, 2H), 3.93-4.16 (m, 4H), 4.89 (s, 2H), 6.78-6.90 (m, 3H), 6.96-7.09 (m, 1H), 7.10-7.26 (m, 5H), 7.49 (d, 2H).

Example 13(14)

4-(3-carboxymethyl)-4-{2-[4-(3-cyclohexylpropoxy)phenyl]ethyl}-1H-indol-1-yl)butanoic acid TLC: Rf 0.48 (dichloromethane:methanol=9:1); $^1$H-NMR (DMSO-$d_6$): δ 0.77-0.98 (m, 2H), 1.07-1.38 (m, 6H), 1.54-1.79 (m, 7H), 1.85-2.00 (m, 2H), 2.19 (t, 2H), 2.74-2.85 (m, 2H), 3.03-3.15 (m, 2H), 3.78 (s, 2H), 3.89 (t, 2H), 4.12 (t, 2H), 6.78-6.87 (m, 3H), 7.03 (t, 1H), 7.10-7.33 (m, 4H), 1221 (s, 2H).

Example 13(15)

4-[3-carboxymethyl)-4-(2-{4-[4-(4-methoxyphenyl)butoxy]phenyl}ethyl)-1H-indol-1-yl]butanoic acid TLC: Rf 0.48 (dichloromethane:methanol=9:1); $^1$H-NMR (DMSO-$d_6$): δ 1.58-1.77 (m, 4H), 1.86-2.00 (m, 2H), 2.19 (t, 2H), 2.52-2.62 (m, 2H), 2.74-2.85 (m, 2H), 3.04-3.15 (m, 2H) 3.70 (s, 3H), 3.78 (s, 2H), 3.87-3.99 (m, 2H), 4.12 (t, 2H), 6.76-6.89 (m, 5H), 7.03 (dd, 1H), 7.07-7.23 (m, 5H), 7.28 (d, 1H), 12.21 (s, 2H).

Example 13(16)

2,2'-(4-{2-[4-(4-phenoxybutoxy)phenyl]ethyl}-1H-indol-1,3-diyl)diacetic acid

TLC 0.50 (dichloromethane:methanol:acetic acid=18:1:1); $^1$H-NMR (DMSO-$d_6$): δ 1.80-1.91 (m, 4H), 2.75-2.86 (m, 2H), 3.05-3.17 (m, 2H), 3.80 (s, 2H), 3.95-4.07 (m, 4H), 4.93 (s, 2H), 6.80-6.90 (m, 3H), 6.89-6.97 (m, 3H), 7.02 (dd, 1H), 7.11-7.32 (m, 6H), 12.27 (s, 1H), 12.87 (s, 1H).

Example 13(17)

2,2'-(4-{2-[4-(2,3-dihydro-1H-inden-2-ylmethoxy)phenyl]ethyl}-1H-indol-1,3-diyl)diacetic acid TLC: Rf 0.26 (dichloromethane:methanol:acetic acid=90:10:1); $^1$H-NMR (DMSO-$d_6$): δ 2.69-2.96 (m, 5H), 2.99-3.16 (m, 4H), 3.78 (s, 2H), 3.94 (d, 2H), 4.77 (s, 2H), 6.76-6.92 (m, 3H), 6.99 (t, 1H), 7.05-7.28 (m, 8H).

Example 13(18)

4-[3-(carboxymethyl)-4-(2-{4-[4-(2,6-dimethylphenoxy)butoxy]phenyl}ethyl)-1H-indol-1-yl]butanoic acid TLC: Rf 0.54 (dichloromethane: methanol:acetic acid=9:1:0.05); $^1$H-NMR(DMSO-$d_6$): δ 1.81-2.00 (m, 6H), 2.13-2.24 (m, 8H), 2.75-2.85 (m, 2H), 3.03-3.16 (m, 2H), 3.73-3.82 (m, 4H), 4.02 (t, 2H), 4.12 (t, 2H), 6.78-6.92 (m, 4H), 6.96-7.07 (m, 3H), 7.15-7.23 (m, 3H), 7.28 (d, 1H), 12.16 (s, 2H).

Example 13(19)

2,2'-(4-{2-[4-(3-phenoxypropoxy)phenyl]ethyl}-1H-indol-1,3-diyl)diacetic acid

TLC: Rf 0.49 (dichloromethane:methanol:acetic acid=18:1:1); $^1$H-NMR (DMSO-$d_6$): δ 2.08-2.21 (m, 2H), 2.74-2.88 (m, 2H), 3.05-3.17 (m, 2H), 3.79 (s, 2H), 4.04-4.17 (m, 4H), 4.93 (s, 2H), 6.80-6.98 (m, 6H), 6.98-7.06 (m, 1H), 7.13-7.23 (m, 4H), 7.23-7.32 (m, 2H), 12.31 (s, 1H), 12.84 (s, 1H).

Example 14 methyl 4-[4-bromo-3-(3-methoxy-3-oxopropyl)-1H-indol-1-yl]butanoate

To a tetrahydrofuran (6.00 mL) solution of the compound prepared in Example 11 (256 mg), nickel chloride (II) hexahydrate (160 mg) was added at 0° C., followed by stirring for 5 minutes. To the mixture, a methanol (6.00 mL) suspension of sodium borohydride (128 mg) was added at 0° C., followed by stirring for 30 minutes. To the reaction mixture, an aqueous saturated ammonium chloride solution was added, followed by extraction with ethyl acetate. The organic layer was washed with saturated saline, dried and then concentrated. The residue was purified by the column chromatography to obtain the titled compound having the following physical properties (116 mg).

TLC: Rf 0.45 (n-hexane:ethyl acetate=2:1); $^1$H-NMR ($CDCl_3$): δ 2.11 (m, 2H), 2.26 (t, 2H), 2.75 (t, 2H), 3.32 (t, 2H), 3.666 (s, 3H), 3.669 (s, 3H), 4.12 (t, 2H), 6.94 (s, 1H), 7.00 (dd, 1H), 7.23-7.27 (m, 2H).

Example 15

4-(3-(2-carboxyethyl)-4-{(E)-2-[4-(4-phenylbutoxy)phenyl]vinyl}-1H-indol-1-yl)butanoic acid

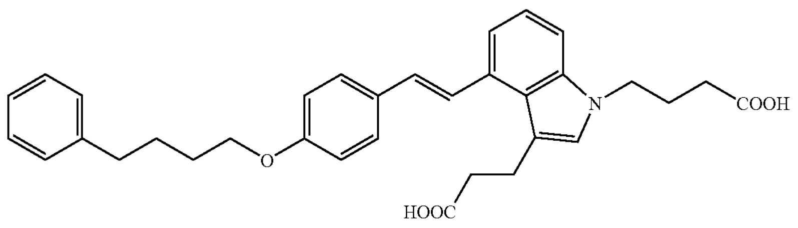

The same operation as in Example 3→Example 4→Example 5→Example 6 was conducted to obtain the titled compound having the following physical properties. In the step corresponding to Example 3 in the operation, the compound prepared in Example 14 was used in place of the compound prepared in Example 2.

TLC: Rf 0.41 (chloroform:methanol:acetic acid=90:10:1); $^1$H-NMR (DMSO-$d_6$): δ 1.68-1.78 (m, 4H), 1.92 (quint, 2H), 2.17 (t, 2H), 2.50-2.68 (m, 4H), 3.16 (t, 2H), 3.97-4.02 (m, 2H), 4.11 (t, 2H), 6.92 (d, 2H), 7.04-7.34 (m, 10H), 7.52 (d, 2H), 7.67 (d, 1H), 12.08 (bs, 2H).

Example 16 ethyl 1-methyl-7-nitro-1H-indole-2-carboxylate

The same operation as in Example 2 was conducted to obtain the titled compound having the following physical properties. Ethyl 7-nitro-1H-indole-2-carboxylate was used in place of the compound prepared in Example 1 and methyl iodide was used in place of methyl 4-bromobutyrate.

TLC: Rf 0.45 (ethyl acetate: n-hexane=1:9); $^1$H-NMR (DMSO-$d_6$): δ 1.43 (t, 3H), 4.00 (s, 3H) 4.41 (q, 2H), 7.19 (dd, 1H), 7.43 (s, 1H), 7.87 (d, 1H), 7.91 (d, 1H).

Example 17 ethyl 3-(4-methoxy-4-oxobutanoyl)-1-methyl-7-nitro-1H-indole-2-carboxylate

To a 1,2-dichloroethane (15 mL) suspension of aluminum chloride (793 mg), methyl 4-chloro-4-oxobutanoate (898 mg) was added dropwise at 0° C. and the mixture was stirred for 5 minutes. To the mixture, the compound prepared in Example 16 (740 mg) was added at 0° C., followed by stirring at 60° C. for 90 minutes. The reaction mixture was cooled, poured into ice water and then extracted with dichloromethane. The organic layer was washed in turn with an aqueous saturated sodium hydrogen carbonate solution and saturated saline, dried and then concentrated. The residue was purified by the column chromatography to obtain the titled compound having the following physical properties (695 mg).

TLC: Rf 0.29 (ethyl acetate: n-hexane=3:7); $^1$H-NMR ($CDCl_3$): δ 1.45 (t, 3H), 2.79 (t, 2H), 3.22 (t, 2H), 3.71 (s, 3H), 3.81 (s, 3H), 4.54 (q, 2H), 7.34 (t, 1H), 7.89 (d, 1H), 8.41 (d, 1H).

Example 18 ethyl 7-amino-3-(4-methoxy-4-oxobutanoyl 1-methyl-1H-indole-2-carboxylate

The same operation as in Example 13 was conducted to obtain the titled compound having the following physical properties. In place of the compound prepared in Example 6(3), the compound prepared in Example 17 was used.

TLC: Rf 0.32 (ethyl acetate: n-hexane=1:1); $^1$H-NMR ($CDCl_3$): δ 1.39 (t, 3H), 2.77 (t, 2H), 3.23 (t, 2H), 3.70 (s, 3H), 3.77 (brs, 2H), 4.16 (s, 3H), 4.47 (q, 2H), 6.61 (d, 1H), 7.04 (dd, 1H), 7.48 (d, 1H).

Example 19 ethyl 3-(4-methoxy-4-oxobutanoyl)-1-methyl-7-{[4-(4-phenylbutoxy)benzoyl]amino}-1H-indole-2-carboxylate To a dichloromethane (3 mL) solution of 4-(4-phenylbutoxy)benzoic acid (68 mg), oxalyl chloride (64 mg) and N,N-dimethylformamide (10 μL) were added at 0° C., followed by stirring at room temperature for one hour. The reaction mixture was concentrated. The residue was added to a dichloromethane (5 mL) solution of the compound prepared in Example 18 (70 mg) and triethylamine (35 mg) at 0° C. and the mixture was stirred at room temperature for 24 hours. To the reaction mixture, water was added, followed by extraction with dichloromethane. The organic layer was washed in turn with water and saturated saline, dried and then concentrated.

The residue was purified by the column chromatography to obtain the titled compound having the following physical properties (72 mg).

TLC: Rf 0.33 (ethyl acetate: n-hexane=4:6); $^1$H-NMR ($CDCl_3$): δ 1.38 (t, 3H), 1.82-1.88 (m, 4H), 2.72 (t, 2H), 2.77 (t, 2H), 3.21 (t, 2H), 3.69 (s, 3H), 3.83 (s, 3H), 4.05 (t, 2H), 4.44 (q, 2H), 6.97 (d, 2H), 7.09-7.33 (m, 7H), 7.87-7.93 (m, 3H), 8.09 (m, 1H).

Example 20

3-(3-carboxypropanoyl)-1-methyl-7-{[4-(4-phenylbutoxy)benzoyl]amino}-1H-indole-2-carboxylic acid

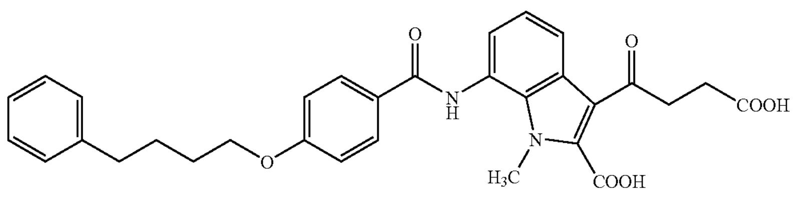

The same operation as in Example 6 was conducted to obtain the titled compound having the following physical properties. In place of the compound prepared in Example 5, the compound prepared in Example 19 was used.

TLC: Rf 0.18 (methanol: dichloromethane:acetic acid=1: 9:0.5); $^1$H-NMR (DMSO-$d_6$): δ 1.66-1.82 (m, 4H), 2.57 (t, 2H), 2.65 (t, 2H), 3.08-3.22 (m, 2H), 3.83 (s, 3H), 3.98-4.19 (m, 2H), 7.06 (d, 2H), 7.13-7.33 (m, 7H), 7.99 (d, 2H), 8.05 (d, 1H), 10.24 (s, 1H), 12.10 (brs, 2H).

Example 20(1)

7-{[4-benzyloxy)benzoyl]amino}-3(3-carboxypropanoyl)-1-methyl-1H-indole-2-carboxylic acid The same operation as in Example 19→Example 20 was conducted to obtain the titled compound having the following physical properties. In the step corresponding to Example 19 in the operation, 4-benzyloxybenzoic acid was used in place of 4-(4-phenylbutoxy)benzoic acid.

TLC: Rf 0.16 (methanol: dichloromethane:acetic acid=1: 9:0.5); $^1$H-NMR (DMSO-$d_6$): δ 2.49-2.61 (m, 2H), 3.17 (t, 2H), 3.77 (s, 3H), 5.21 (s, 2H), 7.07 (d, 1H), 7.12-7.24 (m, 3H), 7.34-7.50 (r, 5H), 8.01 (d, 2H), 8.10 (d, 1H), 10.23 (s, 1H), 12.04 (brs, 2H).

Example 21 methyl 4-bromo-1-methyl-1H-indole-2-carboxylate

The same operation as in Example 2 was conducted to obtain the titled compound having the following physical properties. In place of the compound prepared in Example 1,4-bromo-1H-indole-2-carboxylic acid was used.

TLC: Rf 0.47 (n-hexane:ethyl acetate=2:1); $^1$H-NMR ($CDCl_3$): δ 3.93 (s, 3H), 4.08 (s, 3H), 7.21 (d, 1H), 7.32-7.35 (m, 3H).

Example 22 methyl 4-bromo-3-formyl-1-methyl-1H-indole-2-carboxylate

Phosphorus oxychloride (900 mg) was added dropwise to N,N-dimethylformamide (2 mL) at 0° C., followed by stirring at room temperature for 5 minutes. To the reaction mixture, an N,N-dimethylformamide (3 mL) solution of the compound (484 mg) prepared in Example 21 was added and the mixture was stirred at 90° C. for 16 hours. The reaction mixture was cooled to room temperature, poured into ice water, neutralized with an aqueous saturated sodium carbonate solution and then extracted with ethyl acetate. The organic layer was washed with saturated saline, dried and then concentrated. The residue was purified by the column chromatography to obtain the titled compound having the following physical properties (195 mg).

TLC: Rf 0.56 (n-hexane:ethyl acetate=2:1); $^1$H-NMR ($CDCl_3$): δ 3.86 (s, 3H), 4.04 (s, 3H), 721-7.26 (m, 1H), 7.38-7.41 (m, 1H), 7.53-7.56 (m, 1H), 10.92 (s, 1H).

Example 23

3-[(E)-2-carboxyvinyl]-1-methyl-4-{(E)-2-[4-(4-phenylbutoxy)phenyl]vinyl}-1H-indole-2-carboxylic acid

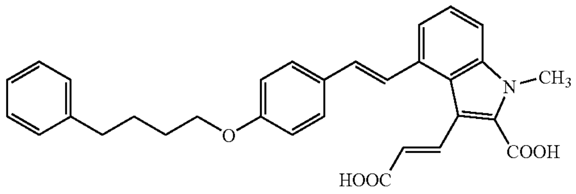

The operation was conducted in the same manner as in Example 10→Example 3→Example 4→Example 5→Example 6 to obtain the titled compound having the following physical properties. In the step corresponding to Example 10 in the operation, the compound prepared in Example 22 was used in place of 4-bromo-H-indole-3-carbaldehyde.

TLC: Rf 0.34 (chloroform:methanol:acetic acid=90:10:1); $^1$H-NMR (DMSO-$d_6$): δ 1.68-1.77 (m, 4H), 2.64 (t, 2H), 3.96

(s, 3H), 4.00 (t, 2H), 6.03 (d, 1H), 6.89 (d, 2H), 7.08 (d, 1H), 7.17-7.31 (m, 5H), 7.35-7.60 (m, 6H) 8.26 (d, 1H), 12.28 (bs, 2H).

Example 24 ethyl 4-(3-cyanomethyl)-4-{(E)-2-[4-(4-phenylbutoxy)phenyl]vinyl}-1H-indol-1-yl)butanoate The same operation as in Example 2→Example 3 was conducted to obtain the titled compound having the following physical properties. In the step corresponding to Example 2 in the operation, 24-bromo-1H-indol-3-yl)acetonitrile was used in place of the compound prepared in Example 1, ethyl 4-bromobutyrate was used in place of methyl 4-bromobutyrate and, in the step corresponding to Example 3, 1-(4-phenylbutoxy)-4-vinylbenzene was used in place of 4-vinylphenyl acetate.

TLC: Rf 0.48 (toluene: ethyl acetate=5:1); $^1$H-NMR ($CDCl_3$): δ 1.25 (t, 3H), 1.71-1.91 (m, 4H), 2.10-2.19 (m, 2H), 2.29 (t, 2H), 2.70 (t, 2H), 3.98-4.03 (m, 4H), 4.10-4.20 (m, 4H), 6.91 (d, 2H) 6.98 (d, 1H), 7.15-7.34 (m, 9H), 7.47 (d, 2H), 7.53 (d, 1H).

Example 25 ethyl 4-[4-{(E)-2-[4-(4-phenylbutoxy)phenyl]vinyl}-3-(1H-tetrazol-5-ylmethyl)-1H-indol-1-yl]butanoate To a toluene (2 mL) solution of the compound (150 mg) prepared in Example 24, trimethyl silylazide (100 mg) and di-n-butyltin oxide (14 mg) were added, followed by stirring at 110° C. for 8.5 hours. An aqueous saturated sodium hydrogen carbonate solution was poured into the reaction, followed by extraction with ethyl acetate. The organic layer was washed in turn with water, an aqueous saturated ammonium chloride solution and saturated saline, dried and then concentrated. The residue was purified by the column chromatography to obtain the titled compound having the following physical properties (113 mg).

TLC: Rf 0.47 (dichloromethane:methanol=90:10); $^1$H-NMR ($CDCl_3$): δ 0.78 (t, 3H), 1.71-1.96 (m, 4H), 2.25-2.43 (m, 4H), 2.62-2.75 (m, 2H), 3.09 (q, 2H), 4.00 (t, 2H), 4.24 (t, 2H), 4.61 (s, 2H), 6.84-6.91 (m, 3H), 7.06-7.12 (m, 2H), 7.15-7.32 (m, 8H), 7.38 (d, 2H).

Example 26

4-[4-{(E)-2-[4-(4-phenylbutoxy)phenyl]vinyl}-3-1H-tetrazol-5-ylmethyl)-1H-indol-1-yl]butanoic acid The same operation as in Example 6 was conducted to obtain the titled compound having the following physical properties. In place of the compound prepared in Example 5, the compound prepared in Example 25 was used.

TLC: Rf 0.53 (dichloromethane:methanol:acetic acid=90:10:1); $^1$H-NMR (DMSO-$d_6$): δ 1.60-1.80 (m, 4H), 1.86-2.05 (m, 2H), 2.24 (t, 2H), 2.58-2.69 (m, 2H), 3.93-4.06 (m, 2H), 4.15 (t, 2H), 4.56 (s, 2H), 6.91 (d, 2H), 6.99 (d, 1H), 7.08-7.57 (m, 12H).

Example 26(1)

4-[4-{2-[4-(4-phenylbutoxy)phenyl]ethyl}-3-(1H-tetrazol-5-ylmethyl)-1H-indol-1-yl]butanoic acid

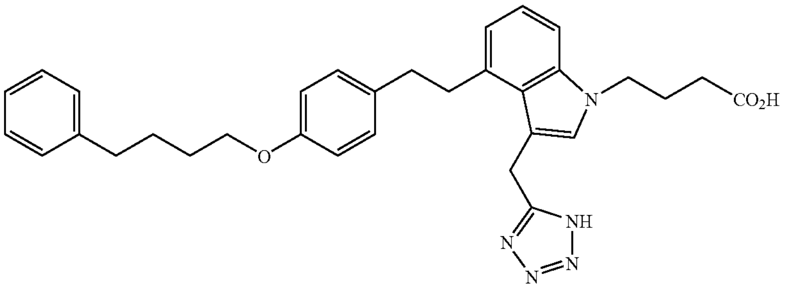

The same operation as in Example 13 was conducted to obtain the titled compound having the following physical properties. In place of the compound prepared in Example 6(3), the compound prepared in Example 26 was used.

TLC: Rf 0.52 (dichloromethane:methanol:acetic acid=90:10:0.5); $^1$H-NMR (DMSO-$d_6$): δ 1.53-1.80 (m, 4H), 1.81-2.05 (m, 2H), 2.11-2.30 (m, 2H), 2.55-2.85 (m, 4H), 2.94-3.11 (m, 2H), 3.82-4.01 (m, 2H), 4.12 (t, 2H), 4.51 (s, 2H), 6.65-6.92 (m, 3H), 6.95-7.41 (m, 10H).

Example 27 ethyl 3-(4-methoxy-4-methoxy-4-oxobutyl-1H-indole-2-carboxylate

To a trifluoroacetic acid (2 mL) solution of ethyl 3-(4-methoxy-4-oxobutanoyl)-1H-indole-2-carboxylate (200 mg), triethylsilyl hydride (306 mg) was added at room temperature and the mixture was stirred at room temperature for 3 hours. The reaction mixture was concentrated. To the residue, water was added, followed by extraction with ethyl acetate. The organic layer was washed in turn with water and saturated saline, dried and then concentrated to obtain the titled compound having the following physical properties.

TLC: Rf 0.29 (ethyl acetate: n-hexane=3:7); $^1$H-NMR ($CDCl_3$): δ 1.44 (t, 3H), 1.99-2.09 (m, 2H), 2.38 (t, 2H), 3.17 (t, 2H), 3.65 (s, 3H), 4.42 (q, 2H), 7.14 (dd, 1H), 7.31 (d, 1H) 7.37 (dd, 1H) 7.69 (d, 1H), 8.73 (brs, 1H).

Example 28

3-(3-carboxypropyl)-1-(3-phenylpropyl)-1H-indole-2-carboxylic acid

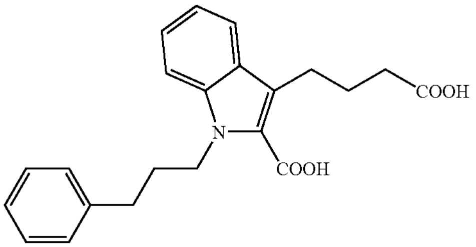

The same operation as in Example 2→Example 6 was conducted to obtain the titled compound having the following physical properties. In the step corresponding to Example 2 in the operation, the compound prepared in Example 27 was used in place of the compound prepared in Example 1 and (3-bromopropyl)benzene was used in place of methyl 4-bromobutyrate.

TLC: Rf 0.54 (dichloromethane:methanol=9:1); $^1$H-NMR (DMSO-$d_6$): δ 1.73-1.88 (m, 2H), 1.89-2.03 (m, 2H), 2.20 (t, 2H), 2.56 (t, 2H), 3.04 (t, 2H), 4.52 (t, 2H), 7.04-7.20 (m, 4H), 7.21-7.34 (m, 3H), 7.42 (d, 1H), 7.68 (d, 1H), 12.45 (brs, 2H).

Example 29 methyl 4-[4-{(E)-2-[4-(4-{[tert-butyl(dimethyl)silyl]oxy}butoxy) phenyl]vinyl}-3-(2-methoxy-2-oxoethyl)-1H-indol-1-yl]butanoate The same operation as in Example 5 was conducted to obtain the titled compound having the following physical properties. Methyl 4-[4-[(E)-2-(4-hydroxyphenyl)vinyl]-3-(2-methoxy-2-oxoethyl)-1H-indol-1-yl]butanoate was used in place of the compound prepared in Example 4 and tert-butyl(4-iodobutoxy)dimethylsilane (obtained by conducting the same operation as in Example 2→Example 3→Example 4 using the compound prepared in Example 7) was used in place of 1-chloro-4-phenylbutane.

TLC: Rf 0.47 (n-hexane:ethyl acetate=2:1); $^1$H-NMR ($CDCl_3$): δ-0.07 (s, 6H), 0.84 (s, 9H), 1.55-1.69 (m, 2H), 1.72-1.87 (m, 2H), 2.02-2.15 (m, 2H), 2.25 (t, 2H), 3.56 (s, 3H), 3.59-3.61 (m, 3H), 3.61-3.67 (m, 2H), 3.88 (s, 2H), 3.95 (t, 2H), 4.08 (q, 2H), 6.84 (d, 2H), 6.90 (d, 1H), 6.98 (s, 1H), 7.07-7.17 (m, 2H), 7.25 (dd, 1H), 7.38-7.46 (m, 2H), 7.60 (d, 1H).

Example 30 methyl 4-[4-{(E)-2-[4-(4-hydroxybutoxy)phenyl]vinyl}-3-(2-methoxy-2-oxoethyl)-1H-indol-1-yl]butanoate To a tetrahydrofuran (8 mL) solution of the compound (1.4 g) prepared in Example 29, tetrabutylammonium fluoride (1M tetrahydrofuran solution; 3.1 mL) was added under ice cooling, followed by stirring at room temperature for 1.5 hours. The reaction mixture was poured into water and then extracted with ethyl acetate. The organic layer was washed in turn with water and saturated saline, dried and then concentrated. The residue was purified by the column chromatography to obtain the titled compound having the following physical properties (1.0 g).

TLC: Rf 0.31 (n-hexane:ethyl acetate=1:2); $^1$H-NMR ($CDCl_3$): δ 1.74-1.82 (m, 2H), 1.87-1.93 (m, 2H), 2.13-2.20 (m, 2H), 2.32 (t, 2H), 3.63 (s, 3H), 3.67 (s, 3H), 3.75 (t, 2H), 3.95 (s, 2H), 4.05 (t, 2H), 4.16 (t, 2H), 6.90-6.93 (m, 2H), 6.97 (d, 1H), 7.05 (s, 1H), 7.17-7.33 (m, 3H), 7.48-7.51 (m, 2H), 7.68 (d, 1H).

Example 31

4-(3-carboxymethyl-4-{(E)-2-[4-(4-hydroxybutoxy)phenyl]vinyl}-1H-indol-1-yl)butanoic acid

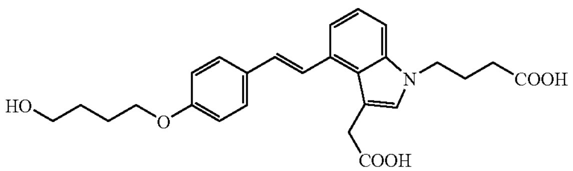

The same operation as in Example 6 was conducted to obtain the titled compound having the following physical properties. In place of the compound prepared in Example 5, the compound prepared in Example 30 was used.

TLC: Rf 0.33 (dichloromethane:methanol:acetic acid=9:1:0.05); $^1$H-NMR (DMSO-$d_6$): δ 1.49-1.62 (m, 2H), 1.68-1.81 (m, 2H), 1.89-2.00 (m, 2H), 2.20 (t, 2H), 3.39-3.50 (m, 2H), 3.83 (s, 2H), 3.99 (t, 2H), 4.14 (t, 2H), 4.44 (t, 1H), 6.92 (d, 2H), 7.06 (d, 1H), 7.13 (dd, 1H), 7.26 (s, 1H), 7.32 (d, 1H), 7.36 (d, 1H), 7.52 (d, 2H), 7.62 (d, 1H), 12.24 (s, 2H).

Example 32

Allyl 4-(3-[2-allyloxy)-2-oxoethyl]-4-{(E)-2-[4-(4-phenylbutoxy)phenyl]vinyl}-1H-indol-1-yl)-4-oxobutanoate Using allyl 4-bromo-1H-indole-3-acetate in place of the compound prepared in Example 1 and 1×4-phenylbutoxy)-4-vinylbenzene in place of 4-vinylphenyl acetate, the same operation as in Example 3 was conducted to obtain allyl 4-(3-[2-allyloxy-2-oxoethyl]-4-{(E)-2-[4-(4-phenylbutoxy)phenyl]vinyl}-1H-indol-1-yl)-4-oxobutanoate. Subsequently, to an ethyl acetate (0.5 mL)-acetonitrile (0.5 mL) solution of this compound (200 mg), triethylamine (0.18 mL), 4-dimethylaminopyridine (8 mg) and allyl 4-chloro-4-oxobutanoate (38 mg) were sequentially added, followed by stirring at 40° C. for 5 hours. To the reaction mixture, water was added, followed by extraction with ethyl acetate. The organic layer was washed in turn with water and saturated saline, dried and then concentrated. The residue was purified by the column chromatography to obtain the titled compound having the following physical properties (100 mg).

TLC: Rf 0.68 (toluene: ethyl acetate=4:1); $^1$H-NMR ($CDCl_3$): δ 1.71-1.91 (m, 4H), 2.70 (t, 2H), 2.87 (t, 2H), 3.26 (t, 2H), 3.94 (s, 2H), 4.00 (t, 2H), 4.54-4.58 (m, 2H), 4.63-4.66 (m, 2H), 5.17-5.38 (m, 4H), 5.78-6.01 (m, 2H), 6.89 (d, 2H), 6.95 (d, 1H), 7.16-7.36 (m, 6H), 7.44-7.55 (m, 5H), 8.40 (d, 1H).

Example 33

4-(3-carboxymethyl)-4-{(E)-2-[4-(4-phenylbutoxy)phenyl]vinyl}-1H-indol-1-yl)-4-oxobutanoic acid

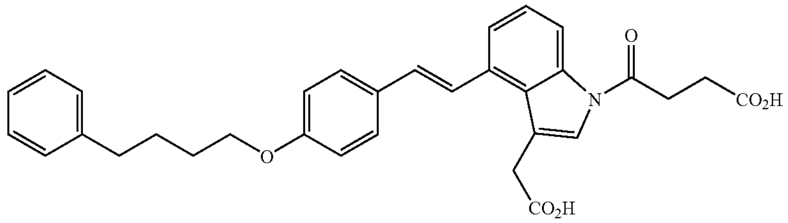

To a tetrahydrofuran (1.5 mL) solution of the compound (100 mg) prepared in Example 32, morpholine (14 μL) and tetrakistriphenylphosphine palladium (19 mg) were sequentially added and the mixture was stirred at room temperature for one hour. To the reaction mixture, 1M hydrochloric acid (0.17 mL) and water were added, followed by extraction with ethyl acetate. The organic layer was washed in turn with water and saturated sale, dried and then concentrated. The residue was purified by the column chromatography to obtain the titled compound having the following physical properties (4 mg).

TLC: Rf 0.48 (methylene chloride:methanol:acetic acid=90:10:0.5); $^1$H-NMR (DMSO-$d_6$): δ 1.54-1.80 (m, 4H), 2.56-2.71 (m, 4H), 3.21 (t, 2H), 3.91 (s, 2H), 3.96-4.09 (m, 2H), 6.93 (d, 2H), 7.01-7.40 (m, 7H), 7.44-7.66 (m, 4H), 7.81-7.99 (s, 1H), 8.29 (d, 1H), 12.42 (brs, 2H).

Example 34

4-{3-carboxymethyl)-4-[2-(4-{4-[2-(1-hydroxyethyl)phenoxy]butoxy}phenyl)ethyl]-1H-indol-1-yl}butanoic acid

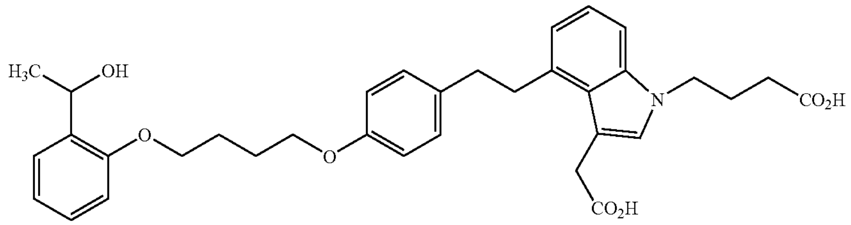

A methanol (1.0 mL)-tetrahydrofuran (1.0 mL) solution of the compound (55 mg) prepared in Example 8(20) and 10% palladium-carbon (50% wet, 10 mg) was stirred under a hydrogen atmosphere at room temperature for 2 hours. The reaction mixture was filtered and then the filtrate was concentrated. The residue was dissolved in a methanol (1.0 mL)-dichloromethane (1.0 mL) solution and sodium tetrahydroborate (28 mg) was added, and then the mixture was stirred at room temperature for 3 hours. To the reaction mixture, an aqueous saturated ammonium chloride solution was added, followed by extraction with ethyl acetate. The organic layer was washed in turn with water and saturated saline, dried and then concentrated. The residue was purified by the column chromatography to obtain the titled compound having the following physical properties (15 mg).

TLC: Rf 0.30 (dichloromethane:methanol=9:1); $^1$H-NMR (DMSO-$d_6$): δ 1.25 (d, 3H), 1.63-2.04 (m, 6H), 2.20 (t, 2H), 2.72-2.88 (m, 2H), 3.01-3.20 (m, 2H), 3.79 (s, 2H), 3.87-4.23 (m, 6H), 4.73-5.16 (m, 2H), 6.77-6.97 (m, 5H), 6.98-7.08 (m, 1H), 7.09-7.24 (m, 4H), 7.28 (d, 1H), 7.42 (dd, 1H) 12.19 (brs, 2H).

Example 35

4-(3-carboxymethyl)-4-{2-[4-(4-hydroxybutoxy)phenyl]ethyl}-1H-indol-1-yl)butanoic acid

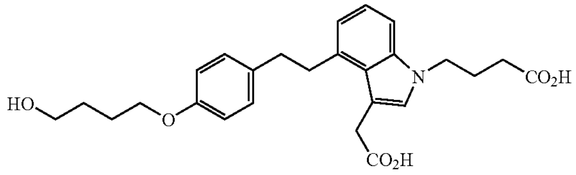

The same operation as in Example 13 was conducted to obtain the titled compound having the following physical properties. In place of the compound prepared in Example 6(3), the compound prepared in Example 31 was used.

TLC: Rf 0.30 (dichloromethane:methanol:acetic acid=90:10:1); $^1$H-NMR (DMSO-$d_6$): δ 1.47-1.61 (m, 2H), 1.64-1.79 (m, 2H), 1.86-2.03 (m, 2H), 2.19 (t, 2H), 2.73-2.87 (m, 2H), 3.02-3.16 (m, 2H), 3.44 (t, 2H), 3.78 (s, 2, 3.93 (t, 2H), 4.12 (t, 2H), 6.78-6.88 (m, 3H), 7.03 (t, 1H), 7.10-7.23 (m, 3H), 7.28 (d, 1H).

Example 36

4-(3-carboxymethyl)-4-{[4-(4-phenylbutoxy)benzyl]oxy}-1H-indol-1-yl)butanoic acid

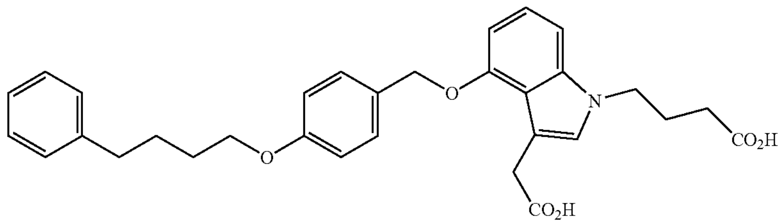

The same operation as in Example 6→Example 7→Example 2→Example 13→Example 5→Example 6 was conducted to obtain the titled compound having the following physical properties. In the step corresponding to Example 6 in the operation, 2-[4-benzyloxy)-1H-indol-3-yl]acetonitrile was used in place of the compound prepared in Example 5, a methanol-dioxane (volume ratio: 5:2) solution of 40% sodium hydroxide was used in place of an aqueous 2M sodium hydroxide solution and, in the step corresponding to Example 5, 1-(chloromethyl)-4-(4-phenylbutoxy)benzene was used in place of 1-chloro-4-phenylbutane.

TLC: Rf 0.42 (dichloromethane:methanol=9:1); $^1$H-NMR (DMSO-$d_6$): δ 1.59-1.81 (m, 4H) 1.82-1.99 (m, 2H), 2.17 (t, 2H), 2.50-2.69 (m, 2H), 3.73 (s, 2H), 3.97 (t, 2H), 4.08 (t, 2H), 5.05 (s, 2H), 6.49-6.54 (m, 1H), 6.86-7.08 (m, 4H), 7.11-7.31 (m, 6H), 7.38 (d, 2H), 12.07 (brs, 2H).

Example 37 ethyl 7-bromo-3-[4-(ethyloxy)-4-oxobutanoyl]-1-methyl-1H-indole-2-carboxylate

To an N,N-dimethylformamide (3 mL) solution of ethyl 7-bromo-3-[4-ethyloxy)-4-oxobutanoyl]-1H-indole-2-carboxylate (310 mg), cesium carbonate (510 mg) and methyl iodide (111 mg) were added and the mixture was stirred at room temperature for 2 hours. Water was poured into the reaction mixture, followed by extraction with n-hexane/ethyl acetate (1/1). The organic layer was washed in turn with water and saturated saline, dried with anhydrous sodium sulfate and then concentrated to obtain the titled compound having the following physical properties (301 mg).

TLC: Rf 0.49 (n-hexane:ethyl acetate 1:1); $^1$H-NMR ($CDCl_3$): δ 1.25 (t, 3H), 1.43 (t, 3H), 2.75 (t, 2H), 3.20 (t, 2H), 4.15 (q, 2H), 4.21 (s, 3H), 4.50 (q, 2H), 7.09 (t, 1H), 7.50 (dt, 1H), 8.05 (d, 1H).

Example 38

3-(3-carboxypropanoyl)-1-methyl-7-{(E)-2-[4-(4-phenoxybutoxy) phenyl]vinyl}-1H-indole-2-carboxylic acid

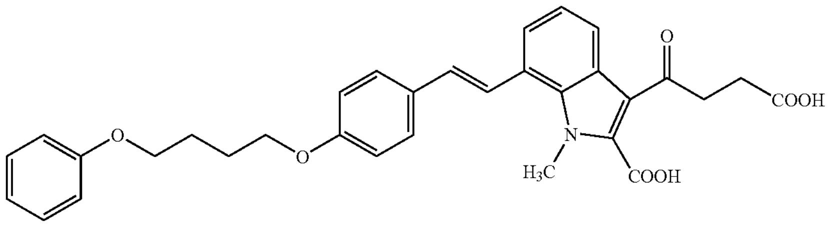

The same operation as in Example 3→Example 6 was conducted to obtain the titled compound having the following physical properties. In the step corresponding to Example 3, the compound prepared in Example 37 was used in place of the compound prepared in Example 2 and 1-ethenyl-4-{[4-phenyloxy)butyl]oxy}benzene was used in place of 4-vinylphenyl acetate.

TLC: Rf 0.43 (dichlorometaane:methanol:acetic acid=85:15:1); $^1$H-NMR (DMSO-$d_6$): δ 1.82-1.93 (m, 4H), 2.56 (t, 2H), 3.14 (t, 2H), 3.97-4.12 (m, 7H), 6.86-7.02 (m, 6H), 7.20-7.32 (m, 3H), 7.42 (d, 1H), 7.59 (d, 2H), 7.86 (d, 1H), 8.03 (d, 1H), 12.10 (s, 1H), 14.50 (s, 1H).

Example 39(1) to Example 39(3)

The same operation as in Example 13 was conducted to obtain the titled compound having the following physical properties. In place of the compound prepared in Example 6(3), the compound prepared in Example 8(46), 8(47) or 8(50) was used.

Example 39(1)

2,2'-[4-(2-{4-[4-(3-methylphenoxy)butoxy] phenyl}ethyl)-1H-indol-1,3-diyl]diacetic acid

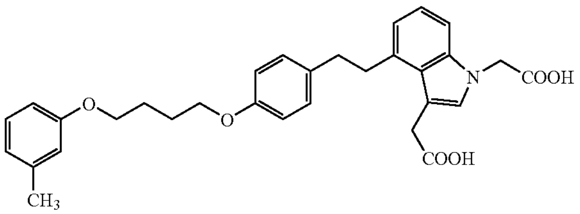

TLC: Rf 0.48 (dichloromethane:methanol:acetic acid=18:1:1); $^1H$-NMR (DMSO-$d_6$): δ 1.79-1.90 (m, 4H), 2.26 (s, 3H), 2.75-2.87 (m, 2H), 3.05-3.17 (m, 2H), 3.80 (s, 2H), 3.93-4.05 (m, 4H), 4.94 (s, 2H), 6.66-6.79 (m, 3H), 6.81-6.90 (m, 3H), 7.02 (dd, 1H), 7.07-7.25 (m, 5H), 12.27 (m, 5H), 12.89 (s, 1H).

Example 39(2)

2,2'-[4-(2-{4-[4-(4-methylphenoxy)butoxy] phenyl}ethyl)-1H-indol-1,3-diyl]diacetic acid TLC: Rf 0.48 (dichloromethane:methanol:acetic acid=18:1:1); $^1H$-NMR (DMSO-$d_6$): δ 1.76-1.91 (m, 4H), 2.21 (s, 3H), 2.75-2.86 (m, 2H), 3.03-3.18 (m, 2H), 3.80 (s, 2H), 3.90-4.06 (m, 4H), 4.94 (s, 2H), 6.75-6.91 (m, 5H), 6.96-7.10 (m, 3H), 7.11-7.26 (m, 4H), 12.26 (s, 1H), 12.90 (s, 1H).

Example 39(3)

2,2'-[4-(2-{4-[4-(2-propylphenoxy)butoxy] phenyl}ethyl)-1H-indol-1,3-diyl]diacetic acid TLC: Rf 0.48 (dichloromethane:methanol:acetic acid=18:1:1); $^1H$-NMR (DMSO-$d_6$): δ 0.86 (t, 3H), 1.45-1.61 (m, 2H), 1.84-1.93 (m, 4H), 2.48-2.57 (m, 2H), 2.74-2.88 (m, 2H), 3.04-3.17 (m, 2H), 3.80 (s, 2H), 3.91-4.11 (m, 4H), 4.94 (s, 2H), 6.78-6.89 (m, 4H), 6.92 (d, 1H), 7.02 (dd, 1H), 7.06-7.26 (m, 6H), 12.27 (s, 1H), 12.89 (s, 1H).

Example 40(1) to Example 40(98)

The same operation as in Example 2→Example 3→Example 4→Example 5→Example 6 was conducted to obtain the titled compound having the following physical properties. In the step corresponding to Example 2 in the operation, methyl (4-bromo-1H-indol-3-yl)acetate) or a corresponding compound was used in place of the compound prepared in Example 1 and, in the step corresponding to Example 2, methyl 4-bromobutyrate or a corresponding compound was used and, in the step corresponding to Example 5, 1-chloro-4-phenylbutane or a corresponding compound was used.

Example 40(1)

6-(3-carboxymethyl)-4-{(E)-2-[4-(4-phenylbutoxy) phenyl]vinyl}-1H-indol-1-yl)hexanoic acid

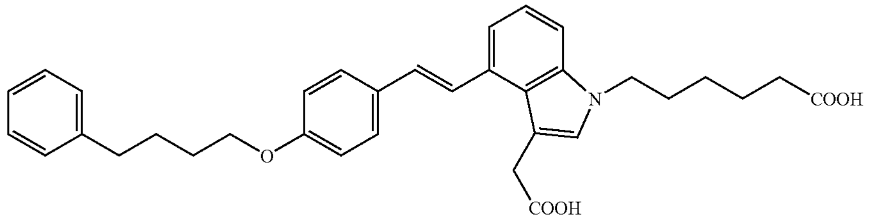

TLC: Rf 0.41 (dichloromethane:methanol:acetic acid=9:1:0.05); $^1H$-NMR (DMSO-$d_6$): δ 1.14-1.36 (m, 2H), 1.43-1.59 (m, 2H), 1.64-1.80 (m, 6H), 2.17 (t, 2H), 2.59-2.69 (m, 2H), 3.82 (s, 2H), 3.95-4.04 (m, 2H), 4.05-4.19 (m, 2H), 6.92 (d, 2H), 6.99-7.40 (m, 10H), 7.51 (d, 2H), 7.62 (d, 1H), 12.15 (s, 2H).

Example 40(2)

(1-{[1-carboxymethyl)cyclopropyl]methyl}-4-{(E)-2-[4-(4-phenylbutoxy)phenyl]vinyl}-1H-indol-3-yl) acetic acid TLC: Rf 0.38 (dichloromethane:methanol=9:1); $^1H$-NMR (DMSO-$d_6$): δ 0.41-0.54 (m, 2H), 0.60-0.73 (m, 2H), 1.62-1.79 (m, 4H), 2.05 (s, 2H), 2.57-2.74 (m, 2H), 3.85 (s, 2H), 3.93-4.06 (m, 2H), 4.16 (s, 2H), 6.92 (d, 2H), 6.98-7.39 (m, 10H), 7.52 (d, 2H), 7.63 (d, 1H), 12.26 (brs, 2H).

Example 40(3)

4-(3-carboxymethy)-4-{(E)-2-[4-(4-oxo-4-phenylbutoxy)phenyl]vinyl}-1H-indol-1-yl)butanoic acid TLC: Rf 0.46 (dichloromethane:methanol:acetic acid=9:1:0.05); $^1H$-NMR (DMSO-$d_6$): δ 1.88-2.00 (m, 2H), 2.02-2.13 (m, 2H), 2.19 (t, 2H), 3.21 (t, 2H), 3.83 (s, 2H), 4.07 (t, 2H), 4.14 (t, 2H), 6.93 (d, 2H), 7.05 (d, 1H), 7.12 (dd, 1H), 7.26 (s, 1H), 7.29-7.39 (m, 2H), 7.48-7.57 (m, 4H), 7.59-7.72 (m, 2H), 7.96-8.03 (m, 2H), 12.23 (s, 2H).

Example 40(4)

4-[3-carboxymethy)-4-((E)-2-{4-[4-(2-chloro-6-methylphenoxy)butoxy]phenyl}vinyl)-1H-indol-1-yl]butanoic acid TLC: Rf 0.48 (dichloromethane:methanol:acetic acid=9:1:0.05); $^{1}$H-NMR (DMSO-$d_6$): δ 1.87-2.03 (m, 6H), 2.20 (t, 2H), 2.28 (s, 3H), 3.84 (s, 2H), 3.93 (t, 2H), 4.09 (t 2H), 4.14 (t, 2H), 6.90-7.22 (m, 6H), 7.23-7.42 (m, 4H), 7.53 (d, 2H), 7.63 (d, 1H), 12.23 (s, 2H).

Example 40(5)

4-[4-((E)-2-{4-[4-(2-acetyl-4-fluorophenoxy)butoxy]phenyl}vinyl)-3-(carboxymethyl)-1H-indol-1-yl]butanoic acid TLC: Rf 0.60 (methanol: dichloromethane:acetic acid=1:9:0.05); $^{1}$H-NMR (DMSO-$d_6$): δ 1.85-2.02 (m, 6H), 2.20 (t, 2H), 2.56 (s, 3H), 3.84 (s, 2H), 4.01-4.24 (m, 6H), 6.94 (d, 2H), 7.06 (d, 1H), 7.10-7.24 (m, 2H), 7.27 (s, 1H), 7.30-7.44 (m, 4H), 7.53 (d, 2H), 7.63 (d, 1H), 12.23 (brs, 2H).

Example 40(6)

4-[4-((E)-2-{4-[4-(4-acetylphenoxy)butoxy]phenyl}vinyl)-3-(carboxymethyl)-1H-indol-1-yl]butanoic acid TLC: Rf 0.38 (dichloromethane:methanol=9:1); $^{1}$H-NMR (DMSO-$d_6$): δ 1.79-2.00 (m, 6H), 2.19 (t 2H), 2.49 (s, 3H), 3.82 (s, 2H), 4.00-4.22 (m, 6H), 6.93 (d, 2H), 6.98-7.19 (m, 4H), 7.21-7.39 (m, 3H), 7.52 (d, 2H), 7.62 (d, 1H), 7.90 (d, 2H), 12.23 (brs, 2H).

Example 40(7)

4-[3-(carboxymethyl)-4-((E)-2-{4-[4-(2-chloro-6-fluorophenoxy)butoxy]phenyl}vinyl)-1H-indol-1-yl]butanoic acid TLC: Rf 0.62 (methanol: dichloromethane:acetic acid=1:9:0.05); $^{1}$H-NMR (DMSO-$d_6$): δ 1.81-2.03 (m, 6H), 2.20 (t, 2H), 3.84 (s, 2H), 4.01-4.19 (m, 6H), 6.94 (d, 2H), 7.06 (d, 1H), 7.10-7.18 (m, 2H), 7.24-7.40 (m, 5H), 7.53 (d, 2H), 7.63 (d, 1H), 12.25 (s, 2H).

Example 40(8)

4-[3-(carboxymethyl)-4-((E)-2-{4-[4-(2-methoxy-6-methylphenoxy)butoxy]phenyl}vinyl)-1H-indol-1-yl]butanoic acid TLC: Rf 0.58 (methanol: dichloromethane:acetic acid=1:9:0.05); $^{1}$H-NMR (DMSO-$d_6$): δ 1.77-2.00 (m, 6H), 2.15-2.24 (m, 2H), 2.19 (s, 3H), 3.75 (s, 3H), 3.84 (s, 2H), 3.90 (t 2H), 4.07 (t, 2H), 4.14 (t, 2H), 6.72-6.78 (m, 1H), 6.84 (d, 1H), 6.89-6.98 (m, 3H), 7.06 (d, 1H), 7.13 (t, 1H), 7.27 (s, 1H), 7.32 (d, 1H), 7.36 (d, 1H), 7.53 (d, 2H), 7.63 (d, 1H), 1226 (brs, 2H).

Example 40(9)

4-[4-((E)-2-{4-[4-(2-acetyl-4,6-difluorophenoxy)butoxy]phenyl}vinyl)-3-carboxymethyl)-1H-indol-1-yl]butanoic acid TLC: Rf 0.71 (methanol: dichloromethane:acetic acid=1:9:0.05); $^{1}$H-NMR (DMSO-$d_6$): δ 1.83-2.01 (m, 6H), 2.20 (t, 2H), 2.59 (s, 3H), 3.84 (s, 2H), 4.01-4.21 (m, 6H), 6.94 (d, 2H), 7.06 (d, 1H), 7.13 (t, 1H), 7.24-7.29 (m, 2H), 7.32 (d, 1H), 7.36 (d, 1H), 7.53 (d, 2H), 7.55-7.64 (m, 1H), 7.63 (d, 1H), 12.24 (brs, 2H).

Example 40(10)

4-[4-((E)-2-{4-[4-(2-acetyl-5-fluorophenoxy)butoxy]phenyl}vinyl)-3-carboxymethyl)-1H-indol-1-yl]butanoic acid TLC: Rf 0.58 (methanol: dichloromethane:acetic acid=1:9:0.01); $^{1}$H-NMR (DMSO-$d_6$): δ 1.86-2.00 (m, 6H), 2.20 (t, 2H), 2.53 (s, 3H), 3.83 (s, 2H), 4.04-4.24 (m, 6H), 6.80-6.89 (m, 1H), 6.94 (d, 2H), 7.02-7.17 (m, 3H), 7.27 (s, 1H), 7.32 (d, 1H), 7.36 (d, 1H), 7.53 (d, 2H), 7.63 (d, 1H), 7.69 (dd, 1H), 12.23 (brs, 2H).

Example 40(11)

4-[3-(carboxymethyl)-4-((E)-2-{4-[4-(3-methylphenoxy)butoxy]phenyl}vinyl)-3-carboxymethyl)-1H-indol-1-yl]butanoic acid TLC: Rf 0.60 (methanol: dichloromethane:acetic acid=1:9:0.01); $^{1}$H-NMR (DMSO-$d_6$): δ 1.82-2.00 (m, 6H), 2.20 (t, 2H), 2.26 (s, 3H), 3.84 (s, 2H), 3.96-4.09 (m, 4H), 4.14 (t, 2H), 6.69-6.77 (m, 3H), 6.94 (d, 2H), 7.06 (d, 1H), 7.10-7.18 (m, 2H), 7.27 (s, 1H), 7.32 (d, 1H), 7.36 (d, 1H), 7.53 (d, 2H), 7.63 (d, 1H), 12.22 (b, 2H).

Example 40(12)

4-[4-((E)-2-{4-[4-(2-acetyl-5-)butoxy]phenyl}vinyl)-3-carboxymethyl)-1H-indol-1-yl]butanoic acid TLC: Rf 0.55 (dichloromethane:methanol:acetic acid=9:1:0.05); $^{1}$H-NMR (DMSO-$d_6$): δ 1.88-2.02 (m, 6H), 2.20 (t, 2H), 2.33 (s, 3H), 2.52 (s, 3H), 3.84 (s, 2H), 4.04-4.21 (m, 6H), 6.82 (d, 1H), 6.90-7.01 (m, 3H), 7.06 (d, 1H), 7.10-7.17 (m, 1H), 7.27 (s, 1H), 7.32 (d, 1H), 7.36 (d, 1H), 7.47-7.57 (m, 3H), 7.63 (d, 1H), 12.20 (s, 2H).

Example 40(13):4-[4-((E)-2-{4-[4-(2-acetyl-3-methoxyphenoxy)butoxy]phenyl}vinyl)-3-(carboxymethyl-1H-indol-1-yl]butanoic acid TLC: Rf 0.57 (methanol: dichloromethane:acetic acid=1:9:0.05); $^{1}$H-NMR (DMSO-$d_6$): δ 1.78-1.87 (m, 4H), 1.88-2.02 (m, 2H), 2.20 (t, 2H), 2.35 (s, 3H), 3.74 (s, 3H), 3.83 (s, 2H), 3.99-4.08 (m, 4H), 4.14 (t, 2H) 6.68 (d, 1H), 6.70 (d, 1H), 6.93 (d, 2H), 7.06 (d, 1H), 7.13 (t, 1H), 7.26 (s, 1H), 7.28-7.39 (m, 3H), 7.52 (d, 2H), 7.63 (d, 1H), 12.22 (brs, 2H).

Example 40(14)

4-(3-carboxymethyl)-4-{(E)-2-[4-(4-phenylbutoxy)phenyl]vinyl}-1H-indol-1-yl-2,2-dimethylbutanoic acid TLC: Rf 0.50 (dichloromethane:methanol=9:1); $^{1}$H-NMR ($DMSO-d_6$): δ 1.18 (s, 6H), 1.65-1.77 (m, 4H), 1.81-1.97 (m, 2H), 2.63 (t, 2H), 3.82 (s, 2H), 3.93-4.16 (m, 4H), 6.91 (d, 2H), 6.99-7.38 (m, 10H), 7.51 (d, 2H), 7.61 (d, 1H), 12.36 (brs, 2H).

Example 40(15)

4-{3-(carboxymethyl)-4-[(E)-2-(4-{4-[(4-fluorophenyl)thio]butoxy}phenyl)vinyl]-1H-indol-1-yl}butanoic acid TLC: Rf 0.63 (methanol: dichloromethane:acetic acid=1:9:0.05); $^{1}$H-NMR ($DMSO-d_6$): δ 1.61-2.04 (m, 6H), 2.20 (t, 2H), 3.01 (t, 2H), 3.83 (s, 2H), 4.00 (t, 2H), 4.14 (t, 2H), 6.91 (d, 2H), 7.06 (d, 1H), 7.10-7.21 (m, 3H), 7.26 (s, 1H), 7.29-7.44 (m, 4H), 7.52 (d, 2H), 7.63 (d, 1H), 12.24 (brs, 2H).

Example 40(16)

4-[3-(carboxymethyl)-4-((E)-2-{4-[4-(2,6-difluorophenoxy)butoxy]phenyl}vinyl)-1H-indol-1-yl]butanoic acid TLC: Rf 0.54 (methanol: dichloromethane=1:9); $^{1}$H-NMR ($DMSO-d_6$): δ 1.77-2.03 (m, 6H), 2.20 (t, 2H), 3.84 (s, 2H), 3.99-4.24 (m, 6H), 6.93 (d, 2H), 7.01-7.21 (m, 5H), 7.27 (s, 1H), 730-7.41 (m, 2H), 7.53 (d, 2H), 7.63 (d, 1H), 12.26 (brs, 2H).

Example 40(17)

4-[3-(carboxymethyl)-4-((E)-2-{4-[4-(4-fluoro-2-methylphenoxy)butoxy]phenyl}vinyl)-1H-indol-1-yl]butanoic acid TLC: Rf 0.49 (methanol: dichloromethane=1:9); $^{1}$H-NMR ($DMSO-d_6$): δ 1.84-2.00 (m, 6H), 2.15 (s, 3H), 2.20 (t, 2H), 3.83 (s, 2H), 3.98-4.10 (m, 4H), 4.14 (t, 2H), 6.89-7.03 (m, 5H), 7.06 (d, 1H), 7.13 (t, 1H), 7.26 (s, 1H), 7.32 (d, 1H), 7.36 (d, 1H), 7.53 (d, 2H), 7.63 (d, 1H), 12.23 (brs, 2H).

Example 40(18)

4-[3-(carboxymethyl)-4-((E)-2-{4-[(4-ethylbenzyl)oxy]phenyl}vinyl)-1H-indol-1-yl]butanoic acid TLC: Rf 0.66 (dichloromethane:methanol:acetic acid=90:10:1); $^{1}$H-NMR ($DMSO-d_6$): δ 1.16 (t, 3H), 1.76-2.06 (m, 2H), 2.20 (t, 2H), 2.60 (q, 2H), 3.83 (s, 2H), 4.14 (t, 2H), 5.09 (s, 2H), 6.92-7.17 (m, 4H), 7.17-7.43 (m, 7H), 7.53 (d, 2H), 7.63 (d, 1H), 12.24 (brs, 2H).

Example 40(19)

4-[3-(carboxymethyl)-4-((E)-2-{4-[(4-isobutylbenzyl)oxy]phenyl}vinyl)-1H-indol-1-yl]butanoic acid TLC: Rf 0.66 (dichloromethane:methanol:acetic acid=90:10:1) $^{1}$H-NMR ($DMSO-d_6$): δ 0.86 (d, 6H), 1.72-2.03 (m, 3H), 2.20 (t, 2H), 2.45 (d, 2H), 3.83 (s, 2H), 4.14 (t, 2H), 5.08 (s, 2H), 6.94-7.22 (m, 6H), 7.26 (s, 1H), 7.29-7.41 (m, 4H), 7.53 (d, 2H), 7.64 (d, 1H), 12.24 (brs, 2H).

Example 40(20)

4-[4-((E)-2-{4-[(4-butylbenzyl)oxy]phenyl}vinyl)-3-carboxymethyl)-1H-indol-1-yl]butanoic acid TLC: Rf 0.38 (dichloromethane:methanol=9:1); $^{1}$H-NMR ($DMSO-d_6$): δ 0.88 (t, 3H), 1.21-1.37 (m, 2H), 1.47-1.63 (m, 2H), 1.94 (t, 2H), 2.20 (t, 2H), 2.54-2.62 (m, 2H), 3.83 (s, 2H), 4.14 (t, 2H), 5.08 (s, 2H), 6.95-7.39 (m, 1H), 7.53 (d, 2H), 7.64 (d, 1H), 12.23 (s, 2H).

Example 40(21)

4-[3-(carboxymethyl)-4-((E)-2-{4-[(4-isopropylbenzyl)oxy]phenyl}vinyl)-1H-indol-1-yl]butanoic acid TLC: Rf 0.39 (dichloromethane:methanol=9:1); $^{1}$H-NMR ($DMSO-d_6$): δ 1.18 (s, 3H), 1.21 (s, 3H), 1.88-2.01 (m, 2H), 2.20 (t, 2H), 2.83-2.95 (m, 1H), 3.83 (s, 2H), 4.14 (t, 2H), 5.08 (s, 2H), 6.96-7.16 (m, 4H), 7.23-7.40 (m, 7H), 7.53 (d, 2H), 7.64 (d, 1H), 12.23 (s, 2H).

Example 40(22)

4-[4-{(E)-2-[4-(4-biphenylylmethoxy)phenyl]vinyl}-3-carboxymethyl)-1H-indol-1-yl]butanoic acid TLC: Rf 0.47 (dichloromethane:methanol:acetic acid=9:1:0.05); $^{1}$H-NMR ($DMSO-d_6$): δ 1.87-2.01 (m, 2H), 2.20 (t, 2H), 3.83 (s, 2H), 4.14 (t, 2H), 5.19 (s, 2H), 7.01-7.16 (m, 4H), 7.26 (s, 1H), 7.29-7.40 (m, 3H), 7.42-7.50 (m, 2H), 7.55 (d, 4H), 7.60-7.74 (m, 5H), 12.24 (s, 2H).

Example 40(23)

4-[4-{(E)-2-[4-(3-biphenylylmethoxy)phenyl]vinyl}-3-(carboxymethyl)-1H-indol-1-yl]butanoic acid TLC: Rf 0.43 (dichloromethane:methanol:acetic acid=9:1:0.05); $^{1}$H-NMR ($DMSO-d_6$): δ 1.87-2.04 (m, 2H), 2.20 (t, 2H), 3.83 (s, 2H), 4.14 (t, 2H), 5.22 (s, 2H), 6.99-7.17 (m, 4H), 7.26 (s, 1H), 7.29-7.41 (m, 3H), 7.41-7.81 (m, 11H), 12.23 (s, 2H).

Example 40(24)

4-{3-(carboxymethyl)-4-[(E)-2-(4-{4-[(2-methylphenyl)thio]butoxy}phenyl)vinyl]-1H-indol-1-yl}butanoic acid TLC: Rf 0.63 (methanol: dichloromethane=1:9); $^{1}$H-NMR ($DMSO-d_6$): δ 1.68-2.01 (m, 6H), 2.20 (t, 2H), 2.27 (s, 3H), 3.01 (t, 2H), 3.83 (s, 2H), 4.02 (t, 2H), 4.14 (t, 2H), 6.92 (d, 2H), 7.01-7.39 (m, 9H), 7.52 (d, 2H), 7.63 (d, 1H), 12.25 (brs, 2H).

Example 40(25)

4-[4-((E)-2-{4-[4-(2-acetyl-4-fluorophenoxy)butoxy]phenyl}vinyl)-3-carboxymethyl)-1H-indol-1-yl]-2-methylbutanoic acid TLC: Rf 0.39 (dichloromethane:methanol=9:1); $^{1}$H-NMR ($DMSO-d_6$): δ 1.12 (d, 3H), 1.63-2.17 (m, 6H), 2.20-2.42 (m, 1H), 2.56 (s, 3H), 3.83 (s, 2H),4.00-4.22 (m, 6H), 6.94 (d, 2H), 7.00-7.46 (m, 8H), 7.53 (d, 2H), 7.63 (d, 1H), 12.30 (brs, 2H).

Example 40(26)

4-[3-(carboxymethyl)-4-((E)-2-{4-[(3-isobutylbenzyl)oxy]phenyl}vinyl)-1H-indol-1-yl]butanoic acid TLC: Rf 0.30 (dichloromethane:methanol=9:1); $^1$H-NMR ($DMSO-d_6$): δ 0.86 (d, 6H), 1.73-2.03 (m, 3H), 2.20 (t, 2H), 2.46 (d, 2H), 3.83 (s, 2H), 4.14 (t, 2H), 5.10 (s, 2H), 6.94-7.18 (m, 5H), 7.19-7.42 (m, 6H), 7.53 (d, 2H), 7.64 (d, 1H), 12.24 (brs, 2H).

Example 40(27)

4-[3-(carboxymethyl)-4-((E)-2-{4-[(4-pentylbenzyl)oxy]phenyl}vinyl)-1H-indol-1-yl]butanoic acid TLC: Rf 0.54 (dichloromethane:methanol:acetic acid=9:1:0.05); $^1$H-NMR ($DMSO-d_6$): δ 0.82-0.88 (m, 3H), 1.20-1.35 (m, 4H), 1.50-1.61 (m, 2H), 1.87-2.01 (m, 2H), 2.20 (t, 2H), 2.52-2.62 (m, 2H), 3.83 (s, 2H), 4.14 (t, 2H), 5.08 (s, 2H), 6.97-7.38 (m, 11H), 7.53 (d, 2H), 7.64 (d, 1H),12.23 (s, 2H).

Example 40(28)

4-{3-(carboxymethyl)-4-[(E)-2-(4-{[4-trifluoromethyl)benzyl]oxy}phenyl)vinyl]-1H-indol-1-yl}butanoic acid TLC: Rf 0.54 (dichloromethane:methanol:acetic acid=9:1:0.05); $^1$H-NMR ($DMSO-d_6$): δ 1.86-2.02 (m, 2H), 2.19 (t, 2H), 3.83 (s, 2H), 4.14 (t, 2H), 5.26 (s, 2H), 6.99-7.18 (m, 4H), 7.26 (s, 1H), 7.28-7.42 (m, 2H), 7.55 (d, 2H), 7.60-7.72 (m, 3H), 7.73-7.81 (m, 2H), 12.25 (s, 2H).

Example 40(29)

4-[3-(carboxymethyl)-4-4((E)-2-{4-[4-(2-propionylphenoxy)butoxy]phenyl}vinyl)-1H-indol-1-yl]butanoic acid TLC: Rf 0.65 (methanol: dichloromethane=1:9); $^1$H-NMR ($DMSO-d_6$): δ 1.04 (t, 3H), 1.82-2.01 (m, 6H), 2.20 (t, 2H), 2.94 (q, 2H), 3.84 (s, 2H), 4.03-4.20 (m, 6H), 6.94 (d, 2H), 6.97-7.18 (m, 4H), 7.27 (s, 1H), 7.32 (d, 1H), 7.36 (d, 1H), 7.45-7.57 (m, 4H), 7.63 (d, 1H), 12.23 (brs, 2H).

Example 40(30)

4-(3-carboxymethy)-4-{(E)-2-[4-({2-[(phenylsulfonyl)methyl]benzyl}oxy)phenyl]vinyl}-1H-indol-1-yl)butanoic acid TLC: Rf 0.45 (dichloromethane:methanol:acetic acid=9:1:0.05); $^1$H-NMR ($DMSO-d_6$): δ 1.88-1.99 (m, 2H), 2.20 (t, 2H), 3.84 (s, 2H), 4.14 (t, 2H), 4.82 (s, 2H), 5.13 (s, 2H), 6.92-7.17 (m, 5H), 7.21-7.41 (m, 5H), 7.45-7.83 (m, 9H), 12.24 (s, 2H).

Example 40(31)

4-{3-(carboxymethy)-4-[(E)-2-(4-{[3-(trifluoromethyl)benzyl]oxy}phenyl)vinyl]-1H-indol-1-yl}butanoic acid TLC: Rf 0.53 (dichloromethane:methanol:acetic acid=9:1:0.05); $^1$H-NMR ($DMSO-d_6$): δ 1.87-2.03 (m, 2H), 2.20 (t, 2H), 3.84 (s, 2H), 4.14 (t, 2H), 5.25 (s, 2H), 6.99-7.18 (m, 4H), 7.27 (s, 1H), 7.32 (d, 1H), 7.34-7.38 (m, 1H), 7.56 (d, 2H), 7.59-7.87 (m, 5H), 12.22 (s, 2H).

Example 40(32)

4-[3-(carboxymethy)-4-((E)-2-{4-[4-(2-chlorophenoxy)butoxy]phenyl}vinyl)-1H-indol-1-yl]butanoic acid TLC: Rf 0.47 (dichloromethane:methanol:acetic acid=9:1:0.05); $^1$H-NMR ($DMSO-d_6$): δ 1.86-1.99 (m, 6H), 2.19 (t, 2H), 3.83 (s, 2H), 4.04-4.18 (m, 6H), 6.89-6.98 (m, 3H), 7.05 (d, 1H), 7.09-7.18 (m, 2H), 7.26 (s, 1H), 7.27-7.37 (m, 3H), 7.40 (dd, 1H), 7.52 (d, 2H), 7.62 (d, 1H), 12.21 (s, 2H).

Example 40(33)

4-[3-(carboxymethy)-4-((E)-2-{4-[4-(2-chloro-2,6-dimethylphenoxy)butoxy]phenyl}vinyl)-1H-indol-1-yl]butanoic acid TLC: Rf 0.52 (methanol: dichloromethane=1:9); $^1$H-NMR ($DMSO-d_6$): δ 1.83-2.02 (m, 6H), 2.16-2.24 (m, 2H), 2.21 (s, 6H), 3.79 (t, 2H), 3.83 (s, 2H), 4.08 (t, 2H), 4.14 (t, 2H), 6.95 (d, 2H), 7.06 (d, 1H), 7.09 (s, 2H), 7.13 (t, 1H), 7.26 (s, 1H), 7.32 (d, 1H), 7.36 (d, 1H), 7.53 (d, 2H), 7.64 (d, 1H) 12.21 (brs, 2H).

Example 40(34)

4-[3-(carboxymethy)-4-((E)-2-{4-[4-(2-(2,3,6-trimethylphenoxy)butoxy]phenyl}vinyl)-1H-indol-1-yl]butanoic acid TLC: Rf 0.52 (methanol: dichloromethane=1:9); $^1$H-NMR ($DMSO-d_6$): δ 1.84-2.01 (m, 6H), 2.08-2.24 (m, 2H), 2.12 (s, 3H), 2.16 (s, 3H), 2.18 (s, 3H), 3.73 (t, 2H), 3.84 (s, 2H), 4.04-4.20 (m, 4H), 6.80 (d, 1H), 6.89 (d, 1H), 6.95 (d, 2H), 7.06 (d, 1H), 7.13 (t, 1H), 7.26 (s, 1H), 7.32 (d, 1H), 7.36 (d, 1H), 7.54 (d, 2H), 7.64 (d, 1H), 12.22 (brs, 2H).

Example 40(35)

4-[3-(carboxymethy)-4-((E)-2-{4-[4-chloro-2-methylphenoxy)butoxy]phenyl}vinyl)-1H-indol-1-yl]butanoic acid TLC: Rf 0.35 (methanol: dichloromethane=1:9); $^1$H-NMR ($DMSO-d_6$): δ 1.84-2.01 (m, 6H), 2.13 (s, 3H), 2.20 (t, 2H), 3.83 (s, 2H), 3.99-4.10 (m, 4H), 4.14 (t, 2H), 6.90-6.97 (m, 3H), 7.06 (d, 1H), 7.10-7.22 (m, 3H), 7.26 (s, 1H), 7.32 (d, 1H), 7.36 (d, 1H), 7.53 (d, 2H), 7.63 (d, 1H), 12.22 (brs, 2H).

Example 40(36)

4-[3-(carboxymethy)-4-((E)-2-{4-[4-(2,4-dimethylphenoxy)butoxy]phenyl}vinyl)-1H-indol-1-yl] butanoic acid TLC: Rf 0.30 (dichloromethane:methanol:acetic acid=9:1:0.05); $^1$H-NMR (DMSO-$d_6$): δ 1.82-2.02 (m, 6H), 2.11 (s, 3H), 2.15-2.27 (m, 5H), 3.83 (s, 2H), 3.92-4.01 (m, 2H), 4.06 (t, 2H), 4.14 (t, 2H), 6.74-6.83 (m, 1H), 6.87-7.00 (m, 4H), 7.06 (d, 1H), 7.13 (dd, 1H), 7.26 (s, 1H), 7.32 (d, 1H), 7.36 (d, 1H), 7.53 (d, 2H), 7.63 (d, 1H), 12.22 (s, 2H).

Example 40(37)

4-[3-(carboxymethy)-4-((E)-2-{4-[4-(mesityloxy) butoxy]phenyl}vinyl)-1H-indol-1-yl]butanoic acid TLC: Rf 0.28 (dichloromethane:methanol:acetic acid=9:1:0.05); $^1$H-NMR (DMSO-$d_6$): δ 1.81-2.01 (m, 6H), 2.13-2.25 (m, 1H), 3.74 (t, 2H), 3.83 (s, 2H), 4.07 (t, 2H), 4.11-4.17 (m, 2H), 6.80 (s, 2H), 6.95 (d, 2H), 7.06 (d, 1H), 7.13 (d, 1H), 7.26 (s, 1H), 7.32 (d, 1H), 7.35 (d, 1H), 7.53 (d, 2H), 7.63 (d, 1H), 12.23 (s, 2H).

Example 40(38)

4-[4-((E)-2-{4-[4-(4-acetyl-2-methylphenoxy)butoxy]phenyl}vinyl)-3-(carboxymethyl)-1H-indol-1-yl]butanoic acid TLC: Rf 0.60 (dichloromethane:methanol:acetic acid=9:1:0.05); $^1$H-NMR (DMSO-$d_6$): δ 1.87-2.01 (m, 6H), 2.15-2.25 (m, 5H), 2.48-2.49 (m, 3H), 3.83 (s, 2H), 4.02-4.21 (m, 6H), 6.94 (d, 2H), 7.02-7.09 (m, 2H), 7.13 (dd, 1H), 7.26 (s, 1H), 7.32 (d, 1H), 7.36 (d, 1H), 7.53 (d, 2H), 7.63 (d, 1H), 7.73-7.84 (m, 2H), 12.23 (s, 2H).

Example 40(39)

4-[4-((E)-2-{4-[4-(2-acetyl-5-methoxyphenoxy)butoxy]phenyl}vinyl)-3-(carboxymethyl)-1H-indol-1-yl]butanoic acid TLC: Rf 0.46 (dichloromethane:methanol:acetic acid=9:1:0.05); $^1$H-NMR (DMSO-$d_6$): δ 1.88-2.01 (m, 6H), 2.20 (t, 2H), 2.50 (s, 3H), 3.82 (s, 3H), 3.83 (s, 2H), 4.06-4.21 (m, 6H), 6.59 (dd, 1H), 6.65 (d, 1H), 6.94 (d, 2H), 7.06 (d, 1H), 7.13 (dd, 1H), 7.27 (s, 1H), 7.32 (d, 1H), 7.36 (d, 1H), 7.49-7.55 (m, 2H), 7.63 (d, 1H), 7.66 (d, 1H), 1226 (s, 2H).

Example 40(40)

4-[3-(carboxymethyl)-4-((E)-2-{4-[4-(2,5-dimethylphenoxy)butoxy]phenyl}vinyl)-1H-indol-1-yl] butanoic acid TLC: Rf 0.39 (methanol: dichloromethane=1:9); $^1$H-NMR (DMSO-$d_6$): δ 1.82-2.00 (m, 6H), 2.09 (s, 3H), 2.20 (t, 2H), 2.24 (s, 3H), 3.84 (s, 2H), 3.98-4.10 (m, 4H), 4.14 (t, 2H), 6.62 (d, 1H), 6.74 (s, 1H) 6.91-7.01 (m, 3H), 7.06 (d, 1H), 7.13 (t, 1H), 7.26 (s, 1H), 7.32 (d, 1H), 7.36 (d, 1H), 7.53 (d, 2H), 7.58-7.69 (d, 4H), 12.23 (brs, 2H).

Example 40(41)

4-[3-(carboxymethyl)-4-((E)-2-{4-[4-(2-ethyl-6-methylphenoxy)butoxy]phenyl}vinyl)-1H-indol-1-yl]butanoic acid TLC: Rf 0.37 (methanol: dichloromethane=1:9); $^1$H-NMR (DMSO-$d_6$): δ 1.15 (t, 3H), 1.83-2.03 (m, 6H), 2.20 (t 2H), 2.23 (s, 3H), 2.60 (q, 2H), 3.79 (t, 2H), 3.84 (s, 2H), 4.09 (t, 2H), 4.14 (t 2H), 6.89-7.05 (m, 5H), 7.06 (d, 1H), 7.13 (t, 1H), 7.26 (s, 1H), 7.32 (d, 1H), 7.36 (d, 1H), 7.54 (d, 2H), 7.64 (d, 1H) 12.22 (brs, 2H).

Example 40(42)

4-[3-carboxymethyl)-4-((E)-2-{4-[4-(2-methyl-6-propylphenoxy)butoxy]phenyl}vinyl)-1H-indol-1-yl] butanoic acid TLC: Rf 0.58 (dichloromethane:methanol:acetic acid=9:1:0.05); $^1$H-NMR (DMSO-$d_6$): δ 0.90 (t, 3H), 1.47-1.63 (m, 2H), 1.83-2.01 (m, 6H), 2.15-2.24 (m, 5H), 2.51-2.58 (m, 2H), 3.78 (t 2H), 3.83 (s, 2H), 4.06-4.11 (m, 2H), 4.14 (t, 2H), 6.88-7.03 (m, 5H), 7.06 (d, 1H), 7.13 (dd, 1H), 7.26 (s, 1H), 7.32 (d, 1H),7.36 (d, 1H), 7.53 (d, 1H), 7.54 (d, 1H), 7.64 (d, 1H), 12.22 (s, 2H).

Example 40(43)

4-[3-carboxymethyl)-4-((E)-2-{4-[4-(4-chloro-2-fluorophenoxy)butoxy]phenyl}vinyl)-1H-indol-1-yl] butanoic acid TLC: Rf 0.44 (methanol: dichloromethane=1:9); $^1$H-NMR (DMSO-$d_6$): δ 1.81-2.03 (m, 6H), 2.20 (t, 2H), 3.84 (s, 2H), 3.99-4.21 (m, 6H), 6.93 (d, 2H), 7.06 (d, 1H), 7.13 (t, 1H), 7.18-7.23 (m, 2H), 7.26 (s, 1H), 7.32 (d, 1H), 7.36 (d, 1H), 7.38-7.45 (m, 1H), 7.53 (d, 2H), 7.63 (d, 1H), 12.23 (brs, 2H).

Example 40(44)

4-[4-((E)-2-{4-[4-(2-allyl-6-methylphenoxy)butoxy] phenyl}vinyl)-3-(carboxymethyl)-1H-indol-1-yl] butanoic acid TLC: Rf 0.51 (dichloromethane:methanol:acetic acid=9:1:0.05); $^1$H-NMR (DMSO-$d_6$): δ 1.85-2.02 (m, 6H), 2.20 (t, 2H), 2.23 (s, 3H), 3.43-3.48 (m, 2H), 3.79 (t, 2H), 3.84 (s, 2H), 4.08 (t, 2H), 4.14 (t, 2H), 4.99-5.11 (m, 2H), 5.86-6.03 (m, 1H), 6.88-7.09 (m, 6H), 7.13 (dd, 1H), 7.26 (s, 1H), 7.32 (d, 1H), 7.36 (d, 1H), 7.53 (d, 2H), 7.64 (d, 1H), 12.25 (s, 2H).

Example 40(45)

4-[4-((E)-2-{4-[4-(2-acetyl-4-chloro-5-methylphenoxy)butoxy]phenyl}vinyl)-3-(carboxymethyl)-1H-indol-1-yl]butanoic acid TLC: Rf 0.48 (dichloromethane:methanol:acetic acid=9:1:0.05); $^1$H-NMR (DMSO-$d_6$): δ 1.87-2.02 (m, 6H), 2.20 (t, 2H), 2.35 (s, 3H), 2.53 (s, 3H), 3.83 (s, 2H), 4.08 (t, 2H), 4.11-4.24 (m, 4H), 6.94 (d, 2H), 7.06 (d, 1H), 7.13 (dd, 1H), 7.22 (s, 1H), 7.26 (s, 1H), 7.32 (d, 1H), 7.36 (d, 1H), 7.53 (d, 2H), 7.55 (s, 1H), 7.64 (d, 1H), 12.20 (s, 2H).

Example 40(46)

4-[3-carboxymethyl)-4-((E)-2-{4-[4-(2-chloro-4-fluorophenoxy)butoxy]phenyl}vinyl)-1H-indol-1-yl]butanoic acid TLC: Rf 0.44 (methanol: dichloromethane=1:9); $^1$H-NMR (DMSO-$d_6$): δ 1.84-2.01 (m, 6H), 2.20 (t, 2H), 3.84 (s, 2H), 4.01-4.21 (m, 6H), 6.94 (d, 2H), 7.06 (d, 1H), 7.09-7.20 (m, 3H), 7.26 (s, 1H), 7.32 (d, 1H), 7.36 (d, 1H), 739-7.45 (m, 1H), 7.53 (d, 2H), 7.63 (d, 1H), 12.23 (brs, 2H).

Example 40(47)

4-[3-carboxymethyl)-4-((E)-2-{4-[4-(2,4-dichloro-6-methylphenoxy)butoxy]phenyl}vinyl)-1H-indol-1-yl]butanoic acid TLC: Rf 0.44 (methanol: dichloromethane=1:9); $^1$H-NMR ($CD_3OD$): δ 2.01-2.21 (m, 6H), 2.30-2.39 (m, 2H), 2.35 (s, 3H), 3.97 (s, 2H), 4.03 (t, 2H), 4.15 (t, 2H), 4.24 (t, 2H), 6.97 (d, 2H), 7.04 (d, 1H), 7.15-7.24 (m, 3H), 7.29-7.40 (m, 3H), 7.56 (d, 2H), 7.76 (d, 1H).

Example 40(48)

4-[3-carboxymethyl)-4-((E)-2-{4-[4-(2-chloro-4-methoxyphenoxy)butoxy]phenyl}vinyl)-1H-indol-1-yl]butanoic acid TLC: Rf 0.37 (methanol: dichloromethane=1:9); $^1$H-NMR (DMSO-$d_6$): δ 1.82-2.01 (m, 6H), 2.20 (t, 2H), 3.71 (s, 3H), 3.83 (s, 2H), 4.00-4.11 (m, 4H), 4.14 (t, 2H), 6.86 (dd, 1H), 6.94 (d, 2H), 7.03 (d, 1H), 7.06-7.17 (m, 3H), 7.26 (s, 1H), 7.32 (d, 1H), 7.35 (d, 1H), 7.53 (d, 2H), 7.63 (d, 1H), 12.21 (brs, 2H).

Example 40(49)

4-[3-carboxymethyl)-4-((E)-2-{4-[4-(2,3-dichlorophenoxy)butoxy]phenyl}vinyl)-1H-indol-1-yl]butanoic acid TLC: Rf 0.49 (dichloromethane:methanol:acetic acid=9:1:0.05); $^1$H-NMR (DMSO-$d_6$): δ 1.87-1.96 (m, 6H), 2.20 (t, 2H), 3.83 (s, 2H), 3.99-4.22 (m, 6H), 6.89-6.98 (m, 2H), 7.01-7.23 (m, 4H), 7.24-7.39 (m, 4H), 7.53 (d, 2H), 7.63 (d, 1H), 12.22 (s, 2H).

Example 40(50)

4-[3-(carboxymethyl)-4-((E)-2-{4-[4-(2,4-dichlorophenoxy)butoxy]phenyl}vinyl)-1H-indol-1-yl]butanoic acid TLC: Rf 0.47 (dichloromethane:methanol:acetic acid=9:1:0.05); $^1$H-NMR (DMSO-$d_6$): δ 1.82-1.97 (m, 6H), 2.20 (t, 2H), 3.83 (s, 2H), 4.02-4.20 (m, 6H), 6.94 (d, 2H), 7.06 (d, 1H), 7.13 (dd, 1H), 7.18 (d, 1H), 7.26 (s, 1H), 7.29-7.39 (m, 3H), 7.48-7.57 (m, 3H), 7.63 (d, 1H), 12.23 (s, 2H).

Example 40(51)

4-[3-(carboxymethyl)-4-((E)-2-{4-[4-(2-chloro-5-methylphenoxy)butoxy]phenyl}vinyl)-1H-indol-1-yl]butanoic acid TLC: Rf 0.60 (dichloromethane:methanol:acetic acid=9:1:0.05); $^1$H-NMR (DMS (16): δ 1.83-2.03 (m, 6H), 2.20 (t, 2H), 2.28 (s, 3H), 3.83 (s, 2H), 4.01-4.18 (m, 6H), 6.67-6.78 (m, 1H), 6.85-7.00 (m, 3H), 7.06 (d, 1H), 7.13 (dd, 1H), 7.21-7.40 (m, 4H), 7.49-7.56 (m, 2H), 7.63 (d, 1H), 12.21 (s; 2H).

Example 40(52)

4-[4((E)-2-{4-[4-(2-acetyl-4,6-dimethylphenoxy)butoxy]phenyl}vinyl)-1H-indol-1-yl]butanoic acid TLC: Rf 0.64 (dichloromethane:methanol:acetic acid=9:1:0.05); $^1$H-NMR (DMSO-$d_6$): δ 1.83-2.01 (m, 6H), 2.16-2.30 (m, 8H), 2.54 (s, 3H), 3.79 (t, 2H), 3.84 (s, 2H), 4.06 (t, 2H), 4.14 (t, 2H), 6.90-6.98 (m, 2H), 7.06 (d, 1H), 7.10-7.23 (m, 3H), 7.27 (s, 1H), 7.32 (d, 1H), 7.36 (d, 1H), 7.53 (d, 2H), 7.63 (d, 1H), 12.22 (s, 2H).

Example 40(53)

4-[3-carboxymethyl)-4-((E)-2-{4-[4-(5-fluoro-2-methylphenoxy)butoxy]phenyl}vinyl)-1H-indol-1-yl]butanoic acid TLC: Rf 0.63 (dichloromethane:methanol:acetic acid=9:1:0.05); $^1$H-NMR (DMSO-$d_6$): δ 1.84-2.02 (m, 6H), 2.10 (s, 3H), 2.20 (t, 2H), 3.84 (s, 2H), 3.97-4.10 (m, 4H), 4.14 (t, 2H), 6.63 (ddd, 1H), 6.82 (dd, 1H), 6.94 (d, 2H), 7.01-7.19 (m, 3H), 7.26 (s, 1H), 7.32 (d, 1H), 7.36 (d, 1H), 7.53 (d, 2H), 7.63 (d, 1H), 12.24 (s, 2H).

Example 40(54)

4-[3-(carboxymethyl)-4-((E)-2-{4-[4-(2-chloro-5-fluorophenoxy)butoxy]phenyl}vinyl)-1H-indol-1-yl]butanoic acid TLC: Rf 0.49 (dichloromethane:methanol:acetic acid=9:1:0.05); $^1$H-NMR (DMSO-$d_6$): δ 1.82-2.02 (m, 6H), 2.20 (t, 2H), 3.83 (s, 2H), 4.04-4.24 (m, 6H), 6.75-6.85 (m, 1H), 6.94 (d, 2H), 7.01-7.19 (m, 3H), 7.26 (s, 1H), 7.29-7.39 (m, 2H), 7.40-7.48 (m, 1H), 7.53 (d, 2H), 7.63 (d, 1H), 12.22 (s, 2H).

Example 40(55)

4-[3-(carboxymethyl)-4-((E)-2-{4-[4-(2-chloro-4-methylphenoxy) butoxy]phenyl}vinyl)-1H-indol-1-yl]butanoic acid TLC: Rf 0.52 (methanol: dichloromethane=1:9); $^1$H-NMR (DMSO-$d_6$): δ 1.83-2.00 (m, 6H), 2.16-2.24 (m, 2H), 2.22 (s, 3H), 3.84 (s, 2H), 3.99-4.20 (m, 6H), 6.94 (d, 2H), 7.00-7.17 (m, 4H), 7.19-7.28 (m, 2H), 7.32 (d, 1H), 7.36 (d, 1H), 7.53 (d, 2H), 7.63 (d, 1H), 12.19 (brs, 2H).

Example 40(56)

4-[3-(carboxymethyl)-4-((E)-2-{4-[4-(3-chloro-2-methylphenoxy)butoxy]phenyl}vinyl)-1H-indol-1-yl]butanoic acid TLC: Rf 0.50 (methanol: dichloromethane=1:9); $^1$H-NMR (DMSO-$d_6$): δ 1.86-2.01 (m, 6H), 2.15-2.24 (m, 2H), 2.20 (s, 3H), 3.84 (s, 2H), 4.02-4.10 (m, 4H), 4.14 (t, 2H), 6.91-7.05 (m, 4H), 7.07-7.20 (m, 3H), 7.27 (s, 1H), 7.32 (d, 1H), 7.36 (d, 1H), 7.53 (d, 2H), 7.63 (d, 1H), 12.24 (brs, 2H).

Example 40(57)

4-[3-(carboxymethyl)-4-((E)-2-{4-[4-(2,3,5-trimethylphenoxy)butoxy]phenyl}vinyl)-1H-indol-1-yl]butanoic acid TLC: Rf 0.48 (methanol: dichloromethane=1:9); $^1$H-NMR (DMSO-$d_6$): δ 1.85-2.00 (m, 6H), 2.02 (s, 3H), 2.15 (s, 3H), 2.17-2.24 (m, 2H), 2.20 (s, 3H), 3.84 (s, 2H), 3.94-4.03 (m, 2H), 4.04-4.10 (m, 2H), 4.14 (t, 2H), 6.55 (s, 1H), 6.60 (s, 1H), 6.94 (d, 2H), 7.06 (d, 1H), 7.13 (t, 1H), 7.27 (s, 1H), 7.32 (d, 1H), 7.36 (d, 1H), 7.53 (d, 2H), 7.63 (d, 1H), 12.24 (brs, 2H).

Example 40(58)

4-[3-(carboxymethyl)-4-((E)-2-{4-[4-(3-chlorophenoxy)butoxy]phenyl}vinyl)-1H-indol-1-yl]butanoic acid TLC: Rf 0.54 (dichloromethane:methanol:acetic acid=9:1:0.05); $^1$H-NMR (DMSO-$d_6$): δ 1.78-2.01 (m, 6H), 2.20 (t, 2H), 3.83 (s, 2H), 3.97-4.09 (m, 4H), 4.10-4.17 (m, 2H), 6.78-7.03 (m, 5H), 7.06 (d, 1H), 7.13 (dd, 1H), 7.26 (d, 1H), 7.28-7.41 (m, 3H), 7.53 (d, 2H), 7.63 (d, 1H), 12.20 (s, 2H).

Example 40(59)

4-{3-(carboxymethyl)-4-[(E)-2-(4-{4-[2-trifluoromethyl)phenoxy]butoxy}phenyl)vinyl]1H-indol-1-yl}butanoic acid TLC: Rf 0.44 (dichloromethane:methanol:acetic acid=9:1:0.05); $^1$H-NMR (DMSO-$d_6$): δ 1.81-2.01 (m, 6H), 2.20 (t 2H), 3.83 (s, 2H), 3.99-4.08 (m, 2H), 4.10-4.21 (m, 4H), 6.93 (d, 2H), 7.01-7.16 (m, 3H), 7.23-7.40 (m, 4H), 7.53 (d, 2H), 7.57-7.70 (m, 3H), 12.23 (s, 2H).

Example 40(60)

4-[3-(carboxymethyl)-4-((E)-2-{4-[4-(4-ethylphenoxy)butoxy]phenyl}vinyl)-1H-indol-1-yl]butanoic acid TLC: Rf 0.46 (methanol: dichloromethane=1:9); $^1$H-NMR (DMSO-$d_6$): δ 1.13 (t, 3H), 1.75-2.01 (m, 6H), 2.20 (t 2H), 2.50-2.58 (m, 2H), 3.83 (s, 2H), 3.96-4.02 (m, 2H), 4.03-4.09 (m, 2H), 4.14 (t, 2H), 6.84 (d, 2H), 6.94 (d, 2H), 7.01-7.18 (m, 1H), 7.26 (s, 1H), 7.32 (d, 1H), 7.36 (d, 1H), 7.53 (d, 2H), 7.63 (d, 1H), 12.22 (brs, 2H).

Example 40(61)

4-[3-(carboxymethyl)-4-((E)-2-{4-[4-(4-methoxyphenoxy)butoxy]phenyl}vinyl)-1H-indol-1-yl]butanoic acid TLC: Rf 0.57 (ethyl acetate); $^1$H-NMR (DMSO-$d_6$): δ 1.76-2.02 (m, 6H), 2.20 (t, 2H), 3.68 (s, 3H), 3.83 (s, 2H), 3.96 (t, 2H), 4.05 (t, 2H), 4.14 (t, 2H), 6.80-6.90 (m, 4H), 6.94 (d, 2H), 7.06 (ds 1H), 7.13 (t, 1H), 7.26 (s, 1H), 7.32 (d, 1H), 7.35 (d, 1H), 7.53 (d, 2H), 7.63 (d, 1H), 12.23 (brs, 2H).

Example 40(62)

4-[3-(carboxymethyl)-4-((E)-2-{4-[4-(2,3-difluorophenoxy)butoxy]phenyl}vinyl)-1H-indol-1-yl]butanoic acid TLC: Rf 0.50 (dichloromethane:methanol:acetic acid=9:1:0.05); $^1$H-NMR (DMSO-$d_6$): δ 1.84-2.01 (m, 6H), 2.20 (t, 2H), 3.83 (s, 2H), 4.04-4.21 (m, 6H), 6.90-7.19 (m, 7H), 7.26 (s, 1H), 7.32 (d, 1H), 7.35 (d, 1H), 7.53 (d, 2H), 7.63 (d, 1H), 12.24 (s, 2H).

Example 40(63)

4-{3-(carboxymethyl)-4-[(E)-2-(4-{4-[2-chloro-3-(trifluoromethyl)phenoxy]butoxy}phenyl)vinyl]-1H-indol-1-yl}butanoic acid TLC: Rf 0.52 (dichloromethane:methanol:acetic acid=9:1:0.05); $^1$H-NMR (DMSO-$d_6$): δ 1.88-2.01 (m, 6H), 2.20 (t, 2H), 3.83 (s, 2H), 4.05-4.18 (m, 4H), 4.19-4.27 (m, 2H), 6.94 (d, 2H), 7.06 (d, 1H), 7.13 (dd, 1H), 7.26 (s, 1H), 730-7.44 (m, 3H), 7.47-7.56 (m, 4H), 7.63 (d, 1H), 12.22 (s, 2H).

Example 40(64)

4-[3-(carboxymethyl)-4-((E)-2-{4-[4-(6-chloro-2-fluoro-3-methylphenoxy)butoxy]phenyl}vinyl)-1H-indol-1-yl]butanoic acid TLC: Rf 0.53 (dichloromethane:methanol:acetic acid=9:1:0.05); $^1$H-NMR (DMSO-$d_6$): δ 1.86-2.01 (m, 6H), 2.16-2.24 (m, 5H), 3.84 (s, 2H), 4.03-4.20 (m, 6H), 6.94 (d, 2H), 6.98-7.09 (m, 2H), 7.13 (dd, 1H), 7.20 (dd, 1H), 7.26 (s, 1H), 7.32 (d, 1H), 7.36 (d, 1H), 7.53 (d, 2H), 7.63 (d, 1H), 12.24 (s, 2H).

Example 40(65)

4-[3-(carboxymethyl)-4-((E)-2-{4-[4-(2-chloro-6-fluoro-3-methylphenoxy)butoxy]phenyl}vinyl)-1H-indol-1-yl]butanoic acid TLC: Rf 0.49 (dichloromethane:methanol:acetic acid=9:1:0.05); $^1$H-NMR (DMSO-$d_6$): δ 1.85-2.01 (m, 6H), 2.20 (t, 2H), 2.29 (s, 3H), 3.84 (s, 2H), 4.03-4.19 (m, 6H), 6.94 (d, 2H), 7.01-7.23 (m, 4H), 7.25-7.27 (m, 1H), 7.30-7.34 (m, 1H), 7.36 (d, 1H), 7.53 (d, 2H), 7.63 (d, 1H), 12.21 (s, 2H).

Example 40(66)

4-[3-(carboxymethyl)-4-((E)-2-{4-[4-(4,5-difluoro-2-methylphenoxy)butoxy]phenyl}vinyl)-1H-indol-1-yl]butanoic acid TLC: Rf 0.34 (methanol: dichloromethane=1:9); $^1$H-NMR (DMSO-$d_6$): δ 1.84-2.02 (m, 6H), 2.10 (s, 3H), 2.20 (t, 2H), 3.83 (s, 2H), 3.98-4.09 (m, 4H), 4.14 (t, 2H), 6.94 (d, 2H), 7.01-7.24 (m, 4H), 7.26 (s, 1H), 7.32 (d, 1H), 7.36 (d, 1H), 7.53 (d, 2H), 7.63 (d, 1H), 12.22 (brs, 2H).

Example 40(67)

4-[3-(carboxymethyl)-4-((E)-2-{4-[4-(2,3-dimethylphenoxy)butoxy]phenyl}vinyl)-1H-indol-1-yl]butanoic acid TLC: Rf 0.52 (dichloromethane:methanol:acetic acid=9:1:0.05); $^1$H-NMR (DMSO-$d_6$): δ 1.85-2.01 (m, 6H), 2.07 (s, 3H), 2.16-2.24 (m, 5H), 3.83 (s, 2H), 3.94-4.04 (m, 2H), 4.07 (t 2H), 4.14 (t, 2H), 6.73 (d, 1H) 6.78 (d, 1H), 6.94 (d, 2H), 6.99 (d, 1H), 7.06 (d, 1H), 7.13 (dd, 1H), 7.26 (s, 1H), 7.32 (d, 1H), 7.36 (d, 1H), 7.53 (d, 2H), 7.63 (d, 1H), 12.23 (s, 2H).

Example 40(68)

4-[3-(carboxymethyl)-4-((E)-2-{4-[4-(2-chloro-3,5-dimethylphenoxy)butoxy]phenyl}vinyl)-1H-indol-1-yl]butanoic acid TLC: Rf 0.55 (dichloromethane:methanol:acetic acid=9:1:0.05); $^1$H-NMR (DMSO-$d_6$): δ 1.87-2.01 (m, 6H), 2.20 (t, 2H), 3.83 (s, 2H), 4.04-4.23 (m, 6H), 6.94 (d, 2H), 6.99-7.09 (m, 3H), 7.13 (dd, 1H), 7.26 (s, 1H), 7.32 (d, 1H), 7.36 (d, 1H), 7.53 (d, 2H), 7.63 (d, 1H), 12.22 (s, 2H).

Example 40(69)

4-[4-((E)-2-{4-[3-(4-acetyl-3-hydroxy-2-propylphenoxy)propoxy]phenyl}vinyl)-3-(carboxymethyl)-1H-indol-1-yl]butanoic acid TLC: Rf 0.45 (methanol: dichloromethane=1:9); $^1$H-NMR (DMSO-$d_6$): δ 0.85 (t, 3), 137-1.53 (m, 2H), 1.88-2.02 (m, 2H), 2.14-2.31 (m, 4H), 2.51-2.56 (m, 2H), 2.57 (s, 3H), 3.83 (s, 2H), 4.10-4.22 (m, 4H), 4.26 (t, 2H), 6.68 (d, 1H), 6.95 (d, 2H), 7.06 (d, 1H), 7.13 (t, 1H), 7.26 (s, 1H), 7.32 (d, 1H), 7.36 (d, 1H), 7.54 (d, 2H), 7.64 (d, 1H), 7.80 (d, 1H), 12.22 (brs, 2H), 12.82 (s, 1H).

Example 40(70)

4-[4-((E)-2-{4-[4-(2-acetyl-6-chlorophenoxy)butoxy]phenyl}vinyl-3-carboxymethyl)-1H-indol-1-yl]butanoic acid TLC: Rf 0.55 (dichloromethane:methanol:acetic acid=9:1:0.05); $^1$H-NMR (DMSO-$d_6$): δ 1.85-2.01 (m, 6H),2.20 (t, 2H), 2.58 (s, 3H), 3.84 (s, 2H), 4.00 (t, 2H), 4.07 (t, 2H), 4.14 (t, 2H), 6.94 (d, 2H), 7.06 (dc, 1H) 7.13 (dd, 1H), 7.19-7.41 (m, 4H), 7.47-7.75 (m, 5H), 12.24 (s, 2H).

Example 40(71)

4-[3-carboxymethyl)-4-((E)-2-{4-[4-(2,6-dichloro-4-methylphenoxy)butoxy]phenyl}vinyl)-1H-indol-1-yl]butanoic acid TLC: Rf 0.42 (dichloromethane:methanol:acetic acid=9:1:0.05); $^1$H-NMR (DMSO-$d_6$): δ 1.88-2.01 (m, 6H), 2.20 (t, 2H), 2.26 (s, 3H), 3.83 (s, 2H), 4.00 (t, 2H), 4.08 (t, 2H), 4.14 (t, 2H), 6.94 (d, 2H), 7.06 (d, 1H), 7.13 (dd, 1H), 7.26 (s, 1H), 7.29-7.39 (m, 4H), 7.53 (d, 2H), 7.64 (d, 1H), 12.22 (s, 2H).

Example 40(72)

4-[3-carboxymethyl)-4-((E)-2-{4-[4-(2,6-dichloro-4-fluorophenoxy)butoxy]phenyl}vinyl)-1H-indol-1-yl]butanoic acid TLC: Rf 0.47 (dichloromethane:methanol:acetic acid=9:1:0.05); $^1$H-NMR (DMSO-$d_6$): δ 1.85-2.00 (m, 6H), 2.20 (t, 2H), 3.83 (s, 2H), 4.02 (t, 2H), 4.08 (t, 2H), 4.14 (t 2H), 6.95 (d, 2H), 7.06 (d, 1H), 7.13 (dd, 1H), 7.26 (s, 1H), 7.32 (d, 1H), 7.36 (d, 1H), 7.48-7.57 (m, 4H), 7.64 (d, 1H), 12.22 (s, 2H).

Example 40(73)

4-[4-((E)-2-{4-[4-(2-acetyl-6-methylphenoxy)butoxy]phenyl}vinyl)-3-(carboxymethyl-1H-indol-1-yl]butanoic acid TLC: Rf 0.49 (dichloromethane:methanol:acetic acid=9:1:0.05); $^1$H-NMR (DMSO-$d_6$): δ 1.83-2.00 (m, 6H), 2.20 (t, 2H), 2.28 (s, 3H), 2.55 (s, 3H), 3.77-3.89 (m, 4H), 4.01-4.08 (m, 2H), 4.14 (t, 2H), 6.90-6.98 (m, 2H), 7.02-7.17 (m, 3H), 7.26 (s, 1H), 7.30-7.44 (m, 4H), 7.50-7.56 (m, 2H), 7.63 (d, 1H), 12.24 (s, 2H).

Example 40(74)

4-[4-((E)-2-{4-[4-(2-acetyl-4-fluoro-6-methylphenoxy)butoxy]phenyl}vinyl)-3-(carboxymethyl)-1H-indol-1-yl]butanoic acid TLC: Rf 0.43 (dichloromethane:methanol:acetic acid=9:1:0.05); $^1$H-NMR (DMSO-$d_6$): δ 1.81-2.01 (m, 6H), 2.20 (t, 2H), 2.28 (s, 3H), 2.56 (s, 3H), 3.77-3.86 (m, 4H), 4.06 (t, 2H), 4.14 (t, 2H), 6.94 (d, 2H), 7.06 (d, 1H), 7.10-7.21 (m, 2H), 7.24-7.39 (m, 4H), 7.53 (d, 2H), 7.63 (d, 1H), 12.22 (s, 2H).

Example 40(75)

4-[4-((E)-2-{4-[4-(2-acetyl-3-fluorophenoxy)butoxy]phenyl}vinyl)-3-carboxymethyl)-1H-indol-1-yl]butanoic acid TLC: Rf 0.46 (dichloromethane:methanol:acetic acid=9:1:0.05); $^1$H-NMR (DMSO-$d_6$): δ 1.81-2.02 (m, 6H), 2.20 (t, 2H), 2.47 (s, 3H), 3.83 (s, 2H), 4.05 (t 2H), 4.09-4.19 (m, 4H), 6.85 (dd, 1H), 6.93 (d, 2H), 6.97 (d, 1H), 7.06 (d, 1H), 7.13 (dd, 1H), 7.26 (s, 1H), 729-7.47 (m, 3H), 7.53 (d, 2H), 7.64 (d, 1H) 12.22 (s, 2H).

Example 40(76)

4-[3-(carboxymethyl)-4-((E)-2-{4-[4-(3,4-dimethylphenoxy)butoxy]phenyl}vinyl)-1H-indol-1-yl]butanoic acid TLC: Rf 0.48 (dichloromethane:methanol:acetic acid=9:1:0.05); $^1$H-NMR (DMSO-$d_6$): δ 1.80-2.00 (m, 6H), 2.12 (s, 3H), 2.16 (s, 3H), 2.20 (t, 2H), 3.83 (s, 2H), 3.93-4.00 (m, 2H), 4.05 (t, 2H), 4.14 (t, 2H), 6.64 (dd, 1H), 6.73 (d, 1H), 6.94 (d, 2H), 7.00 (d, 1H), 7.06 (d, 1H), 7.13 (dd, 1H), 7.26 (s, 1H), 7.32 (d, 1H), 7.35 (d, 1H), 7.53 (d, 2H), 7.64 (d, 1H), 12.20 (s, 2H).

Example 40(77)

4-[3-(carboxymethyl)-4-((E)-2-{4-[4-(3,4,5-trimethylphenoxy)butoxy]phenyl}vinyl)-1H-indol-1-yl]butanoic acid TLC: Rf 0.53 (dichloromethane:methanol:acetic acid=9:1:0.05); $^1$H-NMR (DMSO-$d_6$): δ 1.74-2.00 (m, 6H), 2.02 (s, 3H), 2.13-2.24 (m, 8H), 3.83 (s, 2H), 3.91-3.99 (m, 2H), 4.01-4.08 (m, 2H), 4.14 (t, 2H), 6.57 (s, 2H), 6.94 (d, 2H), 7.06 (d, 1H), 7.13 (dd, 1H), 7.26 (s, 1H), 7.32 (d, 1H), 7.35 (d, 1H), 7.53 (d, 2H), 7.64 (d, 1H), 12.22 (s, 2H).

Example 40(78)

4-[3-(carboxymethyl)-4-((E)-2-{4-[4-(3,5-dimethylphenoxy)butoxy]phenyl}vinyl)-1H-indol-1-yl]butanoic acid TLC: Rf 0.30 (dichloromethane:methanol:acetic acid=9:1:0.05); $^1$H-NMR (DMSO-$d_6$): δ 1.79-1.88 (m, 4H), 1.89-2.03 (m, 2H), 2.16-2.23 (m, 8H), 3.83 (s, 2H), 3.92-4.01 (m, 2H), 4.02-4.08 (m, 2H), 4.14 (t, 2H), 6.54 (s, 3H), 6.94 (d, 2H), 7.06 (d, 1H), 7.12 (dd, 1H), 7.26 (s, 1H), 7.32 (d, 1H), 7.35 (d, 1H), 7.53 (d, 2H), 7.64 (d, 1H), 12.17 (s, 2H).

Example 40(79)

4-[3-(carboxymethyl)-4-((E)-2-{4-[4-(3,4-difluorophenoxy)butoxy]phenyl}vinyl)-1H-indol-1-yl]butanoic acid TLC: Rf 0.36 (dichloromethane:methanol:acetic acid=9:1:0.05); $^1$H-NMR (DMSO-$d_6$): δ 1.82-2.00 (m, 6H), 2.20 (t, 2H), 3.83 (s, 2H), 3.97-4.08 (m, 4H), 4.14 (t, 2H), 6.71-6.83 (m, 1H), 6.94 (d, 2H), 7.01-7.16 (m, 3H), 7.23-7.39 (m, 4H), 7.53 (d, 2H), 7.64 (d, 1H), 12.14 (s, 2H).

Example 40(80)

4-[3-(carboxymethyl)-4-((E)-2-{4-[4-(2,3,4-trifluorophenoxy)butoxy]phenyl}vinyl)-1H-indol-1-yl]butanoic acid TLC: Rf 0.50 (dichloromethane:methanol:acetic acid=9:1:0.05); $^1$H-NMR (DMSO-$d_6$): δ 1.82-2.01 (m, 6H), 2.19 (t, 2H), 3.83 (s, 2H), 4.02-4.09 (m, 2H), 4.10-4.17 (m, 4H), 6.93 (d, 2H), 6.99-7.09 (m, 2H), 7.12 (dd, 1H), 7.18-7.30 (m, 2H), 7.32 (d, 1H), 7.35 (d, 1H), 7.53 (d, 2H), 7.64 (d, 1H), 12.33 (s, 2H).

Example 40(81)

4-[3-(carboxymethyl)-4-((E)-2-{4-[4-(4-fluoro-3-methylphenoxy-butoxy]phenyl}vinyl)-1H-indol-1-yl]butanoic acid TLC: Rf 0.44 (dichloromethane:methanol:acetic acid=9:1:0.05); $^1$H-NMR (DMSO-$d_6$): δ 1.74-2.02 (m, 6H), 2.13-2.24 (m, 5H), 3.83 (s, 2H), 3.94-4.01 (m, 2H), 4.02-4.10 (m, 2H), 4.14 (t, 2H), 6.74 (ddd, 1H), 6.84 (dd, 1H), 6.94 (d, 2H), 6.98-7.09 (m, 2H), 7.13 (dd, 1H), 7.26 (s, 1H), 7.32 (d, 1H), 7.36 (d, 1H), 7.53 (d, 2H), 7.64 (d, 1H), 12.16 (s, 2H).

Example 40(82)

4-[3-(carboxymethyl)-4-((E)-2-{4-[4-(3-fluoro-4-methylphenoxy)butoxy]phenyl}vinyl)-1H-indol-1-yl]butanoic acid TLC: Rf 0.44 (dichloromethane:methanol:acetic acid=9:1:0.05); $^1$H-NMR (DMSO-$d_6$): δ 1.77-2.01 (m, 6H), 2.13 (d, 3H), 2.16-2.23 (m, 2H), 3.83 (s, 2H), 3.95-4.08 (m, 4H), 4.14 (t 2H), 6.69 (dd, 1H), 6.76 (dd, 1H), 6.94 (d, 2H), 7.01-7.19 (m, 3H), 7.26 (s, 1H), 7.32 (d, 1H), 7.36 (d, 1H), 7.53 (d, 2H), 7.64 (d, 1H), 12.24 (s, 2H).

Example 40(83)

4-[3-(carboxymethyl)-4-((E)-2-{4-[4-(2,4,5-trimethylphenoxy)butoxy]phenyl}vinyl)-1H-indol-1-yl]butanoic acid TLC: Rf 0.42 (dichloromethane:methanol:acetic acid=9:1:0.05); $^1$H-NMR (DMSO-$d_6$): δ 1.79-2.00 (m, 6H), 2.07 (s, 3H), 2.09 (s, 3H), 2.15 (s, 3H), 2.20 (t, 2H), 3.83 (s, 2H), 3.92-4.01 (m, 2H), 4.03-4.09 (m, 2H), 4.14 (t, 2H), 6.71 (s, 1H), 6.86 (s, 1H), 6.94 (d, 2H), 7.06 (d, 1H), 7.13 (dd, 1H), 7.26 (s, 1H), 7.32 (d, 1H), 7.35 (d, 1H), 7.53 (d, 2H), 7.63 (d, 1H), 12.21 (s, 2H).

Example 40(84)

4-[3-(carboxymethyl)-4-((E)-2-{4-[4-(2-methoxyphenoxy)butoxy]phenyl}vinyl)-1H-indol-1-yl]butanoic acid TLC: Rf 0.50 (dichloromethane:methanol:acetic acid=9:1:0.05); $^1$H-NMR (DMSO-$d_6$): δ 1.79-2.01 (m, 6H), 2.20 (t, 2H), 3.74 (s, 3H), 3.83 (s, 2H), 3.96-4.03 (m, 2H), 4.05-4.10 (m, 2H), 4.14 (t, 2H), 6.78-6.99 (m, 6H), 7.06 (d, 1H), 7.13 (dd, 1H), 7.26 (s, 1H), 7.32 (d, 1H), 7.35 (d, 1H), 7.53 (d, 2H), 7.64 (d, 1H), 12.17 (s, 2H).

Example 40(85)

4-[4-((E)-2-{4-[4-(3-acetylphenoxy)butoxy]phenyl}vinyl)-3-(carboxymethyl)-1H-indol-1-yl]butanoic acid TLC: Rf 0.48 (dichloromethane:methanol:acetic acid=9:1:0.05); $^1$H-NMR (DMSO-$d_6$): δ 1.84-2.02 (m, 6H), 2.20 (t, 2H), 2.56 (s, 3H), 3.83 (s, 2H), 4.03-4.18 (m, 6H), 6.94 (d, 2H), 7.06 (d, 1H), 7.13 (dd, 1H), 7.18-7.24 (m, 1H), 7.26 (s, 1H), 7.32 (d, 1H), 7.36 (d, 1H), 7.40-7.47 (m, 2H), 7.50-7.57 (m, 3H), 7.63 (d, 1H), 12.21 (s, 2H).

Example 40(86)

4-[3-carboxymethyl-4-((E)-2-{4-[4-(4-chlorophenoxy) butoxy]phenyl}vinyl)-1H-indol-1-yl]butanoic acid TLC: Rf 0.50 (dichloromethane:methanol:acetic acid=9:1:0.05); $^1$H-NMR (DMSO-$d_6$): δ 1.78-2.03 (m, 6H), 2.20 (t, 2H), 3.83 (s, 2H), 3.96-4.09 (m, 4H), 4.14 (t, 2H), 6.88-6.99 (m, 4H), 7.06 (d, 1H), 7.13 (dd, 1H), 7.22-7.39 (m, 5H), 7.53 (d, 2H), 7.64 (d, 1H), 12.17 (s, 2H).

Example 40(87)

4-[3-carboxymethyl-4-((E)-2-{4-[4-(3-ethylphenoxy)butoxy]phenyl}vinyl)-1H-indol-1-yl]butanoic acid TLC: Rf 0.51 (dichloromethane:methanol:acetic acid=9:1:0.05); $^1$H-NMR (DMSO-$d_6$): δ 1.15 (t 3H), 1.78-2.04 (m, 6H), 2.20 (t, 2H), 2.55 (q, 2H), 3.83 (s, 2H), 3.94-4.08 (m, 4H), 4.14 (t, 2H), 6.66-6.82 (m, 3H), 6.94 (d, 2H), 7.06 (d, 1H), 7.10-7.21 (m, 2H), 7.26 (s, 1H), 7.32 (d, 1H), 7.35 (d, 1H), 7.53 (d, 2H), 7.64 (d, 1H), 12.22 (s, 2H).

Example 40(88)

4-[3-carboxymethyl-4-((E)-2-{4-[4-(3-methoxyphenoxy)butoxy]phenyl}vinyl)-1H-indol-1-yl]butanoic acid TLC: Rf 0.55 (dichloromethane:methanol:acetic acid=9:1:0.05); $^1$H-NMR (DMSO-$d_6$): δ 1.79-2.01 (m, 6H), 2.20 (t, 2H), 3.72 (s, 3H), 3.83 (s, 2H), 3.98-4.10 (m, 4H), 4.14 (t, 2H), 6.46-6.59 (m, 3H), 6.94 (d, 2H), 7.06 (d, 1H), 7.10-7.20 (m, 2H), 7.26 (s, 1H), 7.32 (d, 1H), 7.36 (d, 1H), 7.53 (d, 2H), 7.64 (d, 1H), 12.20 (s, 2H).

Example 40(89)

[1-{[1-(carboxymethyl)cyclopropyl]methyl}-4-((E)-2-{4-[4-(mesityloxy)butoxy]phenyl}vinyl)-1H-indol-3-yl]acetic acid TLC: Rf 0.45 (dichloromethane:methanol:acetic acid=90:10:1); $^1$H-NMR (DMSO-$d_6$): δ 0.4-40.54 (m, 2H), 0.61-0.71 (m, 2H), 1.77-2.00 (m, 4H), 2.05 (s, 2H), 2.17 (s, 9H), 3.74 (t, 2H), 3.85 (s, 2), 4.07 (t, 2H), 4.16 (s, 214), 6.80 (s, 2H), 6.95 (d, 2H), 7.06 (d, 1H), 7.12 (d, 1H), 7.26-7.38 (m, 31H), 7.53 (d, 2H), 7.64 (d, 1H), 12.27 (brs, 2H).

Example 40(90)

4-[3-(carboxymethyl)-4-((E)-2-{4-[4-(4-fluorophenoxy)butoxy]phenyl}vinyl)-1H-indol-1-yl]butanoic acid TLC: Rf 0.53 (dichloromethane:methanol:acetic acid=9:1:0.05); $^1$H-NMR (DMSO-$d_6$): δ 1.74-2.06 (m, 6H), 2.20 (t, 2H), 3.83 (s, 2H), 3.95-4.09 (m, 4H), 4.14 (t, 2H), 6.88-7.17 (m, 8H), 7.26 (s, 1H), 7.32 (d, 1H), 7.35 (d, 1H), 7.53 (d, 2H), 7.64 (d, 1H), 12.35 (s, 2H).

Example 40(91)

4-[3-(carboxymethyl)-4-((E)-2-{4-[4-(3-fluorophenoxy)butoxy]phenyl}vinyl)-1H-indol-1-yl]butanoic acid TLC: Rf 0.51 (dichloromethane:methanol:acetic acid=9:1:0.05); $^1$H-NMR (DMSO-$d_6$): δ 1.76-2.02 (m, 6H), 2.19 (t, 2H), 3.83 (s, 2H), 3.99-4.09 (m, 4H), 4.14 (t, 2H), 6.58-6.85 (m, 3H), 6.94 (d, 2H), 7.06 (d, 1H), 7.12 (dd, 1H), 7.22-7.34 (m, 3H), 7.35 (d, 1H), 7.53 (d, 2H), 7.64 (d, 1H), 12.23 (s, 2H).

Example 40(92)

4-[3-(carboxymethyl)-4-((E)-2-{4-[4-(2,3-difluoro-4-methylphenoxy)butoxy]phenyl}vinyl)-1H-indol-1-yl]butanoic acid TLC: Rf 0.49 (dichloromethane:methanol:acetic acid=9:1:0.05); $^1$H-NMR (DMSO-$d_6$): δ 1.79-2.00 (m, 6H), 2.13-2.26 (m, 5H), 3.83 (s, 2H), 3.97-4.18 (m, 6H), 6.84-7.01 (m, 4H), 7.06 (d, 1H), 7.12 (d, 1H), 7.26 (s, 1H), 7.32 (d, 1H), 7.36 (d, 1H), 7.53 (d, 2H), 7.64 (d, 1H), 11.97 (s, 2H).

Example 40(93)

4-[3-(carboxymethyl)-4-((E)-2-{4-[4-(3-chloro-2-fluorophenoxy)butoxy]phenyl}vinyl)-1H-indol-1-yl]butanoic acid TLC: Rf 0.41 (methanol: dichloromethane:acetic acid=1:9:0.1); $^1$H-NMR (DMSO-$d_6$): δ 12.24 (brs, 2H), 7.64 (d, 1H), 7.53 (d, 2H), 7.34 (dd, 2H), 7.27 (s, 1H), 7.23-7.00 (m, 5H), 6.93 (d, 2H), 422-3.98 (m, 6H), 3.84 (s, 2H), 2.20 (t, 2H), 2.03-1.80 (m, 6H).

Example 40(94)

4-(3-(carboxymethyl)-4-{(E)-2-[4-(2,3-dihydro-1H-inden-2-ylmethoxy)phenyl]vinyl}-1H-indol-1-yl) butanoic acid TLC: Rf 0.48 (methanol: dichloromethane:acetic acid=1:9:0.1); $^1$H-NMR (DMSO-$d_6$): δ 1220 (brs, 2H), 7.63 (d, 1H), 7.53 (d, 2H), 7.40-7.29 (m, 2H), 7.29-7.18 (m, 3H), 7.18-7.01 (m, 4H), 6.96 (d, 2H), 4.13 (m, 2H), 4.00 (d, 2H), 3.83 (s, 2H), 3.08 (dd, 2H), 2.98-2.82 (m, 1H), 2.79 (dd, 2H), 2.20 (t, 2H), 1.94 (quintet, 2H).

Example 40(95)

4-[3-(carboxymethyl)-4-((E)-2-{4-[2-(2,3-dihydro-1H-inden-2-yl)ethoxy]phenyl}vinyl)-1H-indol-1-yl] butanoic acid TLC: Rf 0.47 (methanol: dichloromethane:acetic acid=1:9:0.1); $^1$H-NMR (DMSO-$d_6$): δ 12.24 (brs, 2H), 7.64 (d, 1H), 7.54 (d, 2H), 7.40-7.29 (m, 2H), 7.27 (s, 1H), 7.23-7.01 (m, 6H), 6.96 (d, 2H), 4.14 (t, 2H), 4.09 (t, 2H), 3.84 (s, 2H), 3.12-2.95 (m, 2H), 2.70-2.50 (m, 3H), 2.20 (t, 2H), 2.02-1.86 (m, 4H).

Example 40(96)

4-[3-(carboxymethyl)-4-((E)-2-{4-[3-(2,3-dihydro-1H-inden-2-yl)propoxy]phenyl}vinyl)-1H-indol-1-yl]butanoic acid TLC: Rf 0.57 (methanol: dichloromethane:acetic acid=1:9:0.1); $^1$H-NMR (DMSO-$d_6$): δ 12.23 (brs, 2H), 7.63 (d, 1H), 7.53 (d, 2H), 7.36 (d, 1H), 7.32 (d, 1H), 7.26 (s, 1H), 7.23-7.00 (m, 6H), 6.93 (d, 2H), 4.14 (t, 2H), 4.02 (t, 2H), 3.84 (s, 2H), 3.02 (dd, 2H), 2.55 (dd, 2H), 2.54-2.34 (m, 1H), 2.20 (t, 2H), 1.94 (quintet, 2H), 1.87-1.73 (m, 2H), 1.68-1.54 (m, 2H).

Example 40(97)

4-[3-carboxymethyl)-4-((E)-2-{4-[4-(4-fluoro-2,6-dimethylphenoxy)butoxy]phenyl}vinyl)-1H-indol-1-yl]butanoic acid TLC: Rf 0.47 (dichloromethane:methanol:acetic acid=9:1:0.05); $^1$H-NMR (DMSO-$d_6$): δ 1.83-2.02 (m, 6H), 2.16-2.25 (m, 8H), 3.76 (t, 2H), 3.83 (s, 2H), 4.07 (t, 2H), 4.14 (t, 2H), 6.85 (d, 2H), 6.95 (d, 2H), 7.06 (d, 1H), 7.13 (dd, 1H), 7.26 (s, 1H), 7.32 (d, 1H), 7.36 (d, 1H), 7.53 (d, 2H), 7.64 (d, 1H), 12.30 (s, 2H).

Example 40(98)

4-[3-carboxymethyl)-4-((E)-2-{4-[4-(3-fluoro-2-methylphenoxy)butoxy]phenyl}vinyl)-1H-indol-1-yl]butanoic acid TLC: Rf 0.48 (dichloromethane:methanol:acetic acid=9:1:0.05); $^1$H-NMR (DMSO-$d_6$): δ 1.83-2.01 (m, 6H), 2.05 (d, 3H), 2.20 (t, 2H), 3.83 (s, 2H), 4.00-4.11 (m, 4H), 4.14 (t, 2H), 6.73 (dd, 1H), 6.81 (d, 1H), 6.94 (d, 2H), 7.06 (d, 1H), 7.09-7.20 (m, 2H), 7.26 (s, 1H), 7.32 (d, 1H), 7.36 (d, 1H), 7.53 (d, 2H), 7.63 (d, 1H),12.25 (s, 2H).

Example 41 ethyl 4-(7-bromo-1H-indol-3-yl)-4-oxobutanoate

To a dichloromethane (50 mL) solution of aluminum chloride (6.80 g), succinic acid monoethyl ester chloride (8.39 g) was added under ice cooling and the mixture was stirred for 30 minutes. To the mixture, 7-bromoindole (5.0 g) was added, followed by stirring at room temperature for 5 hours. To the reaction mixture, ice water and ethyl acetate were added, followed by extraction with ethyl acetate. The organic layer was washed in turn with water and saturated saline, dried over anhydrous sodium sulfate and then concentrated. The residue was washed with diisopropyl ether to obtain the titled compound having the following physical properties (6.04 g).

TLC: Rf 0.53 (n-hexane:ethyl acetate 1:1); $^1$H-NMR ($CDCl_3$): δ 1.27 (t, 3H), 2.79 (t, 2H), 3.23 (t, 2H), 4.17 (q, 2H), 7.16 (t, 1H), 7.43 (dd, 1H), 7.96 (d, 1H), 8.32 (dd, 1H), 8.72 (1H).

Example 42 ethyl 4-(7-bromo-1H-indol-3-yl)butanoate

To a tetrahydrofuran (20 mL) solution of the compound (700 mg) prepared in Example 41, sodium borohydride (106 mg) was added at −30° C. and a boron trifluoride-diethyl ether complex (0.82 mL) was further added dropwise at −30° C., and then the mixture was stirred at 0° C. for 2 hours. To the reaction mixture, an aqueous saturated ammonium chloride solution was added, followed by extraction with ethyl acetate. The organic layer was washed in turn with water and saturated saline, dried over anhydrous sodium sulfate and then concentrated. The residue was purified by silica gel column chromatography (n-hexane:ethyl acetate=90:10→85:15) to obtain the titled compound having the following physical properties (483 mg).

TLC: Rf 0.53 (n-hexane:ethyl acetate=2:1); $^1$H-NMR ($CDCl_3$): δ 1.24 (t, 3H), 1.98-2.08 (m, 2H), 2.36 (t, 2H), 2.78 (t, 2H), 4.12 (q, 2H), 6.99 (t, 1H), 7.04-7.08 (m, 1H), 7.34 (dd, 1H), 7.54 (dd, 1H).

Example 43 ethyl 4-{7-bromo-1-[2-(ethyloxy)-2-oxoethyl]-1H-indol-3-yl}butanoate

The same operation as in Example 37 was conducted to obtain the titled compound. In place of ethyl 7-bromo-3-[4-(ethyloxy)-4-oxobutanoyl]-1H-indole-2-carboxylate, the compound prepared in Example 42 was used and methyl 2-bromoacetate was used in place of methyl iodide.

Example 44

4-(1-(carboxymethyl)-7-{(E)-2-[4-(4-phenoxybutoxy)phenyl]vinyl}-1H-indol-3-yl)butanoic acid

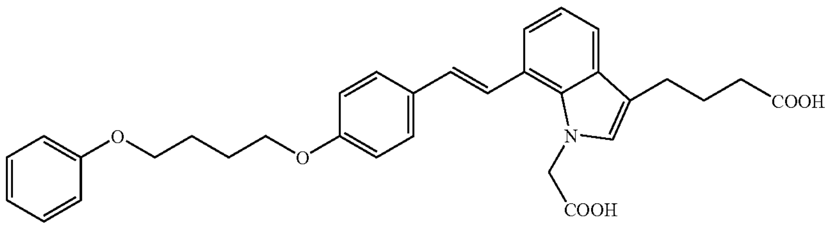

The same operation as in Example 3→Example 6 was conducted to obtain the titled compound having the following physical properties. In the step corresponding to Example 3 in the operation, the compound prepared in Example 43 was used in place of the compound prepared in Example 2 and 1-(4-phenoxybutoxy)-4-vinylbenzene was used in place of 4-vinylphenyl acetate.

TLC: Rf 0.50 (dichloromethane:methanol:acetic acid=90:10:1); $^1$H-NMR (DMSO-$d_6$): δ 1.73-1.94 (, 6H), 2.28 (t, 2H), 2.67 (t, 2H), 3.92-4.13 (m, 4H), 5.12 (s, 2H), 6.84-6.98 (m, 6H), 7.02 (t, 1H), 7.08 (s, 1H), 7.21-7.33 (m, 3H), 7.40-7.60 (m, 4H).

Example 44(1) to Example 44(95)

Using a corresponding compound, the same operation as in Example 41→Example 42→Example 43→Example 44 was conducted to obtain the titled compound having the following physical properties.

Example 44(1)

4-[1-carboxymethyl)-7-((E)-2-{4-[4-(mesityloxy)butoxy]phenyl}vinyl)-1H-indol-3-yl]butanoic acid TLC: Rf 0.44 (dichloromethane:methanol:acetic acid=90:10:1); $^1$H-NMR (DMSO-$d_6$): δ 1.76-2.00 (m, 6H), 2.16 (s, 9H), 2.27 (t, 2H), 2.66 (t, 2H), 3.73 (t, 2H), 4.07 (t, 2H), 5.11 (s, 2H), 6.79 (s, 2H), 6.86-6.98 (m, 3H), 7.01 (t, 1H), 7.07 (s, 1H), 7.25 (d, 1H), 7.40-7.57 (m, 4H).

Example 44(2)

4-[1-(carboxymethyl)-7-((E)-2-{4-[4-(2-chlorophenoxy)butoxy]phenyl}vinyl)-1H-indol-3-yl]butanoic acid

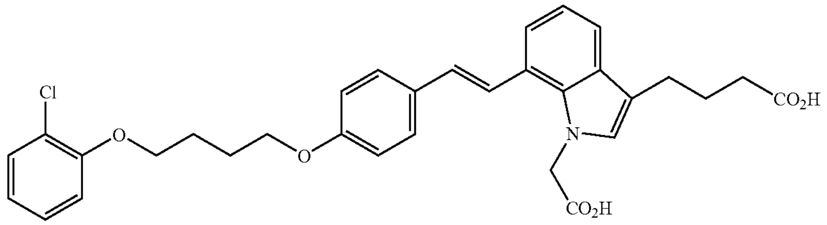

TLC: Rf 0.48 (dichloromethane:methanol:acetic acid=90:10:1); $^1$H-NMR (DMSO-$d_6$): δ 1.75-2.01 (m, 6H), 2.28 (t, 2H), 2.67 (t, 2H), 3.99-4.21 (m, 4H), 5.12 (s, 2H), 6.87-6.97 (m, 4H), 7.02 (t, 1H) 7.08 (s, 1H), 7.13-7.18 (m, 1H), 7.23-7.34 (m, 2H), 7.38-7.58 (m, 5H).

Example 44(3)

4-[1-(carboxymethyl)-7-((E)-2-{4-[4-(2,3-difluorophenoxy)butoxy]phenyl}vinyl)-1H-indol-3-yl]butanoic acid

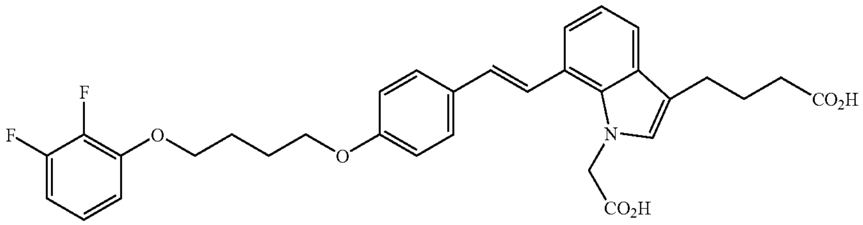

TLC: Rf 0.45 (dichloromethane:methanol:acetic acid=90:10:1); $^1$H-NMR (DMSO-$d_6$): δ 1.77-1.96 (m, 6H), 2.28 (t, 2H), 2.66 (t, 2H), 4.06 (t, 2H), 4.16 (t, 2H), 5.09 (s, 2H), 6.86-7.19 (m, 8H) 7.26 (d, 1H), 7.41-7.58 (m, 4H).

Example 44(4)

4-[1-(carboxymethyl)-7-((E)-2-{4-[4-(3-chloro-2-methylphenoxy)butoxy]phenyl}vinyl)-1H-indol-3-yl]butanoic acid TLC: Rf 0.31 (dichloromethane:methanol=9:1); $^1$H-NMR (DMSO-$d_6$-): δ 1.75-1.99 (m, 6H), 2.20 (s, 3H), 2.28 (t, 2H), 2.67 (t, 2H), 4.07 (s, 4H), 5.13 (s, 2H), 6.81-7.10 (m, 7H), 7.16 (t, 1H), 7.26 (d, 1H), 7.39-7.59 (m, 4H).

Example 44(5)

4-[1-(carboxymethyl)-7-((E)-2-{4-[4-(2-chloro-3,6-difluorophenoxy)butoxy]phenyl}vinyl)-1H-indol-3-yl]butanoic acid TLC: Rf 0.31 (dichloromethane:methanol=9:1); $^1$H-NMR (DMSO-$d_6$): δ 1.76-2.01 (m, 6H), 2.28 (t, 2H), 2.67 (t 2H), 4.02-4.12 (m, 2H), 4.15-4.25 (m, 2H), 5.13 (s, 2H), 6.85-6.97 (m, 3H), 7.02 (t, 1H), 7.08 (s, 1H), 7.15-7.31 (m, 2H), 7.31-7.43 (m, 1H), 7.43-7.57 (m, 4H).

Example 44(6)

4-[1-(carboxymethyl)-7-((E)-2-{4-[4-(mesityloxy) butoxy]phenyl}vinyl)-1H-indol-3-yl]butanoic acid TLC: RF 0.53 dichloromethane:methanol:acetic acid=90: 10:1); $^1$H-NMR (DMSO-$d_6$): δ 1.74-2.01 (m, 6H), 2.17 (s, 9H), 2.26 (t, 2H), 2.74 (t, 2H), 3.74 (t, 2H), 4.06 (t, 2H), 5.10 (s, 2H), 6.71-6.82 (m, 3H), 6.85 (d, 1H), 6.94 (d, 2H), 7.08 (s, 1H), 7.17 (dd, 1H), 7.41-7.54 (m, 3H).

Example 44(7)

4-[1-(carboxymethyl)-7-((E)-2-{4-[4-(2,3-difluorophenoxy-butoxy]phenyl}vinyl)-4-fluoro-1H-indol-3-yl]butanoic acid

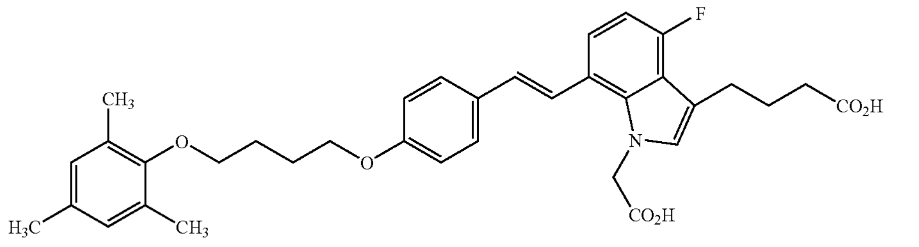

TLC: Rf 0.46 (dichloromethane:methanol:acetic acid=90: 10:1); $^1$H-NMR (DMSO-$d_6$): δ 1.75-2.02 (m, 6H), 2.26 (t 2H), 2.74 (t, 2H),4.05 (t 2H), 4.16 (t 2H), 5.09 (s, 2H), 6.76 (dd, 1H), 6.85 (d, 1H), 6.89-7.22 (m, 7H), 7.40-7.52 (m, 3H).

Example 44(8)

4-[1-(carboxymethyl)-7-((E)-2-{4-[4-(2-chloro-3,5-difluorophenoxy)butoxy]phenyl}vinyl)-1H-indol-3-yl]butanoic acid

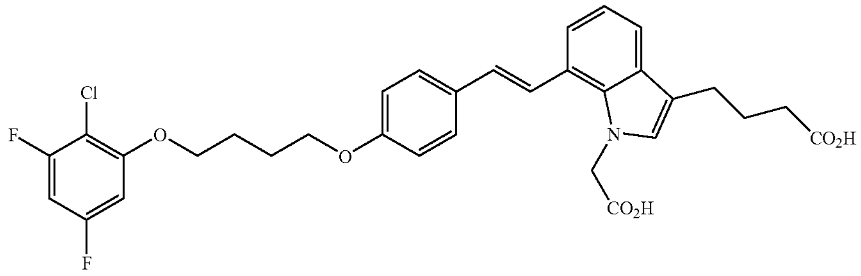

TLC: Rf 0.32 (dichloromethane:methanol=9:1); $^1$H-NMR (DMSO-$d_6$): δ 1.78-1.98 (m, 6H), 2.28 (t, 2H), 2.67 (t, 2H), 4.02-4.13 (m, 2H), 4.14-4.23 (m, 2H), 5.13 (s, 2H), 6.93 (d, 1H), 6.94 (d, 2H), 6.97-7.12 (m, 4H), 7.26 (d, 1H), 7.46 (d, 1H), 7.49 (d, 2H), 7.51 (d, 1H), 12.02 (s, 1H), 12.98 (s, 1H).

Example 44(9)

4-[1-carboxymethyl)-7-((E)-2-{4-[4-(2,3-dichlorophenoxy)butoxy]phenyl}vinyl)-1H-indol-3-yl] butanoic acid TLC: Rf 0.38 (dichloromethane:methanol=9:1); $^1$H-NMR (DMSO-$d_6$): δ 1.77-1.98 (m, 6H), 2.28 (t 2H), 2.67 (t 2H), 4.03-4.12 (m, 2H), 4.12-4.21 (m, 2H), 5.13 (s, 2H), 6.92 (d, 1H), 6.94 (d, 2H), 7.02 (t, 1H), 7.08 (s, 1H), 7.15 (dd, 1H), 7.19 (dd, 1H), 7.26 (d, 1H), 7.32 (t, 1H), 7.45 (dd, 1H), 7.49 (d, 2H), 7.52 (d, 1H), 12.05 (s, 1H), 12.95 (s, 1H).

Example 44(10)

4-[1-carboxymethyl)-7-((E)-2-{4-[4-(2,6-dichlorophenoxy)butoxy]phenyl}vinyl)-1H-indol-3-yl] butanoic acid TLC: Rf 0.34 (dichloromethane:methanol=9:1); $^1$H-NMR (DMSO-$d_6$): δ 1.77-2.03 (m, 6H), 2.28 (t 2H), 2.67 (t, 2H), 3.96-4.17 (m, 4H), 5.13 (s, 2H), 6.92 (d, 1H), 6.95 (d, 2H), 7.02 (t, 1H), 7.08 (s, 1H), 7.17 (dd, 1H), 7.26 (d, 1H), 7.39-7.59 (m, 6H), 12.05 (s, 1H), 12.95 (s, 1H).

Example 44(11)

4-[1-(carboxymethyl)-7-((E)-2-{4-[4-(2-methylphenoxy)butoxy]phenyl}vinyl)-1H-indol-3-yl]butanoic acid TLC: Rf 0.55 (methanol: dichloromethane:acetic acid=1:9:0.1); $^1$H-NMR (DMSO-$d_6$): δ 12.41 (brs, 2H), 7.52 (d, 1H), 7.49 (d, 2H), 7.45 (d, 1H), 7.26 (d, 1H), 7.18-7.06 (m, 3H), 7.02 (t, 1H), 6.98-6.86 (m, 4H), 6.81 (t, 1H), 5.12 (s, 2H), 4.12-3.96 (m, 4H), 2.67 (t, 2H), 2.28 (t 2H), 2.14 (s, 3H), 1.96-1.78 (m, 6H).

Example 44(12)

4-[1-(carboxymethyl)-7-((E)-2-{4-[4-(4-fluorophenoxy)butoxy]phenyl}vinyl)-1H-indol-3-yl]butanoic acid TLC: Rf 0.56 (methanol: dichloromethane:acetic acid=1:9:0.1); $^1$H-NMR (DMSO-$d_6$): δ 12.34 (brs, 2H), 7.54 (d, 1H), 7.49 (d, 2H), 7.44 (d, 1H), 7.25 (d, 1H), 7.16-6.86 (m, 9H), 5.08 (s, 2H), 4.11-3.93 (m, 4H), 2.66 (t 2H), 2.28 (t 2H), 1.93-1.77 (m, 6H).

Example 44(13)

4-[1-(carboxymethyl)-7-((E)-2-{4-[4-(4-fluoro-2-methylphenoxy)butoxy]phenyl}vinyl)-1H-indol-3-yl]butanoic acid TLC: Rf 0.55 (methanol: dichloromethane:acetic acid=1:9:0.1); $^1$H-NMR (DMSO-$d_6$): δ 1228 (brs, 2H), 7.52 (d, 1H), 7.49 (d, 2H), 7.45 (d, 1H), 7.26 (d, 1H), 7.11-6.85 (m, 8H), 5.12 (s, 2H), 4.12-3.95 (m, 4H), 2.67 (t, 2H), 2.28 (t, 2H), 2.15 (s, 3H), 1.96-1.77 (m, 6H).

Example 44(14)

4-[1-(carboxymethyl)-7-((E)-2-{4-[4-(2,4-dichloro-6-methylphenoxy)butoxy]phenyl}vinyl)-1H-indol-3-yl]butanoic acid TLC: Rf 0.56 (methanol: dichloromethane:acetic acid=1:9:0.1); $^1$H-NMR (DMSO-$d_6$): δ 1232 (brs, 2H), 7.52 (d, 1H), 7.49 (d, 2H), 7.45 (d, 1H), 7.44 (d, 1H), 7.31 (d, 1H), 7.26 (d, 1H), 7.08 (s, 1H), 7.02 (t, 1H), 6.95 (d, 2H), 6.92 (d, 1H), 5.12 (s, 2H), 4.07 (t, 2H), 3.93 (t, 2H), 2.67 (t, 2H), 2.28 (t, 2H), 2.27 (s, 3H), 2.01-1.77 (m, 6H).

Example 44(15)

4-[1-(carboxymethyl)-7-((E)-2-{4-[4-(4,5-difluoro-2-methylphenoxy)butoxy]phenyl}vinyl)-1H-indol-3-yl]butanoic acid TLC: Rf 0.32 (dichloromethane:methanol=9:1); $^1$H-NMR (DMSO-$d_6$): δ 1.75-1.95 (m, 6H), 2.10 (s, 3H), 2.28 (t, 2H), 2.67 (t, 2H), 3.96-4.14 (m, 4H), 5.13 (s, 1H), 6.92 (d, 1H), 6.94 (d, 2H), 7.02 (t, 1H), 7.06 (dd, 1H), 7.08 (s, 1H), 7.25 (dd, 1H), 7.26 (d, 1H), 7.45 (dd, 1H), 7.49 (d, 2H), 7.51 (d, 1H), 12.07 (s, 1H), 12.93 (s, 1H).

Example 44(16)

4-[1-(carboxymethyl)-7-((E)-2-{4-[4-(2-chloro-6-fluorophenoxy)butoxy]phenyl}vinyl)-1H-indol-3-yl]butanoic acid TLC: Rf 0.32 (dichloromethane:methanol=9:1); $^1$H-NMR (DMSO-$d_6$): δ 1.77-2.00 (m, 6H),2.28 (t, 2H), 2.67 (t, 2H), 4.07 (t, 2H), 4.13 (t, 2H), 5.13 (s, 2H), 6.92 (d, 1H), 6.94 (d, 2H), 7.02 (t, 1H), 7.08 (s, 1H), 7.09-7.18 (m, 1H), 7.22-7.35 (m, 3H), 7.45 (dd, 1H), 7.49 (d, 2H), 7.51 (d, 1H), 12.03 (s, 1H), 13.00 (s, 1H).

Example 44(17)

4-[1-(carboxymethyl)-7-((E)-2-{4-[4-(2-fluorophenoxy)butoxy]phenyl}vinyl)-1H-indol-3-yl]butanoic acid TLC: Rf 0.34 (dichloromethane:methanol=9:1); $^1$H-NMR (DMSO-$d_6$): δ 1.75-1.98 (m, 6H), 2.28 (t, 2H), 2.67 (t, 2H), 4.01-4.17 (m, 4H), 5.13 (s, 2H), 6.85-6.98 (m, 4H), 7.02 (t, 1H), 7.08 (s, 1H), 7.10-7.24 (m, 3H), 7.26 (d, 1H), 7.45 (d, 1H), 7.49 (d, 2H), 7.52 (d, 1H), 12.06 (s, 1H), 12.92 (s, 1H).

Example 44(18)

4-[1-(carboxymethyl)-7-((E)-2-{4-[4-(3-fluorophenoxy)butoxy]phenyl}vinyl)-1H-indol-3-yl]butanoic acid TLC: Rf 0.34 (dichloromethane:methanol=9:1); $^1$H-NMR (DMSO-$d_6$): δ 1.77-1.95 (m, 6H), 2.28 (t 2H), 2.67 (t 2H), 4.00-4.12 (m, 4H), 5.13 (s, 2H), 6.68-6.86 (m, 3H), 6.92 (d, 1H), 6.94 (d, 2H), 7.02 (t, 1H), 7.08 (s, 1H), 7.20-7.35 (m, 2H), 7.45 (dd, 1H), 7.49 (d, 2H), 7.52 (d, 1H), 12.09 (s, 1H), 12.98 (s, 1H).

Example 44(19)

4-[1-(carboxymethyl)-7-((E)-2-{4-[4-(4-fluoro-2,6-dimethylphenoxy)butoxy]phenyl}vinyl)-1H-indol-3-yl]butanoic acid TLC: Rf 0.42 (dichloromethane:methanol:acetic acid=9:1:0.05); $^1$H-NMR (DMSO-$d_6$): δ 1.71-2.01 (m, 6H), 2.22 (s, 6H), 2.28 (t, 2H), 2.67 (t, 2H), 3.76 (t, 2H), 4.07 (t 2H), 5.13 (s, 2H), 6.72-6.98 (m, 5H), 7.02 (dd, 1H), 7.08 (s, 1H), 7.26 (d, 1H), 7.39-7.60 (m, 4H), 12.05 (s, 1H), 12.92 (s, 1H).

Example 44(20)

4-[1-(carboxymethyl)-7-((E)-2-{4-[4-(2,4-dichlorophenoxy)butoxy]phenyl}vinyl)-1H-indol-3-yl]butanoic acid TLC: Rf 0.41 (dichloromethane:methanol=9:1); $^1$H-NMR (DMSO-$d_6$): δ 1.77-1.95 (m, 6H), 2.28 (t 2H), 2.67 (t, 2H), 4.04-4.11 (m, 2H), 4.10-4.18 (m, 2H), 5.13 (s, 2H), 6.92 (d, 1H), 6.94 (d, 2H), 7.02 (t, 1H), 7.08 (s, 1H), 7.18 (d, 1H), 7.26 (d, 1H), 7.36 (dd, 1H), 7.45 (dd, 1H), 7.49 (d, 2H), 7.51 (d, 1H), 7.56 (d, 1H), 12.02 (s, 1H), 12.99 (s, 1H).

Example 44(21)

4-[1-(carboxymethyl)-7-((E)-2-{4-[4-(2-chloro-4-methylphenoxy)butoxy]phenyl}vinyl)-1H-indol-3-yl]butanoic acid TLC: Rf 0.41 (dichloromethane:methanol=9:1); $^1$H-NMR (DMSO-$d_6$): δ 1.78-1.97 (m, 6H), 2.22 (s, 3H), 2.28 (t 2H), 2.67 (t, 2H), 3.93-4.19 (m, 4H), 5.13 (s, 2H), 6.92 (d, 1H), 6.94 (d, 2H), 6.98-7.12 (m, 4H), 7.23 (d, 1H), 7.26 (d, 1H), 7.45 (d, 1H), 7.49 (d, 2H), 7.51 (d, 1H), 12.06 (s, 1H), 12.97 (s, 1H).

Example 44(22)

4-[7-((E)-2-{4-[4-(2-chloro-5-methylphenoxy)butoxy]phenyl}vinyl)-1-(carboxymethyl)-1H-indol-3-yl]butanoic acid TLC: Rf 0.49 (methanol: dichloromethane:acetic acid=1:9:0.1); $^1$H-NMR(DMSO-$d_6$): δ 12.68 (brs, 2H), 7.52 (d, 1H), 7.49 (d, 2H), 7.45 (d, 1H), 7.26 (d, 1H), 7.22 (s, 1H), 7.08 (s, 1H), 7.02 (t 1H), 6.94 (d, 2H), 6.92 (d, 1H), 5.12 (s, 2H), 4.17 (t 2H), 4.07 (t 2H), 2.67 (t, 2H), 2.53 (s, 3H), 2.35 (s, 3H), 2.28 (t, 2H), 2.03-1.77 (m, 6H).

Example 44(23)

4-[1-(carboxymethyl)-7-((E)-2-{4-[4-(2,3,4-trifluorophenoxy)butoxy]phenyl}vinyl)-1H-indol-3-yl]butanoic acid TLC: Rf 0.49 (methanol: dichloromethane:acetic acid=1:9:0.1); $^1$H-NMR (DMSO-$d_6$): δ 12.25 (brs, 2H), 7.52 (d, 1H), 7.49 (d, 2H), 7.45 (d, 1H), 7.31-7.18 (m, 2H), 7.11-6.98 (m, 1H), 7.08 (s, 1H), 7.02 (t, 1H), 6.93 (d, 2H), 6.92 (d, 1H), 5.12 (s, 2H), 4.14 (t 2H), 4.06 (t, 2H), 2.67 (t, 2H), 2.28 (t, 2H), 1.97-1.76 (m, 6H).

Example 44(24)

4-[1-(carboxymethyl)-7-((E)-2-{4-[4-(2,6-dichloro-4-fluorophenoxy)butoxy]phenyl}vinyl)-1H-indol-3-yl]butanoic acid TLC: Rf 0.51 (methanol: dichloromethane:acetic acid=1:9:0.1); $^1$H-NMR (DMSO-$d_6$): δ 12.24 (brs, 2H), 7.57 (s, 1H), 7.54 (s, 1H), 7.52 (d, 1H), 7.49 (d, 2H), 7.45 (d, 1H), 7.26 (d, 1H), 7.08 (s, 1H), 7.02 (t, 1H), 6.95 (d, 2H), 6.92 (d, 1H), 5.12 (s, 2H), 4.08 (t, 2H), 4.02 (t, 2H), 2.67 (t, 2H), 2.28 (t 2H), 2.02-1.77 (m, 6H).

Example 44(25)

4-[1-(carboxymethyl)-7-((E)-2-{4-[4-(2-chloro-6-fluoro-3-methylphenoxy)butoxy]phenyl}vinyl)-1H-indol-3-yl]butanoic acid TLC: Rf 0.41 (dichloromethane:methanol=9:1); $^1$H-NMR (DMSO-$d_6$): δ 1.77-2.00 (m, 6H), 2.28 (t, 2H), 2.29 (s, 3H), 2.67 (t, 2H), 4.01-4.15 (m, 4H), 5.13 (s, 2H), 6.92 (d, 1H), 6.94 (d, 2H), 7.02 (t, 1H), 7.10 (dd, 1H), 7.08 (s, 1H), 7.19 (dd, 1H), 7.26 (d, 1H), 7.45 (dd, 1H), 7.49 (d, 2H), 7.52 (d, 1H), 12.07 (s, 1H),12.93 (s, 1H).

Example 44(26)

4-[1-(carboxymethyl)-7-((E)-2-{4-[4-(6-chloro-2-fluoro-3-methylphenoxy)butoxy]phenyl}vinyl)-1H-indol-3-yl]butanoic acid TLC: Rf 0.41 (dichloromethane:methanol=9:1); $^1$H-NMR (DMSO-$d_6$): δ 1.77-2.00 (m, 6H), 2.22 (d, 3H), 2.28 (t, 2H), 2.67 (t, 2H), 4.02-4.14 (m, 4H), 5.13 (s, 2H), 6.92 (d, 1H), 6.94 (d, 2H), 6.98-7.06 (m, 2H), 7.08 (s, 1H), 7.20 (dd, 1H), 7.26 (d, 1H), 7.45 (dd, 1H), 7.49 (d, 2H), 7.52 (d, 1H), 12.09 (s, 1H), 12.90 (s, 1H).

Example 44(27)

4-[1-(carboxymethyl)-7-((E)-2-{4-[4-(2,3,6-trimethylphenoxy)butoxy]phenyl}vinyl)-1H-indol-3-yl]butanoic acid TLC: Rf 0.28 (methanol: dichloromethane=1:9); $^1$H-NMR (DMSO-$d_6$): δ 1.78-2.01 (m, 6H), 2.12 (s, 3H), 2.16 (s, 3H), 2.17 (s, 3H), 2.28 (t, 2H), 2.67 (t, 2H), 3.73 (t, 2H), 4.08 (t, 2H), 5.12 (s, 2H), 6.80 (d, 1H), 6.87-6.98 (m, 4H), 7.02 (t, 1H), 7.08 (s, 1H), 7.26 (d, 1H), 7.38-7.60 (m, 4H).

Example 44(28)

4-[1-(carboxymethyl)-7-((E)-2-{4-[4-(2,3-difluoro-4-methylphenoxy)butoxy]phenyl}vinyl)-1H-indol-3-yl]butanoic acid TLC: Rf 0.44 (methanol: dichloromethane=1:9); $^1$H-NMR (DMSO-$d_6$): δ 1.78-1.95 (m, 6H), 2.19 (d, 3H), 2.28 (t, 2H), 2.66 (t, 2H), 4.02-4.09 (m, 2H), 4.09-4.16 (m, 2H), 5.12 (s, 2H), 6.85-7.11 (m, 7H), 7.26 (d, 1H), 7.40-7.58 (m, 4H).

Example 44(29)

4-[1-(carboxymethyl)-7-((E)-2-{4-[4-(2-ethyl-6-methylphenoxy)butoxy]phenyl}vinyl)-1H-indol-3-yl]butanoic acid TLC: Rf 0.30 (methanol: dichloromethane=1:9); $^1$H-NMR (DMSO-$d_6$): δ 1.15 (t 3H), 1.77-2.02 (m, 6H), 2.23 (s, 3H), 2.24-2.32 (m, 2H), 2.54-2.79 (m, 4H), 3.79 (t, 2H), 4.08 (t, 2H), 5.12 (s, 2H), 6.86-7.10 (m, 8H), 7.26 (d, 1H), 7.39-7.60 (m, 4H).

Example 44(30)

4-[1-(carboxymethyl)-7-((E)-2-{4-[4-(3-chloro-2-fluorophenoxy)butoxy]phenyl}vinyl)-1H-indol-3-yl]butanoic acid TLC: Rf 0.31 (methanol: dichloromethane=1:9); $^1$H-NMR (DMSO-$d_6$): δ 1.76-1.97 (m, 6H), 2.28 (t, 2H), 2.67 (t, 2H), 4.06 (t, 2H), 4.16 (t, 2H), 5.12 (s, 2H), 6.92 (d, 1H), 6.94 (d, 2H), 7.02 (t, 1H), 7.08 (s, 1H), 7.09-7.23 (m, 3H), 7.26 (d, 1H), 7.45 (d, 1H), 7.49 (d, 2H), 7.52 (d, 1H).

Example 44(31)

4-[1-(carboxymethyl)-7-((E)-2-{4-[4-(2,6-dichloro-4-methylphenoxy)butoxy]phenyl}vinyl)-1H-indol-3-yl]butanoic acid

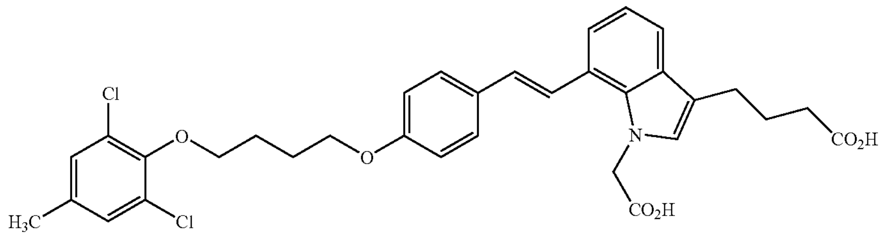

TLC: Rf 0.41 (dichloromethane:methanol=9:1); $^1$H-NMR (DMSO-$d_6$): δ 1.78-2.01 (m, 6H), 2.26 (s, 3H), 2.28 (t, 2H), 2.67 (t, 2H), 4.00 (t 2H), 4.08 (t, 2H), 5.13 (s, 2H), 6.92 (d, 1H), 6.95 (d, 2H), 7.02 (t, 1H), 7.08 (s, 1H), 7.26 (d, 1H), 7.31 (s, 2H), 7.45 (dd, 1H), 7.49 (d, 1H), 7.52 (d, 2H), 12.08 (s, 1H), 12.95 (s, 1H).

Example 44(32)

4-[1-(carboxymethyl)-7-((E)-2-{4-[4-(2-chloro-4,5-dimethylphenoxy)butoxy]phenyl}vinyl)-1H-indol-3-yl]butanoic acid TLC: Rf 0.39 (dichloromethane:methanol=9:1); $^1$H-NMR (DMSO-$d_6$): δ 1.75-1.98 (m, 6H), 2.12 (s, 3H), 2.18 (s, 3H), 2.28 (t, 2H), 2.67 (t 2H), 3.99-4.15 (m, 4H), 5.13 (s, 2H), 6.92 (d, 1H), 6.91-6.98 (m, 3H), 7.02 (t, 1H), 7.08 (s, 1H), 7.16 (s, 1H), 7.26 (d, 1H), 7.45 (dd, 1H), 7.49 (d, 2H), 7.52 (d, 1H), 12.07 (s, 1H), 12.94 (s, 1H).

Example 44(33)

4-[1-(carboxymethyl)-7-((E)-2-{4-[4-(2-chloro-5-methylphenoxy)butoxy]phenyl}vinyl)-1H-indol-3-yl]butanoic acid TLC: Rf 0.37 (methanol: dichloromethane:acetic acid=5:95:0.1); $^1$H-NMR(DMSO-$d_6$): δ 12.14 (brs, 2H), 7.52 (d, 1H), 7.49 (d, 2H), 7.45 (dd, 1H), 7.30-7.22 (m, 2H), 7.07 (s, 1H), 7.02 (t, 1H) 6.97 (d, 1H), 6.94 (d, 2H), 6.91 (d, 1H), 6.75 (ddd, 1H), 5.12 (s, 2H), 4.16-4.02 (m, 4H), 2.67 (t, 2H), 2.28 (t, 2H), 2.28 (s, 3H), 1.94-1.77 (m, 6H).

Example 44(34)

4-[7-((E)-2-{4-[4-(2-acetyl-4-fluorophenoxy)butoxy]phenyl}vinyl)-1-carboxymethyl)-1H-indol-3-yl]butanoic acid TLC: Rf 0.35 (methanol: dichloromethane:acetic acid=5:95:0.1); $^1$H-NMR (DMSO-$d_6$): δ 12.26 (brs, 2H), 7.52 (d, 1H), 7.49 (d, 2H), 7.45 (d, 1H), 7.43-7.30 (m, 2H), 7.26 (d, 1H), 7.20 (dd, 1H), 7.08 (s, 1H), 7.02 (t, 1H), 6.94 (d, 2H), 6.92 (d, 1H), 5.12 (s, 2H), 4.22-4.01 (m, 4H), 2.67 (t 2H), 2.56 (s, 3H), 2.28 (t, 2H), 2.02-1.76 (m, 6H).

Example 44(35)

4-[1-(carboxymethyl)-7-((E)-2-{4-[4-(2-chloro-5-fluorophenoxy)butoxy]phenyl}vinyl)-1H-indol-3-yl]butanoic acid TLC: Rf 0.37 (methanol: dichloromethane:acetic acid=5:95:0.1); $^1$H-NMR (DMSO-$d_6$): δ 12.25 (brs, 2H), 7.52 (d, 1H), 7.49 (d, 2H), 7.47-7.38 (m, 2H), 7.26 (d, 1H), 7.11 (dd, 1H), 7.08 (s, 1H), 7.02 (t, 1H), 6.94 (d, 2H), 6.91 (d, 1H), 6.80 (t, 1H), 5.12 (s, 2H), 4.22-4.02 (m, 4H), 2.67 (t, 2H), 2.28 (t, 2H), 1.99-1.78 (m, 6H).

Example 44(36)

4-[1-(carboxymethyl)-7-((E)-2-{4-[4-(2,3,5-trifluorophenoxy)butoxy]phenyl}vinyl)-1H-indol-3-yl]butanoic acid TLC: Rf 0.37 (methanol: dichloromethane=1:9); $^1$H-NMR (DMSO-$d_6$): δ 1.77-1.95 (m, 6H), 2.28 (t, 2H), 2.67 (t, 2H), 4.06 (t, 2H), 4.17 (t, 2H), 5.12 (s, 2H), 6.86-7.11 (m, 7H), 7.26 (d, 1H), 7.45 (d, 1H), 7.49 (d, 2H), 7.51 (d, 1H).

Example 44(37)

4-(1-(carboxymethyl)-7-{(E)-2-[4-(4-phenylbutoxy)phenyl]vinyl}-1H-indol-3-yl)butanoic acid TLC: Rf 0.38 (methanol: dichloromethane=1:9); $^1$H-NMR (DMSO-$d_6$): δ 1.66-1.78 (m, 4H), 1.78-1.93 (m, 2H), 2.28 (t, 2H), 2.58-2.76 (m, 4H), 3.91-4.10 (m, 2H), 5.11 (s, 2H), 6.87-6.95 (m, 4H), 7.01 (t, 1H), 7.07 (s, 1H), 7.14-7.32 (m, 6H), 7.41-7.57 (m, 3H).

Example 44(38)

3-(1-(carboxymethyl)-7-{(E)-2-[4-(4-phenoxybutoxy)phenyl]vinyl}-1H-indol-3-yl)propanoic acid TLC: Rf 0.46 (dichloromethane:methanol:acetic acid=9:1:0.05); $^1$H-NMR (DMSO-$d_6$): δ 1.80-1.94 (m, 4H), 2.57 (t, 2H), 2.90 (t, 2H), 3.98-4.10 (m, 4H), 5.09 (s, 2H), 6.83-6.96 (m, 6H), 7.02 (dd, 1H), 7.07 (s, 1H), 7.22-7.33 (m, 3H), 7.40-7.57 (m, 4H), 12.08 (s, 2H).

Example 44(39)

3-[1-(carboxymethyl)-7-((E)-2-{4-[4-(2,3-difluorophenoxy)butoxy]phenyl}vinyl)-1H-indol-3-yl]propanoic acid TLC: Rf 0.47 (dichloromethane:methanol:acetic acid=9:1:0.05); $^1$H-NMR (DMSO-$d_6$): δ 1.82-1.98 (m, 4H), 2.57 (t, 2H), 2.90 (t, 2H), 4.07 (t, 2H), 4.12-4.23 (m, 2H), 5.10 (s, 2H), 6.80-7.15 (m, 8H), 7.26 (d, 1H), 7.40-7.58 (m, 4H), 12.09 (s, 2H).

Example 44(40)

4-[1-(carboxymethyl)-5-chloro-7-((E)-2-{4-[4-(mesityloxy)butoxy]phenyl}vinyl)-1H-indol-3-yl]butanoic acid TLC: Rf 0.46 (dichlorometane:methanol:acetic acid=90:10:1); $^1$H-NMR (DMSO-$d_6$): δ 1.74-2.00 (m, 6H), 2.17 (s, 9H), 2.27 (t, 2H), 2.64 (t, 2H), 3.74 (t, 2H), 4.06 (t, 2H), 5.11 (s, 2H), 6.80 (s, 2H), 6.95 (d, 2H), 7.01 (d, 1H), 7.15 (s, 1H), 7.25 (d, 1H), 7.43-7.56 (m, 4H).

Example 44(41)

4-(1-(carboxymethyl)-5-chloro-7-{(E)-2-[4-(4-phenoxybutoxy)phenyl]vinyl}-1H-indol-3-yl)butanoic acid TLC: Rf 0.47 (dichloromethane:methanol:acetic acid=90:10:1); $^1$H-NMR (DMSO-$d_6$): δ 1.73-1.93 (m, 6H), 2.27 (t, 2H), 2.64 (t, 2H), 3.97-4.12 (m, 4H), 5.10 (s, 2H), 6.87-6.97 (m, 5H), 7.01 (d, 1H), 7.15 (s, 1H), 7.23-7.31 (m, 3H), 7.43-7.57 (m, 4H).

Example 44(42)

4-[1-(carboxymethyl)-5-chloro-7-((E)-2-{4-[4-(2,3-difluorophenoxy)butoxy]phenyl}vinyl)-1H-indol-3-yl]butanoic acid TLC: Rf 0.45 (dichloromethane:methanol:acetic acid=90:10:1); $^1$H-NMR (DMSO-$d_6$): δ 1.73-1.96 (m, 6H), 2.27 (t, 2H), 2.64 (t, 2H), 4.05 (t, 2H), 4.16 (t, 2H), 5.09 (s, 2H), 6.88-7.18 (m, 7H), 7.24 (d, 1H), 7.43-7.56 (m, 4H).

Example 44(43)

4-(1-(carboxymethyl)-5-methyl-7-{(E)-2-[4-(4-phenoxybutoxy)phenyl]vinyl}-1H-indol-3-yl)butanoic acid TLC: Rf 0.57 (methanol: dichloromethane:acetic acid=1:9:0.1); $^1$H-NMR (DMSO-$d_6$): δ 12.40 (brs, 2H), 7.49 (d, 2H), 7.48 (d, 1H), 7.32-7.20 (m, 3H), 7.10 (s, 1H), 7.02 (s, 1H), 6.98-6.86 (m, 6H), 5.08 (s, 2H), 4.12-3.96 (m, 4H), 2.63 (t, 2H), 2.39 (s, 3H), 2.27 (t, 2H), 1.94-1.76 (m, 6H).

Example 44(44)

4-[1-(carboxymethyl)-7-((E)-2-{4-[4-(2,3-difluorophenoxy)butoxy]phenyl}vinyl)-5-methyl-1H-indol-3-yl]butanoic acid TLC: Rf 0.55 (methanol: dichloromethane:acetic acid=1:9:0.1); $^1$H-NMR (DMSO-$d_6$): δ 12.34 (brs, 2H), 7.49 (d, 2H), 7.48 (d, 1H), 7.23 (s, 1H), 7.19-6.86 (m, 8H), 5.08 (s, 2H), 4.16 (t, 2H), 4.06 (t, 2H), 2.63 (t, 2H), 2.39 (s, 3H), 2.27 (t, 2H), 1.98-1.76 (m, 6H).

Example 44(45)

5-(1-(carboxymethyl)-7-((E)-2-{4-(4-phenoxybutoxy)phenyl}vinyl)-1H-indol-3-yl)pentanoic acid TLC: Rf 0.52 (dichloromethane:methanol:acetic acid=9:1:0.05); $^1$H-NMR (DMSO-$d_6$): δ 1.52-1.69 (m, 4H), 1.80-2.03 (m, 4H), 2.25 (t, 2H), 2.65 (t, 2H), 3.94-4.17 (m, 4H), 5.10 (s, 2H), 6.64-7.10 (m, 8H), 7.20-7.34 (m, 3H), 7.37-7.62 (m, 4H), 12.01 (s, 2).

Example 44(46)

5-[1-(carboxymethyl)-7-((E)-2-{4-[4-(2,3-difluorophenoxy)butoxy]phenyl}vinyl)-1H-indol-3-yl]pentanoic acid TLC: Rf 0.40 (dichloromethane:methanol:acetic acid=9:1:0.05); $^1$H-NMR (DMSO-$d_6$): δ 1.52-1.71 (m, 4H), 1.82-1.98 (m, 4H), 2.25 (t, 2H), 2.65 (t, 2H), 4.06 (t, 2H), 4.12-4.20 (m, 2H), 5.11 (s, 2H), 6.86-7.07 (m, 7H), 7.12 (ddd, 1H), 7.25 (d, 1H), 7.43 (dd, 1H), 7.46-7.63 (m, 3H), 12.03 (s, 1H), 12.97 (s, 1H).

Example 44(47)

4-[1-(carboxymethyl)-7-((E)-2-{4-[4-(2,3-difluorophenoxy)butoxy]phenyl}vinyl)-5-(trifluoromethoxy)-1H-indol-3-yl]butanoic acid TLC: Rf 0.40 (dichloromethane:methanol:acetic acid=90:10:1); $^1$H-NMR (DMSO-$d_6$): δ 1.72-1.97 (m, 6H), 2.28 (t, 2H), 2.65 (t, 2H), 4.06 (t, 2H), 4.16 (t, 2H), 5.12 (s, 2H), 6.88-7.19 (m, 6H), 7.21 (s, 2H), 7.40 (s, 1H), 7.46-7.58 (m, 3H).

Example 44(48)

4-(1-(carboxymethyl)-7-((E)-2-{4-[4-phenoxybutoxy)phenyl]vinyl}-1H-indol-3-yl)butanoic acid TLC: Rf 0.55 (dichloromethane:methanol:acetic acid=90:10:1); $^1$H-NMR (DMSO-$d_6$): δ 1.65-1.82 (m, 2H), 1.82-1.94 (m, 4H), 2.15-2.30 (m, 5H), 2.67 (t, 2H), 3.97-4.10 (m, 4H), 5.00 (s, 2H), 6.83-7.03 (m, 7H), 7.15 (d, 1H), 7.23-7.33 (m, 2H), 7.39 (d, 1H), 7.44-7.58 (m, 3H).

Example 44(49)

4-(1-(carboxymethyl)-5-fluoro-7-{(E)-2-[4-(4-phenoxybutoxy)phenyl]vinyl}-1H-indol-3-yl)butanoic acid TLC: Rf 0.56 (methanol: dichloromethane:acetic acid=1:9:0.1); $^1$H-NMR (DMSO-$d_6$): δ 12.31 (brs, 2H), 7.51 (d, 2H), 7.47 (d, 1H), 7.34-7.08 (m, 5H), 7.02 (d, 1H), 7.00-6.86 (m, 5H), 5.15 (s, 2H), 4.11-3.96 (m, 4H), 2.63 (t, 2H), 2.28 (t, 2H), 1.95-1.74 (m, 6H).

Example 44(50)

4-[1-(carboxymethyl)-7-((E)-2-{4-[4-(2,3-difluorophenoxy)butoxy]phenyl}vinyl)-5-fluoro-1H-indol-3-yl]butanoic acid TLC: Rf 0.56 (methanol: dichloromethane:acetic acid=1:9:0.1); $^1$H-NMR (DMSO-$d_6$): δ 12.40 (brs, 2H), 7.51 (d, 2H), 7.47 (d, 1H), 7.26-6.90 (m, 9H), 5.15 (s, 2H), 4.16 (t, 2H), 4.07 (t, 2H), 2.63 (t, 2H), 2.27 (t, 2H), 1.97-1.75 (m, 6H).

Example 44(51)

4-(1-(carboxymethyl)-6-methyl-7-{(E)-2-[4-(4-phenoxybutoxy)phenyl]vinyl}-1H-indol-3-yl)butanoic acid TLC: Rf 0.57 (methanol: dichloromethane:acetic acid=1:9:0.1); $^1$H-NMR (DMSO-$d_6$): δ 12.28 (brs, 2H), 7.47 (d, 2H), 7.36-7.22 (m, 3H), 7.19 (d, 1H), 7.00-6.85 (m, 7H), 6.49 (d, 1H), 4.95 (s, 2H), 4.12-3.94 (m, 4H), 2.64 (t, 2H), 2.33 (s, 3H), 2.27 (t, 2H), 1.95-1.74 (m, 6H).

Example 44(52)

4-[1-(carboxymethyl)-7-((E)-2-{4-[4-(2,3-difluorophenoxy)butoxy]phenyl}vinyl)-6-methyl-1H-indol-3-yl]butanoic acid TLC: Rf 0.57 (methanol: dichloromethane:acetic acid=1:9:0.1); $^1$H-NMR (DMSO-$d_6$): δ 12.29 (brs, 2H), 7.47 (d, 2H), 7.32 (d, 1H), 7.19 (d, 1H), 7.16-6.86 (m, 7H), 6.49 (d, 1H), 4.95 (s, 2H), 4.16 (t, 2H), 4.06 (t, 2H), 2.64 (t, 2H), 2.33 (s, 3H), 2.27 (t, 2H), 1.98-1.76 (m, 6H).

Example 44(53)

4-(1-(carboxymethyl)-7-{2-[4-(4-phenoxybutoxy)phenyl]ethyl}-1H-indol-3-yl)butanoic acid TLC: Rf 0.45 (dichloromethane:methanol:acetic acid=90:10:1); $^1$H-NMR (DMSO-$d_6$): δ 1.75-1.93 (m, 6H), 2.27 (t, 2H), 2.65 (t, 2H), 2.75-2.87 (m, 2H), 2.98-3.11 (m, 2H), 3.93-4.07 (m, 4H), 5.04 (s, 2H), 6.81-6.96 (m, 7H), 7.04 (s, 1H), 7.18 (d, 2H), 7.22-7.31 (m, 2H), 7.32-7.37 (m, 1H).

Example 44(54)

4-[1-(carboxymethyl)-7-((E)-2-{4-[4-(2,3-difluorophenoxy)butoxy]phenyl}vinyl)-2-methyl-1H-indol-3-yl]butanoic acid

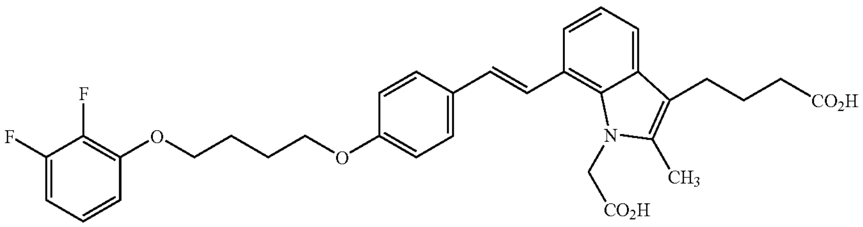

TLC: Rf 0.56 (dichloromethane:methanol:acetic acid=90:10:1); $^1$H-NMR (DMSO-$d_6$): δ 1.64-1.96 (m, 6H), 2.15-2.30 (m, 5H), 2.67 (t, 2H), 4.06 (t, 2H), 4.16 (t, 2H), 5.00 (s, 2H), 6.80-7.22 (m, 8H), 7.39 (d, 1H), 7.44-7.58 (m, 3H).

Example 44(55)

4-(1-(carboxymethyl)-7-{(E)-2-[6-(4-phenoxybutoxy)-3-pyridinyl]vinyl}-1H-indol-3-yl)butanoic acid TLC: Rf 0.46 (dichloromethane:methanol:acetic acid=90:10:1); $^1$H-NMR (DMSO-$d_6$): δ 1.63-1.91 (m, 6H), 2.27 (t, 2H), 2.65 (t, 2H), 3.88-4.03 (m, 4H), 5.12 (s, 2H), 6.46 (d, 1H), 6.72 (d, 1H), 6.85-6.94 (m, 3H), 7.00 (t, 1H), 7.06 (s, 1H), 7.18 (d, 1H), 7.21-7.31 (m, 2H), 7.35-7.48 (m, 2H), 7.76-7.90 (m, 2H).

Example 44(56)

4-[1-(carboxymethyl)-7-((E)-2-{4-[4-(2-chloro-3,5-difluorophenoxy)butoxy]phenyl}vinyl)-5-methyl-1H-indol-3-yl]butanoic acid TLC: Rf 0.54 (methanol: dichloromethane:acetic acid=1:9:0.1); $^1$H-NMR (DMSO-$d_6$): δ 12.24 (brs, 2H), 7.49 (d, 2H), 7.48 (d, 1H), 7.23 (s, 1H), 7.15-6.82 (m, 7H), 5.08 (s, 2H), 4.25-4.00 (m, 4H), 2.63 (t, 2H), 2.39 (s, 3H), 2.27 (t, 2H), 2.01-1.75 (m, 6H).

Example 44(57)

4-[1-(carboxymethyl)-7-((E)-2-{4-[4-(2-chloro-3,5-difluorophenoxy)butoxy]phenyl}vinyl)-5-methyl-1H-indol-3-yl]butanoic acid TLC: Rf 0.50 (methanol: dichloromethane:acetic acid=1:9:0.1); $^1$H-NMR (DMSO-$d_6$): δ 12.35 (brs, 2H), 7.51 (d, 2H), 7.47 (d, 1H), 7.21 (dd, 1H), 7.18-6.98 (m, 5H), 6.95 (4, 2H), 5.14 (s, 2H), 4.23-4.03 (m, 4H), 2.63 (t, 2H), 2.27 (t, 2H), 1.98-1.74 (m, 6H).

Example 44(58)

4-[1-(carboxymethyl)-7-((E)-2-{4-[4-(2-chloro-3,5-difluorophenoxy)butoxy]phenyl}vinyl)-6-methyl-1H-indol-3-yl]butanoic acid TLC: Rf 0.51 (methanol: dichloromethane:acetic acid=1:9:0.1); $^1$H-NMR (DMSO-$d_6$): δ 12.34 (brs, 2H), 7.47 (d, 2H), 7.32 (d, 1H), 7.19 (d, 1H), 7.05 (d, 2H), 6.99-6.88 (m, 4H), 6.49 (d, 1H), 4.95 (s, 2H), 4.24-4.02 (m, 4H), 2.64 (t, 2H), 2.33 (s, 3H), 2.27 (t, 2H), 1.98-1.75 (m, 6H).

Example 44(59)

4-(1-(carboxymethyl)-7-{(E)-2-[5-(4-phenoxybutoxy)-2-pyridinyl]vinyl}-1H-indol-3-yl)butanoic acid TLC: Rf 0.50 (dichloromethane:methanol:acetic acid=90:10:1); $^1$H-NMR (DMSO-$d_6$): δ 1.77-1.95 (m, 6H), 2.21-2.32 (m, 2H), 2.67 (t, 2H), 3.97-4.08 (m, 2H), 4.09-4.21 (m, 2H), 5.09 (s, 2H), 6.85-7.13 (m, 6H), 7.22-7.33 (m, 3H), 7.39 (dd, 1H), 7.45-7.57 (m, 2H), 7.94 (d, 1H), 8.27 (d, 1H).

Example 44(60)

(3S)-4-(1-carboxymethyl)-7-{(E)-2-[4-(4-phenoxybutoxy)phenyl]vinyl}-1H-indol-3-yl)-3-methylbutanoic acid TLC: Rf 0.33 (dichloromethane:methanol=9:1); $^1$H-NMR (DMSO-$d_6$): δ 0.91 (d, 3H), 1.79-1.94 (m, 4H), 2.06 (dd, 1H), 2.10-2.23 (m, 1H), 2.28 (dd, 1H), 2.44-2.57 (m, 1H), 2.67 (dd, 1H), 3.93-4.14 (m, 4H), 5.14 (s, 2H), 6.86-6.98 (m, 6H), 7.02 (t, 1H), 7.08 (s, 1H), 7.20-7.33 (m, 3H), 739-7.61 (m, 4H), 12.07 (s, 1H), 13.00 (s, 1H).

Example 44(61)

4-(1-carboxymethyl)-7-{(E)-2-[4-(3-phenylpropoxy)phenyl]vinyl}-1H-indol-3-yl)butanoic acid TLC: Rf 0.55 (methanol: dichloromethane:acetic acid=1:9:0.1); $^1$H-NMR (DMSO-$d_6$): δ 12.30 (brs, 2H), 7.52 (d, 1H), 7.49 (d, 2H), 7.45 (d, 1H), 7.37-7.14 (m, 6H), 7.08 (s, 1H), 7.02 (t, 1H), 6.93 (d, 2H), 6.92 (d, 1H), 5.13 (s, 2H), 3.98 (t, 2H), 2.75 (t, 2H), 2.67 (t, 2H), 2.28 (t, 2H), 2.02 (quintet, 2H), 1.85 (quintet, 2H).

Example 44(62)

4-(1-carboxymethyl)-7-{(E)-2-[4-(3-phenoxypropoxy)phenyl]vinyl}-1H-indol-3-yl)butanoic acid TLC: Rf 0.56 (dichloromethane:methanol:acetic acid=90:10:1); $^1$H-NMR (DMSO-$d_6$): δ 12.34 (brs, 2H), 7.52 (d, 1H), 7.50 (d, 2H), 7.45 (d, 1H), 7.33-7.21 (m, 3H), 7.08 (s, 1H), 7.02 (t, 1H), 7.03-6.86 (m, 6H), 5.12 (s, 2H), 4.16 (t, 2H), 4.13 (t, 2H), 2.66 (t, 2H), 2.28 (t, 2H), 2.17 (quintet, 2H), 1.85 (quintet, 2H).

Example 44(63)

4-(1-carboxymethyl)-7-{(E)-2-[4-(2,3-dihydro-1H-inden-2-ylmethoxy)phenyl]vinyl}-1H-indol-3-yl)butanoic acid TLC: Rf 0.56 (dichloromethane:methanol:acetic acid=90:10:1); $^1$H-NMR (DMSO-$d_6$): δ 12.34 (brs, 2H), 7.52 (d, 1H), 7.49 (d, 2H), 7.45 (d, 1H), 7.30-7.18 (m, 3H), 7.17-7.05 (m, 3H), 7.02 (t, 1H), 6.96 (d, 2H), 6.91 (d, 1H), 5.12 (s, 2H), 4.00 (d, 2H), 3.09 (dd, 2H), 2.97-2.82 (m, 1H), 2.79 (dd, 2H), 2.66 (t, 2H), 2.28 (t, 2H), 1.85 (quintet, 2H).

Example 44(64)

4-[1-carboxymethyl)-7-((E)-2-{4-[3-(3-fluorophenyl)propoxy]phenyl}vinyl)-1H-indol-3-yl]butanoic acid TLC: Rf 0.54 (dichloromethane:methanol:acetic acid=90:10:1); $^1$H-NMR (DMSO-$d_6$): δ 12.35 (brs, 2H), 7.52 (d, 1H), 7.49 (d, 2H), 7.45 (d, 1H), 7.38-7.22 (m, 2H), 7.13-6.96 (m, 5H), 6.94 (d, 2H), 6.92 (d, 1H), 5.13 (s, 2H), 3.98 (t, 2H), 2.77 (t, 2H), 2.67 (t, 2H), 2.28 (t, 2H), 2.11-1.95 (m, 2H), 1.85 (quintet, 2H).

Example 44(65)

4-[1-carboxymethyl)-7-((E)-2-{4-[3-(2-fluorophenyl)propoxy]phenyl}vinyl)-1H-indol-3-yl]butanoic acid TLC: Rf 0.54 (dichloromethane:methanol:acetic acid=90:10:1); $^1$H-NMR (DMSO-$d_6$): δ 12.38 (brs, 2H), 7.52 (d, 1H), 7.49 (d, 2H), 7.45 (d, 1H), 7.37-7.20 (m, 3H), 7.19-7.09 (m, 2H), 7.08 (s, 1H), 7.02 (t, 1H), 6.93 (d, 2H), 6.92 (d, 1H), 5.13 (s, 2H), 4.01 (t, 2H), 2.78 (t, 2H), 2.67 (t, 2H), 2.28 (n 2H), 2.08-1.94 (m, 2H), 1.84 (quintet, 2H).

Example 44(66)

4-[1-carboxymethyl)-7-((E)-2-{4-[3-(2,3-dihydro-1H-inden-2-yl)propoxy]phenyl}vinyl)-1H-indol-3-yl]butanoic acid TLC: Rf 0.53 (dichloromethane:methanol:acetic acid=90:10:1); $^1$H-NMR (DMSO-$d_6$): δ 12.28 (brs, 2H), 7.52 (d, 1H), 7.49 (d, 2H), 7.45 (d, 1H), 7.26 (d, 1H), 7.22-7.13 (m, 2H), 7.13-7.04 (m, 3H), 7.02 (t, 1H), 6.93 (d, 2H), 6.91 (d, 1H), 5.12 (s, 2H), 4.01 (t, 2H), 3.02 (dd, 2H), 2.66 (t, 2H), 2.55 (dd, 2H), 2.50-2.36 (m, 1H), 2.28 (t, 2H), 1.93-1.73 (m, 4H), 1.67-1.54 (m, 2H).

Example 44(67)

4-(1-carboxymethyl)-7-{(E)-2-[3-methyl-4-(4-phenoxybutoxy)phenyl]vinyl}-1H-indol-3-yl)butanoic acid TLC: Rf 0.42 (dichloromethane:methanol=9:1); $^1$H-NMR (DMSO-$d_6$): δ 1.77-1.96 (m, 6H), 2.17 (s, 3H), 2.28 (t, 2H), 2.66 (t, 2H), 3.96-4.13 (m, 4H), 5.11 (s, 2H), 6.84-6.97 (m, 5H), 7.01 (t, 1H), 7.08 (s, 1H), 721-7.53 (m, 7H).

Example 44(68)

4-[7-{(E)-2-[3-acetyl-4-(4-phenoxybutoxy)phenyl]vinyl}-1-(carboxymethyl)-1H-indol-3-yl]butanoic acid TLC: Rf 0.36 (dichloromethane:methanol=9:1); $^1$H-NMR (DMSO-$d_6$): δ 1.77-2.01 (m, 6H), 2.28 (t, 2H), 2.55 (s, 3H), 2.67 (t, 2H), 4.00-4.10 (m, 2H), 4.14-4.29 (m, 2H), 5.12 (s, 2H), 6.86-7.11 (m, 6H), 7.19 (d, 1H), 7.23-7.32 (m, 3H), 7.46 (d, 1H), 7.59 (d, 1H), 7.68-7.81 (m, 2H).

Example 44(69)

4-[1-carboxymethyl)-7-((E)-2-{4-[3-(2-fluorophenoxy)propoxy]phenyl}vinyl)-1H-indol-3-yl]butanoic acid TLC: Rf 0.56 (dichloromethane:methanol:acetic acid=90:10:1); $^1$H-NMR (DMSO-$d_6$): δ 12.26 (brs, 2H), 7.52 (d, 1H), 7.50 (d, 2H), 7.45 (d, 1H), 7.26-7.08 (m, 4H), 7.08 (s, 1H), 7.02 (t, 1H), 7.00-6.86 (m, 4H), 5.13 (s, 2H), 4.21 (t, 2H), 4.16 (t, 2H), 2.67 (t, 2H), 2.28 (t, 2H), 2.20 (quintet, 2H), 1.85 (quintet, 2H).

Example 44(70)

4-[1-carboxymethyl)-7-((E)-2-{4-[3-(2-chlorophenoxy)propoxy]phenyl}vinyl)-1H-indol-3-yl]butanoic acid TLC: Rf 0.54 (dichloromethane:methanol:acetic acid=90:10:1); $^1$H-NMR (DMSO-$d_6$): δ 12.33 (brs, 2H), 7.52 (d, 1H), 7.50 (d, 2H), 7.45 (d, 1H), 7.41 (dd, 1H), 7.33-7.22 (m, 2H), 7.18 (dd, 1H), 7.08 (s, 1H), 7.02 (t, 1H), 7.00-6.86 (m, 4H), 5.13 (s, 2H), 4.22 (t, 2H), 4.19 (t, 2H), 2.67 (t, 2H), 2.28 (t, 2H), 2.20 (quintet, 2H), 1.85 (quintet, 2H).

Example 44(71)

4-[1-carboxymethyl)-7-((E)-2-{4-[3-(4,5-difluoro-2-methylphenoxy)propoxy]phenyl}vinyl)-1H-indol-3-yl]butanoic acid TLC: Rf 0.52 (dichloromethane:methanol:acetic acid=90:10:1); $^1$H-NMR (DMSO-$d_6$): δ 12.37 (brs, 2H), 7.52 (d, 1H), 7.50 (d, 2H), 7.45 (d, 1H), 7.30-7.18 (m, 2H), 7.10 (dd, 1H), 7.08 (s, 1H), 7.02 (t, 1H), 6.96 (d, 2H), 6.92 (d, 1H), 5.13 (s, 2H), 4.17 (t, 2H), 4.12 (t, 2H), 2.67 (t, 2H), 2.28 (t, 2H), 2.18 (quintet, 2H), 1.85 (quintet, 2H).

Example 44(72)

4-[1-carboxymethyl)-7-((E)-2-{4-[3-(3-chloro-2-methylphenoxy)propoxy]phenyl}vinyl)-1H-indol-3-yl]butanoic acid TLC: Rf 0.24 (chloroform:methanol:water=50:10:1); $^1$H-NMR (DMSO-$d_6$-): δ 1.78-1.92 (m, 2H), 2.16-2.25 (m, 2H), 2.21 (s, 3H), 2.28 (t, 2H), 2.66 (t, 2H), 4.16 (t, 2H), 4.18 (t, 2H), 5.12 (s, 2H), 6.92 (d, 1H), 6.95-7.05 (m, 5H), 7.08 (s, 1H), 7.17 (dd, 1H), 7.26 (d, 1H), 7.45 (dd, 1H), 7.50 (d, 2H), 7.52 (d, 1H), 11.51-13.53 (m, 2H).

Example 44(73)

4-[1-carboxymethyl)-7-((E)-2-{4-[3-(2-methylphenoxy)propoxy]phenyl}vinyl)-1H-indol-3-yl]butanoic acid TLC: Rf 0.24 (chloroform:methanol:water=50:10:1); $^1$H-NMR (DMSO-$d_6$): δ 1.77-1.91 (m, 2H), 2.14 (s, 3H), 2.14-2.23 (m, 2H), 2.27 (t, 2H), 2.66 (t, 2H), 4.12 (t, 2H), 4.18 (t, 2H), 5.11 (s, 2H), 6.81 (dt, 1H), 6.86-6.98 (m, 4H), 7.01 (dd, 1H), 7.07 (s, 1H), 7.09-7.17 (m, 2H), 7.25 (d, 1H), 7.44 (d, 1H), 7.49 (d, 2H), 7.48-7.57 (m, 1H), 11.28-13.21 (m, 2H).

Example 44(74)

4-[1-carboxymethyl)-7-((E)-2-{4-[3-(2,3-dichlorophenoxy)propoxy]phenyl}vinyl)-1H-indol-3-yl]butanoic acid TLC: Rf 0.21 (chloroform:methanol:water=50:10:1); $^1$H-NMR (DMSO-$d_6$): δ 1.77-1.92 (m, 2H), 2.14-2.26 (m, 2H), 2.27 (t, 2H), 2.66 (t, 2H), 4.18 (t, 2H),4.25 (t, 2H), 5.10 (s, 2H), 6.86-6.97 (m, 3H), 7.01 (dd, 1H), 7.06 (s, 1H), 7.17 (dd, 1H), 7.19-7.22 (m, 1H), 7.25 (d, 1H), 7.31 (dd, 1H), 7.44 (dd, 1H), 7.49 (d, 2H), 7.52 (d, 1H), 11.32-13.40 (m, 2H).

Example 44(75)

4-[1-carboxymethyl)-7-((E)-2-{4-[3-(2,3-difluorophenoxy)propoxy]phenyl}vinyl)-1H-indol-3-yl]butanoic acid TLC: Rf 0.53 (dichloromethane:methanol:acetic acid=90:10:1); $^1$H-NMR (DMSO-$d_6$): δ 1.85 (quintet, 2H), 2.21 (quintet, 2H), 2.28 (t, 2H), 2.67 (t, 2H), 4.16 (t, 2H), 4.26 (t, 2H), 5.13 (s, 2H), 6.86-7.19 (m, 8H), 7.26 (d, 1H), 7.45 (d, 1H), 7.50 (d, 2H), 7.52 (d, 1H), 12.37 (brs, 2H).

Example 44(76)

4-[1-carboxymethyl)-7-((E)-2-{4-[3-(4-fluoro-2-methylphenoxy)propoxy]phenyl}vinyl)-1H-indol-3-yl]butanoic acid TLC: Rf 0.53 (dichloromethane:methanol:acetic acid=90:10:1); $^1$H-NMR (DMSO-$d_6$): δ 1.85 (quintet, 2H), 2.15 (s, 3H), 2.18 (quintet, 2H), 2.28 (t, 2H), 2.67 (t, 2H), 4.11 (t, 2H), 4.18 (t, 2H), 5.13 (s, 2H), 6.87-7.00 (m, 6H), 7.02 (t, 1H), 7.08 (s, 1H), 7.26 (d, 1H), 7.45 (d, 1H), 7.50 (d, 2H), 7.52 (d, 1H), 12.29 (brs, 2H).

Example 44(77)

4-{1-carboxymethyl)-7-[(E)-2-(4-{[(2E)-4-(2,3-difluorophenoxy)-2-buten-1-yl]oxy}phenyl)vinyl]-1H-indol-3-yl}butanoic acid

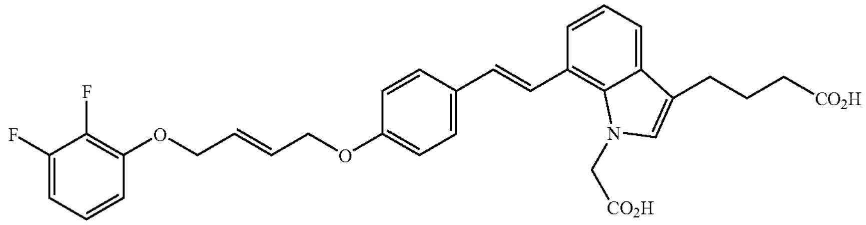

TLC: Rf 0.58 (dichloromethane:methanol:acetic acid=90:10:1); $^1$H-NMR (DMSO-$d_6$): δ 1.85 (quintet, 2H), 2.28 (t, 2H), 2.67 (t, 2H), 4.60-4.68 (m, 2H), 4.68-4.76 (m, 2H), 5.13 (s, 2H), 6.01-6.17 (m, 2H), 6.87-7.18 (m, 8H), 7.26 (d, 1H), 7.45 (d, 1H), 7.49 (d, 2H), 7.53 (d, 1H), 12.32 (brs, 2H).

Example 44(78)

4-(1-(carboxymethyl)-7-{(E)-2-[3-fluoro-4-(4-phenoxybutoxy)phenyl]vinyl}-1H-indol-3-yl)butanoic acid TLC: Rf 0.35 (dichloromethane:methanol=9:1); $^1$H-NMR (DMSO 6): δ 1.77-1.96 (m, 6H), 2.28 (t, 2H), 2.66 (t, 2H), 4.03 (t, 2H), 4.14 (t, 2H), 5.15 (s, 2H), 6.86-6.96 (m, 4H), 7.02 (t, 1H), 7.08 (s, 1H), 7.17 (t, 1H), 7.23-7.33 (m, 4H), 7.43-7.51 (m, 2H), 7.58 (d, 1H).

Example 44(79)

4-(1-(carboxymethyl)-7-{(E)-2-[6-(2-phenoxyethoxy)-1,3-benzothiazol-2-yl]vinyl}-1H-indol-3-yl)butanoic acid TLC: Rf 0.19 (chloroform:methanol:water=50:10:1); $^1$H-NMR (DMSO-$d_6$): δ 1.77-1.92 (m, 2H), 2.28 (t, 2H), 2.68 (t, 2H), 4.30-4.37 (m, 2H), 4.37-4.44 (m, 2H), 5.16 (s, 2H), 6.90-7.02 (m, 3H), 7.08 (dd, 1H), 7.14 (dd, 1H), 7.14 (s, 1H), 7.25-7.34 (m, 3H), 7.45 (d, 1H), 7.58 (dd, 1H), 7.72 (d, 1H), 7.85 ((d, 1H), 7.98 (d, 1H), 11.75-12.47 ((m, 1H), 12.64-13.52 (m, 1H).

Example 44(80)

4-(1-(carboxymethyl)-7-{(E)-2-[6-(4-phenoxybutoxy)-1,3-benzothiazol-2-yl]vinyl}-1H-indol-3-yl)butanoic acid TLC: Rf 0.23 (chloroform:methanol:water=50:10:1); $^1$H-NMR (DMSO-$d_6$): δ 1.78-2.00 (m, 6H), 2.29 (t, 2H), 2.68 (t, 2H), 3.98-4.09 (m, 2H), 4.08-4.16 (m, 2H), 5.16 (s, 2H), 6.86-6.98 (m, 3H), 7.05-7.13 (m, 2H), 7.13-7.15 (m, 1H), 7.23-7.33 (m, 3H), 7.45 (d, 1H), 7.58 (dd, 1H), 7.65 (d, 1H), 7.83 ((d, 1H), 7.98 ((d, 1H), 11.69-12.66 (m, 1H), 12.79-13.48 (m, 1H).

Example 44(81)

4-(1-(carboxymethyl)-7-{(E)-2-[2-fluoro-4-(4-phenoxybutoxy)phenyl]vinyl}-1H-indol-3-yl)butanoic acid TLC: Rf 0.30 (dichloromethane:methanol=9:1); $^1$H-NMR (DMSO-$d_6$): δ 1.78-1.93 (m, 6H), 2.28 (t, 2H), 2.67 (t, 2H), 3.94-4.15 (m, 4H), 5.11 (s, 2H), 6.79-6.97 (m, 6H), 7.03 (t, 1H), 7.08 (s, 1H), 7.22-7.32 (m, 3H), 7.47 (dd, 1H), 7.59-7.70 (m, 2H).

Example 44(82)

4-[1-(carboxymethyl)-7-((E)-2-{5-[4-(2,3-difluorophenoxy)butoxy]-2-pyridinyl}vinyl)-1H-indol-3-yl]butanoic acid TLC: Rf 0.18 (dichloromethane:methanol=9:1); $^1$H-NMR (DMSO-$d_6$): δ 1.78-1.97 (m, 6H), 2.28 (t, 2H), 2.67 (t, 2H), 4.09423 (m, 4H), 5.09 (s, 2H), 6.90-7.18 (m, 6H), 7.28 (d, 1H), 7.39 (dd, 1H), 7.45-7.56 (m, 2H), 7.94 (d, 1H), 8.26 (d, 1H).

Example 44(83)

4-[1-(carboxymethyl)-7-((E)-2-{4-[3-(2,4-dichlorophenoxy)propoxy]phenyl}vinyl)-1H-indol-3-yl]butanoic acid TLC: Rf 0.53 (dichloromethane:methanol:acetic acid=90:10:1); $^1$H-NMR (DMSO-$d_6$): δ 1.84 (quintet, 2H), 2.20 (quintet, 2H), 2.28 (t, 2H), 2.66 (t, 2H), 4.18 (t, 2H), 4.23 (t, 2H), 5.12 (s, 2H), 6.92 (d, 1H), 6.96 (d, 2H), 7.02 (t, 1H), 7.08 (s, 1H), 7.21 (d, 1H), 7.26 (d, 1H), 7.36 (dd, 1H), 7.45 (d, 1H), 7.49 (d, 2H), 7.52 (d, 1H), 7.57 (d, 1H), 12.23 (brs, 2H).

Example 44(84)

4-{1-(carboxymethyl)-7-[(E)-2-(4-{[(2E)-4-phenoxy-2-buten-1-yl]oxy}phenyl)vinyl]-1H-indol-3-yl}butanoic acid TLC: Rf 0.52 (dichloromethane:methanol:acetic acid=90:10:1); $^1$H-NMR (DMSO-$d_6$): δ 1.85 (quintet, 2H), 2.28 (t, 2H), 2.67 (t, 2H), 4.55-4.68 (m, 4H), 5.13 (s, 2H), 5.99-6.15 (m, 2H), 6.87-7.01 (m, 6H), 7.02 (t, 1H), 7.08 (s, 1H), 7.23-7.33 (m, 3H), 7.45 (d, 1H), 7.50 (d, 2H), 7.53 (d, 1H), 12.29 (brs, 2H).

Example 44(85)

4-[1-(carboxymethyl)-7-((E)-2-{5-[4-(2-chlorophenoxy)butoxy]-2-pyridinyl}vinyl)-1H-indol-3-yl]butanoic acid TLC: Rf 0.46 (dichloromethane:methanol=4:1); $^1$H-NMR (DMSO-$d_6$): δ 1.75-2.01 (m, 6H), 2.28 (t 2H), 2.67 (t 2H), 4.05-4.27 (m, 4H), 5.09 (s, 2H), 6.89-7.20 (m, 5H), 7.28 (d, 2H), 7.31-7.57 (m, 4H), 7.94 (d, 1H), 8.26 (d, 1H).

Example 44(86)

4-[1-(carboxymethyl)-7-((E)-2-{5-[4-(2-fluorophenoxy)butoxy]-2-pyridinyl}vinyl)-1H-indol-3-yl]butanoic acid TLC: Rf 0.48 (dichloromethane:methanol=4:1); $^1$H-NMR (DMSO-$d_6$): δ 1.77-1.97 (m, 6H), 2.28 (t, 2H), 2.67 (t, 2H), 4.05-4.21 (m, 4H), 5.07 (s, 2H), 6.87-7.24 (m, 7H), 7.28 (d, 1H), 7.38 (dd, 1H), 7.48 (d, 1H), 7.53 (d, 1H), 7.94 (d, 1H), 8.26 (d, 1H).

Example 44(87)

4-[1-(carboxymethyl)-7-((E)-2-{5-[4-(2-chloro-3,5-difluorophenoxy)butoxy]-2-pyridinyl}vinyl)-1H-indol-3-yl]butanoic acid TLC: Rf 0.51 (dichloromethane:methanol=4:1); $^1$H-NMR (DMSO-$d_6$): δ 1.78-1.97 (m, 6H), 2.28 (t 2H), 2.67 (t, 2H), 4.11-4.23 (m, 4H), 5.08 (s, 2H), 6.96 (d, 1H), 7.00-7.11 (m, 4H), 7.28 (d, 1H), 7.38 (dd, 1H), 7.45-7.50 (m, 1H), 7.53 (d, 1H), 7.94 (d, 1H), 8.26 (d, 1H).

Example 44(88)

4-[1-(carboxymethyl)-7-[(E)-2-(4-{[(2Z)-4-phenoxy-2-buten-1-yl]oxy}phenyl)vinyl]-1H-indol-3-yl]butanoic acid TLC: Rf 0.62 (dichloromethane:methanol:acetic acid=9:1:0.1); $^1$H-NMR (DMSO-$d_6$): δ 1.85 (quintet 2H), 2.28 (t 2H), 2.67 (t 2H), 4.68-4.82 (m, 4H), 5.13 (s, 2H), 5.82-5.94 (m, 2H), 6.86-7.12 (m, 8H), 721-7.35 (m, 3H), 7.45 (d, 1H), 7.51 (d, 2H), 7.53 (d, 1H), 12.33 (brs, 2H).

Example 44(89)

4-(1-carboxymethyl)-7-{(E)-2-[4-({2-[(2,3-difluorophenoxy)methyl]benzyl}oxy)phenyl]vinyl}-1H-indol-3-yl)butanoic acid TLC: Rf 0.60 (dichloromethane:methanol:acetic acid=90:10:1); $^1$H-NMR (DMSO-$d_6$): δ 1.75-1.94 (m, 2H), 2.28 (t, 2H), 2.66 (t, 2H), 5.13 (s, 2H), 5.28 (s, 2H), 5.36 (s, 2H), 6.92 (d, 1H), 6.96-7.17 (m, 7H), 7.26 (d, 1H), 7.35-7.62 (m, 8H), 12.31 (s, 2H).

Example 44(90)

4-{1-(carboxymethyl)-7-[(E)-2-(4-{[(2Z)-4-(2,3-difluorophenoxy)-2-buten-1-yl]oxy}phenyl)vinyl]-1H-indol-3-yl}butanoic acid TLC: Rf 0.58 (dichloromethane:methanol:acetic acid=90:10:1); $^1$H-NMR (DMSO-$d_6$): δ 1.75-1.96 (m, 2H) 2.28 (t, 2H), 2.67 (t, 2H), 4.77 (d, 2H), 4.86 (d, 2H), 5.04-5.22 (m, 2H), 5.83-5.99 (m, 2H), 6.86-7.20 (m, 8H), 7.26 (d, 1H), 7.45 (dd, 1H), 7.51 (d, 2H), 7.53 (d, 1H), 12.31 (s, 2H).

Example 44(91)

4-[1-(carboxymethyl-7-((E)-2-{5-[4-(2,3-dichlorophenoxy)butoxy]-2-pyridinyl}vinyl)-1H-indol-3-yl]butanoic acid TLC: Rf 0.56 (dichloromethane:methanol=4:1); $^1$H-NMR (DMSO-$d_6$): δ 1.77-2.00 (m, 6H), 2.28 (t 2H), 2.67 (t 2H), 4.06-4.24 (m, 4H), 5.06 (s, 2H), 6.95 (d, 1H), 7.03 (t, 1H), 7.08 (s, 1H), 7.12-7.41 (m, 5H), 7.48 (d, 1H), 7.53 (d, 1H), 7.94 (d, 1H), 8.26 (d, 1H).

Example 44(92)

4-[1-(carboxymethyl-7-((E)-2-{5-[4-(4-fluoro-2-methylphenoxy)butoxy]-2-pyridinyl}vinyl)-1H-indol-3-yl]butanoic acid TLC: Rf 0.35 (dichloromethane:methanol=4:1); $^1$H-NMR (DMSO-$d_6$): δ 1.76-2.00 (m, 6H) 2.14 (s, 3H), 2.28 (t, 2H), 2.67 (t, 2H), 3.97-4.06 (m, 2H), 4.09-4.20 (m, 2H), 5.10 (s, 2H), 6.89-7.07 (m, 5H), 7.09 (s, 1H), 7.28 (d, 1H), 7.39 (dd, 1H), 7.46-7.55 (m, 2H), 7.93 (d, 1H), 8.27 (d, 1H).

Example 44(93)

4-{1-(carboxymethyl)-7-[(E)-2-(4-{[(2E)-4-(mesityloxy)-2-buten-1-yl]oxy}phenyl)vinyl]-1H-indol-3-yl}butanoic acid TLC: Rf 0.55 (dichloromethane:methanol:acetic acid=90:10:1); $^1$H-NMR (DMSO-$d_6$): δ 1.78-1.92 (m, 2H), 2.16 (s, 9H), 2.28 (t, 2H), 2.67 (t, 2H), 4.28 (d, 2H), 4.64 (d, 2H), 5.13 (s, 2H), 5.96-6.21 (m, 2H), 6.80 (s, 2H), 6.93 (d, 1H), 6.97 (d, 2H), 7.02 (t, 1H), 7.08 (s, 1H), 7.26 (d, 1H), 7.45 (d, 1H), 7.50 (d, 2H), 7.53 (d, 1H), 12.48 (s, 2H).

Example 44(94)

4-[1-(carboxymethyl-7-[(E)-2-(4-{[(2E)-4-(2-chloro-6-fluoro-3-methylphenoxy)-2-buten-1-yl]oxy}phenyl)vinyl]-1H-indol-3-yl]butanoic acid TLC: Rf 0.56 (dichloromethane:methanol:acetic acid=90:10:1); $^1$H-NMR (DMSO-$d_6$): δ 1.77-1.95 (m, 2H), 2.28 (t, 2H), 2.26-2.30 (m, 3H),2.67 (t, 2H), 4.51-4.74 (m, 4H), 5.13 (s, 2H), 5.94-6.17 (m, 2H), 6.92 (d, 1H), 6.93 (d, 2H), 6.97-7.23 (m, 4H), 7.26 (d, 1H), 7.45 (d, 1H), 7.49 (d, 2H), 7.53 (d, 1H), 12.42 (s, 2H).

Example 44(95)

4-{1-(carboxymethyl-7-[(E)-2-(4-{[(2E)-4-(6-chloro-2-fluoro-3-methylphenoxy)-2-buten-1-yl]oxy}phenyl)vinyl]-1H-indol-3-yl}butanoic acid TLC: Rf 0.49 (dichloromethane:methanol:acetic acid=90:10:0.5); $^1$H-NMR (DMSO-$d_6$): δ 1.63-1.96 (m, 2H), 2.21 (d, 3H), 2.28 (t, 2H), 2.67 (t, 2H) 4.57-4.66 (m, 4H), 5.10 (s, 2H), 6.03-6.09 (m, 2H), 6.87-7.11 (m, 6H), 7.16-7.31 (m, 2H), 7.39-7.60 (m, 4H), 12.15 (s, 2H).

Example 45 ethyl 4-[7-bromo-1-[2-(ethyloxy)-2-oxoethyl]-2-(methylthio)-1H-indol-3-yl]butanoate To a chloroform (0.8 mL) solution of dimethyl disulfide (30 mg), sulfuryl chloride (34 mg) was added at −15° C. and the mixture was stirred at −5° C. for 1.5 hours. To the reaction mixture, a chloroform (0.5 mL) solution of the compound prepared in Example 43, namely, ethyl 4-{7-bromo-1-[2-(ethyloxy)-2-oxoethyl]-1H-indol-3-yl}butanoate (100 mg) was added at −78° C., followed by stirring at room temperature for 3 hours. To the reaction mixture, an aqueous saturated sodium hydrogen carbonate solution was added under ice cooling, followed by extraction with ethyl acetate. The organic layer was washed in turn with an aqueous saturated sodium hydrogen carbonate solution, water and saturated saline, dried over anhydrous magnesium sulfate and then concentrated. The residue was purified by silica gel column chromatography (n-hexane:ethyl acetate=95:5→91:9) to obtain the titled compound having the following physical properties (70 mg).

TLC: Rf 0.45 (n-hexane:ethyl acetate=5:1); $^1$H-NMR ($CDCl_3$): δ 1.23-1.30 (m, 6H), 1.96-2.03 (m, 2H), 2.23 (s, 3H), 2.36 (t, 2H), 2.96 (t, 2H), 4.13 (q, 2H), 4.24 (q, 2H), 5.58 (s, 2H), 6.92-6.97 (m, 1H), 7.37 (dd, 1H), 7.54 (dd, 1H).

Example 46

4-[1-(carboxymethyl-7-((E)-2-{4-[4-(2,3-difluorophenoxy)butoxy]phenyl}vinyl)-2-methylthio)-1H-indol-3-yl]butanoic acid To a dimethoxyethane (6 mL) solution of the compound (95 mg) prepared in Example 45, an aqueous lithium hydroxide solution (1M, 1.5 mL) was added under ice cooling and the mixture was stirred at 50° C. for 5 hours. The reaction mixture was neutralized by adding an aqueous 5% potassium hydrogen sulfate solution under ice cooling and then extracted with ethyl acetate. The organic layer was washed in turn with water and saturated saline, dried over anhydrous magnesium sulfate and then concentrated. The residue was recrystallized from a mixed solvent of ethyl acetate/tetrahydrofuran/n-hexane to obtain a compound (70 mg) of the present invention having the following physical properties.

TLC: Rf 0.50 (methylene chloride:methanol:acetic acid=9:1:0.05); $^1$H-NMR (DMSO-$d_6$): δ 1.75-1.95 (m, 6H), 2.21-2.30 (m, 5H), 2.87 (t, 2H), 4.07 (t, 2H), 4.12-4.21 (m, 2H), 5.28 (s, 2M), 6.85-7.20 (, 7H), 7.31 (d, 1H), 7.46-7.59 (m, 4H), 12.03 (s, 1H), 13.19 (s, 1H).

Example 47

4-[(7-bromo-1H-indol-3-yl)thio]butanoic acid

To a methanol (15 mL) solution of 7-bromoindole (0.98 g) and thiourea (0.46 g), an aqueous 0.2M potassium triiodide solution (30 mL) was added dropwise and the mixture was stirred at room temperature for 2 hours. The reaction mixture was filtered and the filtrate was subjected to deaeration and argon substitution. To the filtrate, a 10 N sodium hydroxide solution (2 mL) was added, followed by stirring at 90° C. for 2 hours. The mixture was air-cooled and a diethyl ether (7.5 mL) solution of methyl bromobutyrate (0.91 g) was added, followed by stirring for one hour. To the reaction mixture, methanol (10 mL) was added, followed by stirring overnight. Furthermore, water was added, followed by extraction with tert-butyl methyl ether. The organic layer was washed in turn with water and saturated saline. The pH of the aqueous layer was adjusted to 2 by adding 1M hydrochloric acid, followed by extraction with ethyl acetate. The organic layer was washed in turn with water and saturated saline, dried over anhydrous magnesium sulfate and then concentrated to obtain the titled compound.

TLC: Rf 0.32 (methylene chloride:methanol=9:1).

Example 48 methyl 4-[(7-bromo-1H-indol-3-yl)thio]butanoate

To the compound prepared in Example 47, methanol (3.5 mL) and ethyl acetate (3.5 mL) were added and 2M (trimethylsilyl)diazomethane (1.4 mL) was added dropwise under ice cooling. The mixture was stirred at room temperature for 30 minutes and then concentrated. The residue was purified by silica gel column chromatography (n-hexane:ethyl acetate=85:15) to obtain the titled compound having the following physical properties (0.31 g).

TLC: Rf 0.44 (n-hexane:ethyl acetate=3:1); $^1$H-NMR ($CDCl_3$): δ 1.79-1.89 (m, 2H), 2.45 (t, 2H) 2.73 (t, 2H), 3.64 (s, 3H), 7.09 (dd, 1H), 7.38-7.41 (m, 2H), 7.68-7.71 (m, 1H), 8.45 (s, 1H).

Example 49

4-[(1-carboxymethyl)-7-{(E)-2-[4-(4-phenoxybutoxy)phenyl]vinyl}-1H-indol-3-yl)thio]butanoic acid

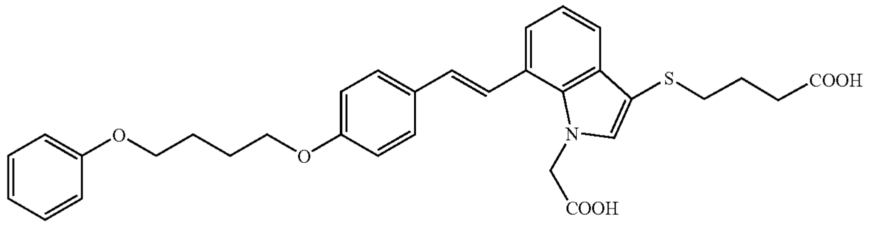

The same operation was conducted in the same manner as in Example 37→Example 3→Example 46 to obtain the titled compound having the following physical properties. In the step corresponding to Example 37, the compound prepared in Example 48 was used in place of ethyl 7-bromo-3-[4-(ethyloxy)-4-oxobutanoyl]-1H-indole-2-carboxylate and ethyl bromoacetate was used in place of methyl iodide.

TLC: Rf 0.47 (dichloromethane:methanol:acetic acid=9:1:0.05); $^1$H-NMR (DMSO-$d_6$): δ 1.61-1.74 (m, 2H), 1.82-1.91

(m, 4H), 2.32 (t, 2H), 2.65 (t, 2H), 3.95-4.14 (m, 4H), 5.20 (s, 2H), 6.84-6.99 (m, 6H), 7.05-7.18 (m, 1H), 7.21-7.37 (m, 3H), 7.44-7.61 (m, 5H), 12.05 (s, 1H), 13.11 (s, 1H).

Example 49(1) to Example 49(25)

Using a corresponding compound, the same operation as in Example 47→Example 48→Example 49 was conducted to obtain the titled compound having the following physical properties.

Example 49(1)

3-[(1-carboxymethyl)-7-{(E)-2-[4-(4-phenoxybutoxy)phenyl]vinyl}-1H-indol-3-yl)thio]propanoic acid TLC: Rf 0.60 (dichloromethane:methanol:acetic acid=9:1:0.05); $^1$H-NMR (DMSO-$d_6$): δ 1.83-1.91 (m, 4H), 2.40 (t, 2H), 2.79 (t, 2H), 3.98-4.12 (m, 4H), 5.22 (s, 2H), 6.83-7.04 (m, 6H), 7.14 (dd, 1H), 7.23-7.36 (m, 3H), 7.45-7.59 (m, 5H), 12.28 (s, 1H), 13.14 (s, 1H).

Example 49(2)

[(1-carboxymethyl)-7-{(E)-2-[4-(4-phenoxybutoxy)phenyl]vinyl}-1H-indol-3-yl)thio]acetic acid TLC: Rf 0.41 (dichloromethane:methanol:acetic acid=9:1:0.05); $^1$H-NMR (DMSO-$d_6$): δ 1.82-1.93 (m, 4H), 3.39 (s, 2H), 3.99-4.10 (m, 4H), 5.17 (s, 2H), 6.85-7.01 (m, 6H), 7.13 (dd, 1H), 7.22-7.39 (m, 3H), 7.46-7.60 (m, 5H).

Example 49(3)

4-{[1-(carboxymethyl)-7-((E)-2-{4-[4-(mesityloxy)butoxy]phenyl}vinyl)-1H-indol-3-yl]thio}butanoic acid TLC: Rf 0.53 (dichloromethane:methanol:acetic acid=9:1:0.05); $^1$H-NMR (DMSO-$d_6$): δ 1.54-1.75 (m, 2H), 1.81-2.02 (m, 4H), 2.17 (s, 9H), 2.32 (t, 2H), 2.65 (t, 2H), 3.74 (t, 2H), 4.07 (t, 2H), 5.18 (s, 2H), 6.80 (s, 2H), 6.89-6.99 (m, 3H), 7.12 (dd, 1H), 7.32 (d, 1H), 7.42-7.58 (m, 5H).

Example 49(4)

{[1-(carboxymethyl)-7-((E)-2-{4-[4-chlorophenoxy)butoxy]phenyl}vinyl)-1H-indol-3-yl]thio}acetic acid TLC: Rf 0.40 (dichloromethane:methanol:acetic acid=9:1:0.05); $^1$H-NMR (DMSO-$d_6$): δ 1.82-1.99 (m, 4H), 3.39 (s, 2H), 4.03-4.17 (m, 4H), 5.20 (s, 2H), 6.87-6.98 (m, 4H), 7.08-7.19 (m, 2H), 7.23-7.37 (m, 2H), 7.41 (dd, 1H), 7.46-7.62 (m, 5H).

Example 49(5)

{[1-(carboxymethyl)-7-((E)-2-{4-[4-(2,3-difluorophenoxy)butoxy]phenyl}vinyl)-1H-indol-3-yl]thio}acetic acid

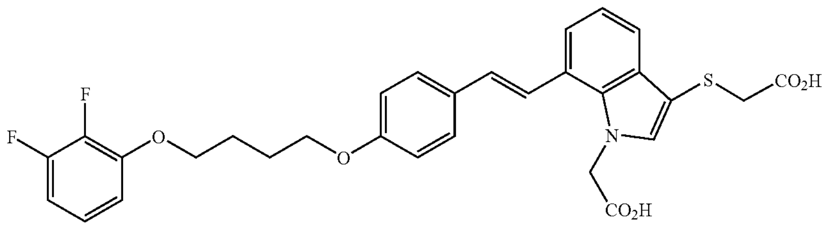

TLC: Rf 0.31 (dichloromethane:methanol:acetic acid=9:1:0.05); $^1$H-NMR (DMSO-$d_6$): δ 1.86-1.92 (m, 4H), 3.39 (s, 2H), 4.07 (t, 2H), 4.16 (t, 2H), 5.21 (s, 2H), 6.88-7.20 (m, 7H), 7.33 (d, 1H), 7.45-7.61 (m, 5H).

Example 49(6)

3-{[1-(carboxymethyl)-7-((E)-2-{4-[4-(2-chlorophenoxy)butoxy]phenyl}vinyl)-1H-indol-3-yl]thio}propanoic acid TLC: Rf 0.61 (dichloromethane:methanol:acetic acid=9:1:0.05); $^1$H-NMR (DMSO-$d_6$): δ 1.85-1.95 (m, 4H), 2.41 (t, 2H), 2.79 (t, 2H), 4.05-4.20 (m, 4H), 5.19 (s, 2H), 6.88-6.99 (m, 4H), 7.08-7.19 (m, 2H), 7.24-7.36 (m, 2H), 7.41 (dd, 1H), 7.47-7.59 (m, 5H).

Example 49(7)

3-{[1-(carboxymethyl)-7-((E)-2-{4-[4-difluorophenoxy)butoxy]phenyl}vinyl)-1H-indol-3-yl]thio}propanoic acid TLC: Rf 0.47 (dichloromethane:methanol:acetic acid=9:1:0.05); $^1$H-NMR (DMSO-$d_6$): δ 1.84-1.94 (m, 4H), 2.40 (t, 2H), 2.79 (t 2H), 4.06 (t 2H), 4.12-4.20 (m, 2H), 5.21 (s, 2H), 6.89-7.19 (m, 7H), 7.33 (d, 1H), 7.45-7.59 (m, 5H), 12.31 (s, 2H).

Example 49(8)

{[1-(carboxymethyl)-7-((E)-2-{4-[4-mesityloxy) butoxy]phenyl}vinyl)-1H-indol-3-yl]thio}acetic acid

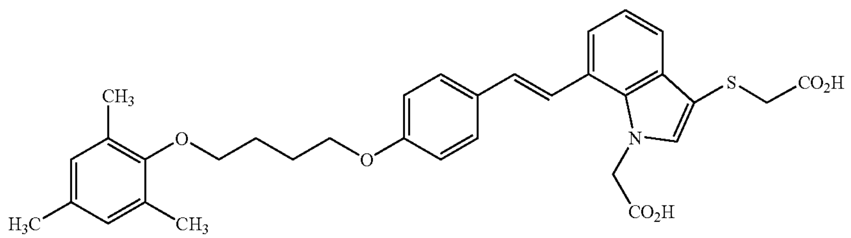

TLC: Rf 0.43 (dichloromethane:methanol:acetic acid=9:1:0.05); $^1$H-NMR (DMSO-$d_6$): δ 1.74-2.00 (m, 4H), 2.17 (s, 9H), 3.39 (s, 2H), 3.74 (t, 2H), 4.07 (t 2H), 5.20 (s, 2H), 6.80 (s, 2H), 6.89-7.01 (m, 3H), 7.13 (dd, 1H), 7.33 (d, 1H), 7.47-7.63 (m, 5H), 12.56 (s, 1H), 13.09 (s, 1H).

Example 49(9)

3-{[1-(carboxymethyl)-7-((E)-2-{4-[4-mesityloxy) butoxy]phenyl}vinyl)-1H-indol-3-yl]thio}propanoic acid TLC: Rf 0.42 (dichloromethane:methanol:acetic acid=9:1:0.05); $^1$H-NMR (DMSO-$d_6$): δ 1.78-2.01 (m, 4H), 2.17 (s, 9H), 2.41 (t, 2H), 2.79 (t 2H), 3.74 (t 2H), 4.08 (t 2H), 5.22 (s, 2H), 6.80 (s, 2H), 6.87-7.03 (m, 3H), 7.14 (dd, 1H), 7.34 (d, 1H), 7.43-7.62 (m, 5H), 12.31 (s, 1H), 12.81 (s, 1H).

Example 49(10)

{[1-(carboxymethyl)-7-((E)-2-{4-[4-(2,4-dichloro-6-methylphenoxy)butoxy]phenyl}vinyl)-1H-indol-3-yl]thio}acetic acid TLC: Rf 0.47 (dichloromethane:methanol:acetic acid=9:1:0.05); $^1$H-NMR (DMSO-$d_6$): δ 1.82-2.01 (m, 4H), 2.24-2.33 (m, 3H), 3.39 (s, 2H), 3.93 (t, 2H), 4.08 (t 2H), 5.20 (s, 2H), 6.87-7.02 (m, 3H), 7.13 (dd, 1H), 7.28-7.37 (m, 2H), 7.41-7.60 (m, 6H), 12.51 (s, 1H), 12.98 (s, 1H).

Example 49(11)

{[1-(carboxymethyl)-7-((E)-2-{4-[4-(2-methylphenoxy)butoxy]phenyl}vinyl)-1H-indol-3-yl]thio}acetic acid TLC: Rf 0.45 (dichloromethane:methanol:acetic acid=9:1:0.05); $^1$H-NMR (DMSO-$d_6$): δ 1.82-1.97 (m, 4H), 2.14 (s, 3H), 3.39 (s, 2H), 3.92-4.19 (m, 4H), 5.19 (s, 2H), 6.74-6.84 (m, 1H), 6.87-7.02 (m, 4H), 7.06720 (m, 3H), 7.33 (d, 1H), 7.43-7.62 (m, 5H), 12.54 (s, 2H).

Example 49(12)

{[1-(carboxymethyl)-7-((E)-2-{4-[4-(2-fluorophenoxy)butoxy]phenyl}vinyl)-1H-indol-3-yl]thio}acetic acid TLC: Rf 0.46 (dichloromethane:methanol:acetic acid=9:1:0.05); $^1$H-NMR (DMSO-$d_6$): δ 1.77-2.00 (m, 4H), 3.39 (s, 2H), 4.01-4.17 (m, 4H), 5.20 (s, 2H), 6.85-6.99 (m, 4H), 7.05-7.25 (m, 4H), 7.33 (d, 1H), 7.45-7.64 (m, 5H), 12.68 (s, 2H).

Example 49(13)

{[1-(carboxymethyl)-7-((E)-2-{4-[4-(2,6-dimethylphenoxy)butoxy]phenyl}vinyl)-1H-indol-3-yl]thio}acetic acid TLC: Rf 0.43 (dichloromethane:methanol:acetic acid=9:1:0.05); $^1$H-NMR (DMSO-$d_6$): δ 1.77-2.02 (m, 4H), 2.22 (s, 6H), 3.39 (s, 2H), 3.79 (t 2H), 4.08 (t, 2H), 5.20 (s, 2H), 6.80-7.04 (m, 6H), 7.13 (dd, 1H), 7.34 (d, 1H), 7.44-7.64 (m, 5H), 12.63 (s, 2H).

Example 49(14)

{[1-(carboxymethyl)-7-((E)-2-{4-[4-chloro-2,6-dimethylphenoxy)butoxy]phenyl}vinyl)-1H-indol-3-yl]thio}acetic acid TLC: Rf 0.39 (dichloromethane:methanol:acetic acid=9:1:0.05); $^1$H-NMR (DMSO-$d_6$): δ 1.82-2.03 (m, 4H), 2.21 (s, 6H), 3.39 (s, 2H), 3.78 (t 2H), 4.07 (t, 2H), 5.19 (s, 2H), 6.86-7.01 (m, 3H), 7.09 (s, 2H), 7.13 (dd, 1H), 7.33 (d, 1H), 7.45-7.61 (m, 5H), 12.64 (s, 2H).

Example 49(15)

3-[(1-(carboxymethyl)-7-{(E)-2-[4-(4-(phenyoxybutoxy)phenyl]vinyl}-1H-indol-3-yl)thio]butanoic acid TLC: Rf 0.25 (dichloromethane:methanol=9:1); $^1$H-NMR (DMSO-$d_6$): δ 1.17 (d, 3H), 1.77-1.95 (m, 4H), 2.28 (dd, 1H), 2.43 (dd, 1H), 3.12-3.24 (m, 1H), 3.89-4.16 (m, 4H), 4.93 (s, 2H), 6.86-6.98 (m, 6H), 7.10 (t, 1H), 722-7.35 (m, 3H), 7.44 (s, 1H), 7.49-7.58 (m, 3H), 7.66 (d, 1H).

Example 49(16)

2-[(1-(carboxymethyl)-7-{(E)-2-[4-(4-(phenyoxybutoxy)phenyl]vinyl}-1H-indol-3-yl)thio]propanoic acid TLC: Rf 0.33 (dichloromethane:methanol=9:1); $^1$H-NMR (DMSO-$d_6$): δ 1.26 (d, 3H), 1.80-1.94 (m, 4H), 3.48 (q, 1H), 3.96-4.14 (m, 4H), 5.25 (s, 2H), 6.87-7.00 (m, 6H), 7.13 (t, 1H), 7.21-7.37 (m, 3H), 7.46-7.60 (m, 5H), 12.47 (s, 1H), 13.13 (s, 1H).

Example 49(17)

2-[(1-(carboxymethyl)-7-((E)-2-{4-[4-(phenoxybutoxy)phenyl]vinyl})-1H-indol-3-yl)thio]butanoic acid TLC: Rf 0.18 (dichloromethane:methanol=9:1); $^1$H-NMR (DMSO-$d_6$): δ 0.93 (t, 3H), 1.55-1.77 (m, 2H), 1.79-1.97 (m, 4H), 3.18-3.28 (m, 1H), 3.96-4.13 (m, 4H), 5.23 (s, 2H), 6.85-7.01 (m, 6H), 7.13 (t, 1H), 7.22-7.38 (m, 3H), 7.43-7.62 (m, 5H), 12.50 (s, 1H), 13.09 (s, 1H).

Example 49(18)

2-{[1-(carboxymethyl)-7-((E)-2-{4-[4-(2,3-difluorophenoxy)butoxy]phenyl}vinyl)-1H-indol-3-yl]thio}propanoic acid TLC: Rf 0.49 (dichloromethane:methanol:acetic acid=9:1:0.05); $^1$H-NMR (DMSO-$d_6$): δ 1.26 (d, 3H), 1.82-1.97 (m, 4H), 3.43-3.53 (m, 1H), 4.07 (t 2H), 4.12-4.20 (m, 2H), 523 (s, 2H), 6.88-7.21 (m, 7H), 7.33 (d, 1H), 7.46-7.59 (m, 5H), 12.50 (s, 1H), 13.06 (s, 1H).

Example 49(19)

2-{[1-(carboxymethyl)-7-((E)-2-{4-[4-(2-chloro-3,5-difluorophenoxy)butoxy]phenyl}vinyl)-1H-indol-3-yl]thio}propanoic acid TLC: Rf 0.40 (dichloromethane:methanol:acetic acid=9:1:0.05); $^1$H-NMR (DMSO-$d_6$): δ 1.26 (d, 3H), 1.76-2.00 (m, 4H), 3.47 (q, 1H), 4.01-4.12 (m, 2H), 4.13-4.26 (m, 2H), 5.23 (s, 2H), 6.83-7.17 (m, 6H), 7.32 (d, 1H), 7.43-7.60 (m, 5H), 12.49 (s, 1H), 13.07 (s, 1H).

Example 49(20)

2-[(1-(carboxymethyl)-7-{(E)-2-[4-(4-phenoxybutoxy)phenyl]vinyl}-1H-indol-3-yl)thio]-2-methylpropanoic acid TLC: Rf 0.18 (dichloromethane:methanol=9:1); $^1$H-NMR (DMSO-$d_6$): δ 1.35 (s, 6H), 1.79-1.97 (m, 4H), 3.94-4.15 (m, 4H), 5.25 (s, 2H), 6.85-7.01 (m, 6H), 7.11 (t, 1H), 7.20-7.37 (m, 3H), 7.42-7.62 (m, 5H), 12.45 (s, 1H), 13.11 (s, 1H).

Example 49(21)

3-{[1-(carboxymethyl)-7-((E)-2-{4-[4-(2,3-difluorophenoxy)butoxy]phenyl}vinyl)-1H-indol-3-yl]thio}butanoic acid TLC: Rf 0.51 (dichloromethane:methanol=9:1); $^1$H-NMR (DMSO-$d_6$): δ 1.17 (d, 3H), 1.83-1.95 (m, 4H), 2.24-2.43 (m, 2H), 3.10-3.23 (m, 1H), 4.07 (t 2H), 4.16 (t, 2H), 5.24 (s, 2H), 6.89-7.19 (m, 7H), 7.30-7.37 (m, 1H), 7.44-7.62 (m, 5H), 12.32 (s, 1H), 13.08 (s, 1H).

Example 49(22)

3-{[1-(carboxymethyl)-7-((E)-2-{4-[4-(2-chloro-3,5-difluorophenoxy)butoxy]phenyl}vinyl)-1H-indol-3-yl]thio}butanoic acid TLC: Rf 0.39 (dichloromethane:methanol=9:1); $^1$H-NMR (DMSO-$d_6$): δ 1.17 (d, 3H), 1.79-2.06 (m, 4H), 2.21-2.46 (m, 2H), 3.11-3.26 (m, 1H), 4.04-4.13 (m, 2H), 4.14-4.23 (m, 2H), 5.24 (s, 2H), 6.87-7.10 (m, 5H), 7.14 (dd, 1H), 7.33 (d, 1H), 7.45-7.61 (m, 5H), 12.31 (s, 2H).

Example 49(23)

3-{[1-(carboxymethyl)-7-((E)-2-{4-[4-(2,3-difluorophenoxy)butoxy]phenyl}vinyl)-1H-indol-3-yl]thio}-2-methylpropanoic acid

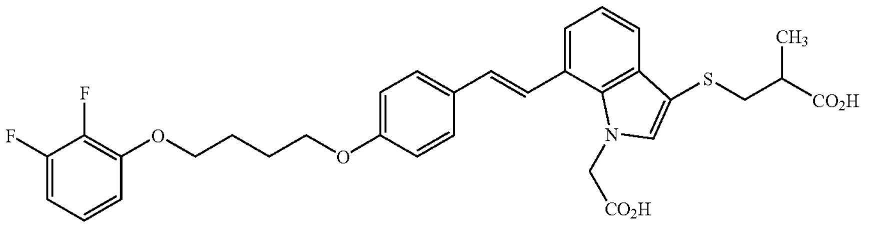

TLC: Rf 0.50 (dichloromethane:methanol:acetic acid=9:1:0.05); $^1$H-NMR (DMSO-$d_6$): δ 1.15 (d, 3H), 1.84-1.97 (m, 4H), 2.41 (q, 1H), 2.57-2.63 (m, 1H), 2.89-2.96 (m, 1H), 4.00-4.10 (m, 2H), 4.12-4.20 (m, 2H), 5.21 (s, 2H), 6.87-7.20 (m, 7H), 7.33 (d, 1H), 7.46-7.59 (m, 5H), 12.31 (s, 1H), 13.05 (s, 1H).

Example 49(24)

3-{[1-(carboxymethyl)-7-((E)-2-{4-[4-(2-chloro-3,5-difluorophenoxy)butoxy]phenyl}vinyl)-1H-indol-3-yl]thiol}-2-methylpropanoic acid TLC: Rf 0.48 (dichloromethane:methanol:acetic acid=9:1:0.05); $^1$H-NMR (DMSO-$d_6$): δ 1.14 (d, 3H), 1.84-2.03 (m, 4H), 2.34-2.45 (m, 1H), 2.54-2.66 (m, 1H), 2.87-2.97 (m, 1H), 4.08 (t, 2H), 4.14-4.23 (m, 2H), 5.17 (s, 2H), 6.87-7.20 (m, 6H), 7.33 (d, 1H), 7.44-7.60 (m, 5H), 12.37 (s, 1H), 13.10 (s, 1H).

Example 49(25)

[(1-(carboxymethyl)-7-{(E)-2-[4-(4-phenoxybutoxy) phenyl]vinyl}-1H-indol-3-yl)thiol](phenyl)acetic acid TLC: Rf 0.20 (dichloromethane:methanol=9:1); $^1$H-NMR (DMSO-$d_6$): δ 1.72-1.98 (m, 4H), 3.88-4.16 (m, 4H), 4.60 (s, 1H), 4.99 (s, 2H), 6.83-6.99 (m, 6H), 7.05 (t, 1H), 7.18-7.32 (m, 6H), 733-7.46 (m, 4H), 7.51 (d, 2H), 7.59 (d, 1H).

Example 50

4-(1-carboxymethyl)-7-{(E)-2-[4-(4-phenylbutoxy) phenyl]vinyl}-1H-indol-3-yl)-4-oxobutanoic acid

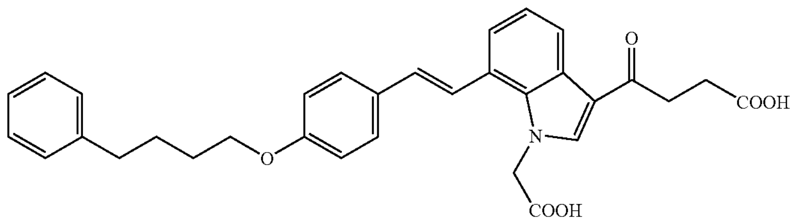

The same operation as in Example 37 was conducted and then the same operation as in Example 3→Example 6 was conducted to obtain a compound of the present invention having the following physical properties. In the step corresponding to Example 37 in the operation, the compound prepared in Example 41 was used in place of ethyl 7-bromo-3-[4-(ethyloxy)-4-oxobutanoyl]-1H-indole-2-carboxylate, methyl 2-bromoacetate was used in place of methyl iodide and, in the step corresponding to Example 3, 1-ethenyl-4-[(4-phenylbutyl)oxy]benzene was used in place of 4-vinylphenyl acetate.

TLC: Rf 0.30 (dichloromethane:methanol=9:1); $^1$H-NMR (DMSO-$d_6$): δ 1.63-1.81 (m, 4H), 2.53-2.70 (m, 4H), 3.09 (t, 2H), 3.87-4.13 (m, 2H), 5.31 (S, 2H), 6.88-7.01 (m, 3H), 7.11-7.33 (m, 6H), 7.37 (d, 1H), 7.45-7.64 (m, 3H), 8.16 (dd, 1H), 8.36 (s, 1H), 12.09 (brs, 1H), 13.30 (brs, 1H).

Example 50(1) to Example 50(24)

Using a corresponding compound, the same operation as in Example 50 was conducted to obtain the titled compound having the following physical properties.

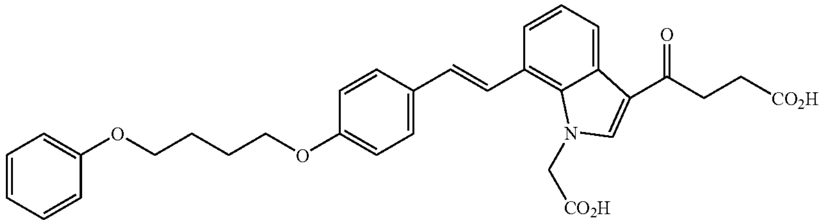

Example 50(1)

4-(1-(carboxymethyl)-7-{(E)-2-[4-(4-phenoxybutoxy)phenyl]vinyl}-1H-indol-3-yl)-4-oxobutanoic acid TLC: Rf 0.49 (dichloromethane:methanol:acetic acid=90:10:1); $^1$H-NMR(DMSO-$d_6$): δ 1.79-1.93 (m, 4H), 2.58 (t, 2H), 3.09 (t, 2H), 3.90-4.16 (m, 4H), 5.30 (s, 2H), 6.85-7.03 (m, 6H), 7.14-732 (m, 3H), 7.37 (d, 1H), 7.46-7.61 (m, 3H), 8.17 (d, 1H), 8.35 (s, 1H), 12.06 (brs, 1H), 13.31 (brs, 1H).

Example 50(2)

4-[7-((E)-2-{4-[4-(2-acetylphenoxy)butoxy]phenyl}vinyl)-1-(carboxymethyl)-1H-indol-3-yl]-4-oxobutanoic acid TLC: Rf 0.39 (dichloromethane:methanol:acetic acid=90:10:1); $^1$H-NMR (DMSO-$d_6$): δ 1.83-2.06 (m, 4H), 2.52-2.63 (m, 5H), 3.09 (t, 2H), 4.09 (t, 2H), 4.17 (t, 2H), 5.31 (s, 2H), 6.88-7.06 (m, 4H), 7.10-7.29 (m, 2H), 7.38 (d, 1H), 7.46-7.62 (m, 5H), 8.17 (d, 1H), 8.36 (s, 1H), 12.08 (brs, 1H), 13.29 (brs, 1H).

Example 50(3)

4-(1-[carboxy(fluoro)methyl]-7-{(E)-2-[4-(4-phenoxybutoxy)phenyl]vinyl}-1H-indol-3-yl)-4-oxobutanoic acid TLC: Rf 0.19 (dichloromethane:methanol:acetic acid=90:10:1); $^1$H-NMR (DMSO-$d_6$): δ 1.78-1.95 (m, 4H), 2.59 (t, 2H), 3.08-3.20 (m, 2H), 3.90-4.17 (m, 4H), 6.82-7.41 (m, 10H), 7.43-7.67 (m, 4H), 8.21 (d, 1H), 8.51 (s, 1H), 12.11 (brs, 2H).

Example 50(4)

4-[1-(carboxymethyl)-7-((E)-2-{4-[4-(2,3,6-trimethylphenoxy)butoxy]phenyl}vinyl)-1H-indol-3-yl]-4-oxobutanoic acid TLC: Rf 0.32 (methanol: dichloromethane:acetic acid=1:9:0.05); $^1$H-NMR (DMSO-$d_6$): δ 1.83-2.01 (m, 4H), 2.12 (s, 3H), 2.17 (s, 3H), 2.18 (s, 3H), 2.59 (t, 2H), 3.09 (t, 2H), 3.73 (t, 2H), 4.09 (t, 2H), 5.32 (m, 2H), 6.80 (d, 1H), 6.89 (d, 1H), 6.93-7.02 (m, 3H), 7.21 (t, 1H), 7.38 (d, 1H), 7.47-7.60 (m, 3H), 8.18 (d, 1H), 8.36 (s, 1H), 12.12 (brs, 1H), 13.19 (brs, 1H).

Example 50(5)

4-[1-(carboxymethyl)-7-((E)-2-{4-[4-(2,6-dimethylphenoxy)butoxy]phenyl}vinyl)-1H-indol-3-yl]-4-oxobutanoic acid TLC: Rf 0.47 (methanol: dichloromethane:acetic acid=1:9:0.05); $^1$H-NMR (DMSO-$d_6$): δ 1.81-2.03 (m, 4H), 2.22 (s, 6H), 2.59 (t, 2H), 3.09 (t, 2H), 3.79 (t, 2H), 4.09 (t 2H), 5.32 (s, 2H), 6.84-7.05 (m, 6H), 7.21 (t, 1H), 7.38 (d, 1H), 7.47-7.60 (m, 3H), 8.17 (dd, 1H), 8.36 (s, 1H), 12.07 (brs, 1H), 13.27 (brs, 1H).

Example 50(6)

4-[1-(carboxymethyl)-7-((E)-2-{4-[4-mesityloxy)butoxy]phenyl}vinyl)-1H-indol-3-yl]-4-oxobutanoic acid TLC: Rf 0.46 (methanol: dichloromethane:acetic acid=1:9:0.05); $^1$H-NMR (DMSO-$d_6$): δ 1.79-2.02 (m, 4H), 2.17 (s, 9H), 2.58 (t, 2H), 3.09 (t, 2H), 3.74 (t, 2H), 4.08 (t, 2H), 5.31 (s, 2H), 6.80 (s, 2H), 6.91-7.03 (m, 3H), 7.21 (t, 1H), 7.37 (d, 1H), 7.47-7.61 (m, 3H), 8.17 (dd, 1H), 8.36 (s, 1H), 12.07 (brs, 1H), 13.29 (brs, 1H).

Example 50(7)

4-[1-(carboxymethyl)-7-((E)-2-{4-[4-(4-chloro-2,6-dimethylphenoxy)butoxy]phenyl}vinyl)-1H-indol-3-yl]-4-oxobutanoic acid TLC: Rf 0.49 (methanol: dichloromethane:acetic acid=1:9:0.1); $^1$H-NMR (DMSO-$d_6$): δ 1.80-2.01 (m, 4H), 2.21 (s, 6H), 2.59 (t, 2H), 3.09 (t, 2H), 3.79 (t, 2H), 4.08 (t, 2H), 5.32 (s, 2H), 6.92-7.01 (m, 3H), 7.09 (s, 2H), 7.21 (t, 1H), 7.38 (d, 1H), 7.48-7.62 (m, 3H), 8.17 (dd, 1H), 8.36 (s, 1H).

Example 50(8)

4-(1-(carboxymethyl)-4-methyl-7-{(E)-2-[4-(4-phenoxybutoxy)phenyl]vinyl}-1H-indol-3-yl)-4-oxobutanoic acid TLC: Rf 0.49 (dichloromethane:methanol:acetic acid=90:10:1); $^1$H-NMR (DMSO-$d_6$): δ 1.78-1.94 (m, 4H), 2.56 (t, 2H), 2.63 (s, 3H), 3.11 (t, 2H), 3.93-4.15 (m, 4H), 5.22 (s, 2H), 6.78-7.02 (m, 7H), 7.17-7.35 (m, 3H), 7.42-7.61 (m, 3H), 8.32 (s, 1H), 12.10 (brs, 2H).

Example 50(9)

4-(1-(carboxymethyl)-4-fluoro-7-{(E)-2-[4-(4-phenoxybutoxy)phenyl]vinyl}-1H-indol-3-yl)-4-oxobutanoic acid TLC: Rf 0.49 (dichloromethane:methanol:acetic acid=90:10:1); $^1$H-NMR (DMSO-$d_6$): δ 1.80-1.93 (m, 4H), 2.55 (t, 2H), 3.10 (t, 2H), 3.96-4.09 (m, 4H), 4.82 (s, 2H), 6.81-6.97 (m, 7H), 7.22-7.33 (m, 3H), 7.53 (d, 2H), 7.64 (d, 1H), 8.27 (s, 1H), 12.06 (brs, 2H).

Example 50(10)

4-(1-(carboxymethyl)-6-methyl-7-{(E)-2-[4-(4-phenoxybutoxy)phenyl]vinyl}-1H-indol-3-yl)-4-oxobutanoic acid TLC: Rf 0.38 (dichloromethane:methanol:acetic acid=90:10:1); $^1$H-NMR (DMSO-$d_6$): δ 1.78-1.94 (m, 4H), 2.35 (s, 3H), 2.56 (t, 2H), 3.06 (t, 2H), 3.94-4.09 (m, 4H), 4.97 (s, 2H), 6.53 (d, 1H), 6.86-6.97 (m, 5H), 7.09 (d, 1H), 7.19-7.34 (m, 3H), 7.51 (d, 2H), 8.02 (d, 1H), 8.21 (s, 1H).

Example 50(11)

4-(1-(carboxymethyl)-5-fluoro-7-{(E)-2-[4-phenoxybutoxy)phenyl]vinyl}-1H-indol-3-yl)-4-oxobutanoic acid TLC: Rf 0.36 (dichloromethane:methanol:acetic acid=90:10:1); $^1$H-NMR (DMSO-$d_6$): δ 1.80-1.96 (m, 4H), 2.58 (t, 2H), 3.08 (t, 2H), 3.95-4.14 (m, 4H), 5.33 (s, 2H), 6.86-7.01 (m, 5H), 7.08 ((d, 1H), 7.22-733 (m, 3H), 7.44-7.59 (m, 3H), 7.84 (dd, 1H), 8.42 (s, 1H), 12.10 (s, 1H), 13.33 (s, 1H).

Example 50(12)

4-[1-carboxymethyl)-7-((E)-2-{4-[4-(2-chlorophenoxy)butyl]phenyl}vinyl)-1H-indol-3-yl]-4-oxobutanoic acid TLC: Rf 0.36 (methanol: dichloromethane:acetic acid=1:9:0.1); $^1$H-NMR (DMSO-$d_6$): δ 1.86-1.97 (m, 4H), 2.59 (t, 2H), 3.09 (t, 2H), 4.03-4.17 (m, 4H), 5.31 (s, 2H), 6.89-7.01 (m, 4H), 7.15 (d, 1H), 7.18-7.33 (m, 2H), 7.37 (d, 1H), 7.41 (dd, 1H), 7.48-7.59 (m, 3H), 8.17 (dd, 1H), 8.36 (s, 1H).

Example 50(13)

4-(1-(1-carboxyethyl)-7-{(E)-2-[4-(4-phenoxybutoxy)phenyl]vinyl}-1H-indol-3-yl)-4-oxobutanoic acid TLC: Rf 0.35 (dichloromethane:methanol:acetic acid=90:10:1); $^1$H-NMR (DMSO-$d_6$): δ 1.80-1.97 (m, 7H), 2.58 (t, 2H), 3.17 (t, 2H), 3.98-4.12 (m, 4H), 5.67 (q, 1H), 6.84-7.02 (m, 6H), 7.15-7.38 (m, 4H), 7.46-7.67 (m, 3H), 8.21 (d, 1H), 8.48 (s, 1H), 12.05 (brs, 1H), 13.38 (brs, 1H).

Example 50(14)

4-[1-(carboxymethyl)-5-fluoro-7-((E)-2-{4-[4-mesityloxy)butoxy]phenyl}vinyl)-1H-indol-3-yl]4-oxobutanoic acid

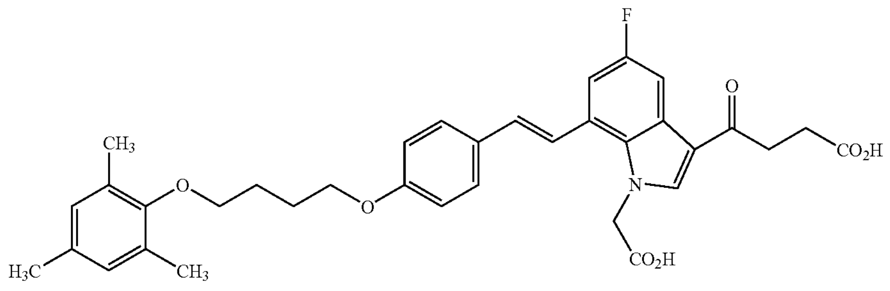

TLC: Rf 0.30 (dichloromethane:methanol:acetic acid=90:10:1); $^1$H-NMR (DMS-$d_6$): δ 1.79-2.01 (m, 4H), 2.17 (s, 9H), 2.58 (t 2H), 3.08 (t, 2H), 3.74 (t, 2H), 4.08 (t, 2H), 5.34 (s, 2H), 6.80 (s, 2H), 6.97 (d, 2H), 7.09 (d, 1H), 7.27 (dd, 1H), 7.41-7.60 (r, 3H), 7.84 (dd, 1H), 8.42 (s, 1H), 12.09 (brs, 1H), 13.31 (m, 1H).

Example 50(15)

4-[1-(carboxymethyl)-7-((E)-2-{4-[4-(mesityloxy)butoxy]phenyl}vinyl)-6-methyl-1H-indol-3-yl]-4-oxobutanoic acid TLC: Rf 0.40 (dichloromethane:methanol:acetic acid=90:10:1); $^1$H-NMR (DMSO-$d_6$): δ 1.82-1.99 (m, 4H), 2.14-2.19 (m, 9H), 2.34 (s, 3H), 2.57 (t, 2H), 3.06 (t, 2H), 3.75 (t, 2H), 4.04-4.13 (m, 2H), 5.12 (s, 2H), 6.53 (d, 1H), 6.80 (s, 2H), 6.96 (d, 2H), 7.11 (d, 1H), 7.19 (d, 1H), 7.50 (d, 2H), 8.03 (d, 1H), 8.26 (s, 1H), 12.06 (brs, 1H), 12.96 (brs, 1H).

Example 50(16)

4-[1-(carboxymethyl)-7-{(E)-2-[4-(4-phenoxybutoxy)phenyl]vinyl}-4-trifluoromethyl)-1H-indol-3-yl]-4-oxobutanoic acid TLC: Rf 0.30 (dichloromethane:methanol:acetic acid=90:10:1); $^1$H-NMR (DMSO-$d_6$): δ 1.81-1.95 (m, 4H), 2.56 (t, 2H), 3.09 (t, 2H), 3.95-4.15 (m, 4H), 5.38 (s, 2H), 6.86-7.10 (m, 6H), 7.22-7.33 (m, 2H), 7.44-7.68 (m, 5H), 8.47 (s, 1H), 12.09 (brs, 1H), 13.34 (brs, 1H).

Example 50(17)

4-[1-(carboxymethyl)-7-((E)-2-{4-[4-(2,4-dichloro-6-methylphenoxy)butoxy]phenyl}vinyl)-1H-indol-3-yl]-4-oxobutanoic acid TLC: Rf 0.48 (methanol: dichloromethane:acetic acid=1:9:0.1); $^1$H-NMR (DMSO-$d_6$): δ 1.82-2.02 (m, 4H), 2.27 (s, 3H), 2.59 (t, 2H), 3.09 (t, 2H), 3.93 (t, 2H), 4.08 (t, 2H), 5.32

(s, 2H), 6.96 (d, 1H) 6.96 (d, 2H) 7.21 (t, 1H), 7.28-7.46 (m, 3H), 7.48-7.61 (m, 3H), 8.17 (dd, 1H), 8.36 (s, 1H), 12.07 (brs, 1H), 13.29 (brs, 1H).

Example 50(18)

4-[1-(carboxymethyl)-7-((E)-2-{4-[4-(2,3-difluorophenoxy)butoxy]phenyl}vinyl)-1H-indol-3-yl]-4-oxobutanoic acid

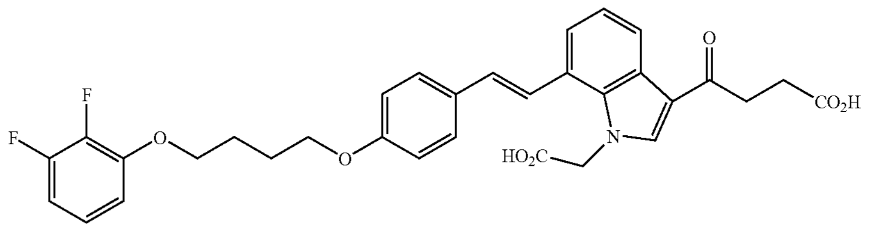

TLC: Rf 0.41 (methanol: dichloromethane:acetic acid=1:9:0.1); $^1$H-NMR (DMSO-$d_6$): δ 12.13 (brs, 2H), 8.36 (s, 1H), 8.17 (dd, 1H), 7.60-7.48 (m, 3H), 7.38 (d, 1H), 7.27-6.89 (m, 7H), 5.32 (s, 2H), 4.16 (t, 2H) 4.07 (t, 2H), 3.09 (t 2H), 2.59 (t 2H), 2.00-1.80 (m, 4H).

Example 50(19)

4-(1-carboxymethyl)-7-{((E)-2-[4-(2,3-dihydro-1H-inden-2-ylmethoxy)phenyl]vinyl}-1H-indol-3-yl)-4-oxobutanoic acid TLC: Rf 0.47 (methanol: dichloromethane:acetic acid=1:9:0.1); $^1$H-NMR (DMSO-$d_6$): δ 12.08 (brs, 2H), 8.36 (s, 1H), 8.17 (dd, 1H), 7.60-7.46 (m, 3H), 7.37 (d, 1H), 7.27-7.17 (m, 3H), 7.17-7.08 (m, 2H), 7.02-6.90 (m, 3H), 5.32 (s, 2H), 4.00 (d, 2H), 3.15-3.01 (m, 4H), 2.98-2.73 (m, 3H), 2.58 (t, 2H).

Example 50(20)

4-[1-(carboxymethyl)-7-((E)-2-{4-[2-(2,3-dihydro-1H-inden-2-yl)ethoxy]phenyl}vinyl)-1H-indol-3-yl]-4-oxobutanoic acid TLC: Rf 0.42 (methanol: dichloromethane:acetic acid=1:9:0.1); $^1$H-NMR (DMSO-$d_6$): δ 12.14 (brs, 2H), 8.36 (s, 1H), 8.17 (dd, 1H), 7.60-7.48 (m, 3H), 7.38 (d, 1H), 7.27-7.14 (m, 3H), 7.14-7.05 (m, 2H), 7.03-6.91 (m, 3H), 5.32 (s, 2H), 4.09 (t, 2H), 3.14-2.96 (m, 4H), 2.70-2.54 (m, 5H), 1.93 (q, 2H).

Example 50(21)

4-[1-carboxymethyl)-7-((E)-2-{4-[3-(2,3-dihydro-1H-inden-2-yl)propoxy]phenyl}vinyl)-1H-indol-3-yl]-4-oxobutanoic acid TLC: Rf 0.44 (methanol: dichloromethane:acetic acid=1:9:0.1); $^1$H-NMR (DMS (d): δ 12.09 (brs, 2H), 8.36 (s, 1H), 8.17 (dd, 1H), 7.6-7.46 (m, 3H), 7.37 (d, 1H), 7.26-7.13 (m, 3H), 7.13-7.04 (m, 2H), 7.01-6.89 (m, 3H), 5.31 (s, 2H), 4.02 (t, 2H), 3.14-2.95 (m, 4H), 2.64-2.36 (m, 5H), 1.87-1.73 (m, 2H), 1.67-1.55 (m, 2H).

Example 50(22)

3-[1-(carboxymethyl)-7-((E)-2-{4-[4-(2,3-difluorophenoxy)butoxy]phenyl}vinyl)-1H-indol-3-yl]-2,2-dimethyl-3-oxopropanoic acid

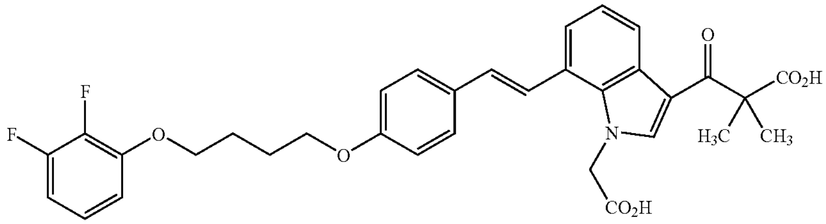

TLC: Rf 0.46 (dichloromethane:methanol:acetic acid=9:1:0.05); $^1$H-NMR (DMSO-$d_6$): 1.45 (s, 6H), 1.84-1.96 (m, 4H), 4.07 (t, 2H), 4.13-4.20 (m, 2H), 5.37 (s, 2H), 6.89-7.19 (m, 6H), 7.22 (dd, 1H), 7.37 (d, 1H), 7.47-7.58 (m, 3H), 8.03 (s, 1H), 8.26 (dd, 1H), 12.72 (s, 1H), 13.22 (s, 1H).

Example 50(23)

1-{[1-(carboxymethyl)-7-((E)-2-{4-[4-(2,3-difluorophenoxy)butoxy]phenyl}vinyl)-1H-indol-3-yl]carbonyl}cyclopropanecarboxylic acid TLC: Rf 0.22 (dichloromethane:methanol:acetic acid=9:1:0.05); $^1$H-NMR (DMSO-$d_6$): δ 1.26-1.50 (m, 4H), 1.85-1.95 (m, 4H), 4.07 (t, 2H), 4.16 (t, 2H), 5.35 (s, 2H), 6.87-7.27 (m, 7H), 7.38 (d, 1H), 7.49-7.62 (m, 3H), 8.11 (d, 1H), 8.20 (s, 1H), 12.74 (s, 1H), 13.23 (s, 1H).

Example 50(24)

2-[(1-carboxymethyl)-7-{((E)-2-[4-(4-phenoxybutoxy)phenyl]vinyl}-1H-indol-3-yl)carbonyl]benzoic acid TLC: Rf 0.31 (chloroform:methanol:water=20:10:1); $^1$H-NMR (DMSO-$d_6$): δ 1.80-1.94 (m, 4H), 3.96-4.12 (m, 4H), 5.26 (s, 2H), 6.85-7.03 (m, 6H), 7.21-7.30 (m, 3H), 7.41 (d, 1H), 7.43-7.56 (m, 4H), 7.59 (ddd, 1H), 7.60 (s, 1H), 7.66 (ddd, 1H), 7.91 (dd, 1H), 8.15 (dd, 1H), 12.41-13.69 (m, 2H).

Example 51

2-(4-bromo-1H-indol-3-yl)propanenitrile

To a tetrahydrofuran solution (10 mL) of 1, -dimethylethyl 4-bromo-3-(cyanomethyl)-1H-indole-1-carboxylate [CAS registration number 151726-05-5, Organic Letters 2003, 5(19), 3519-3522] (1.0 g), lithium diisopropylamide (2M tetrahydrofuran solution; 3.4 mL) was added dropwise at −78° C. and the mixture was stirred at the same temperature for one hour. To the mixture, methyl iodide (0.5 mL) was added, followed by stirring for one hour. The mixture was gradually heated to room temperature and methanol (2 mL) was added. The mixture was stirred overnight at room temperature and water was added under ice cooling, followed by extraction with ethyl acetate. The organic layer was washed in turn with water and saturated saline, dried over anhydrous magnesium sulfate and then concentrated. The residue was purified by silica gel column chromatography (n-hexane: ethyl acetate=80:20 y 70:30) to obtain the titled compound having the following physical properties (0.35 g).

TLC: Rf 0.23 (n-hexane:ethyl acetate=4:1); $^1$H-NMR ($CDCl_3$): δ 1.74-1.77 (m, 3H), 4.86-4.93 (m, 1H), 7.06 (d, 1H), 7.30-7.36 (m, 2H), 7.40-7.41 (m, 1H), 8.29 (s, 1M).

Example 52

2-(4-bromo-1H-indol-3-yl)propanoic acid

The compound prepared in Example 51, namely, 2-(4-bromo-1H-indol-3-yl)propanenitrile (184 mg) was dissolved in a mixture of ethanol (1 mL) and ethylene glycol (1 mL) and an aqueous 20% potassium hydroxide solution (0.5 mL) was added, and then the mixture was stirred overnight at 120° C. The reaction mixture was ice-cooled and then neutralized with 2M hydrochloric acid. The precipitated crystal was collected by filtration to obtain the titled compound having the following physical properties (155 mg).

TLC: Rf 0.38 (methylene chloride:methanol=9:1); $^1$H-NMR (DMSO-$d_6$): δ 1.48 (s, 3H), 4.43-4.48 (m, 1H), 6.92-6.99 (m, 1H), 7.16 (d, 1H), 731-7.39 (m, 2H), 11.29 (s, 1H), 12.12 (s, 1H).

Example 53

4-(3-(1-carboxyethyl)-4-{(E)-2-[4-(4-phenylbutoxy)phenyl]vinyl}-1H-indol-1-yl)butanoic acid

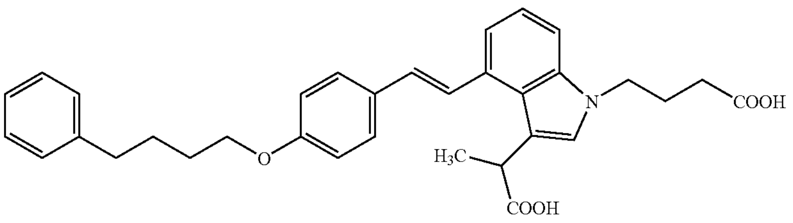

The same operation as in Example 7→Example 37→Example 3→Example 6 was conducted to obtain the titled compound having the following physical properties. In the step corresponding to Example 7 in the operation, the compound prepared in Example 52 was used in place of (4-bromo-1H-indol-3-yl)acetic acid and, in the step corresponding to Example 37, ethyl bromobutyrate was used in place of methyl iodide. In the step corresponding to Example 3, 1-ethenyl-4-[(4-phenylbutyl)oxy]benzene was used in place of 4-vinylphenyl acetate.

TLC: Rf 0.47 (dichloromethane:methanol=9:1); $^1$H-NMR (DMSO-$d_6$): δ 1.52 (d, 3H), 1.66-1.81 (m, 4H), 1.89-2.01 (m, 2H), 2.20 (t, 2H), 2.64 (t, 2H), 3.97-4.05 (m, 2H), 4.10-4.19 (m, 3H), 6.93 (d, 2H), 7.03 (d, 1H), 7.08-7.31 (m, 8H), 7.36 (d, 1H), 7.54 (d, 2H), 7.73 (d, 1H), 12.21 (s, 2H).

Example 54 methyl [4-((E)-2-{4-[(4-phenylbutyl)oxy]phenyl}ethenyl)-1H-indol-3-yl]acetate

Methyl 4-bromoindole-3-acetate (1.5 g) and 4-phenylbutoxy-4-styrene (1.48 g) were dissolved in acetonitrile (31 mL), and then triethylamine (10.6 mL) and tris(o-tolyl)phosphine (1.36 g) were added. After deaeration and argon substitution, palladium acetate (0.25 g) was added and then deaeration and argon substitution were conducted again. The mixture was stirred at 90° C. for 3 hours and the reaction mix was filtered, and then the filtrate was concentrated. The residue was purified by silica gel column chromatography (n-hexane:ethyl acetate=4:1→3:1) to obtain the titled compound having the following physical properties (2.2 g).

TLC: Rf 0.41 (n-hexane:ethyl acetate=3:2); $^1$H-NMR ($CDCl_3$): δ 1.81-1.85 (m, 4H), 2.71 (t, 2H), 3.63 (s, 3H), 3.97

(s, 2H), 4.01 (t, 2H), 6.88-6.92 (m, 2H), 6.98 (d, 1H), 7.16-7.35 (m, 9H), 7.47-7.51 (m, 2H), 7.67 (d, 1H), 8.09 (s, 1H).

Example 55

{-4-{(E)-2-[4-(4-phenylbutoxy)phenyl]vinyl}-1-[3-(1H-tetrazol-5-yl)propyl]-1H-indol-3-yl}acetic acid

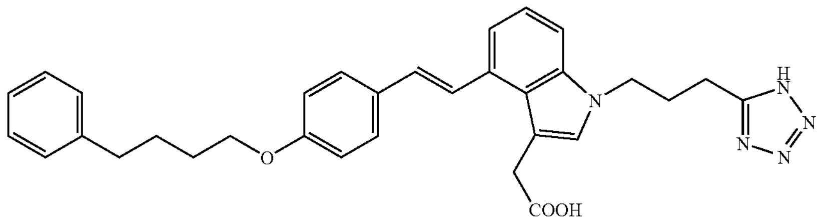

The same operation as in Example 37→Example 25→Example 6 was conducted to obtain the titled compound having the following physical properties. In the step corresponding to Example 37 in the operation, 4-bromobutanenitrile was used in place of methyl iodide and the compound prepared in Example 54 was used in place of ethyl 7-bromo-3-[4-(ethyloxy)-4-oxobutanoyl]-1H-indole-2-carboxylate.

TLC: Rf 0.26 (dichloromethane:methanol=9:1); $^1$H-NMR (DMSO-$d_6$): δ 1.69-1.77 (m, 4H), 2.11-2.23 (m, 2H), 2.64 (t, 2H), 2.85 (t, 2H), 3.84 (s, 2H), 4.01 (t, 2H), 4.24 (t, 2H), 6.92 (d, 2H), 7.06 (d, 1H), 7.10-7.42 (m, 10H), 7.52 (d, 2H), 7.63 (d, 1H), 12.28 (s, 1H).

Example 56

4-[4((E)-2-{4-[4-(2-methylphenoxy)butoxy]phenyl}vinyl)-3-(1H-tetrazol-5-ylmethyl)-1H-indol-1-yl]butanoic acid

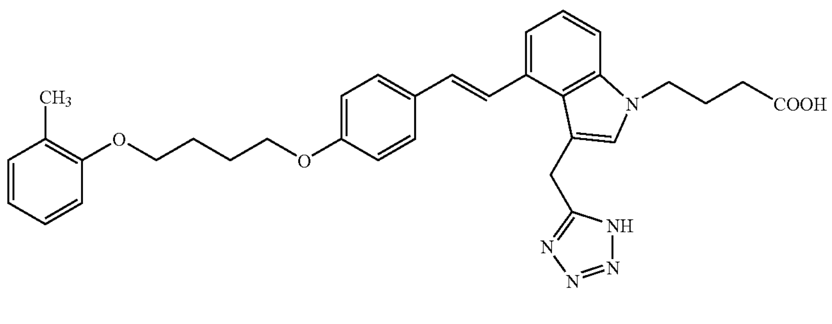

The same operation as in Example 37→Example 3→Example 4→Example 25→Example 6 was conducted to obtain the titled compound having the following physical properties. In the step corresponding to Example 37 in the operation, 4-bromoindole-3-acetonitrile was used in place of methyl iodide and methyl 4-bromobutanoate was used in place of ethyl 7-bromo-3-[4-(ethyloxy)-4-oxobutanoyl]-1H-indole-2-carboxylate. In the step corresponding to Example 3, 1-({4-[(4-ethenylphenyl)oxy]butyl}oxy)-2-methylbenzene was used in place of 4-vinylphenyl acetate.

TLC: Rf 0.26 (dichloromethane:methanol=9:1); $^1$H-NMR (DMSO-$d_6$): δ 1.84-2.01 (m, 6H), 2.14 (s, 3H), 2.24 (t, 2H), 3.96-4.10 (m, 4H), 4.16 (t, 2H), 4.58 (s, 2H), 6.81 (t, 1H), 6.87-7.04 (m, 4H), 7.08-7.20 (m, 3H), 7.23-7.33 (m, 2H), 7.35-7.54 (m, 4H).

Example 57

N,N-dimethyl-1-(2-methyl-4-nitro-1H-indol-3-yl)methanamine

To an acetic acid (5 mL) solution of an aqueous 370% formaldehyde solution (271 mg), an aqueous 50% dimethylamine solution (317 mg) was slowly added dropwise under ice cooling and the mixture was stirred at room temperature for 30 minutes. Furthermore, an acetic acid (1 mL) solution of 2-methyl-4-nitro-1H-indole [Tetrahedron 1, 1999, 5395-5398] (310 mg) was added and the mixture was stirred at room temperature for 24 hours. The pH of the reaction mix was adjusted to 9 using an aqueous 5M sodium hydroxide solution, followed by extraction with dichloromethane three times. The organic layer was washed with saturated saline, dried over anhydrous sodium sulfate and then concentrated. The residue was washed with diisopropyl ether to obtain the titled compound having the following physical properties (303 mg).

TLC: Rf 0.22 (dichloromethane:methanol:acetic acid=80:20:1); $^1$H-NMR ($CDCl_3$): δ 2.07 (s, 6H), 2.46 (s, 3H), 3.51 (s, 2H), 7.11 (t, 1H), 7.46 (dd, 1H), 7.63 (dd, 1H).

Example 58

(2-methyl-4-nitro-1H-indol-3-yl)acetonitrile

To an acetone (5 mL) solution of the compound (300 mg) prepared in Example 57, methyl iodide (2 mL) was added and the mixture was stirred overnight at room temperature. The reaction mixture was concentrated and the residue was dissolved in N,N-dimethylformamide (3 mL) and, after adding the solution to a water (3 mL) solution of sodium cyanide (632 mg), the mixture was stirred at 100° C. for 6 hours. To the reaction mixture, water was added, followed by extraction twice with n-hexane/ethyl acetate=¼. The organic layer was washed in turn with water (twice) and saturated saline, dried over anhydrous sodium sulfate and then concentrated. The residue was washed with diisopropyl ether to obtain the titled compound having the following physical properties (232 mg).

TLC: Rf 0.38 (n-hexane:ethyl acetate=1:2); $^1$H-NMR ($CDCl_3$): δ 2.54 (s, 3H), 3.99 (s, 2H), 7.22 (t, 1H), 7.59 (d, 1H), 7.98 (d, 1H), 8.47 (brs, 1H).

Example 59 methyl 4-[3-(cyanomethyl)-2-methyl-4-nitro-1H-indol-1-yl]butanoate

The same operation as in Example 37 was conducted to obtain the titled compound having the following physical properties. The compound prepared in Example 58 was used in place of ethyl 7-bromo-3-[4-(ethyloxy)-4-oxobutanoyl]-1H-indole-2-carboxylate and methyl bromobutyrate was used in place of methyl iodide.

TLC: Rf 0.38 (toluene:ethyl acetate=2:1); $^1$H-NMR ($CDCl_3$): δ 2.01-2.10 (m, 2H), 2.40 (t 2H), 2.52 (s, 3H), 3.71 (s, 3H), 4.00 (s, 2H), 4.23 (t, 2H), 7.24 (t, 1H), 7.67 (dd, 1H), 7.96 (dd, 1H).

Example 60 methyl 4-[4-amino-3-cyanomethyl)-2-methyl-1H-indol-1-yl]butanoate

To an ethanol (4 mL) solution of the compound (130 mg) prepared in Example 59, tin chloride (1.15 g) was added and the mixture was stirred at 90° C. for one hour. To the reaction mixture, an aqueous solution (12 mL) of a 1M disodium tartrate and an aqueous saturated sodium hydrogen carbonate solution were sequentially added, followed by extraction with ethyl acetate. The organic layer was washed in turn with water and saturated saline, dried over anhydrous sodium sulfate and then concentrated to obtain the titled compound having the following physical properties (112 mg).

TLC: Rf 0.45 (n-hexane:ethyl acetate=1:1); $^1$H-NMR ($CDCl_3$): δ 1.99-2.08 (m, 2H), 2.32-2.40 (m, 5H), 3.68 (s, 3H), 3.92 (brs, 2H), 3.96 (s, 2H), 4.07 (t, 2H), 6.40 (dd, 1H), 6.79 (d, 1H), 6.97 (t, 1H).

Example 61

4-[2-methyl-4-{[4-(4-phenylbutoxy)benzoyl]amino}-3-(1H-tetrazol-5-ylmethyl)-1H-indol-1-yl]butanoic acid

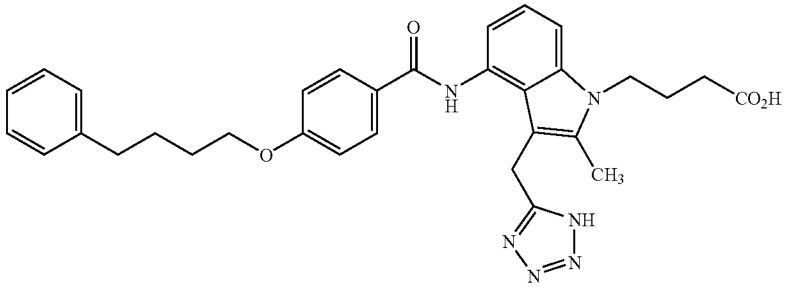

The same operation as in Example 19→Example 25→Example 6 was conducted to obtain the titled compound having the following physical properties. In the step corresponding to Example 19 in the operation, the compound prepared in Example 60 was used in place of the compound prepared in Example 18.

TLC: Rf 0.48 (dichloromethane:methanol:acetic acid=90:10:1); $^1$H-NMR (DMSO-$d_6$): δ 1.63-1.81 (m, 4H), 1.81-1.98 (m, 2H) 2.25-2.38 (m, 5H), 2.65 (m, 2H), 4.06 (t, 2H), 4.15 (t, 2H), 4.33 (s, 2H), 6.89-7.02 (m, 3H), 7.07 (t, 1H), 7.11-7.37 (m, 6H), 7.83 (d, 2H), 10.08 (s, 1H), 12.19 (brs, 1H), 15.63 (brs, 1H).

Example 62

4-[4-{[4-(4-phenylbutoxy)benzoyl]amino}-3-(1H-tetrazol-5-ylmethyl)-1H-indol-1-yl]butanoic acid

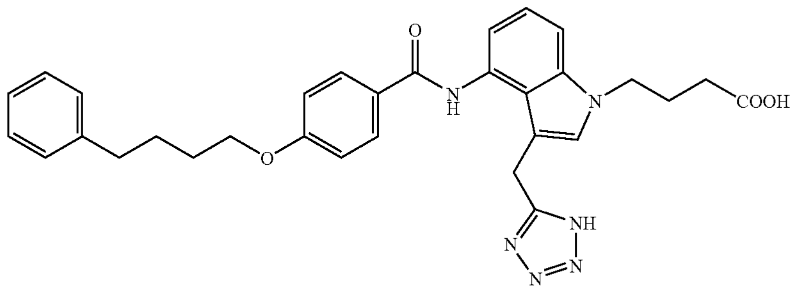

Using a corresponding compound, the same operation as in Example 61 was conducted to obtain the titled compound having the following physical properties.

TLC: Rf 0.49 (dichloromethane:methanol:acetic acid=90:10:1); $^1$H-NMR (DMSO-$d_6$): δ 1.65-1.80 (m, 4H), 1.84-2.02 (m, 2H), 2.21 (t, 2H), 2.65 (t, 2H), 4.05 (t 2H), 4.14 (t, 2H), 4.40 (s, 2H), 6.92-7.02 (m, 3H), 7.05 (s, 1H), 7.11-7.33 (m, 6H), 7.38 (d, 1H), 7.87 (d, 2H), 10.07 (s, 1H), 12.14 (brs, 1H), 15.85 (brs, 1H).

Example 63

(1E)-(7-bromo-1-methyl-1H-indol-2-yl)(oxo)ethanal hydrazone

To a dichloromethane (2 mL) solution of 7-bromo-1-methyl-1H-indole-2-carboxylic acid (200 mg), oxalyl dichloride (0.10 mL) and N,N-dimethylformamide (5 mL) were added and the mixture was stirred at room temperature for 2 hours. The reaction mixture was concentrated, azeotroped twice with toluene to obtain a crude product of 7-bromo-1-methyl-1H-indole-2-carboxylic acid chloride. Separately, a solution was prepared by dissolving 2M trimethylsilyldiazomethane (0.60 mL) and trimethylamine (0.16 mL) in tetrahydrofuran (2 mL)-acetonitrile (2 mL) and a tetrahydrofuran (1 mL)acetonitrile (1 mL) solution of 7-bromo-1-methyl-1H-indole-2-carboxylic acid chloride was added thereto, and then the mixture was stirred at room temperature for 4 hours. To the reaction mixture, an aqueous saturated ammonium chloride solution was added, followed by extraction with ethyl acetate. The organic layer was washed with saturated saline, dried over anhydrous sodium sulfate and then concentrated. The residue was purified by silica gel column chromatography (n-hexane:ethyl acetate=90:10 85:15) to obtain the titled compound having the following physical properties (72 mg).

TLC: Rf 0.52 (n-hexane:ethyl acetate=2:1); $^1$H-NMR ($CDCl_3$): δ 4.44 (s, 3H), 5.87 (s, 1H), 6.90 (s, 1H), 6.96 (t, 1H), 7.50 (dd, 1H), 7.56 (dd, 1H).

Example 64 ethyl (7-bromo-1-methyl-1H-indol-2-yl)acetate

To a tetrahydrofuran (2 mL)methanol (2 mL) solution of the compound (70 mg) prepared in Example 63, trimethylamine (35 μL) and silver acetate (4.2 mg) were added and the mixture was stirred at 50° C. for one hour. To the reaction mixture, an aqueous saturated ammonium chloride solution was added, followed by extraction with ethyl acetate. The organic layer was washed with saturated saline, dried over anhydrous sodium sulfate and then concentrated. The residue was purified by silica gel column chromatography (n-hexane:ethyl acetate=90:10→80:20) to obtain the titled compound having the following physical properties (68 mg).

TLC: Rf 0.53 (n-hexane:ethyl acetate=2:1); $^1$H-NMR ($CDCl_3$): δ 1.28 (t, 3H) 3.80 (s, 2H), 4.07 (s, 3H), 4.22 (d, 2H), 6.40 (s, 1H), 6.89 (t, 1H), 7.32 (dd, 1H), 7.46 (dd, 1H).

Example 65

4-[2-(carboxymethyl)-7-((E)-2-{4-[4-(mesityloxy)butoxy]phenyl}vinyl)-1-methyl-1H-indol-3-yl]-4-oxobutanoic acid

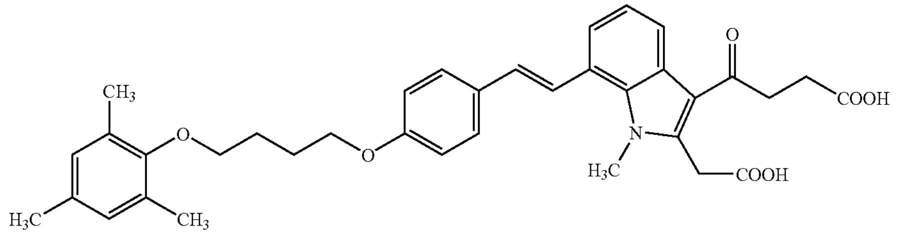

The same operation as in Example 17→Example 3→Example 6 was conducted to obtain the titled compound having the following physical properties. In the step corresponding to Example 17 in the operation, the compound prepared in Example 64 was used in place of the compound prepared in Example 16.

TLC: Rf 0.44 (dichloromethane:methanol:acetic acid=90:10:1); $^1$H-NMR (DMSO-$d_6$): δ 1.78-2.03 (m, 4H), 2.17 (s, 9H), 2.58 (t, 2H), 3.21 (t, 2H), 3.74 (t, 2H), 3.96 (s, 3H), 4.08 (t, 2H), 4.32 (s, 2H), 6.80 (s, 2H), 6.86-7.01 (m, 3H), 7.23 (t, 1H), 7.29-7.35 (m, 1H), 7.60 (d, 2H), 7.82-8.00 (m, 2H).

Example 66 ethyl 4-[7-{(E)-2-[4-(4-phenoxybutoxy)phenyl]vinyl}-1-(1H-tetrazol-5-ylmethyl)-1H-indol-3-yl]butanoate

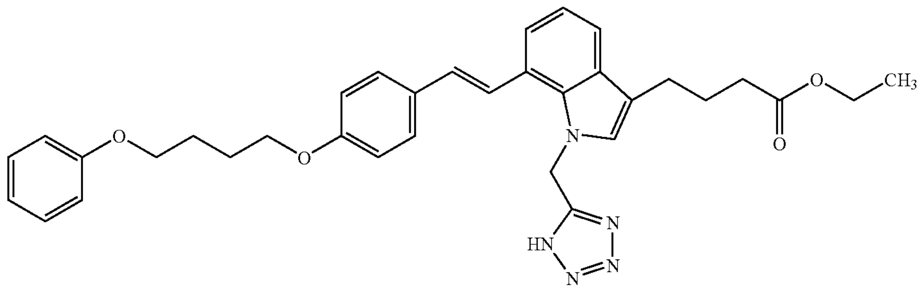

The same operation as in Example 17→Example 42→Example 37→Example 3 was conducted to obtain a compound having the following physical properties. In the step corresponding to Example 17 in the operation, 7-bromoindole was used in place of the compound prepared in Example 16 and, in the step corresponding to Example 37 in the operation, bromoacetonitrile was used in place of ethyl 7-bromo-3-[4-(ethyloxy)-4-oxobutanoyl]-1H-indole-2-carboxylate and, in the step corresponding to Example 3, 1-ethenyl-4-{[4-(phenyloxy)butyl]oxy}benzene was used in place of 4-vinylphenyl acetate.

TLC: Rf 0.45 (dichloromethane:methanol=90:10); $^1$H-NMR ($CDCl_3$): δ 0.90 (t, 3H), 1.89-2.06 (m, 4H), 2.08-2.24 (m, 2H), 2.28-2.40 (m, 2H), 2.79-2.89 (m, 2H), 3.26 (q, 2H) 3.95-4.14 (m, 4H), 5.81 (s, 2H), 6.77 (d, 1H), 6.86-6.98 (m, 6H), 7.11 (t, 1H), 7.16-7.33 (m, 4H), 7.40 (d, 2H), 7.50 (dd, 1H).

Example 67

4-[7-{(E)-2-[4-(4-phenoxybutoxy)phenyl]vinyl}-1-(1H-tetrazol-5-ylmethyl)-1H-indol-3-yl]butanoic acid

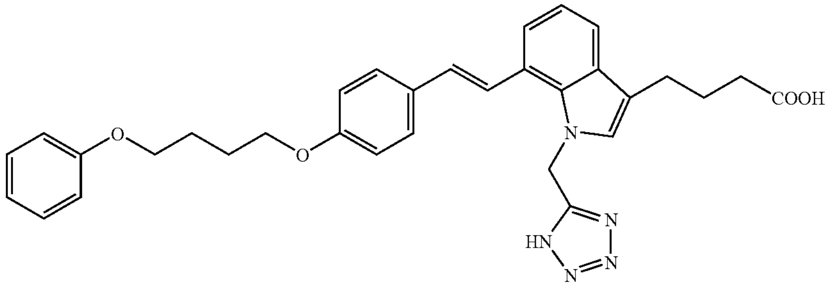

The same operation as in Example 6 was conducted to obtain the titled compound having the following physical properties. In place of the compound prepared in Example 5, the compound prepared in Example 66 was used.

TLC: Rf 0.60 (dichloromethane:methanol:acetic acid=90:10:1); $^1$H-NMR (DMSO-$d_6$): δ 1.77-1.98 (m, 6H), 2.29 (t, 2H), 2.69 (t, 2H), 3.93-4.16 (m, 4H), 5.88 (s, 2H), 6.86 (d, 1H), 6.90-6.98 (m, 5H), 7.04 (t, 1H), 7.20-7.32 (m, 4H), 7.44-7.51 (m, 3H), 7.66 (d, 1H).

Example 68

4-(7-bromo-1H-indol-3-yl)butanenitrile

To an anhydrous toluene (12 mL) solution of 7-bromoindole (1.0 g) and 4-chlorobutyronitrile (0.26 g), ethylmagnesium bromide (3.0M diethyl ether solution; 1.7 mL) was added dropwise under ice cooling and the mixture was heated to reflux for 4.5 hours. To the reaction mixture, an aqueous saturated ammonium chloride solution was added under ice cooling, followed by extraction with ethyl acetate. The organic layer was washed in turn with water and saturated saline, dried over anhydrous magnesium sulfate and then concentrated. The residue was purified by silica gel column chromatography (n-hexane:ethyl acetate=90:10→70:30) to obtain the titled compound having the following physical properties (0.40 g).

TLC: Rf 0.26 (n-hexane:ethyl acetate=4:1); $^1$H-NMR ($CDCl_3$): δ 2.01-2.08 (m, 2H), 2.35 (t, 2H), 2.94 (t, 2H), 7.02 (dd, 1H), 7.11 (d, 1H), 7.36 (d, 1H), 7.53 (dd, 1H), 8.20 (s, 1H).

Example 69

{7-{(E)-2-[4-(4-phenoxybutoxy)phenyl]vinyl}-3-[3-(1H-tetrazol-5-yl)propyl]-1H-indol-1-vinyl}acetic acid

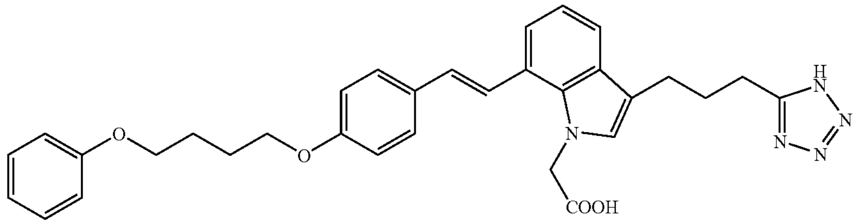

The same operation as in Example 37→Example 3→Example 25→Example 6 was conducted to obtain a compound of the prevent invention having the following physical properties. In the step corresponding to Example 37 in the operation, 4-(7-bromo-1H-indol-3-yl)butanenitrile was used in place of ethyl 7-bromo-3-[4-(ethyloxy)-4-oxobutanoyl]-1H-indole-2-carboxylate and, in the step corresponding to Example 3, 1-ethenyl-4-{[4-(phenyloxy)butyl]oxy}benzene was used in place of 4-vinylphenyl acetate.

TLC: Rf 0.55 (dichloromethane:methanol:acetic acid=9:1:0.05); $^1$H-NMR (DMSO-$d_6$): δ 1.81-1.93 (m, 4H), 1.98-2.13 (m, 2H), 2.67-2.77 (m, 2H), 2.88-2.97 (m, 2H), 3.98-4.13 (m, 4H), 5.12 (s, 2H), 6.85-6.98 (m, 7H), 7.02 (dd, 1H), 7.11 (s, 1H), 7.23-7.33 (m, 3H), 7.40-7.60 (m, 3H).

Example 70

4-[7-((E)-2-{4-[4-(2,3-difluorophenoxy)butoxy]phenyl}vinyl)-2-methyl-1-(1H-tetrazol-5-ylmethyl)-1H-indol-3-yl]butanoic acid

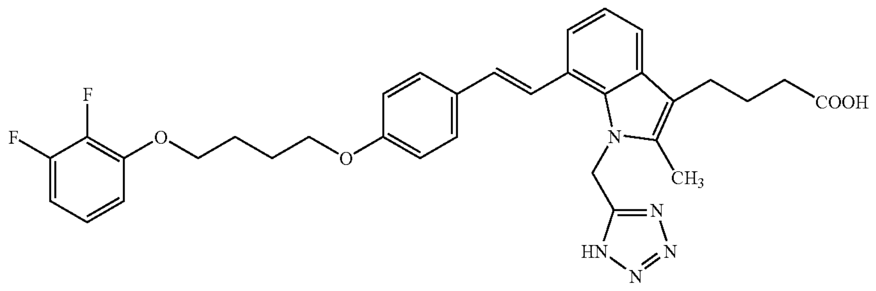

The same operation as in Example 17→Example 41→Example 37→Example 3→Example 6 was conducted to obtain the titled compound having the following physical properties. In the step corresponding to Example 17 in the operation, 7-bromo-2-methylindole was used in place of the compound prepared in Example 16 and, in the step corresponding to Example 37 in the operation, bromoacetonitrile was used in place of ethyl 7-bromo-3-[4-(ethyloxy)-4-oxobutanoyl]-1H-indole-2-carboxylate and, in the step corresponding to Example 3, 1-({4-[(4-ethenylphenyl)oxy]butyl}oxy)-2,3-difluorobenzene was used in place of the compound prepared in Example 2.

TLC: Rf 0.52 (dichloromethane:methanol:acetic acid=90:10:1); $^1$H-NMR (DMSO-$d_6$): δ 1.64-2.00 (m, 6H), 2.23 (t, 2H), 2.35 (s, 3H), 2.69 (t, 2H), 4.06 (t, 2H), 4.16 (t, 2H), 5.79 (s, 2H), 6.83 (d, 1H), 6.88-7.21 (m, 7H), 7.37-7.46 (m, 3H), 7.61 (d, 1H), 12.00 (s, 1H), 16.48 (s, 1H).

Example 71 methyl [4-bromo-2-methyl-5-(methyloxy)-1H-indol-3-yl]acetate

To an acetic acid (12 mL) solution of methyl [2-methyl-5-(methyloxy)-1H-indol-3-yl]acetate (300 mg), bromine (206 mg) was added and the mixture was stirred at room temperature for one hour. To the reaction mixture, water and an aqueous saturated sodium hydrogen carbonate solution were added, followed by extraction with ethyl acetate. The organic layer was washed in turn with an aqueous saturated sodium hydrogen carbonate solution, water and saturated saline, dried over anhydrous sodium sulfate and then concentrated. The residue was purified by silica gel column chromatography (n-hexane:ethyl acetate=65:35→60:40) to obtain the titled compound having the following physical properties (134 mg).

TLC: Rf 0.49 (n-hexane:ethyl acetate=1:1); $^1$H-NMR ($CDCl_3$): δ 2.33 (s, 3H), 3.71 (s, 3H), 3.88 (s, 3H), 3.99 (s, 2H), 6.81 (d, 1H), 7.13 (dd, 1H), 7.84 (brs, 1H).

Example 72

2,2'-(5-methoxy-2-methyl-4-{(E)-2-[4-(4-phenoxybutoxy)phenyl]vinyl}-1H-indol-1,3-diyl)diacetic acid

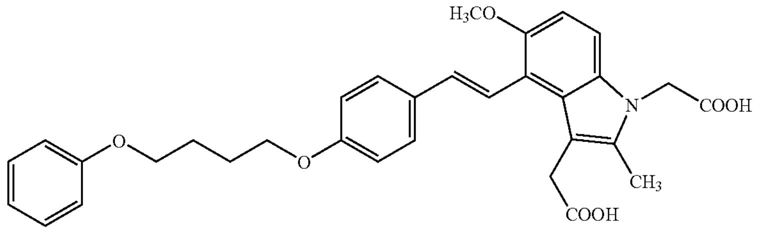

The same operation as in Example 37→Example 3→Example 6 was conducted to obtain the titled compound having the following physical properties. In the step corresponding to Example 37 in the operation, the compound pr in Example 71 was used in place of ethyl 7-bromo-3-[4-(ethyloxy)-4-oxobutanoyl]-1H-indole-2-carboxylate and methyl bromoacetate was used in place of methyl iodide and, in the step corresponding to Example 3, 1-(4-phenoxybutoxy)-4-vinylbenzene was used in place of 4-vinylphenyl acetate.

TLC: Rf 0.33 (dichloromethane:methanol:acetic acid=90:10:1); $^1$H-NMR (DMSO-$d_6$): δ 1.79-1.93 (m, 4H), 2.25 (s, 3H), 3.71 (s, 2H), 3.78 (s, 3H), 3.92-4.18 (m, 4H), 4.89 (s, 2H), 6.79-6.97 (m, 6H), 7.05 (d, 1H), 7.13-7.33 (m, 3H), 7.40 (d, 1H), 7.47 (d, 2H).

Example 72(1)

4-(3-(carboxymethyl)-5-methoxy-2-methyl-4-{(E)-2-[4-(4-phenoxybutoxy)phenyl]vinyl}-1H-indol-1-yl)butanoic acid Using a corresponding compound, the same operation as in Example 72 was conducted to obtain the titled compound having the following physical properties.

TLC: Rf 0.43 (dichloromethane:methanol=9:1); $^1$H-NMR (DMSO-$d_6$): δ 1.74-1.94 (m, 6H), 2.20-2.36 (m, 5H), 3.71 (s, 2H), 3.79 (s, 3H), 3.97-4.20 (m, 6H), 6.83-6.97 (m, 6H), 7.03 (d, 1H), 7.21-7.33 (m, 3H), 7.39 (d, 1H), 7.47 (d, 2H), 12.17 (brs, 2H).

Example 73

(7-bromo-1-methyl-1H-indol-2-yl)methanol

To a tetrahydrofuran (40 mL) solution of ethyl 7-bromo-1-methyl-1H-indole-2-carboxylate (1.99 g), lithium tetrahydroborate (463 mg) was added at 0° C., followed by stirring at room temperature for 5 hours. To the reaction mixture, an aqueous saturated ammonium chloride solution was added, followed by extraction with ethyl acetate. The organic layer was washed in turn with water and saturated saline, dried over anhydrous sodium sulfate and then concentrated. The residue anhydrous sodium sulfate and then concentrated. The residue was purified by silica gel column chromatography (n-hexane:ethyl acetate=90:10-70:30) to obtain the titled compound having the following physical properties (880 mg).

TLC: Rf 0.42 (n-hexane:ethyl acetate=2:1); $^1$H-NMR ($CDCl_3$): δ 1.56 (t, 1H), 4.18 (s, 3H), 4.79 (d, 1H), 6.44 (s, 1H), 6.90 (t, 1H), 7.35 (dd, 1H), 7.49 (dd, 1H).

Example 74

7-bromo-1-methyl-1H-indole-2-carboaldehyde

A dichloromethane (40 mL) solution of oxalyl dichloride (1.2 mL) was cooled to −78° C. and a dichloromethane (5 mL) solution of dimethyl sulfoxide (1.6 mL) was added dropwise, followed by stirring at −78° C. for 30 minutes. To the mixture, a dichloromethane (20 mL) solution of the compound (1.50 g) prepared in Example 73 was added dropwise, followed by stirring at −78° C. for one hour. To the reaction mixture, triethylamine (5.23 mL) was added, followed by heating to room temperature. To the reaction mixture, an aqueous saturated ammonium chloride solution was added, followed by extraction with ethyl acetate. The organic layer was washed in turn with water and saturated saline, dried over anhydrous sodium sulfate and then concentrated. The residue was purified by silica gel column chromatography (n-hexane:ethyl acetate=85:15→75:25) to obtain the titled compound having the following physical properties (707 mg).

TLC: Rf 0.59 (n-hexane:ethyl acetate=3:1); $^1$H-NMR ($CDCl_3$): δ 4.51 (s, 3H), 6.99 (t, 1H), 7.23 (s, 1H), 7.57 (d, 1H), 7.66 (d, 1H), 9.88 (s, 1H).

Example 75 methyl(2E)-3-(7-bromo-1-methyl-1H-indol-2-yl)-2-propanoate

To a tetrahydrofuran (50 mL) solution of sodium hydride (176 mg), trimethyl phosphonoacetate (803 mg) was added dropwise under ice cooling, followed by stirring at 0° C. for 30 minutes. To the mixture, a tetrahydrofuran (10 mL) solution of the compound (700 mg) prepared in Example 74 was added dropwise, followed by stirring at 0° C. for 1.5 hours. To the reaction mixture, an aqueous saturated ammonium chloride solution was added, followed by extraction with ethyl acetate. The organic layer was washed in turn with water and saturated saline, dried over anhydrous sodium sulfate and then concentrated. The residue was purified by silica gel column chromatography (n-hexane:ethyl acetate=85:15 h 75:25) to obtain the titled compound having the following physical properties (707 mg).

TLC: Rf 0.61 (n-hexane:ethyl acetate=4:1); $^1$H-NMR ($CDCl_3$): δ 3.83 (s, 3H), 4.20 (s, 3H), 6.48 (d, 1H), 6.89-6.95 (m, 2H), 7.40 (dd, 1H), 7.52 (dd, 1H), 7.79 (d, 1H).

Example 76 methyl 3-(7-bromo-1-methyl-1H-indol-2-yl)propanoate

To a methanol (29 mL) solution of the compound (860 mg) prepared in Example 75, nickel chloride hexahydrate (125 mg) and sodium tetrahydroborate (277 mg) were added at 0° C., followed by stirring at the same temperature for 45 minutes. To the reaction mixture, an aqueous saturated ammonium chloride solution was added, followed by extraction with ethyl acetate. The organic layer was washed in turn with water and saturated saline, dried over anhydrous sodium sulfate and then concentrated. The residue was purified by silica gel column chromatography (n-hexane:ethyl acetate=90:10-85:15) to obtain the titled compound having the following physical properties (391 mg).

TLC: Rf 0.49 (n-hexane:ethyl acetate=4:1); $^1$H-NMR ($CDCl_3$): δ 2.74-2.79 (m, 2H), 3.03-3.08 (m, 2H), 3.72 (s, 3H), 4.07 (s, 3H), 6.23 (t, 1H), 6.87 (t, 1H), 7.28 (dd, 1H), 7.43 (dd, 1H).

Example 77

4-[2-(2-carboxyethyl)-7-((E)-2-{4-[4-(mesityloxy)butoxy]phenyl}vinyl)-1-methyl-1H-indol-3-yl]-4-oxobutanoic acid

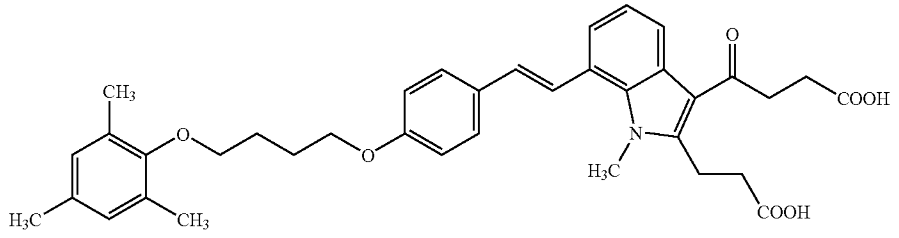

The same operation as in Example 17→Example 3→Example 6 was conducted to obtain the titled compound having the following physical properties. In the step corresponding to Example 17 in the operation, the compound prepared in Example 76 was used in place of the compound prepared in Example 16 and, in the step corresponding to Example 3, 2-({4-[(4-ethenylphenyl)oxy]butyl}oxy)-1,3,5-trimethylbenzene was used in place of 4-vinylphenyl acetate.

TLC: Rf 0.53 (dichloromethane:methanol:acetic acid=90:10:1); $^1$H-NMR (DMSO-$d_6$): δ 1.79-2.01 (m, 4H), 2.17 (s, 9H), 2.49-2.56 (m, 2H), 2.60 (t, 2H), 3.12-3.40 (m, 4H), 3.74 (t, 2H), 3.99 (s, 3H), 4.08 (t, 2H), 6.80 (s, 2H), 6.90 (d, 1H), 6.97 (d, 2H), 7.20 (t, 1H), 7.26-7.32 (m, 1H), 7.59 (d, 2H), 7.80-7.95 (m, 2H).

Example 78

4-[2-(2-(2-carboxyethyl)-7-((E)-2-{4-[4-(2,3-difluorophenoxy)butoxy]phenyl}vinyl)-1-methyl-1H-indol-3-yl]butanoic acid TLC: Rf 0.49 (dichloromethane:methanol:acetic acid=90:10:1); $^1$H-NMR (DMSO-$d_6$): δ 1.76-2.03 (m, 4H), 2.17 (s, 9H), 2.60 (t, 2H), 3.17 (t, 2H), 3.74 (t, 2H), 4.01 (s, 3H), 4.08 (d, 2H), 6.33 (d, 1H) 6.80 (s, 2H), 6.91-7.07 (m, 3H), 7.27 (t, 1H), 7.43 (d, 1H), 7.60 (d, 2H), 7.80 (d, 1H), 7.92-8.08 (m, 2H).

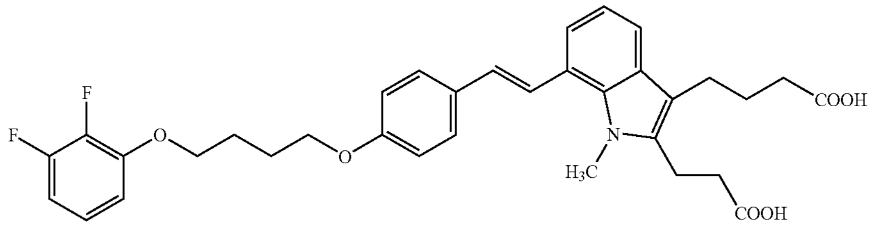

The same operation as in Example 37→Example 73→Example 74→Example 75→Example 14→Example 17→Example 42→Example 3→Example 6 was conducted to obtain the titled compound having the following physical properties. In the step corresponding to Example 37 in the operation, ethyl 7-bromo-H-indole-2-carboxylate was used in place of ethyl 7-bromo-3-[4-ethyloxy)-4-oxobutanoyl]-1H-indole-2-carboxylate.

TLC: Rf 0.37 (dichloromethane:methanol:acetic acid=90:10:1); $^1$H-NMR (DMSO-$d_6$): δ 1.67-1.81 (m, 2H), 1.83-1.97 (m, 4H), 2.22 (t, 2H), 2.41-2.47 (m, 2H), 2.66 (t, 2H), 2.93-3.04 (m, 2H), 3.89 (s, 3), 4.07 (t, 2H), 4.16 (t, 2H), 6.88 (d, 1H), 6.91-7.21 (m, 7H), 7.38 (d, 1H), 7.56 (d, 2H), 7.84 (d, 1H).

Example 79

4-[2-[(E)-2-carboxyvinyl]-7-((E)-2-{4-[4-(mesityloxy)butoxy]phenyl}vinyl)-1-methyl-1H-indol-3-yl]-4-oxobutanoic acid

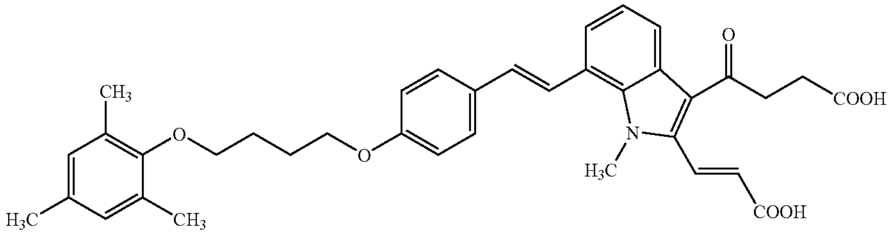

Using a corresponding compound, the same operation as in Example 17→Example 3→Example 6 was conducted to obtain the titled compound having the following physical properties. In the step corresponding to Example 17 in the operation, methyl (2E)-3-(7-bromo-1-methyl-1H-indol-2-yl2-propanoate was used in place of the compound prepared in Example 16 and, in the step corresponding to Example 3, 2-({4-[(4-ethenylphenyl)oxy]butyl}oxy-1,3,5-trimethylbenzene was used in place of 4-vinylphenyl acetate.

Example 80

(3-(5-oxotetrahydro-2-furanyl)-7-{(E)-2-[4-(4-phenoxybutoxy)phenyl]vinyl}-1H-indol-1-yl)acetic acid

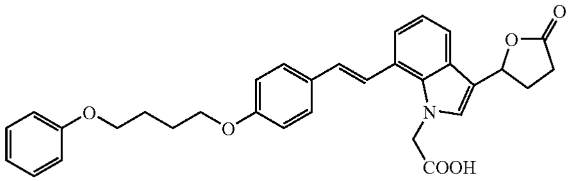

The compound (100 mg) prepared in Example 48(2) was dissolved in a mixture of 1,2-dimethoxyethane (5 mL) and ethanol (5 mL) and sodium borohydride (14 mg) was added at room temperature, followed by stirring at 50° C. for one hour. Purified water (5 mL) was added and sodium borohydride (14 mg) was added every one hour four times, followed by stirring. The reaction mixture was added to an aqueous 5% potassium hydrogen sulfate solution, followed by extraction with ethyl acetate. The organic layer was washed with saturated saline, dried over anhydrous sodium sulfate and then concentrated. The residue was washed with a mixed solvent of diethyl ether and n-hexane to obtain the titled compound having the following physical properties (93 mg).

TLC: Rf 0.42 (dichloromethane:methanol=9:1); $^1$H-NMR (DMSO-$d_6$): δ 1.78-1.98 (m, 4H), 232-2.87 (m, 4H) 3.93-

4.18 (m, 4H), 5.20 (s, 2H), 5.83 (dd, 1H), 6.86-7.02 (m, 6H), 7.09 (t, 1H), 7.20-7.38 (m, 3H), 7.41-7.61 (m, 5H), 13.12 (s, 1H).

Example 81

4-(1-carboxylatemethyl)-7-{(E)-2-[4-(4-phenoxybutoxy)phenyl]vinyl}-1H-indol-3-yl)-4-hydroxybutanoate disodium

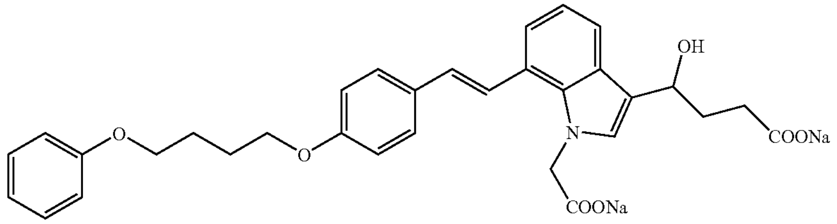

The same operation as in Example 6 was conducted to obtain the titled compound having the following physical properties. In place of the compound prepared in Example 5, the compound prepared in Example 80 was used.

TLC: Rf 0.51 (dichloromethane:methanol=4:1); $^1$H-NMR (DMSO-$d_6$): δ 1.78-1.99 (m, 6H), 2.05-2.20 (m, 2H), 3.95-4.15 (m, 4H), 4.49 (s, 2H), 4.82 (dd, 1H), 6.81-6.98 (m, 8H), 7.18 (d, 1H), 7.23-7.33 (m, 2H), 7.46 (dd, 1H), 7.55 (d, 2H), 7.84 (d, 1H).

Example 82

4-(1-[2-(dimethylamino)-2-oxoethyl]-7-{(E)-2-[4-(4-phenoxybutoxy)phenyl]vinyl}-1H-indol-3-yl)butanoic acid

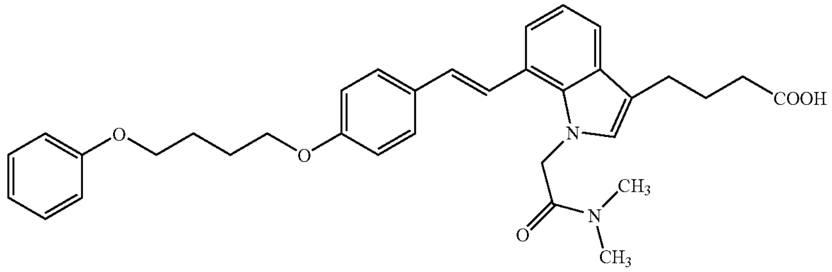

Except for using ethyl 4-(7-bromo-1H-indol-3-yl)butanoate in place of ethyl 7-bromo-3-[4-(ethyloxy)-4-oxobutanoyl]-1H-indole-2-carboxylate, the same operation as in Example 37→Example 3→Example 6 was conducted to obtain the titled compound having the following physical properties. Herein, ethyl 447-bromo-1H-indol-3-yl)butanoate was obtained by the same operation as in Example 17, except for using ethyl 4-chloro-4-oxobutanoate in place of methyl 4-chloro-4-oxobutanoate and 7-bromoindole in place of the compound prepared in Example 16.

TLC: Rf 0.43 (methanol: dichloromethane=1:9); $^1$H-NMR (DMSO-$d_6$): δ 1.76-1.95 (m, 6H), 2.27 (t, 2H), 2.67 (t, 2H), 2.79 (s, 3H), 2.98 (s, 3H), 3.97-4.11 (m, 4H), 5.23 (s, 2H), 6.83 (d, 1H), 6.88-7.02 (m, 7H), 7.18 (d, 1H), 7.23-7.35 (m, 3H), 7.40 (d, 2H), 7.43 (d, 1H).

Example 83

4-(1-(2-carboxyethyl)-7-{(E)-2-[4-(4-phenoxybutoxy)phenyl]vinyl}-2,3-dihydro-1H-indol-3-yl)butanoic acid

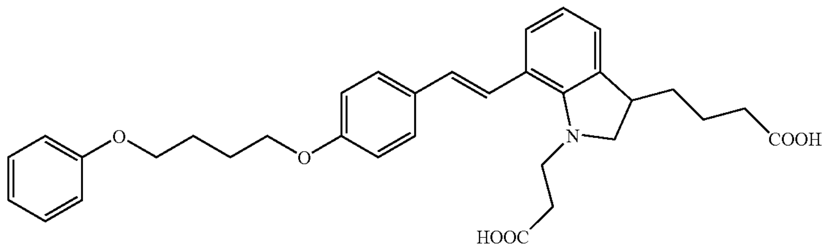

The same operation as in Example 37→Example 3→Example 6 was conducted to obtain the titled compound having the following physical properties. In the step corresponding to Example 37 in the operation, ethyl 4-(7-bromo-2,3-dihydro-1H-indol-3-yl)butanoate was used in place of ethyl 7-bromo-3-[4-ethyloxy)-4-oxobutanoyl]-1H-indole-2-carboxylate and ethyl 3-bromopropionate was used in place of methyl iodide and, in the step corresponding to Example 3, 1-ethenyl-4-{[4-(phenyloxy)butyl]oxy}benzene was used in place of 4-vinylphenyl acetate.

TLC: Rf 0.48 (dichloromethane:methanol=9:1); $^1$H-NMR (DMSO-$d_6$): δ 133-1.63 (m, 3H), 1.66-1.79 (m, 1H), 1.81-1.92 (m, 4H), 2.24 (t, 2H), 2.54 (t, 2H), 3.01 (dd, 1H), 3.10-3.22 (m, 1H), 331-3.39 (m, 1H), 3.42-3.64 (m, 2H), 3.96-4.11 (m, 4H), 6.72 (t, 1H), 6.83-6.99 (m, 7H), 7.17-7.35 (m, 4H), 7.52 (d, 2H), 12.13 (s, 2H).

Example 84 ethyl (7-bromo-1H-indol-3-yl)oxo)acetate

To a diethyl ether (24 mL) solution of 7-bromoindole (2 g), oxalyl chloride (2 mL) was added dropwise under ice cooling and the mixture was stirred at room temperature for 3 hours. The reaction mixture was cooled to 60° C. and sodium ethoxide (20% ethanol solution) (9.7 g) was added. The reaction mixture was stirred at room temperature for 30 minutes and an aqueous saturated sodium hydrogen carbonate solution was added under ice cooling, followed by extraction with ethyl acetate. The organic layer was washed in turn with water and saturated saline, dried over anhydrous magnesium sulfate and then concentrated to obtain the titled compound having the following physical properties (2.88 g).

TLC: Rf 0.52 (n-hexane:ethyl acetate=2:1); $^1$H-NMR ($CDCl_3$): δ 1.43 (t, 3H), 4.42 (q, 2H), 7.22 (dd, 1H), 7.47 (dd, 1H), 8.39 (d, 1H), 8.55 (d, 1H), 9.18 (s, 1H).

Example 85

2,2'-(7-{(E)-2-[4-(4-phenoxybutoxy)phenyl]vinyl}-1H-indol-1,3-diyl)diacetic acid

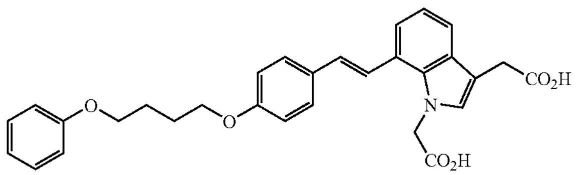

The same operation as in Example 37→Example 27→Example 3→Example 6 was conducted to obtain the titled compound having the following physical properties. In the step corresponding to Example 37 in the operation, the compound prepared in Example 84 was used in place of ethyl 7-bromo-3-[4-(ethyloxy)-4-oxobutanoyl]-1H-indole-2-carboxylate and ethyl bromoacetate was used in place of methyl iodide and, in the step corresponding to Example 3, 1-ethenyl-4-{[4-phenyloxy)butyl]oxy}benzene was used in place of 4-vinylphenyl acetate.

TLC: Rf 0.45 (dichloromethane:methanol:acetic acid=9:1:0.05); $^1$H-NMR (DMSO-$d_6$: δ 1.83-1.93 (m, 4H), 3.62 (s, 2H), 3.99-4.13 (m, 4H), 5.15 (s, 2H), 6.82-6.97 (m, 6H), 7.03 (dd, 1H), 7.21 (s, 1H), 7.23-7.32 (m, 3H), 7.38-7.59 (m, 4H), 12.21 (s, 2H).

Example 85(1) to Example 85(2)

The same operation as in Example 85 was conducted using a corresponding compound to obtain the titled compound having the following physical properties.

Example 85(1)

2,2'-(7-{(E)-2-[4-(4-phenylbutoxy)phenyl]vinyl}-1H-indol-1,3-diyl)diacetic acid

TLC: Rf 0.50 (dichloromethane:methanol:acetic acid=90:10:1); $^1$H-NMR (DMSO-$d_6$): δ 1.63-1.81 (m, 4H), 2.57-2.70 (m, 2H), 3.62 (s, 2H), 3.94-4.08 (m, 2H), 5.16 (s, 2H), 6.87-6.97 (m, 3H), 7.03 (t, 1H), 7.11-7.36 (m, 7H), 736-7.61 (m, 4H), 12.21 (brs, 1H), 13.04 (brs, 1H).

Example 85(2)

2,2'-[7-((E)-2-{4-[4-(2,3-difluorophenoxy)butoxy]phenyl}vinyl)-1H-indol-1,3-diyl]diacetic acid

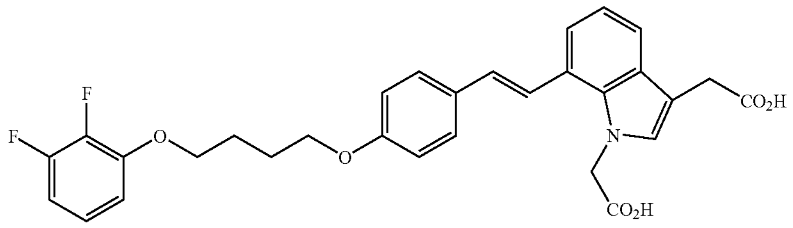

TLC: Rf 0.43 (dichloromethane:methanol:acetic acid=9:1:0.05); $^1$H-NMR (DMSO-$d_6$): δ 1.84-1.97 (m, 4H), 3.62 (s, 2H), 4.06 (t, 2H), 4.16 (t, 2H), 5.15 (s, 2H), 6.85-7.07 (m, 6H), 7.12 (ddd, 1H) 7.21 (s, 1H), 7.27 (d, 1H), 7.43 (d, 1H), 7.47-7.57 (m, 3H), 12.25 (s, 2H).

Example 86

4-(1-(2-carboxyethyl)-7-{(E)-2-[4-(4-phenoxybutoxy)phenyl]vinyl}-1H-indol-3-yl)butanoic acid

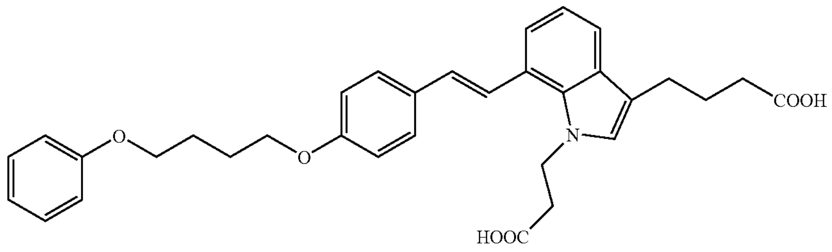

The same operation as in Example 37→Example 3→Example 6 was conducted to obtain the titled compound having the following physical properties. In the step corresponding to Example 37 in the operation, methyl bromopropionate was used in place of ethyl 7-bromo-3-[4-ethyloxy)-4-oxobutanoyl]-1H-indole-2-carboxylate and, in the step corresponding to Example 3, 4-phenoxybutoxy-vinylbenzene was used in place of 4-vinylphenyl acetate.

TLC: Rf 0.38 (methanol: dichloromethane=1:9); $^1$H-NMR (DMSO-$d_6$): δ 1.75-1.92 (m, 6H), 2.26 (t, 2H), 2.65 (t, 2H), 2.74 (t, 2H), 3.95-4.12 (m, 4H), 4.55 (t, 2H), 6.87-7.05 (m, 7H), 7.10 (s, 1H), 7.20-7.32 (m, 3H), 7.43 (d, 1H), 7.56 (d, 2H), 7.73 (d, 1H).

Example 87 ethyl 4-{1-{2-[(1,1-dimethylethyl)oxy]-2-oxoethyl}-7-[(E)-2-(4-{[4-(phenyloxy)butyl]oxy}phenyl)ethenyl]-1H-indol-3-yl}butanoate The same operation as in Example 37→Example 3 was conducted to obtain the titled compound having the following physical properties. In the step corresponding to Example 37 in the operation, the compound prepared in Example 42 was used in place of ethyl 7-bromo-3-[4-ethyloxy)-4-oxobutanoyl]-1H-indole-2-carboxylate and tert-butyl bromoacetate was used in place of methyl iodide and, in the step corresponding to Example 3, 1-(4-phenoxybutoxy)-4-vinylbenzene was used in place of 4-vinylphenyl acetate.

TLC: Rf 0.50 (n-hexane:ethyl acetate=3:1); $^1$H-NMR ($CDCl_3$): δ 1.23-1.28 (m, 3H), 1.42 (s, 9H), 1.99-2.06 (m, 6H), 2.38 (t, 2H), 2.79 (t, 2H), 4.03-4.17 (m, 6H), 4.90 (s, 2H), 6.80-6.97 (m, 7H), 7.07-7.12 (m, 1H), 7.25-7.32 (m, 3H), 7.42-7.53 (m, 4H).

Example 88

{3-[4-(ethyloxy)-4-oxobutyl]-7-[(E)-2-(4-{[4-pheny-loxy)butyl]oxy}phenyl)ethenyl]-1H-indol-1-yl}acetic acid

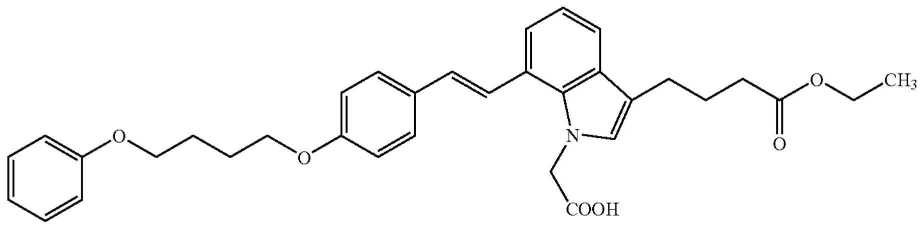

To a methylene chloride solution (1.5 mL) of the compound (130 mg) prepared in Example 87, trifluoroacetic acid (0.2 mL) was added and the mixture was stirred overnight. To the reaction mixture, water was added, followed by extraction with ethyl acetate. The organic layer was washed in turn with water and saturated saline, dried over anhydrous magnesium sulfate and then concentrated. The residue was purified by silica gel column chromatography (n-hexane:ethyl acetate=3:1) to obtain the titled compound having the following physical properties (78 mg).

TLC: Rf 0.48 (methylene chloride:methanol=9:1); $^1$H-NMR ($CDCl_3$): δ 1.16 (t, 2H), 1.83-1.91 (m, 6H), 2.34 (t, 2H), 2.66 (t, 2H), 4.01-4.08 (m, 6H), 5.11 (s, 2H), 6.88-7.07 (m, 8H), 7.24-7.29 (m, 3H), 7.43-7.54 (m, 4H), 13.05 (s, 1H).

Example 88(1)

[7-((E)-2-{4-[4-(2,3-difluorophenoxy)butoxy]phenyl}vinyl)-3-(4-ethoxy-4-oxobutyl-1H-indol-1-yl]acetic acid Using a corresponding compound, the same operation as in Example 88 was conducted to obtain the titled compound having the following physical properties.

TLC: Rf 0.50 (dichloromethane:methanol=9:1); $^1$H-NMR (DMSO-$d_6$): δ 1.17 (t, 3H), 1.80-1.92 (m, 6H), 2.35 (t, 2H), 2.67 (t, 2H), 4.05 (q, 4H), 4.16 (t, 2H), 5.10 (s, 2H), 6.79-7.19 (m, 8H) 7.26 (d, 1H), 7.39-7.59 (m, 4H), 13.04 (s, 1H).

Example 89

4-(7-bromo-1H-indol-3-yl)butanoic acid

To a toluene (7 mL) solution of 447-bromo-1H-indol-3-yl) butanoic acid (0.6 g), N,N-dimethylformamide tert-butylacetal (2.3 mL) was added and the mixture was stirred at 80° C. for 2 hours. After the reaction mixture was air-cooled, saturated sodium bicarbonate water was added, followed by extraction with ethyl acetate. The organic layer was washed in turn with water, an aqueous saturated sodium hydrogen carbonate solution and saturated saline, dried over anhydrous magnesium sulfate and then concentrated to obtain the titled compound having the following physical properties (0.68 g).

TLC: Rf 0.49 (n-hexane:ethyl acetate=5:1); $^1$H-NMR ($CDCl_3$): δ 1.45 (s, 9H), 1.94-2.04 (m, 2H), 2.26-2.31 (m, 2H), 2.75-2.80 (m, 2H), 6.97-7.02 (m, 1H), 7.06 (d, 1H), 7.33-7.35 (m, 1H), 7.55 (d, 1H), 8.13 (s, 1H).

Example 90

4-[7-((E)-2-{4-[4-(2,3-difluorophenoxy)butoxy]phenyl}vinyl)-1-(2-ethoxy-2-oxoethyl)-1H-indol-3-yl]butanoic acid

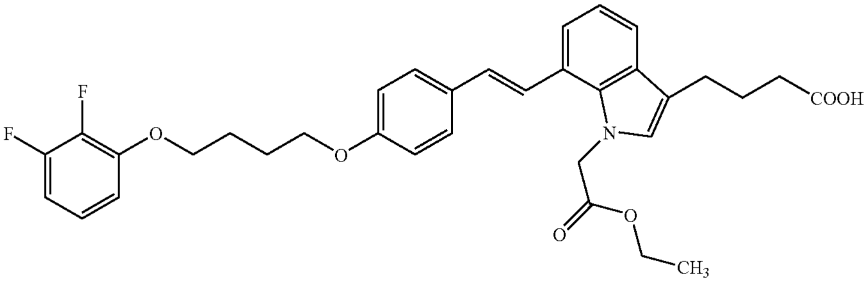

The same operation as in Example 37→Example 3→Example 87 was conducted to obtain the titled compound having the following physical properties. In the step corresponding to Example 37 in the operation, the compound prepared in Example 89 was used in place of ethyl 7-bromo-3-[4-ethyloxy)-4-oxobutanoyl]-1H-indole-2-carboxylate and ethyl bromoacetate was used in place of methyl iodide and, in the step corresponding to Example 3, 1-({4-[(4-ethenylphenyl)oxy]butyl}oxy)-2,3-difluorobenzene was used in place of 4-vinylphenyl acetate.

TLC: Rf 0.49 (dichloromethane:methanol=9:1); $^1$H-NMR (CDCl$_3$): δ 1.19 (t, 3H), 1.95-2.13 (m, 6H), 2.43 (t, 2H), 2.81 (t, 2H), 4.02-4.23 (m, 6H), 4.98 (s, 2H), 6.68-7.02 (m, 7H), 7.09 (dd, 1H), 7.23 (s, 1H), 7.36-7.46 (m, 3H), 7.47-7.54 (m, 1H).

Example 91 ethyl (7-{(E)-2-[4-({4-[(2,3-difluorophenyl)oxy]butyl}oxy)phenyl]ethenyl}-3-{4-[(methylsulfonyl)amino]-4-oxobutyl}-1H-indol-1-yl)acetate To a dichloromethane (1.5 mL) solution of the compound (75 mg) prepared in Example 90, methanesulfonamide (13 mg) and 4-dimethylaminopyridine (19 mg) were added. Furthermore, 1-ethyl-3-(3-dimethylaminopropyl)carbodiimide hydrochloride (29 mg) was added and the mixture was stirred overnight. To the reaction mixture, water was added, followed by extraction with ethyl acetate. The organic layer was washed in turn with water and saturated saline, dried over anhydrous magnesium sulfate and then concentrated. The residue was purified by silica gel column chromatography (methylene chloride:methanol=100:1) to obtain the titled compound having the following physical properties (38 mg).

TLC: Rf 0.21 (n-hexane:ethyl acetate=1:1); $^1$H-NMR (CDCl$_3$): δ 1.20 (t, 3H) 2.02-2.04 (m, 4H), 2.08-2.15 (m, 2H), 2.85 (t, 2H), 3.16-3.19 (m, 3H), 4.09-4.21 (m, 6H) 5.02 (s, 2H), 627-7.01 (m, 8H), 7.11 (dd, 1H), 7.23-7.24 (m, 1H), 7.37-7.50 (m, 4H).

Example 92

(7-{(E)-2-[4-({4-[(2,3-difluorphenyl)oxy]butyl}oxy)phenyl]ethenyl}-3-{4-[(methylsulfonyl)amino]-4-oxobutyl}-1H-indol-1-yl)acetic acid The same operation as in Example 6 was conducted to obtain the titled compound having the following physical properties. In place of the compound prepared in Example 5, the compound prepared in Example 91 was used.

TLC: Rf 0.33 (dichloromethane:methanol=9:1); $^1$H-NMR (DMSO-d$_6$): δ 1.82-1.95 (m, 6H), 2.34 (t, 2H), 2.61-2.70 (m, 2H), 3.20 (s, 3H), 4.07 (t, 2H), 4.16 (t, 2H), 5.13 (s, 2H), 6.86-7.17 (m, 9H), 7.26 (d, 1H), 7.40-7.57 (m, 4H), 11.77 (s, 1H).

Example 93

4-(3-(carboxymethyl)-4-{(E)-2-[4-(4-phenoxybutoxy)phenyl]vinyl}-1H-indol-1-yl)-4-oxobutanoic acid Using a corresponding compound, the same operation as in Example 32→Example 33 was conducted to obtain the titled compound having the following physical properties.

TLC: Rf 0.41 (dichloromethane:methanol:acetic acid=90:10:1); $^1$H-NMR (DMSO-d$_6$): δ 1.80-1.95 (m, 4H), 2.66 (t, 2H), 3.24 (t, 2H), 3.92 (s, 2H), 3.97-4.14 (m, 4H), 6.85-7.00 (m, 5H), 7.13 (d, 1H), 723-7.36 (m, 3H), 7.46-7.60 (m, 4H), 7.89 (s, 1H), 8.29 (d, 1H), 12.41 (s, 2H).

Example 94 ethyl 4-{1-[2-(ethyloxy)-2-oxoethyl]-7-ethynyl-1H-indol-3-yl}butanoate

To an ethanol (2 mL) solution of ethyl 4-{1-[2-(ethyloxy)-2-oxoethyl]-7-[(trimethylsilyl)ethynyl]-1H-indol-3-yl}butanoate (98 mg), potassium carbonate (50 mg) was added and the mixture was stirred at room temperature for 3 hours. To the reaction mixture, water was added, followed by extraction with ethyl acetate. The organic layer was washed with saturated saline, dried over anhydrous sodium sulfate and then concentrated to obtain the titled compound having the following physical properties (74 mg). Herein, ethyl 4-{1-[2-(ethyloxy)-2-oxoethyl]-7-[(trimethylsilyl)ethynyl]-1H-indol-3-yl}butanoate was prepared by the same operation as in Example 3, except for using ethyl 4-{7-bromo-1-[2-(ethyloxy)-2-oxoethyl]-1H-indol-3-yl}butanoate and ethynyl(trimethyl)silane.

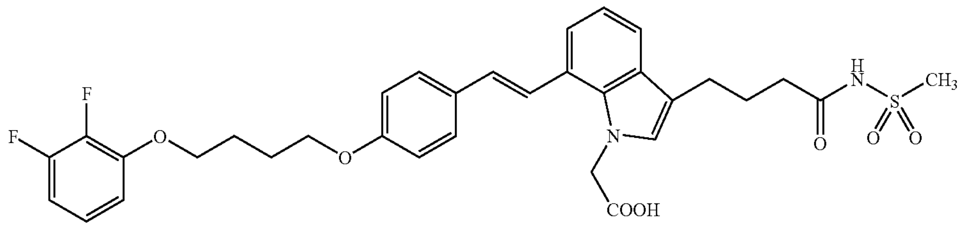

TLC: Rf 0.24 (n-hexane:ethyl acetate=4:1); $^1$H-NMR (CDCl$_3$): δ 1.25 (t, 3H), 1.20-1.30 (m, 3H), 1.95-2.08 (m, 2H), 2.36 (t, 2H), 2.77 (dt, 2H), 3.27 (s, 1H), 4.12 (q, 2H), 4.22

(q, 2H), 5.27 (s, 2H), 6.80 (s, 1H), 7.04 (dd, 1H), 7.35 (dd, 1H), 7.59 (dd, 1H).

Example 95 ethyl 4-{1-[2-(ethyloxy)-2-oxoethyl]-7-[3-(4-{[4-(phenyloxy)butyl]oxy}phenyl)-5-isoxazolyl]-1H-indol-3-yl}butanoate To a dichloromethane (5 mL) solution of 4-{[4-(phenyloxy)butyl]oxy}benzaldehyde (811 mg), pyridine (0.1 mL) and hydroxylamine hydrochloride (219 mg) were added and the mixture was stirred at room temperature for 3 hours and methanol (5 mL) was further added, followed by stirring overnight. To the reaction mixture, an aqueous saturated sodium hydrogen carbonate solution was added, followed by extraction with ethyl acetate. The organic layer was washed with saturated saline, dried over anhydrous sodium sulfate and then concentrated. The resulting solid (285 mg) was dissolved in N,N-dimethylformamide (2 mL) and 1-chlorosuccimide (133 mg) was added at 0° C., followed by stirring overnight at room temperature. To the reaction mixture, water was added and the precipitated solid was filtered and then dried under reduced pressure to obtain a white solid (311 mg). The resulting solid (121 mg) and the compound (108 mg) prepared in Example 94 were dissolved in ethyl acetate (5 mL) and triethylamine (0.097 mL) was added, followed by stirring overnight. To the reaction mixture, water was added, followed by extraction with ethyl acetate. The organic layer was washed with saturated saline, dried over anhydrous sodium sulfate and filtered, and then the filtrate was concentrated under reduced pressure. The residue was purified by silica gel column chromatography (n-hexane:ethyl acetate=95:5-50:50) to obtain the titled compound having the following physical properties (76 mg).

TLC: Rf 0.45 (n-hexane:ethyl acetate=2:1); $^1$H-NMR ($CDCl_3$): δ 1.07 (t, 2H), 1.26 (t, 3H), 1.95-2.13 (m, 6H), 2.40 (t, 2H), 2.82 (t, 2H), 4.01 (q, 2H), 4.03-4.08 (m, 2H), 4.09-4.12 (m, 2H), 4.14 (q, 3H), 4.70 (s, 2H), 6.62 (s, 1H), 6.86 (s, 1H), 6.88-6.98 (m, 3H), 7.00 (d, 2H), 7.18 (dd, 1H), 7.23-7.34 (m, 2H), 7.74 (dd, 1H), 7.77-7.83 (m, 2H).

Example 96

4-(1-(carboxymethyl)-7-{3-[4-(4-phenoxybutoxy)phenyl]-5-isoxazolyl}-1H-indol-3-yl)butanoic acid The same operation as in Example 6 was conducted to obtain the titled compound having the following physical properties. In place of the compound prepared in Example 5, the compound prepared in Example 95 was used.

TLC: Rf 0.31 (chloroform:methanol:water=50:10:1); $^1$H-NMR (DMSO-$d_6$)1.80-1.97 (m, 6H), 2.30 (t, 2H), 2.73 (t, 2H), 3.99-4.08 (m, 2H), 4.08-4.16 (m, 2H), 4.72 (s, 2H), 6.88-6.99 (m, 3H), 7.09 (d, 2H), 7.16 (dd, 1H), 7.17 (dd, 1H), 7.20 (s, 1H), 7.22-7.34 (m, 3H), 7.75 (dd, 1H), 7.85 (d, 2H), 11.61-13.03 (m, 2H).

Example 97(1) to Example 97(3)

The same operation as in Example 2→Example 3→Example 4→Example 5→Example 6 was conducted to obtain the titled compound having the following physical properties. In the step corresponding to Example 2, methyl (4-bromo-1H-indol-3-yl)acetate) was used in place of the compound prepared in Example 1 and, in the step corresponding to Example 2, a corresponding compound was used in place of methyl 4-bromobutyrate. In the step corresponding to Example 5, 1-chloro-4-phenylbutane or a corresponding compound was used.

Example 97(1)

4-{3-(carboxymethyl)-4-[(E)-2-(4-{[(2E)-4-(2,3-difluorophenoxy)-2-buten-1-yl]oxy}phenyl)vinyl]-1H-indol-1-yl}butanoic acid TLC: Rf 0.29 (dichloromethane:methanol=9:1); $^1$H-NMR (DMSO-$d_6$): δ 1.86-2.01 (m, 2H), 2.20 (t, 2H), 3.84 (s, 2H), 4.14 (t, 2H), 4.60-4.64 (m, 2H), 4.69-4.76 (m, 2H), 6.00-6.18 (m, 2H), 6.90-7.19 (m, 7H), 7.27 (s, 1H), 7.30-7.40 (m, 2H), 7.53 (d, 2H), 7.64 (d, 1H), 12.30 (brs, 2H).

Example 97(2)

4-{3-(carboxymethyl)-4-[(E)-2-(4-{[(2E)-4-(mesityloxy)-2-buten-1-yl]oxy}phenyl)vinyl]-1H-indol-1-yl}butanoic acid TLC: Rf 0.29 (dichloromethane:methanol=9:1); $^1$H-NMR (DMSO-$d_6$): δ 1.84-2.02 (m, 2H), 2.13-2.24 (m, 1H), 3.83 (s, 2H), 4.14 (t, 2H), 4.28 (d, 2H), 4.64 (d, 2H), 5.98-6.18 (m, 2H), 6.80 (s, 2H), 6.97 (d, 2H), 7.02-7.18 (m, 2H), 7.26 (s, 1H), 7.30-7.39 (m, 2H), 7.54 (d, 2H), 7.65 (d, 1H).

Example 97(3)

4-{3-(carboxymethyl)-4-[(E)-2-(4-{[(2E)-4-(4-chloro-2,6-dimethylphenoxy)-2-buten-1-yl]oxy}phenyl)vinyl]-1H-indol-1-yl}butanoic acid TLC: Rf 0.29 (dichloromethane:methanol=9:1); $^1$H-NMR (DMSO-$d_6$): δ 1.87-2.01 (m, 2H), 2.10-2.26 (m, 8H), 3.84 (s, 2H), 4.14 (t, 2H), 4.33 (d, 2H), 4.64 (d, 2H), 6.00-6.18 (m, 2H), 6.96 (d, 2H), 7.01-7.19 (m, 4H), 7.27 (s, 1H), 7.30-7.41 (m, 2H), 7.54 (d, 2H), 7.65 (d, 1H), 12.29 (s, 2H).

Example 98(1) to Example 98(137)

Using a corresponding compound, the same operation as in Example 41→Example 42→Example 43→Example 44 was conducted to obtain the titled compound having the following physical properties.

Example 98(1)

4-[1 (carboxymethyl)-7-((E)-2-{5-[4-(2,3-dichlorophenoxy)butoxy]-2-pyridinyl}vinyl)-1H-indol-3-yl]butanoic acid TLC: Rf 0.56 (methanol: dichloromethane=1:4); $^1$H-NMR (DMSO-$d_6$): δ 1.77-2.00 (m, 6H), 2.28 (t, 2H), 2.67 (t, 2H), 4.06-4.24 (m, 4H), 5.06 (s, 2H), 6.95 (d, 1H), 7.03 (t, 1H), 7.08 (s, 1H), 7.12-7.41 (m, 5H), 7.48 (d, 1H), 7.53 (d, 1H), 7.94 (d, 1H), 8.26 (d, 1H).

Example 98(2)

4-[1-(carboxymethyl)-7-((E)-2-{4-[3-(mesityloxy)propoxy]phenyl}vinyl)-1H-indol-3-yl]butanoic acid TLC: Rf 0.57 (methanol: dichloromethane:acetic acid=1:9:0.1); $^1$H-NMR (DMSO-$d_6$): δ 1.78-1.92 (m, 2H), 2.08-2.22

(m, 2H), 2.14 (s, 6H), 2.16 (s, 3H), 2.28 (t, 2H), 2.67 (t, 2H), 3.85 (t, 2H), 4.23 (t, 2H), 5.13 (s, 2H), 6.79 (s, 2H), 6.92 (d, 1H), 6.98 (d, 2H), 7.02 (t, 1H), 7.08 (s, 1H), 7.26 (d, 1H), 7.46 (d, 1H), 7.50 (d, 2H) 7.52 (d, 1H), 12.50 (s, 2H).

Example 98(3)

4-{1-(carboxymethyl)-7-[(E)-2-(4-{[(2E)-4-(2-chloro-3,5-difluorophenoxy)-2-buten-1-yl]oxy}phenyl)vinyl]-1H-indol-3-yl}butanoic acid TLC: Rf 0.63 (methanol: dichloromethane:acetic acid=1:9:0.1); $^1$H-NMR (DMSO-$d_6$): δ 1.76-1.95 (m, 2H), 2.28 (t, 2H), 2.66 (t, 2H), 4.64 (d, 2H), 4.75 (d, 2H), 5.10 (s, 2H), 5.97-6.23 (m, 2H) 6.85-7.15 (m, 7H), 7.26 (d, 1H), 7.45 (d, 1H), 7.50 (d, 2H), 7.54 (d, 1H), 12.46 (s, 2H).

Example 98(4)

4-{1-(carboxymethyl)-7-[(E)-2-(4-{[(2E)-4-(mesityloxy)-2-buten-1-yl]oxy}phenyl)vinyl]-1H-indol-3-yl}butanoic acid TLC: Rf 0.55 (dichloromethane:methanol:acetic acid=90:10:1); $^1$H-NMR (DMSO-$d_6$): δ 1.78-1.92 (m, 2H), 2.16 (s, 9H), 2.28 (t, 2H), 2.67 (t, 2H), 4.28 (d, 2H), 4.64 (d, 2H), 5.13 (s, 2H), 5.96-6.21 (m, 2H) 6.80 (s, 2H), 6.93 (d, 1H), 6.97 (d, 2H), 7.02 (t, 1H), 7.08 (s, 1H), 7.26 (d, 1H), 7.45 (d, 1H), 7.50 (d, 2H), 7.53 (d, 1H) 12.48 (s, 2H).

Example 98(5)

4-{1-(carboxymethyl)-7-[(E)-2-(4-{[(2E)-4-(2-chloro-6-fluoro-3-methylphenoxy)-2-buten-1-yl]oxy}phenyl)vinyl]-1H-indol-3-yl}butanoic acid TLC: Rf 0.56 (dichloromethane:methanol:acetic acid=90:10:1); $^1$H-NMR (DMSO-$d_6$): δ 1.77-1.95 (m, 2H), 2.28 (t, 2H), 2.26-2.30 (m, 3H), 2.67 (t, 2H), 4.51-4.74 (m, 4H), 5.13 (s, 2H), 5.94-6.17 (m, 2H), 6.92 (d, 1H), 6.93 (d, 2H), 6.97-7.23 (m, 4H), 7.26 (d, 1H), 7.45 (d, 1H), 7.49 (d, 2H), 7.53 (d, 1H) 12.42 (s, 2H).

Example 98(6)

4-[1-(carboxymethyl)-7-((E)-2-{5-[4-(4-fluoro-2-methylphenoxy)butoxy]-2-pyridinyl}vinyl)-1H-indol-3-yl]butanoic acid TLC: Rf 0.35 (methanol: dichloromethane=1:4); $^1$H-NMR (DMSO-$d_6$): δ 1.76-2.00 (m, 6H), 2.14 (s, 3H), 2.28 (t, 2H), 2.67 (t, 2H),3.97-4.06 (m, 2H), 4.09-4.20 (m, 2H), 5.10 (s, 2H ),6.89-7.07 (m, 5H), 7.09 (s, 1H), 7.28 (d, 1H), 7.39 (dd, 1H), 7.46-7.55 (m, 2H), 7.93 (d, 1H), 8.27 (d, 1H).

Example 98(7)

4-{1-(carboxymethyl)-7-[(E)-2-(4-{[(2E)-4-(6-chloro-2-fluoro-3-methylphenoxy)-2-buten-1-yl]oxy}phenyl)vinyl]-1H-indol-3-yl}butanoic acid TLC: Rf 0.49 (dichloromethane:methanol:acetic acid=90:10:0.5); $^1$H-NMR (DMSO-$d_6$): δ 1.63-1.96 (m, 2H), 2.21 (d, 3H), 2.28 (t, 2H), 2.67 (t, 2H), 4.57-4.66 (m, 4H), 5.10 (s, 2H), 6.03-6.09 (m, 2H), 6.87-7.11 (m, 6H), 7.16-7.31 (m, 2H), 7.39-7.60 (m, 4H), 12.15 (s, 2H).

Example 98(8)

4-[1-(carboxymethyl)-7-((E)-2-{4-[4-(2-chloro-3,5-difluorophenoxy)butoxy]phenyl}vinyl)-2-methyl-1H-indol-3-yl]butanoic acid TLC: Rf 0.33 (dichloromethane:methanol=9:1); $^1$H-NMR (DMSO-$d_6$): δ 1.67-1.80 (m, 2H), 1.84-1.97 (m, 4H), 2.21 (t, 2H), 2.25 (s, 3H), 2.66 (t 2H), 4.02-4.11 (m, 2H), 4.13-4.24 (m, 2H), 4.99 (s, 2H), 6.88 (d, 1H), 6.91-7.11 (m, 5H), 7.15 (d, 1H), 7.39 (d, 1H), 7.44-7.58 (m, 3H).

Example 98(9)

4-(1-(carboxymethyl)-7-{(E)-2-[4-(5-phenoxypentanoyl)phenyl]vinyl}-1H-indol-3-yl)butanoic acid TLC: Rf 0.22 (chloroform:methanol:water=50:10:1); $^1$H-NMR (DMSO-$d_6$): δ 1.70-1.93 (m, 6H), 2.34 (t, 2H), 2.45-2.49 (m, 2H), 3.98-4.13 (m, 4H), 5.36 (s, 2H), 6.81-7.05 (m, 6H), 7.21-7.32 (m, 3H), 7.40-7.61 (m, 4H), 7.71 (d, 1H), 8.08 (s, 1H), 12.13 (s, 1H), 13.29 (s, 1H).

Example 98(10)

4-[1-(carboxymethyl)-7-((E)-2-{4-[4-(2-chlorophenoxy)butoxy]phenyl}vinyl)-2-methyl-1H-indol-3-yl]butanoic acid TLC: Rf 0.45 (dichloromethane:methanol=9:1); $^1$H-NMR (DMSO-$d_6$): δ 1.68-1.81 (m, 2H), 1.85-1.97 (m, 4H), 2.21 (t, 2H), 2.25 (s, 3H), 2.67 (t, 2H), 4.02-4.18 (m, 4H), 5.01 (s, 2H), 6.87 (d, 1H), 6.90-7.01 (m, 4H), 7.11-7.17 (m, 2H), 7.24-7.33 (m, 1H), 7.34-7.57 (m, 5H).

Example 98(11)

4-(1-(carboxymethyl)-7-{(E)-2-[4-(5-phenoxypentyl)phenyl]vinyl}-1H-indol-3-yl)butanoic acid TLC: Rf 0.26 (chloroform:methanol:water=50:10:1); $^1$H-NMR (DMSO-$d_6$): δ 1.36-1.51 (m, 2H), 1.57-1.69 (m, 2H), 1.68-1.79 (m, 2H), 1.79-1.91 (m, 2H), 2.28 (t, 2H), 2.60 (t, 2H), 2.66 (dd, 2H), 3.94 (t, 2H), 5.12 (s, 2H), 6.84-6.98 (m, 4H), 7.02 (dd, 1H), 7.07 (s, 1H), 7.15-7.31 (m, 5H), 7.42-7.50 (m, 3H), 7.62 (d, 1H).

Example 98(12)

4-{1-(carboxymethyl)-7-[(E)-2-(4-{[(2E)-4-(2,3-difluorophenoxy)-2-buten-1-yl]oxy}phenyl)vinyl]-2-methyl-1H-indol-3-yl}butanoic acid TLC: Rf 0.23 (chloroform:methanol=9:1); $^1$H-NMR (DMSO-$d_6$): δ 1.68-1.80 (m, 2H), 2.21 (t, 2H), 2.25 (s, 3H), 2.67 (t, 2H), 4.64 (d, 2H), 4.72 (d, 2H), 5.02 (s, 2H), 6.01-6.16 (m, 2H), 6.89 (d, 1H), 6.93-7.17 (m, 5H), 6.96 (d, 2H), 7.39 (dd, 1H), 7.49 (d, 2H), 7.51 (d, Example 98(13)

4-{1-(carboxymethyl)-7-[(E)-2-(4-{[(2E)-4-(mesityloxy)-2-buten-1-yl]oxy}phenyl)vinyl]-2-methyl-1H-indol-3-yl}butanoic acid TLC: Rf 0.25 (chloroform:methanol=9:1); $^1$H-NMR (DMSO-$d_6$): δ 1.68-1.81 (m, 2H), 2.16 (s, 9H), 2.21 (t, 2H), 2.26 (s, 3H), 2.67 (t, 2H), 4.28 (d, 2H), 4.64 (d, 2H), 5.02 (s, 2H), 6.00-6.17 (m, 2H), 6.81 (s, 2H), 6.89 (d, 1H), 6.98 (d, 2H), 6.99 (dd, 1H), 7.15 (d, 1H), 7.39 (d, 1H), 7.50 (d, 2H), 7.52 (d, 1H).

Example 98(14)

4-{1-(carboxymethyl)-2-methyl-7-[(E)-2-(4-{[(2E)-4-phenoxy-2-buten-1-yl]oxy}phenyl)vinyl]-1H-indol-3-yl}butanoic acid TLC: Rf 0.16 (chloroform:methanol=9:1); $^1$H-NMR (DMSO-$d_6$): δ 1.67-1.81 (m, 2H), 2.21 (t, 2H), 2.25 (s, 3H), 2.67 (t, 2H), 4.60 (s, 2H), 4.62 (s, 2H), 5.01 (s, 2H), 6.04-6.08 (m, 2H), 6.88 (d, 1H), 6.88-7.01 (m, 4H), 6.94 (d, 2H), 7.14 (d, 1H), 7.27 (dd, 2H), 7.38 (d, 1H), 7.49 (d, 2H), 7.51 (d, 1H).

Example 98(15)

4-[1-(carboxymethyl)-7-((E)-2-{4-[4-(4-chloro-2,6-dimethylphenoxy)butoxy]phenyl}vinyl)-2-methyl-1H-indol-3-yl]butanoic acid TLC: Rf 0.48 (dichloromethane:methanol=9:1); $^1$H-NMR (DMSO-$d_6$): δ 1.67-1.80 (m, 2H), 1.83-1.99 (m, 4H), 2.16-2.24 (m, 2H), 2.21 (s, 6H),2.25 (s, 3H), 2.67 (t, 2H), 3.78 (t 2H), 4.07 (t, 2H), 5.02 (s, 2H), 6.88 (d, 1H), 6.93-7.03 (m, 3H), 7.09 (s, 2H), 7.15 (d, 1H), 7.39 (d, 1H), 7.46-7.57 (m, 3H).

Example 98(16)

4-{1-(carboxymethyl)-7-[(E)-2-(4-{[(2E)-4-(2,6-dimethylphenoxy)-2-buten-1-yl]oxy}phenyl)vinyl]-2-methyl-1H-indol-3-yl}butanoic acid TLC: Rf 0.26 (chloroform:methanol=9:1); $^1$H-NMR (DMSO-$d_6$): δ 1.69-1.79 (m, 1H), 2.21 (t 2H), 2.21 (s, 6H), 2.26 (s, 3H), 2.67 (t, 2H), 4.33 (d, 2H), 4.65 (d, 2H), 5.03 (s, 2H), 6.03-6.18 (m, 2H), 6.89 (d, 1H), 6.91 (dd, 1H), 6.99 (d, 2H), 6.98-7.03 (m, 3H), 7.15 (d, 1H), 7.39 (d, 1H), 7.50 (d, 2H), 7.52 (d, 1H).

Example 98(17)

4-{1-(carboxymethyl)-7-[(E)-2-(4-{[(2E)-4-(4-chloro-2,6-dimethylphenoxy)-2-buten-1-yl]oxy}phenyl)vinyl]-2-methyl-1H-indol-3-yl}butanoic acid TLC: Rf 0.27 (chloroform:methanol=9:1); $^1$H-NMR (DMSO-$d_6$): δ 1.68-1.80 (m, 2H), 2.21 (t 2H), 2.20 (s, 6H), 2.25 (s, 3H), 2.67 (t, 2H),4.33 (d, 2H), 4.64 (d, 2H), 5.03 (s, 2H), 6.01-6.16 (m, 2H), 6.89 (d, 1H), 6.97 (d, 2H), 6.99 (dd, 1H), 7.10 (s, 2H), 7.15 (d, 1H), 7.39 (d, 1H), 7.50 (d, 2H), 7.52 (d, 1H).

Example 98(18)

4-[1-(carboxymethyl)-7-((E)-2-{4-[4-(2,3-difluorophenoxy)butoxy]phenyl}vinyl)-4-fluoro-2-methyl-1H-indol-3-yl]butanoic acid TLC: Rf 0.54 (dichloromethane:methanol:acetic acid=90:10:1); $^1$H-NMR (DMSO-$d_6$): δ 1.68-1.83 (m, 2H), 1.83-1.97 (m, 4H), 2.19 (t, 2H), 2.24 (s, 3H), 2.73 (t, 2H), 4.06 (t 2H), 4.15 (t 2H), 5.03 (s, 2H), 6.74 (dd, 1H), 6.82 (d, 1H), 6.93 (d, 2H), 6.97-7.20 (m, 4H), 7.43 (d, 1H), 7.47 (d, 2H), 12.24 (s, 2H).

Example 98(19)

4-{1-(carboxymethyl)-7-[(E)-2-(4-{[(2E)-4-(2,3-difluorophenoxy)-2-buten-1-yl]oxy}phenyl)vinyl]-5-fluoro-1H-indol-3-yl}butanoic acid TLC: Rf 0.34 (dichloromethane:methanol=9:1); $^1$H-NMR (DMSO-$d_6$): δ 1.74-1.88 (m, 2H), 2.23-2.31 (m, 2H), 2.62 (t, 2H), 4.60-4.67 (m, 2H), 4.69-4.76 (m, 2H), 5.12 (s, 2H), 6.06-6.13 (m, 2H), 6.92-7.17 (m, 8H), 7.21 (dd, 1H), 7.44-7.55 (m, 3H).

Example 98(20)

4-[1-(carboxymethyl)-7-((E)-2-{4-[4-(2,3-difluorophenoxy)butoxy]phenyl}vinyl)-1H-indol-3-yl]butanoic acid TLC: Rf 0.32 (chloroform:methanol:water=50:10:1); $^1$H-NMR (DMSO-$d_6$): δ 1.73 (d, 3H), 1.78-1.98 (m, 6H), 2.27 (t, 2H), 2.68 (t, 2H), 4.02-4.10 (m, 2H), 4.11-4.20 (m, 2H), 5.49 (q, 1H), 6.87 (d, 1H), 6.91-7.16 (m, 6H), 7.19 (d, 1H), 7.23 (s, 1H), 7.45 (dd, 1H), 7.50 (d, 2H), 7.56 (d, 1H).

Example 98(21)

4-{1-(carboxymethyl)-4-fluoro-7-[(E)-2-(4-{[(2E)-4-(mesityloxy)-2-buten-1-yl]oxy}phenyl)vinyl]-2-methyl-1H-indol-3-yl}butanoic acid TLC: Rf 0.59 (dichloromethane:methanol:acetic acid=9:1:0.1); $^1$H-NMR (DMSO-$d_6$): δ 1.69-1.83 (m, 2H), 2.16 (s, 9H), 2.18 (t, 2H), 2.24 (s, 3H), 2.73 (t, 2H), 4.28 (d, 2H), 4.63 (d, 2H), 5.04 (s, 2H), 5.97-6.18 (m, 2H), 6.74 (dd, 1H), 6.80 (s, 2H), 6.82 (d, 1H), 6.96 (d, 2H), 7.07 (dd, 1H), 7.44 (d, 1H), 7.48 (d, 2H), 12.11 (s, 1H), 13.16 (s, 1H).

Example 98(22)

4-{1-(1-carboxymethyl)-7-[(E)-2-(4-{[(2E)-4-phenoxy-2-buten-1-yl]oxy}phenyl)vinyl]-1H-indol-3-yl}butanoic acid TLC: Rf 0.39 (chloroform:methanol:water=50:10:1); $^1$H-NMR (DMSO-$d_6$): δ 1.73 (d, 3H), 1.78-1.93 (m, 2H), 2.27 (t, 2H), 2.68 (t, 2H), 4.51-4.71 (m, 4H), 5.50 (q, 1H), 5.98-6.15 (m, 2H), 6.83-7.07 (m, 7H), 7.17-7.33 (m, 4H), 7.46 (dd, 1H), 7.52 (d, 2H), 7.59 (d, 1H).

Example 98(23)

4-{1-(1-carboxymethyl)-7-[(E)-2-(4-{[(2E)-4-(2,3-difluorophenoxy)-2-buten-1-yl]oxy}phenyl)vinyl]-1H-indol-3-yl}butanoic acid TLC: Rf 0.39 (chloroform:methanol:water=50:10:1); $^1$H-NMR (DMSO-$d_6$): δ 1.72 (d, 3H) 1.77-1.92 (m, 2H) 2.27 (t, 2H) 2.68 (t, 2H), 4.63 (d, 2H), 4.72 (d, 2H), 5.49 (q, 1H), 6.00-6.16 (m, 2H), 6.88 (d, 1H), 6.92-7.17 (m, 6H), 7.19 (d, 1H), 7.24 (s, 1H), 7.46 (dd, 1H), 7.51 (d, 2H), 7.58 (d, 1H).

Example 98(24)

4-{1-(1-carboxymethyl)-7-[(E)-2-(4-{[(2E)-4-(mesityloxy)-2-buten-1-yl]oxy}phenyl)vinyl]-1H-indol-3-yl}butanoic acid TLC: Rf 0.39 (chloroform:methanol:water=50:10:1); $^1$H-NMR (DMSO-$d_6$): δ 1.73 (d, 3H), 1.79-1.93 (m, 2H), 2.16 (s, 9H), 2.28 (t, 2H), 2.69 (t, 2H), 4.28 (d, 2H), 4.64 (d, 2H), 5.51 (q, 1H), 5.99-6.17 (m, 2H), 6.80 (s, 2H), 6.89 (d, 1H), 6.98 (d, 2H), 7.03 (dd, 1H), 7.20 (d, 1H), 7.24 (s, 1H), 7.46 (dd, 1H), 7.53 (d, 2H), 7.59 (d, 1H).

Example 98(25)

4-{1-(carboxymethyl)-5-fluoro-7-[(E)-2-(4-{[(2E)-4-(mesityloxy)-2-buten-1-yl]oxy}phenyl)vinyl]-1H-indol-3-yl}butanoic acid TLC: Rf 0.33 (dichloromethane:methanol=9:1); $^1$H-NMR (DMSO-$d_6$): δ 1.76-1.88 (m, 2H), 2.16 (s, 9H), 2.27 (t, 2H), 2.62 (t, 2H), 4.25-4.31 (m, 2H), 4.59-4.66 (m, 2H), 4.99 (brs, 2H), 6.04-6.12 (m, 2H), 6.80 (s, 2H), 6.96 (d, 2H), 7.01 (d, 1H), 7.07-7.14 (m, 2H), 7.18 (dd, 1H), 7.46-7.60 (m, 3H).

Example 98(26)

4-{1-(carboxymethyl)-7-[(E)-2-(4-{[(2E)-4-(4-chloro-2,6-dimethylphenoxy)-2-buten-1-yl]oxy}phenyl)vinyl]-5-fluoro-1H-indol-3-yl}butanoic acid TLC: Rf 0.28 (dichloromethane:methanol=9:1); $^1$H-NMR (DMSO-$d_6$): δ 1.75-1.88 (m, 2H), 2.20 (s, 6H), 2.27 (t, 2H), 2.62 (t, 2H), 4.30-4.36 (m, 2H), 4.59-4.68 (m, 2H), 5.10 (brs, 2H), 6.06-6.13 (m, 2H), 6.97 (d, 2H), 7.03 (d, 1H), 7.08-7.16 (m, 4H), 7.21 (dd, 1H), 7.45-7.57 (m, 3H).

Example 98(27)

4-{1-(carboxymethyl)-5-fluoro-7-[(E)-2-(4-{[(2E)-4-phenoxy-2-buten-1-yl]oxy}phenyl)vinyl]-1H-indol-3-yl}butanoic acid TLC: Rf 0.23 (dichloromethane:methanol=9:1); $^1$H-NMR (DMSO-$d_6$): δ 1.74-1.88 (m, 2H), 2.27 (t, 2H), 2.62 (t, 2H), 4.54-4.67 (m, 4H), 5.11 (s, 2H), 6.03-6.10 (m, 2H), 6.88-7.33 (m, 11H), 7.43-7.57 (m, 3H).

Example 98(28)

4-{1-(carboxymethyl)-7-[(E)-2-(4-{[(2E)-(2-chloro-3,6-difluorophenoxy)-2-buten-1-yl]oxy}phenyl)vinyl]-1H-indol-3-yl}butanoic acid TLC: Rf 0.22 (chloroform:methanol=9:1); $^1$H-NMR (DMSO-$d_6$): δ 1.77-1.92 (m, 2H), 2.28 (t, 2H), 2.67 (t, 2H), 4.57-4.64 (m, 2H), 4.68-4.74 (m, 2H), 5.12 (s, 2H), 5.98-6.14 (m, 2H), 6.91 (d, 1H), 6.92 (d, 2H), 7.01 (dd, 1H), 7.07 (s, 1H), 7.16-7.25 (m, 1H), 7.25 (d, 1H), 7.36 (ddd, 1H), 7.44 (d, 1H), 7.48 (d, 2H), 7.52 (d, 1H).

Example 98(29)

4-{1-(carboxymethyl)-7-[(E)-2-(4-{[(2E)-4-(2-chloro-3,6-difluorophenoxy)-2-buten-1-yl]oxy}phenyl)vinyl]-2-methyl-1H-indol-3-yl}butanoic acid TLC: Rf 0.26 (chloroform:methanol=9:1); $^1$H-NMR (DMSO-$d_6$): δ 1.68-1.80 (m, 2H), 2.21 (t, 2H), 2.26 (s, 3H), 2.67 (t, 2H), 4.59-4.64 (m, 2H), 4.68-4.74 (m, 2H), 5.02 (s, 2H), 5.98-6.13 (m, 2H), 6.88 (d, 1H), 6.92 (d, 2H), 6.98 (dd, 1H), 7.14 (d, 1H), 7.21 (ddd, 1H), 7.36 (ddd, 1H), 7.38 (d, 1H), 7.47 (d, 2H), 7.50 (d, 1H).

Example 98(30)

4-{1-(carboxymethyl)-7-[(E)-2-(4-{[(2E)-4-(2-chloro-3,5-difluorophenoxy)-2-buten-1-yl]oxy}phenyl)vinyl]-2-methyl-1H-indol-3-yl}butanoic acid TLC: Rf 0.24 (chloroform:methanol=9:1); $^1$H-NMR (DMSO-$d_6$): δ 1.68-1.80 (m, 2H), 2.21 (t, 2H), 2.25 (s, 3H), 2.67 (t, 2H), 4.65 (d, 2H), 4.75 (d, 2H), 5.02 (s, 2H), 6.01-6.18 (m, 2H), 6.88 (d, 1H), 6.96 (d, 2H), 6.98 (dd, 1H), 7.01-7.12 (m, 2H), 7.14 (d, 1H), 7.38 (d, 1H), 7.48 (d, 2H), 7.51 (d, 1H).

Example 98(31)

[3-{[1-(carboxymethyl)cyclopropyl]methyl}-7-((E)-2-{4-[4-(2,3-difluorophenoxy)butoxy]phenyl}vinyl)-1H-indol-1-yl]acetic acid TLC: Rf 0.57 (dichloromethane:methanol:acetic acid=90:10:1); $^1$H-NMR (DMSO-$d_6$): δ 0.34-0.52 (m, 4H), 1.79-1.97 (m, 4H), 2.17 (s, 2H), 2.77 (s, 2H), 4.02-4.10 (m, 2H), 4.11-4.21 (m, 2H), 5.13 (s, 2H), 6.85-7.18 (m, 8H), 7.24 (d, 1H), 7.39-7.60 (m, 4H).

Example 98(32)

{3-{[1-(carboxymethyl)cyclopropyl]methyl}-7-[(E)-2-(4-{[(2E)-4-(2,3-difluorophenoxy)-2-buten-1-yl]oxy}phenyl)vinyl]-1H-indol-1-yl}acetic acid TLC: Rf 0.43 (dichloromethane:methanol:acetic acid=90:10:1); $^1$H-NMR (DMSO-$d_6$): δ 0.31-0.52 (m, 4H), 2.17 (s, 2H), 2.78 (s, 2H), 4.60-4.67 (r, 2H), 4.68-4.75 (m, 2H), 5.13 (s, 2H), 6.05-6.12 (m, 2H), 6.85-7.19 (m, 8H), 7.25 (d, 1H), 7.41-7.59 (m, 4H).

Example 98(33)

4-{1-(carboxymethyl)-7-[(E)-2-(4-{[(2E)-4-(2,3-difluorophenoxy)-2-buten-1-yl]oxy}phenyl)vinyl]-4-fluoro-2-methyl-1H-indol-3-yl}butanoic acid TLC: Rf 0.52 (dichloromethane:methanol:acetic acid=90:10:1); $^1$H-NMR (DMSO-$d_6$): δ 1.68-1.85 (m, 2H), 2.18 (t, 2H), 2.24 (s, 3H), 2.73 (t, 2H), 4.63 (d, 2H), 4.72 (d, 2H), 5.04 (s, 2H), 5.99-6.20 (m, 2H), 6.74 (dd, 1H), 6.83 (d, 1H), 6.90-7.20 (m, 4H), 6.97 (d, 2H), 7.45 (d, 1H), 7.47 (d, 2H), 12.05 (s, 2H).

Example 98(34)

4-{1-(carboxymethyl)-5-fluoro-7-[(E)-2-(4-{[(2E)-4-(mesityloxy)-2-buten-1-yl]oxy}phenyl)vinyl]-2-methyl-1H-indol-3-yl}butanoic acid TLC: Rf 0.56 (dichloromethane:methanol:acetic acid=90:10:1); $^1$H-NMR (DMSO-$d_6$): δ 1.63-1.80 (m, 2H),2.16 (s, 9H), 2.21 (t, 2H), 2.26 (s, 3H), 2.63 (t, 2H), 4.28 (d, 2H), 4.64 (d, 2H), 5.02 (s, 2H) 5.99-6.19 (m, 2H), 6.80 (s, 2H), 6.92-7.07 (m, 4H), 7.16 (dd, 1H), 7.49 (d, 1H), 7.52 (d, 2H), 12.28 (s, 2H).g, Example 98(35)

4-[1-(carboxymethyl)-7-((E)-2-{4-[4-(2,3-difluorophenoxy)butoxy]phenyl}vinyl)-5-fluoro-2-methyl-1H-indol-3-yl]butanoic acid TLC: Rf 0.35 (dichloromethane:methanol=9:1); $^1$H-NMR (DMSO-$d_6$): δ 1.65-1.79 (m, 2H), 1.81-1.98 (m, 4H), 2.21 (t, 2H), 2.25 (s, 3H), 2.63 (t, 2H), 4.02-4.11 (m, 2H), 4.12-4.21 (m, 2H), 5.02 (s, 2H), 6.89-7.20 (m, 8H), 7.40-7.55 (m, 3H), 12.04 (s, 1H), 13.13 (s, 1H).

Example 98(36)

4-{1-(carboxymethyl)-7-[(E)-2-(4-{[(2E)-4-(2-chloro-3,6-difluorophenoxy)-2-buten-1-yl]oxy}phenyl)vinyl]-5-fluoro-1H-indol-3-yl}butanoic acid TLC: Rf 0.35 (dichloromethane:methanol=9:1); $^1$H-NMR (DMSO-$d_6$): δ 1.75-1.90 (m, 2H), 2.27 (t 2H), 2.63 (t, 2H), 4.59-4.64 (m, 2H), 4.69-4.74 (m, 2H), 5.15 (s, 2H), 6.03-6.09 (m, 2H), 6.94 (d, 2H), 7.03 (d, 1H), 7.10-7.27 (m, 4H), 7.31-7.41 (m, 1H), 7.48 (d, 1H), 7.50 (d, 2H).

Example 98(37)

4-{1-(1-carboxymethyl)-7-[(E)-2-(4-{[(2E)-4-(mesityloxy)-2-buten-1-yl]oxy}phenyl)vinyl]-2-methyl-1H-indol-3-yl}butanoic acid TLC: Rf 0.43 (chloroform:methanol:water=50:10:1); $^1$H-NMR (DMSO-$d_6$): δ 1.62 (d, 3H), 1.66-1.81 (m, 2H), 2.16 (s, 6H), 2.16 (s, 3H), 2.21 (t, 2H), 2.27 (s, 3H), 2.66 (t, 2H), 4.28 (d, 2H), 4.63 (d, 2H), 5.42-5.66 (m, 1H), 5.97-6.16 (m, 2H), 6.79 (s, 2H), 6.85-7.06 (m, 4H), 7.09-7.23 (m, 1H), 732-7.56 (m, 4H).

Example 98(38)

4-{1-(1-carboxymethyl)-7-[(E)-2-(4-{[(2E)-4-(2,3-difluorophenoxy)-2-buten-1-yl]oxy}phenyl)vinyl]-5-fluoro-2-methyl-1H-indol-3-yl}butanoic acid TLC: Rf 0.28 (chloroform:methanol:water=50:10:1); $^1$H-NMR (DMSO-$d_6$): δ 1.64-1.79 (m, 2H), 2.21 (t, 2H), 2.25 (s, 3H), 2.63 (t, 2H), 4.63 (d, 2H), 4.72 (d, 2H), 4.99 (s, 2H), 5.98-6.16 (m, 2H), 6.89-7.19 (m, 8H), 7.41-7.57 (m, 3H).

Example 98(39)

4-{1-(carboxymethyl)-5-fluoro-2-methyl-7-[(E)-2-(4-{[(2E)-4-phenoxy-2-buten-1-yl]oxy}phenyl)vinyl]-1H-indol-3-yl}butanoic acid TLC: Rf 0.47 (dichloromethane:methanol:acetic acid=90:10:1); $^1$H-NMR (DMSO-$d_6$): δ 1.63-1.82 (m, 2H), 2.16-2.29 (m, 5H), 2.63 (t 2H), 4.54-4.70 (m, 4H), 5.00 (s, 2H), 6.01-6.12 (m, 2H), 6.88-7.05 (m, 7H), 7.15 (dd, 1H), 7.23-7.32 (m, 2H), 7.44-7.55 (m, 3H).

Example 98(40)

2-{[1-(carboxymethyl)-7-((E)-2-{4-[4-(2,3-difluorophenoxy)butoxy]phenyl}vinyl)-1H-indol-3-yl]methyl}benzoic acid TLC: Rf 0.40 (dichloromethane:methanol:acetic acid=90:10:1); $^1$H-NMR (DMSO-$d_6$): δ 1.79-1.96 (m, 4H), 4.06 (t, 2H), 4.15 (t, 2H), 4.39 (s, 2H), 5.09 (s, 2H), 6.83-7.19 (m, 8H), 7.20-7.32 (m, 3H), 733-7.59 (m, 5H), 7.79 (d, 1H).

Example 98(41)

3-{[1-(carboxymethyl)-7-((E)-2-{4-[4-(2,3-difluorophenoxy)butoxy]phenyl}vinyl)-1H-indol-3-yl]methyl}benzoic acid TLC: Rf 0.40 (dichloromethane:methanol:acetic acid=90:10:1); $^1$H-NMR (DMSO-$d_6$): δ 1.76-1.97 (m, 4H), 4.01-4.11 (m, 4H), 4.12-4.19 (m, 2H), 5.13 (s, 2H), 6.85-7.19 (m, 8H), 7.25 (d, 1H), 733-7.44 (m, 2H) 7.45-7.59 (m, 4H), 7.73 (dt, 1H), 7.83 (t, 1H), 12.96 (brs, 2H).

Example 98(42)

4-{1-carboxymethyl)-7-[(E)-2-(4-{[(2E)-4-(3,4-difluorophenoxy)-2-buten-1-yl]oxy}phenyl)vinyl]-2-methyl-1H-indol-3-yl}butanoic acid TLC: Rf 0.42 (dichloromethane:methanol:acetic acid=90:10:1); $^1$H-NMR (DMSO-$d_6$): δ 1.65-1.81 (m, 2H), 2.14-2.29 (m, 5H), 2.66 (t, 2H), 4.51-4.70 (m, 4H), 5.00 (s, 2H), 5.99-6.09 (m, 2H), 6.73-6.81 (m, 1H), 6.87 (d, 1H), 6.91-7.02 (m, 3H), 7.03-7.17 (m, 2H), 7.25-7.41 (m, 2H), 7.43-7.57 (m, 3H), 12.01 (brs, 1H), 13.12 (brs, 1H).

Example 98(43)

4-{1-(carboxymethyl)-7-[(E)-2-(4-{[(2E)-4-(3-fluorophenoxy)-2-buten-1-yl]oxy}phenyl)vinyl]-2-methyl-1H-indol-3-yl}butanoic acid TLC: Rf 0.25 (dichloromethane:methanol=9:1); $^1$H-NMR (DMSO-$d_6$): δ 1.65-1.83 (m, 2H), 2.21 (t, 2H), 2.25 (s, 3H), 2.67 (t, 2H), 4.51-4.74 (m, 4H), 5.02 (s, 2H), 5.96-6.16 (m, 2H), 6.69-7.04 (m, 7H), 7.14 (d, 1H), 7.23-7.35 (m, 1H), 7.38 (d, 1H), 7.48 (d, 2H), 7.51 (d, 1H), 12.03 (s, 1H), 13.15 (s, 1H).

Example 98(44)

4-{1-(carboxymethyl)-5-fluoro-7-[(E)-2-(4-{[(2E)-4-(3-fluorophenoxy)-2-buten-1-yl]oxy}phenyl)vinyl]-2-methyl-1H-indol-3-yl}butanoic acid TLC: Rf 0.21 (dichloromethane:methanol=9:1); $^1$H-NMR (DMSO-$d_6$): δ 1.63-1.80 (m, 2H), 2.21 (t, 2H), 2.25 (s, 3H), 2.63 (t, 2H), 4.50-4.74 (m, 4H), 5.02 (s, 2H), 5.96-6.16 (m, 2H), 6.70-6.88 (m, 3H), 6.92-7.05 (m, 4H), 7.15 (dd, 1H), 7.23-7.35 (m, 1H) 7.49 (d, 1H), 7.50 (d, 2H) 12.03 (s, 1H), 13.16 (s, 1H).

Example 98(45)

4-{1-(carboxymethyl)-4-fluoro-7-[(E)-2-(4-{[(2E)-4-(3-fluorophenoxy)-2-buten-1-yl]oxy}phenyl)vinyl]-2-methyl-1H-indol-3-yl}butanoic acid TLC: Rf 0.29 (dichloromethane:methanol=9:1); $^1$H-NMR (DMSO-$d_6$): δ 1.67-1.85 (m, 2H), 2.19 (t, 2H), 2.24 (s, 3H), 2.73 (t, 2H), 4.52-4.72 (m, 4H), 5.03 (s, 2H), 5.96-6.15 (m, 2H) 6.67-4.89 (m, 5H), 6.95 (d, 2H), 7.06 (dd, 1H), 7.23-7.35 (m, 1H), 7.38-7.53 (m, 3H), 12.00 (s, 1H), 13.19 (s, 1H).

Example 98(46)

4-{1-(carboxymethyl)-4-fluoro-2-methyl-7-[(E)-2-(4-{[(2E)-4-phenoxy-2-buten-1-yl]oxy}phenyl)vinyl]-1H-indol-3-yl}butanoic acid TLC: Rf 0.29 (dichloromethane:methanol=9:1); $^1$H-NMR (DMSO-$d_6$): δ 1.69-1.84 (m, 2H), 2.19 (t, 2H), 2.24 (s, 3H), 2.73 (t, 2H), 4.51-4.70 (m, 4H), 5.03 (s, 2H), 5.98-6.14 (m, 2H), 6.74 (dd, 1H), 6.82 (d, 1H), 6.87-7.01 (m, 5H), 7.06 (dd, 1H), 7.22-7.32 (m, 2H), 7.37-7.52 (m, 3H), 12.01 (s, 1H), 13.18 (s, 1H).

Example 98(47)

4-{1-(carboxymethyl)-4-fluoro-7-[(E)-2-(4-{[(2E)-4-(4-fluorophenoxy)-2-buten-1-yl]oxy}phenyl)vinyl]-2-methyl-1H-indol-3-yl}butanoic acid TLC: Rf 0.23 (chloroform:methanol:water=50:10:1); $^1$H-NMR (DMSO-$d_6$): δ 1.68-1.84 (m, 2H), 2.19 (t, 2H), 2.24 (s, 3H), 2.73 (t, 2H), 4.54-4.59 (m, 2H), 4.60-4.66 (m, 2H), 5.03 (s, 2H), 5.98-6.12 (m, 2H), 6.74 (dd, 1H), 6.83 (d, 1H), 6.90-7.01 (m, 4H), 7.03-7.17 (m, 3H), 7.38-7.53 (m, 3H).

Example 98(48)

4-{1-(carboxymethyl)-5-fluoro-7-[(E)-2-(4-{[(2E)-4-(4-fluorophenoxy)-2-buten-1-yl]oxy}phenyl)vinyl]-2-methyl-1H-indol-3-yl}butanoic acid TLC: Rf 0.23 (chloroform:methanol:water=50:10:1); $^1$H-NMR (DMSO-$d_6$): δ 1.65-1.79 (m, 2H), 2.21 (t, 2H), 2.25 (s, 3H), 2.63 (t, 2H), 4.54-4.60 (m, 2H), 4.60-4.67 (m, 2H), 5.01 (s, 2H), 5.98-6.13 (m, 2H), 6.91-7.05 (m, 6H), 7.06-7.19 (m, 3H), 7.44-7.55 (m, 3H).

Example 98(49)

4-[1-(carboxymethy)-5-fluoro-7-((E)-2-{4-[4-(mesityloxy)butoxy]phenyl}vinyl)-2-methyl-1H-indol-3-yl]butanoic acid TLC: Rf 0.33 (dichloromethane:methanol=9:1); $^1$H-NMR (DMSO-$d_6$): δ 1.64-1.78 (m, 2H), 1.80-2.01 (m, 4H), 2.17 (s, 9H), 2.21 (t, 2H), 2.25 (s, 3H), 2.63 (t, 2H), 3.74 (t, 2H), 4.07 (t, 2H), 5.02 (s, 2H), 6.80 (s, 2H), 6.92-7.05 (m, 4H), 7.15 (dd, 1H), 7.42-7.55 (m, 3H).

Example 98(50)

4-{1-(carboxymethyl)-7-[(E)-2-(4-{[(2E)-4-(2-chlorophenoxy)-2-buten-1-yl]oxy}phenyl)vinyl]-2-methyl-1H-indol-3-yl}butanoic acid TLC: Rf 0.52 (dichloromethane:methanol:acetic acid=90:10:1); $^1$H-NMR (DMSO-$d_6$): δ 1.64-1.84 (m, 2H), 2.21 (t, 2H), 2.25 (s, 3H), 2.67 (t, 2H), 4.60-4.67 (m, 2H), 4.67-4.75 (m, 2H), 5.02 (s, 2H), 6.02-6.18 (m, 2H), 6.89 (d, 1H), 6.92-7.04 (m, 2H), 6.97 (d, 2H), 7.15 (d, 2H), 7.23-7.35 (m, 1H), 7.35-7.46 (m, 2H), 7.50 (d, 2H), 7.52 (d, 1H), 12.26 (s, 2H).

Example 98(51)

4-{1-(carboxymethyl)-7-[(E)-2-(4-{[(2E)-4-(2-chlorophenoxy)-2-buten-1-yl]oxy}phenyl)vinyl]-4-fluoro-2-methyl-1H-indol-3-yl}butanoic acid TLC: Rf 0.57 (dichloromethane:methanol:acetic acid=90:10:1); $^1$H-NMR (DMSO-$d_6$): δ 1.68-1.85 (m, 2H), 2.19 (t, 2H), 2.24 (s, 3H), 2.73 (t, 2H), 4.60-4.67 (m, 2H), 4.67-4.77 (m, 2H), 5.04 (s, 2H), 5.97-6.20 (m, 2H), 6.75 (dd, 1H), 6.83 (d, 1H), 6.94 (d, 1H), 6.96 (d, 2H), 7.07 (dd, 1H), 7.15 (d, 1H), 7.24-7.35 (m, 1H), 7.39-7.45 (m, 1H), 7.43 (d, 1H), 7.48 (d, 2H), 12.16 (s, 1H), 13.07 (s, 1H).

Example 98(52)

4-{1-(carboxymethyl)-7-[(E)-2-(4-{[(2E)-4-(2-fluorophenoxy)-2-buten-1-yl]oxy}phenyl)vinyl]-1H-indol-3-yl}butanoic acid TLC: Rf 0.24 (dichloromethane:methanol=9:1); $^1$H-NMR (DMSO-$d_6$): δ 1.77-1.92 (m, 2H), 2.28 (t, 2H), 2.66 (t, 2H), 4.60-4.65 (m, 2H), 4.65-4.70 (m, 2H), 5.12 (s, 2H), 6.05-6.12 (m, 2H), 6.87-7.30 (m, 10H), 7.45 (d, 1H), 7.47-7.58 (m, 3H).

Example 98(53)

4-{1-(carboxymethy)-4-fluoro-7-[(E)-2-(4-{[(2E)-4-(2-fluorophenoxy)-2-buten-1-yl]oxy}phenyl)vinyl]-2-methyl-1H-indol-3-yl}butanoic acid TLC: Rf 0.32 (dichloromethane:methanol=9:1); $^1$H-NMR (DMSO-$d_6$): δ 1.68-1.84 (m, 2H), 2.19 (t, 2H), 2.24 (s, 3H), 2.73 (t, 2H), 4.59-4.64 (m, 2H), 4.65-4.70 (m, 2H), 5.02 (s, 2H), 6.04-6.11 (m, 2H), 6.73 (dd, 1H), 6.82 (d, 1H), 6.88-6.99 (m, 3H), 7.02-7.24 (m, 4H), 7.38-7.51 (m, 3H).

Example 98(54)

4-[1-(carboxymethyl)-7-((E)-2-{4-[4-(mesityloxy)butoxy]phenyl}vinyl)-2-methyl-1H-indol-3-yl]butanoic acid TLC: Rf 0.22 (chloroform:methanol=9:1); $^1$H-NMR (DMSO-$d_6$): δ 1.68-1.80 (m, 2H), 1.80-1.99 (m, 4H), 2.17 (s, 9H), 2.21 (t, 2H), 2.25 (s, 3H), 2.67 (t, 2H), 3.74 (m, 2H), 4.07 (t, 2H), 5.02 (s, 2H), 6.80 (s, 2H), 6.88 (d, 1H), 6.96 (d, 2H), 6.99 (dd, 1H), 7.15 (d, 1H), 7.39 (d, 1H), 7.49 (d, 2H), 7.51 (d, 1H).

Example 98(55)

4-[1-(carboxymethyl)-7-((E)-2-{4-[4-(3-fluorophenoxy)butoxy]phenyl}vinyl)-2-methyl-1H-indol-3-yl]butanoic acid TLC: Rf 0.28 (dichloromethane:methanol=9:1); $^1$H-NMR (DMSO-$d_6$): δ 1.66-1.82 (m, 2H), 1.82-1.92 (m, 4H), 2.21 (t, 2H), 2.25 (s, 3H), 2.67 (m, 2H), 3.97-4.12 (m, 4H), 5.02 (s, 2H), 6.69-6.85 (m, 3H), 6.88 (d, 1H), 6.92-7.04 (m, 3H), 7.15 (d, 1H), 7.23-7.35 (m, 1H), 7.39 (d, 1H), 7.43-7.58 (m, 3H), 12.04 (s, 1H), 13.11 (s, 1H).

Example 98(56)

4-(1-(carboxymethyl)-4-fluoro-2-methyl-7-{(E)-2-[4-(4-phenoxybutoxy)phenyl]vinyl}-1H-indol-3-yl)butanoic acid TLC: Rf 0.28 (dichloromethane:methanol=9:1); $^1$H-NMR (DMSO-$d_6$): δ 1.68-1.83 (m, 2H), 1.82-1.93 (m, 4H), 2.19 (t, 2H), 2.24 (s, 3H), 2.73 (t, 2H), 3.94-4.14 (m, 4H), 5.04 (s, 2H), 6.74 (dd, 1H), 6.82 (d, 1H), 6.87-7.00 (m, 5H), 7.07 (dd, 1H), 7.21-7.33 (m, 2H), 7.37-7.54 (m, 3H), 12.00 (s, 1H), 13.18 (s, 1H).

Example 98(57)

4-{1-(carboxymethyl)-7[(E)-2-(4-{[(2E)-4-(2,4-difluorophenoxy)-2-buten-1-yl]oxy}phenyl)vinyl]-2-methyl-1H-indol-3-yl}butanoic acid TLC: Rf 0.20 (chloroform:methanol=9:1); $^1$H-NMR (DMSO-$d_6$): δ 1.68-1.80 (m, 2H), 2.21 (t, 2H), 2.25 (t, 3H), 2.67 (t, 2H), 4.59-4.69 (m, 4H), 5.02 (s, 2H), 5.98-6.13 (m, 2H), 6.89 (d, 1H), 6.96 (d, 2H), 6.99 (d, 1H), 6.99-7.04 (m, 1H), 7.15 (d, 1H), 7.17-7.23 (m, 1H), 7.23-7.33 (m, 1H), 7.39 (d, 1H), 7.49 (d, 2H), 7.52 (d, 1H).

Example 98(58)

4-{1-(carboxymethyl)-7-[(E)-2-(4-{[(2E)-4-(2-chloro-3,5-difluorophenoxy)-2-buten-1-yl]oxy}phenyl)vinyl]-5-fluoro-2-methyl-1H-indol-3-yl}butanoic acid TLC: Rf 0.36 (dichloromethane:methanol=9:1); $^1$H-NMR (DMSO-$d_6$): δ 1.64-1.78 (m, 2H), 2.21 (t, 2H), 2.25 (s, 3H), 2.63 (t, 2H), 4.65 (d, 2H), 4.76 (d, 2H), 5.01 (s, 2H), 6.01-6.20 (m, 2H), 6.91-7.21 (m, 7H), 7.42-7.57 (m, 3H), 12.06 (s, 1H), 13.22 (s, 1H).

Example 98(59)

4-{1-(carboxymethyl)-7-[(E)-2-(4-{[(2E)-4-(2-chloro-3,5-difluorophenoxy)-2-buten-1-yl]oxy}phenyl)vinyl]-4-fluoro-2-methyl-1H-indol-3-yl}butanoic acid TLC: Rf 0.36 (dichloromethane:methanol=9:1); $^1$H-NMR (DMSO-$d_6$): δ 1.67-1.84 (m, 2H), 2.19 (t, 2H), 2.24 (s, 3H), 2.73 (t, 2H), 4.65 (d, 2H), 4.75 (d, 2H), 5.04 (s, 2H), 6.00-6.20 (m, 2H), 6.75 (dd, 1H), 6.83 (d, 1H), 6.97 (d, 2H), 7.01-7.16 (m, 3H), 7.36-7.56 (m, 3H), 12.02 (s, 1H), 13.21 (s, 1H).

Example 98(60)

4-[1-(carboxymethyl)-7-((E)-2-{4-[4-(2-chloro-3,5-difluorophenoxy)butoxy]phenyl}vinyl)-5-fluoro-2-methyl-1H-indol-3-yl]butanoic acid TLC: Rf 0.48 (dichloromethane:methanol:acetic acid=90:10:1); $^1$H-NMR (DMSO-$d_6$): δ 1.59-1.80 (m, 2H), 1.82-2.00 (m, 4H), 2.14-2.30 (m, 5H), 2.63 (t, 2H), 4.00-4.23 (m, 4H), 4.89-5.10 (m, 2H), 6.89-7.11 (m, 6H), 7.14 (dd, 1H), 7.38-7.55 (m, 3H).

Example 98(61)

{3-{[1-(carboxymethyl)cyclopropyl]methyl}-7-[(E)-2-(4-{[(2E)-4-(mesityloxy)-2-buten-1-yl]oxy}phenyl)vinyl]-1H-indol-1-yl}acetic acid TLC: Rf 0.54 (dichloromethane:methanol:acetic acid=90:10:1); $^1$H-NMR (DMSO-$d_6$): δ 0.30-0.51 (m, 4H), 2.16 (s, 9H), 2.77 (s, 2H), 4.27 (d, 2H), 4.63 (d, 2H), 5.01-5.25 (m, 2H), 5.14 (s, 2M 5.98-6.16 (m, 2H), 6.79 (s, 2H), 6.84-7.06 (m, 4H), 7.10 (s, 1H), 7.24 (d, 1H), 7.35-7.63 (m, 4H), 12.05 (brs, 1H), 13.06 (brs, 1H).

Example 98(62)

2-({1-(carboxymethyl)-7-[(E)-2-(4-{[(2E)-4-(mesityloxy)-2-buten-1-yl]oxy}phenyl)vinyl]-1H-indol-3-yl}methyl)benzoic acid TLC: Rf 0.50 (dichloromethane:methanol:acetic acid=90:10:1); $^1$H-NMR (DMSO-$d_6$): δ 2.16 (s, 9H), 4.28 (d, 2H), 4.39 (s, 2H), 4.63 (d, 2H), 5.11 (s, 2H), 5.96-6.18 (m, 2H), 6.80 (s, 2H), 6.85-7.06 (m, 5H), 7.18-7.33 (m, 3H), 7.33-7.60 (m, 5H), 7.78 (dd, 1H), 12.96 (brs, 2H).

Example 98(63)

4-{3-carboxymethyl)-4-[(E)-2-(4-{[(2E)-4-(2,4-dichloro-6-methylphenoxy)-2-buten-1-yl]oxy}phenyl)vinyl]-1H-indol-1-yl}butanoic acid TLC: Rf 0.50 (dichloromethane:methanol:acetic acid=90:10:1); $^1$H-NMR (DMSO-$d_6$): δ 1.83-2.02 (m, 2H), 2.12-2.33 (m, 5H), 3.84 (s, 2H), 4.14 (t 2H), 4.47 (d, 2H), 4.63 (d, 2H), 5.99-6.18 (m, 2H), 6.95 (d, 2H), 7.00-7.19 (m, 2H), 7.22-7.41 (m, 4H), 7.45 (d, 1H), 7.54 (d, 2H), 7.65 (d, 1H), 12.28 (brs, 2H).

Example 98(64)

4-{3-(carboxymethyl)-4-[(E)-2-(4-{[(2E)-4-phenoxy-2-buten-1-yl]oxy}phenyl)vinyl]-1H-indol-1-yl}butanoic acid TLC: Rf 0.50 (dichloromethane:methanol:acetic acid=90:10:1); $^1$H-NMR (DMSO-$d_6$): δ 1.82-2.02 (m, 2H), 2.16 (t, 2H), 3.78 (s, 2H), 4.12 (t, 2H), 4.49-4.69 (m, 4H), 5.97-6.16 (m, 2H), 6.86-6.99 (m, 5H), 7.00-7.17 (m, 2H), 7.17-7.39 (m, 5H), 7.55 (d, 2H), 7.72 (d, 1H).

Example 98(65)

4-{1-(carboxymethyl)-7-[(E)-2-(4-{[(2E)-4-(4-fluorophenoxy)-2-buten-1-yl]oxy}phenyl)vinyl]-2-methyl-1H-indol-3-yl}butanoic acid TLC: Rf 0.23 (chloroform:methanol:water=50:10:1); $^1$H-NMR (DMSO-$d_6$): δ 1.66-1.81 (m, 2H), 2.20 (t, 2H), 2.24 (s, 3H), 2.65 (t, 2H), 4.50-4.65 (m, 4H), 4.87-5.04 (m, 2H), 5.95-6.12 (m, 2H), 6.87 (d, 1H), 6.91-7.01 (m, 5H), 7.05-7.17 (m, 3H), 7.37 (dd, 1H), 7.49 (d, 2H), 7.54 (d, 1H).

Example 98(66)

4-{1-(carboxymethyl)-7-[(E)-2-(4-{[(2E)-4-(4-chloro-2-fluorophenoxy)-2-buten-1-yl]oxy}phenyl)vinyl]-1H-indol-3-yl}butanoic acid TLC: Rf 0.29 (dichloromethane:methanol=9:1); $^1$H-NMR (DMSO-$d_6$): δ 1.78-1.92 (m, 2H), 2.28 (t 2H), 2.66 (t, 2H), 4.58-4.64 (m, 2H), 4.66-4.71 (m, 2H), 5.10 (s, 2H), 6.03-6.10 (m, 2H), 6.86-6.97 (m, 3H), 7.01 (t, 1H), 7.07 (s, 1H), 7.16-7.29 (m, 3H), 7.38-7.58 (m, 5H).

Example 98(67)

4-(1-(carboxymethyl)-5-fluoro-2-methyl-7-{(E)-2-[4-(4-phenoxybutoxy)phenyl]vinyl}-1H-indol-3-yl)butanoic acid TLC: Rf 0.53 (dichloromethane:methanol:acetic acid=90:10:1); $^1$H-NMR (DMSO-$d_6$): δ 1.64-1.78 (m, 2H), 1.81-1.95 (m, 4H), 2.21 (t 2H), 2.25 (s, 3H), 2.63 (t 2H), 3.97-4.14 (m, 4H), 5.02 (s, 2H), 6.84-7.07 (m, 7H), 7.16 (dd, 1H), 7.23-7.34 (m, 2H), 7.48 (d, 1H), 7.50 (d, 2H), 12.22 (s, 1H), 12.86 (s, 1H).

Example 98(68)

4-[1-(carboxymethyl)-4-fluoro-7-((E)-2-{4-[4-(mesityloxy)butoxy]phenyl}vinyl)-2-methyl-1H-indol-3-yl]butanoic acid TLC: Rf 0.53 (dichloromethane:methanol:acetic acid=90:10:1); $^1$H-NMR (DMSO-$d_6$): δ 1.69-1.82 (m, 2H), 1.82-2.00 (m, 4H), 2.19 (t 2H), 2.17 (s, 9H), 2.23 (s, 3H), 2.73 (t 2H), 3.73 (t, 2H), 4.05 (t, 2H), 5.00 (s, 2H), 6.73 (dd, 1H), 6.80 (s, 2H), 6.82 (d, 1H), 6.94 (d, 2H), 7.06 (dd, 1H), 7.45 (d, 1H), 7.48 (d, 2H), 12.17 (s, 2H).

Example 98(69)

4-{3-(carboxymethyl)-4-[(E)-2-(4-{[(2E)-4-(2-chloro-3,5-difluorophenoxy)-2-buten-1-yl]oxy}phenyl)vinyl]-1H-indol-1-yl}butanoic acid TLC: Rf 0.50 (dichloromethane:methanol:acetic acid=90:10:1); $^1$H-NMR (DMSO-$d_6$): δ 1.86-2.01 (m, 2H), 2.19 (t, 2H), 3.83 (s, 2H), 4.14 (t, 2H), 4.65 (d, 2H), 4.75 (d, 2H), 6.00-6.20 (m, 2H), 6.96 (d, 2H), 7.00-7.17 (m, 4H), 7.26 (s, 1H), 7.29-7.41 (m, 2H), 7.53 (d, 2H), 7.64 (d, 1H), 12.24 (brs, 2H).

Example 98(70)

4-{1-(carboxymethy)-7-[(E)-2-(4-{[(2E)-4-(2-chlorophenoxy)-2-buten-1-yl]oxy}phenyl)vinyl]-1H-indol-3-yl}butanoic acid TLC: Rf 0.38 (dichloromethane:methanol=9:1); $^1$H-NMR (DMSO-$d_6$): δ 1.77-1.93 (m, 2H), 2.28 (t, 2H), 2.66 (t, 2H), 4.64 (d, 2H), 4.69 (d, 2H), 5.12 (s, 2H), 6.01-6.17 (m, 2H), 6.86-7.05 (m, 5H), 7.07 (s, 1H), 7.14 (dd, 1H), 7.23-7.33 (m, 2H), 7.38-7.60 (m, 5H), 12.08 (s, 1H), 13.05 (s, 1H).

Example 98(71)

4-[1-(carboxymethy)-7-((E)-2-{4-[4-(2-chloro-3,5-difluorophenoxy)butoxy]phenyl}vinyl)-4-fluoro-2-methyl-1H-indol-3-yl]butanoic acid TLC: Rf 0.36 (dichloromethane:methanol=9:1); $^1$H-NMR (DMSO-$d_6$): δ 1.68-1.83 (m, 2H), 1.81-1.99 (m, 4H), 2.18 (t, 2H), 2.23 (s, 3H), 2.72 (t, 2H), 3.99-4.10 (m, 2H), 4.11-4.24 (m, 2H), 4.95 (s, 2H), 6.72 (dd, 1H), 6.80 (d, 1H), 6.91 (d, 2H), 6.99-7.12 (m, 3H), 7.39-7.55 (m, 3H), 12.02 (s, 2H).

Example 98(72)

4-[1-(carboxymethy)-7-((E)-2-{4-[4-(4-fluorophenoxy)butoxy]phenyl}vinyl)-2-methyl-1H-indol-3-yl]butanoic acid TLC: Rf 0.31 (chloroform:methanol:water=50:10:1); $^1$H-NMR (DMSO-$d_6$): δ 1.67-1.80 (m, 2H), 1.79-1.92 (m, 4H), 2.20 (t, 2H), 2.25 (s, 3H), 2.66 (t, 2H), 3.94-4.11 (m, 4H), 5.01 (s, 2H), 6.87 (d, 1H), 6.91-7.02 (m, 5H), 7.05-7.17 (m, 3H), 7.38 (d, 1H), 7.48 (d, 2H), 7.51 (d, 1H).

Example 98(73)

4-[1-(carboxymethy)-4-fluoro-7-((E)-2-{4-[4-(4-fluorophenoxy)butoxy]phenyl}vinyl)-2-methyl-1H-indol-3-yl]butanoic acid TLC: Rf 0.31 (chloroform:methanol:water=50:10:1); $^1$H-NMR (DMSO-$d_6$): δ 1.67-1.93 (m, 6H), 2.18 (t, 2H), 2.23 (s, 3H), 2.72 (t, 2H), 3.93-4.10 (m, 4H), 5.02 (s, 2H), 6.74 (dd, 1H), 6.78-6.86 (m, 1H), 6.88-7.00 (m, 4H), 7.02-7.16 (m, 3H), 7.37-7.52 (m, 3H).

Example 98(74)

4-[1-(carboxymethy)-5-fluoro-7-((E)-2-{4-[4-(4-fluorophenoxy)butoxy]phenyl}vinyl)-2-methyl-1H-indol-3-yl]butanoic acid TLC: Rf 0.31 (chloroform:methanol:water=50:10:1); $^1$H-NMR (DMSO-$d_6$): δ 1.63-1.78 (m, 2H), 1.78-1.93 (m, 4H), 2.21 (t, 2H), 2.24 (s, 3H), 2.62 (t, 2H), 3.94-4.09 (m, 4H), 5.00 (s, 2H), 6.88-7.04 (m, 6H), 7.04-7.19 (m, 3H), 7.42-7.54 (m, 3H).

Example 98(75)

4-{1-(carboxymethy)-7-[(E)-2-(4-{[(2E)-4-(2,4-difluorophenoxy)-2-buten-1-yl]oxy}phenyl)vinyl]-1H-indol-3-yl}butanoic acid TLC: Rf 0.23 (chloroform:methanol=9:1); $^1$H-NMR (DMSO-$d_6$): δ 1.78-1.91 (m, 2H), 2.28 (t, 2H), 2.66 (t, 2H), 4.59-4.69 (m, 4H), 5.14 (s, 2H), 5.99-6.14 (m, 2H), 6.92 (d, 1H), 6.95 (d, 2H), 6.98-7.05 (m, 2H), 7.08 (s, 1H), 7.16-7.33 (m, 3H), 7.45 (d, 1H), 7.50 (d, 2H), 7.53 (d, 1H).

Example 98(76)

4-{1-(carboxymethy)-7-[(E)-2-(4-{[(2E)-4-(2,4-difluorophenoxy)-2-buten-1-yl]oxy}phenyl)vinyl]-4-fluoro-2-methyl-1H-indol-3-yl}butanoic acid TLC: Rf 0.20 (chloroform:methanol=9:1); $^1$H-NMR (DMSO-$d_6$): δ 1.69-1.82 (m, 2H), 2.19 (t, 2H), 2.24 (s, 3H), 2.73 (t, 2H), 4.57-4.69 (m, 4H), 5.02 (s, 2H), 5.98-6.14 (m, 2H), 6.74 (dd, 1H), 6.82 (d, 1H), 6.95 (d, 2H), 6.97-7.10 (m, 2H), 7.14-7.33 (m, 2H), 7.46 (d, 1H), 7.48 (d, 2H).

Example 98(77)

4-{1-(carboxymethyl)-7-[(E)-2-(4-{[(2E)-4-(4-chloro-2,6-dimethylphenoxy)-2-buten-1-yl]oxy}phenyl)vinyl]-1H-indol-3-yl}butanoic acid TLC: Rf 0.53 (dichloromethane:methanol:acetic acid=90:10:1); $^1$H-NMR (DMSO-$d_6$): δ 1.77-1.92 (m, 2H), 2.20 (s, 6H), 2.28 (t, 2H), 2.66 (t, 2H), 4.32 (d, 2H), 4.63 (d, 2H), 5.13 (s, 2H), 5.97-6.19 (m, 2H), 6.92 (d, 1H), 6.96 (d, 2H), 7.01 (t, 1H), 7.07 (s, 1H), 7.09 (s, 2H), 7.26 (d, 1H), 7.44 (d, 1H), 7.49 (d, 2H), 7.52 (d, 1H), 12.20 (s, 1H), 12.84 (s, 1H).

Example 98(78)

4-{1-(carboxymethyl)-7-[(E)-2-(4-{[(2E)-4-(4-chloro-2,6-dimethylphenoxy)-2-buten-1-yl]oxy}phenyl)vinyl]-4-fluoro-2-methyl-1H-indol-3-yl}butanoic acid TLC: Rf 0.52 (dichloromethane:methanol:acetic acid=90:10:1); $^1$H-NMR (DMSO-$d_6$): δ 1.67-1.84 (m, 2H), 2.20 (t, 2H), 2.20 (s, 6H), 2.24 (s, 3H), 2.73 (t, 2H), 4.32 (d, 2H), 4.63 (d, 2H), 5.03 (s, 2H), 5.98-6.20 (m, 2H), 6.74 (dd, 1H), 6.82 (d, 1H), 6.96 (d, 2H), 7.06 (dd, 1H), 7.09 (s, 2H), 7.44 (d, 1H), 7.48 (d, 2H), 12.15 (s, 1H), 12.99 (s, 1H).

Example 98(79)

4-{1-(carboxymethyl)-7-[(E)-2-(4-{[(2E)-4-(4-chloro-2-fluorophenoxy)-2-buten-1-yl]oxy}phenyl)vinyl]-2-methyl-1H-indol-3-yl}butanoic acid TLC: Rf 0.41 (dichloromethane:methanol=9:1); $^1$H-NMR (DMSO-$d_6$): δ 1.67-1.82 (m, 2H), 2.21 (t, 2H), 2.25 (s, 3H), 2.67 (t, 2H), 4.60-4.65 (m, 2H), 4.67-4.72 (m, 2H), 5.01 (s, 2H), 6.03-6.11 (m, 2H), 6.88 (d, 1H), 6.93-7.02 (m, 3H), 7.15 (d, 1H), 7.18-7.24 (m, 2H), 7.35-7.58 (m, 5H).

Example 98(80)

4-{1-(carboxymethyl)-7-[(E)-2-(4-{[(2E)-4-(4-chloro-2-fluorophenoxy)-2-buten-1-yl]oxy}phenyl)vinyl]-4-fluoro-2-methyl-1H-indol-3-yl}butanoic acid TLC: Rf 0.27 (dichloromethane:methanol=9:1); $^1$H-NMR (DMSO-$d_6$): δ 1.69-1.84 (m, 2H), 2.19 (t, 2H), 2.24 (s, 3H), 2.73 (t, 2H), 4.59-4.65 (m, 2H), 4.66-4.72 (m, 2H), 5.02 (s, 2H), 6.04-6.11 (m, 2H), 6.74 (dd, 1H), 6.82 (d, 1H), 6.95 (d, 2H), 7.07 (dd, 1H), 7.15-7.24 (m, 2H), 7.37-7.52 (m, 4H).

Example 98(81)

4-{1-(carboxymethyl)-7-[(E)-2-(4-{[(2E)-4-(3-chlorophenoxy)-2-buten-1-yl]oxy}phenyl)vinyl]-2-methyl-1H-indol-3-yl}butanoic acid TLC: Rf 0.38 (dichloromethane:methanol=9:1); $^1$H-NMR (DMSO-$d_6$): δ 1.67-1.82 (m, 2H), 2.21 (t, 2H), 2.25 (s, 3H), 2.67 (t 2H), 4.55-4.70 (m, 4H), 5.02 (s, 2H), 5.97-6.15 (m, 2H), 6.81-7.07 (m, 7H), 7.15 (d, 1H), 7.30 (t, 1H), 7.39 (d, 1H), 7.49 (d, 2H), 7.52 (d, 1H).

Example 98(82)

4-{1-(carboxymethyl)-2-methyl-7-[(E)-2-(4-{[(2E)-4-(3-methylphenoxy)-2-buten-1-yl]oxy}phenyl)vinyl]-1H-indol-3-yl}butanoic acid TLC: Rf 0.38 (dichloromethane:methanol=9:1); $^1$H-NMR (DMSO-$D_6$) δ 1.67-1.81 (m, 2H), 2.21 (t, 2H), 2.26 (s, 6H), 2.67 (t, 2H), 4.53-4.59 (m, 2H), 4.59-4.66 (m, 2H), 5.01 (s, 2H), 5.97-6.14 (m, 2H), 6.70-6.79 (m, 3H), 6.88 (d, 1H), 6.97 (d, 2H), 6.98 (t, 1H), 7.15 (d, 1H), 7.15 (t, ), 7.39 (d, ), 7.50 (d, 2H), 7.53 (d, 1H).

Example 98(83)

4-{1-(carboxymethyl)-7-[(E)-2-(4-{[(2E)-4-(3-chlorophenoxy)-2-buten-1-yl]oxy}phenyl)vinyl]-4-fluoro-2-methyl-1H-indol-3-yl}butanoic acid TLC: Rf 0.22 (dichloromethane:methanol=9:1); $^1$H-NMR (DMSO-$d_6$): δ 1.68-1.84 (m, 2H), 2.19 (t, 2H), 2.24 (s, 3H), 2.73 (t 2H), 4.53-4.72 (m, 4H), 5.03 (s, 2H), 5.97-6.14 (m, 2H), 6.74 (dd, 1H), 6.82 (d, 1H), 6.88-7.11 (m, 6H), 7.29 (t, 1H), 7.37-7.53 (m, 3H).

Example 98(84)

4-{1-(carboxymethyl)-4-fluoro-2-methyl-7-[(E)-2-(4-{[(2E)-4-(3-methylphenoxy)-2-buten-1-yl]oxy}phenyl)vinyl]-1H-indol-3-yl}butanoic acid TLC: Rf 0.22 (dichloromethane:methanol=9:1); $^1$H-NMR (DMSO-$d_6$): δ 1.68-1.84 (m, 2H), 2.19 (t, 2H), 2.24 (s, 3H), 2.26 (s, 3H), 2.73 (t, 2H), 4.53-4.60 (m, 2H), 4.59-4.67 (m, 2H), 5.03 (s, 2H), 5.97-6.14 (m, 2H), 6.68-6.78 (m, 4H), 6.82 (d, 1H), 6.95 (d, 2H), 7.06 (dd, 1H), 7.14 (t, 1H), 735-7.55 (m, 3H).

Example 98(85)

4-[1-(carboxymethyl)-7-((E)-2-{4-[4-chloro-2,6-dimethylphenoxy)butoxy]phenyl}vinyl)-4-fluoro-2-methyl-1H-indol-3-yl]butanoic acid TLC: Rf 0.51 (dichloromethane:methanol:acetic acid=90:10:1); $^1$H-NMR (DMSO-$d_6$): δ 1.68-1.84 (m, 2H), 1.84-2.02 (m, 4H), 2.19 (t, 2H), 2.24 (s, 3H), 2.73 (t, 2H), 3.98-4.22 (m, 4H), 5.03 (s, 2H), 6.74 (dd, 1H) 6.82 (d, 1H), 6.89-7.00 (m, 3H), 7.07 (dd, 1H), 7.15 (dd, 1H), 7.23-7.34 (m, 1H), 7.41 (dd, 1H), 7.43 (d, 1H), 7.47 (d, 2H), 12.09 (s, 1H), 13.07 (s, 1H).

Example 98(86)

4-[1-(carboxymethyl)-7-((E)-2-{4-[4-(4-chloro-2,6-dimethylphenoxy)butoxy]phenyl}vinyl)-4-fluoro-2-methyl-1H-indol-3-yl]butanoic acid TLC: Rf 0.52 (dichlomethane:methanol:acetic acid=90:10:1); $^1$H-NMR (DMSO-$d_6$): δ 1.69-1.82 (m, 2H), 1.82-2.01 (m, 4H), 2.19 (t, 2H), 2.21 (s, 6H), 2.24 (s, 3H), 2.73 (t, 2H), 3.78 (t, 2H), 4.05 (t, 2H), 5.00 (s, 2H), 6.73 (dd, 1H), 6.82 (d, 1H), 6.94 (d, 2H), 7.06 (dd, 1H), 7.09 (s, 2H), 7.45 (d, 1H), 7.48 (d, 2H), 12.17 (s, 2H).

Example 98(87)

4-{1-(carboxymethyl)-7-[(E)-2-(4-{[(2E)-4-(4-chlorophenoxy)-2-buten-1-yl]oxy}phenyl)vinyl]-2-methyl-1H-indol-3-yl}butanoic acid TLC: Rf 0.18 (chloroform:methanol=9:1); $^1$H-NMR (DMSO-$d_6$): δ 1.67-1.80 (m, 2H), 2.21 (t, 2H), 2.25 (s, 3H), 2.67 (t 2H), 4.56-4.67 (m, 4H), 5.02 (s, 2H), 6.03-6.08 (m, 2H), 6.89 (d, 1H), 6.96 (d, 2H), 6.98 (d, 2H), 6.97-7.02 (m, 1H), 7.15 (d, 1H), 7.32 (d, 2H), 7.39 (d, 1H), 7.49 (d, 2H), 7.51 (d, 1H).

Example 98(88)

4-{1-(carboxymethyl)-7-[(E)-4-{[(2E)-4-(4-chloro-2-methylphenoxy)-2-buten-1-yl]oxy}phenyl)vinyl]-4-fluoro-2-methyl-1H-indol-3-yl}butanoic acid TLC: Rf 0.57 (dichloromethane:methanol:acetic acid=90:10:1); $^1$H-NMR (DMSO-$d_6$): δ 1.65-1.86 (m, 2H), 2.15 (s, 3H), 2.18 (t, 2H), 2.24 (s, 3H), 2.73 (t, 2H), 4.47-4.74 (m, 4H), 5.03 (s, 2H), 5.97-6.15 (m, 2H), 6.74 (dd, 1H), 6.83 (d, 1H), 6.94 (d, 1H), 6.96 (d, 2H), 7.07 (dd, 1H), 7.12-7.26 (m, 2H), 7.44 (4, 1H), 7.48 (d, 2H), 12.21 (s, 2H).

Example 98(89)

4-{1-(carboxymethyl)-7-[(E)-2-(4-{[(2E)-4-(2,4-dimethylphenoxy)-2-buten-1-yl]oxy}phenyl)vinyl]-4-fluoro-2-methyl-1H-indol-3-yl}butanoic acid TLC: Rf 0.53 (dichloromethane:methanol:acetic acid=90:10:1); $^1$H-NMR (DMSO-$d_6$): δ 1.68-1.84 (m, 2H), 2.12 (s, 3H), 2.17 (t, 2H), 2.18 (s, 3H), 2.24 (s, 3H), 2.73 (t, 2H), 4.50-4.58 (m, 2H), 4.58-4.67 (m, 2H), 5.02 (s, 2H), 5.97-6.15 (m, 2H), 6.74 (dd, 1H), 6.80 (d, 1H), 6.82 (d, 1H), 6.88-7.00 (m, 4H), 7.07 (dd, 1H), 7.45 (d, 1H), 7.48 (d, 2H), 12.26 (s, 2H).

Example 98(90)

4-{1-(carboxymethyl)-7-[(E)-2-(4-{[(2E)-4-(3-chlorophenoxy)-2-buten-1-yl]oxy}phenyl)vinyl]-1H-indol-3-yl}butanoic acid TLC: Rf 0.23 (dichloromethane:methanol=9:1); $^1$H-NMR (DMSO-$d_6$): δ 1.77-1.92 (m, 2H), 2.28 (t, 2H), 2.66 (t, 2H), 4.52-4.74 (m, 4H), 5.12 (s, 2H), 5.97-6.14 (m, 2H), 6.83-7.13 (m, 8H), 721-7.35 (m, 2H), 7.40-7.59 (m, 4H).

Example 98(91)

4-{1-(carboxymethyl)-7-[(E)-2-(4-{[(2E)-4-(3-methylphenoxy)-2-buten-1-yl]oxy}phenyl)vinyl]-1H-indol-3-yl}butanoic acid TLC: Rf 0.23 (dichloromethane:methanol=9:1); $^1$H-NMR (DMSO-$d_6$): δ 1.77-1.93 (m, 2H), 2.21-2.34 (m, 5H), 2.66 (t, 2H), 4.52-4.59 (m, 2H), 4.59-4.68 (m, 2H), 5.13 (s, 2H), 5.96-6.14 (m, 2H), 6.68-6.79 (m, 3H), 6.86-6.98 (m, 3H), 7.01 (t, 1H), 7.07 (s, 1H), 7.14 (t, 1H), 7.25 (d, 1H), 7.44 (d, 1H), 7.49 (d, 2H), 7.52 (d, 1H).

Example 98(92)

4-{1-(carboxymethyl)-7-[(E)-2-(4-{[(2E)-4-(4-chlorophenoxy)-2-buten-1-yl]oxy}phenyl)vinyl]-4-fluoro-2-methyl-1H-indol-3-yl}butanoic acid TLC: Rf 0.28 (chloroform:methanol:water=50:10:1); $^1$H-NMR (DMSO-$d_6$): δ 1.67-1.85 (m, 2H), 2.18 (t, 2H), 2.23 (s, 3H), 2.72 (t, 2H), 4.49-4.70 (m, 4H), 5.01 (s, 2H), 5.94-6.14 (m, 2H), 6.73 (dd, 1H), 6.81 (d, 1H), 6.90-7.00 (m, 4H), 7.06 (dd, 1H), 7.30 (d, 2H), 7.44 (d, 1H), 7.46 (d, 2H).

Example 98(93)

4-(1-(carboxymethyl)-7-{(E)-2-[4-({(2E)-4-[(2,4-dichloro-6-methylphenyl)oxy]-2-buten-1-yl}oxy)phenyl]ethenyl}-2-methyl-1H-indol-3-yl)butanoic acid TLC: Rf 0.58 (dichloromethane:methanol:acetic acid=90:10:1); $^1$H-NMR (DMSO-$d_6$): δ 1.64-1.83 (m, 2H), 2.13-2.30 (m, 8H), 2.61-2.76 (m, 2H), 4.47 (d, 2H), 4.63 (d, 2H), 4.96 (s, 2H), 6.00-6.16 (m, 2H), 6.82-7.03 (m, 4H), 7.15 (d, 1H), 7.31 (d, 1H), 7.38 (d, 1H), 7.43-7.62 (m, 4H).

Example 98(94)

4-(1-(carboxymethyl)-7-{(E)-2-[4-({(2E)-4-[(2,4-dichloro-6-methylphenyl)oxy]-2-buten-1-yl}oxy)phenyl]ethenyl}-4-fluoro-2-methyl-1H-indol-3-yl)butanoic acid TLC: Rf 0.58 (dichloromethane:methanol:acetic acid=90:10:1); $^1$H-NMR (DMSO-$d_6$): δ 1.68-1.83 (m, 2H), 2.13-2.29 (m, 8H), 2.66-2.78 (m, 2H), 4.47 (d, 2H), 4.63 (d, 2H), 5.03 (s, 2H) 5.99-6.17 (m, 2H) 6.74 (dd, 1H), 6.83 (d, 1H), 6.95 (d, 2H), 7.07 (dd, 1H), 7.31 (d, 1H), 7.40-7.52 (m, 4H).

Example 98(95)

4-(1-(carboxymethyl)-4-fluoro-2-methyl-7-{(E)-2-[4-({(2E)-4-[(2-methylphenyl)oxy]-2-buten-1-yl}oxy)phenyl]ethenyl}-1H-indol-3-yl)butanoic acid TLC: Rf 0.32 (dichloromethane:methanol=9:1); $^1$H-NMR (DMSO-$d_6$): δ 1.68-1.83 (m, 2H), 2.16 (s, 3H), 2.20 (t, 2H), 2.24 (s, 3H), 2.73 (t 2H), 4.57-4.61 (m, 2H), 4.62-4.65 (m, 2H), 5.02 (s, 2H), 6.05-6.11 (m, 2H), 6.74 (dd, 1H), 6.79-6.87 (m, 2H), 6.92 (d, 1H), 6.96 (d, 2H), 7.03-7.18 (m, 3H), 7.45 (d, 1H), 7.48 (d, 2H).

Example 98(96)

4-(1-(carboxymethyl)-2-methyl-7-{(E)-2-[4-({(2E)-4-[(2-methylphenyl)oxy]-2-buten-1-yl}oxy)phenyl]ethenyl}-1H-indol-3-yl)butanoic acid TLC: Rf 0.44 (dichloromethane:methanol=9:1); $^1$H-NMR (DMSO-$d_6$): δ 1.66-1.82 (m, 2H), 2.16 (s, 3H), 2.21 (t, 2H), 2.25 (s, 3H), 2.67 (t 2H), 4.57-4.61 (m, 2H), 4.62-4.66 (m, 2H), 5.01 (s, 2H), 6.04-6.13 (m, 2H), 6.79-7.03 (m, 6H), 7.09-7.18 (m, 3H), 7.39 (d, 1H), 7.50 (d, 2H), 7.52 (d, 1H).

Example 98(97)

4-(1-(carboxymethyl)-7-{(E)-2-[4-({(2E)-4-[(4-chloro-2-methylphenyl)oxy]-2-buten-1-yl}oxy)phenyl]ethenyl}-2-methyl-1H-indol-3-yl)butanoic acid TLC: Rf 0.53 (dichloromethane:methanol:acetic acid=90:10:1); $^1$H-NMR (DMSO-$d_6$): δ 1.65-1.84 (m, 2H), 2.16 (s, 3H), 2.21 (t, 2H), 2.26 (s, 3H), 2.67 (t, 2H), 4.53-4.73 (m, 4H), 5.02 (s, 2H), 5.95-6.18 (m, 2H), 6.89 (d, 1H), 6.92-7.05 (m, 4H), 7.10-7.26 (m, 3H), 7.39 (d, 1H), 7.49 (d, 2H), 7.52 (d, 1H), 12.26 (s, 2H).

Example 98(98)

4-(1-(carboxymethyl)-7-{(E)-2-[4-({(2E)-4-[(2,4-dimethylphenyl)oxy]-2-buten-1-yl}oxy)phenyl]ethenyl}-2-methyl-1H-indol-3-yl)butanoic acid TLC: Rf 0.54 (dichloromethane:methanol:acetic acid=90:10:1); $^1$H-NMR (DMSO-$d_6$): δ 1.67-1.84 (m, 2H), 2.13 (s, 3H), 2.18 (s, 3H), 2.21 (t 2H), 2.25 (s, 3H), 2.67 (t, 2H), 4.51-4.59 (m, 2H), 4.59-4.72 (m, 2H), 5.02 (s, 2H), 5.96-6.18 (m, 2H), 6.80 (d, 1H), 6.89 (d, 1H), 6.89-7.04 (m, 5H), 7.15 (d, 1H), 7.39 (d, 1H), 7.49 (d, 2H), 7.51 (d, 1H), 12.22 (s, 1H), 12.86 (s, 1H).

Example 98(99)

(3-{[1-(carboxymethyl)cyclopropyl]methyl}-7-{(E)-2-[4-({4-[(2,3-difluorophenyl)oxy]butyl}oxy)phenyl]ethenyl}-4-fluoro-2-methyl-1H-indol-1-yl)acetic acid TLC: Rf 0.57 (dichloromethane:methanol:acetic acid=90:10:1=9:1:0.1); $^1$H-NMR (DMSO-$d_6$): δ 0.15-0.34 (m, 4H), 1.82-1.96 (m, 4H), 2.23 (s, 3H), 2.23 (s, 2H), 3.00 (s, 2H), 4.06 (t, 2H), 4.15 (t, 2H), 5.04 (s, 2H), 6.73 (dd, 1H), 6.82 (d, 1H), 6.94 (d, 2H), 6.96-7.20 (m, 4H), 7.43 (d, 1H), 7.47 (d, 2H), 12.09 (s, 2H).

Example 98(100)

4-(1-(carboxymethyl)-7-{(E)-2-[4-({4-[(2,6-difluorophenyl)oxy]butyl}oxy)phenyl]ethenyl}-4-fluoro-2-methyl-1H-indol-3-yl)butanoic acid TLC: Rf 0.58 (dichloromethane:methanol:acetic acid=90:10:1); $^1$H-NMR (DMSO-$d_6$): δ 1.66-1.97 (m, 6H), 2.18 (t, 2H), 2.24 (s, 3H), 2.73 (t 2H), 4.04 (t 2H), 4.16 (t, 2H), 5.03 (s, 2H), 6.74 (dd, 1H), 6.82 (d, 1H), 6.93 (d, 2H), 7.07 (dd, 1H), 7.09-7.19 (m, 3H), 7.43 (d, 1H), 7.47 (d, 2H), 12.15 (s, 1H), 13.12 (s, 1H).

Example 98(101)

4-(1-(carboxymethyl)-7-{(E)-2-[4-({4-[(2,6-difluorophenyl)oxy]butyl}oxy)phenyl]ethenyl}-2-methyl-1H-indol-3-yl)butanoic acid TLC: Rf 0.56 (dichloromethane:methanol:acetic acid=90:10:1); $^1$H-NMR (DMSO-$d_6$): δ 1.67-1.97 (m, 6H), 2.21 (t, 2H), 2.25 (s, 3H), 2.67 (t, 2H), 4.05 (t, 2H), 4.16 (t, 2H), 5.02 (s, 2H), 6.88 (d, 1H), 6.94 (d, 2H), 6.98 (t, 1H), 7.06-7.22 (m, 4H), 7.39 (d, 1H), 7.48 (d, 2H), 7.51 (d, 1H), 12.19 (s, 1H), 12.93 (s, 1H).

Example 98(102)

(3-{[1-(carboxymethyl)cyclopropyl]methyl}-7-{(E)-2-[4-({(2E)-4-[(2,3-difluorophenyl)oxy]-2-buten-1-yl}oxy)phenyl]ethenyl}-2-methyl-1H-indol-1-yl) acetic acid TLC: Rf 0.35 (chloroform:methanol:water=50:10:1); $^1$H-NMR (DMSO-$d_6$): δ 0.20-0.38 (m, 4H), 2.17 (s, 2H), 2.24 (s, 3H), 2.87 (s, 2H), 4.59-4.66 (m, 2H), 4.68-4.75 (m, 2H), 5.01 (s, 2H), 6.00 (6.16 (m, 2H), 6.87 (d, 1H), 6.92-7.18 (m, 7H), 7.39 (dd, 1H), 7.49 (d, 2H), 7.52 (d, 1H).

Example 98(103)

(3-{[1-carboxymethyl)cyclopropyl]methyl}-2-methyl-7-{(E)-2-[4-({(2E)-4-[(2,4,6-trimethylphenyl)oxy]-2-buten-1-yl}oxy)phenyl]ethenyl}-1H-indol-1-yl)acetic acid TLC: Rf 0.35 (chloroform:methanol:water=50:10:1); $^1$H-NMR (DMSO-$d_6$): δ 0.18-0.42 (m, 4H), 2.15 (s, 9H), 2.17 (s, 2H), 2.22-2.26 (m, 3H), 2.81-2.93 (m, 2H), 4.24-4.31 (m, 2H), 4.59-4.67 (m, 2H), 5.02 (s, 2H), 5.99-6.17 (m, 2H), 6.78-6.82 (m, 2H), 6.88 (d, 1H), 6.97 (d, 2H), 6.99 (d, 1H), 7.13 (d, 1H), 7.39 (dd, 1H), 7.49 (d, 2H), 7.52 (d, 1H).

Example 98(104)

(3-{[1-(carboxymethyl)cyclopropyl]methyl}-7-{(E)-2-[4-({4-[(2,3-difluorophenyl)oxy]butyl}oxy)phenyl]ethenyl}-2-methyl-1H-indol-1-yl)acetic acid TLC: Rf 0.35 (chloroform:methanol:water=50:10:1); $^1$H-NMR (DMSO-$d_6$): δ 0.21-0.38 (m, 4H), 1.81-1.96 (m, 4H), 2.17 (s, 2H), 2.24 (s, 3H), 2.87 (s, 2H), 4.02-4.09 (m, 2H), 4.10-4.20 (m, 2H), 5.01 (s, 2H), 6.87 (d, 1H), 6.91-7.19 (m, 7H), 7.38 (d, 1H), 7.48 (d, 2H), 7.51 (d, 1H).

Example 98(105)

(3-{[1-(carboxymethyl)cyclopropyl]methyl}-7-{(E)-2-[4-({(2E)-4-[(2,3-difluorophenyl)oxy]-2-buten-1-yl}oxy)phenyl]ethenyl}-4-fluoro-2-methyl-1H-indol-1-yl)acetic acid TLC: Rf 0.33 (chloroform:methanol:water=50:10:1); $^1$H-NMR (DMSO-$d_6$): δ 0.15-0.34 (m, 4H), 2.23 (s, 3H), 2.23 (s, 2H), 3.00 (s, 2H), 4.61-4.66 (m, 2H), 4.69-4.75 (m, 2H), 5.03 (s, 2H), 6.00-6.17 (m, 2H), 6.73 (dd, 1H), 6.82 (d, 1H), 6.96 (d, 2H), 6.97-7.19 (m, 4H), 7.44 (d, 1H), 7.48 (d, 2H).

Example 98(106)

(3-{[1-(carboxymethyl)cyclopropyl]methyl}-4-fluoro-2-methyl-7-{(E)-2-[4-({(2E)-4-[2,4,6-trimethylphenyl)oxy]-2-buten-1-yl}oxy)phenyl]ethenyl}-1H-indol-1-yl)acetic acid TLC: Rf 0.33 (chloroform:methanol:water=50:10:1); $^1$H-NMR (DMSO-$d_6$): δ 0.14-0.34 (m, 4H), 2.15 (s, 6H), 2.16-2.17 (m, 3H), 2.23 (s, 3H), 2.23 (s, 2H), 3.00 (s, 2H), 4.22-4.32 (m, 2H) 4.57-4.68 (m, 2H), 5.03 (s, 2H), 5.97-6.17 (m, 2H), 6.73 (dd, 1H), 6.80 (s, 2H), 6.82 (d, 1H), 6.96 (d, 2H), 7.05 (dd, 1H), 7.39-7.52 (m, 3H).

Example 98(107)

{1-[(1-(carboxymethyl)-7-{(E)-2-[4-({(2E)-4-[(2-chlorophenyl)oxy]-2-buten-1-yl}oxy)phenyl]ethenyl}-4-fluoro-2-methyl-1H-indol-3-yl)methyl]cyclopropyl}acetic acid TLC: Rf 0.33 (chloroform:methanol:water=50:10:1); $^1$H-NMR (DMSO-$d_6$): δ 0.17-0.32 (m, 4H), 2.23 (s, 2H), 2.23 (s, 3H), 3.00 (s, 2H), 4.61-4.67 (m, 2H), 4.67-4.73 (m, 2H), 5.03 (s, 2H), 6.02-6.18 (m, 2H), 6.73 (dd, 1H), 6.82 (d, 1H), 6.91-7.00 (m, 3H), 7.05 (dd, 1H), 7.15 (dd, 1H), 7.29 (ddd, 1H) 7.42 (dd, 1H), 7.45 (d, 1H) 7.48 (d, 2H).

Example 98(108)

{3-{[1-(carboxymethyl)cyclopropyl]methyl}-2-methyl-7-[(E)-2-(4-{[(2E)-4-(phenyloxy)-2-buten-1-yl]oxy}phenyl)ethenyl]-1H-indol-1-yl}acetic acid TLC: Rf 0.26 (chloroform:methanol=9:1); $^1$H-NMR (DMSO-$D_6$): δ 0.27-0.34 (m, 4H), 2.18 (s, 2H), 2.25 (s, 3H), 2.88 (s, 2H), 4.58-4.66 (m, 4H), 5.03 (s, 2H), 6.04-6.10 (m, 2H) 6.85-7.02 (m, 7H), 7.14 (d, 1H), 7.24-7.32 (m, 2H), 7.37-7.42 (m, 1H), 7.49 (d, 2H), 7.52 (d, 1H).

Example 98(109)

{3-{[1-(carboxymethyl)cyclopropyl]methyl}-4-fluoro-2-methyl-7-[(E)-2-(4-{[4-(phenyloxy)butyl]oxy}phenyl)ethenyl]-1H-indol-1-yl}acetic acid TLC: Rf 0.36 (chloroform:methanol:water=50:10:1); $^1$H-NMR (DMSO-$d_6$): δ 0.15-0.34 (m, 4H), 1.82-1.91 (m, 4H), 2.23 (s, 3H), 2.23 (s, 2H), 3.00 (s, 2H), 3.93-4.14 (m, 4H), 5.02 (s, 2H) 6.72 (dd, 1H), 6.81 (d, 1H), 6.86-6.98 (m, 5H), 7.04 (dd, 1H), 7.22-7.31 (m, 2H), 7.38-7.51 (m, 3H).

Example 98(110)

{3-{[1-(carboxymethyl)cyclopropyl]methyl}-4-fluoro-2-methyl-7-[(E)-2-(4-{[(2E)-4-(phenyloxy) -2-buten-1-yl]oxy}phenyl)ethenyl]-1H-indol-1-yl}acetic acid TLC: Rf 0.36 (chloroform:methanol:water=50:10:1); $^1$H-NMR (DMSO-$d_6$): δ 0.16-0.34 (m, 4H), 2.24 (s, 3H), 2.24 (s, 2H), 3.01 (s, 2H), 4.52-4.70 (m, 4H), 5.04 (s, 2H), 5.99-6.14 (m, 2H), 6.73 (dd, 1H), 6.82 (d, 1H), 6.89-7.00 (m, 5H), 7.05 (dd, 1H), 7.23-7.33 (m, 2H), 7.39-7.53 (m, 3H).

Example 98(111)

(3-{[1-(carboxymethyl)cyclopropyl]methyl}-4-fluoro-2-methyl-7-{(E)-2-[4-({4-[(2,4,6-trimethylphenyl)oxy]butyl}oxy)phenyl]ethenyl}-1H-indol-1-yl)acetic acid TLC: Rf 0.36 (chloroform:methanol:water=50:10:1); $^1$H-NMR (DMSO-$d_6$): δ 0.16-0.34 (m, 4H), 1.79-2.00 (m, 4H), 2.17 (s, 6H), 2.17 (s, 3H), 2.24 (s, 3H), 2.24 (s, 2H), 3.00 (s, 2H), 3.74 (t, 2H), 4.07 (t, 2H), 5.04 (s, 2H), 6.73 (dd, 1H), 6.78-6.87 (m, 3H), 6.95 (d, 2H), 7.05 (dd, 1H), 7.38-7.52 (m, 3H).

Example 98(112)

{3-{[1-(carboxymethyl)cyclopropyl]methyl}-7-[(E)-2-(4-{[(2E)-4-(phenyloxy)-2-buten-1-yl]oxy}phenyl)ethenyl]-1H-indol-1-yl}acetic acid TLC: Rf 0.20 (chloroform:methanol=9:1); $^1$H-NMR (DMSO-$d_6$): δ 037-0.50 (m, 4H), 2.17 (s, 2H), 2.78 (s, 2H), 4.57-4.66 (m, 4H), 5.16 (s, 2H), 6.04-6.09 (m, 2H), 6.88-6.98 (m, 6H), 7.01 (dd, 1H), 7.11 (s, 1H), 7.22-7.32 (m, 3H), 7.45 (d, 1H), 7.50 (d, 2H), 7.53 (d, 1H).

Example 98(113)

4-(1-(carboxymethyl)-7-{(E)-2-[4-({(2E)-4-[(2-chloro-5-fluorophenyl)oxy]-2-buten-1-yl}oxy)phenyl]ethenyl}-2-methyl-1H-indol-3-yl)butanoic acid TLC: Rf 0.29 (dichloromethane:methanol=9:1); $^1$H-NMR (DMSO-$d_6$): δ 1.66-1.82 (m, 2H), 2.21 (t, 2H), 2.26 (s, 3H), 2.67 (t, 2H), 4.65 (d, 2H), 4.72 (d, 2H), 5.02 (s, 2H), 5.99-6.19 (m, 2H), 6.81 (td, 1H), 6.88 (d, 1H), 6.93-7.03 (m, 3H), 7.07-7.19 (m, 2H), 7.38 (dd, 1H), 7.41-7.56 (m, 4H).

Example 98(114)

4-(1-(carboxymethyl)-7-{(E)-2-[4-({(2E)-4-[(2-chloro-5-fluorophenyl)oxy]-2-buten-1-yl}oxy)phenyl]ethenyl}-4-fluoro-2-methyl-1H-indol-3-yl)butanoic acid TLC: Rf 0.27 (dichloromethane:methanol=9:1); $^1$H-NMR ($DMSO-d_6$): δ 1.69-1.84 (m, 2H) 2.19 (t, 2H), 2.24 (s, 3H), 2.73 (t, 2H), 4.64 (d, 2H), 4.72 (d, 2H), 5.03 (s, 2H), 6.00-6.19 (m, 2H), 6.68-6.87 (m, 3H), 6.96 (d, 2H), 7.02-7.16 (m, 2H), 7.36-7.54 (m, 4H).

Example 98(115)

4-{1-(carboxymethyl)-7-[(E)-2-(4-{[(2E)-4-(2-chloro-4-methylphenoxy)-2-buten-1-yl]oxy}phenyl)vinyl]-2-methyl-1H-indol-3-yl}butanoic acid TLC: Rf 0.41 (dichloromethane:methanol=9:1); $^1$H-NMR ($DMSO-d_6$): δ 1.68-1.81 (m, 2H), 2.21 (t, 2H), 2.22 (s, 3H), 2.26 (s, 3H), 2.67 (t, 2H), 4.51-4.75 (m, 4H), 5.02 (s, 2H), 5.98-6.17 (m, 2H), 6.88 (d, 1H), 6.93-7.11 (m, 5H), 7.14 (d, 1H), 7.24 (d, 1H), 7.38 (d, 1H), 7.48 (d, 2H), 7.51 (d, 1H).

Example 98(116)

4-{1-(carboxymethyl)-7-[(E)-2-(4-{[(2E)-4-(2-chloro-4-methylphenoxy)-2-buten-1-yl]oxy}phenyl)vinyl]-4-fluoro-2-methyl-1H-indol-3-yl}butanoic acid TLC: Rf 0.35 (dichloromethane:methanol=9:1); $^1$H-NMR ($DMSO-d_6$): δ 1.69-1.83 (m, 2H), 2.19 (t, 2H), 2.22 (s, 3H), 2.24 (s, 3H), 2.73 (t, 2H), 4.54-4.73 (m, 4H), 5.03 (s, 2H), 5.98-6.16 (m, 2H), 6.74 (dd, 1H), 6.82 (d, 1H), 6.95 (d, 2H), 6.99-7.12 (m, 3H), 7.23 (d, 1H), 7.38-7.53 (m, 3H).

Example 98(117)

4-(1-(carboxymethyl)-4-fluoro-2-methyl-7-{(E)-2-[4-({4-[(2,4,6-trifluorophenyl)oxy]butyl}oxy)phenyl]ethenyl}-1H-indol-3-yl)butanoic acid TLC: Rf 0.60 (dichloromethane:methanol:acetic acid=90:10:1); $^1$H-NMR ($DMSO-d_6$): δ 1.67-1.97 (m, 6H), 2.19 (t, 2H), 2.24 (s, 3H), 2.73 (t, 2H), 4.04 (t, 2H), 4.11 (t, 2H), 5.04 (s, 2H), 6.74 (dd, 1H), 6.82 (d, 1H), 6.93 (d, 2H), 7.07 (dd, 1H), 7.25 (t, 2H), 7.43 (d, 1H), 7.47 (d, 2H), 12.13 (s, 1H), 13.12 (s, 1H).

Example 98(118)

4-(1-(carboxymethyl)-2-methyl-7-{(E)-2-[4-({4-[(2,4,6-trifluorophenyl)oxy]butyl}oxy)phenyl]ethenyl}-1H-indol-3-yl)butanoic acid TLC: Rf 0.59 (dichloromethane:methanol:acetic acid=90:10:1); $^1$H-NMR ($DMSO-d_6$): δ 1.66-1.97 (m, 6H), 2.21 (t, 2H), 2.25 (s, 3H), 2.67 (t 2H), 4.05 (t, 2H), 4.12 (t, 2H), 5.02 (s, 2H), 6.88 (d, 1H), 6.93 (d, 2H), 6.98 (t, 1H), 7.15 (d, 1H), 7.25 (t 2H), 7.39 (d, 1H), 7.48 (d, 2H), 7.51 (d, 1H), 12.34 (s, 2H).

Example 98(119)

4-(1-carboxymethyl)-4-fluoro-7-{(E)-2-[4-({4-[(2-fluorophenyl)oxy]butyl}oxy)phenyl]ethenyl}-2-methyl-1H-indol-3-yl)butanoic acid TLC: Rf 0.32 (dichloromethane:methanol=9:1); $^1$H-NMR ($DMSO-d_6$): δ 1.69-1.82 (m, 2H), 1.84-1.93 (m, 4H), 2.18 (t 2H), 2.24 (s, 3H), 2.73 (t, 2H), 4.01-4.16 (m, 4H), 5.02 (s, 2H), 6.74 (dd, 1H), 6.82 (d, 1H), 6.87-6.98 (m, 3H), 7.02-7.25 (m, 4H), 7.39-7.52 (m, 3H).

Example 98(120)

4-(1-(carboxymethyl)-7-{(E)-2-[4-({4-[(2-fluorophenyl)oxy]butyl}oxy)phenyl]ethenyl}-2-methyl-1H-indol-3-yl)butanoic acid TLC: Rf 0.33 (dichloromethane:methanol=9:1); $^1$H-NMR ($DMSO-d_6$): δ 1.67-1.81 (m, 2H), 1.84-1.95 (m, 4H), 2.21 (t 2H), 2.25 (s, 3H), 2.66 (t, 2H), 4.01-4.15 (m, 4H), 5.00 (s, 2H), 6.82-7.02 (m, 5H), 7.05-7.24 (m, 4H), 7.38 (d, 1H), 7.44-7.56 (m, 3H).

Example 98(121)

{1-[(1-(carboxymethyl)-7-{(E)-2-[4-({(2E)-4-[(2-chloro-3,5-difluorophenyl)oxy]-2-buten-1-yl}oxy)phenyl]ethenyl}-4-fluoro-2-methyl-1H-indol-3-yl)methyl]cyclopropyl}acetic acid TLC: Rf 0.36 (chloroform:methanol:water=50:10:1); $^1$H-NMR ($DMSO-d_6$): δ 0.13-0.36 (m, 4H), 2.23 (s, 3H), 2.23 (s, 2H); 3.00 (s, 2H), 4.59-4.68 (m, 2H), 4.71-4.78 (m, 2H), 5.02 (s, 2H), 5.99-6.19 (m, 2H), 6.72 (dd, 1H), 6.81 (d, 1H), 6.91-6.99 (m, 2H), 7.00-7.13 (m, 3H), 7.44 (d, 1H), 7.47 (d, 2H).

Example 98(122)

{3-{[1-(carboxymethyl)cyclopropyl]methyl}-2-methyl-7-[(E)-2-(4-{[4-(phenyloxy)butyl]oxy}phenyl)ethenyl]-1H-indol-1-yl}acetic acid TLC: Rf 0.39 (dichloromethane:methanol=9:1); $^1$H-NMR ($DMSO-d_6$): δ 0.20-0.39 (m, 4H), 1.79-1.96 (m, 4H), 2.18 (s, 2H), 2.25 (s, 3H), 2.88 (s, 2H), 3.97-4.12 (m, 4H), 5.03 (s, 2H), 6.83-7.03 (m, 7H), 7.13 (d, 1H), 7.23-7.32 (m, 2H), 7.39 (d, 1H), 7.48 (d, 2H), 7.51 (d, 1H).

Example 98(123)

{1-[(1-(carboxymethyl)-7-{(E)-2-[4-({4-[(2-chlorophenyl)oxy]butyl}oxy)phenyl]ethenyl}-2-methyl-1H-indol-3-yl)methyl]cyclopropyl}acetic acid TLC: Rf 0.45 (chloroform:methanol:water=50:10:1); $^1$H-NMR ($DMSO-d_6$): δ 0.22-0.36 (m, 4H), 1.83-1.96 (m, 4H), 2.17 (s, 2H), 2.24 (s, 3H), 2.87 (s, 2H), 4.03-4.18 (m, 4H), 5.02 (s, 2H), 6.87 (d, 1H), 6.90-7.01 (m, 4H), 7.10-7.17 (m, 2H), 7.28 (ddd, 1H), 7.36-7.43 (m, 2H), 7.48 (d, 2H), 7.50 (d, 1H).

Example 98(124)

{1-[(1-(carboxymethyl)-7-{(E)-2-[4-({(2E)-4-[(2-chlorophenyl)oxy]-2-buten-1-yl}oxy)phenyl]ethenyl}-2-methyl-1H-indol-3-yl)methyl]cyclopropyl}acetic acid TLC: Rf 0.45 (chloroform:methanol:water=50:10:1); $^1$H-NMR (DMSO-$d_6$): δ 0.21-0.40 (m, 4H), 2.18 (s, 2H), 2.25 (s, 3H), 2.88 (s, 2H), 4.60-4.67 (m, 2H), 4.67-4.73 (m, 2H), 5.02 (s, 2H), 6.01-6.19 (m, 2H), 6.88 (d, 1H), 6.92-7.01 (m, 4H), 7.13 (d, 1H), 7.15 (dd, 1H), 7.29 (ddd, 1H), 7.37-7.41 (m, 1H), 7.42 (dd, 1H), 7.49 (d, 2H), 7.53 (d, 1H).

Example 98(125)

{3-{[1-(carboxymethyl)cyclopropyl]methyl}-7-[(E)-2-(4-{[4-(phenyloxy)butyl]oxy}phenyl)ethenyl]-1H-indol-1-yl}acetic acid TLC: Rf 0.37 (dichloromethane:methanol=9:1); $^1$H-NMR (DMSO-$d_6$): δ 0.37-0.43 (m, 2H), 0.43-0.50 (m, 2H), 1.82-1.94 (m, 4H), 2.17 (s, 2H), 2.78 (s, 2H), 3.96-4.14 (m, 4H), 5.15 (s, 2H), 6.86-6.98 (m, 6H), 7.01 (t, 1H), 7.11 (s, 1H), 7.20-7.34 (m, 3H), 7.45 (d, 1H), 7.49 (d, 2H), 7.53 (d, 1H).

Example 98(126)

{1-[(1-(carboxymethyl)-7-{(E)-2-[4-({(2E)-4-[(2-chlorophenyl)oxy]-2-buten-1-yl}oxy)phenyl]ethenyl}-1H-indol-3-yl)methyl]cyclopropyl}acetic acid TLC: Rf 0.39 (chloroform:methanol:water=50:10:1); $^1$H-NMR (DMSO-$d_6$): δ 0.36-0.43 (m, 2H), 0.43-0.51 (m, 2H), 2.17 (s, 2H), 2.78 (s, 2H), 4.61-4.67 (m, 2H), 4.68-4.72 (m, 2H), 5.15 (s, 2H), 6.02-6.18 (m, 2H), 6.87-7.06 (m, 5H), 7.11 (s, 1H), 7.15 (dd, 1H), 7.22-7.33 (m, 2H), 7.42 (dd, 1H), 7.45-7.59 (m, 4H).

Example 98(127)

{1-[(1-(carboxymethyl)-7-{(E)-2-[4-({4-[(2-chlorophenyl)oxy]butyl}oxy)phenyl]ethenyl}-1H-indol-3-yl)methyl]cyclopropyl}acetic acid TLC: Rf 0.39 (chloroform:methanol:water=50:10:1); $^1$H-NMR (DMSO-$d_6$): δ 036-0.43 (m, 2H), 0.43-0.51 (m, 2H), 1.83-1.99 (m, 4H), 2.17 (s, 2H), 2.78 (s, 2H), 4.04-4.10 (m, 2H), 4.10-4.16 (m, 2H), 5.14 (s, 2H), 6.87-6.97 (m, 4H), 7.01 (dd, 1H), 7.11 (s, 1H), 7.15 (dd, 1H), 7.24 (d, 1H), 7.29 (ddd, 1H), 7.41 (dd, 1H), 7.45 (dd, 1H), 7.47-7.57 (m, 3H).

Example 98(128)

{1-[(1-(carboxymethyl)-7-{(E)-2-[4-({4-[(2-chloro-3,5-difluorophenyl)oxy]butyl}oxy)phenyl]ethenyl}-1H-indol-3-yl)methyl]cyclopropyl}acetic acid TLC: Rf 0.37 (dichloromethane:methanol=9:1); $^1$H-NMR (DMSO-$d_6$): δ 0.35-0.43 (m, 2H), 0.43-0.50 (m, 2H), 1.83-1.98 (m, 4H), 2.17 (s, 2H), 2.78 (s, 2H), 4.04-4.12 (m, 2H), 4.14423 (m, 2H), 5.15 (s, 2H), 6.85-7.15 (m, 7H), 7.24 (d, 1H), 7.45 (d, 1H), 7.49 (d, 2H), 7.53 (d, 1H).

Example 98(129)

{1-[(1-(carboxymethyl)-7-{(E)-2-[4-({4-[(2-chloro-3,5-difluorophenyl)oxy]butyl}oxy)phenyl]ethenyl}-2-methyl-1H-indol-3-yl)methyl]cyclopropyl}acetic acid TLC: Rf 0.39 (dichloromethane:methanol=9:1); $^1$H-NMR (DMSO-$d_6$): δ 0.20-0.38 (m, 4H), 1.84-1.97 (m, 4H), 2.18 (s, 2H), 2.25 (s, 3H), 2.88 (s, 2H), 4.04-4.12 (m, 2H), 4.14-4.22 (m, 2H), 5.03 (s, 2H), 6.88 (d, 1H), 6.91-7.18 (m, 6H), 7.39 (d, 1H), 7.49 (d, 2H), 7.51 (d, 1H).

Example 98(130)

(3-{[1-(carboxymethyl)cyclopropyl]methyl}-7-{(E)-2-[4-({(2E)-4-[(2-fluorophenyl)oxy]-2-buten-1-yl}oxy)phenyl]ethenyl}-2-methyl-1H-indol-1-yl)acetic acid TLC: Rf 0.18 (chloroform:methanol=9:1); $^1$H-NMR (DMSO-$d_6$): δ 0.37-0.49 (m, 4H), 2.17 (s, 2H), 2.78 (s, 2H), 4.60-4.70 (m, 4H), 5.15 (s, 2H), 6.01-6.15 (m, 2H), 6.87-7.04 (m, 5H), 7.06-7.27 (m, 5H), 7.44 (dd, 1H), 7.49 (d 2H), 7.53 (d, 1H).

Example 98(131)

(3-{[1-(carboxymethyl)cyclopropyl]methyl}-7-{(E)-2-[4-({2E)-4-[(2-fluorophenyl)oxy]-2-buten-1-yl}oxy)phenyl]ethenyl}-2-methyl-1H-indol-1-yl)acetic acid TLC: Rf 0.21 (chloroform:methanol=9:1); $^1$H-NMR (DMSO-$d_6$): δ 0.26-0.34 (m, 4H), 2.18 (s, 2H), 2.25 (s, 3H), 2.88 (s, 2H), 4.59-4.71 (m, 4H), 5.02 (s, 2H), 6.01-6.14 (m, 2H), 6.88 (d, 1H), 6.88-7.01 (m, 4H), 7.07-7.24 (m, 4H), 7.38 (d, 1H), 7.48 (d, 2H), 7.51 (d, 1H).

Example 98(132)

4-(1-(carboxymethyl)-7-{(E)-2-[4-({(2E)-4-[(2,6-difluorophenyl)oxy]-2-buten-1-yl}oxy)phenyl]ethenyl}-4-fluoro-2-methyl-1H-indol-3-yl)butanoic acid TLC: Rf 0.53 (dichloromethane:methanol:acetic acid=90:10:1); $^1$H-NMR (DMSO-$d_6$): δ 1.68-1.84 (m, 2H), 2.19 (t, 2H), 2.24 (s, 3H), 2.73 (t, 2H), 4.60 (d, 2H), 4.66 (d, 2H), 5.03 (s, 2H), 5.93-6.14 (m, 2H), 6.74 (dd, 1H), 6.83 (d, 1H), 6.92 (d, 2H), 7.07 (dd, 1H), 7.09-7.19 (m, 3H), 7.45 (d, 1H), 7.47 (d, 2H), 12.11 (s, 2H).

Example 98(133)

4-(1-carboxymethyl)-7-{(E)-2-[4-({(2E)-4-[(2,6-difluorophenyl)oxy]-2-buten-1-yl}oxy)phenyl]ethenyl}-2-methyl-1H-indol-3-yl)butanoic acid TLC: Rf 0.54 (dichloromethane:methanol:acetic acid=90:10:1); $^1$H-NMR (DMSO-$d_6$)1.66-1.83 (m, 2H), 2.21 (t, 2H), 2.25 (s, 3H), 2.67 (t, 2H), 4.55-4.63 (m, 2H), 4.66 (d, 2H), 5.01 (s, 2H), 5.94-6.14 (m, 2H), 6.88 (d, 1H), 6.92 (d, 2H), 6.98 (t, 1H), 7.08-7.21 (m, 4H), 7.39 (d, 1H), 7.48 (d, 2H), 7.52 (d, 1H), 12.39 (s, 2H).

Example 98(134)

4-(1-(carboxymethyl)-2-methyl-7-{(E)-2-[4-({(2E)-4-[(2,4,6-trifluorophenyl)oxy]-2-buten-1-yl}oxy)phenyl]ethenyl}-1H-indol-3-yl)butanoic acid TLC: Rf 0.56 (dichloromethane:methanol:acetic acid=90:10:1); $^1$H-NMR (DMSO-$d_6$): δ 1.67-1.85 (m, 2H), 2.19 (t, 2H), 2.24 (s, 3H), 2.73 (t, 2H), 4.45-4.74 (m, 4H), 5.03 (s, 2H), 5.92-6.12 (m, 2H), 6.74 (dd, 1H), 6.82 (d, 1H), 6.92 (d, 2H), 7.07 (dd, 1H), 7.24 (t, 2H), 7.45 (d, 1H), 7.47 (d, 2H), 12.29 (s, 2H).

Example 98(135)

4-(1-carboxymethyl)-2-methyl-7-{(E)-2-[4-({(2E)-4-[(2,4,6-trifluorophenyl)oxy]-2-buten-1-yl}oxy)phenyl]ethenyl}-1H-indol-3-yl)butanoic acid TLC: Rf 0.55 (dichloromethane:methanol:acetic acid=90:10:1); $^1$H-NMR (DMSO-$d_6$): δ 1.64-1.84 (m, 2H), 2.21 (t, 2H), 2.25 (s, 3H), 2.67 (t, 2H), 4.46-4.75 (m, 4H), 5.01 (s, 2H), 5.89-6.15 (m, 2H), 6.88 (d, 1H), 6.92 (d, 2H), 6.98 (t, 1H), 7.15 (d, 1H), 7.24 (t, 2H), 7.39 (d, 1H), 7.48 (d, 2H), 7.52 (d, 1H), 12.34 (s, 2H).

Example 98(136)

(3-{[1-carboxymethyl)cyclopropyl]methyl}-7-{(E)-2-[4-({4-[(2-fluorophenyl)oxy]butyl}oxy)phenyl]ethenyl}-1H-indol-1-yl)acetic acid TLC: Rf 0.30 (dichloromethane:methanol=9:1); $^1$H-NMR (DMSO-$d_6$): δ 0360.42 (m, 2H), 0.43-0.49 (m, 2H), 1.82-1.95 (m, 4H), 2.17 (s, 2H), 2.78 (s, 2H), 4.01-4.15 (m, 4H), 5.12 (s, 2H), 6.85-6.96 (m, 4H), 7.00 (t, 1H), 7.07-7.28 (m, 5H), 7.45 (d, 1H), 7.47-7.58 (m, 3H).

Example 98(137)

4-(1-(1-carboxyethyl)-7-{(E)-2-[4-({4-[(2,3-difluorophenyl)oxy]butyl}oxy)phenyl]ethenyl}-2-methyl-1H-indol-3-yl)butanoic acid TLC: Rf 0.40 (chloroform:methanol:water=50:10:1); $^1$H-NMR (DMSO-$d_6$): δ 1.62 (d, 3H), 1.67-1.80 (m, 2H), 1.81-1.97 (m, 4H), 2.21 (t, 2H), 2.27 (s, 3H), 2.65 (t, 2H), 4.02-4.11 (m, 2H), 4.11-4.19 (m, 2H), 5.44-5.65 (m, 1H), 6.86-7.17 (m, 8H), 7.33-7.46 (m, 2H), 7.50 (d, 2H).

Example 99

2-[(1-carboxymethyl)-7-{(E)-2-[4-(4-phenoxybutoxy)phenyl]vinyl}-1H-indol-3-yl)carbonyl]benzoic acid Except for using 7-bromoindole in place of the compound prepared in Example 16 and methyl 2-(chlorocarbonyl)benzoate in place of 4-chloro-4-oxobutanoate, the same operation as in Example 17→Example 2 (using methyl bromoacetate in place of methyl 4-bromobutyrate)→Example 3 (using 1-ethenyl-4-{[4-(phenyloxy)butyl]oxy}benzene in place of 4-vinylphenyl acetate)→Example 6 was conducted to obtain the titled compound having the following physical properties.

TLC: Rf 0.31 (chloroform:methanol:water=20:10:1);

$^1$H-NMR (DMSO-$d_6$): δ 1.80-1.94 (m, 4H), 3.96-4.12 (m, 4H), 5.26 (s, 2H), 6.85-7.03 (m, 6H), 7.21-7.30 (m, 3H), 7.41 (d, 1H), 7.43-7.56 (m, 4H), 7.59 (ddd, 1H), 7.60 (s, 1H), 7.66 (ddd, 1H), 7.91 (dd, 1H), 8.15 (d, 1H), 12.41-13.69 (m, 2H).

Example 99(1) to Example 99(3)

Using a corresponding compound, the same operation as in Example 99 was conducted to obtain the titled compound having the following physical properties.

Example 99(1)

4-{1-(carboxymethyl)-7-[(E)-2-(4-{[(2E)-4-(2,3-difluorophenoxy-2-buten-1-yl]oxy}phenyl)vinyl]-4-fluoro-2-methyl-1H-indol-3-yl}-4-oxobutanoic acid TLC: Rf 0.19 (chloroform:methanol:water=50:10:1);

$^1$H-NMR (DMSO-$d_6$): δ 2.44 (s, 3H), 2.56 (t, 2H), 3.10 (t, 2H), 4.59-4.67 (m, 2H), 4.68-4.76 (m, 2H), 5.14 (s, 2H), 6.00-6.17 (m, 2H), 6.86 (d, 1H), 6.92-7.17 (m, 6H), 7.22 (dd, 1H), 7.41-7.53 (m, 3H).

Example 99(2)

4-{1-(carboxymethyl)-4-fluoro-7-[(E)-2-(4-{[2E)-4-mesityloxy)-2-buten-1-yl]oxy}phenyl)vinyl]-2-methyl-1H-indol-3-yl}-4-oxobutanoic acid TLC: Rf 0.19 (chloroform:methanol:water=50:10:1);

$^1$H-NMR (DMSO-$d_6$): δ 2.16 (s, 9H), 2.45 (s, 3H), 2.57 (t, 2H), 3.06-3.15 (m, 2H), 4.28 (d, 2H), 4.64 (d, 2H), 5.15 (s, 2H), 5.99-6.17 (m, 2H), 6.80 (s, 2H), 6.87 (d, 1H), 6.93-7.04 (m, 3H), 7.23 (dd, 1H), 7.41-7.56 (m, 3H).

Example 99(3)

4-[1-carboxymethyl)-7-((E)-2-{4-[4-(2,3-difluorophenoxy)butoxy]phenyl}vinyl)-4-fluoro-2-methyl-1H-indol-3-yl]oxobutanoic acid TLC: Rf 0.19 (chloroform:methanol:water=50:10:1);

$^1$H-NMR (DMSO-$d_6$): δ 1.80-1.99 (m, 4H), 2.45 (s, 3H), 2.57 (t, 2H), 3.06-3.15 (m, 2H), 4.02-4.11 (m, 2H), 4.11-4.20 (m, 2H), 5.15 (s, 2H), 6.86 (d, 1H), 6.91-7.19 (m, 6H), 7.23 (dd, 1H), 7.40-7.55 (m, 3H).

Example 100

{7-((E)-2-{4-[4-(2,3-difluorophenoxy)butoxy]phenyl}vinyl)-3-[4-(dimethylamino)-4-oxobutyl]-1H-indol-1-yl}acetic acid Except for using the compound prepared in Example 42 in place of the compound prepared in Example 2, the same operation as in Example 6→Example 91 (using dimethylamine in place of methanesulfonamide) a Example 2 (using ethyl 2-bromoacetate in place of methyl 4-bromobutyrate)→Example 3 (using 1-({4-(4-[(4-ethynylphenyl)oxy]butyl}oxy)-2,3-difluorobenzene in place of 4-vinylphenyl acetate)→Example 6 was conducted to obtain the titled compound having the following physical properties.

TLC: Rf 0.31 (dichloromethane:methanol=9:1);

$^1$H-NMR (DMSO-$d_6$): δ 1.76-1.98 (m, 6H) 2.35 (t, 2H), 2.66 (t, 2H), 2.81 (s, 3H), 2.91 (s, 3H), 4.03-4.11 (m, 2H), 4.11-4.21 (m, 2H) 5.13 (s, 2H), 6.86-7.19 (m, 8H), 7.26 (d, 1H), 7.40-7.58 (m, 4H), 13.03 (s, 1H).

Example 100(1) to Example 100(4)

Using a corresponding compound, the same operation as in Example 100 was conducted to obtain the titled compound having the following physical properties.

Example 100(1)

{7-((E)-2-{4-[4-(2,3-difluorophenoxy)butoxy] phenyl}vinyl)-3-[4-methylamino-4-oxobutyl]-1H-indol-1-yl}acetic acid TLC: Rf 0.29 (dichloromethane:methanol=9:1);

$^1$H-NMR (DMSO-$d_6$): δ 1.76-1.97 (m, 6H), 2.13 (t, 2H), 2.56 (d, 3H), 2.62 (t, 2H), 4.02-4.11 (m, 2H), 4.12-4.20 (m, 2H), 5.12 (s, 2H), 6.85-7.20 (m, 8H), 7.25 (d, 1H), 7.38-7.59 (m, 4H), 7.65-7.78 (m, 1H), 13.05 (s, 1H).

Example 100(2)

[3-(4-amino-4-oxobutyl)-7-((E)-2-{4-[4-(2,3-difluorophenoxy)butoxy]phenyl}vinyl)-1H-indol-1-yl] acetic acid TLC: Rf 0.16 (dichloromethane:methanol=9:1);

$^1$H-NMR (DMSO-$d_6$): δ 1.75-1.99 (m, 6H), 2.12 (t, 2H), 2.63 (t, 2H), 4.01-4.11 (m, 2H), 4.12-4.20 (m, 2H), 5.13 (s, 2H), 6.73 (s, 1H), 6.84-7.19 (m, 8H), 7.20-7.33 (m, 2H), 7.45 (d, 1H), 7.49 (d, 2H), 7.52 (d, 1H), 13.03 (s, 1H).

Example 100(3)

{7-[(E)-2-(4-{[(2E)-4-mesityloxy)-2-buten-1-yl] oxy}phenyl)vinyl]-3-[4-methylamino)-4-oxobutyl]-1H-indol-1-yl}acetic acid TLC: Rf 0.28 (dichloromethane:methanol=9:1);

$^1$H-NMR (DMSO-$d_6$): δ 1.77-1.92 (m, 2H), 2.08-2.18 (m, 2H), 2.16 (s, 9H), 2.56 (d, 3H), 2.62 (t, 2H), 4.28 (d, 2H), 4.64 (d, 2H), 5.13 (s, 2H), 5.99-6.18 (m, 2H), 6.81 (s, 2H), 6.87-7.06 (m, 4H), 7.07 (s, 1H), 7.26 (d, 1H), 7.44 (dd, 1H), 7.50 (d, 2H), 7.53 (d, 1H), 7.66-7.78 (m, 1H), 13.06 (s, 1H).

Example 100(4)

{3-(4-amino-4-oxobutyl)-7-[(E)-2-(4-{[(2E)-4-mesityloxy)-2-buten-1-yl]oxy}phenyl)vinyl]-1H-indol-1-yl}acetic acid TLC: Rf 0.23 (dichloromethane:methanol=9:1);

$^1$H-NMR (DMSO-$d_6$): δ 1.77-1.91 (m, 2H), 2.12 (t, 2H), 2.16 (s, 9H), 2.63 (t, 2H), 4.28 (d, 2H), 4.64 (d, 2H), 5.13 (s, 2H), 5.99-6.17 (m, 2H), 6.71 (s, 1H), 6.80 (s, 2H), 6.87-7.06 (m, 4H), 7.07 (s, 1H), 7.21-7.31 (m, 2H), 7.45 (dd, 1H), 7.50 (d, 2H), 7.53 (d, 1H), 13.06 (s, 1H).

Example 101

4-(1-carboxymethyl)-7-{[2-hydroxy-4-(4-phenoxybutoxy)phenyl]ethynyl}-1H-indol-3-yl)butanoic acid Except for using the compound prepared in Example 43 in place of the compound prepared in Example 2, the same operation as in Example 3→Example 4→Example 3 (using [(2-bromo-5-{[4-(phenyloxy)butyl]oxy}phenyl)oxy](1,1-dimethylethyl)dimethylsilane in place of the compound prepared in Example 2)→Example 30→Example 6 was conducted to obtain the titled compound having the following physical properties.

TLC: Rf 0.24 (chloroform:methanol:water=50:10:1);

$^1$H-NMR (DMSO-$d_6$): δ 1.76-2.02 (m, 6H), 2.27 (t, 2H), 2.66 (t, 2H), 3.95-4.14 (m, 4H), 5.40 (s, 2H), 6.37 (dd, 1H), 6.46 (d, 1H), 6.83-6.91 (m, 3H), 6.95 (dd, 1H), 7.11 (s, 1H), 7.16-7.24 (m, 3H), 7.29 ((d, 1H), 7.51 (dd, 1H), 9.92 (s, 1H).

Example 102 methyl 4-({7-bromo-1-[2-methyloxy)-2-oxoethyl]-1H-indol-3-yl}thio)butanoate

Except for using the compound prepared in Example 48 in place of the compound prepared in Example 1 and methyl bromoacetate in place of methyl 4-bromobutyrate, the same operation as in Example 2 was conducted to obtain the titled compound having the following physical properties.

TLC: Rf 0.19 (n-hexane:ethyl acetate=3:1);

$^1$H-NMR ($CDCl_3$): δ 1.79-1.89 (m, 2H), 2.45 (t, 2H), 2.71 (t, 2H), 3.64 (s, 3H), 3.78 (s, 3H), 5.73 (s, 2H), 7.04 (dd, 1H), 7.15 (s, 1H), 7.37-7.40 (m, 1H), 7.70 (dd, 1H).

Example 103 methyl 4-({7-bromo-1-[2-methyloxy-2-oxoethyl]-1H-indol-3-yl}sulfonyl)butanoate

To a methylene chloride (3.5 mL) solution of the compound (146 mg) prepared in Example 102, a methylene chloride (1 mL) solution of 3-chloroperbenzoic acid (185 mg) was added dropwise under ice cooling, followed by stirring at room temperature for 50 minutes. To the reaction mixture, an aqueous saturated sodium thiosulfate solution was added under ice cooling, followed by extraction with ethyl acetate. The organic layer was washed in turn with an aqueous saturated sodium hydrogen carbonate solution, water and saturated saline, dried and then concentrated. The residue was purified by silica gel column chromatography (n-hexane: ethyl acetate=75:25 to 50:50) to obtain a compound (160 mg) having the following physical properties.

TLC: Rf 0.27 (n-hexane:ethyl acetate=1:1);

$^1$H-NMR ($CDCl_3$): δ 2.04-2.12 (m, 2H), 2.46 (t 2H), 3.27 (t 2H), 3.62 (s, 3H), 3.80 (s, 3H), 5.33 (s, 2H), 7.12-7.17 (m, 1H), 7.49 (d, 1H), 7.63 (d, 1H), 7.88-7.91 (m, 1H).

Example 104

4-[(1-(carboxymethyl)-7-{(E)-2-[4-(4-phenoxybutoxy)phenyl]vinyl}-1H-indol-3-yl)sulfonyl]butanoic acid Except for using the compound prepared in Example 103 in place of the compound prepared in Example 2 and 1-ethenyl-4-{[4-(phenyloxy)butyl]oxy}benzene in place of 4-vinylphenyl acetate, the same operation as in Example 3→Example 6 was conducted to obtain the titled compound having the following physical properties.

TLC: Rf 0.35 (dichloromethane:methanol:acetic acid=90:10:0.5);

$^1$H-NMR (DMSO-$d_6$): δ 1.70-1.93 (m, 6H), 2.34 (t 2H), 3.21-3.31 (m, 2H), 3.98-4.13 (m, 4H), 5.36 (s, 2H), 6.81-7.05 (m, 6H), 7.21-7.32 (m, 3H), 7.40-7.61 (m, 4H), 7.71 (d, 1H), 8.08 (s, 1H), 12.13 (s, 1H), 13.29 (s, 1H).

Example 104(1)

4-{[1-(carboxymethyl)-7-((E)-2-{4-[4-(2,3-difluorophenoxy)butoxy]phenyl}vinyl)-1H-indol-3-yl]sulfonyl}butanoic acid Using a corresponding compound, the same operation as in Example 104 was conducted to obtain the titled compound having the following physical properties.

TLC: Rf 0.29 (dichloromethane:methanol:acetic acid=90:10:0.5);

$^1$H-NMR (DMSO-$d_6$): δ 1.72-1.96 (m, 6H), 2.34 (t 2H), 3.25-3.29 (m, 2H), 4.06 (t 2H), 4.16 (t 2H), 5.29 (s, 2H), 6.91-7.18 (m, 6H), 7.26 (dd, 1H), 7.39-7.62 (m 4H), 7.70 (d, 1H), 8.06 (s, 1H), 12.40 (s, 2H).

The compounds prepared in Example 40(2) and Example 40(89) can be obtained by using, as starting materials, the compounds prepared in Example 105→Example 106 in place of the compound prepared in Example 1 in the step corresponding to Example 2 in the operation of the Example. Also, the compounds prepared in Example 98(31), Example 98(32), Example 98(61), Example 98(99), Example 98(102) to Example 98(112), Example 98(121) to Example 98(131) and Example 98(136) can be obtained by using the same steps as in the following Example 105→Example 106 in place of the step corresponding to Example 41 in the operation of the Example.

Example 105

{1-[(7-bromo-1H-indol-3-yl)methyl]cyclopropyl}acetonitrile

To a toluene (12 mL) solution of 7-bromoindole (1.00 g), [1-bromomethyl)cyclopropyl]acetonitrile (444 mg) was added and a diethyl ether solution (1.7 mL) of 3M ethylmagnesium bromide was added dropwise under ice cooling, and then the mixture was refluxed for 2.5 hours. To the reaction mixture, an aqueous saturated ammonium chloride solution was added under ice cooling, followed by extraction with ethyl acetate. The organic layer was washed with water and saturated saline, dried over anhydrous sodium sulfate and then filtered. The filtrate was concentrated and the residue was purified by silica gel column chromatography (n-hexane:ethyl acetate=90:10 to 80:20) to obtain the titled compound having the following physical properties (390 mg).

TLC: Rf 0.33 (n-hexane:ethyl acetate=4:1);

$^1$H-NMR ($CDCl_3$): δ 0.61-0.74 (m, 4H), 2.28 (s, 2H), 2.91 (s, 2H), 7.02 (t, 1H), 7.17 (d, 1H), 7.36 (d, 1H), 7.57 (d, 1H), 8.24 (brs, 1H).

Example 106 methyl {1-[(7-bromo-1H-indol-3-yl)methyl]cyclopropyl}acetate

Using the compound prepared in Example 105, the same operation as in Example 52→Example 7 was conducted to obtain the titled compound having the following physical properties.

TLC: Rf 0.53 (n-hexane:ethyl acetate=3:1);

$^1$H-NMR ($CDCl_3$): δ 0.49-0.61 (m, 4H), 2.24 (s, 2H), 2.86 (s, 2H), 3.66 (s, 3H), 6.99 (t, 1H), 7.12 (d, 1H), 7.32 (dd, 1H), 7.57 (dt, 1H), 8.18 (brs, 1H).

Example 107

4-(7-{(E)-2-[4-({4-[(2,3-difluorophenyl)oxy]butyl}oxy)phenyl]ethenyl}-1-{2-[(methylsulfonyl)amino]-2-oxoethyl}-1H-indol-3-yl)butanoic acid Except for using a corresponding compound in place of the compound prepared in Example 90, the same operation as in Example 91B Example 92 was conducted to obtain the titled compound having the following physical properties.

TLC: Rf 0.45 (dichloromethane:methanol:acetic acid=9:1:0.05);

$^1$H-NMR(DMSO-$d_6$): δ 1.78-1.95 (m, 6H), 2.28 (t, 2H), 2.67 (t, 2H), 2.94 (s, 3H), 4.07 (t, 2H), 4.16 (t, 2H), 5.16 (s, 2H), 6.85-7.17 (m, 8H), 7.22 (d, 1H), 7.36-7.49 (m, 2H), 7.55 (d, 2H), 12.02 (s, 1H), 12.24 (s, 1H).

Biological Example

The effects of the compound of the present invention represented by the formula (I) were confirmed by the following Biological Example. The methods are described below, but the present invention is not limited thereto.

Biological Example 1

Effect on OVA-Induced Bronchocontraction Involved in Endogenous Leukotriene in Guinea Pigs Guinea pigs were actively sensitized by intraperitoneal administration of 1 ml of saline containing 1 mg ovalbumin (OVA) containing $5\times10^9$ killed Bordetella pertussis cells. Two or three weeks after the sensitization, the guinea pigs were anesthetized with pentobarbital sodium (75 mg/kg, i.p.), and a polyethylene tube was inserted into the trachea which had been incised. For administration of the compound of the present invention and OVA, the jugular vein was cannulated. One side of the tracheal cannula was connected to a constant volume respirator and the animals were artificially ventilated with a constant volume of 5 mL at a frequency of 70 strokes/min. Bronchocontraction was induced by intravenous administration of OVA, and airway resistance was measured by Konzett & Rössler method. In order to avoid the influence of cyclooxygenase metabolites and histamine, indomethacin (5 mg/kg/mL) and pyrilamine (1 mg/kg/mL) were intravenously administered 3 and 1 minute(s) before OVA challenge. Bronchocontraction was measured until the time of 20 minutes after OVA challenge.

It was revealed from the results that the compound represented by the formula (I) inhibited the contraction of guinea pig tracheal mustle. For example, the compound of Example 44 inhibited the airway contraction at an oral dose of 10 mg/kg.

Formulation Example

The formulations to be used in order to carry out the present invention are shown below.

Formulation Example 1

The following components were admixed by conventional techniques, thereby to give 10,000 tablets each containing 10 mg of active ingredient.

4-(3-carboxymethyl)-4-{(E)-2-[4-(4-phenylbutoxy)phenyl]vinyl}-1H-indol-1-yl)butanoic acid (100 g);

carboxymethyl cellulose calcium (disintegrating agent) (20 g);

magnesium stearate (lubricating agent) (10 g);

microcrystalline cellulose (870 g).

Formulation Example 2

The following components were admixed by conventional method, filtered over a dust-removable filter, and filled 5 ml each in ampoules, and heat-sterilized with an autoclave, giving 10,000 ampoules each containing 20 mg of active ingredient.

4-(3-(carboxymethyl)-4-{(E)-2-[4-(4-phenylbutoxy)phenyl]vinyl}-1H-indol-1-yl)butanoic acid (200 g);

mannitol (2 kg);

distilled water (SOL).

INDUSTRIAL APPLICABILITY

Since the compound of the present invention etc. has low-toxity and an availableness using as drug and also antagonizes leukotriene receptor, it is useful as an inhibitor of airway contraction, an inhibitor of infiltration of inflammatory cells (e.g. eosinophils, neutrophils, lymphocytes, basophils, etc.), an inhibitor of mucus secretion or an inhibitor of increased airway hyperreactivity. And the compound of the present invention etc. is also useful for the prevention and/or treatment of leukotriene receptor-mediated diseases, e.g. respiratory diseases (e.g. bronchial asthma, chronic obstructive pulmonary diseases, lung emphysema, chronic bronchitis, pneumonia (e.g. interstitial pneumonitis, etc.), severe acute respiratory syndrome (SARS), acute respiratory distress syndrome (ARDS), allergic rhinitis, sinusitis (e.g. acute sinusitis, chronic sinusitis, etc.), etc., and as an expectorant or an antitussive agent And the compound of the present invention etc. is also useful as an agent for the improvement of respiratory functions.

Leukotriene receptor-mediated diseases also include cardiovascular diseases, e.g. angina pectoris, cardiac infarction, acute coronary syndromes, heart failure, arrhythmia, cardiomyopathy (dilative cardiomyopathy, hypertrophic cardiomyopathy, etc.), pericarditis, valvulitis, myocarditis, cardiac tamponade, low cardiac output syndrome, mitral stenosis, atherosclerosis, pulmonary fibrosis, cerebral infarction, cerebral edema, aneurysm, headache (migraine, migrainous neuralgia or tension-type headache, etc.), gynecologic disorder (endometriosis, dysmenorrhea, etc.), Meniere's disease, etc. The compound of the present invention etc. is useful for the treatment and/or prevention of these diseases.

The invention claimed is:

1. A compound represented by the formula (I-a-1)

(I-a-1)

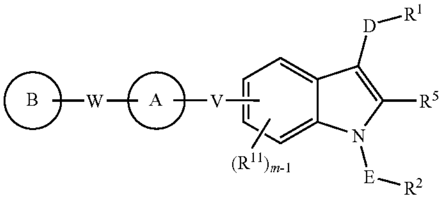

wherein:

$R^{11}$ represents (1) alkyl which may have a substituent(s),
 wherein
 said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, and
 said substituent(s) represent(s) 1 to 4 group(s) selected from the group consisting of (a) hydroxyl, (b) amino, (c) carboxy, (d) nitro, (e) C1-6 alkoxy, (f) C3-7 cycloalkyl-C1-6 alkoxy, (g) C3-7 cycloalkyloxy, (h) C1-6 alkoxycarbonyl, (i) C1-6 acyloxy, (j) C1-4 alkylthio, (k) halogen, (l) C1-4 alkylsulfonyl and (m) acyl,
 wherein said acyl represents
 (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl,
 (ii) alkenylcarbonyl, wherein said alkenyl represents ethenyl, propenyl, butenyl, pentenyl or hexenyl, or
 (iii) alkynylcarbonyl, wherein said alkynyl represents ethynyl, propynyl, butynyl, pentynyl or hexynyl, (2) alkenyl which may have a substituent(s),
 wherein
 said alkenyl represents ethenyl, propenyl, butenyl, pentenyl, or hexenyl, and
 said substituent(s) represent(s) 1 to 4 group(s) selected from the group consisting of (a) hydroxy, (b) amino, (c) carboxy, (d) nitro, (e) C1-6 alkoxy, (f) C3-7 cycloalkyl-C1-6 alkoxy, (g) C3-7 cycloalkyloxy, (h) C1-6 alkoxycarbonyl, (i) C1-6 acyloxy, (j) C1-4 alkylthio, (k) halogen, (l) C1-4 alkylsulfonyl and (m) acyl,
 wherein said acyl represents
 (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl,
 (ii) alkenylcarbonyl, wherein said alkenyl represents ethenyl, propenyl, butenyl, pentenyl or hexenyl, or
 (iii) alkynylcarbonyl, wherein said alkynyl represents ethynyl, propynyl, butynyl, pentynyl or hexynyl, (3) alkynyl which may have a substituent(s),
 wherein
 said alkynyl represents ethynyl, propynyl, butynyl, pentynyl or hexynyl, and
 said substituent(s) represent(s) 1 to 4 group(s) selected from the group consisting of (a) hydroxy, (b) amino, (c) carboxy, (d) nitro, (e) C1-6 alkoxy, (f) C3-7 cycloalkyl-C1-6 alkoxy, (g) C3-7 cycloalkyloxy, (h) C1-6 alkoxycarbonyl, (i) C1-6 acyloxy, (j) C1-4 alkylthio, (k) halogen, (l) C1-4 alkylsulfonyl and (m) acyl, wherein said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl, (4) hydroxy which may be protected by alkyl, alkenyl, alkynyl, alkylsulfonyl or acyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, said alkenyl represents ethenyl, propenyl, butenyl, pentenyl or hexenyl, said alkynyl represents ethynyl, propynyl, butynyl, pentynyl or hexynyl, said alkylsulfonyl represents C1-4 alkylsulfonyl, and said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl, (5) mercapto which may be protected by alkyl, alkenyl, alkynyl, alkylsulfonyl or acyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, said alkenyl represents ethenyl, propenyl, butenyl, pentenyl or hexenyl, said alkynyl represents ethynyl, propynyl, butynyl, pentynyl or hexynyl, said alkylsulfonyl represents C1-4 alkylsulfonyl, and said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl, (6) amino which may be protected by alkyl, alkenyl, alkynyl, alkylsulfonyl or acyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, said alkenyl represents ethenyl, propenyl, butenyl, pentenyl or hexenyl, said alkynyl represents ethynyl, propynyl, butynyl, pentynyl or hexynyl, said alkylsulfonyl represents C1-4 alkylsulfonyl, and said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl, (7) carbamoyl which may have a substituent(s), wherein said carbamoyl which may have a substituent(s) represents carbamoyl which has no substituent, N-mono-C1-4 alkylcarbamoyl, N,N-di-C1-4 alkylcarbamoyl or 1-piperidiylcarbamoyl, (8) sulfamoyl which may have a substituent(s), wherein said sulfamoyl which may have a substituent(s) represents sulfamoyl which has no substituent, N-mono-C1-4 alkylsulfamoyl or N,N-di-C1-4 alkylsulfamoyl, (9) carboxy,

(10) C1-6 alkoxycarbonyl,

(11) sulfo,

(12) sulfino,

(13) nitro,

(14) cyano,

(15) halogen,

(16) C1-4 alkylsulfinyl,

(17) C1-4 alkylsulfonyl, or

(18) acyl, wherein said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl;

$R^5$ represents a hydrogen atom or a substituent selected from the group consisting of hydroxy, methyl, ethyl, propyl, n-butyl, n-pentyl, n-hexyl, fluoro, chloro, bromo, methoxy, ethoxy, propoxy, butoxy, acetyl, propanoyl, trifluoromethyl and methylthio;

m-1 represents 0 or an integer of 1 to 3;

V represents

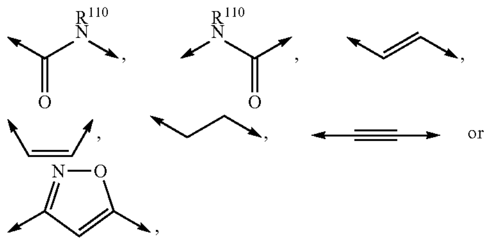

wherein $R^{110}$ represents a hydrogen atom or C1-8 alkyl, and a left arrow binds to ring A;

W represents —O—(C1-6 alkylene)—O—, —O—(C2-6 alkenylene)—O—, —O—(C1-6 alkylene)-C(═O)—, —$CH_2$-phenylene-$CH_2$—, —O—(C1-7 alkylene)- or -(C1-7 alkylene)—O—;

ring A represents cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, pyridine, pyrrole, quinoline, isoquinoline, oxazole, thiazole, benzooxazole or benzothiazole ring, each of which may be substituted with a group(s) selected from the group consisting of C1-8 alkyl which may have a substituent(s), C2-8 alkenyl which may have a substituent(s), C1-8 alkoxy which may have a substituent(s), C2-8 alkenyloxy which may have a substituent(s), C5-10 mono- or bi-cyclic carbocyclic ring which may have a substituent(s), 5 to 10 membered mono- or bi-cyclic heterocyclic ring which may have a substituent(s), hydroxy which may be protected, mercapto which may be protected, amino which may be protected, carbamoyl which may have a substituent(s), carboxy, alkoxycarbonyl, nitro, cyano, halogen, acyl and oxo;

ring B represents cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indan, naphthalene, dihydronaphthalene, tetrahydronaphthalene, perhydronaphthalene, pyridine, pyrrole, quinoline, isoquinoline, oxazole, thiazole, benzooxazole or benzothiazole ring, each of which may be substituted with 1 to 3 group(s) selected from the group consisting of hydroxyl, C1-8 alkyl, C2-8 alkenyl, C2-8 alkynyl, halogen, C1-8 alkoxy, C2-8 alkenyloxy, C2-8 alkynyloxy, C1-8 alkylthio, C1-8 acyl, C1-4 alkyl substituted with 1 to 3 halogen(s), C1-4 alkyl substituted with hydroxy, C1-4 alkyl substituted with mercapto, C1-4 alkoxy substituted with 1 to 3 halogen(s);

D represents a bond, C1-4 alkylene which may have 1 to 2 substituent(s), —C(O)—(C2-4 alkylene)- which may have 1 to 2 substituent(s), —O—(C1-4 alkylene)- which may have 1 to 2 substituent(s) or —S—(C1-4 alkylene)- which may have 1 to 2 substituent(s), provided that each alkylene group binds to $R^1$;

E represents a bond, C1-4 alkylene which may have 1 to 2 substituent(s), —C(O)—(C2-4 alkylene)- which may have 1 to 2 substituent(s), —O—(C1-4 alkylene)- which may have 1 to 2 substituent(s) or —S—(C1-4 alkylene)- which may have 1 to 2 substituent(s), provided that each alkylene group binds to $R^2$; and $R^1$ and $R^2$ each independently represents —$COOR^A$, —$CONR^AR^B$, —$CONR^BSO_2R^C$, —$SO_2NR^BCOR^C$,

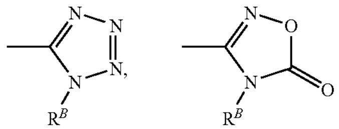

or

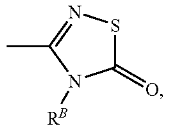

wherein $R^A$ and $R^B$ each independently represents a hydrogen atom or C1-8 alkyl, and $R^C$ represents a hydrocarbon group, or a salt thereof.

2. The compound according to claim 1, wherein D represents

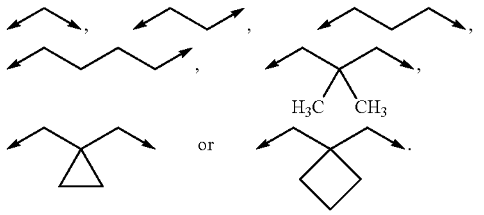

3. The compound according to claim 1, wherein E represents

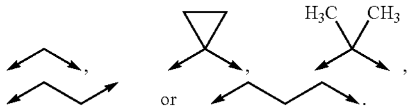

4. A compound represented by the formula (I-a-1-a)

(I-a-1-a)

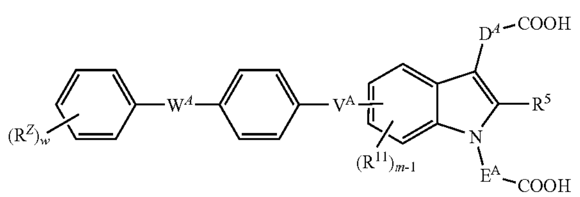

wherein:

$R^{11}$ represents (1) alkyl which may have a substituent(s), wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, and said substituent(s) represent(s) 1 to 4 group(s) selected from the group consisting of (a) hydroxy, (b) amino, (c) carboxy, (d) nitro, (e) C1-6 alkoxy, (f) C3-7 cycloalkyl-C1-6 alkoxy, (g) C3-7 cycloalkyloxy, (h) C1-6 alkoxycarbonyl, (i) C1-6 acyloxy, (j) C1-4 alkylthio, (k) halogen, (l) C1-4 alkylsulfonyl and (m) acyl, wherein said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl, (2) alkenyl which may have a substituent(s), wherein said alkenyl represents ethenyl, propenyl, butenyl, pentenyl, or hexenyl, and said substituent(s) represent(s) 1 to 4 group (s) selected from the group consisting of (a) hydroxy, (b) amino, (c) carboxy, (d) nitro, (e) C1-6 alkoxy, (f) C3-7 cycloalkyl-C1-6 alkoxy, (g) C3-7 cycloalkyloxy, (h) C1-6 alkoxycarbonyl, (i) C1-6 acyloxy, (j) C1-4 alkylthio, (k) halogen, (l) C1-4 alkylsulfonyl and (m) acyl, wherein said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl, (3) alkynyl which may have a substituent(s), wherein said alkynyl represents ethynyl, propynyl, butynyl, pentynyl or hexynyl, and said substituent(s) represent(s) 1 to 4 group (s) selected from the group consisting of (a) hydroxy, (b) amino, (c) carboxy, (d) nitro, (e) C1-6 alkoxy, (f) C3-7 cycloalkyl-C1-6 alkoxy, (g) C3-7 cycloalkyloxy, (h) C1-6 alkoxycarbonyl, (i) C1-6 acyloxy, (j) C1-4 alkylthio, (k) halogen, (l) C1-4 alkylsulfonyl and (m) acyl, wherein said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl, (4) hydroxy which may be protected by alkyl, alkenyl, alkynyl, alkylsulfonyl or acyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, said alkenyl represents ethenyl, propenyl, butenyl, pentenyl or hexenyl, said alkynyl represents ethynyl, propynyl, butynyl, pentynyl or hexynyl, said alkylsulfonyl represents C1-4 alkylsulfonyl, and said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl, (5) mercapto which may be protected by alkyl, alkenyl, alkynyl, alkylsulfonyl or acyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, said alkenyl represents ethenyl, propenyl, butenyl, pentenyl or hexenyl, said alkynyl represents ethynyl, propynyl, butynyl, pentynyl or hexynyl, said alkylsulfonyl represents C1-4 alkylsulfonyl, and said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl, (6) amino which may be protected by alkyl, alkenyl, alkynyl, alkylsulfonyl or acyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, said alkenyl represents ethenyl, propenyl, butenyl, pentenyl or hexenyl, said alkynyl represents ethynyl, propynyl, butynyl, pentynyl or hexynyl, said alkylsulfonyl represents C1-4 alkylsulfonyl, and said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkynylcarbonyl, wherein said alkynyl represents ethynyl, propynyl, butynyl, pentynyl or hexynyl, (7) carbamoyl which may have a substituent(s), wherein said carbamoyl which may have a substituent(s) represents carbamoyl which has no substituent, N-mono-C1-4 alkylcarbamoyl, N,N-di-C1-4 alkylcarbamoyl or 1-piperidiylcarbamoyl, (8) sulfamoyl which may have a substituent(s), wherein said sulfamoyl which may have a substituent(s) represents sulfamoyl which has no substituent, N-mono-C1-4 alkylsulfamoyl or N,N-di-C1-4 alkylsulfamoyl, (9) carboxy,

(10) C1-6 alkoxycarbonyl,

(11) sulfo,

(12) sulfino,

(13) nitro,

(14) cyano,

(15) halogen,

(16) C1-4 alkylsulfinyl,

(17) C1-4 alkylsulfonyl, or

(18) acyl, wherein said acyl represents (i) alkylcarbonyl, wherein said alkyl represents methyl, ethyl, n-propyl, isopropyl, n-butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl or icosyl, (ii) alkenylcarbonyl, wherein said alkenyl represents ethenyl, propenyl, butenyl, pentenyl or hexenyl, or (iii) alkenylcarbonyl, wherein said alkynyl represents ethynyl, propynyl, butynyl, pentynyl or hexynyl;

$V^A$ represents

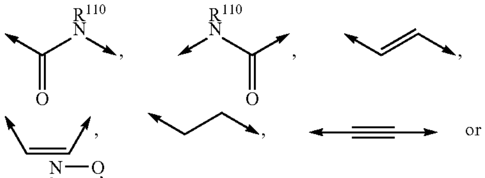

or

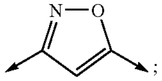

;

$W^A$ represents —O—(C1-6 alkylene)—O—, —O—(C2-6 alkenylene)—O—, —O—(C1-6 alkylene) -C(=O)—, —$CH_2$-phenylene-$CH_2$—, —O—(C1-7 alkylene)- or -(C1-7 alkylene)—O—;

$R^5$ represents a hydrogen atom or a substituent selected from the group consisting of hydroxy, methyl, ethyl, propyl, n-butyl, n-pentyl, n-hexyl, fluoro, chloro, bromo, methoxy, ethoxy, propoxy, butoxy, acetyl, propanoyl, trifluoromethyl and methylthio;

m-1 represents 0 or an integer of 1 to 3;

$R^z$ represents a substituent selected from the group consisting of methyl, ethyl, propyl, butyl, isobutyl, pentyl, trifluoromethyl, benzyl, phenethyl, benzoyl, phenylsulfonyl, vinyl, allyl, phenyl, pyridyl, furyl, thienyl, hydroxy, methoxy, ethoxy, phenoxy, benzyloxy, amino, dimethylamino, diethylamino, carboxy, methoxycarbonyl, ethoxycarbonyl, fluoro, chloro, bromo, iodo, acetyl and propionyl;

w represents 0 or an integer of 1 to 5;

$D^A$ represents

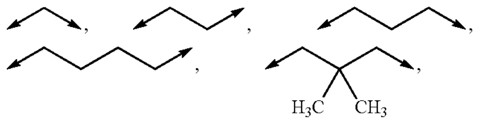

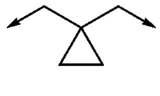

or

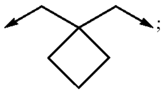

;

$E^A$ represents

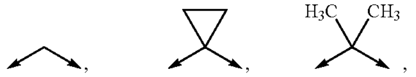

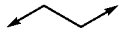

or

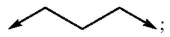

;

and $R^{110}$ represents a hydrogen atom or C1-8 alkyl.

5. The compound according to claim 1, which is selected from the group consisting of:

(1) 1-(3-carboxypropyl)-4-{(E)-2-[4-(4-phenylbutoxy)phenyl]vinyl}-1H-indole-3-carboxylic acid, (2) 4-(3-(carboxymethyl)-4-{(E)-2-[4-(4-phenylbutoxy)phenyl]vinyl}-1H-indol-1-yl)butanoic acid, (3) 4-(3-(carboxymethyl)-4-{(E), 2-[4-(4-phenoxybutoxy)phenyl]vinyl}-1H-indol-1-yl)butanoic acid, (4) 4-(3-(carboxymethyl)-4-{2-[4-(4-phenylbutoxy)phenyl]ethyl}-1H-indol-1-yl)butanoic acid, (5) 4-(3-(carboxymethyl)-4-{2-[4-(4-phenoxybutoxy)phenyl]ethyl}-1H-indol-1-yl)butanoic acid, (6) 4-[4-{(E)-2-[4-(4-phenylbutoxy)phenyl]vinyl}-3-(1H-tetrazol-5-ylmethyl)-1H-indol-1-yl]butanoic acid, (7) 4-[4-{2-[4-(4-phenylbutoxy)phenyl]ethyl}-3-(1H-tetrazol-5-ylmethyl)-1H-indol-1-yl]butanoic acid, (8) 4-(3-(carboxymethyl)-4-{(E)-2-[4-(3-phenoxypropoxy)phenyl]vinyl}-1H-indol-1-yl)butanoic acid, (9) 2,2'-(4-{(E)-2-[4-(4-phenylbutoxy)phenyl]vinyl}-1H-indol-1,3-diyl)diacetic acid,

(10) 4-(3-(carboxymethyl)-4-{(E)-2-[4-(4-phenylbutoxy)phenyl]vinyl}-1H-indol-1-yl)-4-oxobutanoic acid,

(11) 4-(3-(carboxymethyl)-4-{(E)-2-[4-(3-cyclohexylpropoxy)phenyl]vinyl}-1H-indol-1-yl)butanoic acid,

(12) 4-[3-(carboxymethyl)-4-((E)-2-{4-[4-(2-methylphenoxy)butoxy]phenyl}vinyl)-1H-indol-1-yl]butanoic acid,

(13) 4-[4-((E)-2-{4-[4-(2-acetylphenoxy)butoxy]phenyl}vinyl)-3-(carboxymethyl)-1H-indol-1-yl]butanoic acid,

(14) 4-(1-(carboxymethyl)-7-{(E)-2-[4-(4-phenoxybutoxy)phenyl]vinyl}-1H-indol-3-yl)butanoic acid,

(15) 4-[1-(carboxymethyl)-7-((E)-2-{4-[4-(2-chlorophenoxy)butoxy]phenyl}vinyl)-1H-indol-3-yl]butanoic acid,

(16) 4-[1-(carboxymethyl)-7-((E)-2-{4-[4-(2,3-difluorophenoxy)butoxy]phenyl}vinyl)-1H-indol-3-yl]butanoic acid,

(17) 4-[1-(carboxymethyl)-4-fluoro-7-((E)-2-{4-[4-(mesityloxy)butoxy]phenyl}vinyl)-11H-indol-3-yl]butanoic acid,

(18) 4-[1-(carboxymethyl)-7-((E)-2-{4-[4-(2-chloro-3,5-difluorophenoxy)butoxy]phenyl}vinyl)-1H-indol-3-yl]butanoic acid,

(19) 4-[1-(carboxymethyl)-7-((E)-2-{4-[4-(2,6-dichloro-4-methylphenoxy)butoxy]phenyl}vinyl)-1H-indol-3-yl]butanoic acid,

(20) 4-[1-(carboxymethyl)-7-((E)-2-{4-[4-(2,3-difluorophenoxy)butoxy]phenyl}vinyl)-2-methyl-1H-indol-3-yl]butanoic acid,

(21) 4-{1-(carboxymethyl)-7-[(E)-2-(4-{[(2E)-4-(2,3-difluorophenoxy)-2-buten-1-yl]oxy}phenyl)vinyl]-1H-indol-3-yl}butanoic acid,

(22) {[1-(carboxymethyl)-7-((E)-2-{4-[4-(2,3-difluorophenoxy)butoxy]phenyl}vinyl)-1H-indol-3-yl]thio}acetic acid,

(23) {[1-(carboxymethyl)-7-((E)-2-{4-[4-(mesityloxy)butoxy]phenyl}vinyl)-1H-indol-3-yl]thio}acetic acid,

(24) 3-1-{[1-(carboxymethyl)-7-((E)-2-{4-[4-(2,3-difluorophenoxy)butoxy]phenyl}vinyl)-1H-indol-3-yl]thio}-2-methylpropanoic acid,

(25) 4-(1-(carboxymethyl)-7-{(E)-2-[4-(4-phenoxybutoxy)phenyl]vinyl}-1H-indol-3-yl)-4-oxobutanoic acid,

(26) 4-[1-(carboxymethyl)-5-fluoro-7-((E)-2-{4-[4-(mesityloxy)butoxy]phenyl}vinyl)-1H-indol-3-yl]-4-oxobutanoic acid,

(27) 4-[1-(carboxymethyl)-7-((E)-2-{4-[4-(2,3-difluorophenoxy)butoxy]phenyl}vinyl)-1H-indol-3-yl]-4-oxobutanoic acid,

(28) 3-[1-(carboxymethyl)-7-((E)-2-{4-[4-(2,3-difluorophenoxy)butoxy]phenyl}vinyl)-1H-indol-3-yl]-2,2-dimethyl-3-oxopropanoic acid,

(29) 4-{1-(carboxymethyl)-7-[(E)-2-(4-{[(2E)-4-(mesityloxy)-2-buten-1-yl]oxy}phenyl)vinyl]-1H-indol-3-yl}butanoic acid,

(30) 4-{1-(carboxymethyl)-7-[(E)-2-(4-{[(2E)-4-(2,3-difluorophenoxy)-2-buten-1-yl]oxy}phenyl)vinyl]-2-methyl-1H-indol-3-yl}butanoic acid,

(31) [3-{[1-(carboxymethyl)cyclopropyl]methyl}-7-((E)-2-{4-[4-(2,3-difluorophenoxy)butoxy]phenyl}vinyl)-1H-indol-1-yl]acetic acid,

(32) {3-{[1-(carboxymethyl)cyclopropyl]methyl}-7-[(E)-2-(4-{[(2E)-4-(2,3-difluorophenoxy)-2-buten-1-yl]oxy}phenyl)vinyl]-1H-indol-1-yl}acetic acid,

(33) 4-{1-(carboxymethyl)-7-[(E)-2-(4-{[(2E)-4-(2,3-difluorophenoxy)-2-buten-1-yl]oxy}phenyl)vinyl]-4-fluoro-2-methyl-1H-indol-3-yl}butanoic acid,

(34) 4-{1-(carboxymethyl)-7-[(E)-2-(4-{[(2E)-4-(2-chlorophenoxy)-2-buten-1-yl]oxy}phenyl)vinyl]-2-methyl-1H-indol-3-yl}butanoic acid, and

(35) 4-{1-(carboxymethyl)-7-[(E)-2-(4-{[(2E)-4-(2-chlorophenoxy)-2-buten-1-yl]oxy}phenyl)vinyl]-4-fluoro-2-methyl-1H-indol-3-yl}butanoic acid.

6. A pharmaceutical composition comprising the compound represented by the formula (I-a-1), or a salt thereof according to claim 1, and a pharameutically acceptable agent.

* * * * *